US008019552B2

(12) United States Patent
Dai et al.

(10) Patent No.: US 8,019,552 B2
(45) Date of Patent: Sep. 13, 2011

(54) CLASSIFICATION OF BREAST CANCER PATIENTS USING A COMBINATION OF CLINICAL CRITERIA AND INFORMATIVE GENESETS

(75) Inventors: Hongyue Dai, Kenmore, WA (US); Laura J. Van't Veer, Amsterdam (NL); John Lamb, Shoreline, WA (US); Roland Stoughton, San Diego, CA (US); Stephen H. Friend, Philadelphia, PA (US); Yudong He, Kirkland, WA (US)

(73) Assignees: The Netherlands Cancer Institute, Amsterdam (NL); Merck Sharp & Dohme Corp., Rahway, NJ (US)

( * ) Notice: Subject to any disclaimer, the term of this patent is extended or adjusted under 35 U.S.C. 154(b) by 920 days.

(21) Appl. No.: 10/591,800

(22) PCT Filed: Mar. 7, 2005

(86) PCT No.: PCT/US2005/007894

§ 371 (c)(1),
(2), (4) Date: Jul. 9, 2007

(87) PCT Pub. No.: WO2005/086891

PCT Pub. Date: Sep. 22, 2005

(65) Prior Publication Data

US 2008/0187909 A1 Aug. 7, 2008

Related U.S. Application Data

(60) Provisional application No. 60/650,401, filed on Feb. 4, 2005, provisional application No. 60/604,076, filed on Aug. 24, 2004, provisional application No. 60/550,810, filed on Mar. 5, 2004.

(51) Int. Cl.
*G01N 33/48* (2006.01)
*G01N 33/50* (2006.01)

(52) U.S. Cl. .................. 702/19; 703/2; 435/6; 435/7.1; 436/64; 436/86; 436/94

(58) Field of Classification Search ........................ None
See application file for complete search history.

(56) References Cited

U.S. PATENT DOCUMENTS 6,647,341 B1 11/2003 Golub et al.

(Continued)

FOREIGN PATENT DOCUMENTS

WO WO98/33450 8/1998

(Continued)

OTHER PUBLICATIONS

"Patient" definition, Merrian-Webster online dictionary, 2010, on the World Wide Web at http://www.merriam-webster.com/dictionary/patient, 2 pages.*

(Continued)

*Primary Examiner* — Carolyn L. Smith
(74) *Attorney, Agent, or Firm* — Christensen O'Connor Johnson Kindness PLLC

(57) ABSTRACT

The present invention provides prognostic methods for conditions such as cancer, for example, breast cancer, comprising classifying an individual by a plurality of phenotypic, genotypic or clinical characteristics of the condition into a plurality of patient subsets, and analyzing the pattern of expression of prognosis-informative genes identified for that subset in a sample from the individual. The present invention also provides methods for constructing such patient subsets and of identifying prognosis-informative genesets for such subsets. The invention further provides methods of assigning a therapeutic regimen to an individual, microarrays useful for performing prognosis, kits comprising these microarrays, and computer systems and programs for implementing the methods of the invention.

22 Claims, 10 Drawing Sheets

U.S. PATENT DOCUMENTS

Figure 1:
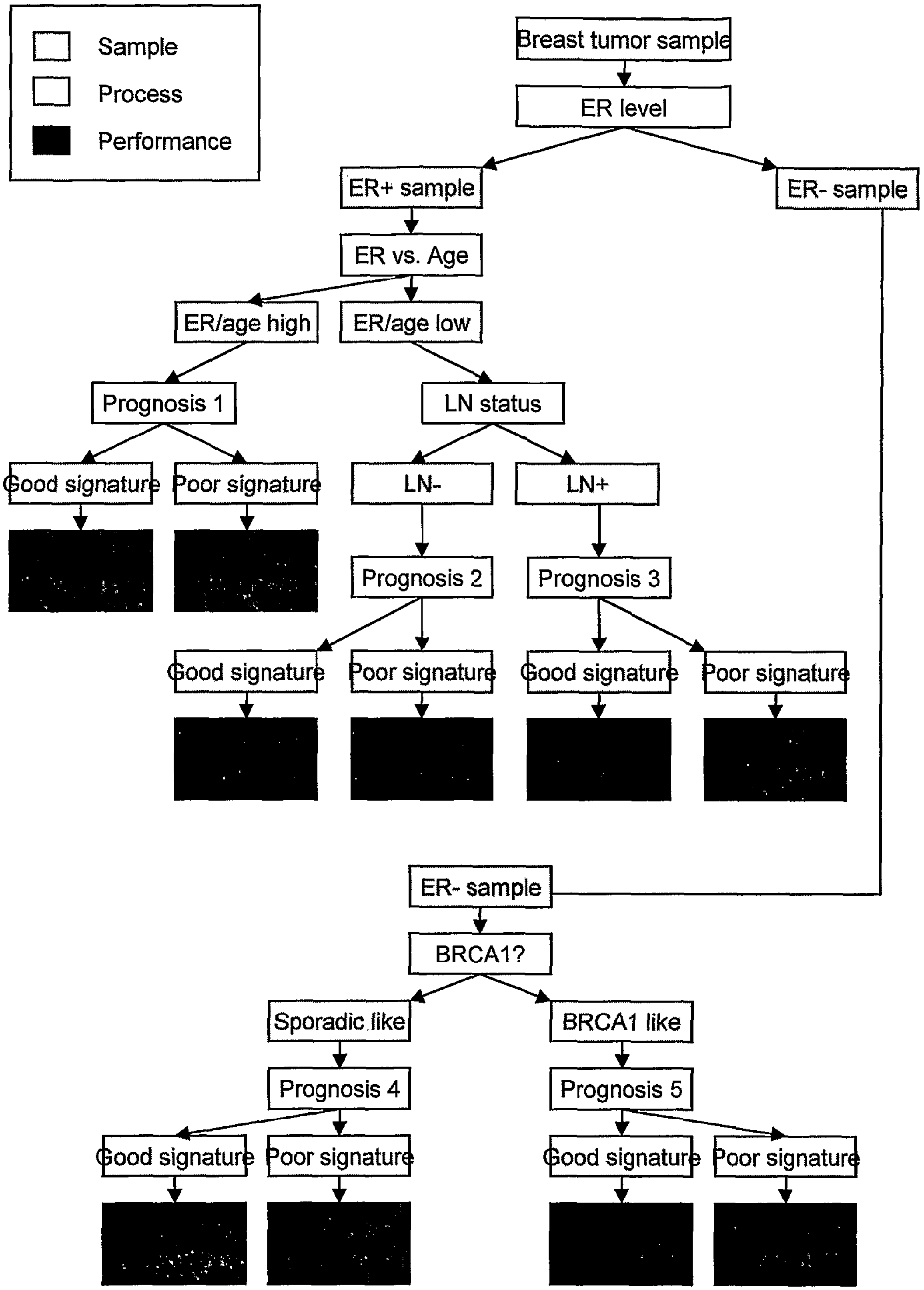

| | | | | |
|---|---|---|---|---|
| 7,171,311 | B2 | 1/2007 | Dai et al. | |
| 2003/0224374 | A1 | 12/2003 | Dai et al. | |
| 2004/0058340 | A1 * | 3/2004 | Dai et al. | 435/6 |
| 2005/0054826 | A1 | 3/2005 | Mao | |
| 2006/0040302 | A1 | 2/2006 | Botstein et al. | |

FOREIGN PATENT DOCUMENTS

| | | |
|---|---|---|
| WO | WO00/39339 | 7/2000 |
| WO | WO02/16650 | 2/2002 |
| WO | WO02/18646 | 3/2002 |
| WO | WO 2006/084272 A2 | 8/2006 |

OTHER PUBLICATIONS

"Individual" definition, Merriam-Webster online dictionary, 2010, on the World Wide Web at http://www.merriam-webster.com/dictionary/individual, 1 page.*

Alizadeh AA, et al., 2000 "Distinct types of diffuse large B-cell lymphoma identified by gene expression profiling" Nature 403(6769):503-511.

Beenken SW, et al., 2001 "Molecular biomarkers for breast cancer prognosis: coexpression of c-erbB-2 and p53" Ann Surg 233(5):630-638.

Biesecker et al., 1993 "Genetic Counseling for Families with Inherited Susceptibility to Breast C and Ovarian Cancer" JAMA 269(15):1970-1974.

Blanchard AP, et al., 1996 "High-density oligonucleotide arrays" Biosensors & Bioelectronics 11(Jun. 7):687-690.

Blanchard AP; (1998) "Synthetic DNA Arrays" Genetic Engineering (Setlow JK;):111-123.

Bonaldo MF, et al., 1996 "Normalization and subtraction: two approaches to facilitate gene discovery" Genome Res 6(9):791-806.

Casey G., 1997 "The BRCA1 and BRCA2 breast cancer genes" Curr Opin Oncol 9(1):88-93.

Collett K, et al., 1996 "Prognostic role of oestrogen and progesterone receptors in patients with breast cancer: relation to age and lymph node status" J Clin Pathol 49(11):920-925.

DeRisi J, et al., 1996 "Use of a cDNA microarray to analyse gene expression patterns in human cancer" Nat Genet 14(4):457-460.

Easton D, et al., 1993 "Inherited susceptibility to breast cancer" Cancer Surv 18:95-113.

Egholm M, et al., 1993 "PNA hybridizes to complementary oligonucleotides obeying the Watson-Crick hydrogen-bonding rules" Nature 365(6446):566-568.

Eifel P, et al., 2001 "National Institutes of Health Consensus Development Conference Statement: adjuvant therapy for breast cancer, Nov. 1-3, 2000" J Natl Cancer Inst 93(13):979-989.

Ferguson JA, et al., 1996 "A fiber-optic DNA biosensor microarray for the analysis of gene expression" Nat Biotechnol 14(13):1681-1684.

Fodor SP, et al.,1991 "Light-directed, spatially addressable parallel chemical synthesis" Science 251(4995):767-773.

Froehler BC, et al., 1986 "Synthesis of DNA via deoxynucleoside H-phosphonate intermediates" Nucleic Acids Res 14(13):5399-5407.

Golub TR, et al., 1999 "Molecular classification of cancer: class discovery and class prediction by gene expression monitoring" Science 286(5439):531-537.

Gruvberger S, et al., 2001 "Estrogen receptor status in breast cancer is associated with remarkably distinct gene expression patterns" Cancer Res 61(16):5979-5984.

Hughes TR, et al., 2001 "Expression profiling using microarrays fabricated by an ink-jet oligonucleotide synthesizer" Nat Biotechnol 19(4):342-347.

Khan J, et al., 1998 "Gene expression profiling of alveolar rhabdomyosarcoma with cDNA microarrays" Cancer Res 58(22):5009-5013.

Kononen J, et al., 1998 "Tissue microarrays for high-throughput molecular profiling of tumor specimens" Nat Med 4(7):844-847.

Lander ES, 1996 "The new genomics: global views of biology" Science 274(5287):536-539.

Lin SY, et al., 2003 "Regulation of ovarian function by the TGF-beta superfamily and follistatin" Reproduction 126(2):133-148.

Lockhart DJ, et al., 1996 "Expression monitoring by hybridization to high-density oligonucleotide arrays" Nat Biotechnol 14(13):1675-1680.

Lukas J, et al., 2001 "Alternative and aberrant messenger RNA splicing of the mdm2 oncogene in invasive breast cancer" Cancer Res 61(7):3212-3219.

Maggard MA, et al., 2003 "Do young breast cancer patients have worse outcomes?" J Surg Res 113(1):109-113.

Marcus JN, et al., 1996 "Hereditary breast cancer: pathobiology, prognosis, and BRCA1 and BRCA2 gene linkage" Cancer 77(4):697-709.

Maskos U and Southern EM, 1992 "Oligonucleotide hybridizations on glass supports: a novel linker for oligonucleotide synthesis and hybridization properties of oligonucleotides synthesised in situ" Nucleic Acids Res 20(7):1679-1684.

McBride LJ and Caruthers MH, 1983 "An investigation of several deoxynucleoside phosphoramidites useful for synthesizing deoxyoligonucleotides" Tetrahedron Letters 24(3):245-2481.

Miki Y, et al., 1994 "A strong candidate for the breast and ovarian cancer susceptibility gene BRCA1" Science 266(5182):66-71.

Pease AC, et al., 1994 "Light-generated oligonucleotide arrays for rapid DNA sequence analysis" Proc Natl Acad Sci U S A 91(11):5022-5026.

Perou CM, et al., 2000 "Molecular portraits of human breast tumours" Nature 406(6797):747-752.

Pichon MF, et al., 1996 "Prognostic value of steroid receptors after long-term follow-up of 2257 operable breast cancers" Br J Cancer 73(12):1545-1551.

Rudolph P, et al., 2001 "Concurrent overexpression of p53 and c-erbB-2 correlates with accelerated cycling and concomitant poor prognosis in node-negative breast cancer" Hum Pathol 32(3):311-319.

Schena M, et al., 1995 "Quantitative monitoring of gene expression patterns with a complementary DNA microarray" Science 270(5235):467-470.

Schena M, et al., 1996 "Parallel human genome analysis: microarray-based expression monitoring of 1000 genes" Proc Natl Acad Sci U S A 93(20):10614-9.

Shalon D, et al., 1996 "A DNA microarray system for analyzing complex DNA samples using two-color fluorescent probe hybridization" Genome Res 6(7):639-645.

Sorlie T, et al., 2003 "Repeated observation of breast tumor subtypes in independent gene expression data sets" Proc Natl Acad Sci U S A 100(14):8418-8423.

Sotiriou C, et al., 2003 "Breast cancer classification and prognosis based on gene expression profiles from a population-based study" Proc Natl Acad Sci U S A 100(18):10393-10398.

Surowiak P, et al., 2001 "Prognostic value of immunocytochemical estimation of estrogen receptor (ER) and of pS2 estrogen-dependent protein in cells of mammary ductal carcinoma. Analysis of five-year course of the disease" Folia Histochem Cytobiol 39(2):143-144.

van't Veer LJ, et al., 2002 "Gene expression profiling predicts clinical outcome of breast cancer" Nature 415(Jan. 31, 2002):530-536.

van de Vijver MJ, et al., 2002 "A gene-expression signature as a predictor of survival in breast cancer" N Engl J Med 347(25):1999-2009.

West M, et al., 2001 "Predicting the clinical status of human breast cancer by using gene expression profiles" Proc Natl Acad Sci U S A 98(20):11462-11467.

Zajchowski DA, et al., 2001 "Identification of gene expression profiles that predict the aggressive behavior of breast cancer cells" Cancer Res 61(13):5168-5178.

(2000) "Life Testing" S_PLUS 2000 Guide to Statistics 2(Chapt 12):368.

Agendia BV, press release dated Feb. 5, 2007, "Agendia's MamaPrint breast cancer prognosis test cleared by U.S. Food and Drug Administration (FDA)—MammaPrint® is the first multi-gene expression test to receive market clearance by the FDA" [online]. Retrieved from the Internet: <http://www.agendia.com/en/Agendia/Press-Releases/Press-Release>, 2 pages.

Alexe et al., 2006, "Breast cancer prognosis by combinatorial analysis of gene expression data," Breast Cancer Research, Current Science 8: 1-20.
Barrett et al., 2003, "Microarrays: the use of oligonucleotides and cDNA for the analysis of gene expression," Drug Discovery Today 8(3): 134-141.
Bertucci et al., 2000, "Gene expression profiling of primary breast cancer carcinomas using arrays of candidate genes," Human Molecular Genetics 9: 2981-2991.
Cooper, 2001, "Applications of microarray technology in breast cancer research," Breast Cancer Research 3: 158-175.
GEO Expression, 2002, "Affymetrix GeneChip Human Genome U133 Array Set HG-U133A" [online]. [Retrieved Mar. 1, 2006]. Retrieved from the Internet: <URL: http://www.ncbi.nlm.nih.gov/projects/geo/query/acc.cgi>.
Gruvberger et al., 2002, "Expression profiling to predict outcome in breast cancer: the influence of sample selection," Breast Cancer Research, Current Science 5(1): 23-26.
Heldenfalk et al., 2001, "Gene-Expression Profiles in Hereditary Breast Cancer," N. Engl. J. Med. 344: 539-548.
Huang et al., 2003, "Gene expression predictors of breast cancer outcomes," The Lancet 361: 1590-96.
International Search Report dated Nov. 23, 2005, issued in International Application No. PCT/US05/07894, 4 pages.
Jahkola et al., 1996, "Expression of tenascin in invasion border of early breast cancer correlates with higher risk of distant metastasis." Intl J. Cancer, 69(6): 445-447.
Keys et al., 1983, "Clinical Oncology, Chapter 12 Breast Cancer," Edited by: Philip Rubin , $6^{th}$ edition, American Cancer Society, pp. 120-128, 133, and 506.
Khan et al., 2001, "Classification and diagnostics prediction of cancers using gene expression profiling and artificial neural networks," Nature Medicine 7: 673-679.
Office Action dated Oct. 19, 2005, in U.S. Appl. No. 10/342,887, filed on Jan. 15, 2003, now U.S. patent No. 7,171,311 B2, issued on Jan. 30, 2007.
Perou et al., 1999, "Distinctive gene expression patterns in human mammary epithelial cells and breast cancers," Proc Natl Acad Sci USA 96: 9212-9217.
Silvestrini et al., 1996, "Validation of P53 accumulation as a predictor of distant metastasis at 10 years of follow-up in 1400 node-negative breast cancers," Clin. Cancer Res. 2: 2007-2013.
Supplementary Partial European Search Report dated Jul. 2, 2007, issued in European Patent Application No. 02746538.4-2204, the European regional phase of PCT/US02/018947, 6 pages.
Supplementary European Search Report dated Aug. 21, 2008, issued in European Patent Application No. 04702566.3-2403, the European regional phase of PCT/US2004/001100, 5 pages.
Supplementary European Search Report dated Aug. 22, 2008, issued in European Patent Application No. 05725207.4-2403, the European regional phase of PCT/US2005/007894, 7 pages.
U.S. Food and Drug Administration, press release dated Feb. 6, 2007, "FDA Clears Breast Cancer Specific Molecular Prognostic Test" [online]. [Retrieved Nov. 28, 2007], Retrieved from the Internet: <http://www.fda.gov/bbs/topics/NEWS/2007/NEW01555.html>, 2 pages.
Van't Veer et al., 2002, "Expression profiling changes treatment in breast cancer," Anal. Cell. Pathol. 25: 227-228.

* cited by examiner

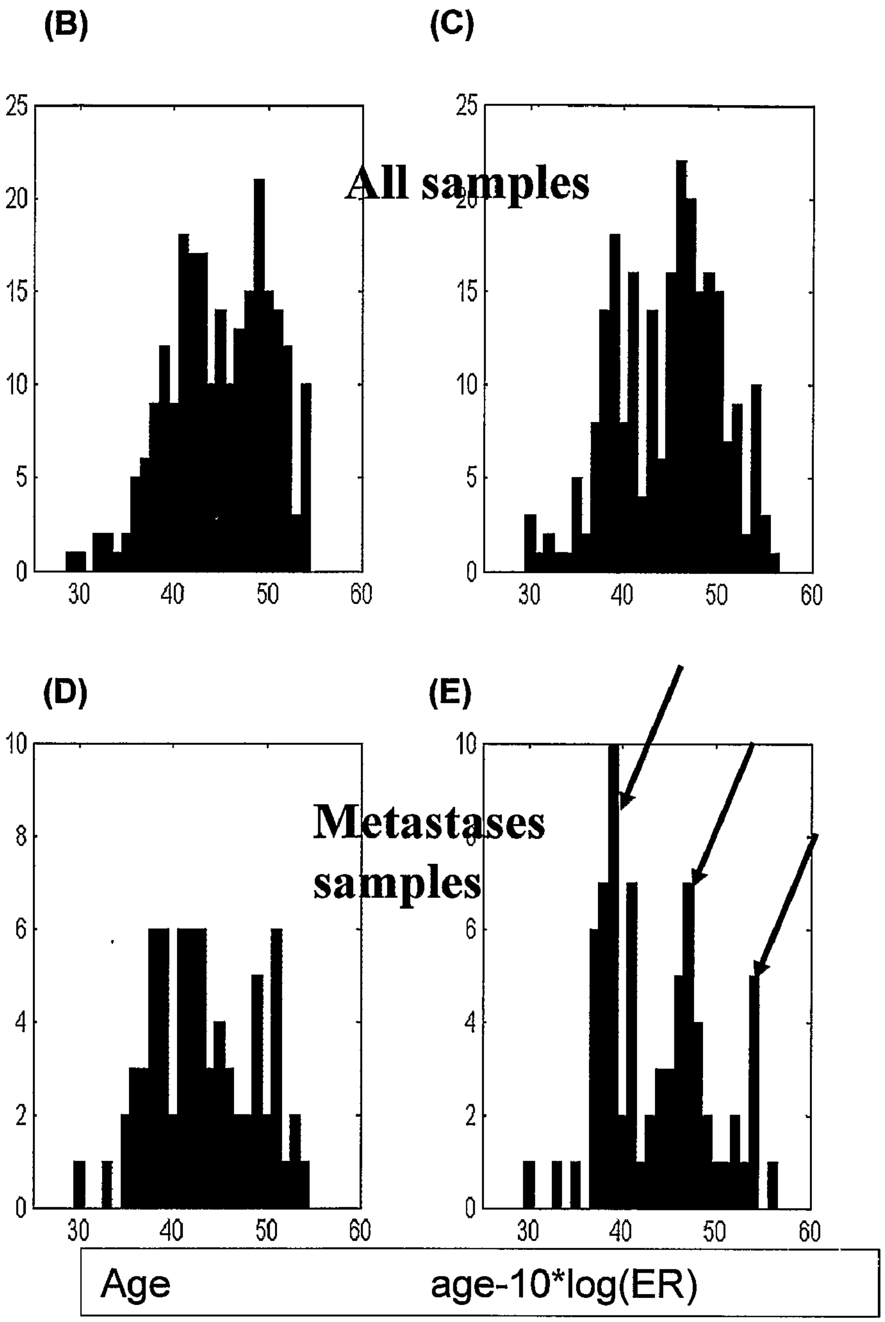
FIGS. 2B-E (A)
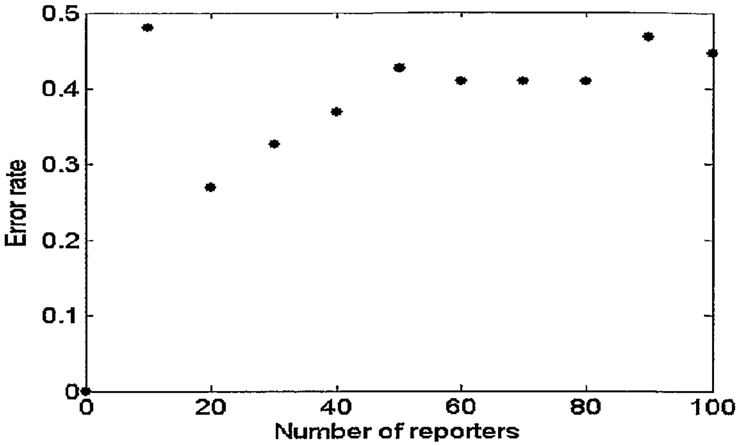
(B)
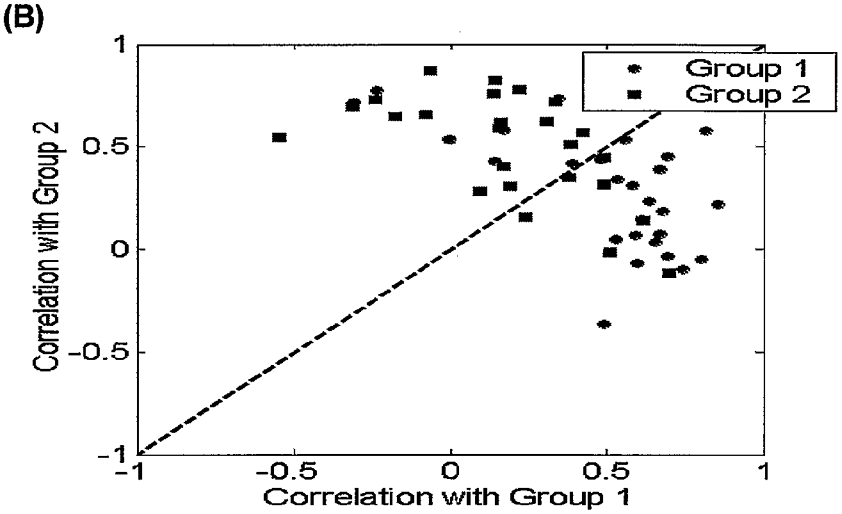
(C)
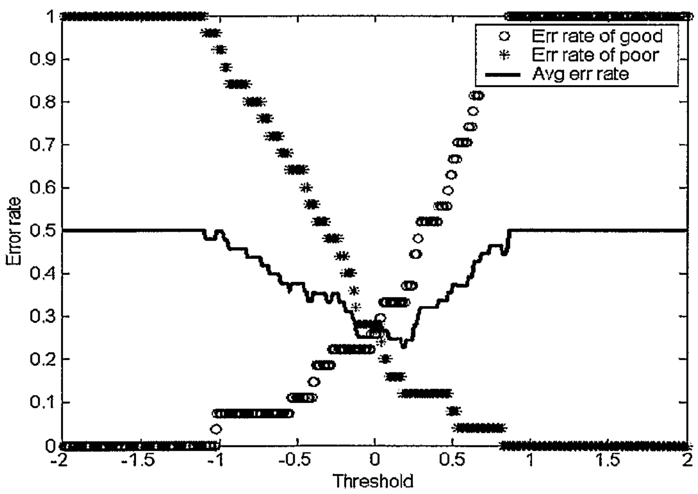
FIGS. 3A-C

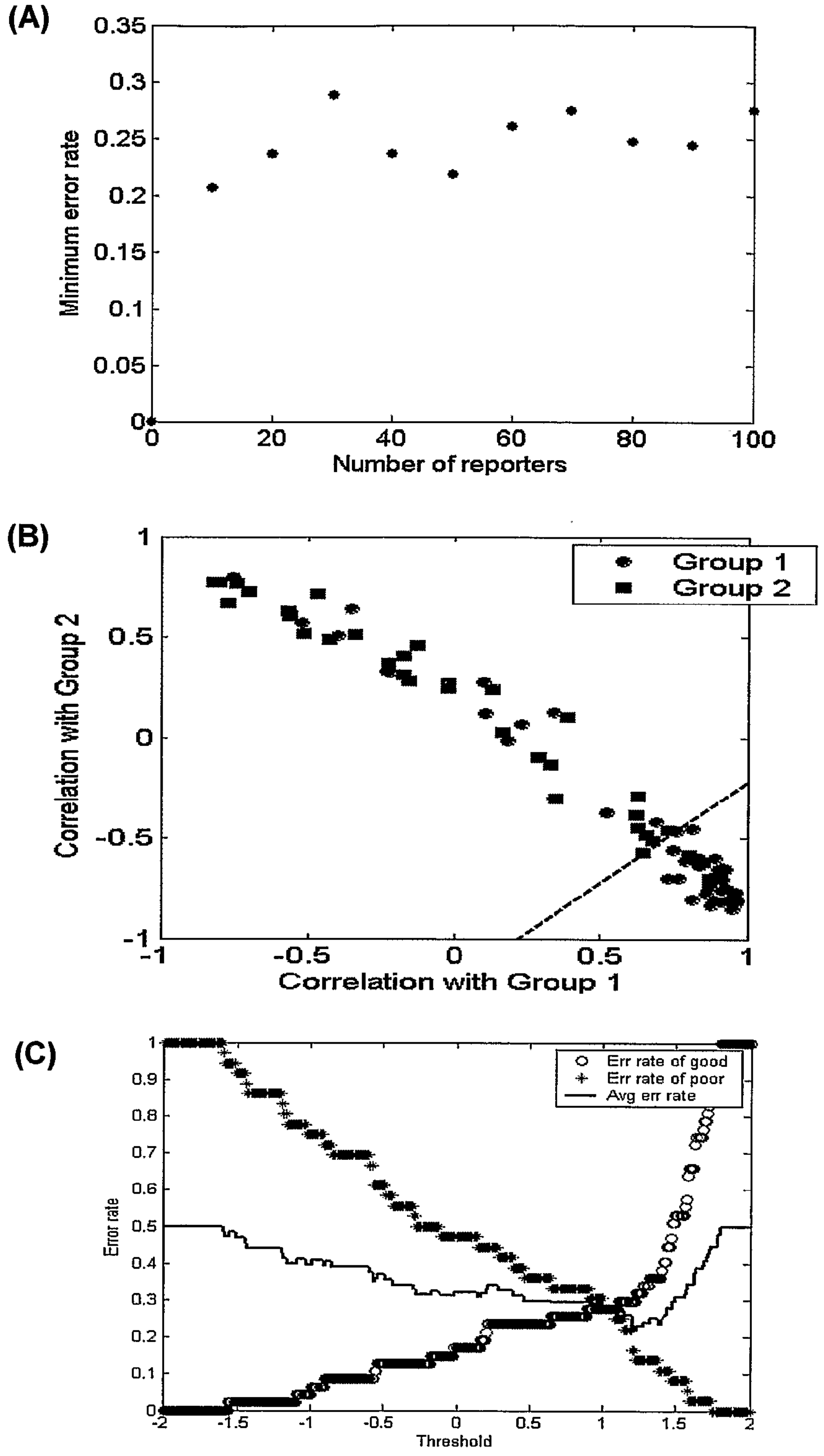
FIGS. 4A-C

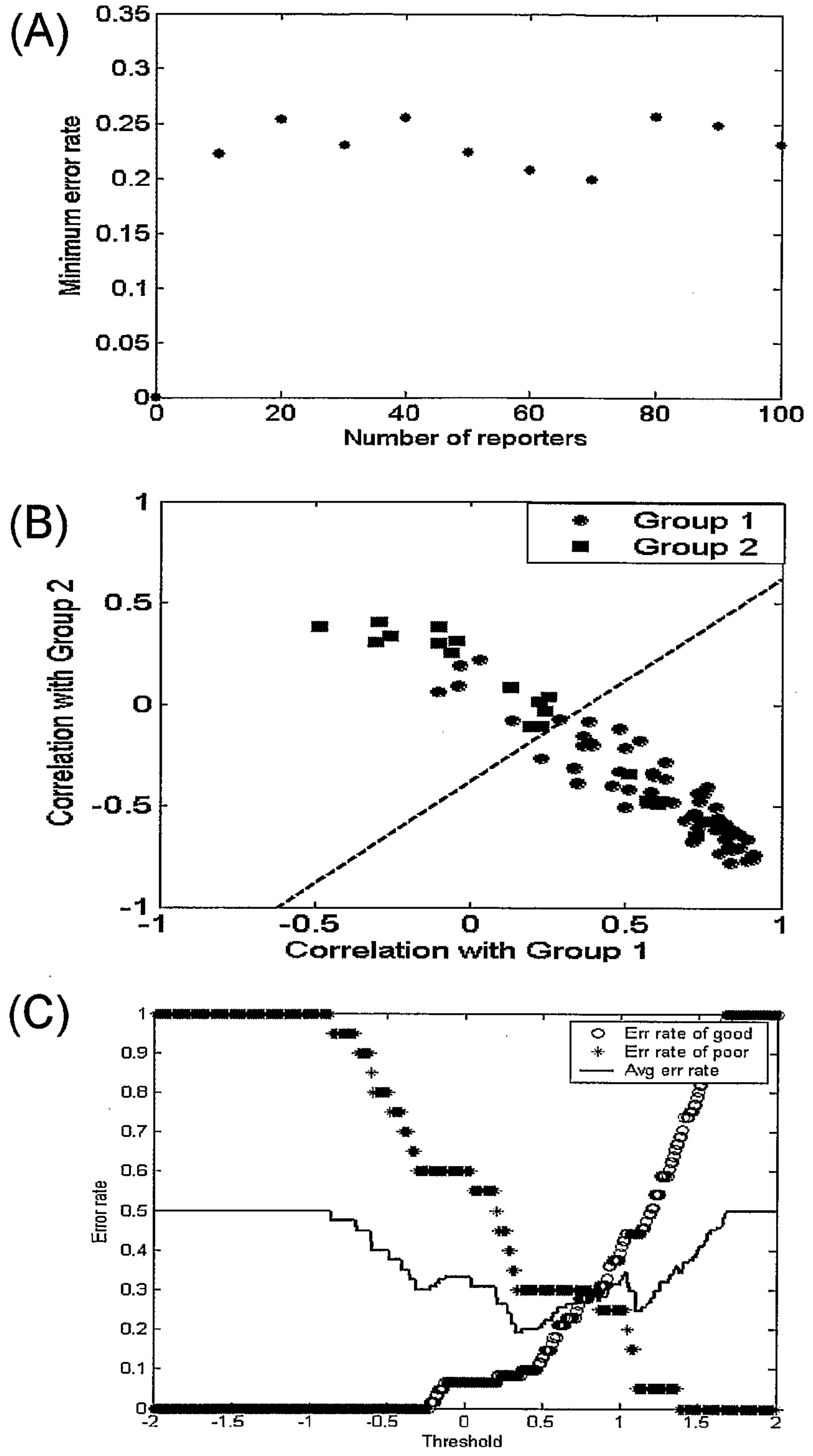
FIGS. 5A-C

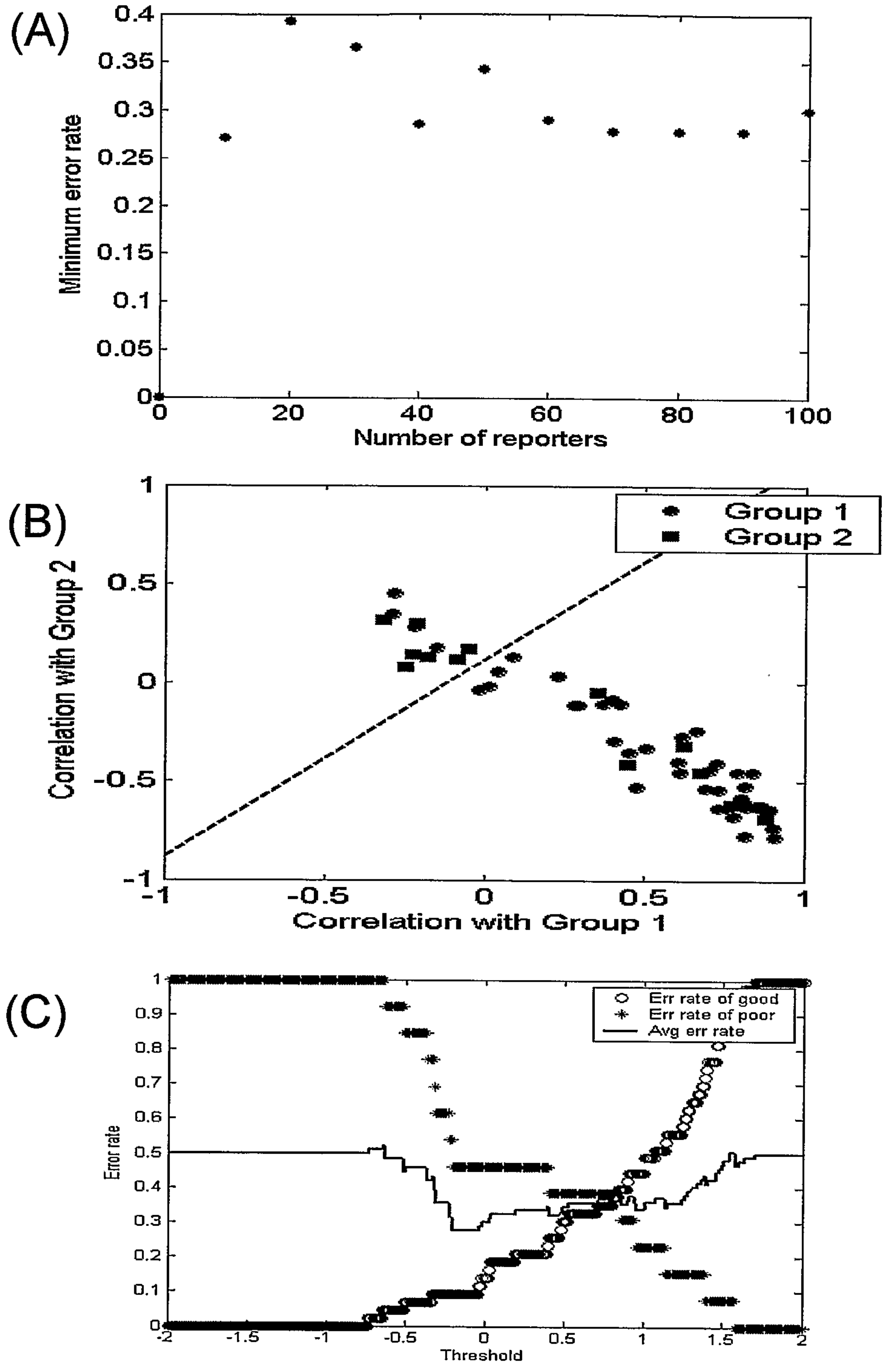
FIGS. 6A-C

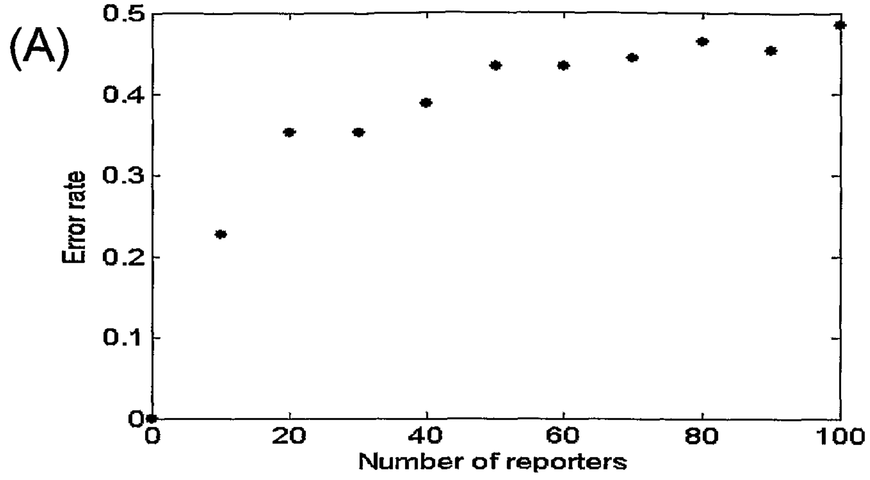
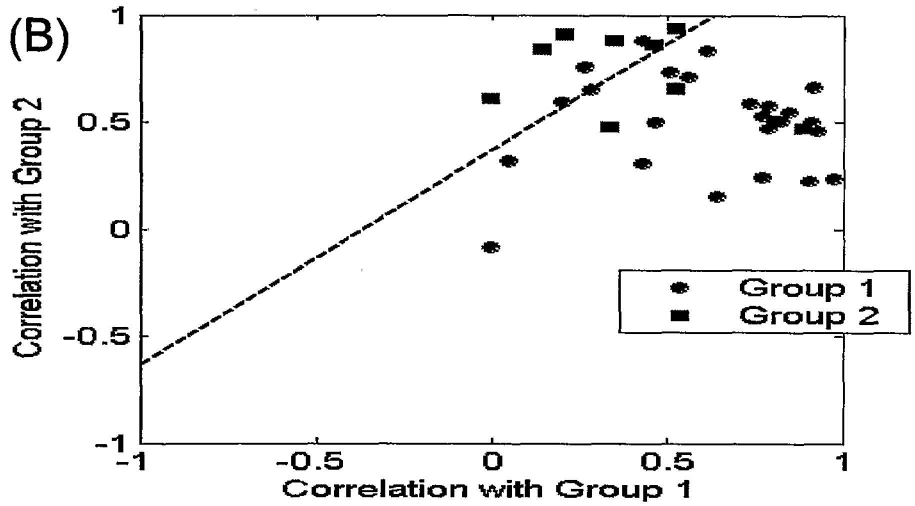
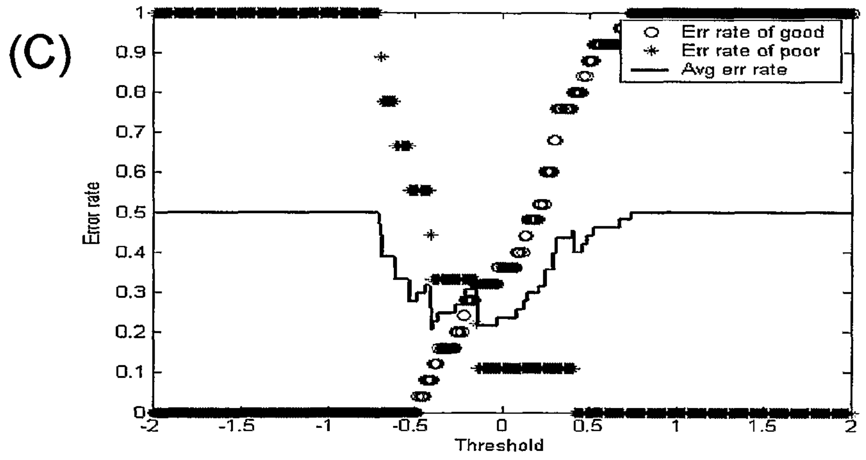
FIGS. 7A-C

Glycolysis subset

CLASSIFICATION OF BREAST CANCER PATIENTS USING A COMBINATION OF CLINICAL CRITERIA AND INFORMATIVE GENESETS

This application claims the benefit under 35 U.S.C. §119 (e) of U.S. Provisional Patent Application No. 60/650,401, filed on Feb. 4, 2005, U.S. Provisional Patent Application No. 60/604,076, filed on Aug. 24, 2004, and U.S. Provisional Patent Application No. 60/550,810, filed on Mar. 5, 2004, each of which is incorporated by reference herein in its entirety.

1. FIELD OF THE INVENTION

The present invention relates to the use of both phenotypic and genotypic aspects of a condition, such as a disease, in order to identify discrete subsets of patients for which specific sets of informative genes are then identified. The invention also relates to the classification of individuals, such as breast cancer patients, into a subset of the condition on the basis of clinical parameters and the status of markers, for example, of genes expression patterns, and the prognosis of those individuals on the basis of markers informative for prognosis within the subset of the condition. The invention also relates to methods of determining a course of treatment or therapy to an individual having, or suspected of having, a condition, such as breast cancer. The invention further relates to methods of structuring a clinical trial, particularly using five breast cancer-specific patient subsets and prognosis-informative genes for each, and of identifying patient populations for clinical trials or for other condition-related, for example, breast cancer-related, research. Finally, the invention relates to computer implementations of the above methods.

2. BACKGROUND OF THE INVENTION

The increased number of cancer cases reported in the United States, and, indeed, around the world, is a major concern. Currently there are only a handful of treatments available for specific types of cancer, and these provide no guarantee of success. In order to be most effective, these treatments require not only an early detection of the malignancy, but a reliable assessment of the severity of the malignancy.

The incidence of breast cancer, a leading cause of death in women, has been gradually increasing in the United States over the last thirty years. Its cumulative risk is relatively high; 1 in 8 women are expected to develop some type of breast cancer by age 85 in the United States. In fact, breast cancer is the most common cancer in women and the second most common cause of cancer death in the United States. In 1997, it was estimated that 181,000 new cases were reported in the U.S., and that 44,000 people would die of breast cancer (Parker et al., *CA Cancer J. Clin.* 47:5-27 (1997); Chu et al., *J. Nat. Cancer Inst.* 88:1571-1579 (1996)). While mechanism of tumorigenesis for most breast carcinomas is largely unknown, there are genetic factors that can predispose some women to developing breast cancer (Miki et al., *Science,* 266:66-71 (1994)).

Sporadic tumors, those not currently associated with a known germline mutation, constitute the majority of breast cancers. It is also likely that other, non-genetic factors also have a significant effect on the etiology of the disease. Regardless of the cancer's origin, breast cancer morbidity and mortality increases significantly if it is not detected early in its progression. Thus, considerable effort has focused on the early detection of cellular transformation and tumor formation in breast tissue.

A marker-based approach to tumor identification and characterization promises improved diagnostic and prognostic reliability. Typically, the diagnosis of breast cancer requires histopathological proof of the presence of the tumor. In addition to diagnosis, histopathological examinations also provide information about prognosis and selection of treatment regimens. Prognosis may also be established based upon clinical parameters such as tumor size, tumor grade, the age of the patient, and lymph node metastasis.

Diagnosis and/or prognosis may be determined to varying degrees of effectiveness by direct examination of the outside of the breast, or through mammography or other X-ray imaging methods (Jatoi, *Am. J. Surg.* 177:518-524 (1999)). The latter approach is not without considerable cost, however. Every time a mammogram is taken, the patient incurs a small risk of having a breast tumor induced by the ionizing properties of the radiation used during the test. In addition, the process is expensive and the subjective interpretations of a technician can lead to imprecision. For example, one study showed major clinical disagreements for about one-third of a set of mammograms that were interpreted individually by a surveyed group of radiologists. Moreover, many women find that undergoing a mammogram is a painful experience. Accordingly, the National Cancer Institute has not recommended mammograms for women under fifty years of age, since this group is not as likely to develop breast cancers as are older women. It is compelling to note, however, that while only about 22% of breast cancers occur in women under fifty, data suggests that breast cancer is more aggressive in pre-menopausal women.

In clinical practice, accurate diagnosis of various subtypes of breast cancer is important because treatment options, prognosis, and the likelihood of therapeutic response all vary broadly depending on the diagnosis. Accurate prognosis, or determination of distant metastasis-free survival could allow the oncologist to tailor the administration of adjuvant chemotherapy, with women having poorer prognoses being given the most aggressive treatment. Furthermore, accurate prediction of poor prognosis would greatly impact clinical trials for new breast cancer therapies, because potential study patients could then be stratified according to prognosis. Trials could then be limited to patients having poor prognosis, in turn making it easier to discern if an experimental therapy is efficacious.

To date, no set of satisfactory predictors for prognosis based on the clinical information alone has been identified. Many have observed that the ER status has a dominant signature in the breast tumor gene expression profiling. See West et al., *Proc. Natl. Acad. Sci. U.S.A.* 98:11462 (2001); van 't Veer et al., *Nature* 415:530 (2002); Sorlie et al., *Proc. Natl. Acad. Sci. U.S.A.* 100:8418 (2003); Perou et al. *Nature* 406:747 (2000); Gruvberger et al., *Cancer Res.* 61:5979 (2001); Sotiriou et al., *Proc. Natl. Acad. Sci. U.S.A.* 100:10393 (2003). It is generally accepted that there is some relationship between patient survival and ER status. van de Vijver et al., *N. Engl. J. Med.* 347:1999 (2002); Surowiak et al, *Folia Histochem. Cytobiol.* 39:143 (2001); Pichon et al. *Br. J Cancer* 73:1545 (1996); Collett et al., *J. Clin. Pathol.* 49:920 (1996). BRCA1 mutations are related to the familial cancer susceptibility. Biesecker et al., *JAMA* 269:1970 (1993); Easton et al., *Cancer Surv.* 18:95 (1993). Age is also considered to be a prognosis factor since young cancer patients tend to have poor tumors. Maggard et al., *J. Surg. Res.* 113:109 (2003).

Lymph node status is a factor in deciding the treatment. Eifel et al., *J. Natl. Cancer Inst.* 93:979 (2001).

The discovery and characterization of BRCA1 and BRCA2 has recently expanded our knowledge of genetic factors which can contribute to familial breast cancer. Germline mutations within these two loci are associated with a 50 to 85% lifetime risk of breast and/or ovarian cancer (Casey, *Curr. Opin. Oncol.* 9:88-93 (1997); Marcus et al., *Cancer* 77:697-709 (1996)). Only about 5% to 10% of breast cancers, however, are associated with breast cancer susceptibility genes, BRCA1 and BRCA2. The cumulative lifetime risk of breast cancer for women who carry the mutant BRCA1 is predicted to be approximately 92%, while the cumulative lifetime risk for the non-carrier majority is estimated to be approximately 10%. BRCA1 is a tumor suppressor gene that is involved in DNA repair and cell cycle control, which are both important for the maintenance of genomic stability. More than 90% of all mutations reported so far result in a premature truncation of the protein product with abnormal or abolished function. The histology of breast cancer in BRCA1 mutation carriers differs from that in sporadic cases, but mutation analysis is the only way to find the carrier. Like BRCA1, BRCA2 is involved in the development of breast cancer, and like BRCA1 plays a role in DNA repair. However, unlike BRCA1, it is not involved in ovarian cancer.

Other genes have been linked to breast cancer, for example c-erb-2 (HER2) and p53 (Beenken et al., *Ann. Surg.* 233(5): 630-638 (2001). Overexpression of c-erb-2 (HER2) and p53 have been correlated with poor prognosis (Rudolph et al., *Hum. Pathol.* 32(3):311-319 (2001), as has been aberrant expression products of mdnm2 (Lukas et al., Cancer Res. 61(7):3212-3219 (2001) and cyclin1 and p27 (Porter & Roberts, International Publication WO98/33450, published Aug. 6, 1998).

The detection of BRCA1 or BRCA2 mutations represents a step towards the design of therapies to better control and prevent the appearance of these tumors. Recently, many studies have used gene expression profiling to analyze various cancers, and those studies have provided new diagnosis and prognosis information in the molecular level. See Zajchowski et al., "Identification of Gene Expression Profiled that Predict the Aggressive Behavior of Breast Cancer Cells," *Cancer Res.* 61:5168 (2001); West et al., "Predicting the Clinical Status of Human Breast Cancer by Using Gene Expression Profiles," *Proc. Natl. Acad. Sci. U.S.A.* 98:11462 (2001); van 't Veer et al., "Gene Expression Profiling Predicts the Outcome of Breast Cancer," *Nature* 415:530 (2002); Roberts et al., "Diagnosis and Prognosis of Breast Cancer Patients," WO 02/103320; Sorlie et al., *Proc. Natl. Acad. Sci. U.S.A.* 100: 8418 (2003); Perou et al., *Nature* 406:747 (2000); Khan et al., *Cancer Res* 58, 5009 (1998); Golub et al., *Science* 286, 531 (1999); DeRisi et al., *Nat. Genet.* 14:457 (1996); Alizadeh et al., *Nature* 403, 503 (2000). Methods for the identification of informative genesets for various cancers have also been described. See Roberts et al., "Diagnosis and Prognosis of Breast Cancer Patients," WO 02/103320; Golub et al., U.S. Pat. No. 6,647,341.

Genesets have been identified that are informative for differentiating individuals having, or suspected of having, breast cancer based on estrogen receptor (ER) status, or BRCA1 mutation vs. sporadic (i.e., other than BRCA1-type) mutation status. See Roberts et al., WO 02/103320; van't Veer et al., *Nature* 415:530 (2001). Genesets have also been identified that enable the classification of sporadic tumor-type individuals as those who will likely have no metastases within five years of initial diagnosis (i.e., individuals with a good prognosis) or those who will likely have a metastasis within five years of initial diagnosis (i.e., those having a poor prognosis). Roberts, supra; van't Veer, supra.

Roberts et al. WO 02/103320 describes a 70-gene set, useful for the prognosis of breast cancer, which outperformed clinical measures of prognosis, and which showed good potential in selecting good outcome patients, thereby avoiding over-treatment. van de Vijver et al., *N. Engl. J. Med.* 347:1999 (2002). The expression of genes with most predictive value, however, were not homogeneous among poor patients, suggesting the need for improvement.

Although the patterns of gene expression as described in Roberts et al. were correlated with existing clinical indicators such as estrogen receptor and BRCA1 status, clinical measures were not incorporated. Furthermore, although the poor-outcome group in particular showed heterogeneity in expression pattern, the best classifier decision rule found during these studies was a fairly simple one based on the similarity of a patient profile to the average profile of a good-outcome training group.

It is evident that breast cancer is the result of more than one type of molecular event. Likewise, a variety of other conditions, such as other cancers; non-cancer diseases such as diabetes, autoimmune or neurodegenerative disorders, obesity; etc., are also the result of more than one molecular event. Moreover, an individual's response to exposure to particular environmental conditions, for example, exposure to natural or man-made agents, such as toxins, pollutants, drugs, food additives, etc., likely result from more than one molecular event. Thus, there exists a need for improved prognostic methods so that appropriate courses of prophylaxis and/or therapy may be provided. Genesets having improved prognostic power can be identified by first identifying discrete subsets of individuals based on genotypic or phenotypic characteristics relevant to the disease or condition, and then identifying genesets informative for prognosis within those subsets of patients. Individuals having the condition, or who are suspected of having the condition, such as breast cancer, would then be provided therapies appropriate to the molecular mechanisms underlying the condition. The present invention provides such methods for breast cancer, and for other cancers, diseases or conditions.

3. SUMMARY OF THE INVENTION

The present invention provides methods of identifying relevant subsets of conditions, and the identification of markers relevant to those subsets, for example, for prognosis of individuals classifiable into one of those subsets. The invention further provides sets of markers useful for the prognosis of individuals having breast cancer, wherein those patients have been classified according to one or more characteristics of breast cancer.

Thus, the present invention provides a method of identifying a set of informative genes or markers for a condition comprising a plurality of phenotypic or genotypic characteristics, comprising: (a) classifying each of a plurality of samples or individuals on the basis of one or more phenotypic or genotypic characteristics of said condition into a plurality of first classes; and (b) identifying within each of said first classes a first set of genes or markers informative for said condition, wherein said first set of genes or markers within each of said first classes is unique to said class relative to other first classes. In a specific embodiment, this method further comprises additionally classifying into a plurality of second classes said samples or individuals in at least one of said first classes on the basis of a phenotypic or genotypic characteristic different that that used in said classifying step (a); and identifying within at least one of said second classes a second set of informative genes or markers, wherein said second set of informative genes or markers within each of said second classes is unique to said second class relative to other first and second classes.

The invention further provides a method of identifying a set of informative genes or markers for a condition comprising a plurality of phenotypic or genotypic characteristics, comprising: (a) classifying each of a plurality of samples or individuals on the basis of one or more phenotypic or genotypic characteristics into a plurality of first classes; (b) classifying at least one of said first classes into a plurality of second classes on the basis of phenotypic or genotypic characteristic different than that used in said classifying step (a); and (c) identifying within at least one of said first classes or said second classes a set of genes or markers informative for said condition, wherein said second set of genes or markers is unique to said class relative to other first and second classes.

The invention further provides a method of identifying a set of informative genes or markers for a condition comprising a plurality of phenotypic or genotypic characteristics, comprising: (a) selecting a first characteristic from said plurality of phenotypic or genotypic characteristics; (b) identifying at least two first condition classes differentiable by said first characteristic; (c) selecting a plurality of individuals classifiable into at least one of said first condition classes; and (d) identifying in samples derived from each of said plurality of individuals a set of genes or markers informative for said condition within said at least one of said first condition classes.

The invention further provides a method of classifying an individual with a condition as having a good prognosis or a poor prognosis, comprising: (a) classifying said individual into one of a plurality of patient classes, said patient classes being differentiated by one or more phenotypic, genotypic or clinical characteristics of said condition; (b) determining the level of expression of a plurality of genes or their encoded proteins in a cell sample taken from the individual relative to a control, said plurality of genes or their encoded proteins comprising genes or their encoded proteins informative for prognosis of the patient class into which said individual is classified; and (c) classifying said individual as having a good prognosis or a poor prognosis on the basis of said level of expression. In a specific embodiment, said condition is cancer, said good prognosis is the non-occurrence of metastases within five years of initial diagnosis, and said poor prognosis is the occurrence of metastases within five years of initial diagnosis. In a more specific embodiment, said cancer is breast cancer. In another specific embodiment, said control is the average level of expression of each of said plurality of genes or their encoded proteins across a plurality of samples derived from individuals identified as having a poor prognosis. In a more specific embodiment, said classifying step (c) is carried out by a method comprising comparing the level of expression of each of said plurality of genes or their encoded proteins to said average level of expression of each corresponding gene or its encoded protein in said control, and classifying said individual as having a poor prognosis if said level of expression correlates with said average level of expression of each of said genes or their encoded proteins in said control more strongly than would be expected by chance. In another specific embodiment, said control is the average level of expression of each of said plurality of genes or their encoded proteins across a plurality of samples derived from individuals identified as having a good prognosis. In a more specific embodiment, said classifying in step (c) is carried out by a method comprising comparing the level expression of each of said plurality of genes or their encoded proteins to said average level of expression of each corresponding gene or its encoded protein in said control, and classifying said individual as having a good prognosis if said level of expression correlates with said average level of expression of each of said genes or their encoded proteins in said control more strongly than would be expected by chance. In another specific embodiment, said plurality of patient classes comprises $ER^-$, BRCAI individuals; $ER^-$, sporadic individuals; ER+, ER/AGE high individuals; ER+, ER/AGE low, LN+ individuals; and ER+, ER/AGE low, $LN^-$ individuals.

The invention further provides a method of classifying a breast cancer patient as having a good prognosis or a poor prognosis comprising: (a) classifying said breast cancer patient as $ER^-$, BRCAI; $ER^-$, sporadic; ER+, ER/AGE high; ER+, ER/AGE low, LN+; or ER+, ER/AGE low, $LN^-$; (b) determining the level of expression of a first plurality of genes in a cell sample taken from said breast cancer patient relative to a control, said first plurality of genes comprising two of the genes corresponding to the markers in Table 1 if said breast cancer patient is classified as $ER^-$, BRCAI; in Table 2 if said breast cancer patient is classified as $ER^-$ sporadic; in Table 3 if said breast cancer patient is classified as ER+, ER/AGE high; in Table 4 if said breast cancer patient is classified as ER+. ER/AGE low, LN+; or in Table 5 if said breast cancer patient is classified as ER+, ER/AGE low, $LN^-$; and (c) classifying said breast cancer patient as having a good prognosis or a poor prognosis on the basis of the level of expression of said first plurality of genes, wherein said breast cancer patient is "ER/AGE high" if the ratio of the $\log_{10}$(ratio) of ER gene expression to age exceeds a predetermined value, and "ER/AGE low" if the ratio of the $\log_{10}$(ratio) of ER gene expression to age does not exceed said predetermined value. In a specific embodiment, said control is the average level of expression of each of said plurality of genes in a plurality of samples derived from $ER^-$, BRCA1 individuals, if said breast cancer patient is $ER^-$, BRCA1; the average level of expression of each of said plurality of genes in a plurality of samples derived from $ER^-$, sporadic individuals if said breast cancer patient is $ER^-$, sporadic; the average level of expression of each of said plurality of genes in a plurality of samples derived from ER+, ER/AGE high individuals, if said breast cancer patient is ER+, ER/AGE high; the average level of expression of each of said plurality of genes in a plurality of samples derived from ER+, ER/AGE low, LN+ individuals where said breast cancer patient is ER+, ER/AGE low, LN+; or the average level of expression of each of said plurality of genes in a plurality of samples derived from ER+, ER/AGE low, $LN^-$ individuals where said breast cancer patient is ER+, ER/AGE low, $LN^-$. In a more specific embodiment, each of said individuals has a poor prognosis. In another more specific embodiment, each of said individuals has a good prognosis. In an even more specific embodiment, said classifying step (c) is carried out by a method comprising comparing the level of expression of each of said plurality of genes or their encoded proteins in a sample from said breast cancer patient to said control, and classifying said breast cancer patient as having a poor prognosis if said level of expression correlates with said average level of expression of the corresponding genes or their encoded proteins in said control more strongly than would be expected by chance. In another specific embodiment, said predetermined value of ER is calculated as ER=0.1 (AGE−42.5), wherein AGE is the age of said individual. In another specific embodiment, said individual is $ER^-$, BRCA1, and said plurality of genes comprises two of the genes for which markers are listed in Table 1. In another specific embodiment, said individual is $ER^-$, BRCA1, and said plurality of genes comprises all of the genes for which markers are listed in Table 1. In another specific embodiment, said individual is $ER^-$, sporadic, and said plurality of genes comprises two of the genes for which markers are listed in Table 2. said individual is $ER^-$, sporadic, and said plurality of genes comprises all of the genes for which markers are listed in Table 2. In another specific embodiment, said individual is ER+, ER/AGE high, and said plurality of genes comprises two of the genes for which markers are listed in Table 3. said individual is ER+, ER/AGE high, and said plurality of genes comprises all of the genes for which markers are listed in Table 3. In another specific embodiment, said individual is ER+, ER/AGE low, LN+, and said plurality of genes comprises two of the genes for which markers are listed in Table 4. In another specific embodiment, said individual is ER+, ER/AGE low, LN+, and said plurality of genes comprises all of the genes for which markers are listed in Table 4. In another specific embodiment, said individual is ER+, ER/AGE low, $LN^-$, and said plurality of genes comprises two of the genes for which markers are listed in Table 4. In another specific embodiment, said individual is ER+, ER/AGE low, $LN^-$, and said plurality of genes comprises all of the genes for which markers are listed in Table 4. In another specific embodiment, the method further comprises determining in said cell sample the level of expression, relative to a control, of a second plurality of genes for which markers are not found in Tables 1-5, wherein said second plurality of genes is informative for prognosis.

In another embodiment, the invention provides a method for assigning an individual to one of a plurality of categories in a clinical trial, comprising: (a) classifying said individual as $ER^-$, BRCA1, $ER^-$, sporadic; ER+, ER/AGE high; ER+, ER/AGE low, LN+; or ER+, ER/AGE low, $LN^-$; (b) determining for said individual the level of expression of at least two genes for which markers are listed in Table 1 if said individual is classified as $ER^-$, BRCA1; Table 2 if said individual is classified as $ER^-$, sporadic; Table 3 if said individual is classified as ER+, ER/AGE high; Table 4 if said individual is classified as ER+, ER/AGE low, LN+; or Table 5 if said individual is classified as ER+, ER/AGE low, $LN^-$; (c) determining whether said individual has a pattern of expression of said at least two genes that correlates with a good prognosis or a poor prognosis; and (d) assigning said individual to one category in a clinical trial if said individual has a good prognosis, and assigning said individual to a second category in said clinical trial if said individual has a poor prognosis. In a specific embodiment, said individual is additionally assigned to a category in said clinical trial on the basis of the classification of said individual as determined in step (a). In another specific embodiment, said individual is additionally assigned to a category in said clinical trial on the basis of any other clinical, phenotypic or genotypic characteristic of breast cancer. In another specific embodiment, said method further comprises determining in said cell sample the level of expression, relative to a control, of a second plurality of genes for which markers are not found in Tables 1-5, wherein said second plurality of genes is informative for prognosis of breast cancer, and determining from the expression of said second plurality of genes, in addition to said first plurality of genes, whether said individual has a good prognosis or a poor prognosis.

The invention further provides a microarray comprising probes complementary and hybridizable to a plurality of the genes for which markers are listed in any of Tables 1-5. The invention further provides a microarray comprising probes complementary and hybridizable to a plurality of the genes for which markers are listed in Table 1, each of the genes for which markers are listed in Table 1, a plurality of the genes for which markers are listed in Table 2, each of the genes for which markers are listed in Table 2, a plurality of the genes for which markers are listed in Table 3, each of the genes for which markers are listed in Table 3, a plurality of the genes for which markers are listed in Table 4, each of the genes for which markers are listed in Table 4, a plurality of the genes for which markers are listed in Table 5, or each of the genes for which markers are listed in Table 5. The invention further provides any one of the above microarrays, wherein said probes are at least 50% of the probes on said microarray. The invention further provides any one of the above microarrays, wherein said probes are at least 90% of the probes on said microarray. The invention further provides microarray comprising probes complementary and hybridizable to a plurality of the genes for which markers are listed in any of Tables 1-5, wherein said probes are complementary and hybridizable to at least 75% of the genes for which markers are listed in Table 1; are complementary and hybridizable to at least 75% of the genes for which markers are listed in Table 2; are complementary and hybridizable to at least 75% of the genes for which markers are listed in Table 3; are complementary and hybridizable to at least 75% of the genes for which markers are listed in Table 4; and are complementary and hybridizable to at least 75% of the genes for which markers are listed in Table 5, wherein said probes, in total, are at least 50% of the probes on said microarray.

The invention further comprises a kit comprising any one of the above microarrays in a sealed container.

The invention further provides a method of identifying a set of genes informative for a condition, said condition having a plurality of phenotypic or genotypic characteristics such that samples may be categorized by at least one of said phenotypic or genotypic characteristics into at least one characteristic class, said method comprising: (a) selecting a plurality of samples from individuals having said condition; (b) identifying a first set of genes informative for said characteristic class using said plurality of samples; (c) predicting the characteristic class of each of said plurality of samples; (d) discarding samples for which said characteristic class is incorrectly predicted; (e) repeating steps (c) and (d) at least once; and (f) identifying a second set of genes informative for said characteristic class using samples in said plurality of samples remaining after step (e).

The invention further provides a method for assigning an individual to one of a plurality of categories in a clinical trial, comprising: (a) classifying the individual into one of a plurality of condition categories differentiated by at least one genotypic or phenotypic characteristic of the condition; (b) determining the level of expression, in a sample derived from said individual, of a plurality of genes informative for said condition category; (c) determining whether said level of expression of said plurality of genes indicates that the individual has a good prognosis or a poor prognosis; and (d) assigning the individual to a category in a clinical trial on the basis of prognosis.

The invention also provides a method for identifying one or more sets of informative genes or markers for a condition in an organism, comprising: (a) subdividing a plurality of individuals or samples derived therefrom of the organism subject to the condition into a plurality of classes based on one or more clinical, phenotypic or genotypic characteristics of the organism, wherein each class consists of a plurality of individuals or samples derived therefrom of the organism each of which having one or more clinical, phenotypic or genotypic characteristics specific for the class; and (b) attempting to identify for each of one or more of said plurality of classes a set of genes or markers informative for said condition in individuals in said class, wherein, if a set of genes or markers informative for said condition in individuals in said class is obtained for any of said one or more of said plurality of classes, said set of genes or markers is taken as a set of informative genes or markers for said condition in said organism.

In one embodiment, the method further comprises, for each of one or more of said classes in which a set of genes or markers informative for said condition in individuals in said class cannot be obtained, repeating said steps (a) and (b) on said plurality of individuals or samples derived therefrom in said class such that said plurality of individuals or samples derived therefrom in said class is subdivided into a plurality of additional classes based on one or more clinical, phenotypic or genotypic characteristics of said organism which are different from those used for defining said class, wherein for each of said plurality of additional classes, if a set of genes or markers informative for said condition in individuals in said class is obtained, said set of genes or markers is taken as a set of informative genes or markers for said condition in said organism.

The invention also provides a method for identifying one or more sets of informative genes or markers for a condition in an organism, comprising: (a) subdividing a plurality of individuals or samples derived therefrom of said organism subject to said condition into a plurality of classes based on one or more clinical, phenotypic or genotypic characteristics of said organism, wherein each said class consists of a plurality of individuals or samples derived therefrom of said organism each having said one or more clinical, phenotypic or genotypic characteristics specific for said class; (b) attempting to identify for each of one or more of said plurality of classes a set of genes or markers informative for said condition in individuals in said class, wherein if a set of genes or markers informative for said condition in individuals in said class is identified for any of said one or more of said classes, said set of genes or markers is taken as a set of informative genes or markers for a condition in said organism; and (c) for each of one or more of said classes in which a set of genes or markers informative for said condition in individuals in said class cannot be obtained, repeating said steps (a) and (b) on said plurality of individuals or samples derived therefrom in said class such that said plurality of samples or individuals in said class is subdivided into a plurality of additional classes based on one or more clinical, phenotypic or genotypic characteristics of said organism which are different from those used those used for defining said class, wherein for each of one or more of said plurality of additional classes, if a set of genes or markers informative for said condition in individuals in said class is obtained, said set of genes or markers is taken as a set of informative genes or markers for a condition in said organism.

In the methods of the invention, the condition can be a type of cancer. In such an embodiment, each of said sets of genes or markers can be informative of prognosis of individuals in a corresponding class. In one embodiment, the condition is breast cancer, and the one or more clinical, phenotypic or genotypic characteristics comprise age, ER level, ER/AGE, BRAC1 status, and lymph node status.

In one embodiment, the methods of the invention further comprise generating a template profile comprising measurements of levels of genes or markers of the set of informative genes or markers for said class representative of levels of the genes or markers in a plurality of patients having a chosen prognosis level.

The invention also provides a method for predicting a breast cancer patient as having a good prognosis or a poor prognosis, comprising: (a) classifying said breast cancer patient into one of the following classes: (a1) $ER^-$, BRCAI; (a2) $ER^-$, sporadic; (a3) ER+, ER/AGE high; (a4) ER+, ER/AGE low, LN+; or (a5) ER+, ER/AGE low, $LN^-$; (b) determining a profile comprising measurements of a plurality of genes or markers in a cell sample taken from said breast cancer patient, said plurality of genes markers comprising at least two of the genes or markers corresponding to the markers in (b1) Table 1 if said breast cancer patient is classified as $ER^-$, BRCAI; (b2) Table 2 if said breast cancer patient is classified as $ER^-$ sporadic; (b3) Table 3 if said breast cancer patient is classified as ER+, ER/AGE high; (b4) Table 4 if said breast cancer patient is classified as ER+, ER/AGE low, LN+; or (b5) Table 5 if said breast cancer patient is classified as ER+, ER/AGE low, $LN^-$; and (c) classifying said breast cancer patient as having a good prognosis or a poor prognosis based on said profile of said plurality of genes or markers, wherein $ER^+$ designates a high ER level and $ER^-$ designates a low ER level, wherein said ER/AGE is a metric of said ER level relative to the age of said patient, and wherein $LN^+$ designates a greater than 0 lymph nodes status in said patient and $LN^-$ designates a 0 lymph nodes status in said patient.

In one embodiment, step (c) is carried out by a method comprising comparing said profile to a good prognosis template and/or a poor prognosis template, and wherein said patient is classified as having a good prognosis if said profile has a high similarity to a good prognosis template or has a low similarity to a poor prognosis template or as having a poor prognosis if said profile has a low similarity to a good prognosis template or has a high similarity to a poor prognosis template. A good prognosis template comprises measurements of said plurality of genes or markers representative of levels of said genes or markers in a plurality of good outcome patients, while a poor prognosis template comprises measurements of said plurality of genes or markers representative of levels of said genes or markers in a plurality of poor outcome patients. Here a good outcome patient is a breast cancer patient who has non-reoccurrence of metastases within a first period of time after initial diagnosis, while a poor outcome patient is a patient who has reoccurrence of metastases within a second period of time after initial diagnosis.

In another embodiment, the methods for predicting the prognosis of a breast cancer patient further comprise determining said profile, said ER level, said LN status, and/or, said ER/AGE. In one embodiment, said profile is an expression profile comprising measurements of a plurality of transcripts in a sample derived from said patient, wherein said good prognosis template comprises measurements of said plurality of transcripts representative of expression levels of said transcripts in said plurality of good outcome patients, and wherein said poor prognosis template comprises measurements of said plurality of transcripts representative of expression levels of said transcripts in said plurality of poor outcome patients.

In one embodiment, said expression profile is a differential expression profile comprising differential measurements of said plurality of transcripts in said sample derived from said patient versus measurements of said plurality of transcripts in a control sample.

In one embodiment, the measurement of each said transcript in said good prognosis template is an average of expression levels of said transcript in said plurality of good outcome patients.

In one embodiment, the similarity of said expression profile to said good or poor prognosis template is represented by a correlation coefficient between said expression profile and said good or poor prognosis template, respectively, and a correlation coefficient greater than a correlation threshold, e.g., 0.5, indicates a high similarity and said correlation coefficient equal to or less than said correlation threshold indicates a low similarity.

In another embodiment, the similarity of said expression profile to said good or poor prognosis template is represented by a distance between said cellular constituent profile and said good or poor prognosis template, respectively, and a distance less than a given value indicates a high similarity and said distance equal to or greater than said given value indicates a low similarity.

In another embodiment, said profile comprises measurements of a plurality of protein species in a sample derived from said patient, wherein said good prognosis template comprises measurements of said plurality of protein species representative of levels of said protein species in said plurality of good outcome patients, and wherein said poor prognosis template comprises measurements of said plurality of protein species representative of levels of said protein species in said plurality of poor outcome patients.

In one embodiment, said ER level is determined by measuring an expression level of a gene encoding said estrogen receptor, e.g., the estrogen receptor $\alpha$ gene, in said patient relative to expression level of said gene in said control sample, and said ER level is classified as $ER^+$ if log 10(ratio) of said expression level is greater than −0.65, and said ER level is classified as $ER^-$ if log 10(ratio) of said expression level is equal to or less than −0.65.

In one embodiment, said ER/AGE is classified as high if said ER level is greater than $c\cdot(AGE-d)$, and said ER/AGE is classified as low if said ER level is equal to or less than $c\cdot(AGE-d)$, wherein c is a coefficient, AGE is the age of said patient, and d is an age threshold.

In a specific embodiment, said estrogen receptor level is measured by a polynucleotide probe that detects a transcript corresponding to the gene having accession number NM_000125, said control sample is a pool of breast cancer cells of different patients, and c=0.1 and d=42.5.

In one embodiment, said control sample is generated by pooling together cDNAs of said plurality of transcripts from a plurality of breast cancer patients. In another embodiment, said control sample is generated by pooling together synthesized cDNAs of said plurality of transcripts and said transcript of said gene encoding said estrogen receptor.

In one embodiment, said individual is $ER^-$, BRCA1, and said plurality of genes comprises at least two of the genes for which markers are listed in Table 1. In one embodiment, said individual is $ER^-$, BRCA1, and said plurality of genes comprises all of the genes for which markers are listed in Table 1.

In another embodiment, the individual is $ER^-$, sporadic, and said plurality of genes comprises at least two of the genes for which markers are listed in Table 2. In one embodiment, said individual is $ER^-$, sporadic, and said plurality of genes comprises all of the genes for which markers are listed in Table 2.

In still another embodiment, said individual is ER+, ER/AGE high, and said plurality of genes comprises at least two of the genes for which markers are listed in Table 3. In one embodiment, said individual is ER+, ER/AGE high, and said plurality of genes comprises all of the genes for which markers are listed in Table 3.

In still another embodiment, said individual is ER+, ER/AGE low, LN+, and said plurality of genes comprises at least two of the genes for which markers are listed in Table 4.

In one embodiment, said individual is ER+, ER/AGE low, LN+, and said plurality of genes comprises all of the genes for which markers are listed in Table 4.

In still another embodiment, said individual is ER+, ER/AGE low, $LN^-$, and said plurality of genes comprises at least two of the genes for which markers are listed in Table 4. In one embodiment, the individual is ER+, ER/AGE low, $LN^-$, and said plurality of genes comprises all of the genes for which markers are listed in Table 4.

In one embodiment, said profile further comprises one or more genes for which markers are not found in Tables 1-5, which are informative for prognosis.

The invention also provides a method for assigning an individual to one of a plurality of categories in a clinical trial, comprising assigning said individual to one category in a clinical trial if said individual has a good prognosis as determined by any one of the methods described above, and assigning said individual to a second category in said clinical trial if said individual has a poor prognosis as determined by any one of the methods described above.

In one embodiment, said individual is additionally assigned to a category in said clinical trial on the basis of the classification of said individual based on said profile, said ER level, said LN status, and/or, said ER/AGE.

In one embodiment, said individual is additionally assigned to a category in said clinical trial on the basis of one or more other clinical, phenotypic or genotypic characteristic of breast cancer.

In one embodiment, the method further comprises determining in said cell sample the levels of expression of said one or more genes for which markers are not found in Tables 1-5, and determining from said expression levels of said one or more genes, whether said individual has a good prognosis or a poor prognosis.

4. BRIEF DESCRIPTION OF THE DRAWINGS

FIG. 1 depicts the decision tree that resulted in the five patient subsets used to identify informative prognosis-related genes.

FIG. 2: Relationship between ER level and age. (A) Scatter plot of ER vs. age for ER+ patients. Black dots indicate metastases free samples, and gray dots indicate metastases samples. It appears that patients of ER+ group can be subdivided into "ER+, ER/AGE high" group (above the black line) and "ER+, ER/AGE low" (below the black line) group. The black line is approximated by ER=0.1*(AGE-42.5), and the dashed line by ER=0.1*(age−50). Within each population, the ER level also increases with age. (B) Age distribution of all patients in ER+ samples. A bimodal distribution is observed. (C) ER-modulated age (age−10*) distribution of all patients in ER+ samples. A bimodal distribution is observed. (D) Age distribution of samples with metastasis. (E) ER-modulated age distribution of samples with metastasis. The three peaks appearing in this distribution suggest a polymorphism.

FIG. 3. Performance of classifier for the "$ER^-$/sporadic" group. (A) Error rate obtained from leave-one-out cross validation (LOOCV) for predicting the disease outcome as a function of the number of reporter genes used in the classifier. (B) Scatter plot between correlation to good group (X axis) and to poor group (Y axis). Circles indicate metastases-free samples, squares indicate samples with metastases. Dashed line: threshold for separating poor from good. (C) Error rate calculated with respect to good outcome group (good outcome misclassified as poor divided by total number of good), or poor outcome group (poor outcome misclassified as good divided by total number of poor), or the average of the two rates.

FIG. 4. Performance of classifier for the "ER+, ER/AGE high" group. (A) Error rate obtained from leave-one-out cross validation (LOOCV) for predicting the disease outcome as a function of the number of reporter genes used in the classifier. (B) Scatter plot between correlation to good group (X axis) and to poor group (Y axis). Circles indicate metastases-free samples, and squares indicate samples with metastases. Dashed line: threshold for separating poor from good. (C) Error rate calculated with respect to good outcome group (good outcome misclassified as poor divided by total number of good), or poor outcome group (poor outcome misclassified as good divided by total number of poor), or the average of the two rates.

FIG. 5. Performance of classifier for the "ER+, ER/AGE low/$LN^-$" group. (A) Error rate obtained from leave-one-out cross validation (LOOCV) for predicting the disease outcome as a function of the number of reporter genes used in the classifier. (B) Scatter plot between correlation to good group (X axis) and to poor group (Y axis). Circles indicate metastases-free samples, and squares indicates samples with metastases. Dashed line indicates the threshold for separating poor from good. (C) Error rate calculated with respect to good outcome group (good outcome misclassified as poor divided by total number of good), or poor outcome group (poor outcome misclassified as good divided by total number of poor), or the average of the two rates.

FIG. 6. Performance of classifier for the "ER+, ER/AGE low/LN+" group. (A) Error rate obtained from leave-one-out cross validation (LOOCV) for predicting the disease outcome as a function of the number of reporter genes used in the classifier. (B) Scatter plot between correlation to good group (X axis) and to poor group (Y axis). Circles indicate metastases free samples, squares indicate samples with metastases. Dashed line: threshold for separating poor from good. (C) Error rate calculated with respect to good outcome group (good outcome misclassified as poor divided by total number of good), or poor outcome group (poor outcome misclassified as good divided by total number of poor), or the average of the two rates.

FIG. 7. Performance of classifier for the "$ER^-$, BRCA1" group. (A) Error rate obtained from leave-one-out cross validation (LOOCV) for predicting the disease outcome as a function of the number of reporter genes used in the classifier. (B) Scatter plot between correlation to good group (X axis) and to poor group (Y axis). Circles indicate metastases free samples, squares indicate samples with metastases. Dashed line: threshold for separating poor from good. (C) Error rate calculated with respect to good outcome group (good outcome misclassified as poor divided by total number of good), or poor outcome group (poor outcome misclassified as good divided by total number of poor), or the average of the two rates.

Figures 8A, 8B:
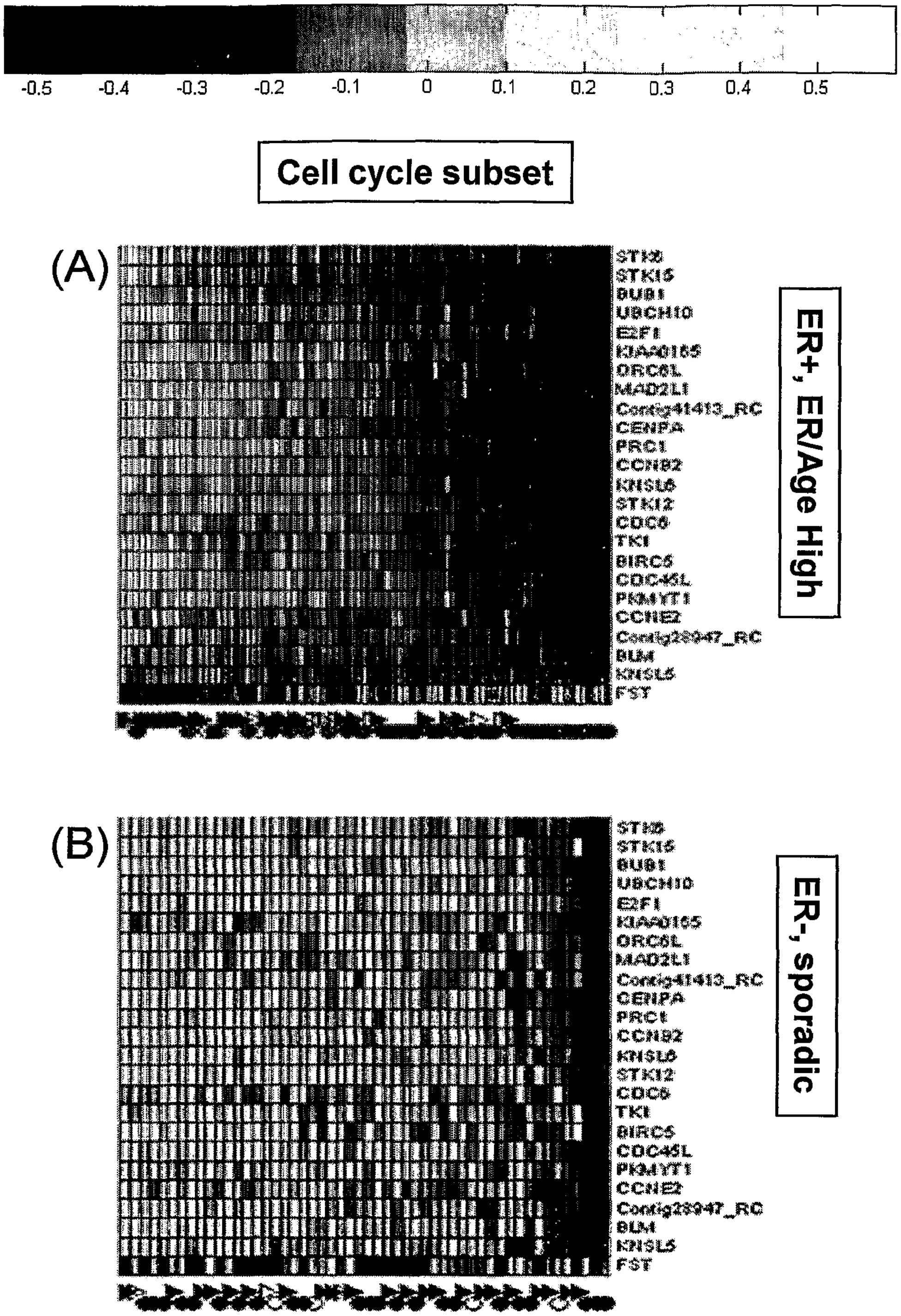
Figure 8C:
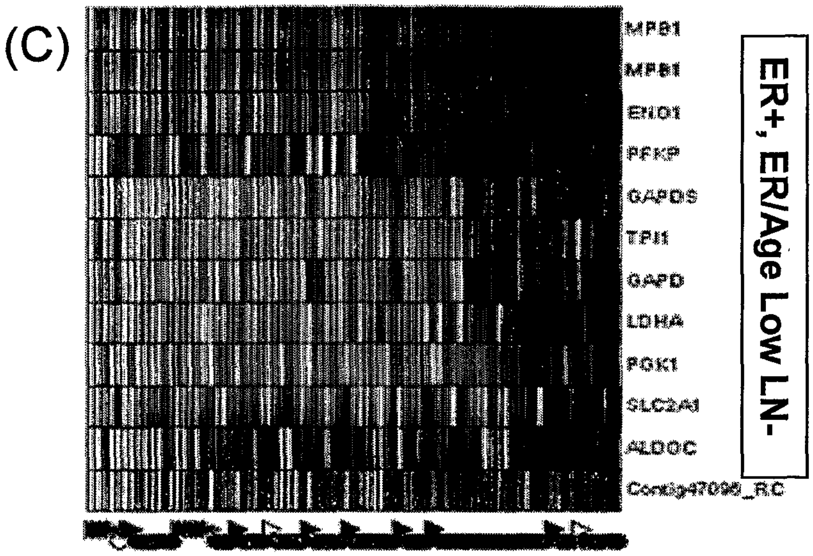
Figure 8D:
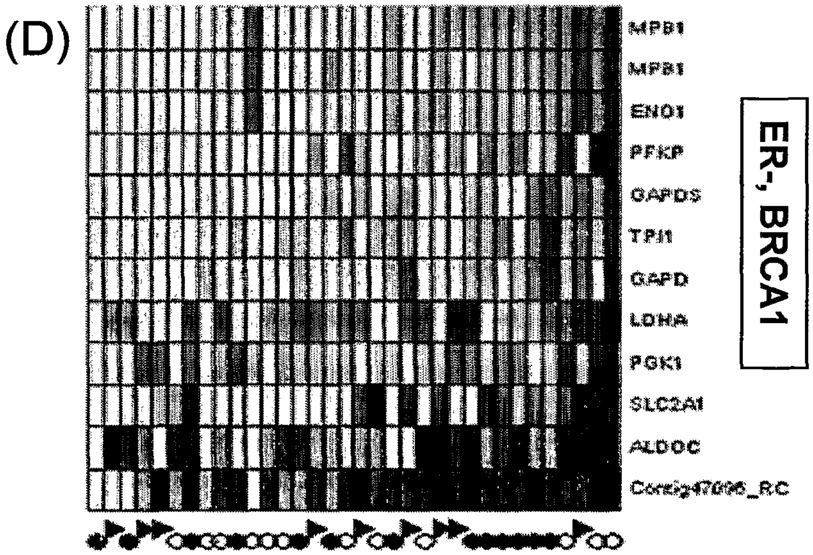

FIG. 8. Heatmaps of genes representing key biological functions in subgroups of patients: A: Cell cycle genes are predictive of outcome in patients with ER/age high. B: Cell cycle genes are not predictive of outcome in "ER− and sporadic" patients C: Glycolysis genes are predictive of outcome in patients with ER/age low and LN−. D: Glycolysis genes are not predictive of outcome in 'ER− & BRCA1" patients.

5. DETAILED DESCRIPTION OF THE INVENTION

5.1 Introduction

The present invention provides methods for classifying individuals having a condition, such as a disease, into one or more subsets of individuals, where individuals in each subset are characterized by one or more phenotypic or genotypic characteristics of the condition. The individuals may be eukaryotes or prokaryotes, may be animals such as mammals, including but not limited to humans, primates, rodents, felines, canines, etc., birds, reptiles, fish, etc. "Individuals" as used herein also encompasses single-celled organisms, or colonies thereof, such as bacteria and yeast. The condition may be a disease, such as cancer, and may be a specific cancer, such as breast cancer. The condition may also be an environmental condition, such as exposure to a toxin, pollutant, drug, proximity to urban or industrial areas, etc.

The present invention provides methods of determining the prognosis of individuals having a condition, such as cancer, for example, breast cancer, or who are suspected of having the condition, by the use of a combination of clinical, biological or biochemical parameters of the condition and gene expression pattern data. For prognosis, the parameters selected preferably relate to or affect the progression and/or outcome of the condition. The pattern of gene expression within a subset of individuals having the particular condition leads to the identification of sets of genes within a subset that is informative for that subset, for example, for prognosis within that subset. In general, the successful identification of sets of genes informative for prognosis within a particular subset justifies the selection of the plurality of clinical, biological or biochemical parameters of the condition on which division of individuals into condition subsets is based.

In the example of breast cancer, patient groups are first classified according to at least one of age, lymph node (LN) status, estrogen receptor (ER) level, and BRCA1 mutation status into discrete patient subsets. These clinical factors have been implicated in tumor etiology as well as differences in disease outcome. These characteristics are not limiting; other genotypic or phenotypic characteristics of breast cancer, for example, tumor grade, tumor size, tumor cell type, etc., may also be used, alone or in combination with those listed herein, in order to classify individuals. The differences in gene expression or in tumor fate related to these parameters likely represent differences in tumor origin and tumor genesis, and are therefore good candidates for tumor stratification. Genesets informative for prognosis within each subset are then identified. New breast cancer patients are then classified using the same criteria, and a prognosis is made based on the geneset specific for the patient subset into which the patient falls. In the process of constructing a prognosis classifier within each patient subset, particular attention is paid to the homogeneous patterns related to the tumor outcome. Emergence of such homogeneous prognosis patterns may indicate the most common mechanism to metastasis within a subset. At the same time, successful identification of such patterns also justifies the parameters being used for the tumor stratification. To differentiate this approach from an mRNA-alone approach, the current approach of integrating clinical data with the gene expression data is referred to herein as a "comprehensive prognosis".

5.2 Definitions

As used herein, "BRCA1 tumor" or "BRCA1 type" means a tumor having cells containing a mutation of the BRCA1 locus.

The "absolute amplitude" of correlation means the absolute value of the correlation; e.g., both correlation coefficients −0.35 and 0.35 have an absolute amplitude of 0.35.

"Marker" means a cellular constituent, or a modification of a cellular constituent (e.g., an entire gene, EST derived from that gene, a protein encoded by that gene, post-translational modification of the protein, etc.) the expression or level of which changes between certain conditions. Where a change in a characteristic of the constituent correlates with a certain condition, the constituent is a marker for that condition.

"Marker-derived polynucleotides" means the RNA transcribed from a marker gene, any cDNA or cRNA produced therefrom, and any nucleic acid derived therefrom, such as synthetic nucleic acid having a sequence derived from the gene corresponding to the marker gene.

A "similarity value" is a number that represents the degree of similarity between two things being compared. For example, a similarity value may be a number that indicates the overall similarity between a patient's expression profile of specific phenotype-related markers and a template specific to that phenotype (for instance, the similarity to a "good prognosis" template, where the phenotype is a good prognosis). The similarity value may be expressed as a similarity metric, such as a correlation coefficient, or may simply be expressed as the expression level difference, or the aggregate of the expression level differences, between a patient sample and a template.

A "patient subset" is a group of individuals, all of whom have a particular condition, or are subject to a particular condition, which is distinguished from other individuals having that condition by one or more phenotypic, genotypic or clinical characteristics of the condition, or of a response to the condition. For example, where the condition is breast cancer, individuals may belong to an "$ER^+$" or an "$ER^-$" patient subset, or may belong to a particular age group patient subset.

A gene and/or marker is "informative" for a condition, phenotype, genotype or clinical characteristic if the expression of the gene or marker is correlated or anticorrelated with the condition, phenotype, genotype or clinical characteristic to a greater degree than would be expected by chance.

An individual of a given age can be classified as "ER/AGE high" if the individual's ER level is higher than a threshold value for the given age. The threshold can be age-dependent, i.e., a different threshold for each different age. In one embodiment, the age-dependent threshold value is calculated as $c\cdot(AGE-d)$, where c is a coefficient, AGE is the age of the patient, and d is an age threshold. The parameters c and d depend on the ER level and AGE used. They can be determined by fitting patients' ER level-age distribution to a bimodal distribution of two subgroups each having a different ER level-age dependence. In a specific embodiment, c=0.1 and d=42.5 is used for ER levels represented by a log(ratio) of ER expression level. Thus, for example, the threshold for a 45-year old individual in this embodiment is 0.1 (45-42.5), or 0.25, and if the log(ratio) of ER expression level of the individual is equal to or greater than 0.25, the individual is classified as "ER/AGE high"; otherwise, the individual is classified as "ER/AGE low."

5.3 Identification of Diagnostic and Prognostic Marker Sets 5.3.1 Identification of Condition Subsets The present invention provides methods of identifying sets of genes and/or markers useful in the diagnosis and prognosis of breast cancer. More generally, the invention also provides methods of identifying sets of genes and/or markers useful in the diagnosis or prognosis of other cancers, and even more generally, of identifying sets of genes and/or markers useful in the differentiation between subgroups of individuals having a particular condition, such as a disease or exposure to a particular environmental condition.

The method may be applied to any condition for which a plurality of phenotypic or genotypic subsets may be identified. The condition may be a disease; for example, the condition may be cancer, an autoimmune disease, an inflammatory disease, an infectious disease, a neurological disease, a degenerative disease, etc. The condition may be environmental; for example, the condition may be a particular diet, geographic location, etc.; the condition may be exposure to a compound, including, for example, a drug, a toxin, a carcinogen, a foodstuff, a poison, an inhaled compound, an ingested compound, etc.; the condition may be a particular genetic background or predisposition to a medical condition; etc.

Where the condition is cancer, the condition may be any cancer, for example, without limitation: leukemias, including acute leukemia, acute lymphocytic leukemia, acute myelocytic leukemia, myeloblastic leukemia, promyelocytic leukemia, myelomonocytic leukemia, monocytic leukemia, and erythroleukemia; chronic leukemia, such as chronic myelocytic (granulocytic) leukemia or chronic lymphocytic leukemia; polycythemia vera; lymphomas, such as Hodgkin's disease and non-Hodgkin's disease; multiple myeloma; Waldenström's macroglobulinemia; heavy chain disease; solid tumors, such as sarcomas and carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, or retinoblastoma; etc.

Rather than stratifying individuals, such as patients or tumor samples derived from patients, by gene expression patterns in the first instance, the method of identifying sets of genes informative for a condition begins by identifying phenotypic, genotypic or clinical subsets of individuals within the larger class of individuals having or affected by the condition.

In one embodiment, the condition is cancer, and the subsets are distinguished by phenotypic, genotypic, and/or clinical characteristics of the cancer. In this embodiment, groups of individuals are classified according to one or more phenotypic, genotypic, or clinical characteristics relevant to the cancer into patient subsets. At any step in the process of subdividing a patient population into patient subsets, the expression level of one or more genes may be determined in order to identify whether a prognosis-informative set of genes may be identified for the particular patient subset. If an informative gene set is identified, but is not as informative as desired, the patient subset may be further divided and a new geneset identified. These subsets may be further subdivided. For example, a group of individuals affected by a particular cancer may be classified first on the basis of a phenotypic, genotypic or clinical characteristic A into subsets S1 and S2.

The levels of expression of a plurality of genes are then determined in tumor samples taken from individuals that fall within subsets S1 or S2 in order to identify sets of genes informative for prognosis within these subsets. Subsets S1 and S2 may then each be subdivided into two or more subsets based on other phenotypic, genotypic or clinical characteristics. The basis for subdivision, if performed, need not be the same for S1 and S2. For example, in various embodiments, S1 is not subdivided, while S2 is subdivided on the basis of characteristic B; or S1 is subdivided based on characteristic B while S2 is not subdivided; or S1 and S2 are both subdivided on the basis of characteristic B; or S1 is subdivided based on characteristic B, while S2 is subdivided according to characteristic C; and so on. For a particular decision matrix leading to a plurality of patient subsets, the preferred outcome is a prognosis-informative set of genes for each patient subset. Different decision matrices may lead to different patient subsets, which, in turn, may result in different sets of prognosis-informative genes.

In the specific example of breast cancer, a plurality of phenotypic, genotypic or clinical indications are used to classify a patient as being a member of one of a plurality of patient subsets, wherein the indications are medically, biochemically or genetically relevant to breast cancer. For example, a group of patients may be classified into patient subsets based on criteria including, but not limited to, estrogen receptor (ER) status, type of tumor (i.e., BRCA1-type or sporadic), lymph node status, grade of cancer, invasiveness of the tumor, or age. "BRCA1-type" indicates that the BRCA1 mutation is present. In each classification step, a group of cancer patients may be classified into only two classes, for example, ER+ or $ER^-$, or into three or more subsets (for example, by tumor grade), depending upon the characteristic used to determine the subsets. As used herein, "ER+" indicates that the estrogen receptor is expressed at some elevated level; for example, it may indicate that the estrogen receptor is detectably expressed, or may indicate that more than 10% of cells are histologically stained for the receptor, etc. Conversely, "ER−" indicates that the estrogen receptor is expressed at a reduced level or not at all; for example, it may indicate that the receptor is not detectably expressed, or that 10% or less of cells are histologically stained for the receptor, etc. Marker gene sets optimized for each phenotypic class are preferably determined after the subsets are established. Where informative markers for a particular patient subset, distinguished from another subset by a particular characteristic of the condition of interest, cannot be determined, the subset may be further divided by another characteristic of the condition to create a plurality of second patient subsets, whereupon genes informative for these second patient subsets may be identified.

FIG. 1 depicts the process, described in the Examples, of subdivision of a collection of breast cancer patients according to phenotypic and genotypic characteristics relevant to breast cancer, in preparation for identification of genes informative for prognosis. A collection of breast cancer tumor samples was first subdivided by estrogen receptor status. ER status was chosen because the presence or absence of the estrogen receptor greatly influences the expression of other genes. In the ER+patient subset, it was noted that patients appeared to be bimodally distributed by ER level vs. age; that is, ER level dependence upon age tended to fall within two classes, as separated by the solid line in FIG. 2A. This bimodality was used to further subdivide ER+individuals into "ER+, ER/AGE high" individuals and "ER+, ER/AGE low" individuals. A set of informative genes was identified for the ER+, ER/AGE high patient subset. An informative set was not identified for the ER+, ER/AGE low subset, however, so the subset of patients was further divided into LN+ and LN− individuals. Thus, in one embodiment, the present invention provides a method of identifying a set of informative genes or markers for a condition comprising a plurality of phenotypic or genotypic characteristics, comprising (a) classifying each of a plurality of samples or individuals on the basis of one phenotypic or genotypic characteristic into a plurality of first classes; and (b) identifying within each of said first classes a set of informative genes or markers, wherein said set of informative genes or markers within each said first classes is unique to said class.

5.3.2 Identification of Marker Sets Informative for Patient Subsets

Once a patient subset is identified, markers, such as genes, informative for a particular outcome, such as prognosis, may be identified. In one embodiment, the method for identifying marker sets is as follows. This example describes the use of genes and gene-derived nucleic acids as markers; however, proteins or other cellular constituents may be used as markers of the condition.

After extraction and labeling of target polynucleotides, the expression of a plurality of markers, such as genes, in a sample X is compared to the expression of the plurality markers in a standard or control. In one embodiment, the standard or control comprises target markers, such as polynucleotide molecules, derived from one or more samples from a plurality of normal individuals, or a plurality of individuals not exposed to a particular condition. For example, the control, or normal, individuals may be persons without the particular disease or condition of interest (e.g., individuals not afflicted with breast cancer, where breast cancer is the disease of interest), or may be an individual not exposed to a particular environmental condition. The standard or control may also comprise target polynucleotide molecules, derived from one or more samples derived from individuals having a different form or stage of the same disease; a different disease or different condition, or individuals exposed or subjected to a different condition, than the individual from which sample X was obtained. The control may be a sample, or set of samples, taken from the individual at an earlier time, for example, to assess the progression of a condition, or the response to a course of therapy.

In a preferred embodiment, the standard or control is a pool of target polynucleotide molecules. However, where protein levels, or the levels of any other relevant biomolecule, are to be compared, the pool may be a pool of proteins or the relevant biomolecule. In a preferred embodiment in the context of breast cancer, the pool comprises samples taken from a number of individuals having sporadic-type tumors.

In another preferred embodiment, the pool comprises an artificially-generated population of nucleic acids designed to approximate the level of nucleic acid derived from each marker found in a pool of marker-derived nucleic acids derived from tumor samples. In another embodiment, the pool, also called a "mathematical sample pool," is represented by a set of expression values, rather than a set of physical polynucleotides; the level of expression of relevant markers in a sample from an individual with a condition, such as a disease, is compared to values representing control levels of expression for the same markers in the mathematical sample pool. Such a control may be a set of values stored on a computer. Such artificial or mathematical controls may be constructed for any condition of interest.

In another embodiment specific to breast cancer, the pool is derived from normal or breast cancer cell lines or cell line samples. In a preferred embodiment, the pool comprises samples taken from individuals within a specific patient subset, e.g., "ER+, ER/AGE high" individuals, wherein each of said individuals has a good prognosis, or each of said individuals has a poor prognosis. Of course, where, for example, expressed proteins are used as markers, the proteins are obtained from the individual's sample, and the standard or control could be a pool of proteins from a number of normal individuals, or from a number of individuals having a particular state of a condition, such as a pool of samples from individuals having a particular prognosis of breast cancer.

The comparison may be accomplished by any means known in the art. For example, expression levels of various markers may be assessed by separation of target polynucleotide molecules (e.g., RNA or cDNA) derived from the markers in agarose or polyacrylamide gels, followed by hybridization with marker-specific oligonucleotide probes. Alternatively, the comparison may be accomplished by the labeling of target polynucleotide molecules followed by separation on a sequencing gel. Polynucleotide samples are placed on the gel such that patient and control or standard polynucleotides are in adjacent lanes. Comparison of expression levels is accomplished visually or by means of densitometer. In a preferred embodiment, the expression of all markers is assessed simultaneously by hybridization to a microarray. In each approach, markers meeting certain criteria are identified as informative for the prognosis of breast cancer.

Marker genes are selected based upon significant difference of expression in a condition, such as a disease, as compared to a standard or control condition. Marker genes may be screened, for example, by determining whether they show significant variation within a set of samples of interest. Genes that do not show a significant amount of variation within the set of samples are presumed not to be informative for the disease or condition, and are not selected as markers for the disease or condition. Genes showing significant variation within the sample set are candidate informative genes for the disease or condition. The degree of variation may be estimated by calculating the difference of the expression of the gene, or ratio of expression between sample and control, within the set of samples. The expression, or ratio of expressions, may be transformed by any means, e.g., linear or log transformation. Selection may be made based upon either significant up- or down regulation of the marker in the patient sample. Selection may also be made by calculation of the statistical significance (i.e., the p-value) of the correlation between the expression of the marker and the disease and condition. Preferably, both selection criteria are used. Thus, in one embodiment of the present invention, markers associated with prognosis of breast cancer within a patient subset are selected where the markers show both more than two-fold change (increase or decrease) in expression as compared to a standard, and the p-value for the correlation between the existence of breast cancer and the change in marker expression is no more than 0.01 (i.e., is statistically significant).

In the context of the present invention, "good prognosis" indicates a desired outcome for a particular condition, especially a particular disease, and "poor prognosis" indicates an undesired outcome of the condition. For example, where the condition is cancer, a "good prognosis" may mean partial or complete remission, and "poor prognosis" may mean reappearance of the cancer after treatment. What constitutes "good prognosis" and "poor prognosis" is specific to the condition of interest, for example, specific to the particular cancer an individual suffers. For example, "good prognosis" for pancreatic cancer may be survival for one or two years after initial diagnosis, while "good prognosis" for Hodgkin's disease may be survival for five years or more. In the specific example of breast cancer, "good prognosis" means the likelihood of non-reoccurrence of metastases within a period of 1, 2, 3, 4, 5 or more years after initial diagnosis, and "poor prognosis" means the likelihood of reoccurrence of metastasis within that period. In a more specific example, "good prognosis" means the likelihood of non-reoccurrence of metastases within 5 years after initial diagnosis, and "poor prognosis" means the likelihood of reoccurrence of metastasis within that period.

In a more specific embodiment for cancer, for example, breast cancer, using a number of breast cancer tumor samples, markers are identified by calculation of correlation coefficients ρ between the clinical category or clinical parameter(s) $\vec{c}$ and the linear, logarithmic or any transform of the expression ratio $\vec{r}$ across all samples for each individual gene. Specifically, the correlation coefficient may be calculated as:

$$\rho=(\vec{c}\cdot\vec{r})/(\|\vec{c}\|\cdot\|\vec{r}\|) \quad \text{Equation (1)}$$

Markers for which the coefficient of correlation exceeds a cutoff are identified as prognosis-informative markers specific for a particular clinical type, e.g., good prognosis, within a given patient subset. Such a cutoff or threshold may correspond to a certain significance of discriminating genes obtained by Monte Carlo simulations. The threshold depends upon the number of samples used; the threshold can be calculated as $3\times1/\sqrt{n-3}$, where $1/\sqrt{n-3}$ is the distribution width and n=the number of samples. In a specific embodiment, markers are chosen if the correlation coefficient is greater than about 0.3 or less than about −0.3.

Next, the significance of the correlation is calculated. This significance may be calculated by any statistical means by which such significance is calculated. In a specific example, a set of correlation data is generated using a Monte-Carlo technique to randomize the association between the expression difference of a particular marker and the clinical category. The frequency distribution of markers satisfying the criteria in the Monte-Carlo runs is used to determine whether the number of markers selected by correlation with clinical data is significant.

Once a marker set is identified, the markers may be rank-ordered in order of significance of discrimination. One means of rank ordering is by the amplitude of correlation between the change in gene expression of the marker and the specific condition being discriminated. Another, preferred, means is to use a statistical metric. In a specific embodiment, the metric is a t-test-like statistic:

$$t=\frac{(\langle x_1\rangle-\langle x_2\rangle)}{\sqrt{[\sigma_1^2(n_1-1)+\sigma_2^2(n_2-1)]/(n_1+n_2-1)/(1/n_1+1/n_2)}} \quad \text{Equation (2)}$$

In this equation, $\langle x_1\rangle$ is the error-weighted average of the log ratio of transcript expression measurements within a first clinical group (e.g., good prognosis), $\langle x_2\rangle$ is the error-weighted average of log ratio within a second, related clinical group (e.g., poor prognosis), $\sigma_1$ is the variance of the log ratio within the first clinical group (e.g., good prognosis), $n_1$ is the number of samples for which valid measurements of log ratios are available, $\sigma_2$ is the variance of log ratio within the second clinical group (e.g., poor prognosis), and $n_2$ is the number of samples for which valid measurements of log ratios are available. The t-value represents the variance-compensated difference between two means.

The rank-ordered marker set may be used to optimize the number of markers in the set used for discrimination. This is accomplished generally in a "leave one out" method as follows. In a first run, a subset, for example five, of the markers from the top of the ranked list is used to generate a template, where out of X samples, X−1 are used to generate the template, and the status of the remaining sample is predicted. This process is repeated for every sample until every one of the X samples is predicted once. In a second run, additional markers, for example five additional markers, are added, so that a template is now generated from 10 markers, and the outcome of the remaining sample is predicted. This process is repeated until the entire set of markers is used to generate the template. For each of the runs, type 1 error (false negative) and type 2 errors (false positive) are counted; the optimal number of markers is that number where the type 1 error rate, or type 2 error rate, or preferably the total of type 1 and type 2 error rate is lowest.

For prognostic markers, validation of the marker set may be accomplished by an additional statistic, a survival model. This statistic generates the probability of tumor distant metastases as a function of time since initial diagnosis. A number of models may be used, including Weibull, normal, log-normal, log logistic, log-exponential, or log-Rayleigh (Chapter 12 "Life Testing", S-PLUS 2000 Guide to Statistics, Vol. 2, p. 368 (2000)). For the "normal" model, the probability of distant metastases P at time t is calculated as $$P=\alpha\times\exp(-t^2/\tau^2) \qquad \text{Equation (3)}$$

where $\alpha$ is fixed and equal to 1, and $\tau$ is a parameter to be fitted and measures the "expected lifetime".

It is preferable that the above marker identification process be iterated one or more times by excluding one or more samples from the marker selection or ranking (i.e., from the calculation of correlation). Those samples being excluded are the ones that can not be predicted correctly from the previous iteration. Preferably, those samples excluded from marker selection in this iteration process are included in the classifier performance evaluation, to avoid overstating the performance.

It will be apparent to those skilled in the art that the above methods, in particular the statistical methods described above, are not limited to the identification of markers associated with the prognosis of breast cancer within a particular patient subset, but may be used to identify set of marker genes associated with any phenotype or condition, or with any subset of a phenotype or condition defined by one or more characteristics of the phenotype or condition. The phenotype or condition can be the presence or absence of a disease such as cancer, or the presence or absence of any identifying clinical condition associated with that cancer. In the disease context, the phenotype may be a prognosis such as a survival time, probability of distant metastases of a disease condition, or likelihood of a particular response to a therapeutic or prophylactic regimen. The phenotype need not be cancer, or a disease; the phenotype may be a nominal characteristic associated with a healthy individual.

Thus, the invention provides a method of identifying a set of informative genes or markers for a condition comprising a plurality of phenotypic of genotypic characteristics, comprising: (a) classifying each of a plurality of samples or individuals on the basis of one or more phenotypic or genotypic characteristics of said condition into a plurality of first classes; (b) identifying within each of said first classes a first set of genes or markers informative for said condition, wherein said first set of genes or markers within each of said first classes is unique to said class relative to other classes. In a specific embodiment, samples or individuals in at least one of said first classes are additionally classified on the basis of a phenotypic or genotypic characteristic different from that used to distinguish said first classes into a plurality of second classes, and identifying within at least one of said second classes a second set of informative genes or markers, wherein said second set of informative genes or markers within each of said second classes is unique to said second class relative to other classes. In another embodiment, the invention provides a method of identifying a set of informative genes or markers for a condition comprising a plurality of phenotypic or genotypic characteristics, comprising: (a) classifying each of a plurality of samples or individuals on the basis of one or more phenotypic or genotypic characteristics into a plurality of first classes; (b) classifying at least one of said first classes into a plurality of second classes on the basis of phenotypic or genotypic characteristic different than that used to distinguish said plurality of first classes; (c) identifying within at least one of said first classes or said second classes a set of genes or markers informative for said condition, wherein said set of genes or markers is unique to said class relative to other classes. The invention further provides a method of identifying a set of informative genes or markers for a condition comprising a plurality of phenotypic or genotypic characteristics, comprising: (a) selecting a first characteristic from said plurality of phenotypic or genotypic characteristics; (b) identifying at least two first condition classes differentiable by said first characteristic; (c) selecting a plurality of individuals classifiable into at least one of said first condition classes; and (d) identifying in samples derived from each of said plurality of individuals a set of genes or markers informative for said condition within said at least one of said first condition classes.

5.3.3 Classifier Genesets for Five Patient Subsets

The present invention provides sets of markers useful for the prognosis of breast cancer. The markers were identified according to the above methods in specific subsets of individuals with breast cancer. Generally, the marker sets were identified within a population of breast cancer patients that had been first stratified into five phenotypic categories based on criteria relevant to breast cancer prognosis, including estrogen receptor (ER) status, lymph node status, type of mutation(s) (i.e., BRCA1-type or sporadic) and age at diagnosis. More specifically, patients, and tumors from which samples were taken, were classified as $ER^-$, sporadic (i.e., being both estrogen receptor negative and having a non-BRCA1-type tumor); $ER^-$, BRCA1 (i.e., being both estrogen receptor negative and having a BRCA1-type tumor); ER+, ER/AGE high (i.e., estrogen receptor positive with a high ratio of the log (ratio) of estrogen receptor gene expression to age); ER+, ER/AGE low, LN+ (i.e., estrogen receptor positive with a low ratio of the log (ratio) of estrogen receptor gene expression to age, lymph node positive); and $ER^+$, ER/AGE low, $LN^-$ (i.e., estrogen receptor positive with a low ratio of the log (ratio) of estrogen receptor gene expression to age, lymph node negative). The rationale for subdivision of the original patient set into these five subsets is detailed in the Examples (Section 6). The marker sets useful for each of the subsets above are provided in Tables 1-5, respectively.

TABLE 1

Geneset of 20 markers used to classify $ER^-$, sporadic individuals.

| Accession/ Contig No. | Gene | Avg good xdev | Avg poor xdev | Correlation | Description | Sp_xref_keyword_list | SEQ ID |
|---|---|---|---|---|---|---|---|
| AF055033 | IGFBP5 | −2.12 | 0.88 | 0.54 | insulin-like growth factor binding protein 5 | Growth factor binding, Glycoprotein, Signal, 3D-structure | 11 |
| NM_000599 | IGFBP5 | −3.41 | 0.43 | 0.53 | insulin-like growth factor binding protein 5 | Growth factor binding, Glycoprotein, Signal, 3D-structure | 51 |
| L27560 | IGFBP5 | −4.55 | 0 | 0.52 | EST | Hypothetical protein | 29 |
| AF052162 | FLJ12443 | −0.27 | 1.6 | 0.52 | EST | Hypothetical protein | 9 |
| NM_001456 | FLNA | −0.61 | 2.47 | 0.52 | filamin A, alpha (actin binding protein 280) | Hypothetical protein, Actin-binding, Phosphorylation, Repeat, Polymorphism, Disease mutation | 73 |
| NM_002205 | ITGA5 | −0.37 | 2.08 | 0.49 | integrin, alpha 5 (fibronectin receptor, alpha polypeptide) | Integrin, Cell adhesion, Receptor, Glycoprotein, Transmembrane, Signal, Calcium, Repeat | 93 |
| NM_013261 | PPARGC1 | 0.09 | 1.54 | 0.47 | peroxisome proliferative activated receptor, gamma, coactivator 1 | | 231 |
| NM_001605 | AARS | 0.39 | 2.36 | 0.51 | alanyl-tRNA synthetase | Aminoacyl-tRNA synthetase, Protein biosynthesis, Ligase, ATP-binding | 77 |
| X87949 | HSPA5 | −0.03 | 2.03 | 0.49 | heat shock 70 kDa protein 5 (glucose-regulated protein, 78 kDa) | ATP-binding, Hypothetical protein, Endoplasmic reticulum, Signal | 273 |
| Contig50950_RC | NGEF | −1.17 | 3.2 | 0.52 | neuronal guanine nucleotide exchange factor | | 337 |
| NM_005689 | ABCB6 | −0.51 | 2.26 | 0.48 | ATP-binding cassette, sub-family B (MDR/TAP), member 6 | ATP-binding, Transport, Transmembrane, Mitochondrion, Inner membrane, Transit peptide, Hypothetical protein | 187 |
| NM_004577 | PSPH | −0.56 | 3.05 | 0.51 | phosphoserine phosphatase | Hydrolase, Serine biosynthesis, Magnesium, Phosphorylation | 151 |
| NM_003832 | PSPHL | −2.08 | 2.18 | 0.5 | phosphoserine phosphatase-like | | 131 |
| NM_002422 | MMP3 | −0.96 | 2.54 | 0.5 | matrix metalloproteinase 3 (stromelysin 1, progelatinase) | Hydrolase, Metalloprotease, Glycoprotein, Zinc, Zymogen, Calcium, Collagen degradation, Extracellular matrix, Signal, Polymorphism, 3D-structure | 101 |
| Contig37562_RC | | −3.42 | −6.02 | −0.59 | ESTs | | 293 |
| NM_018465 | MDS030 | −0.82 | −3.28 | −0.58 | uncharacterized hematopoietic stem/progenitor cells protein MDS030 | Hypothetical protein | 267 |
| Contig54661_RC | | −0.79 | −2.08 | −0.54 | ESTs | | 349 |
| AB032969 | KIAA1143 | −0.6 | −2.85 | −0.53 | KIAA1143 protein | Hypothetical protein | 1 |
| Contig55353_RC | KIAA1915 | −0.27 | −1.82 | −0.47 | KIAA1915 protein | Hypothetical protein | 353 |
| NM_005213 | CSTA | 2.11 | −3.4 | −0.49 | cystatin A (stefin A) | Thiol protease inhibitor, 3D-structure | 175 |

TABLE 2

Geneset of 10 markers used to classify ER⁻, BRCA1 individuals.

| Accession/ Contig No. | Gene | Avg good xdev | Avg poor xdev | Correlation | Sequence name | Description | Sp_xref_keyword_list | SEQ ID |
|---|---|---|---|---|---|---|---|---|
| AF005487 | | 6.08 | 0.5 | −0.79 | HLA-DRB6 | *Homo sapiens* MHC class II antigen (DRB6) mRNA, HLA-DRB6*0201 allele, sequence. | MHC | 3 |
| Contig50728_RC | | 4.02 | 0.25 | −0.77 | | ESTs, Weakly similar to S26650 DNA-binding protein 5 - human [*H. sapiens*] | | 333 |
| Contig53598_RC | | 8.41 | 3.26 | −0.77 | FLJ11413 | hypothetical protein FLJ11413 | Hypothetical protein | 343 |
| NM_002888 | RARRES1 | 6.9 | 0.05 | −0.87 | RARRES1 | retinoic acid receptor responder (tazarotene induced) 1 | Receptor, Transmembrane, Signal-anchor | 109 |
| NM_005218 | DEFB1 | 5.14 | −3.02 | −0.81 | DEFB1 | defensin, beta 1 | Antibiotic, Signal, 3D-structure | 177 |
| U17077 | BENE | 2.72 | −1.72 | −0.77 | BENE | BENE protein | Transmembrane | 271 |
| Contig14683_RC | | 1.29 | −2.31 | −0.74 | | ESTs | | 279 |
| Contig53641_RC | | −3.29 | 4.23 | 0.75 | MAGE-E1 | MAGE-E1 protein | Hypothetical protein | 345 |
| Contig56678_RC | | −6.7 | −9.73 | −0.82 | | ESTs, Highly similar to THYA_HUMAN Prothymosin alpha [*H. sapiens*] | | 357 |
| NM_005461 | KRML | 0.88 | −3.38 | −0.75 | MAFB | v-maf musculoaponeurotic fibrosarcoma oncogene homolog B (avian) | Transcription regulation, Repressor, DNA-binding, Nuclear protein, Hypothetical protein | 181 |

TABLE 3

Geneset of 50 markers used to classify ER+, ER/AGE high individuals.

| Accession/ Contig No. | Gene | Avg good xdev | Avg poor xdev | Correlation | Description | Sp_xref_keyword_list | SEQ ID |
|---|---|---|---|---|---|---|---|
| NM_003600 | STK15 | −2.93 | 2.08 | 0.8 | serine/threonine kinase 6 | ATP-binding, Kinase, Serine/threonine-protein kinase, Transferase | 125 |
| NM_003158 | STK6 | −1.57 | 1.42 | 0.78 | serine/threonine kinase 6 | ATP-binding, Kinase, Serine/threonine-protein kinase, Transferase | 113 |
| NM_007019 | UBCH10 | −2.98 | 2.62 | 0.81 | ubiquitin-conjugating enzyme E2C | Hypothetical protein, UbI conjugation pathway, Ligase, Multigene family, Mitosis, Cell cycle, Cell division | 217 |
| NM_013277 | ID-GAP | −2.43 | 2.43 | 0.77 | Rac GTPase activating protein 1 | Hypothetical protein | 233 |
| NM_004336 | BUB1 | −2.04 | 1.39 | 0.77 | BUB1 budding uninhibited by benzimidazoles 1 homolog (yeast) | Transferase, Serine/threonine-protein kinase, ATP-binding, Cell cycle, Nuclear protein, Mitosis, Phosphorylation, Polymorphism | 147 |
| NM_006607 | PTTG2 | −1.71 | 1.49 | 0.72 | pituitary tumor-transforming 2 | | 211 |
| AK001166 | FLJ11252 | −1.33 | 0.99 | 0.71 | hypothetical protein FLJ11252 | Hypothetical protein | 13 |
| NM_004701 | CCNB2 | −4.62 | 2.01 | 0.81 | cyclin B2 | Cyclin, Cell cycle, Cell division, Mitosis | 153 |

TABLE 3-continued

Geneset of 50 markers used to classify ER+, ER/AGE high individuals.

| Accession/ Contig No. | Gene | Avg good xdev | Avg poor xdev | Correlation | Description | Sp_xref_keyword_list | SEQ ID |
|---|---|---|---|---|---|---|---|
| Contig57584_RC | | −3.68 | 2.04 | 0.78 | likely ortholog of mouse gene rich cluster, C8 gene | | 359 |
| NM_006845 | KNSL6 | −4.13 | 1.05 | 0.73 | kinesin-like 6 (mitotic centromere-associated kinesin) | Hypothetical protein, Motor protein, Microtubules, ATP-binding, Coiled coil, Nuclear protein | 215 |
| Contig38901_RC | | −3.08 | 1.15 | 0.75 | hypothetical protein MGC45866 | Hypothetical protein | 299 |
| NM_018410 | DKFZp762E1312 | −4.38 | 1.49 | 0.75 | hypothetical protein DKFZp762E1312 | Hypothetical protein | 263 |
| NM_003981 | PRC1 | −3.52 | 2.17 | 0.78 | protein regulator of cytokinesis 1 | | 133 |
| NM_001809 | CENPA | −5.04 | 0.98 | 0.75 | centromere protein A, 17 kDa | Hypothetical protein, Chromosomal protein, Nuclear protein, DNA-binding, Centromere, Antigen | 81 |
| NM_003504 | CDC45L | −2.67 | 1.22 | 0.73 | CDC45 cell division cycle 45-like (*S. cerevisiae*) | DNA replication, Cell cycle, Nuclear protein, Cell division | 123 |
| Contig41413_RC | | −5.43 | 2.15 | 0.74 | ribonucleotide reductase M2 polypeptide | Oxidoreductase, DNA replication, Iron | 305 |
| NM_004217 | STK12 | −2.17 | 0.73 | 0.72 | serine/threonine kinase 12 | Hypothetical protein, ATP-binding, Kinase, Serine/threonine-protein kinase, Transferase | 143 |
| NM_002358 | MAD2L1 | −2.65 | 2.27 | 0.83 | MAD2 mitotic arrest deficient-like 1 (yeast) | Cell cycle, Mitosis, Nuclear protein, 3D-structure | 99 |
| NM_014321 | ORC6L | −2.73 | 1.8 | 0.75 | origin recognition complex, subunit 6 homolog-like (yeast) | Hypothetical protein, DNA replication, Nuclear protein, DNA-binding | 241 |
| NM_012291 | KIAA0165 | −1.52 | 1.55 | 0.71 | extra spindle poles like 1 (*S. cerevisiae*) | Hypothetical protein | 229 |
| NM_004203 | PKMYT1 | −3.64 | 2.2 | 0.7 | retinoblastoma-like 2 (p130) | ATP-binding, Kinase, Serine/threonine-protein kinase, Transferase, Transcription regulation, DNA-binding, Nuclear protein, Cell cycle, Phosphorylation, Anti-oncogene | 137 |
| M96577 | E2F1 | −2.14 | 1.42 | 0.75 | E2F transcription factor 1 | Transcription regulation, Activator, DNA-binding, Nuclear protein, Phosphorylation, Cell cycle, Apoptosis, Polymorphism | 33 |
| NM_002266 | KPNA2 | −3.77 | 1.78 | 0.71 | karyopherin alpha 2 (RAG cohort 1, importin alpha 1) | Transport, Protein transport, Repeat, Nuclear protein, Polymorphism | 95 |
| Contig31288_RC | | −2.63 | 0.7 | 0.68 | ESTs, Weakly similar to hypothetical protein FLJ20489 [*Homo sapiens*] [*H. sapiens*] | | 289 |
| NM_014501 | E2-EPF | −1.55 | 1.93 | 0.7 | ubiquitin carrier protein | Ubl conjugation pathway, Ligase, Multigene family | 247 |
| NM_001168 | BIRC5 | −5.76 | 2.01 | 0.78 | baculoviral IAP repeat-containing 5 (survivin) | Apoptosis, Thiol protease inhibitor, Alternative splicing, 3D-structure, Hypothetical | 63 |

TABLE 3-continued

Geneset of 50 markers used to classify ER+, ER/AGE high individuals.

| Accession/ Contig No. | Gene | Avg good xdev | Avg poor xdev | Correlation | Description | Sp_xref_keyword_list | SEQ ID |
|---|---|---|---|---|---|---|---|
| | | | | | | protein, Protease, Receptor | |
| NM_003258 | TK1 | −4.57 | 1.38 | 0.71 | thymidine kinase 1, soluble | Transferase, Kinase, DNA synthesis, ATP-binding | 115 |
| NM_001254 | CDC6 | −2.46 | 0.28 | 0.72 | CDC6 cell division cycle 6 homolog (*S. cerevisiae*) | ATP-binding, Cell division | 67 |
| NM_004900 | DJ742C19.2 | −2.96 | 0.13 | 0.69 | apolipoprotein B mRNA editing enzyme, catalytic polypeptide-like 3B | Hydrolase | 161 |
| NM_004702 | CCNE2 | −3.12 | 2.13 | 0.81 | cyclin E2 | Cell cycle, Cell division, Cyclin, Hypothetical protein, Phosphorylation, Alternative splicing, Nuclear protein | 155 |
| AL160131 | | −3.07 | 2.42 | 0.7 | hypothetical protein MGC861 | Hypothetical protein | 21 |
| NM_016359 | LOC51203 | −3.22 | 2.61 | 0.76 | nucleolar protein ANKT | Hypothetical protein, Nuclear protein | 253 |
| NM_004856 | KNSL5 | −1.52 | 1.1 | 0.71 | kinesin-like 5 (mitotic kinesin-like protein 1) | Motor protein, Cell division, Microtubules, ATP-binding, Coiled coil, Mitosis, Cell cycle, Nuclear protein | 159 |
| NM_000057 | BLM | −1.54 | 0.76 | 0.71 | Bloom syndrome | Hydrolase, Helicase, ATP-binding, DNA-binding, Nuclear protein, DNA replication, Disease mutation | 35 |
| NM_018455 | BM039 | −2.44 | 1.18 | 0.7 | uncharacterized bone marrow protein BM039 | | 265 |
| NM_002106 | H2AFZ | −2.49 | 1.53 | 0.72 | H2A histone family, member Z | Chromosomal protein, Nucleosome core, Nuclear protein, DNA-binding, Multigene family | 91 |
| Contig64688 | | −2.68 | 3.1 | 0.73 | hypothetical protein FLJ23468 | Hypothetical protein | 365 |
| Contig44289_RC | | −1.65 | 1.6 | 0.67 | ESTs | | 315 |
| Contig28552_RC | | −1.37 | 1.53 | 0.68 | diaphanous homolog 3 (*Drosophila*) | Hypothetical protein, Coiled coil, Repeat, Alternative splicing | 281 |
| Contig46218_RC | | −1.31 | 1.56 | 0.68 | ESTs, Weakly similar to T19201 hypothetical protein C11G6.3 - *Caenorhabditis elegans* [*C. elegans*] | | 321 |
| Contig28947_RC | | −1.3 | 0.98 | 0.67 | cell division cycle 25A | Hypothetical protein, Cell division, Mitosis, Hydrolase, Alternative splicing, Multigene family, 3D-structure | 283 |
| NM_016095 | LOC51659 | −1.4 | 2.13 | 0.67 | HSPC037 protein | Hypothetical protein | 249 |
| NM_003090 | SNRPA1 | −3.26 | 0.95 | 0.7 | small nuclear ribonucleoprotein polypeptide A' | Hypothetical protein, Nuclear protein, RNA-binding, Ribonucleoprotein, Leucine-rich repeat, Repeat, 3D-structure | 111 |
| NM_002811 | PSMD7 | −2.48 | 1.89 | 0.7 | proteasome (prosome, macropain) 26S subunit, non-ATPase, 7 (Mov34 homolog) | Proteasome | 107 |
| Contig38288_RC | | −2.34 | 0.97 | 0.67 | hypothetical protein DKFZp762A2013 | Hypothetical protein | 297 |
| NM_003406 | YWHAZ | −1.5 | 2.79 | 0.68 | tyrosine 3-monooxygenase/tryptophan | Brain, Neurone, Phosphorylation, | 121 |

TABLE 3-continued

Geneset of 50 markers used to classify ER+, ER/AGE high individuals.

| Accession/ Contig No. | Gene | Avg good xdev | Avg poor xdev | Correlation | Description | Sp_xref_keyword_list | SEQ ID |
|---|---|---|---|---|---|---|---|
| | | | | | 5-monooxygenase activation protein, zeta polypeptide | Acetylation, Multigene family, 3D-structure | |
| AL137540 | NTN4 | 2.13 | −4.61 | −0.69 | netrin 4 | Hypothetical protein, Laminin EGF-like domain, Signal | 19 |
| AL049367 | | 1.9 | −3.2 | −0.68 | EST | Transducer, Prenylation, Lipoprotein, Multigene family, Acetylation | 15 |
| NM_013409 | FST | 1.04 | −5.78 | −0.69 | follistatin | Glycoprotein, Repeat, Signal, Alternative splicing | 235 |
| NM_000060 | BTD | 3.1 | −1.45 | −0.67 | biotinidase | Hydrolase, Glycoprotein, Signal, Disease mutation | 37 |

TABLE 4

Geneset of 50 markers used to classify ER+, ER/AGE low, LN+ individuals.

| Accession/ Contig No. | Gene | Avg good xdev | Avg poor xdev | Correlation | Description | Sp_xref_keyword_list | SEQ ID |
|---|---|---|---|---|---|---|---|
| NM_006417 | MTAP44 | −1.5 | 3 | 0.69 | Fc fragment of IgG, low affinity IIb, receptor for (CD32) | Hydrolase, Hypothetical protein, Immunoglobulin domain, IgG-binding protein, Receptor, Transmembrane, Glycoprotein, Signal, Repeat, Multigene family, Polymorphism, NAD, One-carbon metabolism, Serine protease, Zymogen, Protease, Alternative splicing, Chromosomal translocation, Proto-oncogene, Galaptin, Lectin, Antigen | 205 |
| NM_006820 | GS3686 | −4.3 | 4.06 | 0.69 | chromosome 1 open reading frame 29 | Hypothetical protein | 213 |
| NM_001548 | IFIT1 | −3.4 | 4.27 | 0.71 | Interferon-induced protein with tetratricopeptide repeats 1 | Repeat, TPR repeat, Interferon induction | 75 |
| Contig41538_RC | | −2.5 | 3.16 | 0.68 | ESTs, Moderately similar to hypothetical protein FLJ20489 [*Homo sapiens*] | | 307 |
| NM_016816 | OAS1 | −1.7 | 3.29 | 0.75 | 2',5'-oligoadenylate synthetase 1, 40/46 kDa | RNA-binding, Transferase, Nucleotidyltransferase, Interferon induction, Alternative splicing | 255 |
| Contig51660_RC | | −2.1 | 2.65 | 0.66 | 28 kD interferon responsive protein | Transmembrane | 339 |
| Contig43645_RC | | −4.8 | 1.44 | 0.63 | *Homo sapiens*, clone IMAGE: 4428577, mRNA, partial cds | Hypothetical protein | 313 |
| AF026941 | | −4.6 | 2.71 | 0.63 | EST, Weakly similar to 2004399A chromosomal | Hypothetical protein | 5 |

TABLE 4-continued

Geneset of 50 markers used to classify ER+, ER/AGE low, LN+ individuals.

| Accession/ Contig No. | Gene | Avg good xdev | Avg poor xdev | Correlation | Description | Sp_xref_keyword_list | SEQ ID |
|---|---|---|---|---|---|---|---|
| | | | | | protein [*Homo sapiens*] | | |
| NM_007315 | STAT1 | −3.5 | 1.8 | 0.59 | signal transducer and activator of transcription 1, 91 kDa | Transcription regulation, DNA-binding, Nuclear protein, Phosphorylation, SH2 domain, Alternative splicing, 3D-structure | 225 |
| NM_002038 | G1P3 | −4.1 | 5.64 | 0.79 | interferon, alpha-inducible protein (clone IFI-6-16) | Interferon induction, Transmembrane, Signal, Alternative splicing | 85 |
| NM_005101 | ISG15 | −5.6 | 5.34 | 0.77 | interferon-stimulated protein, 15 kDa | Interferon induction, Repeat | 169 |
| NM_002462 | MX1 | −6.1 | 0.83 | 0.56 | myxovirus (influenza virus) resistance 1, interferon-inducible protein p78 (mouse) | Hypothetical protein, Interferon induction, GTP-binding, Multigene family, Antiviral | 103 |
| NM_005532 | IFI27 | −5.8 | 2.81 | 0.59 | interferon, alpha-inducible protein 27 | Interferon induction, Transmembrane | 183 |
| NM_002346 | LY6E | −2.1 | 3.58 | 0.75 | lymphocyte antigen 6 complex, locus E | Signal, Antigen, Multigene family, Membrane, GPI-anchor | 97 |
| NM_016817 | OAS2 | −3.6 | 1.89 | 0.59 | 2'-5'-oligoadenylate synthetase 2, 69/71 kDa | RNA-binding, Transferase, Nucleotidyltransferase, Repeat, Interferon induction, Alternative splicing, Myristate | 257 |
| Contig44909_RC | | −2.3 | 1.13 | 0.55 | hypothetical protein BC012330 | Hypothetical protein | 317 |
| NM_017414 | USP18 | −4.1 | 3.37 | 0.72 | ubiquitin specific protease 18 | Ubl conjugation pathway, Hydrolase, Thiol protease, Multigene family | 259 |
| NM_004029 | IRF7 | −2.4 | 3.67 | 0.66 | interferon regulatory factor 7 | Collagen, Transcription regulation, DNA-binding, Nuclear protein, Activator, Alternative splicing | 135 |
| NM_004335 | BST2 | −3.2 | 3.22 | 0.57 | bone marrow stromal cell antigen 2 | Transmembrane, Glycoprotein, Signal-anchor, Polymorphism | 145 |
| NM_002759 | PRKR | −2.4 | 1.8 | 0.58 | protein kinase, interferon-inducible double stranded RNA dependent | Transferase, Serine/threonine-protein kinase, ATP-binding, Repeat, Phosphorylation, Interferon induction, RNA-binding, 3D-structure | 105 |
| NM_006332 | IFI30 | −3.8 | 2.65 | 0.64 | interferon, gamma-inducible protein 30 | Oxidoreductase, Interferon induction, Glycoprotein, Lysosome, Signal, Hypothetical protein | 203 |
| NM_009587 | LGALS9 | −3.2 | 2.08 | 0.6 | lectin, galactoside-binding, soluble, 9 (galectin 9) | Galaptin, Lectin, Repeat, Alternative splicing | 227 |
| NM_003641 | IFITM1 | −2.4 | 5.54 | 0.63 | interferon induced transmembrane protein 1 (9-27) | Interferon induction, Transmembrane | 127 |
| NM_017523 | HSXIAPAF1 | −1 | 2.84 | 0.7 | XIAP associated factor-1 | Hypothetical protein | 261 |

TABLE 4-continued

Geneset of 50 markers used to classify ER+, ER/AGE low, LN+ individuals.

| Accession/ Contig No. | Gene | Avg good xdev | Avg poor xdev | Correlation | Description | Sp_xref_keyword_list | SEQ ID |
|---|---|---|---|---|---|---|---|
| NM_014314 | RIG-I | −1.3 | 3.55 | 0.62 | RNA helicase | ATP-binding, Helicase, Hydrolase, Hypothetical protein | 239 |
| Contig47563_RC | | −2.2 | 3.11 | 0.56 | ESTs | | 325 |
| AI497657_RC | | −4.4 | 5.61 | 0.74 | guanine nucleotide binding protein 4 | Transducer, Prenylation, Lipoprotein, Multigene family | 335 |
| NM_000735 | CGA | −4.3 | 2.5 | 0.58 | glycoprotein hormones, alpha polypeptide | Hormone, Glycoprotein, Signal, 3D-structure | 53 |
| NM_004988 | MAGEA1 | −1.4 | 6.31 | 0.64 | melanoma antigen, family A, 1 (directs expression of antigen MZ2-E) | Antigen, Multigene family, Polymorphism, Tumor antigen | 163 |
| Contig54242_RC | | −1.2 | 4.1 | 0.65 | chromosome 17 open reading frame 26 | Hypothetical protein | 347 |
| NM_004710 | SYNGR2 | −1.4 | 3.01 | 0.54 | synaptogyrin 2 | Transmembrane | 157 |
| NM_001168 | BIRC5 | −3.7 | 3.39 | 0.64 | baculoviral IAP repeat-containing 5 (survivin) | Hypothetical protein, Protease, Receptor, Apoptosis, Thiol protease inhibitor, Alternative splicing, 3D-structure | 63 |
| Contig41413_RC | | −4.4 | 2.61 | 0.57 | ribonucleotide reductase M2 polypeptide | Oxidoreductase, DNA replication, Iron | 305 |
| NM_004203 | PKMYT1 | −3.4 | 3.79 | 0.6 | retinoblastoma-like 2 (p130) | ATP-binding, Kinase, Serine/threonine-protein kinase, Transferase, Transcription regulation, DNA-binding, Nuclear protein, Cell cycle, Phosphorylation, Anti-oncogene | 137 |
| Contig48913_RC | | −3.1 | 1.72 | 0.55 | *Homo sapiens*, Similar to hypothetical protein PRO1722, clone MGC: 15692 IMAGE: 3351479, mRNA, complete cds | | 327 |
| NM_005804 | DDXL | −2.5 | 1.42 | 0.58 | DEAD/H (Asp-Glu-Ala-Asp/His) box polypeptide 39 | ATP-binding, Helicase, Hydrolase, Hypothetical protein | 191 |
| NM_016359 | LOC51203 | −1.7 | 3.6 | 0.57 | nucleolar protein ANKT | Hypothetical protein, Nuclear protein | 253 |
| NM_001645 | APOC1 | −2.9 | 3.43 | 0.58 | apolipoprotein C-I | Plasma, Lipid transport, VLDL, Signal, 3D-structure, Polymorphism | 79 |
| Contig37895_RC | | −2 | 2.05 | 0.55 | ESTs | | 295 |
| NM_005749 | TOB1 | −1.3 | 4.96 | 0.59 | transducer of ERBB2, 1 | Phosphorylation | 189 |
| NM_000269 | NME1 | −1.3 | 2.98 | 0.55 | non-metastatic cells 1, protein (NM23A) expressed in | Transferase, Kinase, ATP-binding, Nuclear protein, Anti-oncogene, Disease mutation | 39 |
| NM_014462 | LSM1 | −1 | 4.5 | 0.57 | Lsm1 protein | Nuclear protein, Ribonucleoprotein, mRNA splicing, mRNA processing, RNA-binding | 245 |
| Contig31221_RC | | −1.4 | 3.83 | 0.56 | HTPAP protein | | 287 |
| NM_005326 | HAGH | −1.9 | 4.29 | 0.57 | hydroxyacyl glutathione hydrolase | Hydrolase, Zinc, 3D-structure | 179 |
| Contig42342_RC | | 0.78 | −3.2 | −0.6 | *Homo sapiens* cDNA FLJ39417 fis, clone PLACE6016942 | Hypothetical protein | 311 |

TABLE 4-continued

Geneset of 50 markers used to classify ER+, ER/AGE low, LN+ individuals.

| Accession/ Contig No. | Gene | Avg good xdev | Avg poor xdev | Correlation | Description | Sp_xref_keyword_list | SEQ ID |
|---|---|---|---|---|---|---|---|
| AL137540 | NTN4 | 2.24 | −3.9 | −0.6 | netrin 4 | Laminin EGF-like domain, Signal, Hypothetical protein | 19 |
| Contig40434_RC | | 1.64 | −5.6 | −0.6 | wingless-type MMTV integration site family, member 5A | Developmental protein, Glycoprotein, Signal | 301 |
| Contig1632_RC | | 1.03 | −3.9 | −0.6 | hypothetical protein MGC17921 | Hypothetical protein | 275 |
| NM_014246 | CELSR1 | 0.95 | −4.6 | −0.6 | cadherin, EGF LAG seven-pass G-type receptor 1 (flamingo homolog, *Drosophila*) | G-protein coupled receptor, Transmembrane, Glycoprotein, EGF-like domain, Calcium-binding, Laminin EGF-like domain, Repeat, Developmental protein, Hydroxylation, Signal, Alternative splicing, Hypothetical protein | 237 |
| NM_005139 | ANXA3 | 1.26 | −6.2 | −0.6 | annexin A3 | Annexin, Calcium/phospholipid-binding, Repeat, Phospholipase A2 inhibitor, 3D-structure, Polymorphism | 171 |

TABLE 5

Geneset of 65 markers used to classify ER+, ER/AGE low, LN⁻ individuals.

| Accession/ Contig No. | Gene | Avg good xdev | Avg poor xdev | Correlation | Sequence name | Description | Sp_xref_keyword_list | SEQ ID |
|---|---|---|---|---|---|---|---|---|
| M55914 | MPB1 | −2.82 | 1.25 | 0.5 | ENO1 | enolase 1, (alpha) | DNA-binding, Transcription regulation, Repressor, Nuclear protein, Lyase, Glycolysis, Magnesium, Multigene family, Hypothetical protein | 31 |
| NM_005945 | MPB1 | −3.06 | 1.19 | 0.49 | ENO1 | *Homo sapiens* enolase 1, (alpha) (ENO1), mRNA. | Glycolysis, Hypothetical protein, Lyase, Magnesium, DNA-binding, Transcription regulation, Repressor, Nuclear protein, Multigene family | 193 |
| NM_001428 | ENO1 | −2.53 | 1.18 | 0.46 | ENO1 | enolase 1, (alpha) | DNA-binding, Transcription regulation, Repressor, Nuclear protein, Lyase, Glycolysis, Magnesium, Multigene family, Hypothetical protein | 71 |
| NM_001216 | CA9 | −4.72 | 1.49 | 0.6 | CA9 | carbonic anhydrase IX | Lyase, Zinc, Transmembrane, Glycoprotein, | 65 |

TABLE 5-continued

Geneset of 65 markers used to classify ER+, ER/AGE low, $LN^-$ individuals.

| Accession/ Contig No. | Gene | Avg good xdev | Avg poor xdev | Correlation | Sequence name | Description | Sp_xref_keyword_list | SEQ ID |
|---|---|---|---|---|---|---|---|---|
| | | | | | | | Antigen, Signal, Nuclear protein, Polymorphism | |
| NM_001124 | ADM | −5.68 | 2.99 | 0.56 | ADM | Adrenomedullin | Hormone, Amidation, Cleavage on pair of basic residues, Signal | 61 |
| NM_000584 | IL8 | −2.45 | 2.04 | 0.54 | IL8 | interleukin 8 | Cytokine, Chemotaxis, Inflammatory response, Signal, Alternative splicing, 3D-structure | 49 |
| D25328 | PFKP | −4.19 | 3.29 | 0.56 | PFKP | Phosphofructo-kinase, platelet | Kinase, Transferase, Glycolysis, Repeat, Allosteric enzyme, Phosphorylation, Magnesium, Multigene family | 25 |
| NM_006096 | NDRG1 | −5.45 | 5.97 | 0.77 | NDRG1 | N-myc downstream regulated gene 1 | Hypothetical protein, Nuclear protein, Repeat | 199 |
| NM_004994 | MMP9 | −5.53 | 1.07 | 0.49 | MMP9 | matrix metalloproteinase 9 (gelatinase B, 92 kDa gelatinase, 92 kDa type IV collagenase) | Hydrolase, Metalloprotease, Glycoprotein, Zinc, Zymogen, Calcium, Collagen degradation, Extracellular matrix, Repeat, Signal, Polymorphism, 3D-structure | 165 |
| NM_003311 | TSSC3 | −4.57 | 5.58 | 0.68 | TSSC3 | tumor suppressing subtransferable candidate 3 | | 117 |
| NM_006086 | TUBB4 | −5.19 | 2.85 | 0.59 | TUBB4 | tubulin, beta, 4 | G-protein coupled receptor, Transmembrane, Glycoprotein, Phosphorylation, Lipoprotein, Palmitate, Polymorphism, Hypothetical protein, GTP-binding, Receptor, Microtubules, Multigene family | 197 |
| NM_006115 | PRAME | −4.48 | 2.77 | 0.61 | PRAME | preferentially expressed antigen in melanoma | Antigen | 201 |
| NM_004345 | CAMP | −2.02 | 1.37 | 0.49 | CAMP | cathelicidin antimicrobial peptide | Antibiotic, Signal | 149 |
| NM_018455 | BM039 | −2.34 | 0.76 | 0.47 | BM039 | uncharacterized bone marrow protein BM039 | | 265 |
| Contig49169_RC | | −1.17 | 1.5 | 0.46 | SUV39H2 | suppressor of variegation 3-9 (*Drosophila*) homolog 2; hypothetical protein FLJ23414 | Hypothetical protein, Nuclear protein | 329 |
| Contig45032_RC | | −1.37 | 0.77 | 0.45 | FLJ14813 | hypothetical protein FLJ14813 | Hypothetical protein, ATP-binding, Kinase, Serine/threonine-protein kinase, Transferase | 319 |
| NM_000917 | P4HA1 | −1.54 | 4.31 | 0.62 | P4HA1 | procollagen-proline, 2-oxoglutarate 4- | Dioxygenase, Collagen, Oxidoreductase, | 57 |

TABLE 5-continued

Geneset of 65 markers used to classify ER+, ER/AGE low, LN⁻ individuals.

| Accession/ Contig No. | Gene | Avg good xdev | Avg poor xdev | Correlation | Sequence name | Description | Sp_xref_keyword_list | SEQ ID |
|---|---|---|---|---|---|---|---|---|
| | | | | | | dioxygenase (proline 4-hydroxylase), alpha polypeptide I | Iron, Vitamin C, Alternative splicing, Glycoprotein, Endoplasmic reticulum, Signal | |
| NM_002046 | GAPD | −2.51 | 3.42 | 0.6 | GAPD | glyceraldehyde-3-phosphate dehydrogenase | Glycolysis, NAD, Oxidoreductase, Hypothetical protein, Multigene family | 87 |
| NM_000365 | TPI1 | −1.81 | 2.94 | 0.56 | TPI1 | triosephosphate isomerase 1 | Fatty acid biosynthesis, Gluconeogenesis, Glycolysis, Isomerase, Pentose shunt, Disease mutation, Polymorphism, 3D-structure | 45 |
| NM_014364 | GAPDS | −1.08 | 2.88 | 0.58 | GAPDS | glyceraldehyde-3-phosphate dehydrogenase, testis-specific | Glycolysis, Oxidoreductase, NAD | 243 |
| NM_005566 | LDHA | −2.01 | 4.01 | 0.59 | LDHA | lactate dehydrogenase A | Oxidoreductase, NAD, Glycolysis, Multigene family, Disease mutation, Polymorphism | 185 |
| NM_000291 | PGK1 | −2.28 | 1.68 | 0.51 | PGK1 | phosphoglycerate kinase 1 | Kinase, Transferase, Multigene family, Glycolysis, Acetylation, Disease mutation, Polymorphism, Hereditary hemolytic anemia | 41 |
| NM_016185 | LOC51155 | −2.33 | 2.82 | 0.59 | HN1 | hematological and neurological expressed 1 | | 251 |
| NM_001168 | BIRC5 | −4.33 | 2.78 | 0.55 | BIRC5 | baculoviral IAP repeat-containing 5 (survivin) | Apoptosis, Thiol protease inhibitor, Alternative splicing, 3D-structure, Hypothetical protein, Protease, Receptor | 63 |
| NM_002266 | KPNA2 | −3.75 | 1.34 | 0.47 | KPNA2 | karyopherin alpha 2 (RAG cohort 1, importin alpha 1) | Transport, Protein transport, Repeat, Nuclear protein, Polymorphism | 95 |
| Contig31288_RC | | −2.1 | 1.27 | 0.5 | | ESTs, Weakly similar to hypothetical protein FLJ20489 [*Homo sapiens*] [*H. sapiens*] | | 289 |
| NM_000269 | NME1 | −2.15 | 3.43 | 0.55 | NME1 | non-metastatic cells 1, protein (NM23A) expressed in | Transferase, Kinase, ATP-binding, Nuclear protein, Anti-oncogene, Disease mutation | 39 |
| NM_003158 | STK6 | −1.23 | 1.73 | 0.45 | STK6 | serine/threonine kinase 6 | ATP-binding, Kinase, Serine/threonine-protein kinase, Transferase | 113 |
| NM_007274 | HBACH | −1.83 | 2.73 | 0.51 | BACH | brain acyl-CoA hydrolase | Hydrolase, Serine esterase, Repeat | 223 |
| Contig55188_RC | | −2.36 | 3.28 | 0.47 | FLJ22341 | hypothetical protein FLJ22341 | Hypothetical protein | 351 |
| NM_002061 | GCLM | −1.06 | 1.76 | 0.48 | GCLM | glutamate-cysteine ligase, modifier subunit | Ligase, Glutathione biosynthesis | 89 |
| NM_004207 | SLC16A3 | −3.11 | 5.07 | 0.67 | SLC16A3 | solute carrier family 16 (monocarboxylic | Transport, Symport, | 139 |

TABLE 5-continued

| Accession/ Contig No. | Gene | Avg good xdev | Avg poor xdev | Correlation | Sequence name | Description | Sp_xref_keyword_list | SEQ ID |
|---|---|---|---|---|---|---|---|---|
| Geneset of 65 markers used to classify ER+, ER/AGE low, LN⁻ individuals. | | | | | | | | |
| | | | | | | acid transporters), member 3 | Transmembrane, Multigene family | |
| NM_000582 | SPP1 | −5.09 | 5.47 | 0.53 | SPP1 | secreted phosphoprotein 1 (osteopontin, bone sialoprotein I, early T-lymphocyte activation 1) | Hypothetical protein, Glycoprotein, Sialic acid, Biomineralization, Cell adhesion, Phosphorylation, Signal, Alternative splicing | 47 |
| NM_001109 | ADAM8 | −2.5 | 3.74 | 0.45 | ADAM8 | a disintegrin and metalloproteinase domain 8 | Hydrolase, Metalloprotease, Zinc, Signal, Glycoprotein, Transmembrane, Antigen | 59 |
| D50402 | SLC11A1 | −1.05 | 3.46 | 0.53 | SLC11A1 | solute carrier family 11 (proton-coupled divalent metal ion transporters), member 1 | Transport, Iron transport, Transmembrane, Glycoprotein, Macrophage, Polymorphism | 27 |
| AL080235 | DKFZP586E1621 | −1.23 | 1.96 | 0.51 | RIS1 | Ras-induced senescence 1 | Hypothetical protein | 17 |
| Contig40552_RC | | −1.26 | 3.96 | 0.54 | FLJ25348 | hypothetical protein FLJ25348 | Hypothetical protein | 303 |
| Contig52490_RC | | −0.64 | 3.33 | 0.61 | LOC116238 | hypothetical protein BC014072 | | 341 |
| NM_006461 | DEEPEST | −2.1 | 1.85 | 0.46 | SPAG5 | sperm associated antigen 5 | Hypothetical protein | 207 |
| Contig56503_RC | | −4.3 | 3.39 | 0.55 | MGC9753 | hypothetical gene MGC9753 | Hypothetical protein | 355 |
| Contig63525 | | −1.91 | 3.34 | 0.5 | FLJ13352 | hypothetical protein FLJ13352 | Hypothetical protein | 363 |
| NM_001909 | CTSD | −0.83 | 4.6 | 0.51 | CTSD | cathepsin D (lysosomal aspartyl protease) | Hydrolase, Aspartyl protease, Glycoprotein, Lysosome, Signal, Zymogen, Polymorphism, Alzheimer's disease, 3D-structure | 83 |
| NM_005063 | SCD | −2.57 | 5.15 | 0.48 | SCD | stearoyl-CoA desaturase (delta-9-desaturase) | Hypothetical protein, Endoplasmic reticulum, Fatty acid biosynthesis, Iron, Oxidoreductase, Transmembrane | 167 |
| NM_005165 | ALDOC | −2.43 | 5.02 | 0.48 | ALDOC | aldolase C, fructose-bisphosphate | Lyase, Schiff base, Glycolysis, Multigene family | 173 |
| NM_000363 | TNNI3 | −0.54 | 3.58 | 0.48 | TNNI3 | troponin I, cardiac | Hypothetical protein, Muscle protein, Actin-binding, Acetylation, Disease mutation, Cardiomyopathy, Receptor, Signal | 43 |
| AF035284 | | −1.63 | 3.28 | 0.47 | FADS1 | EST | Heme, Hypothetical protein | 7 |
| Contig30875_RC | | −0.88 | 3 | 0.6 | | ESTs | | 285 |
| NM_018487 | HCA112 | −0.7 | 3.54 | 0.58 | HCA112 | hepatocellular carcinoma-associated antigen 112 | Hypothetical protein | 269 |
| NM_001323 | CST6 | −1.63 | 3.84 | 0.57 | CST6 | cystatin E/M | Thiol protease inhibitor, Signal, Glycoprotein | 69 |
| NM_006516 | SLC2A1 | −1.66 | 2.22 | 0.46 | SLC2A1 | solute carrier family 2 (facilitated glucose | Transmembrane, Sugar transport, Transport, Glycoprotein, | 209 |

TABLE 5-continued

| Geneset of 65 markers used to classify ER+, ER/AGE low, LN⁻ individuals. | | | | | | | | |
|---|---|---|---|---|---|---|---|---|
| Accession/ Contig No. | Gene | Avg good xdev | Avg poor xdev | Correlation | Sequence name | Description | Sp_xref_keyword_list | SEQ ID |
| | | | | | | transporter), member 1 | Multigene family, Disease mutation | |
| NM_007267 | LAK-4P | −1.04 | 3.28 | 0.61 | EVIN1 | expressed in activated T/LAK lymphocytes | Hypothetical protein | 221 |
| NM_004710 | SYNGR2 | −0.84 | 4.81 | 0.56 | SYNGR2 | synaptogyrin 2 | Transmembrane | 157 |
| Contig63649_RC | | −1.34 | 6.3 | 0.75 | | ESTs, Weakly similar to 2004399A chromosomal protein [*Homo sapiens*] [*H. sapiens*] | | 361 |
| NM_003376 | VEGF | −2.12 | 2.42 | 0.46 | VEGF | vascular endothelial growth factor | Hypothetical protein, Mitogen, Angiogenesis, Growth factor, Glycoprotein, Signal, Heparin-binding, Alternative splicing, Multigene family, 3D-structure | 119 |
| NM_000799 | EPO | −0.75 | 4.01 | 0.69 | EPO | erythropoietin | Erythrocyte maturation, Glycoprotein, Hormone, Signal, Pharmaceutical, 3D-structure | 55 |
| NM_006014 | DXS9879E | −1.85 | 3.44 | 0.54 | DXS9879E | DNA segment on chromosome X (unique) 9879 expressed sequence | | 195 |
| NM_007183 | PKP3 | −0.91 | 4.14 | 0.48 | PKP3 | plakophilin 3 | Cell adhesion, Cytoskeleton, Structural protein, Nuclear protein, Repeat | 219 |
| D13642 | SF3B3 | −0.65 | 2.28 | 0.48 | SF3B3 | splicing factor 3b, subunit 3, 130 kDa | Hypothetical protein, Spliceosome, mRNA processing, mRNA splicing, Nuclear protein | 23 |
| NM_003756 | EIF3S3 | −1.85 | 2.19 | 0.46 | EIF3S3 | eukaryotic translation initiation factor 3, subunit 3 gamma, 40 kDa | Initiation factor, Protein biosynthesis | 129 |
| Contig47096_RC | | −0.41 | 4.52 | 0.54 | PFKFB4 | 6-phosphofructo-2-kinase/fructose-2,6-biphosphatase 4 | Kinase, Multifunctional enzyme, Transferase, Hydrolase, ATP-binding, Phosphorylation, Multigene family | 323 |
| NM_004209 | SYNGR3 | −0.31 | 3.67 | 0.53 | SYNGR3 | synaptogyrin 3 | Transmembrane | 141 |
| Contig3464_RC | | 0.99 | −5.81 | −0.52 | | ESTs | | 277 |
| Contig31646_RC | | 1.1 | −7.76 | −0.5 | COL14A1 | collagen, type XIV, alpha 1 (undulin) | Extracellular matrix, Glycoprotein, Hypothetical protein, Collagen, Signal | 291 |
| Contig49388_RC | | 1.73 | −1.75 | −0.51 | FLJ13322 | hypothetical protein FLJ13322 | Hypothetical protein | 331 |
| Contig41887_RC | | 0.37 | −5.74 | −0.47 | LOC124220 | similar to common salivary protein 1 | Hypothetical protein | 309 |

5.4 Diagnostic and Prognostic Methods 5.4.1 Sample Collection

In the present invention, markers, such as target polynucleotide molecules or proteins, are extracted from a sample taken from an individual afflicted with a condition such as breast cancer. The sample may be collected in any clinically acceptable manner, but must be collected such that marker-derived polynucleotides (i.e., RNA) are preserved (if gene expression is to be measured) or proteins are preserved (if encoded proteins are to be measured). For example, mRNA or nucleic acids derived therefrom (i.e., cDNA or amplified DNA) are preferably labeled distinguishably from standard or control polynucleotide molecules, and both are simultaneously or independently hybridized to a microarray comprising some or all of the markers or marker sets or subsets described above. Alternatively, mRNA or nucleic acids derived therefrom may be labeled with the same label as the standard or control polynucleotide molecules, wherein the intensity of hybridization of each at a particular probe is compared. A sample may comprise any clinically relevant tissue sample, such as a tumor biopsy or fine needle aspirate, or a sample of bodily fluid, such as blood, plasma, serum, lymph, ascitic fluid, cystic fluid, urine or nipple exudate. The sample may be taken from a human, or, in a veterinary context, from non-human animals such as ruminants, horses, swine or sheep, or from domestic companion animals such as felines and canines.

Methods for preparing total and poly(A)+ RNA are well known and are described generally in Sambrook et al., MOLECULAR CLONING—A LABORATORY MANUAL (2ND ED.), Vols. 1-3, Cold Spring Harbor Laboratory, Cold Spring Harbor, N.Y. (1989)) and Ausubel et al., CURRENT PROTOCOLS IN MOLECULAR BIOLOGY, vol. 2, Current Protocols Publishing, New York (1994)).

RNA may be isolated from eukaryotic cells by procedures that involve lysis of the cells and denaturation of the proteins contained therein. Cells of interest include wild-type cells (i.e., non-cancerous), drug-exposed wild-type cells, tumor- or tumor-derived cells, modified cells, normal or tumor cell line cells, and drug-exposed modified cells. Preferably, the cells are breast cancer tumor cells.

Additional steps may be employed to remove DNA. Cell lysis may be accomplished with a nonionic detergent, followed by microcentrifugation to remove the nuclei and hence the bulk of the cellular DNA. In one embodiment, RNA is extracted from cells of the various types of interest using guanidinium thiocyanate lysis followed by CsCl centrifugation to separate the RNA from DNA (Chirgwin et al., *Biochemistry* 18:5294-5299 (1979)). Poly(A)+ RNA is selected by selection with oligo-dT cellulose (see Sambrook et al., MOLECULAR CLONING—A LABORATORY MANUAL (2ND ED.), Vols. 1-3, Cold Spring Harbor Laboratory, Cold Spring Harbor, N.Y. (1989). Alternatively, separation of RNA from DNA can be accomplished by organic extraction, for example, with hot phenol or phenol/chloroform/isoamyl alcohol.

If desired, RNase inhibitors may be added to the lysis buffer. Likewise, for certain cell types, it may be desirable to add a protein denaturation/digestion step to the protocol.

For many applications, it is desirable to preferentially enrich mRNA with respect to other cellular RNAs, such as transfer RNA (tRNA) and ribosomal RNA (rRNA). Most mRNAs contain a poly(A) tail at their 3' end. This allows them to be enriched by affinity chromatography, for example, using oligo(dT) or poly(U) coupled to a solid support, such as cellulose or SEPHADEX® (see Ausubel et al., CURRENT PROTOCOLS IN MOLECULAR BIOLOGY, vol. 2, Current Protocols Publishing, New York (1994)). Once bound, poly(A)+ mRNA is eluted from the affinity column using 2 mM EDTA/0.1% SDS.

The sample of RNA can comprise a plurality of different mRNA molecules, each different mRNA molecule having a different nucleotide sequence. In a specific embodiment, the mRNA molecules in the RNA sample comprise at least 5, 10, 15, 20, 25, 30, 40 or 50 different nucleotide sequences. More preferably, the mRNA molecules of the RNA sample comprise mRNA molecules corresponding to each of the marker genes. In another specific embodiment, the RNA sample is a mammalian RNA sample.

In a specific embodiment, total RNA or mRNA from cells are used in the methods of the invention. The source of the RNA can be cells of a plant or animal, human, mammal, primate, non-human animal, dog, cat, mouse, rat, bird, yeast, eukaryote, prokaryote, etc. In specific embodiments, the method of the invention is used with a sample containing total mRNA or total RNA from $1\times10^6$ cells or less. In another embodiment, proteins can be isolated from the foregoing sources, by methods known in the art, for use in expression analysis at the protein level.

Probes to the homologs of the marker sequences disclosed herein can be employed preferably when non-human nucleic acid is being assayed.

The methods of the invention may employ any molecule suitable as a marker. For example, sets of proteins informative for a particular condition, including a disease, may be determined. As for gene-based markers, levels of variations of different proteins in samples may be determined for phenotypic or genotypic subsets of the condition, and proteins showing significant variation in either level (abundance) or activity, or both, may be identified in order to create a set of proteins informative for one or more of these subsets. Such proteins may be identified, for example, by use of gel electrophoresis, such as one-dimensional polyacrylamide gel electrophoresis, two-dimensional polyacrylamide gel electrophoresis, nondenaturing polyacrylamide gel electrophoresis; isoelectric focusing gels, etc., by use of antibody arrays, etc. Of course, the particular template(s) used to classify the individual depends upon the type(s) of cellular constituents used as markers. For example, where nucleic acids (e.g., genes or nucleic acids derived from expressed genes) are used as markers, the template comprises nucleic acids (or the level of expression or abundance thereof); where proteins are used as markers, the template comprises proteins, for example, the level or abundance of those proteins in a set of individuals; etc.

5.4.2 Use of Prognostic Genesets for Breast Cancer

According to the present invention, once genesets informative for a plurality of subsets of a condition are identified, an individual is classified into one of these subsets and a prognosis is made based on the expression of the genes, or their encoded proteins, in the geneset for that subset in a breast cancer tumor sample taken from the individual.

For example, a particular hypothetical condition has three relevant phenotypic characteristics, A, B and C. In this example, based on these characteristics, genesets informative for prognosis of four patient subsets $A^+B^+$; $A^+B^-C^+$; $A^+B^-C^-$; and $A^-$ are identified by the method described above. Thus, an individual having the condition would first be classified according to phenotypes A-C into one of the four patient subsets. In one embodiment, therefore, the invention provides for the classification of an individual having a condition into one of a plurality of patient subsets, wherein a set of genes informative for prognosis for the subset has been identified. A sample is then taken from the individual, and the expression of the prognostically-informative genes in the sample is analyzed and compared to a control. In various embodiments, the control is the average expression of informative genes in a pool of samples taken from good prognosis individuals classifiable into that patient subset; the average expression of informative genes in a pool of samples taken from poor prognosis individuals classifiable into that patient subset; a set of mathematical values that represent gene expression levels of good prognosis individuals classifiable into that patient subset; etc.

In another embodiment, a sample is taken from the individual, and the levels of expression of the prognostically-informative genes in the sample is analyzed. In one embodiment, the expression level of each gene can be compared to the expression level of the corresponding gene in a control of reference sample to determine a differential expression level. The expression profile comprising expression levels or differential expression levels of the plurality of genes is then compared to a template profile. In various embodiments, the template profile is a good prognosis template comprising the average expression of informative genes in samples taken from good prognosis individuals classifiable into that patient subset; or a poor prognosis template comprising the average expression of informative genes in samples taken from poor prognosis individuals classifiable into that patient subset; or a good prognosis profile comprising a set of mathematical values that represent gene expression levels of good prognosis individuals classifiable into that patient subset; etc.

In a specific embodiment, the condition is breast cancer, and the phenotypic, genotypic and/or clinical classes are: $ER^-$, BRCA1 individuals; $ER^-$, sporadic individuals; ER+, ER/AGE high individuals; ER+, ER/AGE low, LN+ individuals; and ER+, ER/AGE low, $LN^-$ individuals. In this embodiment, an individual may be classified as ER+ or $ER^-$. If the individual is $ER^-$, the individual is additionally classified as having a BRCA1-type or sporadic tumor. $ER^-$ individuals are thus classified as $ER^-$, BRCA1 or $ER^-$, sporadic. Alternatively, if the individual is classified as ER+, the individual is additionally classified as having a high or low ratio of the log (ratio) of the level of expression of the gene encoding the estrogen receptor to the individual's age. Individuals having a low ratio are additionally classified as LN+ or LN−. ER+individuals are thus classified as ER+, ER/AGE high; ER+, ER/AGE low, LN+, or ER+, ER/AGE low, $LN^-$. Of course, the individual's ER status, tumor type, age and LN status may be identified in any order, as long as the individual is classified into one of these five subsets.

Thus, in one embodiment, the invention provides a method of classifying an individual with a condition as having a good prognosis or a poor prognosis, comprising: (a) classifying said individual into one of a plurality of patient classes, said patient classes being differentiated by one or more phenotypic, genotypic or clinical characteristics of said condition; (b) determining the level of expression of a plurality of genes or their encoded proteins in a cell sample taken from the individual relative to a control, said plurality of genes or their encoded proteins comprising genes or their encoded proteins in a cell sample taken from the individual relative to a control, said plurality of genes or their encoded proteins comprising genes or their encoded proteins informative for prognosis of the patient class into which said individual is classified; and (c) classifying said individual as having a good prognosis or a poor prognosis on the basis of said level of expression. In a specific embodiment, said condition is breast cancer, said good prognosis is the non-occurrence of metastases within five years of initial diagnosis, and said poor prognosis is the occurrence of metastases within five years of initial diagnosis. In an more specific embodiment, said classifying said individual with a condition as having a good prognosis or a poor prognosis is carried out by comparing the level expression of each of said plurality of genes or their encoded proteins to said average level of expression of each corresponding gene or its encoded protein in said control, and classifying said individual as having a good prognosis poor prognosis if said level of expression correlates with said average level of expression of each of said genes or their encoded proteins in a good prognosis control or a poor prognosis control, respectively, more strongly than would be expected by chance. In a more specific embodiment of the method, said plurality of patient subsets comprises $ER^-$, BRCA1 individuals; $ER^-$, sporadic individuals; ER+, ER/AGE high individuals; ER+, ER/AGE low, LN+ individuals; and ER+, ER/AGE low, $LN^-$ individuals. In another embodiment, said control is the average level of expression of each of said plurality of genes informative for prognosis in a pool of tumor samples from individuals classified into said subset who have a good prognosis or good outcome, or who have a poor prognosis or good outcome. In another specific embodiment, said control is a set of mathematical values representing the average level of expression of genes informative for prognosis in tumor samples of individuals classifiable into said subset who have a good prognosis, or who have a poor prognosis.

It is evident that the different patient subsets described herein reflect different molecular mechanisms of the initiation of tumor formation and metastasis. Thus, the genesets listed in tables 1-5 are also useful for diagnosing a person as having a particular type of breast cancer in the first instance. Thus, the invention also provides a method of diagnosing an individual as having a particular subtype of breast cancer, comprising determining the level of expression in a sample from said individual of a plurality of the genes for which markers are listed in Tables 1-5; and comparing said expression to a control, where said control is representative of the expression of said plurality of genes in a breast cancer sample of said subtype of cancer, and on the basis of said comparison, diagnosing the individual as having said subtype of breast cancer. In a specific embodiment, said subtype of cancer is selected from the group consisting of $ER^-$, BRCA1 type; $ER^-$, sporadic type; ER+, ER/AGE high type; ER+, ER/AGE low, LN+ type; and ER/AGE low, $LN^-$ type. In another specific embodiment, said control is the average level of expression of a plurality of the genes for which markers are listed in Table 1, Table 2, Table 3, Table 4 or Table 5. In another specific example, said comparing comprises determining the similarity of the expression of the genes for which markers are listed in each of Tables 1-5 in said sample taken from said individual to a control level of expression of the same genes for each of Tables 1-5, and determining whether the level of expression of said genes in said sample is most similar to said control expression of the genes for which markers are listed in Table 1, Table 2, Table 3, Table 4 or Table 5.

In another embodiment, the invention provides a method of classifying an individual as having a good prognosis or a poor prognosis, comprising: (a) classifying said individual as $ER^-$, BRCA1; $ER^-$, sporadic; ER+, ER/AGE high; ER+, ER/AGE low, LN+; or ER+, ER/AGE low, $LN^-$; (b) determining the level of expression of a first plurality of genes in a cell sample taken from the individual relative to a control, said first plurality of genes comprising two of the genes corresponding to the markers Table 1 if said individual is classified as $ER^-$, BRCA1; Table 2 if said individual is classified as $ER^-$, sporadic; Table 3 if said individual is classified as ER+, ER/AGE high; Table 4 if said individual is classified as ER+, ER/AGE low, LN+; or Table 5 if said individual is classified as ER+, ER/AGE low, $LN^-$, wherein said individual is "ER/AGE high" if the ratio of ER expression to age exceeds a predetermined value, and "ER/AGE low" if the ratio of ER expression to age does not exceed said predetermined value. In a specific embodiment of this method, said predetermined value of ER calculated as $ER=0.1(AGE-42.5)$, wherein AGE is the age of said individual. In another specific embodiment, said individual is $ER^-$, BRCA1, and said plurality of genes comprises (i.e., contains at least) 1, 2, 3, 4, 5, 10 or all of the genes for which markers are listed in Table 1. In another specific embodiment, said individual is $ER^-$, sporadic, and said plurality of genes comprises (i.e., contains at least) 1, 2, 3, 4, 5, 10 or all of the genes for which markers are listed in Table 2. In another specific embodiment, said individual is ER+, ER/AGE high, and said plurality of genes comprises (i.e., contains at least) 1, 2, 3, 4, 5, 10 or all of the genes for which markers are listed in Table 3. In another specific embodiment, said individual is ER+, ER/AGE low, LN+, and said plurality of genes comprises (i.e., contains at least) 1, 2, 3, 4, 5, 10 or all of the genes for which markers are listed in Table 4. In another specific embodiment, said individual is ER+, ER/AGE low, $LN^-$, and said plurality of genes comprises (i.e., contains at least) 1, 2, 3, 4, 5, 10 or all of the genes for which markers are listed in Table 5. In another specific embodiment, the method additionally comprises determining in said cell sample the level of expression, relative to a control, of a second plurality of genes for which markers are not found in Tables 1-5, wherein said second plurality of genes is informative for prognosis.

In one embodiment, the invention provides a method of classifying an individual with a condition as having a good prognosis or a poor prognosis, comprising: (a) classifying said individual into one of a plurality of patient classes, said patient classes being differentiated by one or more phenotypic, genotypic or clinical characteristics of said condition; (b) determining the levels of expression of a plurality of genes or their encoded proteins in a cell sample taken from the individual, optionally relative to a control, said plurality of genes or their encoded proteins comprising genes or their encoded proteins informative for prognosis of the patient class into which said individual is classified; and (c) classifying said individual as having a good prognosis or a poor prognosis on the basis of said levels of expression. In a specific embodiment, said condition is breast cancer, said good prognosis is the non-occurrence of metastases within five years of initial diagnosis, and said poor prognosis is the occurrence of metastases within five years of initial diagnosis. In an more specific embodiment, said classifying said individual with a condition as having a good prognosis or a poor prognosis is carried out by comparing the patient's expression profile of said plurality of genes or their encoded proteins to a good and/or poor prognosis template profile of expression levels of said plurality of genes or their encoded proteins, and classifying said individual as having a good prognosis or poor prognosis if said patient expression profile has a high similarity to a good prognosis template or a poor prognosis template, respectively. In a more specific embodiment of the method, said plurality of patient subsets comprises $ER^-$, BRCA1 individuals; $ER^-$, sporadic individuals; ER+, ER/AGE high individuals; ER+, ER/AGE low, LN+ individuals; and ER+, ER/AGE low, $LN^-$ individuals. In another embodiment, said good prognosis template comprises the average level of expression of each of said plurality of genes informative for prognosis in tumor samples from individuals classified into said subset who have a good prognosis or good outcome, while said poor prognosis template comprises the average level of expression of each of said plurality of genes informative for prognosis in tumor samples from individuals classified into said subset who have a poor prognosis or poor outcome. In another specific embodiment, said good or poor prognosis template is a set of mathematical values representing the average level of expression of genes informative for prognosis in tumor samples of individuals classifiable into said subset who have a good prognosis, or who have a poor prognosis, respectively.

It is evident that the different patient subsets described herein reflect different molecular mechanisms of the initiation of tumor formation and metastasis. Thus, the genesets listed in tables 1-5 are also useful for diagnosing a person as having a particular type of breast cancer in the first instance. Thus, the invention also provides a method of diagnosing an individual as having a particular subtype of breast cancer, comprising determining an expression profile of a plurality of the genes for which markers are listed in Tables 1-5 in a sample from said individual; and comparing said expression profile to a template profile, where said template is representative of the expression of said plurality of genes in a breast cancer sample of said subtype of cancer, and on the basis of said comparison, diagnosing the individual as having said subtype of breast cancer. In a specific embodiment, said subtype of cancer is selected from the group consisting of $ER^-$, BRCA1 type; $ER^-$, sporadic type; ER+, ER/AGE high type; ER+, ER/AGE low, LN+ type; and ER/AGE low, $LN^-$ type. In another specific embodiment, said template comprises the average levels of expression of a plurality of the genes for which markers are listed in Table 1, Table 2, Table 3, Table 4 or Table 5. In another specific example, said comparing comprises determining the similarity of the expression profile of the genes for which markers are listed in each of Tables 1-5 in said sample taken from said individual to a template profile comprising levels of expression of the same genes for each of Tables 1-5, and determining whether the pattern of expression of said genes in said sample is most similar to the pattern of expression of the genes for which markers are listed in Table 1, Table 2, Table 3, Table 4 or Table 5.

In another embodiment, the invention provides a method of classifying an individual as having a good prognosis or a poor prognosis, comprising: (a) classifying said individual as $ER^-$, BRCA1; $ER^-$, sporadic; ER+, ER/AGE high; ER+, ER/AGE low, LN+; or ER+, ER/AGE low, $LN^-$; (b) determining an expression profile of a first plurality of genes in a cell sample taken from the individual relative to a control, said first plurality of genes comprising at least two of the genes corresponding to the markers Table 1 if said individual is classified as $ER^-$, BRCA1; Table 2 if said individual is classified as $ER^-$, sporadic; Table 3 if said individual is classified as ER+, ER/AGE high; Table 4 if said individual is classified as ER+, ER/AGE low, LN+; or Table 5 if said individual is classified as ER+, ER/AGE low, $LN^-$, wherein said individual is "ER/AGE high" if the ER level of the individual exceeds a predetermined value, and "ER/AGE low" if the ER level of the individual does not exceed said predetermined value. In a specific embodiment of this method, said predetermined value of ER is calculated as $ER=0.1(AGE-42.5)$, wherein AGE is the age of said individual. In another specific embodiment, said individual is $ER^-$, BRCA1, and said plurality of genes comprises at least 1, 2, 3, 4, 5, 10 or all of the genes for which markers are listed in Table 1. In another specific embodiment, said individual is $ER^-$, sporadic, and said plurality of genes comprises at least 1, 2, 3, 4, 5, 10 or all of the genes for which markers are listed in Table 2. In another specific embodiment, said individual is ER+, ER/AGE high, and said plurality of genes comprises at least 1, 2, 3, 4, 5, 10 or all of the genes for which markers are listed in Table 3. In another specific embodiment, said individual is ER+, ER/AGE low, LN+, and said plurality of genes comprises at least 1, 2, 3, 4, 5, 10 or all of the genes for which markers are listed in Table 4. In another specific embodiment, said individual is ER+, ER/AGE low, $LN^-$, and said plurality of genes comprises at least 1, 2, 3, 4, 5, 10 or all of the genes for which markers are listed in Table 5. In another specific embodiment, the method additionally comprises determining in said cell sample the level of expression, relative to a control, of a second plurality of genes for which markers are not found in Tables 1-5, wherein said second plurality of genes is informative for prognosis.

Where information is available regarding the LN status of a breast cancer patient, the patient may be identified as having a "very good prognosis," an "intermediate prognosis," or a poor prognosis, which enables the refinement of treatment. In one embodiment, the invention provides a method of assigning a therapeutic regimen to a breast cancer patient, comprising: (a) classifying said patient as having a "poor prognosis," "intermediate prognosis," or "very good prognosis" on the basis of the levels of expression of at least five genes for which markers are listed in Table 1, Table 2, Table 3, Table 4 or Table 5; and (b) assigning said patient a therapeutic regimen, said therapeutic regimen (i) comprising no adjuvant chemotherapy if the patient is lymph node negative and is classified as having a good prognosis or an intermediate prognosis, or (ii) comprising chemotherapy if said patient has any other combination of lymph node status and expression profile.

In another embodiment, a breast cancer patient is assigned a prognosis by a method comprising (a) determining the breast cancer patient's age, ER status, LN status and tumor type; (b) classifying said patient as $ER^-$, sporadic; $ER^-$, BRCA1; ER+, ER/AGE high; ER+, ER/AGE low, LN+; or ER+, ER/AGE low, $LN^-$; (c) determining an expression profile comprising at least five genes in a cell sample taken from said breast cancer patient wherein markers for said at least five genes are listed in Table 1 if said patient is classified as $ER^-$, sporadic; Table 2 if said patient is classified as $ER^-$, BRCA1; Table 3 if said patient is classified as ER+, ER/AGE high; Table 4 if said patient is classified as ER+, ER/AGE low, LN+; or Table 5 if said patient is classified as ER+, ER/AGE high, $LN^-$; (d) determining the similarity of the expression profile of said at least five genes to a template profile comprising levels of expression of said at least five genes to obtain a patient similarity value; (e) comparing said patient similarity value to selected first and second threshold values of similarity, respectively, wherein said second similarity threshold indicates greater similarity to said template expression profile than does said first similarity threshold; and (f) classifying said breast cancer patient as having a first prognosis if said patient similarity value exceeds said second threshold similarity values, a second prognosis if said patient similarity value exceeds said first threshold similarity value but does not exceed said second threshold similarity value, and a third prognosis if said patient similarity value does not exceed said first threshold similarity value. In a specific embodiment of the method, said first prognosis is a "very good prognosis," said second prognosis is an "intermediate prognosis," and said third prognosis is a "poor prognosis," wherein said breast cancer patient is assigned a therapeutic regimen comprising no adjuvant chemotherapy if the patient is lymph node negative and is classified as having a good prognosis or an intermediate prognosis, or comprising chemotherapy if said patient has any other combination of lymph node status and expression profile.

The invention also provides a method of assigning a therapeutic regimen to a breast cancer patient, comprising: (a) determining the lymph node status for said patient; (b) determining the expression of at least five genes for which markers are listed in Table 5 in a cell sample from said patient, thereby generating an expression profile; (c) classifying said patient as having a "poor prognosis," "intermediate prognosis," or "very good prognosis" on the basis of said expression profile; and (d) assigning said patient a therapeutic regimen, said therapeutic regimen comprising no adjuvant chemotherapy if the patient is lymph node negative and is classified as having a good prognosis or an intermediate prognosis, or comprising chemotherapy if said patient has any other combination of lymph node status and classification. In a specific embodiment of this method, said therapeutic regimen assigned to lymph node negative patients classified as having an "intermediate prognosis" additionally comprises adjuvant hormonal therapy. In another specific embodiment of this method, said classifying step (c) is carried out by a method comprising: (a) rank ordering in descending order a plurality of breast cancer tumor samples that compose a pool of breast cancer tumor samples by the degree of similarity between the expression profile of said at least five genes in each of said tumor samples and the expression profile of said at least five genes across all remaining tumor samples that compose said pool, said degree of similarity being expressed as a similarity value; (b) determining an acceptable number of false negatives in said classifying step, wherein a false negative is a breast cancer patient for whom the expression levels of said at least five genes in said cell sample predicts that said breast cancer patient will have no distant metastases within the first five years after initial diagnosis, but who has had a distant metastasis within the first five years after initial diagnosis; (c) determining a similarity value above which in said rank ordered list said acceptable number of tumor samples or fewer are false negatives; (d) selecting said similarity value determined in step (c) as a first threshold similarity value; (e) selecting a second similarity value, greater than said first similarity value, as a second threshold similarity value; and (f) determining the similarity between the expression profile of said at least five genes in a breast cancer tumor sample from the breast cancer patient and the expression profile of said respective at least five genes in said pool, to obtain a patient similarity value, wherein if said patient similarity value equals or exceeds said second threshold similarity value, said patient is classified as having a "very good prognosis"; if said patient similarity value equals or exceeds said first threshold similarity value, but is less than said second threshold similarity value, said patient is classified as having an "intermediate prognosis"; and if said patient similarity value is less than said first threshold similarity value, said patient is classified as having a "poor prognosis." Another specific embodiment of this method comprises determining the estrogen receptor (ER) status of said patient, wherein if said patient is ER positive and lymph node negative, said therapeutic regimen assigned to said patient additionally comprises adjuvant hormonal therapy.

A patient in any patient subset or clinical class, e.g., any one of the classes described above, can be classified as having a particular prognosis level, e.g., a good prognosis or a poor prognosis, based on the similarity of the patient's cellular constituent profile to an appropriate template profile for the prognosis level of patients in the clinical class. In one embodiment, a cellular constituent profile corresponding to a certain prognosis level, e.g., a profile comprising measurements of the plurality of cellular constituents representative of levels of the cellular constituents in a plurality of patients having the prognosis level is used as a template for the prognosis level. For example, a good prognosis template profile comprising measurements of the plurality of cellular constituents representative of levels of the cellular constituents in a plurality of good outcome patients or a poor prognosis template profile comprising measurements of the plurality of cellular constituents representative of levels of the cellular constituents in a plurality of poor outcome patients, can be used for determining whether a patient have good or poor prognosis. Here, a good outcome patient is a patient who has non-reoccurrence of metastases within a period of time after initial diagnosis, e.g., a period of 1, 2, 3, 4, 5 or 10 years. In contrast, a poor outcome patient is a patient who has reoccurrence of metastases within a period of time after initial diagnosis, e.g., a period of 1, 2, 3, 4, 5 or 10 years. In a preferred embodiment, both periods are 10 years. Tables 1-5 show exemplary template profiles for the respective patient classes. For example, the expression profile of a patient with a combination of ER+, ER/AGE low, LN+can be compared with the good prognosis template of Table 4 to determine if the patient has good prognosis or poor prognosis.

The degree of similarity of the patient's cellular constituent profile to a template of a particular prognosis can be used to indicate whether the patient has the particular prognosis. For example, a high degree of similarity indicates that the patient has the particular prognosis, whereas a low degree of similarity indicates that the patient does not have the particular prognosis. In a preferred embodiment, a patient is classified as having a good prognosis profile if the patient's cellular constituent profile has a high similarity to a good prognosis template and/or has a low similarity to a poor prognosis template. In another embodiment, a patient is classified as having a poor prognosis profile if the patient's cellular constituent profile has a low similarity to a good prognosis template and/or has a high similarity to a poor prognosis template. In embodiments for predicting the responsiveness of a breast cancer patient under the age of 55, the patients in the good and poor outcome patient populations used to generate the templates are preferably also under the age of 55 at the time of diagnosis of breast cancer.

The degree of similarity between a patient's cellular constituent profile and a template profile can be determined using any method known in the art. In one embodiment, the similarity is represented by a correlation coefficient between the patient's profile and the template. In one embodiment, a correlation coefficient above a correlation threshold indicates high similarity, whereas a correlation coefficient below the threshold indicates low similarity. In preferred embodiments, the correlation threshold is set as 0.3, 0.4, 0.5 or 0.6. In another embodiment, similarity between a patient's profile and a template is represented by a distance between the patient's profile and the template. In one embodiment, a distance below a given value indicates high similarity, whereas a distance equal to or greater than the given value indicates low similarity.

As an illustration, in one embodiment, a template for a good prognosis is defined as $\vec{z}_1$ (e.g., a profile consisting of the xdev's listed in the good prognosis column of one of Tables 1-5) and/or a template for poor prognosis is defined as $\vec{z}_2$ (e.g., a profile consisting of the xdev's listed in the poor prognosis column of one of Tables 1-5). Either one or both of the two classifier parameters ($P_1$ and $P_2$) can then be used to measure degrees of similarities between a patient's profile and the respective templates: $P_1$ measures the similarity between the patient's profile $\vec{y}$ and the good prognosis template $\vec{z}_1$, and $P_2$ measures the similarity between $\vec{y}$ and the poor prognosis template $\vec{z}_2$. In embodiments which employ correlation coefficients, the correlation coefficient $P_i$ can be calculated as:

$$P_i=(\vec{z}_i\cdot\vec{y})/(\|\vec{z}_i\|\cdot\|\vec{y}\|) \quad (4)$$

where i=1 and 2.

Thus, in one embodiment, $\vec{y}$ is classified as a good prognosis profile if $P_1$ is greater than a selected correlation threshold or if $P_2$ is equal to or less than a selected correlation threshold. In another embodiment, $\vec{y}$ is classified as a poor prognosis profile if $P_1$ is less than a selected correlation threshold or if $P_2$ is above a selected correlation threshold. In still another embodiment, $\vec{y}$ is classified as a good prognosis profile if $P_1$ is greater than a first selected correlation threshold and $\vec{y}$ is classified as a poor prognosis profile if $P_2$ is greater than a second selected correlation threshold.

In a preferred embodiment, the cellular constituent profile is an expression profile comprising measurements of a plurality of transcripts (e.g., measured as mRNAs or cDNAs) in a sample derived from a patient, e.g., the plurality of transcripts corresponding to the markers in all or a portion of one of Tables 1-5. In this embodiment, the good prognosis template can be a good prognosis expression template comprising measurements of the plurality of transcripts representative of expression levels of the transcripts in a plurality of good prognosis patients, and the poor prognosis template can be a poor prognosis expression template comprising measurements of the plurality of transcripts representative of expression levels of the transcripts in a plurality of poor prognosis patients. In a preferred embodiment, measurement of each transcript in the good or poor prognosis expression template is an average of expression levels of the transcript in the plurality of good or poor prognosis patients, respectively.

In another embodiment, the expression profile is a differential expression profile comprising differential measurements of the plurality of transcripts in a sample derived from the patient versus measurements of the plurality of transcripts in a control sample. The differential measurements can be xdev, log(ratio), error-weighted log(ratio), or a mean subtracted log(intensity) (see, e.g., Stoughton et al., PCT publication WO 00/39339, published on Jul. 6, 2000; U.S. patent application Ser. No. 10/848,755, filed May 18, 2004, by Mao et al., each of which is incorporated herein by reference in its entirety).

5.4.3 Improving Sensitivity to Expression Level Differences

In using the markers disclosed herein, and, indeed, using any sets of markers, e.g., to compare profiles or to differentiate an individual having one phenotype from another individual having a second phenotype, one can compare the profile comprising absolute expression levels of the markers in a sample to a template; for example, a template comprising the average levels of expression of the markers in a plurality of individuals. To increase the sensitivity of the comparison, however, the expression level values are preferably transformed in a number of ways. Also, to differentiate an individual having one phenotype from another individual having a second phenotype using any sets of markers, one can compare the absolute expression of each of the markers in a sample to a control; for example, the control can be the average level of expression of each of the markers, respectively, in a pool of individuals.

For example, the expression level of each of the markers can be normalized by the average expression level of all markers the expression level of which is determined, or by the average expression level of a set of control genes. Thus, in one embodiment, the markers are represented by probes on a microarray, and the expression level of each of the markers is normalized by the mean or median expression level across all of the genes represented on the microarray, including any non-marker genes. In a specific embodiment, the normalization is carried out by dividing the median or mean level of expression of all of the genes on the microarray. In another embodiment, the expression levels of the markers is normalized by the mean or median level of expression of a set of control markers. In a specific embodiment, the control markers comprise a set of housekeeping genes. In another specific embodiment, the normalization is accomplished by dividing by the median or mean expression level of the control genes.

The sensitivity of a marker-based assay will also be increased if the expression levels of individual markers are compared to the expression of the same markers in a pool of samples. Preferably, the comparison is to the mean or median expression level of each the marker genes in the pool of samples. Such a comparison may be accomplished, for example, by dividing by the mean or median expression level of the pool for each of the markers from the expression level each of the markers in the sample. This has the effect of accentuating the relative differences in expression between markers in the sample and markers in the pool as a whole, making comparisons more sensitive and more likely to produce meaningful results that the use of absolute expression levels alone. The expression level data may be transformed in any convenient way; preferably, the expression level data for all is log transformed before means or medians are taken.

In performing comparisons to a pool, two approaches may be used. First, the expression levels of the markers in the sample may be compared to the expression level of those markers in the pool, where nucleic acid derived from the sample and nucleic acid derived from the pool are hybridized during the course of a single experiment. Such an approach requires that new pool nucleic acid be generated for each comparison or limited numbers of comparisons, and is therefore limited by the amount of nucleic acid available. Alternatively, and preferably, the expression levels in a pool, whether normalized and/or transformed or not, are stored on a computer, or on computer-readable media, to be used in comparisons to the individual expression level data from the sample (i.e., single-channel data).

The current invention also provides the following method of classifying a first cell or organism as having one of at least two different phenotypes, where the different phenotypes comprise a first phenotype and a second phenotype. The level of expression of each of a plurality of markers in a first sample from the first cell or organism is compared to the level of expression of each of said markers, respectively, in a pooled sample from a plurality of cells or organisms, the plurality of cells or organisms comprising different cells or organisms exhibiting said at least two different phenotypes, respectively, to produce a first compared value. The first compared value is then compared to a second compared value, wherein said second compared value is the product of a method comprising comparing the level of expression of each of said markers in a sample from a cell or organism characterized as having said first phenotype to the level of expression of each of said markers, respectively, in the pooled sample. The first compared value is then compared to a third compared value, wherein said third compared value is the product of a method comprising comparing the level of expression of each of the markers in a sample from a cell or organism characterized as having the second phenotype to the level of expression of each of the markers, respectively, in the pooled sample. In specific embodiments, the marker can be a gene, a protein encoded by the gene, etc. Optionally, the first compared value can be compared to additional compared values, respectively, where each additional compared value is the product of a method comprising comparing the level of expression of each of said markers in a sample from a cell or organism characterized as having a phenotype different from said first and second phenotypes but included among the at least two different phenotypes, to the level of expression of each of said genes, respectively, in said pooled sample. Finally, a determination is made as to which of said second, third, and, if present, one or more additional compared values, said first compared value is most similar, wherein the first cell or organism is determined to have the phenotype of the cell or organism used to produce said compared value most similar to said first compared value.

The sensitivity of a marker-based assay will also be increased if the expression levels of individual markers are compared to the expression of the same markers in a control sample, e.g., a sample comprises a pool of samples, to generate a differential expression profile. Such a comparison may be accomplished, for example, by determining a ratio between expression level of each marker in the sample and the expression level of the corresponding marker in the control sample. This has the effect of accentuating the relative differences in expression between markers in the sample and markers in the control as a whole, making subsequent comparisons to a template more sensitive and more likely to produce meaningful results than the use of absolute expression levels alone. The comparison may be performed in any convenient way, e.g., by taking difference, ratio, or log(ratio).

In performing comparisons to a control sample, two approaches may be used. First, the expression levels of the markers in the sample may be compared to the expression level of those markers in the control sample, where nucleic acid derived from the sample and nucleic acid derived from the control are hybridized during the course of a single experiment. Such an approach requires that new control sample of nucleic acid be generated for each comparison or limited numbers of comparisons, and is therefore limited by the amount of nucleic acid available. Alternatively, the expression levels in a control sample, whether normalized and/or transformed or not, are stored on a computer, or on computer-readable media, to be used in comparisons to the individual expression level data from the sample (i.e., single-channel data).

The methods of the invention preferably use a control or reference sample, which can be any suitable sample against which changes in cellular constituents can be determined. In one embodiment, the control or reference sample is generated by pooling together the plurality of cellular constituents, e.g., a plurality of transcripts or cDNAs, or a plurality of protein species, from a plurality of breast cancer patients. Alternatively, the control or reference sample can be generated by pooling together purified or synthesized cellular constituents, e.g., a plurality of purified or synthesized transcripts or cDNAs, a plurality of purified or synthesized protein species. In one embodiment, synthetic RNAs for each transcripts or cDNAs are pooled to form the control or reference sample. Preferably, the abundances of synthetic RNAs are approximately the abundances of the corresponding transcripts in a real tumor pool. The differential expression of marker genes for each individual patient sample is measured against this control sample. In one embodiment, 60-mer oligonucleotides corresponding to the probe sequences on a microarray used to assay the expression levels of the diagnostic/prognostic transcripts are synthesized and cloned into PBLUESCRIPT® SK− vector (Stratagene, La Jolla, Calif.), adjacent to the T7 promotor sequence. Individual clones are isolated, and the sequences of their inserts are verified by DNA sequencing. To generate synthetic RNAs, clones are linearized with EcoRI and a T7 in vitro transcription (IVT) reaction is performed by MEGASCRIPT® kit (Ambion, Austin, Tex.), followed by DNase treatment of the product. Synthetic RNAs are purified on RNEASY® columns (Qiagen, Valencia, Calif.). These synthetic RNAs are transcribed, amplified, labeled, and mixed together to make the reference pool. The abundance of those synthetic RNAs are chosen to approximate the abundances of the transcripts of the corresponding marker genes in the real tumor pool.

The current invention provides the following method of classifying a first cell or organism as having one of at least two different phenotypes, where the different phenotypes comprise a first phenotype and a second phenotype. The level of expression of each of a plurality of markers in a first sample from the first cell or organism is compared to the level of expression of each of said markers, respectively, in a pooled sample from a plurality of cells or organisms, the plurality of cells or organisms comprising different cells or organisms exhibiting said at least two different phenotypes, respectively, to produce a first compared value so that a first differential profile comprising a plurality of first compared values for said plurality of markers is generated. The first differential profile is then compared to a second differential profile comprising a plurality of second compared values, wherein each said second compared value is the product of a method comprising comparing the level of expression of each of said markers in a sample from a cell or organism characterized as having said first phenotype to the level of expression of each of said markers, respectively, in the pooled sample. The first differential profile is then compared to a third differential profile comprising a plurality of third compared values, wherein each said third compared value is the product of a method comprising comparing the level of expression of each of the markers in a sample from a cell or organism characterized as having the second phenotype to the level of expression of each of the markers, respectively, in the pooled sample. In specific embodiments, each marker can be a gene, a protein encoded by the gene, etc. Optionally, the first differential profile can be compared to additional expression profiles each of which comprising additional compared values, respectively, where each additional compared value is the product of a method comprising comparing the level of expression of each of said markers in a sample from a cell or organism characterized as having a phenotype different from said first and second phenotypes but included among the at least two different phenotypes, to the level of expression of each of said genes, respectively, in said pooled sample. Finally, a determination is made as to which of said second, third, and, if present, one or more additional differential profiles, said first differential profile is most similar, wherein the first cell or organism is determined to have the phenotype of the cell or organism used to produce said differential profile most similar to said first differential profile.

In a specific embodiment of this method, the compared values are each ratios of the levels of expression of each of said genes. In another specific embodiment, each of the levels of expression of each of the genes in the pooled sample are normalized prior to any of the comparing steps. In a more specific embodiment, the normalization of the levels of expression is carried out by dividing by the median or mean level of the expression of each of the genes or dividing by the mean or median level of expression of one or more housekeeping genes in the pooled sample from said cell or organism. In another specific embodiment, the normalized levels of expression are subjected to a log transform, and the comparing steps comprise subtracting the log transform from the log of the levels of expression of each of the genes in the sample. In another specific embodiment, the two or more different phenotypes are different stages of a disease or disorder. In still another specific embodiment, the two or more different phenotypes are different prognoses of a disease or disorder. In yet another specific embodiment, the levels of expression of each of the genes, respectively, in the pooled sample or said levels of expression of each of said genes in a sample from the cell or organism characterized as having the first phenotype, second phenotype, or said phenotype different from said first and second phenotypes, respectively, are stored on a computer or on a computer-readable medium.

In another specific embodiment, the two phenotypes are good prognosis and poor prognosis. In a more specific embodiment, the two phenotypes are good prognosis and poor prognosis for an individual that is identified as having $ER^-$, BRCA1 status, $ER^-$, sporadic status, ER+, ER/AGE high status, ER+, ER/AGE low, LN+ status, or ER+, ER/AGE low, LN+ status.

In another specific embodiment, the comparison is made between the expression profile of the genes in the sample and the expression profile of the same genes in a pool representing only one of two or more phenotypes. In the context of prognosis-correlated genes, for example, one can compare the expression levels of prognosis-related genes in a sample to the average levels of the expression of the same genes in a plurality of "good prognosis" samples (as opposed to a plurality of samples that include samples from patients having poor prognoses and good prognoses). Thus, in this method, a sample is classified as having a good prognosis if the expression profile of prognosis-correlated genes exceeds a chosen coefficient of correlation to the average "good prognosis" expression profile (e.g., the profile comprising average levels of expression of prognosis-correlated genes in samples from a plurality of patients having a "good prognosis"). Patients whose expression profiles correlate more poorly with the "good prognosis" expression profile (e.g., whose correlation coefficient fails to exceed the chosen coefficient) are classified as having a poor prognosis.

Where individuals are classified on the basis of phenotypic, genotypic, or clinical characteristics into patient subsets, the pool of samples may be a pool of samples for the phenotype that includes samples representing each of the patient subsets. Alternatively, the pool of samples may be a pool of samples for the phenotype representing only the specific patient subset. For example, where an individual is classified as ER+, sporadic, the pool of samples to which the individual's sample is compared may be a pool of samples from ER+, sporadic individuals having a good prognosis only, or may be a pool of samples of individuals having a good prognosis, without regard to ER status or mutation type.

The method can be applied to a plurality of patient subsets. For example, in a specific embodiment, the phenotype is good prognosis, and the individual is classified into one of the following patient subsets: $ER^-$, BRCA1 status, $ER^-$, sporadic status, ER+, ER/AGE high status, ER+, ER/AGE low, LN+ status, or ER+, ER/AGE low, LN+ status. A set of markers informative for prognosis for the patient subset into which the individual is classified is then used to determine the likely prognosis for the individual. A sample is classified as coming from an individual having a good prognosis if the expression profile of prognosis-correlated genes for the particular subset into which the individual is classified exceeds a chosen coefficient of correlation to the average "good prognosis" expression profile (e.g., the levels of expression of prognosis-correlated genes in a plurality of samples from patients within the subclass having a "good prognosis"). Patients whose expression levels correlate more poorly with the "good prognosis" expression profile (e.g., whose correlation coefficient fails to exceed the chosen coefficient) are classified as having a poor prognosis.

Of course, single-channel data may also be used without specific comparison to a mathematical sample pool. For example, a sample may be classified as having a first or a second phenotype, wherein the first and second phenotypes are related, by calculating the similarity between the expression profile of at least 5 markers in the sample, where the markers are correlated with the first or second phenotype, to a first phenotype template and a second phenotype template each comprising the expression levels of the same markers, by (a) labeling nucleic acids derived from a sample with a fluorophore to obtain a pool of fluorophore-labeled nucleic acids; (b) contacting said fluorophore-labeled nucleic acid with a microarray under conditions such that hybridization can occur, detecting at each of a plurality of discrete loci on the microarray a fluorescent emission signal from said fluorophore-labeled nucleic acid that is bound to said microarray under said conditions; and (c) determining the similarity of marker gene expression in the individual sample to the first and second templates, wherein if said expression is more similar to the first template, the sample is classified as having the first phenotype, and if said expression is more similar to the second template, the sample is classified as having the second phenotype.

In a specific embodiment of the above method, the first phenotype is a good prognosis of breast cancer, the sample is a sample from an individual that has been classified into a patient subset, and the first and second templates are templates for the phenotype for the particular patient subset. In a more specific embodiment, for example, the first phenotype is a good prognosis, the second phenotype is a poor prognosis, the patient is classified into an $ER^-$, sporadic patient subset, an $ER^-$, BRCA1 subset, an ER+, ER/AGE high subset, an ER+, ER/AGE low, LN+ subset, or an ER+, ER/AGE low, LN+ subset, and said first and second templates are templates derived from the expression of the marker genes in individuals having a good prognosis and a poor prognosis, respectively, wherein said individuals are all of the patient subset into which said patient is classified.

5.5 Determination of Marker Gene Expression Levels 5.5.1 Methods

The expression levels of the marker genes in a sample may be determined by any means known in the art. The expression level may be determined by isolating and determining the level (i.e., amount) of nucleic acid transcribed from each marker gene. Alternatively, or additionally, the level of specific proteins encoded by a marker gene may be determined.

The level of expression of specific marker genes can be accomplished by determining the amount of mRNA, or polynucleotides derived therefrom, present in a sample. Any method for determining RNA levels can be used. For example, RNA is isolated from a sample and separated on an agarose gel. The separated RNA is then transferred to a solid support, such as a filter. Nucleic acid probes representing one or more markers are then hybridized to the filter by northern hybridization, and the amount of marker-derived RNA is determined. Such determination can be visual, or machine-aided, for example, by use of a densitometer. Another method of determining RNA levels is by use of a dot-blot or a slot-blot. In this method, RNA, or nucleic acid derived therefrom, from a sample is labeled. The RNA or nucleic acid derived therefrom is then hybridized to a filter containing oligonucleotides derived from one or more marker genes, wherein the oligonucleotides are placed upon the filter at discrete, easily-identifiable locations. Hybridization, or lack thereof, of the labeled RNA to the filter-bound oligonucleotides is determined visually or by densitometer. Polynucleotides can be labeled using a radiolabel or a fluorescent (i.e., visible) label.

These examples are not intended to be limiting; other methods of determining RNA abundance are known in the art.

The level of expression of particular marker genes may also be assessed by determining the level of the specific protein expressed from the marker genes. This can be accomplished, for example, by separation of proteins from a sample on a polyacrylamide gel, followed by identification of specific marker-derived proteins using antibodies in a western blot. Alternatively, proteins can be separated by two-dimensional gel electrophoresis systems. Two-dimensional gel electrophoresis is well-known in the art and typically involves isoelectric focusing along a first dimension followed by SDS-PAGE electrophoresis along a second dimension. See, e.g., Hames et al, 1990, Gel Electrophoresis of Proteins: A Practical Approach, IRL Press, New York; Shevchenko et al., *Proc. Nat'l Acad. Sci. USA* 93:1440-1445 (1996); Sagliocco et al., *Yeast* 12:1519-1533 (1996); Lander, *Science* 274:536-539 (1996). The resulting electropherograms can be analyzed by numerous techniques, including mass spectrometric techniques, western blotting and immunoblot analysis using polyclonal and monoclonal antibodies.

Alternatively, marker-derived protein levels can be determined by constructing an antibody microarray in which binding sites comprise immobilized, preferably monoclonal, antibodies specific to a plurality of protein species encoded by the cell genome. Preferably, antibodies are present for a substantial fraction of the marker-derived proteins of interest. Methods for making monoclonal antibodies are well known (see, e.g., Harlow and Lane, 1988, Antibodies: A Laboratory Manual, Cold Spring Harbor, N.Y., which is incorporated in its entirety for all purposes). In one embodiment, monoclonal antibodies are raised against synthetic peptide fragments designed based on genomic sequence of the cell. With such an antibody array, proteins from the cell are contacted to the array, and their binding is assayed with assays known in the art. Generally, the expression, and the level of expression, of proteins of diagnostic or prognostic interest can be detected through immunohistochemical staining of tissue slices or sections.

Finally, expression of marker genes in a number of tissue specimens may be characterized using a "tissue array" (Kononen et al., *Nat. Med* 4(7):844-7 (1998)). In a tissue array, multiple tissue samples are assessed on the same microarray. The arrays allow in situ detection of RNA and protein levels; consecutive sections allow the analysis of multiple samples simultaneously.

5.5.2 Microarrays

In preferred embodiments, polynucleotide microarrays are used to measure expression so that the expression status of each of the markers above is assessed simultaneously. Generally, microarrays according to the invention comprise a plurality of markers informative for prognosis, or outcome determination, for a particular disease or condition, and, in particular, for individuals having specific combinations of genotypic or phenotypic characteristics of the disease or condition (i.e., that are prognosis-informative for a particular patient subset).

The microarrays of the invention preferably comprise at least 2, 3, 4, 5, 7, 10, 15, 20, 25, 30, 35, 40, 45, 50, 75, 100, 150, 200 or more of markers, or all of the markers, or any combination of markers, identified as prognosis-informative within a patient subset. The actual number of informative markers the microarray comprises will vary depending upon the particular condition of interest, the number of markers identified, and, optionally, the number of informative markers found to result in the least Type I error, Type II error, or Type I and Type II error in determination of prognosis. As used herein, "Type I error" means a false positive and "Type II error" means a false negative; in the example of prognosis of beast cancer, Type I error is the mis-characterization of an individual with a good prognosis as having a poor prognosis, and Type II error is the mis-characterization of an individual with a poor prognosis as having a good prognosis.

In specific embodiments, the invention provides polynucleotide arrays in which the prognosis markers identified for a particular patient subset comprise at least 50%, 60%, 70%, 80%, 85%, 90%, 95% or 98% of the probes on said array. In another specific embodiment, the microarray comprises a plurality of probes, wherein said plurality of probes comprise probes complementary and hybridizable to at least 75% of the prognosis-informative markers identified for a particular patient subset. Microarrays of the invention, of course, may comprise probes complementary and hybridizable to prognosis-informative markers for a plurality of the patient subsets, or for each patient subset, identified for a particular condition. In another embodiment, therefore, the microarray of the invention comprises a plurality of probes complementary and hybridizable to at least 75% of the prognosis-informative markers identified for each patient subset identified for the condition of interest, and wherein said probes, in total, are at least 50% of the probes on said microarray.

In yet another specific embodiment, microarrays that are used in the methods disclosed herein optionally comprise markers additional to at least some of the markers identified by the methods disclosed elsewhere herein. For example, in a specific embodiment, the microarray is a screening or scanning array as described in Altschuler et al., International Publication WO 02/18646, published Mar. 7, 2002 and Scherer et al., International Publication WO 02/16650, published Feb. 28, 2002. The scanning and screening arrays comprise regularly-spaced, positionally-addressable probes derived from genomic nucleic acid sequence, both expressed and unexpressed. Such arrays may comprise probes corresponding to a subset of, or all of, the markers identified for the patient subset(s) for the condition of interest, and can be used to monitor marker expression in the same way as a microarray containing only prognosis-informative markers otherwise identified.

In yet another specific embodiment, the microarray is a commercially-available cDNA microarray that comprises at least five markers identified by the methods described herein. Preferably, a commercially-available cDNA microarray comprises all of the markers identified by the methods described herein as being informative for a patient subset for a particular condition. However, such a microarray may comprise at least 5, 10, 15 or 25 of such markers, up to the maximum number of markers identified.

In an embodiment specific to breast cancer, the invention provides for oligonucleotide or cDNA arrays comprising probes hybridizable to the genes corresponding to each of the marker sets described above (i.e., markers informative for $ER^-$, sporadic individuals, markers informative for $ER^-$, BRCA1 individuals, markers informative for ER+, ER/AGE high individuals, markers informative for ER+, ER/AGE low, LN+ individuals, and markers informative for ER+, ER/AGE low, $LN^-$ individuals, as shown in Tables 1-5). Any of the microarrays described herein may be provided in a sealed container in a kit.

The invention provides microarrays containing probes useful for the prognosis of any breast cancer patient, or for breast cancer patients classified into one of a plurality of patient subsets. In particular, the invention provides polynucleotide arrays comprising probes to a subset or subsets of at least 5, 10, 15, 20, 25 or more of the genetic markers, or up to the full set of markers, in any of Tables 1-5, which distinguish between patients with good and poor prognosis. In certain embodiments, therefore, the invention provides microarrays comprising probes for a plurality of the genes for which markers are listed in Tables 1, 2, 3, 4 or 5. In a specific embodiment, the microarray of the invention comprises 1, 2, 3, 4, 5 or 10 of the markers in Table 1, at least five of the markers in Table 2; 1, 2, 3, 4, 5 or 10 of the markers in Table 3; 1, 2, 3, 4, 5 or 10 of the markers in Table 4; or 1, 2, 3, 4, 5 or 10 of the markers in Table 1. In other embodiments, the microarray comprises probes for 1, 2, 3, 4, 5, or 10 of the markers shown in any two, three or four of Tables 1-5, or all of Tables 1-5. In other embodiments, the microarray of the invention contains each of the markers in Table 1, Table 2, Table 3, Table 4, or Table 5. In another embodiment, the microarray contains all of the markers shown in Tables 1-5. In specific embodiments, the array comprises probes derived only from the markers listed in Table 1, Table 2, Table 3, Table 4, or Table 5; probes derived from any two of Tables 1-5; any three of Tables 1-5; any four of Tables 1-5; or all of Tables 1-5.

In other embodiments, the array comprises a plurality of probes derived from markers listed in any of Tables 1-5 in combination with a plurality of other probes, derived from markers not listed in any of Tables 1-5, that are identified as informative for the prognosis of breast cancer.

In specific embodiments, the invention provides polynucleotide arrays in which the breast cancer prognosis markers described herein in Tables 1, 2, 3, 4 and/or 5 comprise at least 50%, 60%, 70%, 80%, 85%, 90%, 95% or 98% of the probes on said array. In another specific embodiment, the microarray comprises a plurality of probes, wherein said plurality of probes comprise probes complementary and hybridizable to at least 75% of the genes for which markers are listed in Table 1; probes complementary and hybridizable to at least 75% of the genes for which markers are listed in Table 2; probes complementary and hybridizable to at least 75% of the genes for which markers are listed in Table 3; probes complementary and hybridizable to at least 75% of the genes for which markers are listed in Table 4; and probes complementary and hybridizable to at least 75% of the genes for which markers are listed in Table 5, wherein said probes, in total, are at least 50% of the probes on said microarray.

In yet another specific embodiment, microarrays that are used in the methods disclosed herein optionally comprise markers additional to at least some of the markers listed in Tables 1-5. For example, in a specific embodiment, the microarray is a screening or scanning array as described in Altschuler et al., International Publication WO 02/18646, published Mar. 7, 2002 and Scherer et al., International Publication WO 02/16650, published Feb. 28, 2002. The scanning and screening arrays comprise regularly-spaced, positionally-addressable probes derived from genomic nucleic acid sequence, both expressed and unexpressed. Such arrays may comprise probes corresponding to a subset of, or all of, the markers listed in Tables 1-5, or a subset thereof as described above, and can be used to monitor marker expression in the same way as a microarray containing only markers listed in Tables 1-5.

In yet another specific embodiment, the microarray is a commercially-available cDNA microarray that comprises at least five of the markers listed in Tables 1-5. Preferably, a commercially-available cDNA microarray comprises all of the markers listed in Tables 1-5. However, such a microarray may comprise at least 5, 10, 15 or 25 of the markers in any of Tables 1-5, up to the maximum number of markers in a Table, and may comprise all of the markers in any one of Tables 1-5, and a subset of another of Tables 1-5, or subsets of each as described above. In a specific embodiment of the microarrays used in the methods disclosed herein, the markers that are all or a portion of Tables 1-5 make up at least 50%, 60%, 70%, 80%, 90%, 95% or 98% of the probes on the microarray.

General methods pertaining to the construction of microarrays comprising the marker sets and/or subsets above are described in the following sections.

5.5.2.1 Construction of Microarrays

Microarrays are prepared by selecting probes which comprise a polynucleotide sequence, and then immobilizing such probes to a solid support or surface. For example, the probes may comprise DNA sequences, RNA sequences, or copolymer sequences of DNA and RNA. The polynucleotide sequences of the probes may also comprise DNA and/or RNA analogues, or combinations thereof. For example, the polynucleotide sequences of the probes may be full or partial fragments of genomic DNA. The polynucleotide sequences of the probes may also be synthesized nucleotide sequences, such as synthetic oligonucleotide sequences. The probe sequences can be synthesized either enzymatically in vivo, enzymatically in vitro (e.g., by PCR), or non-enzymatically in vitro.

The probe or probes used in the methods of the invention are preferably immobilized to a solid support which may be either porous or non-porous. For example, the probes of the invention may be polynucleotide sequences which are attached to a nitrocellulose or nylon membrane or filter covalently at either the 3' or the 5' end of the polynucleotide. Such hybridization probes are well known in the art (see, e.g., Sambrook et al., Molecular Cloning—A Laboratory Manual (2nd Ed.), Vols. 1-3, Cold Spring Harbor Laboratory, Cold Spring Harbor, N.Y. (1989). Alternatively, the solid support or surface may be a glass or plastic surface. In a particularly preferred embodiment, hybridization levels are measured to microarrays of probes consisting of a solid phase on the surface of which are immobilized a population of polynucleotides, such as a population of DNA or DNA mimics, or, alternatively, a population of RNA or RNA mimics. The solid phase may be a nonporous or, optionally, a porous material such as a gel.

In preferred embodiments, a microarray comprises a support or surface with an ordered array of binding (e.g., hybridization) sites or "probes" each representing one of the markers described herein. Preferably the microarrays are addressable arrays, and more preferably positionally addressable arrays. More specifically, each probe of the array is preferably located at a known, predetermined position on the solid support such that the identity (i.e., the sequence) of each probe can be determined from its position in the array (i.e., on the support or surface). In preferred embodiments, each probe is covalently attached to the solid support at a single site.

Microarrays can be made in a number of ways, of which several are described below. However produced, microarrays share certain characteristics. The arrays are reproducible, allowing multiple copies of a given array to be produced and easily compared with each other. Preferably, microarrays are made from materials that are stable under binding (e.g., nucleic acid hybridization) conditions. The microarrays are preferably small, e.g., between 1 $cm^2$ and 25 $cm^2$, between 12 $cm^2$ and 13 $cm^2$, or 3 $cm^2$. However, larger arrays are also contemplated and may be preferable, e.g., for use in screening arrays. Preferably, a given binding site or unique set of binding sites in the microarray will specifically bind (e.g., hybridize) to the product of a single gene in a cell (e.g., to a specific mRNA, or to a specific cDNA derived therefrom). However, in general, other related or similar sequences will cross hybridize to a given binding site.

The microarrays of the present invention include one or more test probes, each of which has a polynucleotide sequence that is complementary to a subsequence of RNA or DNA to be detected. Preferably, the position of each probe on the solid surface is known. Indeed, the microarrays are preferably positionally addressable arrays. Specifically, each probe of the array is preferably located at a known, predetermined position on the solid support such that the identity (i.e., the sequence) of each probe can be determined from its position on the array (i.e., on the support or surface).

According to the invention, the microarray is an array (i.e., a matrix) in which each position represents one of the markers described herein. For example, each position can contain a DNA or DNA analogue based on genomic DNA to which a particular RNA or cDNA transcribed from that genetic marker can specifically hybridize. The DNA or DNA analogue can be, e.g., a synthetic oligomer or a gene fragment. In one embodiment, probes representing each of the markers is present on the array. In a preferred embodiment, the array comprises probes for each of the markers listed in Tables 1-5.

5.5.2.2 Preparing Probes for Microarrays

As noted above, the "probe" to which a particular polynucleotide molecule specifically hybridizes according to the invention contains a complementary genomic polynucleotide sequence. The probes of the microarray preferably consist of nucleotide sequences of no more than 1,000 nucleotides. In some embodiments, the probes of the array consist of nucleotide sequences of 10 to 1,000 nucleotides. In a preferred embodiment, the nucleotide sequences of the probes are in the range of 10-200 nucleotides in length and are genomic sequences of a species of organism, such that a plurality of different probes is present, with sequences complementary and thus capable of hybridizing to the genome of such a species of organism, sequentially tiled across all or a portion of such genome. In other specific embodiments, the probes are in the range of 10-30 nucleotides in length, in the range of 10-40 nucleotides in length, in the range of 20-50 nucleotides in length, in the range of 40-80 nucleotides in length, in the range of 50-150 nucleotides in length, in the range of 80-120 nucleotides in length, and most preferably are 60 nucleotides in length.

The probes may comprise DNA or DNA "mimics" (e.g., derivatives and analogues) corresponding to a portion of an organism's genome. In another embodiment, the probes of the microarray are complementary RNA or RNA mimics. DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone. Exemplary DNA mimics include, e.g., phosphorothioates.

DNA can be obtained, e.g., by polymerase chain reaction (PCR) amplification of genomic DNA or cloned sequences. PCR primers are preferably chosen based on a known sequence of the genome that will result in amplification of specific fragments of genomic DNA. Computer programs that are well known in the art are useful in the design of primers with the required specificity and optimal amplification properties, such as Oligo version 5.0 (National Biosciences). Typically each probe on the microarray will be between 10 bases and 50,000 bases, usually between 300 bases and 1,000 bases in length. PCR methods are well known in the art, and are described, for example, in Innis et al., eds., PCR Protocols: A Guide to Methods and Applications, Academic Press Inc., San Diego, Calif. (1990). It will be apparent to one skilled in the art that controlled robotic systems are useful for isolating and amplifying nucleic acids.

An alternative, preferred means for generating the polynucleotide probes of the microarray is by synthesis of synthetic polynucleotides or oligonucleotides, e.g., using N-phosphonate or phosphoramidite chemistries (Froehler et al., *Nucleic Acid Res.* 14:5399-5407 (1986); McBride et al., *Tetrahedron Lett.* 24:246-248 (1983)). Synthetic sequences are typically between about 10 and about 500 bases in length, more typically between about 20 and about 100 bases, and most preferably between about 40 and about 70 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm et al., *Nature* 363:566-568 (1993); U.S. Pat. No. 5,539,083).

Probes are preferably selected using an algorithm that takes into account binding energies, base composition, sequence complexity, cross-hybridization binding energies, and secondary structure. See Friend et al., International Patent Publication WO 01/05935, published Jan. 25, 2001; Hughes et al., *Nat. Biotech.* 19:342-7 (2001).

A skilled artisan will also appreciate that positive control probes, e.g., probes known to be complementary and hybridizable to sequences in the target polynucleotide molecules, and negative control probes, e.g., probes known to not be complementary and hybridizable to sequences in the target polynucleotide molecules, should be included on the array. In one embodiment, positive controls are synthesized along the perimeter of the array. In another embodiment, positive controls are synthesized in diagonal stripes across the array. In still another embodiment, the reverse complement for each probe is synthesized next to the position of the probe to serve as a negative control. In yet another embodiment, sequences from other species of organism are used as negative controls or as "spike-in" controls.

5.5.2.3 Attaching Probes to the Solid Surface

The probes are attached to a solid support or surface, which may be made, e.g., from glass, plastic (e.g., polypropylene, nylon), polyacrylamide, nitrocellulose, gel, or other porous or nonporous material. A preferred method for attaching the nucleic acids to a surface is by printing on glass plates, as is described generally by Schena et al, *Science* 270:467-470 (1995). This method is especially useful for preparing microarrays of cDNA (See also, DeRisi et al, *Nature Genetics* 14:457-460 (1996); Shalon et al., *Genome Res.* 6:639-645 (1996); and Schena et al., *Proc. Natl. Acad. Sci. U.S.A.* 93:10539-11286 (1995)).

A second preferred method for making microarrays is by making high-density oligonucleotide arrays. Techniques are known for producing arrays containing thousands of oligonucleotides complementary to defined sequences, at defined locations on a surface using photolithographic techniques for synthesis in situ (see, Fodor et al., 1991, *Science* 251:767-773; Pease et al., 1994, *Proc. Natl. Acad. Sci. U.S.A.* 91:5022-5026; Lockhart et al., 1996, *Nature Biotechnology* 14:1675; U.S. Pat. Nos. 5,578,832; 5,556,752; and 5,510,270) or other methods for rapid synthesis and deposition of defined oligonucleotides (Blanchard et al., *Biosensors & Bioelectronics* 11:687-690). When these methods are used, oligonucleotides (e.g., 60-mers) of known sequence are synthesized directly on a surface such as a derivatized glass slide. Usually, the array produced is redundant, with several oligonucleotide molecules per RNA.

Other methods for making microarrays, e.g., by masking (Maskos and Southern, 1992, *Nuc. Acids. Res.* 20:1679-1684), may also be used. In principle, and as noted supra, any type of array, for example, dot blots on a nylon hybridization membrane (see Sambrook et al., MOLECULAR CLONING—A LABORATORY MANUAL (2ND ED.), Vols. 1-3, Cold Spring Harbor Laboratory, Cold Spring Harbor, N.Y. (1989)) could be used. However, as will be recognized by those skilled in the art, very small arrays will frequently be preferred because hybridization volumes will be smaller.

In one embodiment, the arrays of the present invention are prepared by synthesizing polynucleotide probes on a support. In such an embodiment, polynucleotide probes are attached to the support covalently at either the 3' or the 5' end of the polynucleotide.

In a particularly preferred embodiment, microarrays of the invention are manufactured by means of an ink jet printing device for oligonucleotide synthesis, e.g., using the methods and systems described by Blanchard in U.S. Pat. No. 6,028,189; Blanchard et al., 1996, *Biosensors and Bioelectronics* 11:687-690; Blanchard, 1998, in Synthetic DNA Arrays in Genetic Engineering, Vol. 20, J. K. Setlow, Ed., Plenum Press, New York at pages 111-123. Specifically, the oligonucleotide probes in such microarrays are preferably synthesized in arrays, e.g., on a glass slide, by serially depositing individual nucleotide bases in "microdroplets" of a high surface tension solvent such as propylene carbonate. The microdroplets have small volumes (e.g., 100 pL or less, more preferably 50 pL or less) and are separated from each other on the microarray (e.g., by hydrophobic domains) to form circular surface tension wells which define the locations of the array elements (i.e., the different probes). Microarrays manufactured by this ink-jet method are typically of high density, preferably having a density of at least about 2,500 different probes per 1 $cm^2$. The polynucleotide probes are attached to the support covalently at either the 3' or the 5' end of the polynucleotide.

5.5.2.4 Target Polynucleotide Molecules

The polynucleotide molecules which may be analyzed by the present invention (the "target polynucleotide molecules") may be from any clinically relevant source, but are expressed RNA or a nucleic acid derived therefrom (e.g., cDNA or amplified RNA derived from cDNA that incorporates an RNA polymerase promoter), including naturally occurring nucleic acid molecules, as well as synthetic nucleic acid molecules. In one embodiment, the target polynucleotide molecules comprise RNA, including, but by no means limited to, total cellular RNA, poly$(A)^+$ messenger RNA (mRNA) or fraction thereof, cytoplasmic mRNA, or RNA transcribed from cDNA (i.e., cRNA; see, e.g., Linsley & Schelter, U.S. patent application Ser. No. 09/411,074, filed Oct. 4, 1999, or U.S. Pat. Nos. 5,545,522, 5,891,636, or 5,716,785). Methods for preparing total and poly$(A)^+$ RNA are well known in the art, and are described generally, e.g., in Sambrook et al., MOLECULAR CLONING—A LABORATORY MANUAL (2ND ED.), Vols. 1-3, Cold Spring Harbor Laboratory, Cold Spring Harbor, N.Y. (1989). In one embodiment, RNA is extracted from cells of the various types of interest in this invention using guanidinium thiocyanate lysis followed by CsCl centrifugation (Chirgwin et al., 1979, *Biochemistry* 18:5294-5299). In another embodiment, total RNA is extracted using a silica gel-based column, commercially available examples of which include RNEASY® (Qiagen, Valencia, Calif.) and STRATAPREP® (Stratagene, La Jolla, Calif.). In an alternative embodiment, which is preferred for *S. cerevisiae*, RNA is extracted from cells using phenol and chloroform, as described in Ausubel et al., eds., 1989, CURRENT PROTOCOLS IN MOLECULAR BIOLOGY, Vol. III, Green Publishing Associates, Inc., John Wiley & Sons, Inc., New York, at pp. 13.12.1-13.12.5). Poly$(A)^+$ RNA can be selected, e.g., by selection with oligo-dT cellulose or, alternatively, by oligo-dT primed reverse transcription of total cellular RNA. In one embodiment, RNA can be fragmented by methods known in the art, e.g., by incubation with $ZnCl_2$, to generate fragments of RNA. In another embodiment, the polynucleotide molecules analyzed by the invention comprise cDNA, or PCR products of amplified RNA or cDNA.

In one embodiment, total RNA, mRNA, or nucleic acids derived therefrom, is isolated from a sample taken from a person afflicted with breast cancer. Target polynucleotide molecules that are poorly expressed in particular cells may be enriched using normalization techniques (Bonaldo et al., 1996, *Genome Res.* 6:791-806).

As described above, the target polynucleotides are detectably labeled at one or more nucleotides. Any method known in the art may be used to detectably label the target polynucleotides. Preferably, this labeling incorporates the label uniformly along the length of the RNA, and more preferably, the labeling is carried out at a high degree of efficiency. One embodiment for this labeling uses oligo-dT primed reverse transcription to incorporate the label; however, conventional methods of this method are biased toward generating 3' end fragments. Thus, in a preferred embodiment, random primers (e.g., 9-mers) are used in reverse transcription to uniformly incorporate labeled nucleotides over the full length of the target polynucleotides. Alternatively, random primers may be used in conjunction with PCR methods or T7 promoter-based in vitro transcription methods in order to amplify the target polynucleotides.

In a preferred embodiment, the detectable label is a luminescent label. For example, fluorescent labels, bioluminescent labels, chemiluminescent labels, and colorimetric labels may be used in the present invention. In a highly preferred embodiment, the label is a fluorescent label, such as a fluorescein, a phosphor, a rhodamine, or a polymethine dye derivative. Examples of commercially available fluorescent labels include, for example, fluorescent phosphoramidites such as FLUOREPRIME® (Amersham Pharmacia, Piscataway, N.J.), FLUOREDITE™ (Millipore, Bedford, Mass.), FAM™ (ABI, Foster City, Calif.), and CY3™ or CY5™ (Amersham Pharmacia, Piscataway, N.J.). In another embodiment, the detectable label is a radiolabeled nucleotide.

In a further preferred embodiment, target polynucleotide molecules from a patient sample are labeled differentially from target polynucleotide molecules of a standard. The standard can comprise target polynucleotide molecules from normal individuals (i.e., those not afflicted with breast cancer). In a highly preferred embodiment, the standard comprises target polynucleotide molecules pooled from samples from normal individuals or tumor samples from individuals having sporadic-type breast tumors. In another embodiment, the target polynucleotide molecules are derived from the same individual, but are taken at different time points, and thus indicate the efficacy of a treatment by a change in expression of the markers, or lack thereof, during and after the course of treatment (i.e., chemotherapy, radiation therapy or cryotherapy), wherein a change in the expression of the markers from a poor prognosis pattern to a good prognosis pattern indicates that the treatment is efficacious. In this embodiment, different timepoints are differentially labeled.

5.5.2.5 Hybridization to Microarrays

Nucleic acid hybridization and wash conditions are chosen so that the target polynucleotide molecules specifically bind or specifically hybridize to the complementary polynucleotide sequences of the array, preferably to a specific array site, wherein its complementary DNA is located.

Arrays containing double-stranded probe DNA situated thereon are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self complementary sequences.

Optimal hybridization conditions will depend on the length (e.g., oligomer versus polynucleotide greater than 200 bases) and type (e.g., RNA, or DNA) of probe and target nucleic acids. One of skill in the art will appreciate that as the oligonucleotides become shorter, it may become necessary to adjust their length to achieve a relatively uniform melting temperature for satisfactory hybridization results. General parameters for specific (i.e., stringent) hybridization conditions for nucleic acids are described in Sambrook et al., Molecular Cloning—A Laboratory Manual (2nd Ed.), Vols. 1-3, Cold Spring Harbor Laboratory, Cold Spring Harbor, N.Y. (1989), and in Ausubel et al., Current Protocols in Molecular Biology, vol. 2, Current Protocols Publishing, New York (1994). Typical hybridization conditions for the cDNA microarrays of Schena et al. are hybridization in 5×SSC plus 0.2% SDS at 65° C. for four hours, followed by washes at 25° C. in low stringency wash buffer (1×SSC plus 0.2% SDS), followed by 10 minutes at 25° C. in higher stringency wash buffer (0.1×SSC plus 0.2% SDS) (Schena et al, *Proc. Natl. Acad. Sci. U.S.A.* 93:10614 (1993)). Useful hybridization conditions are also provided in, e.g., Tijessen, 1993, Hybridization With Nucleic Acid Probes, Elsevier Science Publishers B. V.; and Iricka, 1992, Nonisotopic DNA Probe Techniques, Academic Press, San Diego, Calif.

Particularly preferred hybridization conditions include hybridization at a temperature at or near the mean melting temperature of the probes (e.g., within 51° C., more preferably within 21° C.) in 1 M NaCl, 50 mM MES buffer (pH 6.5), 0.5% sodium sarcosine and 30% formamide.

5.5.2.6 Signal Detection and Data Analysis

When fluorescently labeled probes are used, the fluorescence emissions at each site of a microarray may be, preferably, detected by scanning confocal laser microscopy. In one embodiment, a separate scan, using the appropriate excitation line, is carried out for each of the two fluorophores used. Alternatively, a laser may be used that allows simultaneous specimen illumination at wavelengths specific to the two fluorophores and emissions from the two fluorophores can be analyzed simultaneously (see Shalon et al. 1996, "A DNA microarray system for analyzing complex DNA samples using two-color fluorescent probe hybridization," *Genome Research* 6:639-645, which is incorporated by reference in its entirety for all purposes). In a preferred embodiment, the arrays are scanned with a laser fluorescent scanner with a computer controlled X-Y stage and a microscope objective. Sequential excitation of the two fluorophores is achieved with a multi-line, mixed gas laser and the emitted light is split by wavelength and detected with two photomultiplier tubes. Fluorescence laser scanning devices are described in Schena et al., *Genome Res.* 6:639-645 (1996), and in other references cited herein. Alternatively, the fiber-optic bundle described by Ferguson et al., *Nature Biotech.* 14:1681-1684 (1996), may be used to monitor mRNA abundance levels at a large number of sites simultaneously.

Signals are recorded and, in a preferred embodiment, analyzed by computer, e.g., using a 12 or 16 bit analog to digital board. In one embodiment the scanned image is despeckled using a graphics program (e.g., HIJAAK® Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the transcript array, a ratio of the emission of the two fluorophores can be calculated. The ratio is independent of the absolute expression level of the cognate gene, but is useful for genes whose expression is significantly modulated in association with the different breast cancer-related condition.

5.6 Therapeutic Regimens Specific to Patient Subsets

The benefit of identifying subsets of individuals that have a common condition, followed by identification of sets of genes informative for those particular subsets of individuals, is that such subdivision and identification tends to more accurately identify the subset of genes responsible for, or most closely associated with, a particular form of the condition. For example, breast cancer is a complex condition brought about by several different molecular mechanisms. ER+ individuals, particularly ER+, ER/AGE high individuals, show an increased level of expression of cell cycle-control genes, and the expression of these genes is highly informative for prognosis in this patient subset (see Examples). In $ER^-$ individuals, however, the expression of these genes is not informative for prognosis.

The set of informative markers, therefore, can be used to assign a particular course of therapy to an individual, e.g., an individual having breast cancer, depending upon the condition subset into which the individual is classified. In one embodiment, therefore, the invention provides a method of assigning a course of therapy to an individual having a condition, said method comprising classifying the individual into one of a plurality of subsets of a condition, wherein a plurality of informative genes has been identified for at least one of said subsets; and assigning a course of therapy known or suspected to be effective for treating the subset of the condition associated with those genes. In a specific embodiment, said condition is breast cancer, said patient subset is ER+, ER/AGE high status, and said course of therapy comprises the administration of one or more compounds known or suspected to be effective at arresting the cell cycle. In a more specific embodiment, said one or more compounds comprises taxol or a vinca alkaloid.

Of course, any course of therapy selected or assigned on the basis of the above phenotypes and gene expression may be supplemented by other treatments or courses of therapy relevant to or known or suspected to be effective in the treatment of the condition. For example, the treatment of breast cancer may additionally comprise surgery, either tissue-preserving or radical, radiation treatment, chemotherapy other than that suggested by gene expression analysis, or any other therapy or treatment known or suspected to be effective.

5.7 Clinical Trials and Epidemiological Studies

The method of the present invention may also be used to assign individuals to categories within a clinical trial, epidemiological study or the like. For example, individuals may be distinguished according to a characteristic of a condition, such as the presence or absence of specific proteins (e.g., estrogen receptor) or tissue structures (e.g., lymph nodes), and with prognosis, and the results of the trial correlated with prognosis. In a specific example, the condition is breast cancer, the characteristic is the presence of the estrogen receptor, and the outcome is prognosis is the expected reoccurrence or non-reoccurrence of metastases within a given period, for example, five years, after initial diagnosis. In another specific example, the condition is obesity, the characteristics are 24-hour energy expenditure, and the prognosis is the expected occurrence of heart disease or diabetes. In another specific example, the condition is a neurodegenerative disease, the characteristic is exposure to a particular range of concentration of an environmental toxin, and the prognosis is expected occurrence or degree of loss of motor function. In each case, the characteristics and expected outcome are used to assign the individual to a category within a clinical trial or epidemiological study.

Thus, the invention provides a method for assigning an individual to one of a plurality of categories in a clinical trial, comprising classifying the individual into one of a plurality of condition categories differentiated by at least one genotypic or phenotypic characteristic of the condition; determining the level of expression, in a sample derived from said individual, of a plurality of genes informative for said condition category; determining whether said level of expression of said plurality of genes indicates that the individual has a good prognosis or a poor prognosis; and assigning the individual to a category in a clinical trial on the basis of prognosis.

In a specific embodiment, the invention provides a method of assigning an individual to a category in a breast cancer clinical trial, said method comprising: (a) classifying said individual as $ER^-$, BRCA1, $ER^-$, sporadic; ER+, ER/AGE high; ER+, ER/AGE low, LN+; or ER+, ER/AGE low, $LN^-$; (b) determining for said individual the level of expression of at least two genes for which markers are listed in Table 1 if said individual is classified as $ER^-$, BRCA1; Table 2 if said individual is classified as $ER^-$, sporadic; Table 3 if said individual is classified as ER+, ER/AGE high; Table 4 if said individual is classified as ER+, ER/AGE low, LN+; or Table 5 if said individual is classified as ER+, ER/AGE low, $LN^-$; (c) determining whether said individual has a pattern of expression of said at least two genes that correlates with a good prognosis or a poor prognosis; and (d) assigning said individual to at least one category in a clinical trial if said individual has a good prognosis, and assigning said individual to a second category in said clinical trial if said individual has a poor prognosis. In a more specific embodiment, said individual is additionally assigned to a category in said clinical trial on the basis of the classification of said individual as determined in step (a). In another more specific embodiment, said individual is additionally assigned to a category in said clinical trial on the basis of any other clinical, phenotypic or genotypic characteristic of breast cancer. In another more specific embodiment, the method additionally comprises determining in said cell sample the level of expression, relative to a control, of a second plurality of genes for which markers are not found in Tables 1-5, wherein said second plurality of genes is informative for prognosis of breast cancer, and determining from the expression of said second plurality of genes, in addition to said first plurality of genes, whether said individual has a good prognosis or a poor prognosis.

5.8 Kits

The present invention further provides for kits comprising the marker sets described above. The components of the kits of the present invention are preferably contained in sealed containers. In a preferred embodiment, the kit comprises a microarray ready for hybridization to target polynucleotide molecules. In specific embodiments, the kit may comprise any of the microarrays described in detail in Section 5.5.2. Where proteins are the target molecules, the kit preferably comprises a plurality of antibodies for binding to specific condition-related proteins, and means for identifying such binding (e.g., means for performing a sandwich assay, ELISA, RIA, etc.). Such antibodies may be provided, for example, individually or as part of an antibody array. The kit may additionally comprise software for the data analyses described above, as described in detail in Section 5.9. The kit preferably contains one or more control samples. Such a control sample may be an artificial population of marker-related or marker-derived polynucleotides suitable for hybridization to a microarray, wherein the markers are related to or relevant to the condition of interest (for example, breast cancer). The control may also, or alternatively, be a set of expression values stored on a computer disk or other storage medium.

The kits of the invention may be primarily diagnostic in nature; that is, they may assist a physician or researcher in determining a characteristic, for example, the prognosis, of a condition of interest, the likely response to a therapeutic regimen, the likely outcome of exposure to an environmental condition, such as toxin exposure, etc. The kits of the invention may also be used to classify individuals, for example, to place individuals into different groups in a clinical trial. The use of each kit is determined by the markers, microarrays, controls, etc. included.

COMPUTER-FACILITATED ANALYSIS. The analytic methods described in the previous sections can be implemented by use of the following computer systems and according to the following programs and methods. A computer system comprises internal components linked to external components. The internal components of a typical computer system include a processor element interconnected with a main memory. For example, the computer system can be based on an Intel 8086-, 80386-, 80486-, PENTIUM®, or PENTIUM®-based processor with preferably 32 MB or more of main memory. The computer system may also be a MACINTOSH® or a MACINTOSH®-based system, but may also be a minicomputer or mainframe.

The external components preferably include mass storage. This mass storage can be one or more hard disks (which are typically packaged together with the processor and memory). Such hard disks are preferably of 1 GB or greater storage capacity. Other external components include a user interface device, which can be a monitor, together with an inputting device, which can be a "mouse", or other graphic input devices, and/or a keyboard. A printing device can also be attached to the computer.

Typically, a computer system is also linked to network link, which can be part of an Ethernet link to other local computer systems, remote computer systems, or wide area communication networks, such as the Internet. This network link allows the computer system to share data and processing tasks with other computer systems.

Loaded into memory during operation of this system are several software components, which are both standard in the art and special to the instant invention. These software components collectively cause the computer system to function according to the methods of this invention. These software components are typically stored on the mass storage device. A software component comprises the operating system, which is responsible for managing computer system and its network interconnections. This operating system can be, for example, of the MICROSOFT® WINDOWS® family, such as WINDOWS® 3.1, WINDOWS® 95, WINDOWS® 98, WINDOWS® 2000, or WINDOWS NT®, or may be of the MACINTOSH® OS family, or may be UNIX, a UNIX derivative such as LINUX, or an operating system specific to a minicomputer or mainframe. The software component represents common languages and functions conveniently present on this system to assist programs implementing the methods specific to this invention. Many high or low level computer languages can be used to program the analytic methods of this invention. Instructions can be interpreted during run-time or compiled. Preferred languages include C/C++, FORTRAN and JAVA. Most preferably, the methods of this invention are programmed in mathematical software packages that allow symbolic entry of equations and high-level specification of processing, including some or all of the algorithms to be used, thereby freeing a user of the need to procedurally program individual equations or algorithms. Such packages include MATLAB® from Mathworks (Natick, Mass.), MATHEMATICA® from Wolfram Research (Champaign, Ill.), or S-PLUS® from Math Soft (Cambridge, Mass.). Specifically, the software component includes the analytic methods of the invention as programmed in a procedural language or symbolic package.

The software to be included with the kit comprises the data analysis methods of the invention as disclosed herein. In particular, the software may include mathematical routines for marker discovery, including the calculation of similarity values between clinical categories (e.g., prognosis) and marker expression. The software may also include mathematical routines for calculating the similarity between sample marker expression and control marker expression, using array-generated fluorescence data, to determine the clinical classification of a sample.

Additionally, the software may also include mathematical routines for determining the prognostic outcome, and recommended therapeutic regimen, for an individual with a condition of interest. In the specific example of breast cancer, the mathematical routines would determine the prognostic outcome and recommended therapeutic regimen for an individual having breast cancer. Such breast cancer-specific software would include instructions for the computer system's processor to receive data structures that include the level of expression of five or more of the marker genes listed in any of Tables 1-5 in a breast cancer tumor sample obtained from the breast cancer patient; the mean level of expression of the same genes in a control or template; and the breast cancer patient's clinical information, including age, lymph node status and ER status. The software may additionally include mathematical routines for transforming the hybridization data and for calculating the similarity between the expression levels for the marker genes in the patient's breast cancer tumor sample and a control or template. In a specific embodiment, the software includes mathematical routines for calculating a similarity metric, such as a coefficient of correlation, representing the similarity between the expression levels for the marker genes in the patient's breast cancer tumor sample and the control or template, and expressing the similarity as that similarity metric.

The software preferably would include decisional routines that integrate the patient's clinical and marker gene expression data, and recommend a course of therapy. In one embodiment, for example, the software causes the processor unit to receive expression data for prognosis-related genes in the patient's tumor sample, calculate a metric of similarity of these expression values to the values for the same genes in a template or control, compare this similarity metric to a pre-selected similarity metric threshold or thresholds that differentiate prognostic groups, assign the patient to the prognostic group, and, on the basis of the prognostic group, assign a recommended therapeutic regimen. In a specific example, the software additionally causes the processor unit to receive data structures comprising clinical information about the breast cancer patient. In a more specific example, such clinical information includes the patient's age, estrogen receptor status, and lymph node status.

The software preferably causes the processor unit to receive data structures comprising relevant phenotypic and/or genotypic characteristics of the particular condition of interest, and/or of an individual having that condition, and classifies the individual into a condition subset according to those characteristics. The software then causes the processor to receive values for subset-specific markers, to calculate a metric of similarity of the values associated with those markers (e.g., level, abundance, activity, etc.) from the individual to a control, compare this similarity metric to a pre-selected similarity metric threshold or thresholds that differentiate prognostic groups, assign the patient to a prognostic group, and, on the basis of the prognostic group, assign a recommended therapeutic regimen. In the specific example of breast cancer and a breast cancer patient, the software, in one embodiment, causes the processor unit to receive data structures comprising the patient's age, estrogen receptor status, and lymph node status, and on the basis of this data, to classify the patient into one of the following patient subsets: $ER^-$, sporadic; $ER^-$, BRCA1; ER+, AR/AGE high; ER+, ER/AGE low, LN+; or ER+, ER/AGE low, $LN^-$. The software then causes the processor to receive expression values for subset-specific prognosis-informative gene expression in the patient's tumor sample, calculate a metric of similarity of these expression values to the values for the same genes in a patient subset-specific template or control, compare this similarity metric to a pre-selected similarity metric threshold or thresholds that differentiate prognostic groups, assign the patient to the prognostic group, and, on the basis of the prognostic group, assign a recommended therapeutic regimen.

Where the control is an expression template comprising expression values for marker genes within a group of patients, e.g., breast cancer patients, the control can comprise either hybridization data obtained at the same time (i.e., in the same hybridization experiment) as the patient's individual hybridization data, or can be a set of hybridization or marker expression values stores on a computer, or on computer-readable media. If the latter is used, new patient hybridization data for the selected marker genes, obtained from initial or follow-up tumor samples, or suspected tumor samples, can be compared to the stored values for the same genes without the need for additional control hybridizations. However, the software may additionally comprise routines for updating the control data set, e.g., to add information from additional breast cancer patients or to remove existing members of the control data set, and, consequently, for recalculating the average expression level values that comprise the template. In another specific embodiment, said control comprises a set of single-channel mean hybridization intensity values for each of said at least five of said genes, stored on a computer-readable medium.

Clinical data relating to a breast cancer patient, or a patient having another type of condition, and used by the computer program products of the invention, can be contained in a database of clinical data in which information on each patient is maintained in a separate record, which record may contain any information relevant to the patient, the patient's medical history, treatment, prognosis, or participation in a clinical trial or study, including expression profile data generated as part of an initial diagnosis or for tracking the progress of the condition, for example, breast cancer, during treatment.

Thus, one embodiment of the invention provides a computer program product for classifying a breast cancer patient according to prognosis, the computer program product for use in conjunction with a computer having a memory and a processor, the computer program product comprising a computer readable storage medium having a computer program mechanism encoded thereon, wherein said computer program product can be loaded into the one or more memory units of a computer and causes the one or more processor units of the computer to execute the steps of (a) receiving a first data structure comprising said breast cancer patient's age, ER status, LN status and tumor type; (b) classifying said patient as $ER^-$, sporadic; $ER^-$, BRCA1; ER+, ER/AGE high; ER+, ER/AGE low, LN+; or ER+, ER/AGE low, $LN^-$; (c) receiving a first data structure comprising the level of expression of at least two genes in a cell sample taken from said breast cancer patient wherein markers for said at least two genes are listed in Table 1 if said patient is classified as $ER^-$, sporadic; Table 2 if said patient is classified as $ER^-$, sporadic; Table 3 if said patient is classified as ER+, ER/AGE high; Table 4 if said patient is classified as ER+, ER/AGE low, LN+; or Table 5 if said patient is classified as ER+, ER/AGE high, $LN^-$; (d) determining the similarity of the level of expression of said at least two genes to control levels of expression of said at least two genes to obtain a patient similarity value; (e) comparing said patient similarity value to selected first and second threshold values of similarity of said level of expression of said genes to said control levels of expression to obtain first and second similarity threshold values, respectively, wherein said second similarity threshold indicates greater similarity to said control levels of expression than does said first similarity threshold; and (f) classifying said breast cancer patient as having a first prognosis if said patient similarity value exceeds said first and said second threshold similarity values, a second prognosis if said patient similarity value exceeds said first threshold similarity value but does not exceed said second threshold similarity value, and a third prognosis if said patient similarity value does not exceed said first threshold similarity value or said second threshold similarity value. In a specific embodiment of said computer program product, said first threshold value of similarity and said second threshold value of similarity are values stored in said computer. In another more specific embodiment, said first prognosis is a "very good prognosis," said second prognosis is an "intermediate prognosis," and said third prognosis is a "poor prognosis," and wherein said computer program mechanism may be loaded into the memory and further cause said one or more processor units of said computer to execute the step of assigning said breast cancer patient a therapeutic regimen comprising no adjuvant chemotherapy if the patient is lymph node negative and is classified as having a good prognosis or an intermediate prognosis, or comprising chemotherapy if said patient has any other combination of lymph node status and expression profile. In another specific embodiment, said computer program mechanism may be loaded into the memory and further cause said one or more processor units of the computer to execute the steps of receiving a data structure comprising clinical data specific to said breast cancer patient. In a more specific embodiment, said single-channel hybridization intensity values are log transformed. The computer implementation of the method, however, may use any desired transformation method. In another specific embodiment, the computer program product causes said processing unit to perform said comparing step (e) by calculating the difference between the level of expression of each of said genes in said cell sample taken from said breast cancer patient and the level of expression of the same genes in said control. In another specific embodiment, the computer program product causes said processing unit to perform said comparing step (e) by calculating the mean log level of expression of each of said genes in said control to obtain a control mean log expression level for each gene, calculating the log expression level for each of said genes in a breast cancer sample from said breast cancer patient to obtain a patient log expression level, and calculating the difference between the patient log expression level and the control mean log expression for each of said genes. In another specific embodiment, the computer program product causes said processing unit to perform said comparing step (e) by calculating similarity between the level of expression of each of said genes in said cell sample taken from said breast cancer patient and the level of expression of the same genes in said control, wherein said similarity is expressed as a similarity value. In more specific embodiment, said similarity value is a correlation coefficient. The similarity value may, however, be expressed as any art-known similarity metric.

Of course, the above breast cancer-specific examples are not limiting; analogous computer systems, software, and data analysis methods may be utilized for any condition of interest. For example, analogous software may be used to determine the prognosis of any other type of cancer, or of any other non-cancer diseases or conditions, using markers, expression level data and controls specific for that cancer, non-cancer disease or condition.

In an exemplary implementation, to practice the methods of the present invention, a user first loads experimental data into the computer system. These data can be directly entered by the user from a monitor, keyboard, or from other computer systems linked by a network connection, or on removable storage media such as a CD-ROM, floppy disk (not illustrated), tape drive (not illustrated), ZIP® drive (not illustrated) or through the network. Next the user causes execution of expression profile analysis software which performs the methods of the present invention.

In another exemplary implementation, a user first loads experimental data and/or databases into the computer system. This data is loaded into the memory from the storage media or from a remote computer, preferably from a dynamic geneset database system, through the network. Next the user causes execution of software that performs the steps of the present invention.

Additionally, because the data obtained and analyzed in the software and computer system products of the invention may be confidential, the software and/or computer system preferably comprises access controls or access control routines, such as password protection and preferably, particularly if information is to be transmitted between computers, for example, over the Internet, encryption of the data by a suitable encryption algorithm (e.g., PGP®).

Alternative computer systems and software for implementing the analytic methods of this invention will be apparent to one of skill in the art and are intended to be comprehended within the accompanying claims. In particular, the accompanying claims are intended to include the alternative program structures for implementing the methods of this invention that will be readily apparent to one of skill in the art.

6. EXAMPLE

Identification of Phenotypic Subsets and Informative Genesets for Each

Materials and Methods

Tumor Samples:

311 cohort samples were collected from breast cancer patients. Selection criteria for sporadic patients (i.e., those not identified as having a BRCA1-type tumor; n=291) included: primary invasive breast carcinoma less than 5 cm (T1 or T2); no axillary metastases (N0); age at diagnosis of less than 55 years; calendar year of diagnosis 1983-1996; and no previous malignancies. All patients were treated by modified radical mastectomy or breast-conserving treatment. See van't Veer et al., *Nature* 415:530 (2002). Selection criteria for hereditary (i.e., BRCA1-type; n=20) tumors included: carriers of germline mutation in BRCA1 or BRCA2, and primary invasive breast carcinoma. van't Veer, supra. Additionally, for development of a classifier for the BRCA1 group, 14 BRCA1 samples previously identified (see van't Veer, supra) were added to the 20 BRCA1 type samples to increase sample size. Those 14 samples also satisfy the conditions that they are ER negative and age less than 55 years old.

Data Analysis:

Sample sub-grouping: As shown in FIG. 1, tumor samples were first divided into ER+ and $ER^-$ branches since this is the dominant gene expression pattern. In the $ER^-$ branch, the samples were further divided into "BRCA1 mutation like" and "Sporadic like" categories using the expression templates and 100 genes previously identified as optimal for determining BRCA1 status. See van't Veer et al., *Nature* 415:530 (2002). In the ER+category, samples were divided by ER vs. age distribution (see below) into two groups, "ER/AGE low" and "ER/AGE high." Within the "ER/AGE low" group, samples were further divided according to the lymph node status into two sub-groups: lymph node negative (0 lymph nodes; LN−) and positive (>0 lymph nodes; LN+) group.

The result of these divisions was five distinctive subgroups: "$ER^-$, sporadic" (n=52), "$ER^-$, BRCA1" (n=34), "ER+, ER/AGE high" (n=83), "ER+, ER/AGE low, $LN^-$" (n=81), and "ER+, ER/AGE low, LN+" (n=75). A few samples with a specific ER vs. age distribution in "ER+, ER/AGE low, LN+" group were further excluded to develop a classifier, see below for details.

Estrogen receptor level: Estrogen receptor gene expression level was measured by a 60mer oligo-nucleotide on a microarray. Since every individual sample was compared to a pool of all samples, the ratio to pool was used to measure the relative level. A threshold of −0.65 on $\log_{10}$(ratio) was used to separate the ER+ group from $ER^-$ group. See van't Veer et al., *Nature* 415:530 (2002).

Grouping by ER vs. age distribution: Samples were not uniformly distributed in ER vs. age space among the ER+ samples (FIG. 2). First, it appeared that the ER level increases with age, as there were few samples from young individuals having a high ER expression level. For example, in the 35 to 40 years age group, samples having a log(ratio) of ER>0.2 are relatively few as compared to the 40 to 45 age group. In the set of samples used, the 40<age≦45 group contains 30 samples having log(ratio) ER values between −0.2 to 0.2, and 28 samples having values greater than 0.2, whereas the 35<age≦40 group includes 24 samples with values between −0.2 to 0.2, but only 6 samples with values of greater than 0.2 (Fisher's exact test P-value: 1%). The increasing ER level with age may simply due to the fact that estrogen levels decrease with age, and the estrogen receptor level rises in compensation.

Figure 2A:
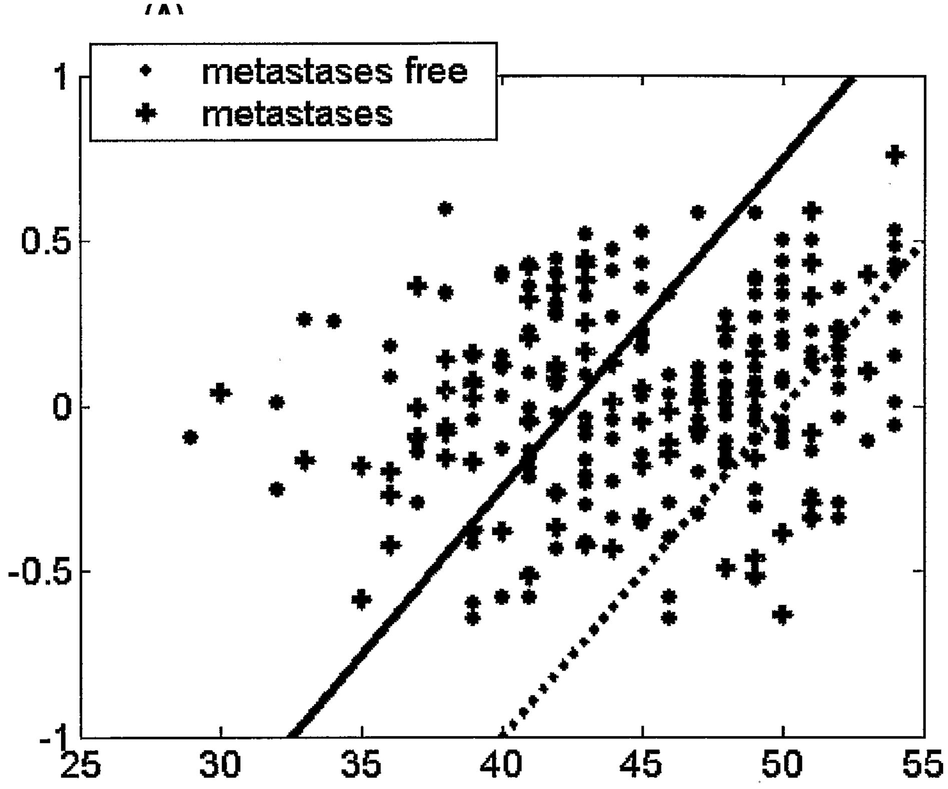

There also appeared to be at least two groups of patients, as indicated by the solid line separating the two in FIG. 2A. A bimodality test of the separation indicated by the solid line yielded P-value $<10^{-4}$. Each of these two groups has its own trend between the ER level and age. The solid line can be approximated by ER=0.1 (age−42.5). Patients having values above the solid line are referred to as the "ER/AGE high" group, and the patients below the line as the "ER/AGE low" group.

Prognosis in Each Group:

Feature selection and performance evaluation: For the prognosis in each group, non-informative genes were filtered in each group of patients. Specifically, only genes with $|\log_{10}(\text{ratio})|>\log_{10}(2)$ and P-value (for log(ratio)≠0)<0.01 in more than 3 experiments were kept. This step removed all genes that never had any significant change across all samples. The second step used a leave-one-out cross validation (LOOCV) procedure to optimize the number of reporter genes (features) in the classifier and to estimate the performance of the classifier in each group. The feature selection was included inside the loop of each LOOCV process. The final "optimal" reporter genes were selected using all of the "training samples" as the result of "re-substitution" because one classifier was needed for each group.

Selection of training samples: Only the samples from patients who had metastases within 5 years of initial diagnosis (3 years for "$ER^-$, sporadic" samples; i.e., the "poor outcome" group), or who were metastases-free with more than 5 years of follow-up time (i.e., the "good outcome" group, were used as the training set. Because the average expression levels for informative genes among patients who were metastasis-free, or who had early metastases, were used as expression templates for prediction, the training samples for the ER+ samples were further limited to those samples that could also be correctly classified by the first round of LOOCV process. For the "ER$^-$, sporadic" samples, no such iteration was done because no improvement was observed. For the "ER$^-$, BRCA1" samples, an iteration was done, but the training samples in the second iteration were limited to the correctly predicted good outcome samples from the first round of LOOCV, and all the poor outcome samples with metastases time less than 5 years. Further limitation of the poor outcome samples was not performed because of the small number of poor samples and the absence of improvement by such limitation. In the first round of LOOCV, except for the "ER$^-$, sporadic" group, the number of features was fixed at 50 genes. A patient was predicted to have a favorable outcome, that is, no metastases within five years of initial diagnosis, if the expression of the reporter genes in a sample from the individual was more similar to the "average good profile" than the "average poor profile", and a poor outcome, that is, a metastasis within five years, if the expression of the reporter genes in the sample was more similar to the "average poor profile" than the "average good profile".

The justification for such an iteration operation is three-fold. First, biologically, there are always a few individuals with specific reasons (different from the vast majority) to stay metastases free or to develop metastases. Second, statistically, most groups of patients include outliers that don't follow the distribution of the majority of samples. Third, methodologically, the iteration operation is very similar to the idea of "boosting", but instead of increasing the weights of the samples predicted wrong, emphasis is placed on the well behaved samples for selecting features and training the classifier. Since this process was used to select "training samples", and the performance was evaluated using the LOOCV (including the feature selection) after the training sample being fixed, there is no issue of over-fitting involved in our procedures. This method of iteration is thus more likely to reveal the dominant mode to metastases within each group.

Error rate and odds ratio, threshold in the final LOOCV: Unless otherwise stated, the error rate was the average error rate from two populations: (1) the number of poor outcome samples misclassified as good outcome samples, divided by the total number of poor outcome samples; and (2) the total number of good outcome samples misclassified as poor outcome samples, divided by the total number of good samples. Two odds ratios were reported for a given threshold: (1) the overall odds ratio and (2) the 5 year odds ratio. The 5 year odds ratio was calculated from samples from individuals that were metastases free for more than five years, and who experienced metastasis within 5 years. The threshold was applied to cor1-cor2, where "cor1" stands for the correlation to the "average good profile" in the training set, and "cor2" stands for the correlation to the "average poor profile" in the training set.

The threshold in the final round of LOOCV was defined using the following steps: (1) For each of the N sample i left out for training, features based on the training set were selected, (2) given a feature set, an incomplete LOOCV with N−1 samples was performed (only the "average poor profile" and "average good profile" is varied depending on whether the left out sample is in the training set or not), (3) the threshold based on the minimum error rate from N−1 samples was determined, and that threshold was assigned to sample i in step (1), (4) the median threshold from all N samples was taken, and designated the final threshold. FIGS. 3-7 present detailed information about classifiers for the 5 groups: "ER$^-$, sporadic", "ER$^-$, BRCA1", "ER+, ER/age high", "ER+, ER/age low, LN$^-$", "ER+, ER/age low, LN+". Tables 1-5 (see Section 5.3) list the final optimal reporter genes for each of the 5 classifiers for each of the five patient subsets. Table 6, below, summarizes the performance of each of the five classifiers together with thresholds used in each classifier.

TABLE 6

Performance of classifiers for each patient subset.

| Classifier | Optimal # of Genes | (C1-C2) Threshold | Metastasis Free | # of Samples | TP | FP | FN | TN | Odds Ratio | 95% C.I. |
|---|---|---|---|---|---|---|---|---|---|---|
| ER+, ER/AGE | 50 | 1.22 | Overall | 83 | 31 | 14 | 5 | 33 | 14.61 | 4.71-45.36 |
| high | | | 5 year | 71 | 24 | 11 | 3 | 33 | 24.00 | 6.03-95.46 |
| ER+, ER/AGE | 65 | 0.38 | Overall | 81 | 14 | 6 | 6 | 55 | 21.39 | 5.98-76.52 |
| low, LN− | | | 5 year | 73 | 11 | 4 | 5 | 53 | 29.15 | 6.73-126.33 |
| ER+, ER/AGE | 50 | −0.12 | Overall | 56 | 7 | 4 | 6 | 39 | 11.38 | 2.54-50.94 |
| low, LN+ | | | 5 year | 48 | 5 | 4 | 3 | 36 | 15.00 | 2.57-87.64 |
| ER−, sporadic | 20 | −0.01 | Overall | 52 | 18 | 7 | 7 | 29 | 7.35 | 2.16-25.04 |
| | | | 5 year | 45 | 16 | 5 | 6 | 18 | 9.60 | 2.45-37.58 |
| ER−, BRCA1 | 10 | −0.37 | Overall | 34 | 6 | 3 | 3 | 22 | 14.67 | 2.34-92.11 |
| | | | 5 year | 22 | 6 | 1 | 3 | 12 | 24.00 | 2.04-282.68 |

TP: True positive
FP: False positive
FN: False negative
TN: True negative

Classification method: All classifiers described herein, feature selection and optimization were included inside the LOOCV loop. Classifier performance was based on the LOOCV results. The profile based on the selected features from each patient was compared to the "average good profile" and "average poor profile" (by correlation) to determine its predicted outcome.

Correlation calculation: The correlation between each gene's expression log(ratio) and the endpoint data (final outcome) was calculated using the Pearson's correlation coefficient. The correlation between each patient's profile and the "average good profile" and "average poor profile" was the cosine product (no mean subtraction).

Results:

The comprehensive prognosis strategy was employed on microarray expression profiles of 311 patients diagnosed before age 55 that were all part of previous studies establishing and validating a 70-gene prognosis profile. See van 't Veer et al., *Nature* 415:530 (2002); van de Vijver et al., *N. Engl. J.*

*Med.* 347:1999 (2002). In addition, 14 known BRCA1 samples from the *Nature* study were included in defining the prognosis classifier for the BRCA1 group. The overview of the stratifications is shown in FIG. 1. In each of the patient subsets, prognosis classifiers were developed and performance was evaluated by leave-one-out cross-validation. The biological make up of each of the classifiers was also examined.

During the process to decide whether a particular clinical parameter should be used for the next stratification, our objectives were twofold: (1) identification of homogeneous prognosis patterns; and/or (2) improved prognosis in the subsets. There is a subtle balance between these two objectives because smaller groups will likely lead to uniform patterns within the group but have increasingly limited predictive power. With the exception of the BRCA1 subset, each group in our stratification contained 50 or more samples.

The first layer of stratification was based on the estrogen receptor level. It was previously observed that estrogen receptor expression has a dominant effect on overall gene expression in breast cancer as seen in hierarchical clustering. van 't Veer et al., *Nature* 415:530 (2002); Perou et al, *Nature* 406: 747 (2000); Gruvberger et al., *Cancer Res.* 61:5979 (2001). In previous analysis up to 2500 genes were significantly correlated with ER expression levels in tumor. See, van 't Veer et al., *Nature* 415:530 (2002). According to the threshold defined previously (van de Vijver et al, *N. Engl. J. Med.* 347:1999 (2002)), samples were first divided into two groups according to the estrogen receptor level as measured by the oligo probe (accession number: NM_000125) on the array; samples with log(ratio)>−0.65 belong to the ER+ group, and the rest belong to $ER^-$ group). This resulted in 239 samples in the ER+ group and 72 samples in the $ER^-$ group.

In the ER+ branch it was observed that when displaying ER expression level as a function of age, at least two subgroups appeared to exist. (In general, any bimodality in the clinical data is useful.) The tumors were stratified according this bimodality (see FIG. 2). The group of ER+ patients having a high ER/AGE ratio was designated the "ER/AGE high" group (83 samples), and the remaining group of patients was designated "ER/AGE low" group (156 samples).

Within the "ER/age high" group, a group of prognosis reporter genes that highly correlated with the outcome is identified (see Table 3). Moreover, the expression of these genes appeared to be very homogeneous, as indicated by high similarity in expression among those genes. See FIG. 2A. Leave-one-out cross validation including reporter selection yielded an odds ratio of 14.6 (95% CI: 4.7-45.4) and 5 year odds ratio of 24.0 (95% CI: 6.0-95.5). Examination of those reporter genes reveals they are mostly the cell cycle genes which are highly expressed in the poor outcome tumors. It is worth noting that even though this group includes LN+ and LN− individuals, and mixed treatment, the incidence of distant metastases is predicted by a biologically uniform set of genes, possibly indicating that proliferation is the prime driving force for disease progression. Also even though variation in these genes is observed in other tumor subgroups this is generally not correlated with outcome in those settings (see below).

In the "ER/age low" group, no predictive pattern was found in the whole group; thus, the samples were further stratified into LN− (81 samples, referred to as "ER/age low $LN^-$") and LN+ (75 samples, referred to as "ER/age low LN+") group.

Within the "ER/age low $LN^-$" group, a group of genes was identified that was uniformly co-regulated, and which correlated with the outcome. Leave-one-out cross-validation (including feature selection) yielded an odds ratio of 21.4 (95% CI: 6.0-76.5) and 5 year odds ratio of 29.2 (95% CI: 6.7-126.3). This group of genes is also enriched for individual biological functions (see below).

For the "ER/age low LN+" subset, an informative set of genes (see Table 4) was obtained after exclusion of several samples from older individuals having low ER levels. These samples are indicated in FIG. 2A as those lying below the dashed line (approximated as ER<0.1*(age-50). 56 samples remained after the exclusion. This sample set allowed the identification of a group of genes with a highly homogeneous pattern that is useful for prognosis (overall odds ratio: 11.4 (2.5-50.9), 5 year odds ratio: 15.0 (2.6-87.6)). This suggests again that ER vs. age is an important combination for stratifying breast cancer patients. The reporter genes involved in this classifier also correlated with the clinical measure of the degree of lymphocytic infiltration (data not shown). The prediction in this group was not as strong as other positive groups, which may indicate the primary tumor carries weaker information about the metastases for this group of patients, and the metastases may be started from or influenced by tumors already in lymph nodes.

In the $ER^-$ branch, because a portion of the samples are "BRCA1-like," it is natural to divide the samples into "BRCA1-like" and "sporadic like". To perform the classification, the BRCA1/sporadic tumor type classifier described in Roberts et al., "Diagnosis and Prognosis of Breast Cancer Patients," International Publication No. WO 02/103320, which is hereby incorporated by reference in its entirety, to segregate the $ER^-$ cohort samples. 52 out of the 72 $ER^-$ samples were found to be "sporadic like" and 20 were found to be "BRCA1-like". Interestingly, the "sporadic like" group was enriched for erbb2 mutations (data not shown).

Within the "$ER^-$, sporadic" group, no homogeneous prognosis pattern was identified; however, 20 genes were identified that are highly predictive of the tumor outcome (see Table 2). Leave-one-out cross-validation including feature selection yielded an odds ratio of 7.4 (95% CI 2.2-25.0) and 5 year odds ratio 9.6 (2.5-37.6). This result represents a significant improvement in prognosis compared to the previously-identified 70 gene prognosis classifier (see Roberts et al., International Publication No. WO 02/103320; van 't Veer et al., *Nature* 415:530 (2002)) which has no within-group prognostic power for the $ER^-$ patient subset. The fact that 20 genes predict outcome and that there is no homogeneous (and apparent biological) pattern in this group probably indicates multiple mechanisms of metastasis in this group. Gene annotation indicates that genes included may be involved in invasion, energy metabolism and other functions.

For the "$ER^-$, BRCA1-like" group, we added 14 BRCA1 mutation carrier samples from a previous study were added to increase the number of samples. Those 14 extra samples also satisfied the following selection criteria: ER negative and age less than 55 years. The leave-one-out cross validation process identified 10 genes that are predictive of final outcomes. The overall odds ratio is 14.7 (95% CI: 2.3-92.1) and the 5 year odds ratio is 24.0 (95% CI: 2.0-282.7).

Because no homogeneous gene expression patterns were found in $ER^-$ branch, the predictive power of those genes was further validated. One means of further validation was to review the different classifier gene sets for biological interpretations and to identify genes within each classifier that gave indications as to the origins of the tumors.

The "ER+, ER/AGE high" group yielded a classifier highly enriched for cell cycle genes with both G1/S and G2/M phases represented. In this group, over-expression of 46 of the 50 genes was associated with disease progression including all the known cell cycle genes. This is consistent with rapid growth being the determinant of metastatic potential. Four genes in this classifier were anti-correlated with outcome and cell cycle. One of these genes encodes follistatin, which binds to and inhibits activin and other members of the TGFβ family (Lin et al., *Reproduction* 126:133 (2003)), the members of which have many functions, including growth stimulation. Tumor grade also accurately predicted metastatic potential in this group (overall odds ratio: 5.9, 95% CI: 2.0-18.0, 5 year odds ratio: 12.5, 95% CI: 2.6-59.3) and was also correlated with the expression level of these genes, which is consistent with rate of growth being the primary determinant of disease progression. This set of genes had a significantly lower correlation with outcome in the other patient subsets, even though coordinate and similarly variable expression was seen. For example, many tumors in the "ER$^-$, sporadic" group had high cell cycle and low FST expression, but the expression of these genes in these groups was minimally correlated with outcome, indicating that growth was not the primary determinant of outcome here (see FIGS. 8A and 8B).

The ER+, ER/AGE low, LN$^-$ group yielded a classifier rich in both genes for glycolytic enzymes (12 of 56) and genes induced by hypoxia and/or angiogenesis (14 of 56) with 5 genes falling into both categories. These genes were positively correlated with poor outcome, implying that energy metabolism (glycolysis), angiogenesis and adaptation to hypoxia were critical pathways in this subgroup of tumors. None of these genes appeared in the classifiers for the other patient subsets, and there was a much reduced predictive value of these genes in the other tumors, even though coordinate and similarly variable expression was seen (see FIGS. 8C and 8D).

The implication of the above analyses is that certain well known functions (growth, angiogenesis, energy metabolism) are important in certain tumor types and not in others, and therefore therapies that target these functions will be likely be similarly effective in some tumor subgroups and not in others. For example therapies that target cell cycle progression, such as taxol or the vinca alkaloids, may be optimally effective in the ER+, ER/AGE high group, where overexpression of cell cycle genes predominates in the classifier. In contrast, tumor subgroups in which variation in cell cycle expression is not correlated with outcome may be less sensitive to taxol or the vinca alkaloids.

The "comprehensive prognosis" approach significantly improved the prediction error rate when compared with 70 gene classifier (Table 7). To make the comparison fair, we listed two sets of results from the 70 gene classifier. The first results from the use of the same threshold applied to all the patient subsets (threshold previously optimized for false negative rate); the second one results from the use of a threshold optimized for each patient subset (optimized for average error rate). The comprehensive approach lowered the error rate by at least 6%.

TABLE 7

Average error rate for the patient subset approach compared with the previously-described 70 gene classifier.

| Prognosis method | over all error rate | 5 year error rate |
|---|---|---|
| 70 gene, fix thresh | 30.90% | 25.70% |
| 70 gene, opt thresh | 28.60% | 27.60% |
| Comprehensive | 21.50% | 19.30% |

Fix thresh: use of a fixed threshold in the classifier as previously determined.
Opt threshold: use of a threshold optimized for each sub-group. For the "ER/Age low, LN+" subgroup, 56 samples used for developing the classifier were included here, resulted in 306 samples in total.

7. REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of the present invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

This application includes a Sequence Listing submitted on compact disc, recorded on two compact discs, including one duplicate, containing Filename SEQLIST 9301-251-999(as filed).txt, of size 434,401 bytes, created Sep. 1, 2006. The Sequence Listing on the compact discs is incorporated by reference herein in its entirety.

What is claimed is:

1. A method for predicting a human breast cancer patient as having a good prognosis or a poor prognosis, comprising:

(a) classifying said breast cancer patient into one of the following classes:

(a1) $ER^-$ and sporadic;

(a2) $ER^-$ and BRCA1;

(a3) ER+ and ER/AGE high;

(a4) ER+, ER/AGE low and LN+; or (a5) ER+, ER/AGE low and $LN^-$;

wherein $ER^+$ designates a high ER level and $ER^-$ designates a low ER level, wherein said ER/AGE is a metric of said ER level relative to the age of said patient, and wherein $LN^+$ designates a greater than 0 lymph nodes status in said patient and $LN^-$ designates a 0 lymph nodes status in said patient, and wherein said ER/AGE is classified as high if said ER level is greater than $c\cdot(AGE-d)$, and wherein said ER/AGE is classified as low if said ER level is equal to or less than $c\cdot(AGE-d)$, wherein c is a coefficient, AGE is the age of said patient, and d is an age threshold;

(b) determining a profile comprising measurements of levels of transcripts of, or proteins encoded by, respective genes in a plurality of genes in a cell sample taken from said breast cancer patient, said respective genes comprising:

(b1) at least five of the genes for which markers are listed in Table 1 if said breast cancer patient is classified as $ER^-$ and sporadic;

(b2) at least two of the genes for which markers are listed in Table 2 if said breast cancer patient is classified as $ER^-$ and BRCA1, (b3) at least two of the genes for which markers are listed in Table 3 if said breast cancer patient is classified as ER+ and ER/AGE high;

(b4) at least two of the genes for which markers are listed in Table 4 if said breast cancer patient is classified as ER+, ER/AGE low and LN+; or (b5) at least two of the genes for which markers are listed in Table 5 if said breast cancer patient is classified as ER+, ER/AGE low and $LN^-$; and (c) comparing, on a computer, said profile to a good prognosis template and/or a poor prognosis template, wherein said good prognosis template comprises measurements of average levels of transcripts of, or proteins encoded by, said respective genes in a plurality of good outcome patients, and said poor prognosis template comprises measurements of average levels of transcripts of, or proteins encoded by, said respective genes in a plurality of poor outcome patients, and wherein a good outcome patient is a breast cancer patient who has non-reoccurrence of metastases within a first period of time after initial diagnosis and a poor outcome patient is a patient who has reoccurrence of metastases within a second period of time after initial diagnosis; and (d) classifying said breast cancer patient (i) as having a good prognosis if said profile has a high similarity to said good prognosis template, has a low similarity to said poor prognosis template, or has a higher similarity to said good prognosis template than to said poor prognosis template, wherein said profile has a high similarity to said good prognosis template if the similarity to said good prognosis template is above a predetermined threshold or has a low similarity to said poor prognosis template if the similarity to said poor prognosis template is below said predetermined threshold, or (ii) as having a poor prognosis if said profile has a high similarity to said poor prognosis template, has a low similarity to said good prognosis template, or has a higher similarity to said poor prognosis template than to said good prognosis template, wherein said profile has a high similarity to said poor prognosis template if the similarity to said poor prognosis template is above said predetermined threshold, or has a low similarity to said good prognosis template if the similarity to said good prognosis template is below said predetermined threshold.

2. The method of claim 1, wherein said individual is $ER^-$ and sporadic, and said plurality of genes comprises at least ten of the genes for which markers are listed in Table 1.

3. The method of claim 1, wherein said individual is $ER^-$ and sporadic, and said plurality of genes comprises all of the genes for which markers are listed in Table 1.

4. The method of claim 1, wherein said individual is $ER^-$ and BRCA1, and said plurality of genes comprises at least five of the genes for which markers are listed in Table 2.

5. The method of claim 1, wherein said individual is $ER^-$ and BRCA1, and said plurality of genes comprises all of the genes for which markers are listed in Table 2.

6. The method of claim 1, wherein said individual is ER+ and ER/AGE high, and said plurality of genes comprises at least five of the genes for which markers are listed in Table 3.

7. The method of claim 1, wherein said individual is ER+ and ER/AGE high, and said plurality of genes comprises all of the genes for which markers are listed in Table 3.

8. The method of claim 1, wherein said individual is ER+, ER/AGE low and LN+, and said plurality of genes comprises at least five of the genes for which markers are listed in Table 4.

9. The method of claim 1, wherein said individual is ER+, ER/AGE low and LN+, and said plurality of genes comprises all of the genes for which markers are listed in Table 4.

10. The method of claim 1, wherein said individual is ER+, ER/AGE low and $LN^-$, and said plurality of genes comprises at least five of the genes for which markers are listed in Table 5.

11. The method of claim 1, wherein said individual is ER+, ER/AGE low and $LN^-$, and said plurality of genes comprises all of the genes for which markers are listed in Table 5.

12. A computer-implemented method for predicting a human breast cancer patient as having a good prognosis or a poor prognosis, comprising:

(a) classifying, on a computer, said patient as having a good prognosis or a poor prognosis based on a profile comprising measurements of levels of transcripts of, or proteins encoded by, respective genes in a plurality of genes in a cell sample taken from said patient, said plurality of genes comprising:

(b1) at least five of the genes for which markers are listed in Table 1 if said patient is $ER^-$ and sporadic;

(b2) at least two of the genes for which markers are listed in Table 2 if said patient is $ER^-$ and BRCA1;

(b3) at least two of the genes for which markers are listed in Table 3 if said patient is ER+ and ER/AGE high;

(b4) at least two of the genes for which markers are listed in Table 4 if said patient is ER+, ER/AGE low and LN+; or (b5) at least two of the genes for which markers are listed in Table 5 if said patient is ER+, ER/AGE low and $LN^-$, wherein ER+ designates a high ER level and $ER^-$ designates a low ER level, wherein said ER/AGE is a metric of said ER level relative to the age of said patient, wherein $LN^+$ designates a greater than 0 lymph nodes status in said patient and $LN^-$ designates a 0 lymph nodes status in patient, and wherein said ER/AGE is classified as high if said ER level is greater than $c \cdot (AGE-d)$, and wherein said ER/AGE is classified as low if said ER level is equal to or less than $c \cdot (AGE-d)$, wherein c is a coefficient, AGE is the age of said patient, and d is an age threshold, wherein said classifying is carried out by a method comprising comparing said profile to a good prognosis template and/or a poor prognosis template, wherein said good prognosis template comprises measurements of average levels of transcripts of, or proteins encoded by, said respective genes in a plurality of good outcome patients, and said poor prognosis template comprises measurements of average levels of transcripts of, or proteins encoded by, said respective genes in a plurality of poor outcome patients, and wherein a good outcome patient is a breast cancer patient who has non-reoccurrence of metastases within a first period of time after initial diagnosis and a poor outcome patient is a breast cancer patient who has reoccurrence of metastases within a second period of time after initial diagnosis, and wherein:

(i) said individual is classified as having a good prognosis if said profile has a high similarity to said good prognosis template, has a low similarity to said poor prognosis template, or has a higher similarity to said good prognosis template than to said poor prognosis template, wherein said profile has a high similarity to said good prognosis template if the similarity to said good prognosis template is above a predetermined threshold, or has a low similarity to said poor prognosis template if the similarity to said poor prognosis template is below said predetermined threshold, or (ii) said individual is classified as having a poor prognosis if said profile has a high similarity to said poor prognosis template, has a low similarity to said good prognosis template, or has a higher similarity to said poor prognosis template than to said good prognosis template, wherein said profile has a high similarity to said poor prognosis template if the similarity to said poor prognosis template is above said predetermined threshold, or has a low similarity to said good prognosis template if the similarity to said good prognosis template is below said predetermined threshold.

13. The method of claim 12, wherein said individual has been classified as $ER^-$ and sporadic, and said plurality of genes comprises at least ten of the genes for which markers are listed in Table 1.

14. The method of claim 12, wherein said individual has been classified as $ER^-$ and sporadic, and said plurality of genes comprises all of the genes for which markers are listed in Table 1.

15. The method of claim 12, wherein said individual has been classified as $ER^-$ and BRCA1, and said plurality of genes comprises at least five of the genes for which markers are listed in Table 2.

16. The method of claim 12, wherein said individual has been classified as $ER^-$ and BRCA1, and said plurality of genes comprises all of the genes for which markers are listed in Table 2.

17. The method of claim 12, wherein said individual has been classified as ER+ and ER/AGE high, and said plurality of genes comprises at least five of the genes for which markers are listed in Table 3.

18. The method of claim 12, wherein said individual has been classified as ER+ and ER/AGE high, and said plurality of genes comprises all of the genes for which markers are listed in Table 3.

19. The method of claim 12, wherein said individual has been classified as ER+; ER/AGE low and LN+, and said plurality of genes comprises at least five of the genes for which markers are listed in Table 4.

20. The method of claim 12, wherein said individual has been classified as ER+, ER/AGE low and LN+, and said plurality of genes comprises all of the genes for which markers are listed in Table 4.

21. The method of claim 12, wherein said individual has been classified as ER+, ER/AGE low and $LN^-$, and said plurality of genes comprises at least five of the genes for which markers are listed in Table 5.

22. The method of claim 12, wherein said individual has been classified as ER+, ER/AGE low and $LN^-$, and said plurality of genes comprises all of the genes for which markers are listed in Table 5.

* * * * *

UNITED STATES PATENT AND TRADEMARK OFFICE

CERTIFICATE OF CORRECTION

PATENT NO. : 8,019,552 B2
APPLICATION NO. : 10/591800
DATED : September 13, 2011
INVENTOR(S) : H. Dai et al.

It is certified that error appears in the above-identified patent and that said Letters Patent is hereby corrected as shown below:

| **COLUMN** | **LINE** | |
|---|---|---|
| 457 (Claim 12) | 50 | "status in patient" should read --status in said patient-- |
| 458 (Claim 19) | 51 | "ER+;" should read --ER+,-- |

Signed and Sealed this
Seventh Day of February, 2012

David J. Kappos
*Director of the United States Patent and Trademark Office*

SEQUENCE LISTING

```
<160> NUMBER OF SEQ ID NOS: 366

<210> SEQ ID NO 1
<211> LENGTH: 4946
<212> TYPE: DNA
<213> ORGANISM: Homo sapiens
<220> FEATURE:
<223> OTHER INFORMATION: AB032969

<400> SEQUENCE: 1

cagcctcagc ccccagatga agatggggat cacagtgaca aagaagatga acagcctcaa     60

gtggtggttt taaaaaaggg agacctgtca gttgaagaag tcatgaaaat taaagcagaa    120

ataaaggctg ccaaagcaga tgaagaacca actccagccg atggaagaat catatatcga    180

aaaccagtca agcatccctc agatgaaaaa tattcaggtt taacagcaag ctcaaaaaag    240

aagaagccaa atgaagatga agtaaatcag gactcggtca aaaagaactc acaaaaacaa    300

attaaaaata gtagcctcct ttcttttgac aacgaagatg aaaatgagta agtgtaaata    360
```

ttttgaattt agtctacttt gaaagtatat ggagtgttca ttaaaatcac atttttttcct 420 attataaaga tactacaagt tctttataga aagtttagga aatagagaaa aaaatttaat 480
aaactacatc tattcatcaa taccccctctg acttaaaatg ccaactctat agaaattagc 540
tagtattaac attttgttat ttcccttgtg tggttgtata tatatgtaaa ttatattttt 600
aagcaaaata catttttttgt gtgtaaacaa aattttataa atacaactgt attgcaaatg 660
ttctttgtcc tgcttctcac ttgacattgc attatgagta ttcttccagg tcagtaaatt 720
tcaaaaacct gacattaata gctacagata atttcataaa catctcattg tatctttttc 780
attagcaata gctccacttt gggtggggga gatgataatg tgccttgtta aaaatacctc 840
cccaactcct gctaagggtg gccatgagac tcagctctgg caagttaaga aatacaggtg 900
gaattctgct tgataaagct gctgggtttt ttgttacaaa aggacagact tggcaaacat 960
gagcctttgc tcttatcttt tcatcctact tggagtgcag agataaaacc tgagtaccag 1020
agccactttt aggcataagg aaggcagcca tgtgctttgg gtcatgttag taaaaagact 1080
cagagcttgg ctccttgctg acatgcctgg aggagctgct acaccagctt ggattgctga 1140
cctctgactt cttggtagtg agaagaataa acactgtgct taattaggcc ttggtcaggt 1200
ttcttttata tgcagccaaa tgcagtccta agtaatacaa taaataactg gtcaaactgt 1260
tactggtgga gggtgtccag gttcttggca ttttggacaa ataattgaac aaaacgcaca 1320
aagcaatgaa tatcctctag aggtttgcca ttggttactt ggcgtacacc ctgtgtaaat 1380
gaagtagtgg cccgtgacct gtctgattgg tgcagaaagt gaccaatcag aggctgaagt 1440
gaagttacaa agttatactc ctgtgtaaat gaggacttgg cctatgacca gtctgattgg 1500
ttgcaggagg ggaccaatca gaggcacttt catttttcat ctgcaatgca gaaaaggcaa 1560
ggggattgca aagggagtag cctctgatcc ttttgttact taggtatgga gaggtggggt 1620
tttccttttg attcagttct aggaagtcaa tgtgaatcag ccttaggttc cctgtctcca 1680
gaccctattc tcctgcctca ttttccccct gagagacgtg atcctcgtaa atctttatgg 1740
gaggctgaga gactgagggt ctttcttctg taactgcttc atgctaactt gggacacagt 1800
ccctacctat tggagatcac gtaactctca ccctgctttg tctaggggag acagggtagc 1860
ttcttgatgg ccggtggtgt cttctcctga aactggctag aaatcttgtc acatgatcat 1920
ctaacttggt ggtctctagg caaaaggaaa tggatttggt taaaagattt aacagatatg 1980
gtccaaaaac caaggcaaat ataatcatta ataatgggct ggccaaggga gggagccatg 2040
aaacccaact tagtgccctt taggtgcccc agctgttgtc atattttaga ggcccagtca 2100
gctagttttc aggtggtgtc ccttactaat cctgattggt tgacatcaaa acagcattct 2160
tcttctagga aaatacataa gccacctgtt tcagcagtta ggagatctag tccccttcga 2220
ttttgcaaag cgaccactgc caaggagcct atccgaattt gtaaggtgac aatactttga 2280
gcaatgttat ccaggctttc cataaaatcc ttggacaagc gttggtaata ggatagggaa 2340
gttgcaatcc cgctaactcc cattcctacc tctgctgtta ttcctagccg ttgtgtctgg 2400
tggttgcagt taaaggtata atgagggatt ggttgttggg agctatatta atttagggac 2460
atacaatatt tctgtctcca gtctaccact tccaccaaag acaaatcaca gcagaaccga 2520
cctaacttca aaataaactg cagtcccata tactgggcct gattacccac acaaagtgca 2580
acaagaatca ttgtccatat agactctcct agattggctt tgctagaaca tttcacaagg 2640
ccatttcagt caaagtcctg agaaagtaac cggtttcaat tgtgccctat tacaaaagaa 2700
aacgtggtta ttaactttat acagacaaat gccatgaatt aagaatattc ataaatagtt 2760

```
tacaaattct ggagaaatta gaatactcaa tacacttaaa gtgtatttca aggctataaa   2820

tagctcaaaa taaaaagatt attcagactc tgaaaaaaca aaaagaagta gcaatatttc   2880

aaacaacaaa agccatacaa attatttcag tcttccatta gttcatttca gtccatgtaa   2940

tcaactcctg ctctacttca tattcatctt tatgaacaca tcagcctttc aattagtgcc   3000

ttggaagttt tctgtctaat ccaatggcac actctccaaa gttaccagaa acctgcattc   3060

aagagttctt ttcatgaact ccaaagaagt aagccttgga ctgtagctga ttataagtca   3120

cttttttttt ttgagaagga tcaaagcaaa acatcaatta tggatgacaa aagtcttaag   3180

acagccataa agacacagtt gacaaatgtg gctatttctg tggcttacaa caatttaaca   3240

taatcattac aacatatatt aagacatatc agaattttag aactctcata caatcctgga   3300

acacatatta acaacaaatc tctatcagta taacccaaag gaagctaaac accacctcac   3360

acttgacaat gtttcctgta taattcaaac attacaaata agcctaatat aagcctaata   3420

tgtcactctt gaacttcagg aagcctaata tccaaaaagt tagtttaagg tcaaaagttt   3480

ttgaattaac ttttttccat tagtatggtc atatctttct tactaatttg taagttatgt   3540

aatttatcaa tttttttttg ttgttctgtt tcccaacctc tatgtcagat aaagaatcac   3600

ccaggccaga cacagtggct catgcttgtg gtcccagcac tttgggaagc caaggtggga   3660

gaattgcttg aagccaggaa tctgagccca gcctgggcga caaagcaata cccctatctc   3720

tacaaaaaat aaaaaatagc caggtgtggc gacacacacc tgtggtccca gctgctcggg   3780

aggctgagcg ggaggatggc ttgggcccag gggttcaacg ctgcagtgag ctgtgattgc   3840

gccactgcac tccagcctgg gcaacagagt aagaactgtc tcaaaaaaaa taaaaaatag   3900

aaataaattt taaaaaaaga attacccata ttctctttgt ttttgtttat tcacattaac   3960

ctttattcta tctggaattt atttgagtat acttttttct caaataatca attgtcctag   4020

aaccatgtgt ttctcattta tttgaaaggc catctagtga gagatttctc caaatgttgg   4080

ggtagggaag ggaggggaag cactttaaag tctgagcctt tagaggtgat tcctcaagac   4140

cctgcttaat cctaacaatt ttcctcatta gtaaaagtca gcccaaactg ggggcttgtt   4200

aagatcctta ccagccacat ccatctgaaa ttatgaattt caaagtatct tacaaatttg   4260

gtgccacatt atctttttta agtttgtttt gttttgtttt tttgagacag agtctcgctc   4320

tgtcacccgg gctggagtgc agtggcgcga tctcagctca ctgcaagctc cgcctcctgg   4380

gttcacacca ttctcttgcc tcggcctccc aagtatctgg gactgcagtc gcccgccacc   4440

acgcccggct aatttttttg tatttttaat agagacgggg tttcactttg ttagccagga   4500

tggtctcaat ctcctgacct catgatccac ctgcctcggc ctcccaaagt gctgggatta   4560

caggcaggag ccaccgcgcc tggccctttt tttaagtttt aagtacctat aaagaacact   4620

gaaaggtgat gtgtgtggat gagctaggaa gacctgaaat aggctctctc taaattaatc   4680

aaattaatcc tgaagccatt ctgcaatact gtctttaatg tatactcact tgttatagaa   4740

gccagggttt tttcccctaa tttgtatcat tgctatatgt gttattgtac caaactacac   4800

tgttttaatt gctgtaaatt ttaatatgtc ttagtatctg ggtgtgggaa tcttgaaagc   4860

atggagtttg tgttattcac cactgtattc tcaaatatca gaagagtatc tggcctacta   4920

agtgcacaat aaacatagtt aaaatg                                        4946
```

<210> SEQ ID NO 2
<211> LENGTH: 60
<212> TYPE: DNA
<213> ORGANISM: Homo sapiens

<220> FEATURE:
<223> OTHER INFORMATION: AB032969

<400> SEQUENCE: 2
taatcctgaa gccattctgc aatactgtct ttaatgtata ctcacttgtt atagaagcca 60

<210> SEQ ID NO 3
<211> LENGTH: 1007
<212> TYPE: DNA
<213> ORGANISM: Homo sapiens
<220> FEATURE:
<223> OTHER INFORMATION: AF005487

<400> SEQUENCE: 3
gaatacagaa tgtgggcaaa ctcgcttctg tgccggccgc cagaaggttt gctgagggca 60
atcactccct ggtgccgggc tccttgaggt tatgcactgg gacatctaga gcctattgtt 120
tgaggaatgc agtcttgcaa gcctgctctg gatcaagcca cagactgaaa cacccccgaa 180
gagcaagcac gtttcttgga gcaggctaag tgtgagtgtc atatcttcaa tgggatgaag 240
cgggtgcagt acctgaacag atacatccat aaacgggagg agaacctgcg cttcgacagc 300
aacgtggagg agttccaggc agttacggaa ctggggcggc ctgtcgcaga gaactggaac 360
agccagaagg gcatcccgga ggagaagcgg gacaagatgg acgactactg cagatacaat 420
tacggggttt tttgagagct tcacagtgca gccgcgagtc catcctaagg tgactgtgta 480
tcctgcaaag acccagcccc tgcatcaccg caaccccctg gtcggctctg tgagtggttt 540
ctatccaggc agcattaaag tcaggtggtt ccagaatggt caggaagaga aggctgcggt 600
ggtctccata ggcctgatcc agaatggaga ttggaccttc cagaccctgg tgatgctgga 660
aacagttcct cggagtggag aggtttacac ctgccaagtg gagcatccaa gcgtgacgag 720
ccctctcaca gtggaatgga gtacacggac tgaatctgca cagagcaaga tgctgagtgg 780
agtcgggggc tttgtgctgg gcctgctctt ccttgggaca gggctgttca tctacttcag 840
gaatcagaaa ggacactctg gacttcagcc aacaggactc ctgcgctgga ctcctgagct 900
gaagtgcaca tgaccacatt caaggaagaa ccttctgcca cagctttgca ggatgaaaag 960
ctttcccact tggctcttat tcttccacaa gagctctctc aggacca 1007

<210> SEQ ID NO 4
<211> LENGTH: 60
<212> TYPE: DNA
<213> ORGANISM: Homo sapiens
<220> FEATURE:
<223> OTHER INFORMATION: AF005487

<400> SEQUENCE: 4
tttgcaggat gaaaagcttt cccacttggc tcttattctt ccacaagagc tctctcagga 60

<210> SEQ ID NO 5
<211> LENGTH: 3200
<212> TYPE: DNA
<213> ORGANISM: Homo sapiens
<220> FEATURE:
<223> OTHER INFORMATION: AF026941

<400> SEQUENCE: 5
caggaagggc catgaagatt aataaagatt tggactcagg gcaaatattt acttagtagc 60
aataactcaa agaattactg ttgaataaat aagccaatta agcagccaat cacgtactat 120
gcggatgcac acaaatgaaa ccctcacttc aacctgaaga cattcgcaca tgagttacgt 180
agagggacct gcaggaagcg gtagagaaaa cataaggctt atgcgtttaa tttccacacc 240

```
aatttcagga tctttgtcac tgacagcagc actaagactt gttaacttta tatagttaag    300
aagaacaagg ctgagcgcga tgactcacgc ctgtaagcct agaactttgg gaggccaaag    360
caggcagact gcttgagccc aggagttcca gaccagcctg ggcaacatgg caacacccca    420
tctctacaaa aaaatacaag aatcagctgg gcgtggtgat gtgttcctgt aatctcagct    480
actcgggagg cagaggcagg aggattgctt gaacccggga ggcagaggtt gtagttagcc    540
gagatctcgc cactgcactc cagtctggac gacagagtga gactcagtct caaataaata    600
aataaataca taaatataag gaaaaaaata aagctgcttt ctcctcttcc tcctctttgg    660
tctcatctgg ctctgctcca ggcatctgcc acaatgtggg tgcttacacc tgctgctttt    720
gctgggaagt tcttgagtgt gttcaggcaa cctctgagct ctctgtggag gagcctggtc    780
ccgctgttct gctggctgag ggcaaccttc tggctgctag ctaccaagag gagaaagcag    840
cagctggtcc tgagagggcc agatgagacc aaagaggagg aagaggaccc tcctctgccc    900
accaccccaa ccagcgtcaa ctatcacttc actcgccagt gcaactacaa atgcggcttc    960
tgtttccaca cagccaaaac atcctttgtg ctgccccttg aggaagcaaa gagaggattg   1020
cttttgctta aggaagctgg tatggagaag atcaactttt caggtggaga gccatttctt   1080
caagaccggg gagaatacct gggcaagttg gtgaggttct gcaaagtaga gttgcggctg   1140
cccagcgtga gcatcgtgag caatggaagc ctgatccggg agaggtggtt ccagaattat   1200
ggtgagtatt tggacattct cgctatctcc tgtgacagct ttgacgagga agtcaatgtc   1260
cttattggcc gtggccaagg aaagaagaac catgtggaaa accttcaaaa gctgaggagg   1320
tggtgtaggg attatagaat ccctttcaag ataaattctg tcattaatcg tttcaacgtg   1380
gaagaggaca tgacggaaca gatcaaagca ctaaaccctg tccgctggaa agtgttccag   1440
tgcctcttaa ttgaaggtga gaattgtgga gaagatgctc taagagaagc agaaagattt   1500
gttattggtg atgaagaatt tgaaagattc ttggagcgcc acaaagaagt gtcctgcttg   1560
gtgcctgaat ctaaccagaa gatgaaagac tcctacctta ttctggatga atatatgcgc   1620
tttctgaact gtagaaaggg acggaaggac ccttccaagt ccatcctgga tgttggtgta   1680
gaagaagcta taaaattcag tggatttgat gaaaagatgt ttctgaagcg aggaggaaaa   1740
tacatatgga gtaaggctga tctgaagctg gattggtaga gcggaaagtg gaacgagact   1800
tcaacacacc agtgggaaaa ctcctagagt aactgccatt gtctgcaata ctatcccgtt   1860
ggtatttccc agtggctgaa aacctgattt tctgctgcac gtggcatctg attacctgtg   1920
gtcactgaac acacgaataa cttggatagc aaatcctgag acaatggaaa accattaact   1980
ttacttcatt ggcttataac cttgttgtta ttgaaacagc acttctgttt ttgagtttgt   2040
tttagctaaa aagaaggaat acacacagga ataatgaccc caaaaatgct tagataaggc   2100
ccctatacac aggacctgac atttagctca atgatgcgtt tgtaagaaat aagctctagt   2160
gatatctgtg ggggcaatat ttaatttgga tttgattttt taaaacaatg tttactgcga   2220
tttctatatt tccattttga aactatttct tgttccaggt ttgttcattt gacagagtca   2280
gtattttttg ccaaatatcc agataaccag ttttcacatc tgagacatta caaagtatct   2340
gcctcaatta tttctgctgg ttataatgct ttttttttt tttgctttta tgccattgca    2400
gtcttgtact ttttactgtg atgtacagaa atagtcaaca gatgtttcca agaacatatg   2460
atatgataat cctaccaatt ttcaagaagt ctctagaaag agataacaca tggaaagacg   2520
gcgtggtgca gcccagccca cggtgcctgt tccatgaatg ctggctacct atgtgtgtgg   2580
tacctgttgt gtccctttct cttcaaagat ccctgagcaa aacaaagata cgctttccat   2640
```

ttgatgatgg agttgacatg gaggcagtgc ttgcattgct ttgttcgcct atcatctggc 2700
cacatgaggc tgtcaagcaa aagaatagga gtgtagttga gtagctggtt ggccctacat 2760
ttctgagaag tgacgttaca ctgggttggc ataagatatc ctaaaatcac gctggaacct 2820
tgggcaagga agaatgtgag caagagtaga gagagtgcct ggatttcatg tcagtgaagc 2880
catgtcacca tatcatattt ttgaatgaac tctgagtcag ttgaaatagg gtaccatcta 2940
ggtcagttta agaagagtca gctcagagaa agcaagcata agggaaaatg tcacgtaaac 3000
tagatcaggg aacaaaatcc tctccttgtg gaaatatccc atgcagtttg ttgatacaac 3060
ttagtatctt attgcctaaa aaaaaatttc ttatcattgt ttcaaaaaag caaaatcatg 3120
gaaaattttt gttgtccagg caaataaaag gtcattttaa tttaaaaaaa aaaaaaaaaa 3180
aaaaaaaaaa aaaaaggcca 3200

<210> SEQ ID NO 6
<211> LENGTH: 60
<212> TYPE: DNA
<213> ORGANISM: Homo sapiens
<220> FEATURE:
<223> OTHER INFORMATION: AF026941

<400> SEQUENCE: 6
atttttgaat gaactctgag tcagttgaaa tagggtacca tctaggtcag tttaagaaga 60

<210> SEQ ID NO 7
<211> LENGTH: 1799
<212> TYPE: DNA
<213> ORGANISM: Homo sapiens
<220> FEATURE:
<223> OTHER INFORMATION: AF035284

<400> SEQUENCE: 7
gcttgaaccg gggaggtgga ggttgcagtg agctgagatc acgccattgt actccagcct 60
gggcgacaga gcaagactcc atttcaaaaa aaaaaaaaaa aaaaaaaatc cactcatata 120
aaaggtgagc tcagctcact ggtccatttc tcagtggctt ctccatcctc atttgcaaac 180
ctcagaggga taaggcagtt gaacctgatg agcaagaatt ataacagcaa ggaaacatta 240
atgcttagaa ttctgagatc cagcacaact cagtctgtgg gagctcagct cgctgcccag 300
ggataggtat gacctatgtc tgccttaggc tgctgggaga tgccattctc cagtttcaga 360
agcaggcagg gcaaaggtca agactgtggt attggggtct tttggctctg aaggatcctg 420
gaaccactga ttttggttta ttccctccag ggtctaaaga gaacaagagg tgctagctct 480
taccaaaaca gatggtagag agagttgctg gctatttaaa aagctctttc atcttttaat 540
tcacctcttc ttttcacctc tttaaccact cctcaggaac agaacacttc taggactggg 600
ggtcttttag ctccataagc aagtgagcag atgggacaag ttagtctttt ctccctagaa 660
acaaagggga tgcccagtgg tttccctttg cttcccaacc taaaatttca agtttaataa 720
aatagcaatt agcagaagtg accaaattgg gagataatta tcagtcatga ggaaagacac 780
agatttcggt cataaagaat gtaagggcta taagtagaaa ctttctataa cctaaatgat 840
gttatagaat tatttttgag caggagcaga aagattaaat atgatcactt catacttcta 900
aatcagaaat aggaagatta aaaccacaga acagtttgtg atttctattg ctggtagcta 960
ggtatcttac tctgtccact cttgttcaag tatctaactc ttctggaaac caaataggct 1020
ttagaagaga ttatcctata ttcctatcag tataatacta aaatgtaact ttttaatcat 1080
ctggttttta aaagataaac agtttagccc atctctccag agagcaaaca taggaatatg 1140
actcaggagc ctcctagggc ttatcatcag ccctcacacc cgcttccccc tccaacccac 1200
agcctttgct tccaggtggc aggattacta ctttgcctct tcagcagcat ctactctagg 1260
catattgatc attttagaca ctgggagaag agaacctcaa actaggagga aaagacagag 1320
cctccactta gttttgggag gggatggcag acagtcaagg agatgagcgt cctaaggcat 1380
gttgggatag ggtcagatgc accacccatg gagaggtttg tcaacacaaa gacatggaag 1440
gttagaggtt tgtcaacaaa aagacatgga aggttaggtt tgtcaacaca aagacatgga 1500
agattagagg tttgtcaaca caaagataca ggaagaatgg gctgcagaag atttagatgt 1560
tttccatttg ggcacatttt acttagctgg agaactaggt ttaaaacagc ctgggtagga 1620
aaattagaag caagctggat gcagtggctc atgcctgtaa tcccaacact tttgggaggt 1680
ccaggcagga ggatcacttg ggcccaggag gtcaagcctg cagcgagctg agatcacacc 1740
actgcactcc agcctggggt gatagaacaa gaccctgtct caaaaaaaaa aaaaaaaaa 1799

<210> SEQ ID NO 8
<211> LENGTH: 60
<212> TYPE: DNA
<213> ORGANISM: Homo sapiens
<220> FEATURE:
<223> OTHER INFORMATION: AF035284

<400> SEQUENCE: 8
caaaaagaca tggaaggtta ggtttgtcaa cacaaagaca tggaagatta gaggtttgtc 60

<210> SEQ ID NO 9
<211> LENGTH: 1380
<212> TYPE: DNA
<213> ORGANISM: Homo sapiens
<220> FEATURE:
<223> OTHER INFORMATION: AF052162

<400> SEQUENCE: 9
gtcaaaggat atttatttat aggccttttt ttttttaata tagaatctga ggctgtttgg 60
gctttgactt aaatttccat caggcctctc tccagcaggt aatccctctc cttccgctgg 120
gtcccctggg gaggtgtgaa ctcaagggcc tagccccaaa acactttttc tgcttttctt 180
aatccttttc cagtcccctc tttttttata aacgttggca gtttgatgtt tctgtttcgg 240
cataacgtaa tccatttcac tgtagcctaa actccagtcc gaggttggat attgttcaaa 300
tgagcagggc ccgagctgga agcgcaaggc agccgccgcc gtgccgctcc tcccttgccc 360
tcaggccagg tccctgctgg aagcggctgc atcttcctgt cagccctggt ttccatggtg 420
actggcgtca cgcagccacc cgagtatggc tgaccttcct gcagagagag gagccgcagt 480
cttttgcttg tggaaggaga cgctgggctg tgcggtgcgg agggtgatga ggatgtctgg 540
tgacagccgt gcggacacca ctcctctctg cagcactgcc tcccagcgcc agggtcgcgg 600
gcacatccca ctgagagcgg gggtcctgcc ccatcttaga gtcaaaggca gaggggcttc 660
caggccctgg atggggtatt ttggtgtcac ctgaagtccc tctgacatca ccttgtttca 720
tcatttttta tgacagaatt agaaacccat ccttcaagca caataatcat cacagacttg 780
agtttgcttc ctaaagcaaa ggctccgggt ttgtttggaa aattttttttg atttctgaaa 840 tgaattgatt tttatatttg gggcatctct atagaaagtg accaccaagg ccagtaagta 900
cgggaaaaaa tgtttactaa cttcctcaga gattcgtgat acgcgtttct ccactgacag 960
acatttaaaa acaaccttca gctccgtttc aatcaatcac ctcgacttgt tttttagcat 1020
ggacactgcc agcaggacag acagggatgg agtaaaccga agtcaatttc agggctcttg 1080
gcgtgttgga cacagaagaa atcctagtgc agcctttggt agctaacagt cactgatttt 1140
ataattggag aatgcgtaaa gattcatttt tcaaggagaa gagcctgcaa atggccaatg 1200
aaggaggtaa ataaactaag atattccgag ggaagggacc caggccacct cccttccgca 1260
ggtctgcaga tgaagggttt tttgaatgaa atgccactgt gcattttcag aaaaaaaaat 1320
ctctgataaa cagactttga atggaaaaaa aaaaaaaaaa aaaaaaaaaa aaaaaaaaaa 1380

<210> SEQ ID NO 10
<211> LENGTH: 60
<212> TYPE: DNA
<213> ORGANISM: Homo sapiens
<220> FEATURE:
<223> OTHER INFORMATION: AF052162

<400> SEQUENCE: 10
cagtaagtac gggaaaaaat gtttactaac ttcctcagag attcgtgata cgcgtttctc 60

<210> SEQ ID NO 11
<211> LENGTH: 1722
<212> TYPE: DNA
<213> ORGANISM: Homo sapiens
<220> FEATURE:
<223> OTHER INFORMATION: AF055033

<400> SEQUENCE: 11
ggggaaaaga gctaggaaag agctgcaaag cagtgtgggc tttttccctt tttttgctcc 60
ttttcattac ccctcctccg ttttcaccct tctccggact tcgcgtagaa cctgcgaatt 120
tcgaagagga ggtggcaaag tgggagaaaa gaggtgttag ggtttggggt ttttttgttt 180
ttgtttttgt tttttaattt cttgatttca acattttctc ccaccctctc ggctgcagcc 240
aacgcctctt acctgttctg cggcgccgcg caccgctggc agctgagggt tagaaagcgg 300
ggtgtatttt agattttaag caaaaatttt aaagataaat ccatttttct ctcccacccc 360
caacgccatc tccactgcat ccgatctcat tatttcggtg gttgcttggg ggtgaacaat 420
tttgtggctt tttttcccct ataattctga cccgctcagg cttgagggtt tctccggcct 480
ccgctcactg cgtgcacctg gcgctgccct gcttccccca acctgttgca aggctttaat 540
tcttgcaact gggacctgct cgcaggcacc ccagccctcc acctctctct acatttttgc 600
aagtgtctgg gggagggcac ctgctctacc tgccagaaat tttaaaacaa aaacaaaaac 660
aaaaaaatct ccgggggccc tcttggcccc tttatccctg cactctcgct ctcctgcccc 720
accccgaggt aaagggggcg actaagagaa gatggtgttg ctcaccgcgg tcctcctgct 780
gctggccgcc tatgcggggc cggcccagag cctgggctcc ttcgtgcact gcgagccctg 840
cgacgagaaa gccctctcca tgtgcccccc cagccccctg ggctgcgagc tggtcaagga 900
gccgggctgc ggctgctgca tgacctgcgc cctggccgag gggcagtcgt gcggcgtcta 960
caccgagcgc tgcgcccagg ggctgcgctg cctcccccgg caggacgagg agaagccgct 1020
gcacgccctg ctgcacggcc gcggggtttg cctcaacgaa aagagctacc gcgagcaagt 1080
caagatcgag agagactccc gtgagcacga ggagcccacc acctctgaga tggccgagga 1140
gacctactcc cccaagatct tccggcccaa acacacccgc atctccgagc tgaaggctga 1200
agcagtgaag aaggaccgca gaaagaagct gacccagtcc aagtttgtcg gggagccga 1260 gaacactgcc cacccccgga tcatctctgc acctgagatg agacaggagt ctgagcaggg 1320
cccctgccgc agacacatgg aggcttccct gcaggagctc aaagccagcc cacgcatggt 1380
gccccgtgct gtgtacctgc ccaattgtga ccgcaaagga ttctacaaga gaaagcagtg 1440
caaaccttcc cgtggccgca agcgtggcat ctgctggtgc gtggacaagt acgggatgaa 1500
gctgccaggc atggagtacg ttgacgggga ctttcagtgc cacaccttcg acagcagcaa 1560
cgttgagtga tgcgtccccc cccaaccttt ccctcacccc ctcccacccc cagccccgac 1620
tccagccagc gcctccctcc accccaggac gccactcatt tcatctcatt taagggaaaa 1680
atatatatct atctatttga ggaaaaaaaa aaaaaaaaaa aa 1722

<210> SEQ ID NO 12
<211> LENGTH: 60
<212> TYPE: DNA
<213> ORGANISM: Homo sapiens
<220> FEATURE:
<223> OTHER INFORMATION: AF055033

<400> SEQUENCE: 12
tccaccccag gacgccactc atttcatctc atttaaggga aaaatatata tctatctatt 60

<210> SEQ ID NO 13
<211> LENGTH: 1411
<212> TYPE: DNA
<213> ORGANISM: Homo sapiens
<220> FEATURE:
<223> OTHER INFORMATION: AK001166

<400> SEQUENCE: 13
aaacaaagag atgccacccc tgtgtgatgg ctttggtacc cgaacactga tggttcagac 60
attttcccgt tgcatcttgt gttccaagga tgaagtggac ttggatgagt tattagctgc 120
tagattggta acgtttctga tggacaatta ccaggaaatt ctgaaagtcc ctttggcctt 180
gcagacctct atagaggagc gtgtggctca tctacgaaga gtccagataa aatacccagg 240
agctgatatg gatatcactt tatctgctcc atcattttgc cgtcaaatta gtccagagga 300
atttgaatat caaagatcat atggctctca ggaacctctg gcagccttgt tggaggaagt 360
cataacagat gccaaactct ccaacaaaga gaaaaagaag aaactgaagc agtttcagaa 420
atcctatcct gaagtctatc aagaacgatt tcctacacca gaaagtgcag cacttctgtt 480
tcctgaaaaa cccaaaccga aaccacagct gctaatgtgg gcactaaaga agcctttcca 540
accatttcaa agaactagaa gttttcgaat gtaataatac ttccacagca acaggtgcta 600
gagaccactg ttgttgtttt gagtgaatgg tggttaggag aaagactttg gtggtggaag 660
aaagaaaagc ataaaacaaa gactactgaa atatagataa agattgcctt agtttttaaa 720
aatgtttggc cattagtatt tttataaaac tcaatgctag ttttaagtgt ataaattggt 780
taaaatttat gagtcaaata tatagtgata atgttaacat gtttgtaatt gctacagaat 840
ttaagggtat ttttatctct gtgctttctt tttcatggtg tttattaaat aattgtgtat 900
atacatccta gctactgata tctttattat agccttaaga cttaatttta agtcttaaaa 960
atagcgtgta tacttgaata agaaagacac tgggtactgt tactgtgatg ctattgactt 1020
agtagccaat tatcatttct cctgtataaa ttccagtttt tattgctgca cataaatttt 1080
ttaatgtctt atattgtgat agctatgtct tttattgcag atttattgga tgttatgaca 1140
gattttacta aagctagtgt ttttataaca tatatattag ttgatgttta cctataagtg 1200
gagtagattt tcatctgcct gcaatggtat aatttcagtc ttagctaaaa atggaaagtt 1260
gaactggata aattctttgg gtacccttag acctctgatt ctaagtcaaa tgcaaatggg 1320
ttaaataaaa tgagactact tcctttataa atatattttc atccttttga aagtaagtga 1380
aatgtaaata aacttatttt ttttaaaaat g 1411

<210> SEQ ID NO 14
<211> LENGTH: 60
<212> TYPE: DNA
<213> ORGANISM: Homo sapiens
<220> FEATURE:
<223> OTHER INFORMATION: AK001166

<400> SEQUENCE: 14
acccttagac ctctgattct aagtcaaatg caaatgggtt aaataaaatg agactacttc 60

<210> SEQ ID NO 15
<211> LENGTH: 2352
<212> TYPE: DNA
<213> ORGANISM: Homo sapiens
<220> FEATURE:
<223> OTHER INFORMATION: AL049367

<400> SEQUENCE: 15
ggcaaacccc ttttaaaatc taatgtctgg gctttgagta ttagctcatt tagggtggac 60
aaatgcatta ctgttttcaa actgctcaca tttattcagt atttctccaa gttgctatct 120
actcagcctt atgaatgccc ctcgcttttc taaggccatg tgaaaatcac ggcactgccc 180
ttagccttgt gtcatctgct ttttcgttct gcgatatgcc cagttcccaa atcaattata 240
ggtacctgtt taggagagag gaagatttta cctctcaaag ggtgagattt gaaatttaca 300
ctaaaaagac aactttacat ttaatgcttc acttaatgag acattctttt ttttataagt 360
ctatttttct actcagtttc agaacactaa tctgattttc actctgattt ttaacgtttc 420
tttaaatatt tataatgtag cttctttcaa aatattttca tgaaaaatta cttttattat 480
accattatgt gcatgttatt ggtagcaggc atagtttatt atttagtact gaaacatgct 540
cttttaccta acagtaaaca agtatgtttt gatatatatc tgttaatatg cttatagtgg 600
taagaaatgg acttgaggtc ccaggagatt tcattttatt caccctggtc agatacaata 660
aaggctatga gtataaatac ataacttcct aaccaggtgt agggcatgtt catgaatatc 720
aaatcttttg atgctggacc caagagagga aaagttgtag ctaaatgttg atttacttat 780
aactagacgt ctatgtgaga aaatatatgt atacatatat atgatatgca gaagtcactt 840
tttttatcag gctttattct ccttacaaag ccacagttta actgtctgca acagttggtt 900
tatgttaatg atagacaaat acccagtgtt tgttactttt tccaactacc actgtaatga 960
taatctttct cacgtatata catgcaactt cttggcttca tttccatgaa gctgtttcaa 1020
tatattcagt atactttgtc cttaatgctg cttctgttaa cagtgatctc tttctttttt 1080
tcattcttat atcttcatta gttcatcata aatctgtcca gttgaggcct caggaccacg 1140
gcatgatttc atgactccga agtattttac agaaacattt tttaaataag ggaaatattt 1200
tatataccag atggttcaca agtgatggct catagctagt tttttttttt tcttctaaaa 1260
aatgtcaggt ttttaaaatc atttacctta ttaaaatgaa aagtgccata cttaactttt 1320
aaaggaaaga cctgacttgc tttttctcta tttagactgt ttttgtactt tactaatctt 1380
taaactatca ggaaaaaaac caaaacttta taccaatgat ttagtaattt tgaggcatag 1440
ggtagcttac gtagtggagg atgtgccaaa tattctcttc aaatgccacc ttctcaattt 1500
ataactaaaa tagtgttatc tgactaattc ctctgaattt tgatgtaaga tctatatagg 1560
cccccaaaat gatcgtagta catgccagtc atttctcagt gaaataaata caataccaga 1620
gtacattatg ggttttattg ctttctttta tggtagacct gttaatgggg aaaaaataca 1680
tcaaatcaaa tagaatctta tatctgtatg ttaaaataga gcacttacct gaagtcagtg 1740
gcctggatca tagccctgga tcatttccca gtctgtcctg tgctgtgtga ccttggacaa 1800
ggcgcttcat ctctctgggc ctctatttct ccatttgtaa aacaagtggc tgcagtagat 1860
gatggctgag agcccttcct gttcccagat gccttggtcc aaagacccca cccctctgct 1920
ggtcctgcca acgtgttggt gctataagct gcttcagata taaaattggt ttatctataa 1980
tgtttgttca tttaatagct tctaaaaggc ctttttgtta tacagtgctt tttttctagt 2040
tttatggact tgattactgt aataatgtct tgtttttagc catgtaacta caaacagata 2100
ttctcttgat gtcttagtaa atttgcattt gatatatcat tgatgagatt ttgttgttat 2160
gtaatattct ttggctacgc atctgtccag catcttatta accataatac tgtgatcatt 2220
atttggaaat atgtcctatg gaaagaataa aagcatgtac ttcacagcta gcatgttcac 2280
agatttgaaa gaagtttcat taaaagcacc attgctttct gtaaaaaaaa aaaaaaaaaa 2340
aaaaaaaaaa aa 2352

<210> SEQ ID NO 16
<211> LENGTH: 60
<212> TYPE: DNA
<213> ORGANISM: Homo sapiens
<220> FEATURE:
<223> OTHER INFORMATION: AL049367

<400> SEQUENCE: 16
atttggaaat atgtcctatg gaaagaataa aagcatgtac ttcacagcta gcatgttcac 60

<210> SEQ ID NO 17
<211> LENGTH: 1130
<212> TYPE: DNA
<213> ORGANISM: Homo sapiens
<220> FEATURE:
<223> OTHER INFORMATION: AL080235

<400> SEQUENCE: 17
ggtcgccgca ccggccgcct ccggcccgcc gccgccccca gcgccgccgc cgccaccgcc 60
ggggcgccca ccgcgctgcc agcctacccc gcggccgagc cgcccgggcc gctgtggctg 120
cagggcgagc cgctgcattt ctgctgccta gacttcagcc tggaggagct gcagggcgag 180
ccgggctggc ggctgaaccg taagcccatt gagtccacgc tggtggcctg cttcatgacc 240
ctggtcatcg tggtgtggag cgtggccgcc ctcatctggc cggtgcccat catcgccggc 300
ttcctgccca acggcatgga acagcgccgg accaccgcca gcaccaccgc agccaccccc 360
gccgcagtgc ccgcagggac caccgcagcc gccgccgccg ccgccgctgc cgccgccgcc 420
gcggccgtca cttcgggggt ggcgaccaag tgacccgctc cgctcctccc tgtgtccgtc 480
ctgtgtccgc gcgcgcgggt gcctttcccg ccggggactc ggccggtgtg cttcgtgctg 540
tagttatcgt tagttcctct tcccgagatg gggccgccga gagaccccag cgcctttgaa 600
aagcaaggtt tgtgctgcgc ttccagttcc gaaaagcaga tgtttaagcc cttggactga 660
gggtgggatc gcagctccga agacggagag gagggaaatg gggccctttc ccctctattg 720
catccccctg cccgactcct tccccgcacc cacgtgccct agattcatgg cagaaaatga 780
ccaaatcctg tgtatttgtt ttatatattt aataactgtt ttaaatgaaa gttttagtaa 840
aaaaaataca aaacaaaaag attaaattgc tattgctgta gtaagagaag ctctttgtat 900
ctgaacatag ttgtatttga aatttgtggt tttttaattt atttaaaatt ggggggaggg 960
catgggaagg atttaacacc gatatattgt taccgctgaa aatgaacttt atgaaccttt 1020
tccaagttga tctatccagt gacgtggcct ggtgggcgtt tcttcttgta cttatgtggt 1080
tttttggctt ttaatacaga cattttcctc caaaaaaaaa aaaaaaaagg 1130

<210> SEQ ID NO 18
<211> LENGTH: 60
<212> TYPE: DNA
<213> ORGANISM: Homo sapiens
<220> FEATURE:
<223> OTHER INFORMATION: AL080235

<400> SEQUENCE: 18
ctttgaaaag caaggtttgt gctgcgcttc cagttccgaa aagcagatgt ttaagccctt 60

<210> SEQ ID NO 19
<211> LENGTH: 2498
<212> TYPE: DNA
<213> ORGANISM: Homo sapiens
<220> FEATURE:
<223> OTHER INFORMATION: AL137540

<400> SEQUENCE: 19
gctgaaacga cagtcttgtc cctgtcagag aaatgacctg aacgaagagc ctcaacattt 60
tacacactat gcaatctatg atttcattgt caagggcagc tgcttctgca atggccacgc 120
tgatcaatgc atacctgttc atggcttcag acctgtcaag gccccaggaa cattccacat 180
ggtccatggg aagtgtatgt gtaagcacaa cacagcaggc agccactgcc agcactgtgc 240
cccgttatac aatgaccggc catgggaggc agctgatggc aaaacggggg ctcccaacga 300
gtgcagaacc tgcaagtgta atgggcatgc tgatacctgt cacttcgacg ttaatgtgtg 360
ggaggcatca gggaatcgta gtggtggtgt ctgtgatgac tgtcagcaca acacagaagg 420
acagtattgc cagaggtgca agccaggctt ctatcgtgac ctgcggagac ccttctcagc 480
tccagatgct tgcaaaccgt gttcctgcca tccagtagga tcagctgtcc ttcctgccaa 540
ctcagtgacc ttctgcgacc ccagcaatgg tgactgccct tgcaagcctg ggtggcaggg 600
gcgacgttgt gacaggtgca tggtgggata ctggggcttc ggagactatg gctgtcgacc 660
atgtgactgt gcggggagct gtgaccctat caccggagac tgcatcagca gccacacaga 720
catagactgg tatcatgaag ttcctgactt ccgtcccgtg cacaataaga gcgaaccagc 780
ctgggagtgg gaggatgcgc aggggttttc tgcacttcta cactcaggta aatgcgaatg 840
taaggaacag acattaggaa atgccaaggc attctgtgga atgaaatatt catatgtgct 900
aaaaataaag attttatcag ctcatgataa aggtactcat gttgaggtca atgtgaagat 960
taaaaaggtc ttaaaatcta ccaaactgaa gattttccga ggaaagcgaa cattatatcc 1020
agaatcatgg acggacagag gatgcacttg tccaatcctc aatcctggtt tggaatacct 1080
tgtagcagga catgaggata taagaacagg caaactaatt gtgaatatga aaagctttgt 1140
ccagcactgg aaaccttctc ttggaagaaa agtcatggat attttaaaaa gagagtgcaa 1200
gtagcattaa gatggatagc acataatggc acttgtctat gtacaaaaca caaactttag 1260
agcaagaaga cctcagacag gaaactggaa ttttttaaag tgccaaaaca tatagaaatg 1320
tttgaatgca tgggtcttat ctaacttatc tcttctggac ccatgtttaa atacagtttt 1380
atttcatgaa gagaaatgaa aacccctaca ctgatatctg ttttctatgg gactgattct 1440
gaaattctta actattaaga atattttaat agcagcatga catttagcag taatccatta 1500
agggcagtac ctctaacaag gacgccttcc agcttcagcg atgttactta cgtttgatgc 1560
tacttaaagt aatgaatgac gttttaagga atccctaacc ctactatcag aaaaggtgtt 1620
tgttaaagag ccttctcttg tgtgttacgc atgaactttg gtctgtaggt gttaaatgga 1680
acctctccat gtgtatatag tatttccttg tataaagcac tttactacct accacttgtg 1740
ttgtgaacgt ttggtgactg ctgttgaaag aaggaaaagg gtgtgtgaga aagcctactg 1800
aagcagcagc actgccacta catgtggaca aaagtgacca tataaaagaa gttgtgctat 1860
ttaactctga atacttggag aaactaggtg aagatgcaac cagaaaggag aatatgtatg 1920
cgtgaagtct cagctttgag ctggaggcta gattccaaga tgacagccat gatgaaactt 1980
tttaaaaaac taaaccagaa gagactttaa aataagagaa agaaatcata aatgtagaca 2040
tatgcttggc taaaggggaa atggacttta aattttaaag agctcatttg caatgcactt 2100
gtatacactt caaaaattat tgtagacaca gaatttgtta tatttttgtg cttagtattt 2160
aaacctgaac attgaaacag ttttcctcct tgtctttctt aacagtaata gtcattatat 2220
ttacctgttt tttaacacaa tgtatgtgat agtcaaaaaa tcacagtttt tcattattat 2280
tcatcttctg tacccacgca taaccactat acatagtttc ttttgtactt gaatatacaa 2340
aacatgaaca cagtgccata tgaataattt cacatacaga accttttttt ctctgaagtc 2400
ctgtggactt gcaaatatat atatatattg ctttgttaat ttgtttttat atttcatata 2460
tgtaataaag gaatatgatc tgaaaaaaaa aaaaaaaa 2498

<210> SEQ ID NO 20
<211> LENGTH: 60
<212> TYPE: DNA
<213> ORGANISM: Homo sapiens
<220> FEATURE:
<223> OTHER INFORMATION: AL137540

<400> SEQUENCE: 20
tggaggctag attccaagat gacagccatg atgaaacttt ttaaaaaact aaaccagaag 60

<210> SEQ ID NO 21
<211> LENGTH: 914
<212> TYPE: DNA
<213> ORGANISM: Homo sapiens
<220> FEATURE:
<223> OTHER INFORMATION: AL160131

<400> SEQUENCE: 21
cgcaccgcag gagcaacggt tggtcctgcg gctgtgatgt cggtgttgag gcccctggac 60
aagctgcccg gcctgaacac ggccaccatc ttgctggtgg gcacggagga tgctcttctg 120
cagcagctgg cggactcgat gctcaaagag gactgcgcct ccgagctgaa ggtccacttg 180
gcaaagtccc tccctttgcc ctccagtgtg aatcggcccc gaattgacct gatcgtgttt 240
gtggttaatc ttcacagcaa atacagtctc cagaacacag aggagtccct gcgccatgtg 300
gatgccagct tcttcttggg gaaggtgtgt ttcctcgcca caggtgctgg gcgggagagc 360
cactgcagca ttcaccggca caccgtggtg aagctggccc acacctatca aagccccctg 420
ctctactgtg acctggaggt ggaaggcttt agggccacca tggcgcagcg cctggtgcgc 480
gtgctgcaga tctgtgctgg ccacgtgccc ggtgtctcag ctctgaacct gctgtccctg 540
ctgagaagct ctgagggccc ctccctggag gacctgtgag ggtggctggc ccctgggctg 600
ccccttctca tggcttcgtg ctgactccat aaacattctc tgttgaggat gtccagtcag 660
ggcttgacag gcccaggctc agcccgccgt ggctgggaag gttccctgca gtgccagtgc 720
tgcagcaggg agagctgggc agaagcagcg agggggccca gctggcgaga ctgtagcccc 780
ctcccactcc cacactcact cttgcagagc ctgtgtcttt aagcagctgg cgtgttacat 840
ctccatttaa ggtttccttt gaacaaaagg tctgtggcta aaaaaagttt aaaaatcact 900
ggtctcattc acca 914

<210> SEQ ID NO 22
<211> LENGTH: 60
<212> TYPE: DNA
<213> ORGANISM: Homo sapiens
<220> FEATURE:
<223> OTHER INFORMATION: AL160131

<400> SEQUENCE: 22
agctggcgtg ttacatctcc atttaaggtt tcctttgaac aaaaggtctg tggctaaaaa 60

<210> SEQ ID NO 23
<211> LENGTH: 4753
<212> TYPE: DNA
<213> ORGANISM: Homo sapiens
<220> FEATURE:
<223> OTHER INFORMATION: D13642

<400> SEQUENCE: 23
cttcaatcaa gtagccttcc cactgcagta cacacccagg aaatttgtca tccaccctga 60
gagtaacaac cttattatca ttgaaacgga ccacaatgcc tacactgagg ccacgaaagc 120
tcagagaaag cagcagatgg cagaggaaat ggtggaagca gcaggggagg atgagcggga 180
gctggccgca gagatggcag cagcattcct caatgaaaac ctccctgaat ccatctttgg 240
agctcccaag gctggcaatg ggcagtgggc ctctgtgatc cgagtgatga atcccattca 300
agggaacaca ctggaccttg tccagctgga acagaatgag gcagctttta gtgtggctgt 360
gtgcaggttt tccaacactg gtgaagactg gtatgtgctg gtgggtgtgg ccaaggacct 420
gatactaaac cccccgatctg tggcaggggg cttcgtctat acttacaagc ttgtgaacaa 480
tggggaaaaa ctggagtttt tgcacaagac tcctgtggaa gaggtccctg ctgctattgc 540
cccattccag gggagggtgt tgattggtgt ggggaagctg ttgcgtgtct atgacctggg 600
aaagaagaag ttactccgaa aatgtgagaa taagcatatt gccaattata tctctgggat 660
ccagactatt ggacataggg taattgtatc tgatgtccaa gaaagtttca tctgggttcg 720
ctacaagcgt aatgaaaacc agcttatcat ctttgctgat gatacctacc cccgatgggt 780
cactacagcc agcctcctgg actatgacac tgtggctggg gcagacaagt ttggcaacat 840
atgtgtggtg aggctcccac ctaacaccaa tgatgaagta gatgaggatc ctacaggaaa 900
caaagccctg tgggaccgtg gcttgctcaa tggggcctcc cagaaggcag aggtgatcat 960
gaactaccat gtcggggaga cggtgctgtc cttgcagaag accacgctga tccctggagg 1020
ctcagaatca cttgtctata ccaccttgtc tggaggaatt ggcatccttg tgccattcac 1080
gtcccatgag gaccatgact tcttccagca tgtggaaatg cacctgcggt ctgaacatcc 1140
ccctctctgt gggcgggacc acctcagctt tcgctcctac tacttccctg tgaagaatgt 1200
gattgatgga gacctctgtg agcagttcaa ttccatggaa cccaacaaac aaaagaacgt 1260
ctctgaagaa ctggaccgaa ccccacccga agtgtccaag aaactcgagg atatccggac 1320
ccgctacgcc ttctgagccc tcctttcccg gtggggcttg ccagagactg tgtgttttgt 1380
ttcccccacc accatcactg ccacctggct tctgccatgt ggcaggaggg tgactggata 1440
attaagactg cattatgaaa gtcaacagct ctttcccctc agctcttctc ctggaatgac 1500
tggcttcccc tcaaattggc actgagattt gctacacttc tccccacctg gtacatgata 1560
catgacccca ggttccagtg tagaacctga gtcccccatt ccccaaagcc atccctgcat 1620
tgatatgtct tgactctcct gtctactttt gcacacaccc ttaattttta attggttttc 1680

-continued

```
ttgtaaatac agttttgtac aatgttatct ctgtgggagg aaggaggcag gctgtggtgg   1740
gactgggtag ggtatagtat cactcctgag ttccactgct ctagaatcta accagaaata   1800
gaaacctagt ttttaaggtg actggcatcc atgtgtcttg ttctggagat gaggatgtag   1860
gtgggaggtt tgaacccaag ttagagcagg aagaactgag tagactcctt ccttccagat   1920
accgacttgg acttgcggca ctctgtggct ccccaccccc aggtctgtgg tggtttcttt   1980
gtttttttcct ggttcttttt gctgtgctga tgaaacatga cctcaataac catgtgtata   2040
cccacccctc ttcccactgg gtattgagga agggtggctg attcttcctc ctcttctact   2100
ctgaggatgt tagtatgggg attttagcat gaattccagc tggggagtct taacagatgc   2160
ccctttact gatagagcac ctaaagcgat ctttggctcc ataggaccat aggaagggtc   2220
agtacagaag aacctagata ctgccctgcc cctgagaact gtgtatatgt ggggcctgtc   2280
tgcagcaccc atctcaggtg ggttccagag ggcctttagg gtataatgag agcctgttag   2340
gtggaagagg cccagttcca gaaatgttcc agcccacccc tgagaattcc tcctgtttag   2400
ttgtgtggga agccctcgtc ttccaggctg tccttgcgcc ttgaacctgg agaagtgagc   2460
tcactgttct caatacttca caaatgtaaa actttctttc gtctgcatgt gctcagccat   2520
ctaaattgag caaatgatct ggtgagcact gggttagaat caggaatggt ggaatacaat   2580
ctgaacctct cagagcccag aacagagggt tcctgacact gtgacactgt ctcctggaac   2640
taagtatctc ttgaatcatg acttggtttt agatcagtca agagagaccc aggttttgcc   2700
aggaatcgaa tccctaaata acatgttttt ttctcactta gctcatgaat ttgcatagta   2760
gacagtagtt ctgaattaga ttttgaaaac ctaatttcag ggctcatttt ttcctgtggc   2820
cctaaatcca ttctatcaaa ttgtgtgata ctgacatgca gtcatctgag gaactcagcg   2880
tagatacttg agcagctcct cgcctctttt ctaactcaag tttgactaaa atacatacac   2940
tccgtacaga aggtaggggg ttatgtaaga aaggaaaacc taatctatgg aatcaggagt   3000
tgtcaccacc gagcttcctc tggaagtctg cccatcagct tgcttgttct ctgttaagag   3060
gaagggctag gacaaggatt tgggcttgaa tatgtggaaa ggaattttca tagttgttgc   3120
tgcaggacct acaaaagttt aaaattagat tggatgtgac tcaatgacaa gtcccatctg   3180
tgtaattgtt aaggggacct gattgactcc tgtggtttga ttgagcaacc aggtaaatag   3240
agacctctct ccagctttgg caaaacccat cagaggctgc tgcagaactc agacagaggg   3300
atctgccctt gggtttgctt ccatcctgtt ccattgctaa gcccttgtga cttggatcct   3360
aggactgaaa agtttttagc tgcctcagct ttcccctgac cttactggca gaggttctgc   3420
agatgtttcc tttggaagat ctcttgccaa gaatagcatt cctttggagg aggggggttc   3480
tagttggaat gttgcttttc ttggttagtg taaatgtatt gctagtgaga cagctgccgg   3540
cgctggaaaa ggctcgtctc acagggagag tgctggtccc cagaatgtgt gctgttccca   3600
cgctgctgcc tttcttgagc ttgttagagg aaagccagaa aggcattcag atgggatcag   3660
tctggctttc aaattttttt taattcctaa gttctgtttt attttttaat tttttaaaaa   3720
aaattttatt agagacagtc tctctctctt gcctagctgg gagtgcagtg gagtgatcat   3780
agctcactga ggcttgaact cctgggctcg agcaatccac ctcagcctcc agagtagggg   3840
agactacaga tgtgtgccac catactcagc tagtttttaa actttcgtag agacagggtc   3900
tccctgtgtt gcccaggctg gcctcgaact cctgacctca aaaaatcttc ctgccttggc   3960
ctcccagcgc tttgagaggc tgaggcagga ggatcccttg agcccaggag tttgagacca   4020
gcctgggcaa catgacaaaa ccccatctct ccaaaaatac aaaaattggc caggcatggt   4080
```

ggtgcacact tgtagtccca gtaattaggg ggctgagaca ggaggatcac ttcagcctat 4140
gagtttgagg ctgcagtgag ctgtgattgc gccactacac tccagcctgg atgacaggac 4200
gaaacctgtc tcaaaaacac caaaaaacaa aaaccggtct cctggggtca tggtagcaca 4260
aacgcacatg actgagtgct caggggttct gaggcttgtc cgctgacctg gggctctggc 4320
cctgggagat ctgggggacc tgctgtccta tatgtgatgc tttgaaagaa aggggcatca 4380
ttccaagcca agaggcccca gagagggcac cgtggggtgt tcaggcttct gtgaggcccc 4440
agtgagatcc tgtggctgtg cccccatcac ctccacccac tctgccctcc cactagctgc 4500
ccaacggatg aatcaacgcc ttggcagagt tttccagcag ggccttgcag agagtgtgtg 4560
tgacctgtgt ggccactgcc ttggggacgg gtgaggagtt agcctggaac attccagcgt 4620
gggcattatt gtcctgttgc aagttcaggg caaaaccagg aatccagttt tgtcgatcca 4680
attgagaaaa catttcatga acaactactt gtggcatgca ttggcactcg gaataaagcg 4740
cactattgtc act 4753

<210> SEQ ID NO 24
<211> LENGTH: 60
<212> TYPE: DNA
<213> ORGANISM: Homo sapiens
<220> FEATURE:
<223> OTHER INFORMATION: D13642

<400> SEQUENCE: 24
aaaccaggaa tccagttttg tcgatccaat tgagaaaaca tttcatgaac aactacttgt 60

<210> SEQ ID NO 25
<211> LENGTH: 2591
<212> TYPE: DNA
<213> ORGANISM: Homo sapiens
<220> FEATURE:
<223> OTHER INFORMATION: D25328

<400> SEQUENCE: 25
cccggacgtg cggctcccct cggcctcctc gccatggacg cggacgactc ccgggccccc 60
aagggctcct tgcggaagtt cctggagcac ctctccgggg ccggcaaggc catcggcgtg 120
ctgaccagcg gcggggatgc tcaaggtatg aacgctgccg tccgtgccgt ggtgcgcatg 180
ggtatctacg tgggggccaa ggtgtacttc atctacgagg gctaccaggg catggtggac 240
ggaggctcaa acatcgcaga ggccgactgg gagagtgtct ccagcatcct gcaagtgggc 300
gggacgatca ttggcagtgc gcggtgccag gccttccgca cgcgggaagg ccgcctgaag 360
gctgcttgca acctgctgca gcgcggcatc accaacctgt gtgtgatcgg cggggacggg 420
agcctcaccg gggccaacct cttccggaag gagtggagtg ggctgctgga ggagctggcc 480
aggaacggcc agatcgataa ggaggccgtg cagaagtacg cctacctcaa cgtggtgggc 540
atggtgggct ccatcgacaa tgatttctgc ggcaccgaca tgaccatcgg cacggactcc 600
gccctgcaca ggatcatcga ggtcgtcgac gccatcatga ccacggccca gagccaccag 660
aggaccttcg ttctggaggt gatgggacga cactgtgggt acctggccct ggtgagtgcc 720
ttggcctgcg gtgcggactg ggtgttcctt ccagaatctc caccagagga aggctgggag 780
gagcagatgt gtgtcaaact ctcggagaac cgtgcccgga aaaaaaggct gaatattatt 840
attgtggctg aaggagcaat tgatacccaa aataaaccca tcacctctga gaaaatcaaa 900
gagcttgtcg tcacgcagct gggctatgac acacgtgtga ccatcctcgg gcacgtgcag 960
agaggaggga ccccttcggc attcgacagg atcttggcca gccgcatggg agtggaggca 1020
gtcatcgcct tgctagaggc caccccggac accccagctt gcgtcgtgtc actgaacggg 1080
aaccacgccg tgcgcctgcc gctgatggag tgcgtgcaga tgactcagga tgtgcagaag 1140
gcgatggacg agaggagatt tcaagatgcg gttcgactcc gagggaggag ctttgcgggc 1200
aacctgaaca cctacaagcg acttgccatc aagctgccgg atgatcagat cccaaagacc 1260
aattgcaacg tagctgtcat caacgtgggg gcacccgcgg ctgggatgaa cgcggccgta 1320
cgctcagctg tgcgcgtggg cattgccgac ggccacagga tgctcgccat ctatgatggc 1380
tttgacggct tcgccaaggg ccagatcaaa gaaatcggct ggacagatgt cgggggctgg 1440
accggccaag gaggctccat tcttgggaca aaacgcgttc tcccggggaa gtacttggaa 1500
gagatcgcca cacagatgcg cacgcacagc atcaacgcgc tgctgatcat cggtggattc 1560
gaggcctacc tgggactcct ggagctgtca gccgcccggg agaagcacga ggagttctgt 1620
gtccccatgg tcatggttcc cgctactgtg tccaacaatg tgccgggttc cgatttcagc 1680
atcggggcag acaccgccct gaacactatc accgacacct gcgaccgcat caagcagtcc 1740
gccagcggaa ccaagcggcg cgtgttcatc atcgagacca tgggcggcta ctgtggctac 1800
ctggccaaca tgggggggct cgcggccgga gctgatgccg catacatttt cgaagagccc 1860
ttcgacatca gggatctgca gtccaacgtg gagcacctga cggagaaaat gaagaccacc 1920
atccagagag gccttgtgct cagaaatgag agctgcagtg aaaactacac caccgacttc 1980
atttaccagc tgtattcaga agagggcaaa ggcgtgtttg actgcaggaa gaacgtgctg 2040
ggtcacatgc agcagggtgg ggcaccctct ccatttgata gaaactttgg aaccaaaatc 2100
tctgccagag ctatggagtg gatcactgca aaactcaagg aggcccgggg cagaggaaaa 2160
aaatttacca ccgatgattc catttgtgtg ctgggaataa gcaaaagaaa cgttattttt 2220
caacctgtgg cagagctgaa gaagcaaacg gattttgagc acaggattcc caaagaacag 2280
tggtggctca agctacggcc cctcatgaaa atcctggcca agtacaaggc cagctatgac 2340
gtgtcggact caggccagct ggaacatgtg cagccctgga gtgtctgacc cagtcccgcc 2400
tgcatgtgcc tgcagccacc gtggactgtc tgtttttgta acacttaagt tattttatca 2460
gcactttatg cacgtattat tgacattaat acctaatcgg cgagtgccca tctgccccac 2520
cagctccagt gcgtgctgtc tgtggagtgt gtctcatgct ttcagatgtg catatgagca 2580
gaattaatta a 2591

<210> SEQ ID NO 26
<211> LENGTH: 60
<212> TYPE: DNA
<213> ORGANISM: Homo sapiens
<220> FEATURE:
<223> OTHER INFORMATION: D25328

<400> SEQUENCE: 26
tattttatca gcactttatg cacgtattat tgacattaat acctaatcgg cgagtgccca 60

<210> SEQ ID NO 27
<211> LENGTH: 2573
<212> TYPE: DNA
<213> ORGANISM: Homo sapiens
<220> FEATURE:
<223> OTHER INFORMATION: D50402

<400> SEQUENCE: 27
gaatcggccg atgtgaaccg aatgttgatg taagaggcag ggcactcggc tgcggatggg 60
taacagggcg tgggctggca cacttacttg caccagtgcc cagagagggg gtgcaggctg 120
aggagctgcc cagagcaccg ctcacactcc cagagtacct gaagtcggca tttcaatgac 180
aggtgacaag ggtccccaaa ggctaagcgg gtccagctat ggttccatct ccagcccgac 240
cagcccgacc agcccagggc cacggcaagc acctcccaga gagacctacc tgagtgagaa 300
gatccccatc ccagacacaa aaccgggcac cttcagcctg cggaagctat gggccttcac 360
ggggcctggc ttcctcatga gcattgcttt cctggaccca ggaaacatcg agtcagatct 420
tcaggctggc gccgtggcgg gattcaaact tctctgggtg ctgctctggg ccaccgtgtt 480
gggcttgctc tgccagcgac tggctgcacg tctgggcgtg gtgacaggca aggacttggg 540
cgaggtctgc catctctact accctaaggt gccccgcacc gtcctctggc tgaccatcga 600
gctagccatt gtgggctccg acatgcagga agtcatcggc acggccattg cattcaatct 660
gctctcagct ggacgaatcc cactctgggg tggcgtcctc atcaccatcg tggacacctt 720
cttcttcctc ttcctcgata actacgggct gcggaagctg gaagcttttt ttggactcct 780
tataaccatt atggccttga cctttggcta tgagtatgtg gtggcgcgtc ctgagcaggg 840
agcgcttctt cggggcctgt tcctgccctc gtgcccgggc tgcggccacc ccgagctgct 900
gcaggcggtg ggcattgttg gcgccatcat catgccccac aacatctacc tgcactcggc 960
cctggtcaag tctcgagaga tagaccgggc ccgccgagcg gacatcagag aagccaacat 1020
gtacttcctg attgaggcca ccatcgccct gtccgtctcc tttatcatca acctctttgt 1080
catggctgtc tttgggcagg ccttctacca gaaaaccaac caggctgcgt tcaacatctg 1140
tgccaacagc agcctccacg actacgccaa gatcttcccc atgaacaacg ccaccgtggc 1200
cgtggacatt taccaggggg gcgtgatcct gggctgcctg ttcggccccg cggccctcta 1260
catctgggcc ataggtctcc tggcggctgg gcagagctcc accatgacgg gcacctacgc 1320
gggacagttc gtgatggagg gcttcctgag gctgcggtgg tcacgcttcg cccgtgtcct 1380
cctcacccgc tcctgcgcca tcctgcccac cgtgctcgtg gctgtcttcc gggacctgag 1440
ggacttgtcg ggcctcaatg atctgctcaa cgtgctgcag agcctgctgc tcccgttcgc 1500
cgtgctgccc atcctcacgt tcaccagcat gcccaccctc atgcaggagt ttgccaatgg 1560
cctgctgaac aaggtcgtca cctcttccat catggtgcta gtctgcgcca tcaacctcta 1620
cttcgtggtc agctatctgc ccagcctgcc ccaccctgcc tacttcggcc ttgcagcctt 1680
gctggccgca gcctacctgg gcctcagcac ctacctggtc tggacctgtt gccttgccca 1740
cggagccacc tttctggccc acagctccca ccaccacttc ctgtatgggc tccttgaaga 1800
ggaccagaaa ggggagacct ctggctaggc ccacaccagg gcctggctgg gagtggcatg 1860
tatgacgtga ctggcctgct ggatgtggag ggggcgcgtg caggcagcag gatggagtgg 1920
gacagttcct gagaccagcc aacctggggg ctttagggac ctgctgtttc ctagcgcagc 1980
catgtgatta ccctctgggt ctcagtgtcc tcatctgtaa aatggagacg ccaccacccct 2040
tgccatggag gttaagcact ttaacacagt gtctggcact tgggacaaaa acaaacaaac 2100
aaacaaaaaa catttcaaaa ggtatttatt gagcacctgc aggcgtgacc tgacagccca 2160
agggtgggtg gggtgagggc ttgaggactt gggcgggaca caggctccaa actggagctt 2220
gaaatagtgt ctgatgaatg ttaaattatc tatctatcta tttatttatt tatttgagac 2280
agggaaaggg tctccctctg ttgccaaggc tggagtgcag tggcgcaatc ttaactcatt 2340
gcaacctcca ccttctgggt tcaagcgatt ctctttattc agccccggga gtggcgcgcg 2400
ccaccacgcc cagctaattt gtgtattttc agcagagacg ggtttgccca tgctggccag 2460
gctggtctcg aactgctgga ttcaagtgat ccgcccatct ccgtctccca aagtgctggg 2520
aattacaggc gtgagccacc aaaacccggc ctgattaaag ttaaataaat acg 2573

<210> SEQ ID NO 28
<211> LENGTH: 60
<212> TYPE: DNA
<213> ORGANISM: Homo sapiens
<220> FEATURE:
<223> OTHER INFORMATION: D50402

<400> SEQUENCE: 28
tggaggttaa gcactttaac acagtgtctg gcacttggga caaaaacaaa caaacaaaca 60

<210> SEQ ID NO 29
<211> LENGTH: 3672
<212> TYPE: DNA
<213> ORGANISM: Homo sapiens
<220> FEATURE:
<223> OTHER INFORMATION: L27560

<400> SEQUENCE: 29
acatgtgcat atttcattcc ccaggcagac attttttaga aatcaataca tgccccaata 60
ttggaaagac ttgttcttcc acggtgacta cagtacatgc tgaagcgtgc cgtttcagcc 120
ctcatttaat tcaatttgta agtagcgcac gagcctctgt gggggaggat aggctgaaaa 180
aaaaaagtgg gctcgtattt atctacagga ctccatatag tcatatatag gcatataaat 240
ctatgctttt tctttgtttt tttctttctt cctttctttc aaaggtttgc attaactttt 300
caaagtagtt cctatagggg cattgaggag cttcctcatt ctgggaaaac tgagaaaacc 360
catattctcc taatacaacc cgtaatagca tttttgcctg cctcgaggca gagtttcccg 420
tgagcaataa actcagcttt tttgtggggc acagtactgg atttgacagt gattccccac 480
gtgtgttcat ctgcacccac cgagccaggc agaggccagc cctccgtggt gcacacagca 540
cgcgcctcag tccatcccat tttagtcttt aaaccctcag gaagtcacag tctccggaca 600
ccacaccaca ttgagcccaa caggtccacg atggatccac ctagtcccac cccagccttt 660
ttctttcatc tgaacagaat gtgcattttt ggaagcctcc ctcactctcc atgctggcag 720
agcaggaggg agactgaagt aagagatggc agagggagat ggtggcaaaa aggtttagat 780
gcaggagaac agtaagatgg atggttccgg ccagagtcga tgtggggagg aacagagggc 840
tgaagggaga gggggctgac tgttccattc tagctttggc acaaagcagc agaaaggggg 900
aaaagccaat agaaatttcc ttagcttccc caccatatgt attttcatgg atttgagagg 960
aaagagagga aaatggggga atgggttgca aaatagaaat gagcttaatc caggccgcag 1020
agccagggaa ggtgagtaac cttaggaggg tgctagactt tagaagccag ataggaagaa 1080
tcagtctaaa ctggccatgc tttggaaggg acaagactat gtgctccgct gcccaccttc 1140
agcctgcaat gagggactga ggcccacgag tctttccagc tcttcctcca ttctggccag 1200
tccctgcatc ctccctgggg tggaggatgg aaggaaagct gggacaagca gggaacgcat 1260
gattcaggga tgctgtcact cggcagccag attccgaaac tcccattctc caatgacttc 1320
ctcaaccaat gggtggcctt gtgactgttc tttaaggctg aagatatcca ggaaaggggg 1380
cttggacact ggccaaggag accccttcgt gctgtggaca cagctctctt cactctttgc 1440
tcatggcatg acacagcgga gaccgcctcc aacaacgaat ttggggctac gaagaggaat 1500
agcgaaaaag caaatctgtt tcaactgatg ggaaccctat agctatagaa cttgggggct 1560
atctcctatg cccctggaca ggacagttgg ctggggacag gagaagtgct caatcttcat 1620
gagacaaagg ggcccgatca aggcagccac aaggccttga cctgccgagt cagcatgccc 1680
catctctctc gacagctgtc ccctaaaccc aactcacgtt tctgtatgtc ttaggccagt 1740
atcccaaacc tcttccacgt cactgttctt tccacccatt ctccctttgc atcttgagca 1800
gttatccaac taggatctgc caagtggata ctggggtgcc actcccctga gaaaagactg 1860
agccaggaac tacaagctcc ccccacattc ctcccagcct ggacctaatt cttgagaggg 1920
gctctctctt cacggactgt gtctggactt tgagcaggct tctgcccctt gcgttggctc 1980
tttgctgcca gccatcaggt gggggattag agcctggtgt aagtgcgcca gactcttccg 2040
gtttccaaag ttcgtgcctg cgaacccaaa cctgtgagtc tcttctgcat gcaggagttt 2100
ctcctgggca gctggtcact ccccagagaa gctgggcctt catggacaca tggaactaag 2160
cctcccaaat gggagttctg gctgagccca gggtggggag atcctgggaa gggaggcact 2220
ggaggaagac ggcacctctt cccccatggc agggtgtgag ggaggcaggt ttggaatggt 2280
gcgagtatgg caatctaagc aggggtctgg tctctttgac tccaggctcg ctttggccga 2340
ctgtctgctc acccagagac cttggactcc ggactatcca tggctccgaa tctaagtgct 2400
gcccactccc atgctcacac ccacagaagg tcttcccatc ccctttagat tcgtgcctca 2460
ctccaccagt gaggaagatg cctctgtctt tcccacgact gccaggagat agggaagccc 2520
agccaggact gaccctcctt cctccagcct gccctgaccc acctggcaaa gcagggcaca 2580
tggggaggaa gagactggaa cctttctttg acagccaggc ctagacagac aggcctgggg 2640
acactggccc atgaggggag gaaggcaggc gcacgaggtc cagggaggcc cttttctgat 2700
catgcccctt ctctcccacc ccatctcccc accaccacct ctgtggcctc catggtaccc 2760
ccacagggct ggcctcccct agagggtggg cctcaaccac ctcgtcccgc cacgcaccgg 2820
ttagtgagac agggctgcca cgcaaccgcc aagccccccct caaggtggga cagtaccccg 2880
gacccatcca ctcactcctg agaggctccg gcccagaatg ggaacctcag agaagagctc 2940
taaggagaag aaaccccata gcgtcagaga ggatatgtct ggcttccaag agaaaggagg 3000
ctccgttttg caaagtggag gagggacgag ggacaggggt ttcaccagcc agcaacctgg 3060
gccttgtact gtctgtgttt ttaaaaccac taaagtgcaa gaattacatt gcactgtttc 3120
tccacttttt attttctctt aggcttttgt ttctatttca aacatacttt cttggttttc 3180
taatggagta tatagtttag tcatttcaca gactctggcc tcctctcctg aaatcctttt 3240
ggatggggaa agggaaggtg gggagggtcc gaggggaagg ggaccccagc ttccctgtgc 3300
ccgctcaccc cactccacca gtccccggtc gccagccgga gtctcctctc taccgccact 3360
gtcacaccgt agcccacatg gatagcacag ttgtcagaca agattccttc agattccgag 3420
ttgctaccgg ttgttttcgt tgttgttgtt gttgttttttc tttttctttt tttttttgaa 3480
gacagcaata accacagtac atattactgt agttctctat agttttacat acattcatac 3540
cataactctg ttctctcctc ttttttgttt tcaactttaa aaacaaaaat aaacgatgat 3600
aatctttact ggtgaaaagg atggaaaaat aaatcaacaa atgcaaccag tttgtgagaa 3660
aaaaaaaaaa aa 3672

<210> SEQ ID NO 30
<211> LENGTH: 60
<212> TYPE: DNA
<213> ORGANISM: Homo sapiens
<220> FEATURE:
<223> OTHER INFORMATION: L27560

<400> SEQUENCE: 30
agcaacctgg gccttgtact gtctgtgttt ttaaaaccac taaagtgcaa gaattacatt 60

<210> SEQ ID NO 31
<211> LENGTH: 1416
<212> TYPE: DNA
<213> ORGANISM: Homo sapiens
<220> FEATURE:
<221> NAME/KEY: Modified_base
<222> LOCATION: 1 ... 1416
<223> OTHER INFORMATION: n = a,c,g, or t
<220> FEATURE:
<223> OTHER INFORMATION: M55914

<400> SEQUENCE: 31
aggaattccg gaattccgga attccgatgg atggaacaga aaataaatct aagtttggtg 60
cgaacgccat tctgggggtg tcccttgccg tctgcaaagc tggtgccgtt gagaaggggg 120
tcccctgtac cgccacatcg cgtacttggc tggcaacttc gaagtcatcc tgccagtccc 180
ggcgttcaag tgtcatcatc aatggcggtt ctcatgctgg caacaagctg gccatgcaga 240
gtctgtcctc ccagtcggtg cagcaaactc agggaagcca tgccgcattg gagcagaggt 300
ttaccacaac ctgaagaatg tcatcaagga gaaatatggg aaagatgcca ccaatgtggg 360
gatttgcgcg ggtttgctcc caacatcctg gagaataaag aaggcctgga gctgctgaag 420
actgctattg gaaagcctgg cctacactgt aaaggtggtc atggcatgga cgtagcggcc 480
tccgagttct tcaggtcagg gaactatgac ctggacttca agtctcccga tgaccccagc 540
aggtacatct cgcctgacca gctggctgac ctgtacaagt ccttcatcaa ggactaccca 600
gtggtgtcta tcgaagatcc ctttgaccag gatgactggg gagcttcaga agttcacagc 660
cagtgcagga atccaggtag tggggggatg actcacagtg accaacccaa agaggatcgc 720
caaggcgtga acgagaagtc ctgcaactgc ctcctgctca aagtcaacca gattggctcc 780
gtgaccgagt ctcttcaggc gtgcaagctg gcccaggcca atggttgggg cgtcatggtg 840
tctcatcgtt cgggggagac tgaagatacc ttcatcgctg acctggttgt ggggctgtgc 900
actggggcag atcaagactg gtgccccttg ccgatcacgc gcttggccaa gtacaaccag 960
ctcctcagaa ttgaagagga gctgggcagc aaggctaagt ttgccggcag gaacttcaga 1020
aaccccttgg ccaagtaagc tgtgggcagg caagccttcg gtcacctgtt ggctacagac 1080
ccctcccctg gtgtcagctc aggcagctcg aggcccccga ccaacacttg caggggtccc 1140
tgctagttag cgcccaccgc cgtggagttc gtaccgcttc cttagaactc tacagaagcc 1200
aagctccctg gaagccctgt tggcagctct agctttgcag ttgtgtaatt ggcccaagtc 1260
attgtttttc tcgccttact ttccaccaag tgtctagagt catgtgagcc tngtgtcatc 1320
tccggggtgg ccacaggcta gatccccggt ggttttgtgc tcaaaataaa aagcctcagt 1380
gacccatgaa aaaaaaaaag gaattccgga attccg 1416

<210> SEQ ID NO 32
<211> LENGTH: 60
<212> TYPE: DNA
<213> ORGANISM: Homo sapiens
<220> FEATURE:
<223> OTHER INFORMATION: M55914

<400> SEQUENCE: 32
gtaccgcttc cttagaactc tacagaagcc aagctccctg gaagccctgt tggcagctct 60

<210> SEQ ID NO 33
<211> LENGTH: 2517
<212> TYPE: DNA
<213> ORGANISM: Homo sapiens

<220> FEATURE:
<223> OTHER INFORMATION: M96577

<400> SEQUENCE: 33

```
ggaattccgt ggccgggact ttgcaggcag cggcggccgg gggcggagcg ggatcgagcc     60
ctcgccgagg cctgccgcca tgggcccgcg ccgccgccgc cgcctgtcac ccgggccgcg    120
cgggccgtga gcgtcatggc cttggccggg gcccctgcgg gcggcccatg cgcgccggcg    180
ctggaggccc tgctcggggc cggcgcgctg cggctgctcg actcctcgca gatcgtcatc    240
atctccgccg cgcaggacgc cagcgccccg ccggctccca ccggccccgc ggcgcccgcc    300
gccggcccct gcgaccctga cctgctgctc ttcgccacac cgcaggcgcc ccggcccaca    360
cccagtgcgc cgcggcccgc gctcggccgc ccgccggtga agcggaggct ggacctggaa    420
actgaccatc agtacctggc cgagagcagt gggccagctc ggggcagagg ccgccatcca    480
ggaaaaggtg tgaaatcccc gggggagaag tcacgctatg agacctcact gaatctgacc    540
accaagcgct tcctggagct gctgagccac tcggctgacg gtgtcgtcga cctgaactgg    600
gctgccgagg tgctgaaggt gcagaagcgg cgcatctatg acatcaccaa cgtccttgag    660
ggcatccagc tcattgccaa gaagtccaag aaccacatcc agtggctggg cagccacacc    720
acagtgggcg tcggcggacg gcttgagggg ttgacccagg acctccgaca gctgcaggag    780
agcgagcagc agctggacca cctgatgaat atctgtacta cgcagctgcg cctgctctcc    840
gaggacactg acagccagcg cctggcctac gtgacgtgtc aggaccttcg tagcattgca    900
gaccctgcag agcagatggt tatggtgatc aaagcccctc ctgagaccca gctccaagcc    960
gtggactctt cggagaactt tcagatctcc cttaagagca aacaaggccc gatcgatgtt   1020
ttcctgtgcc ctgaggagac cgtaggtggg atcagccctg ggaagacccc atcccaggag   1080
gtcacttctg aggaggagaa cagggccact gactctgcca ccatagtgtc accaccacca   1140
tcatctcccc cctcatccct caccacagat cccagccagt ctctactcag cctggagcaa   1200
gaaccgctgt tgtcccggat gggcagcctg cgggctcccg tggacgagga ccgcctgtcc   1260
ccgctggtgg cggccgactc gctcctggag catgtgcggg aggacttctc cggcctcctc   1320
cctgaggagt tcatcagcct ttccccaccc cacgaggccc tcgactacca cttcggcctc   1380
gaggagggcg agggcatcag agacctcttc gactgtgact ttggggacct caccccccctg   1440
gatttctgac agggcttgga gggaccaggg tttccagagt agctcacctt gtctctgcag   1500
ccctggagcc ccctgtccct ggccgtcctc ccagcctgtt tggaaacatt taatttatac   1560
ccctctcctc tgtctccaga agcttctagc tctggggtct ggctaccgct aggaggctga   1620
gcaagccagg aagggaagga gtctgtgtgg tgtgtatgtg catgcagcct acacccacac   1680
gtgtgtaccg gggtgaatg tgtgtgagca tgtgtgtgtg catgtaccgg ggaatgaagg   1740
tgaacataca cctctgtgtg tgcactgcag acacgcccca gtgtgtccac atgtgtgtgc   1800
atgagtccat ctctgcgcgt ggggggctc taactgcact ttcggcccttt ttgctcgtgg   1860
ggtcccacaa ggcccagggc agtgcctgct cccagaatct ggtgctctga ccaggccagg   1920
tggggaggct ttggctggct gggcgtgtag gacggtgaga gcacttctgt cttaaaggtt   1980
ttttctgatt gaagctttaa tggagcgtta tttatttatc gaggcctctt tggtgagcct   2040
ggggaatcag caaaagggga ggagggggtgt ggggttgata ccccaactcc ctctaccctt   2100
gagcaagggc aggggtccct gagctgttct tctgccccat actgaaggaa ctgaggcctg   2160
ggtgatttat ttattgggaa agtgagggag ggagacagac tgactgacag ccatgggtgg   2220
tcagatggtg gggtgggccc tctccagggg gccagttcag ggcccagctg ccccccagga   2280
```

tggatatgag atgggagagg tgagtggggg accttcactg atgtgggcag gaggggtggt 2340
gaaggcctcc cccagcccag accctgtggt ccctcctgca gtgtctgaag cgcctgcctc 2400
cccactgctc tgccccaccc tccaatctgc actttgattt gcttcctaac agctctgttc 2460
cctcctgctt tggttttaat aaatattttg atgacgttaa aaaaaggaat tcgatat 2517

<210> SEQ ID NO 34
<211> LENGTH: 60
<212> TYPE: DNA
<213> ORGANISM: Homo sapiens
<220> FEATURE:
<223> OTHER INFORMATION: M96577

<400> SEQUENCE: 34
gtaggacggt gagagcactt ctgtcttaaa ggtttttttct gattgaagct ttaatggagc 60

<210> SEQ ID NO 35
<211> LENGTH: 4437
<212> TYPE: DNA
<213> ORGANISM: Homo sapiens
<220> FEATURE:
<223> OTHER INFORMATION: NM_000057

<400> SEQUENCE: 35
gcgcggcggc cgtggttgcg gcgcgggaag tttggatcct ggttccgtcc gctaggagtc 60
tgcgtgcgag gattatggct gctgttcctc aaaataatct acaggagcaa ctagaacgtc 120
actcagccag aacacttaat aataaattaa gtctttcaaa accaaaattt tcaggtttca 180
cttttaaaaa gaaaacatct tcagataaca atgtatctgt aactaatgtg tcagtagcaa 240
aaacacctgt attaagaaat aaagatgtta atgttaccga agacttttcc ttcagtgaac 300
ctctacccaa caccacaaat cagcaaaggg tcaaggactt ctttaaaaat gctccagcag 360
gacaggaaac acagagaggt ggatcaaaat cattattgcc agatttcttg cagactccga 420
aggaagttgt atgcactacc caaaacacac caactgtaaa gaaatcccgg gatactgctc 480
tcaagaaatt agaatttagt tcttcaccag attctttaag taccatcaat gattgggatg 540
atatggatga ctttgatact tctgagactt caaaatcatt tgttacacca ccccaaagtc 600
actttgtaag agtaagcact gctcagaaat caaaaaaggg taagagaaac ttttttaaag 660
cacagcttta tacaacaaac acagtaaaga ctgatttgcc tccaccctcc tctgaaagcg 720
agcaaataga tttgactgag gaacagaagg atgactcaga atggttaagc agcgatgtga 780
tttgcatcga tgatggcccc attgctgaag tgcatataaa tgaagatgct caggaaagtg 840
actctctgaa aactcatttg gaagatgaaa gagataatag cgaaaagaag aagaatttgg 900
aagaagctga attacattca actgagaaag ttccatgtat tgaatttgat gatgatgatt 960
atgatacgga ttttgttcca ccttctccag aagaaattat ttctgcttct tcttcctctt 1020
caaaatgcct tagtacgtta aaggaccttg acacatctga cagaaaagag gatgttctta 1080
gcacatcaaa agatcttttg tcaaaacctg agaaaatgag tatgcaggag ctgaatccag 1140
aaaccagcac agactgtgac gctagacaga taagtttaca gcagcagctt attcatgtga 1200
tggagcacat ctgtaaatta attgatacta ttcctgatga taaactgaaa cttttggatt 1260
gtgggaacga actgcttcag cagcggaaca taagaaggaa acttctaacg gaagtagatt 1320
ttaataaaag tgatgccagt cttcttggct cattgtggag atacaggcct gattcacttg 1380
atggccctat ggagggtgat tcctgcccta cagggaattc tatgaaggag ttaaattttt 1440
cacaccttcc ctcaaattct gtttctcctg ggactgttt actgactacc accctaggaa 1500

-continued

```
agacaggatt ctctgccacc aggaagaatc tttttgaaag gcctttattc aatacccatt   1560
tacagaagtc ctttgtaagt agcaactggg ctgaaacacc aagactagga aaaaaaaatg   1620
aaagctctta tttcccagga aatgttctca caagcactgc tgtgaaagat cagaataaac   1680
atactgcttc aataaatgac ttagaaagag aaacccaacc ttcctatgat attgataatt   1740
ttgacataga tgactttgat gatgatgatg actgggaaga cataatgcat aatttagcag   1800
ccagcaaatc ttccacagct gcctatcaac ccatcaagga aggtcggcca attaaatcag   1860
tatcagaaag actttcctca gccaagacag actgtcttcc agtgtcatct actgctcaaa   1920
atataaactt ctcagagtca attcagaatt atactgacaa gtcagcacaa aatttagcat   1980
ccagaaatct gaaacatgag cgtttccaaa gtcttagttt tcctcataca aaggaaatga   2040
tgaagatttt tcataaaaaa tttggcctgc ataattttag aactaatcag ctagaggcga   2100
tcaatgctgc actgcttggt gaagactgtt ttatcctgat gccgactgga ggtggtaaga   2160
gtttgtgtta ccagctccct gcctgtgttt ctcctggggt cactgttgtc atttctccct   2220
tgagatcact tatcgtagat caagtccaaa agctgacttc cttggatatt ccagctacat   2280
atctgacagg tgataagact gactcagaag ctacaaatat ttacctccag ttatcaaaaa   2340
aagacccaat cataaaactt ctatatgtca ctccagaaaa gatctgtgca agtaacagac   2400
tcatttctac tctggagaat ctctatgaga ggaagctctt ggcacgtttt gttattgatg   2460
aagcacattg tgtcagtcag tggggacatg attttcgtca agattacaaa agaatgaata   2520
tgcttcgcca gaagtttcct tctgttccgg tgatggctct tacggccaca gctaatccca   2580
gggtacagaa ggacatcctg actcagctga agattctcag acctcaggtg tttagcatga   2640
gctttaacag acataatctg aaatactatg tattaccgaa aaagcctaaa aaggtggcat   2700
ttgattgcct agaatggatc agaaagcacc acccatatga ttcagggata atttactgcc   2760
tctccaggcg agaatgtgac accatggctg acacgttaca gagagatggg ctcgctgctc   2820
ttgcttacca tgctggcctc agtgattctg ccagagatga agtgcagcag aagtggatta   2880
atcaggatgg ctgtcaggtt atctgtgcta caattgcatt tggaatgggg attgacaaac   2940
cggacgtgcg atttgtgatt catgcatctc tccctaaatc tgtggagggt tactaccaag   3000
aatctggcag agctggaaga gatggggaaa tatctcactg cctgcttttc tatacctatc   3060
atgatgtgac cagactgaaa agacttataa tgatggaaaa agatggaaac catcatacaa   3120
gagaaactca cttcaataat ttgtatagca tggtacatta ctgtgaaaat ataacggaat   3180
gcaggagaat acagcttttg gcctactttg gtgaaaatgg atttaatcct gatttttgta   3240
agaaacaccc agatgtttct tgtgataatt gctgtaaaac aaaggattat aaaacaagag   3300
atgtgactga cgatgtgaaa agtattgtaa gatttgttca agaacatagt tcatcacaag   3360
gaatgagaaa tataaaacat gtaggtcctt ctggaagatt tactatgaat atgctggtcg   3420
acattttctt ggggagtaag agtgcaaaaa tccagtcagg tatatttgga aaaggatctg   3480
cttattcacg acacaatgcc gaaagacttt ttaaaaagct gatacttgac aagattttgg   3540
atgaagactt atatatcaat gccaatgacc aggcgatcgc ttatgtgatg ctcggaaata   3600
aagcccaaac tgtactaaat ggcaatttaa aggtagactt tatggaaaca gaaaattcca   3660
gcagtgtgaa aaaacaaaaa gcgttagtag caaaagtgtc tcagagggaa gagatggtta   3720
aaaaatgtct tggagaactt acagaagtct gcaaatctct ggggaaagtt tttggtgtcc   3780
attacttcaa tatttttaat accgtcactc tcaagaagct tgcagaatct ttatcttctg   3840
atcctgaggt tttgcttcaa attgatggtg ttactgaaga caaactggaa aaatatggtg   3900
```

cggaagtgat ttcagtatta cagaaatact ctgaatggac atcgccagct gaagacagtt 3960
ccccagggat aagcctgtcc agcagcagag gccccggaag aagtgccgct gaggagcttg 4020
acgaggaaat acccgtatct tcccactact ttgcaagtaa aaccagaaat gaaaggaaga 4080
ggaaaaagat gccagcctcc caaaggtcta agaggagaaa aactgcttcc agtggttcca 4140
aggcaaaggg ggggtctgcc acatgtagaa agatatcttc caaaacgaaa tcctccagca 4200
tcattggatc cagttcagcc tcacatactt ctcaagcgac atcaggagcc aatagcaaat 4260
tggggattat ggctccaccg aagcctataa atagaccgtt tcttaagcct tcatatgcat 4320
tctcataaca accgaatctc aatgtacata gaccctcttt cttgtttgtc agcatctgac 4380
catctgtgac tataaagctg ttattcttgt tataccaaaa aaaaaaaaaa aaaaaaa 4437

<210> SEQ ID NO 36
<211> LENGTH: 60
<212> TYPE: DNA
<213> ORGANISM: Homo sapiens
<220> FEATURE:
<223> OTHER INFORMATION: NM_000057

<400> SEQUENCE: 36
taagccttca tatgcattct cataacaacc gaatctcaat gtacatagac cctctttctt 60

<210> SEQ ID NO 37
<211> LENGTH: 2016
<212> TYPE: DNA
<213> ORGANISM: Homo sapiens
<220> FEATURE:
<223> OTHER INFORMATION: NM_000060

<400> SEQUENCE: 37
gccagctgga gcgttttcgg ggctgtaaag ggagaatggc gcatgcgcat attcagggcg 60
gaaggcgcgc taagagcaga tttgtggtct gcattatgtc tggagccaga agtaagcttg 120
ctcttttcct ctgcggctgt tacgtggttg ccctgggagc ccacaccggg gaggagagcg 180
tggctgacca tcacgaggct gaatattatg tggctgccgt gtatgagcat ccatccatcc 240
tgagtctgaa ccctctggct ctcatcagcc gccaagaggc cttggagctc atgaaccaga 300
accttgacat ctatgaacag caagtgatga ctgcagccca aaaggatgta cagattatag 360
tgtttccaga agatggcatt catggattca actttacaag aacatccatt tatccatttt 420
tggacttcat gccgtctccc caggtggtca ggtggaaccc atgcctggag cctcaccgct 480
tcaatgacac agaggtgctc cagcgcctga gttgtatggc catcagggga gatatgttct 540
tggtggccaa tcttgggaca aaggagcctt gtcatagcag tgacccaagg tgcccaaaag 600
atgggagata ccagttcaac acaaatgtcg tgttcagcaa taatggaacc cttgttgacc 660
gctaccgtaa acacaacctc tactttgagg cagcattcga tgttcctctt aaagtggatc 720
tcatcacctt tgataccccc tttgctggca ggtttggcat cttcacatgc tttgatatat 780
tgttctttga ccctgccatc agagtcctca gagactacaa ggtgaagcat gttgtgtacc 840
caactgcctg gatgaaccag ctcccactct tggcagcaat tgagattcag aaagcttttg 900
ctgttgcctt tggcatcaac gttctggcag ctaatgtcca ccacccagtt ctggggatga 960
caggaagtgg catacacacc cctctggagt cctttttggta ccatgacatg gaaaatccca 1020
aaagtcacct tataattgcc caggtggcca aaaatccagt gggtctcatt ggtgcagaga 1080
atgcaacagg tgaaacggac ccatcccata gtaagttttt aaaaattttg tcaggcgatc 1140
cgtactgtga gaaggatgct caggaagtcc actgtgatga ggccaccaag tggaacgtga 1200
atgctcctcc cacatttcac tctgagatga tgtatgacaa tttcaccctg gtccctgtct 1260
ggggaaagga aggctatctc cacgtctgtt ccaatggcct ctgctgttat ttactttacg 1320
agaggcccac cttatccaaa gagctgtatg ccctgggggt ctttgatggg cttcacacag 1380
tacatggcac ttactacatc caagtgtgtg ccctggtcag gtgtgggggt cttggcttcg 1440
acacctgcgg acaggaaatc acagaggcca cggggatatt tgagtttcac ctgtggggca 1500
acttcagtac ttcctatatc tttcctttgt ttctgacctc agggatgacc ctagaagtcc 1560
ctgaccagct tggctgggag aatgaccact atttcctgag gaaaagtagg ctgtcctctg 1620
ggctggtgac ggcggctctc tatgggcgct tgtatgagag ggactaggaa aagtgtgtgg 1680
tctgtggggc ggactctggc catcatgttg acagccttgc acttccacag gctacaagcc 1740
ctgggaccat ctttctgcct taagggcagg agcccacttc tgtggcacca gattccaccc 1800
tgggaactgt ggaaaaagta ggagaggcag attccctcag tgtcttcctc ttaaacctca 1860
atcatcgaga cattaggggg tattttctgt tcacatttat ctttttcaag ccacatcttc 1920
ctctaacaaa tctctcagta tgcgattggt ctcaagctaa aacaaaaata aatgtcagtt 1980
tatattttac acatccaaaa aaaaaaaaaa aaaaaa 2016

<210> SEQ ID NO 38
<211> LENGTH: 60
<212> TYPE: DNA
<213> ORGANISM: Homo sapiens
<220> FEATURE:
<223> OTHER INFORMATION: NM_000060

<400> SEQUENCE: 38
tcctctaaca aatctctcag tatgcgattg gtctcaagct aaaacaaaaa taaatgtcag 60

<210> SEQ ID NO 39
<211> LENGTH: 811
<212> TYPE: DNA
<213> ORGANISM: Homo sapiens
<220> FEATURE:
<223> OTHER INFORMATION: NM_000269

<400> SEQUENCE: 39
gcagaagcgt tccgtgcgtg caagtgctgc gaaccacgtg ggtcccgggc gcgtttcggg 60
tgctggcggc tgcagccgga gttcaaacct aagcagctgg aaggaaccat ggccaactgt 120
gagcgtacct tcattgcgat caaaccagat ggggtccagc ggggtcttgt gggagagatt 180
atcaagcgtt ttgagcagaa aggattccgc cttgttggtc tgaaattcat gcaagcttcc 240
gaagatcttc tcaaggaaca ctacgttgac ctgaaggacc gtccattctt tgccggcctg 300
gtgaaataca tgcactcagg gccggtagtt gccatggtct gggaggggct gaatgtggtg 360
aagacgggcc gagtcatgct cggggagacc aaccctgcag actccaagcc tgggaccatc 420
cgtggagact tctgcataca agttggcagg aacattatac atggcagtga ttctgtggag 480
agtgcagaga aggagatcgg cttgtggttt caccctgagg aactggtaga ttacacgagc 540
tgtgctcaga actggatcta tgaatgacag gagggcagac cacattgctt ttcacatcca 600
tttcccctcc ttcccatggg cagaggacca ggctgtagga aatctagtta tttacaggaa 660
cttcatcata atttggaggg aagctcttgg agctgtgagt tctccctgta cagtgttacc 720
atccccgacc atctgattaa aatgcttcct cccagcatag gattcattga gttggttact 780
tcatattgtt gcattgcttt tttttccttc t 811

<210> SEQ ID NO 40
<211> LENGTH: 60
<212> TYPE: DNA
<213> ORGANISM: Homo sapiens
<220> FEATURE:
<223> OTHER INFORMATION: NM_000269

<400> SEQUENCE: 40
gtctgaaatt catgcaagct tccgaagatc ttctcaagga acactacgtt gacctgaagg 60

<210> SEQ ID NO 41
<211> LENGTH: 2338
<212> TYPE: DNA
<213> ORGANISM: Homo sapiens
<220> FEATURE:
<223> OTHER INFORMATION: NM_000291

<400> SEQUENCE: 41
agcgcacgtc ggcagtcggc tccctcgttg accgaatcac cgacctctct ccccagctgt 60
atttccaaaa tgtcgctttc taacaagctg acgctggaca agctggacgt taaagggaag 120
cgggtcgtta tgagagtcga cttcaatgtt cctatgaaga acaaccagat aacaaacaac 180
cagaggatta aggctgctgt cccaagcatc aaattctgct tggacaatgg agccaagtcg 240
gtagtcctta tgagccacct aggccggcct gatggtgtgc ccatgcctga caagtactcc 300
ttagagccag ttgctgtaga actcaaatct ctgctgggca aggatgttct gttcttgaag 360
gactgtgtag gcccagaagt ggagaaagcc tgtgccaacc cagctgctgg gtctgtcatc 420
ctgctggaga acctccgctt tcatgtggag gaagaaggga agggaaaaga tgcttctggg 480
aacaaggtta aagccgagcc agccaaaata gaagctttcc gagcttcact ttccaagcta 540
ggggatgtct atgtcaatga tgcttttggc actgctcaca gagcccacag ctccatggta 600
ggagtcaatc tgccacagaa ggctggtggg tttttgatga agaaggagct gaactacttt 660
gcaaaggcct tggagagccc agagcgaccc ttcctggcca tcctgggcgg agctaaagtt 720
gcagacaaga tccagctcat caataaatatg ctggacaaag tcaatgagat gattattggt 780
ggtggaatgg cttttacctt ccttaaggtg ctcaacaaca tggagattgg cacttctctg 840
tttgatgaag agggagccaa gattgtcaaa gacctaatgt ccaaagctga gaagaatggt 900
gtgaagatta ccttgcctgt tgactttgtc actgctgaca agtttgatga gaatgccaag 960
actggccaag ccactgtggc ttctggcata cctgctggct ggatgggctt ggactgtggt 1020
cctgaaagca gcaagaagta tgctgaggct gtcactcggg ctaagcagat tgtgtggaat 1080
ggtcctgtgg gggtatttga atgggaagct tttgcccggg gaaccaaagc tctcatggat 1140
gaggtggtga aagccacttc taggggctgc atcaccatca taggtggtgg agacactgcc 1200
acttgctgtg ccaaatggaa cacggaggat aaagtcagcc atgtgagcac tgggggtggt 1260
gccagtttgg agctcctgga aggtaaagtc cttcctgggg tggatgctct cagcaatatt 1320
tagtactttc ctgcctttta gttcctgtgc acagccccta agtcaactta gcattttctg 1380
catctccact tggcattagc taaaaccttc catgtcaaga ttcagctagt ggccaagaga 1440
tgcagtgcca ggaaccctta aacagttgca cagcatctca gctcatcttc actgcaccct 1500
ggatttgcat acattcttca agatcccatt tgaatttttt agtgactaaa ccattgtgca 1560
ttctagagtg catatattta tattttgcct gttaaaaaga aagtgagcag tgttagctta 1620
gttctctttt gatgtaggtt attatgatta gctttgtcac tgtttcacta ctcagcatgg 1680
aaacaagatg aaattccatt tgtaggtagt gagacaaaat tgatgatcca ttaagtaaac 1740
aataaaagtg tccattgaaa ccgtgatttt tttttttttc ctgtcatact ttgttaggaa 1800
gggtgagaat agaatcttga ggaacggatc agatgtctat attgctgaat gcaagaagtg 1860
gggcagcagc agtggagaga tgggacaatt agataaatgt ccattcttta tcaagggcct 1920
actttatggc agacattgtg ctagtgcttt tattctaact tttattttta tcagttacac 1980
atgatcataa tttaaaaagt caaggcttat aacaaaaaag ccccagccca ttcctcccat 2040
tcaagattcc cactccccag aggtgaccac tttcaactct tgagtttttc aggtatatac 2100
ctccatgttt ctaagtaata tgcttatatt gttcacttcc ttttttttta ttttttaaag 2160
aaatctattt cataccatgg aggaaggctc tgttccacat atatttccac ttcttcattc 2220
tctcggtata gttttgtcac aattatagat tagatcaaaa gtctacataa ctaatacagc 2280
tgagctatgt agtatgctat gattaaattt acttatgtaa aaaaaaaaaa aaaaaaaa 2338

<210> SEQ ID NO 42
<211> LENGTH: 60
<212> TYPE: DNA
<213> ORGANISM: Homo sapiens
<220> FEATURE:
<223> OTHER INFORMATION: NM_000291

<400> SEQUENCE: 42
acttagcatt ttctgcatct ccacttggca ttagctaaaa ccttccatgt caagattcag 60

<210> SEQ ID NO 43
<211> LENGTH: 787
<212> TYPE: DNA
<213> ORGANISM: Homo sapiens
<220> FEATURE:
<223> OTHER INFORMATION: NM_000363

<400> SEQUENCE: 43
ctgaaggtca cccgggcggc cccctcactg accctccaaa cgcccctgtc ctcgccctgc 60
ctcctgccat tcccggcctg agtctcagca tggcggatgg gagcagcgat gcggctaggg 120
aacctcgccc tgcaccagcc ccaatcagac gccgctcctc caactaccgc gcttatgcca 180
cggagccgca cgccaagaaa aaatctaaga tctccgcctc gagaaaattg cagctgaaga 240
ctctgctgct gcagattgca aagcaagagc tggagcgaga ggcggaggag cggcgcggag 300
agaaggggcg cgctctgagc acccgctgcc agccgctgga gttgaccggg ctgggcttcg 360
cggagctgca ggacttgtgc cgacagctcc acgcccgtgt ggacaaggtg gatgaagaga 420
gatacgacat agaggcaaaa gtcaccaaga acatcacgga gattgcagat ctgactcaga 480
agatctttga ccttcgaggc aagtttaagc ggcccaccct gcggagagtg aggatctctg 540
cagatgccat gatgcaggcg ctgctggggg cccgggctaa ggagtccctg gacctgcggg 600
cccacctcaa gcaggtgaag aaggaggaca ccgagaagga aaaccgggag gtgggagact 660
ggcggaagaa catcgatgca ctgagtggaa tggagggccg caagaaaaag tttgagagct 720
gagccttcct gcctactgcc cctgccctga ggagggccac tgaggaataa agcttctctc 780
tgagctg 787

<210> SEQ ID NO 44
<211> LENGTH: 60
<212> TYPE: DNA
<213> ORGANISM: Homo sapiens
<220> FEATURE:
<223> OTHER INFORMATION: NM_000363

<400> SEQUENCE: 44
tgtggacaag gtggatgaag agagatacga catagaggca aaagtcacca agaacatcac 60

<210> SEQ ID NO 45
<211> LENGTH: 1263
<212> TYPE: DNA
<213> ORGANISM: Homo sapiens
<220> FEATURE:
<223> OTHER INFORMATION: NM_000365

<400> SEQUENCE: 45
ggcacgagac cttcagcgcc tcggctccag cgccatggcg ccctccagga agttcttcgt 60
tgggggaaac tggaagatga acgggcggaa gcagagtctg gggagctca tcggcactct 120 gaacgcggcc aaggtgccgg ccgacaccga ggtggtttgt gctcccccta ctgcctatat 180
cgacttcgcc cggcagaagc tagatcccaa gattgctgtg gctgcgcaga actgctacaa 240
agtgactaat ggggctttta ctggggagat cagccctggc atgatcaaag actgcggagc 300
cacgtgggtg gtcctggggc actcagagag aaggcatgtc tttggggagt cagatgagct 360
gattgggcag aaagtggccc atgctctggc agagggactc ggagtaatcg cctgcattgg 420
ggagaagcta gatgaaaggg aagctggcat cactgagaag gttgttttcg agcagacaaa 480
ggtcatcgca gataacgtga aggactggag caaggtcgtc ctggcctatg agcctgtgtg 540
ggccattggt actggcaaga ctgcaacacc ccaacaggcc caggaagtac acgagaagct 600
ccgaggatgg ctgaagtcca acgtctctga tgcggtggct cagagcaccc gtatcattta 660
tggaggctct gtgactgggg caacctgcaa ggagctggcc agccagcctg atgtggatgg 720
cttccttgtg ggtggtgctt ccctcaagcc cgaattcgtg gacatcatca atgccaaaca 780
atgagcccca tccatcttcc ctacccttcc tgccaagcca gggactaagc agcccagaag 840
cccagtaact gccctttccc tgcatatgct tctgatggtg tcatctgctc cttcctgtgg 900
cctcatccaa actgtatctt cctttactgt ttatatcttc accctgtaat ggttgggacc 960
aggccaatcc cttctccact tactataatg gttggaacta aacgtcacca aggtggcttc 1020
tccttggctg agagatggaa ggcgtggtgg gatttgctcc tgggttccct aggccctagt 1080
gagggcagaa gagaaaccat cctctccctt cttacaccgt gaggccaaga tcccctcaga 1140
aggcaggagt gctgccctct cccatggtgc ccgtgcctct gtgctgtgta tgtgaaccac 1200
ccatgtgagg gaataaacct ggcactagga aaaaaaaaaa aaaaaaaaaa aaaaaaaaaa 1260
aaa 1263

<210> SEQ ID NO 46
<211> LENGTH: 60
<212> TYPE: DNA
<213> ORGANISM: Homo sapiens
<220> FEATURE:
<223> OTHER INFORMATION: NM_000365

<400> SEQUENCE: 46
tatcttcacc ctgtaatggt tgggaccagg ccaatccctt ctccacttac tataatggtt 60

<210> SEQ ID NO 47
<211> LENGTH: 1616
<212> TYPE: DNA
<213> ORGANISM: Homo sapiens
<220> FEATURE:
<223> OTHER INFORMATION: NM_000582

<400> SEQUENCE: 47
ctccctgtgt tggtggagga tgtctgcagc agcatttaaa ttctgggagg gcttggttgt 60
cagcagcagc aggaggaggc agagcacagc atcgtcggga ccagactcgt ctcaggccag 120

```
ttgcagcctt ctcagccaaa cgccgaccaa ggaaaactca ctaccatgag aattgcagtg    180

atttgctttt gcctcctagg catcacctgt gccataccag ttaaacaggc tgattctgga    240

agttctgagg aaaagcagct ttacaacaaa tacccagatg ctgtggccac atggctaaac    300

cctgacccat ctcagaagca gaatctccta gccccacaga cccttccaag taagtccaac    360

gaaagccatg accacatgga tgatatggat gatgaagatg atgatgacca tgtggacagc    420

caggactcca ttgactcgaa cgactctgat gatgtagatg acactgatga ttctcaccag    480

tctgatgagt ctcaccattc tgatgaatct gatgaactgg tcactgattt tcccacggac    540

ctgccagcaa ccgaagtttt cactccagtt gtccccacag tagacacata tgatggccga    600

ggtgatagtg tggtttatgg actgaggtca aaatctaaga agtttcgcag acctgacatc    660

cagtaccctg atgctacaga cgaggacatc acctcacaca tggaaagcga ggagttgaat    720

ggtgcataca aggccatccc cgttgcccag gacctgaacg cgccttctga ttgggacagc    780

cgtgggaagg acagttatga aacgagtcag ctggatgacc agagtgctga aacccacagc    840

cacaagcagt ccagattata taagcggaaa gccaatgatg agagcaatga gcattccgat    900

gtgattgata gtcaggaact ttccaaagtc agccgtgaat tccacagcca tgaatttcac    960

agccatgaag atatgctggt tgtagacccc aaaagtaagg aagaagataa acacctgaaa   1020

tttcgtattt ctcatgaatt agatagtgca tcttctgagg tcaattaaaa ggagaaaaaa   1080

tacaatttct cactttgcat ttagtcaaaa gaaaaaatgc tttatagcaa aatgaaagag   1140

aacatgaaat gcttctttct cagtttattg gttgaatgtg tatctatttg agtctggaaa   1200

taactaatgt gtttgataat tagtttagtt tgtggcttca tggaaactcc ctgtaaacta   1260

aaagcttcag ggttatgtct atgttcattc tatagaagaa atgcaaacta tcactgtatt   1320

ttaatatttg ttattctctc atgaatagaa atttatgtag aagcaaacaa aatactttta   1380

cccacttaaa aagagaatat aacattttat gtcactataa tcttttgttt tttaagttag   1440

tgtatatttt gttgtgatta tctttttgtg gtgtgaataa atcttttatc ttgaatgtaa   1500

taagaatttg gtggtgtcaa ttgcttattt gttttcccac ggttgtccag caattaataa   1560

aacataacct tttttactgc ctaaaaaaaa aaaaaaaaaa aaaaaaaaaa aaaaaa       1616


<210> SEQ ID NO 48
<211> LENGTH: 60
<212> TYPE: DNA
<213> ORGANISM: Homo sapiens
<220> FEATURE:
<223> OTHER INFORMATION: NM_000582

<400> SEQUENCE: 48

ggtggtgtca attgcttatt tgttttccca cggttgtcca gcaattaata aaacataacc     60


<210> SEQ ID NO 49
<211> LENGTH: 1666
<212> TYPE: DNA
<213> ORGANISM: Homo sapiens
<220> FEATURE:
<223> OTHER INFORMATION: NM_000584

<400> SEQUENCE: 49

ctccataagg cacaaacttt cagagacagc agagcacaca agcttctagg acaagagcca     60

ggaagaaacc accggaagga accatctcac tgtgtgtaaa catgacttcc aagctggccg    120

tggctctctt ggcagccttc ctgatttctg cagctctgtg tgaaggtgca gttttgccaa    180

ggagtgctaa agaacttaga tgtcagtgca taaagacata ctccaaacct ttccacccca    240
```

aatttatcaa agaactgaga gtgattgaga gtggaccaca ctgcgccaac acagaaatta 300
ttgtaaagct ttctgatgga agagagctct gtctggaccc caaggaaaac tgggtgcaga 360
gggttgtgga gaagtttttg aagagggctg agaattcata aaaaaattca ttctctgtgg 420
tatccaagaa tcagtgaaga tgccagtgaa acttcaagca aatctacttc aacacttcat 480
gtattgtgtg ggtctgttgt agggttgcca gatgcaatac aagattcctg gttaaatttg 540
aatttcagta aacaatgaat agtttttcat tgtaccatga aatatccaga acatacttat 600
atgtaaagta ttatttattt gaatctacaa aaaacaacaa ataattttta aatataagga 660
ttttcctaga tattgcacgg gagaatatac aaatagcaaa attgaggcca agggccaaga 720
gaatatccga actttaattt caggaattga atgggtttgc tagaatgtga tatttgaagc 780
atcacataaa aatgatggga caataaattt tgccataaag tcaaatttag ctggaaatcc 840
tggatttttt tctgttaaat ctggcaaccc tagtctgcta gccaggatcc acaagtcctt 900
gttccactgt gccttggttt ctcctttatt tctaagtgga aaaagtatta gccaccatct 960
tacctcacag tgatgttgtg aggacatgtg gaagcacttt aagtttttc atcataacat 1020 aaattatttt caagtgtaac ttattaacct atttattatt tatgtattta tttaagcatc 1080
aaatatttgt gcaagaattt ggaaaaatag aagatgaatc attgattgaa tagttataaa 1140
gatgttatag taaatttatt ttattttaga tattaaatga tgttttatta gataaatttc 1200
aatcagggtt tttagattaa acaaacaaac aattgggtac ccagttaaat tttcatttca 1260
gataaacaac aaataatttt ttagtataag tacattattg tttatctgaa attttaattg 1320
aactaacaat cctagtttga tactcccagt cttgtcattg ccagctgtgt tggtagtgct 1380
gtgttgaatt acggaataat gagttagaac tattaaaaca gccaaaactc cacagtcaat 1440
attagtaatt tcttgctggt tgaaacttgt ttattatgta caaatagatt cttataatat 1500
tatttaaatg actgcatttt taaatacaag gctttatatt tttaacttta agatgttttt 1560
atgtgctctc caaatttttt ttactgtttc tgattgtatg gaaatataaa agtaaatatg 1620
aaacatttaa aatataattt gttgtcaaag taaaaaaaaa aaaaaa 1666

<210> SEQ ID NO 50
<211> LENGTH: 60
<212> TYPE: DNA
<213> ORGANISM: Homo sapiens
<220> FEATURE:
<223> OTHER INFORMATION: NM_000584

<400> SEQUENCE: 50
tggtagtgct gtgttgaatt acggaataat gagttagaac tattaaaaca gccaaaactc 60

<210> SEQ ID NO 51
<211> LENGTH: 1722
<212> TYPE: DNA
<213> ORGANISM: Homo sapiens
<220> FEATURE:
<223> OTHER INFORMATION: NM_000599

<400> SEQUENCE: 51
ggggaaaaga gctaggaaag agctgcaaag cagtgtgggc tttttccctt tttttgctcc 60
ttttcattac ccctcctccg ttttcaccct tctccggact tcgcgtagaa cctgcgaatt 120
tcgaagagga ggtggcaaag tgggagaaaa gaggtgttag ggtttggggt ttttttgttt 180
ttgtttttgt tttttaattt cttgatttca acattttctc ccaccctctc ggctgcagcc 240
aacgcctctt acctgttctg cggcgccgcg caccgctggc agctgagggt tagaaagcgg 300

```
ggtgtatttt agattttaag caaaaatttt aaagataaat ccatttttct ctcccacccc    360

caacgccatc tccactgcat ccgatctcat tatttcggtg gttgcttggg ggtgaacaat    420

tttgtggctt tttttcccct ataattctga cccgctcagg cttgagggtt tctccggcct    480

ccgctcactg cgtgcacctg gcgctgccct gcttccccca acctgttgca aggctttaat    540

tcttgcaact gggacctgct cgcaggcacc ccagccctcc acctctctct acatttttgc    600

aagtgtctgg gggagggcac ctgctctacc tgccagaaat tttaaaacaa aaacaaaaac    660

aaaaaaatct ccgggggccc tcttggcccc tttatccctg cactctcgct ctcctgcccc    720

accccgaggt aaagggggcg actaagagaa gatggtgttg ctcaccgcgg tcctcctgct    780

gctggccgcc tatgcggggc cggcccagag cctgggctcc ttcgtgcact gcgagccctg    840

cgacgagaaa gccctctcca tgtgcccccc cagcccctg ggctgcgagc tggtcaagga    900

gccgggctgc ggctgctgca tgacctgcgc cctggccgag gggcagtcgt gcggcgtcta    960

caccgagcgc tgcgcccagg ggctgcgctg cctcccccgg caggacgagg agaagccgct   1020

gcacgccctg ctgcacggcc gcggggtttg cctcaacgaa aagagctacc gcgagcaagt   1080

caagatcgag agagactccc gtgagcacga ggagcccacc acctctgaga tggccgagga   1140

gacctactcc cccaagatct tccggcccaa acacacccgc atctccgagc tgaaggctga   1200

agcagtgaag aaggaccgca gaaagaagct gacccagtcc aagtttgtcg gggagccgga   1260

gaacactgcc cacccccgga tcatctctgc acctgagatg agacaggagt ctgagcaggg   1320

cccctgccgc agacacatgg aggcttccct gcaggagctc aaagccagcc cacgcatggt   1380

gccccgtgct gtgtacctgc ccaattgtga ccgcaaagga ttctacaaga gaaagcagtg   1440

caaaccttcc cgtggccgca agcgtggcat ctgctggtgc gtggacaagt acgggatgaa   1500

gctgccaggc atggagtacg ttgacgggga ctttcagtgc cacaccttcg acagcagcaa   1560

cgttgagtga tgcgtccccc cccaaccttt ccctcacccc ctcccacccc cagccccgac   1620

tccagccagc gcctccctcc accccaggac gccactcatt tcatctcatt taagggaaaa   1680

atatatatct atctatttga ggaaaaaaaa aaaaaaaaaa aa                     1722
```

<210> SEQ ID NO 52
<211> LENGTH: 60
<212> TYPE: DNA
<213> ORGANISM: Homo sapiens
<220> FEATURE:
<223> OTHER INFORMATION: NM_000599

<400> SEQUENCE: 52

```
ccaggacgcc actcatttca tctcatttaa gggaaaaata tatatctatc tatttgagga     60
```

<210> SEQ ID NO 53
<211> LENGTH: 704
<212> TYPE: DNA
<213> ORGANISM: Homo sapiens
<220> FEATURE:
<223> OTHER INFORMATION: NM_000735

<400> SEQUENCE: 53

```
gcagttactg agaactcata agacgaagct aaaatccctc ttcggatcca cagtcaaccg     60

ccctgaacac atcctgcaaa aagcccagag aaaggagcgc catggattac tacagaaaat    120

atgcagctat ctttctggtc acattgtcgg tgtttctgca tgttctccat tccgctcctg    180

atgtgcagga ttgcccagaa tgcacgctac aggaaaaccc attcttctcc cagccgggtg    240

ccccaatact tcagtgcatg ggctgctgct tctctagagc atatcccact ccactaaggt    300
```

ccaagaagac gatgttggtc caaaagaacg tcacctcaga gtccacttgc tgtgtagcta 360
aatcatataa cagggtcaca gtaatggggg gtttcaaagt ggagaaccac acggcgtgcc 420
actgcagtac ttgttattat cacaaatctt aaatgtttta ccaagtgctg tcttgatgac 480
tgctgatttt ctggaatgga aaattaagtt gtttagtgtt tatggctttg tgagataaaa 540
ctctcctttt ccttaccata ccactttgac acgcttcaag gatatactgc agctttactg 600
ccttcctcct tatcctacag tacaatcagc agtctagttc ttttcatttg gaatgaatac 660
agcattaagc ttgttccact gcaaataaag ccttttaaat catc 704

<210> SEQ ID NO 54
<211> LENGTH: 60
<212> TYPE: DNA
<213> ORGANISM: Homo sapiens
<220> FEATURE:
<223> OTHER INFORMATION: NM_000735

<400> SEQUENCE: 54
tgagataaaa ctctcctttt ccttaccata ccactttgac acgcttcaag gatatactgc 60

<210> SEQ ID NO 55
<211> LENGTH: 1342
<212> TYPE: DNA
<213> ORGANISM: Homo sapiens
<220> FEATURE:
<223> OTHER INFORMATION: NM_000799

<400> SEQUENCE: 55
cccggagccg gaccggggcc accgcgcccg ctctgctccg acaccgcgcc ccctggacag 60
ccgccctctc ctccaggccc gtggggctgg ccctgcaccg ccgagcttcc cgggatgagg 120
gcccccggtg tggtcacccg gcgcgcccca ggtcgctgag ggacccccggc caggcgcgga 180 gatgggggtg cacgaatgtc ctgcctggct gtggcttctc ctgtccctgc tgtcgctccc 240
tctgggcctc ccagtcctgg gcgcccccacc acgcctcatc tgtgacagcc gagtcctgga 300
gaggtacctc ttggaggcca aggaggccga gaatatcacg acgggctgtg ctgaacactg 360
cagcttgaat gagaatatca ctgtcccaga caccaaagtt aatttctatg cctggaagag 420
gatggaggtc gggcagcagg ccgtagaagt ctggcagggc ctggccctgc tgtcggaagc 480
tgtcctgcgg ggccaggccc tgttggtcaa ctcttcccag ccgtgggagc ccctgcagct 540
gcatgtggat aaagccgtca gtggccttcg cagcctcacc actctgcttc gggctctgcg 600
agcccagaag gaagccatct cccctccaga tgcggcctca gctgctccac tccgaacaat 660
cactgctgac actttccgca aactcttccg agtctactcc aatttcctcc ggggaaagct 720
gaagctgtac acaggggagg cctgcaggac aggggacaga tgaccaggtg tgtccacctg 780
ggcatatcca ccacctccct caccaacatt gcttgtgcca caccctcccc cgccactcct 840
gaaccccgtc gaggggctct cagctcagcg ccagcctgtc ccatggacac tccagtgcca 900
gcaatgacat ctcaggggcc agaggaactg tccagagagc aactctgaga tctaaggatg 960
tcacagggcc aacttgaggg cccagagcag gaagcattca gagagcagct ttaaactcag 1020
ggacagagcc atgctgggaa gacgcctgag ctcactcggc accctgcaaa atttgatgcc 1080
aggacacgct ttggaggcga tttacctgtt ttcgcaccta ccatcaggga caggatgacc 1140
tggagaactt aggtggcaag ctgtgacttc tccaggtctc acgggcatgg gcactccctt 1200
ggtggcaaga gcccccttga caccggggtg gtgggaacca tgaagacagg atgggggctg 1260
gcctctggct ctcatggggt ccaagttttg tgtattcttc aacctcattg acaagaactg 1320
aaaccaccaa aaaaaaaaaa aa 1342

<210> SEQ ID NO 56
<211> LENGTH: 60
<212> TYPE: DNA
<213> ORGANISM: Homo sapiens
<220> FEATURE:
<223> OTHER INFORMATION: NM_000799

<400> SEQUENCE: 56
tcatggggtc caagttttgt gtattcttca acctcattga caagaactga aaccaccaaa 60

<210> SEQ ID NO 57
<211> LENGTH: 2722
<212> TYPE: DNA
<213> ORGANISM: Homo sapiens
<220> FEATURE:
<223> OTHER INFORMATION: NM_000917

<400> SEQUENCE: 57
gagcgggctg agggtaggaa gtagccgctc cgagtggagg cgactggggg ctgaagagcg 60
cgccgccctc tcgtcccact ttccaggtgt gtgatcctgt aaaattaaat cttccaagat 120
gatctggtat atattaatta taggaattct gcttccccag tctttggctc atccaggctt 180
ttttacttca attggtcaga tgactgattt gatccatact gagaaagatc tggtgacttc 240
tctgaaagat tatattaagg cagaagagga caagttagaa caaataaaaa aatgggcaga 300
gaagttagat cggctaacta gtacagcgac aaaagatcca gaaggatttg ttgggcatcc 360
agtaaatgca ttcaaattaa tgaaacgtct gaatactgag tggagtgagt tggagaatct 420
ggtccttaag gatatgtcag atggctttat ctctaaccta accattcaga gaccagtact 480
ttctaatgat gaagatcagg ttggggcagc caaagctctg ttacgtctcc aggataccta 540
caatttggat acagatacca tctcaaaggg taatcttcca ggagtgaaac acaaatcttt 600
tctaacggct gaggactgct ttgagttggg caaagtggcc tatacagaag cagattatta 660
ccatacggaa ctgtggatgg aacaagccct aaggcaactg gatgaaggcg agatttctac 720
catagataaa gtctctgttc tagattattt gagctatgcg gtatatcagc agggagacct 780
ggataaggca cttttgctca caaagaagct tcttgaacta gatcctgaac atcagagagc 840
taatggtaac ttaaaatatt ttgagtatat aatggctaaa gaaaaagatg tcaataagtc 900
tgcttcagat gaccaatctg atcagaaaac tacaccaaag aaaaaagggg ttgctgtgga 960
ttacctgcca gagagacaga agtacgaaat gctgtgccgt ggggagggta tcaaaatgac 1020
ccctcggaga cagaaaaaac tcttttgccg ctaccatgat ggaaaccgta atcctaaatt 1080
tattctggct ccagctaaac aggaggatga atgggacaag cctcgtatta ttcgcttcca 1140
tgatattatt tctgatgcag aaattgaaat cgtcaaagac ctagcaaaac caaggctgag 1200
ccgagctaca gtacatgacc ctgagactgg aaaattgacc acagcacagt acagagtatc 1260
taagagtgcc tggctctctg gctatgaaaa tcctgtggtg tctcgaatta atatgagaat 1320
acaagatcta acaggactag atgtttccac agcagaggaa ttacaggtag caaattatgg 1380
agttggagga cagtatgaac cccattttga ctttgcacgg aaagatgagc cagatgcttt 1440
caaagagctg gggacaggaa atagaattgc tacatggctg ttttatatga gtgatgtgtc 1500
tgcaggagga gccactgttt ttcctgaagt tggagctagt gtttggccca aaaaaggaac 1560
tgctgttttc tggtataatc tgtttgccag tggagaagga gattatagta cacggcatgc 1620
agcctgtcca gtgctagttg gcaacaaatg ggtatccaat aaatggctcc atgaacgtgg 1680
acaagaattt cgaagacctt gtacgttgtc agaattggaa tgacaaacag gcttcccttt 1740
ttctcctatt gttgtactct tatgtgtctg atatacacat ttccatagtc ttaactttca 1800
ggagtttaca attgactaac actccatgat tgattcagtc atgaacctca tcccatgttt 1860
catctgtgga caattgctta ctttgtgggt tcttttaaaa gtaacacgaa atcatcatat 1920
tgcataaaac cttaaagttc tgttggtatc acagaagaca aggcagagtt taaagtgagg 1980
aattttatat ttaaagaact ttttggttgg ataaaaacat aatttgagca tccagtttta 2040
gtatttcact acatctcagt tggtgggtgt taagctagaa tgggctgtgt gataggaaac 2100
aaatgcctta cagatgtgcc taggtgttct gtttacctag tgtcttactc tgttttctgg 2160
atctgaagac tagtaataaa ctaggacact aactgggttc catgtgattg ccctttcata 2220
tgatcttcta agttgatttt tttcctccca agtctttttt aaagaaagta tactgtattt 2280
taccaacccc ctctcttttc ttttagctcc tctgtggtga attaaacgta cttgagttaa 2340
aatatttcga tttttttttt ttttttaatg gaaagtcctg cataacaaca ctgggccttc 2400
ttaactaaaa tgctcaccac ttagcctgtt tttttatccc ttttttaaaa tgacagatga 2460
ttttgttcag gaattttgct gtttttctta gtgctaatac cttgcctctt attcctgcta 2520
cagcagggtg gtaatattgg cattctgatt aaatactgtg ccttaggaga ctggaagttt 2580
aaaaatgtac aagtcctttc agtgatgagg gaattgattt tttttaaaag tctttttctt 2640
agaaagccaa aatgtttgtt tttttaagat tctgaaatgt gttgtgacaa caatgaccta 2700
tttatgatct taaatctttt tt 2722

<210> SEQ ID NO 58
<211> LENGTH: 60
<212> TYPE: DNA
<213> ORGANISM: Homo sapiens
<220> FEATURE:
<223> OTHER INFORMATION: NM_000917

<400> SEQUENCE: 58
tcttactctg ttttctggat ctgaagacta gtaataaact aggacactaa ctgggttcca 60

<210> SEQ ID NO 59
<211> LENGTH: 3236
<212> TYPE: DNA
<213> ORGANISM: Homo sapiens
<220> FEATURE:
<223> OTHER INFORMATION: NM_001109

<400> SEQUENCE: 59
gacccggcca tgcgcggcct cgggctctgg ctgctgggcg cgatgatgct gcctgcgatt 60
gcccccagcc ggccctgggc cctcatggag cagtatgagg tcgtgttgcc gcggcgtctg 120
ccaggccccc gagtccgccg agctctgccc tcccacttgg gcctgcaccc agagagggtg 180
agctacgtcc ttggggccac agggcacaac ttcaccctcc acctgcggaa gaacagggac 240
ctgctgggtt ccggctacac agagacctat acggctgcca atggctccga ggtgacggag 300
cagcctcgcg ggcaggacca ctgcttatac cagggccacg tagaggggta cccggactca 360
gccgccagcc tcagcacctg tgccggcctc aggggtttct tccaggtggg gtcagacctg 420
cacctgatcg agcccctgga tgaaggtggc gagggcggac ggcacgccgt gtaccaggct 480
gagcacctgc tgcagacggc cgggacctgc ggggtcagcg acgacagcct gggcagcctc 540
ctgggacccc ggacggcagc cgtcttcagg cctcggcccg gggactctct gccatcccga 600
gagacccgct acgtggagct gtatgtggtc gtggacaatg cagagttcca gatgctgggg 660

```
agcgaagcag ccgtgcgtca tcgggtgctg gaggtggtga atcacgtgga caagctatat    720
cagaaactca acttccgtgt ggtcctggtg ggcctggaga tttggaatag tcaggacagg    780
ttccacgtca gccccgaccc cagtgtcaca ctggagaacc tcctgacctg gcaggcacgg    840
caacggacac ggcggcacct gcatgacaac gtacagctca tcacgggtgt cgacttcacc    900
gggactactg tggggtttgc cagggtgtcc gccatgtgct cccacagctc aggggctgtg    960
aaccaggacc acagcaagaa ccccgtgggc gtggcctgca ccatggccca tgagatgggc   1020
cacaacctgg gcatggacca tgatgagaac gtccagggct gccgctgcca ggaacgcttc   1080
gaggccggcc gctgcatcat ggcaggcagc attggctcca gtttccccag gatgttcagt   1140
gactgcagcc aggcctacct ggagagcttt ttggagcggc cgcagtcggt gtgcctcgcc   1200
aacgcccctg acctcagcca cctggtgggc ggccccgtgt gtgggaacct gtttgtggag   1260
cgtggggagc agtgcgactg cggcccccc gaggactgcc ggaaccgctg ctgcaactct   1320
accacctgcc agctggctga gggggcccag tgtgcgcacg gtacctgctg ccaggagtgc   1380
aaggtgaagc cggctggtga gctgtgccgt cccaagaagg acatgtgtga cctcgaggag   1440
ttctgtgacg gccggcaccc tgagtgcccg gaagacgcct tccaggagaa cggcacgccc   1500
tgctccgggg gctactgcta caacggggcc tgtcccacac tggcccagca gtgccaggcc   1560
ttctgggggc caggtgggca ggctgccgag gagtcctgct tctcctatga catcctacca   1620
ggctgcaagg ccagccggta cagggctgac atgtgtggcg ttctgcagtg caagggtggg   1680
cagcagcccc tggggcgtgc catctgcatc gtggatgtgt gccacgcgct caccacagag   1740
gatggcactg cgtatgaacc agtgcccgag ggcacccggt gtggaccaga gaaggtttgc   1800
tggaaaggac gttgccagga cttacacgtt tacagatcca gcaactgctc tgcccagtgc   1860
cacaaccatg ggtgtgcaa ccacaagcag gagtgccact gccacgcggg ctgggccccg   1920
ccccactgcg cgaagctgct gactgaggtg cacgcagcgt ccgggagcct ccccgtcctc   1980
gtggtggtgg ttctggtgct cctggcagtt gtgctggtca ccctggcagg catcatcgtc   2040
taccgcaaag cccggagccg catcctgagc aggaacgtgg ctcccaagac cacaatgggg   2100
cgctccaacc ccctgttcca ccaggctgcc agccgcgtgc cggccaaggg cggggctcca   2160
gccccatcca ggggccccca agagctggtc cccaccaccc acccgggcca gcccgcccga   2220
cacccggcct cctcggtggc tctgaagagg ccgccccctg ctcctccggt cactgtgtcc   2280
agcccaccct tcccagttcc tgtctacacc cggcaggcac caaagcaggt catcaagcca   2340
acgttcgcac ccccagtgcc cccagtcaaa cccggggctg gtgcggccaa ccctggtcca   2400
gctgagggtg ctgttggccc aaaggttgcc ctgaagcccc ccatccagag gaagcaagga   2460
gccggagctc ccacagcacc ctagggggc acctgcgcct gtgtggaaat ttggagaagt   2520
tgcggcagag aagccatgcg ttccagcctt ccacggtcca gctagtgccg ctcagcccta   2580
gaccctgact ttgcaggctc agctgctgtt ctaacctcag taatgcatct acctgagagg   2640
ctcctgctgt ccacgccctc agccaattcc ttctccccgc cttggccacg tgtagcccca   2700
gctgtctgca ggcaccaggc tgggatgagc tgtgtgcttg cgggtgcgtg tgtgtgtacg   2760
tgtctccagg tggccgctgg tctcccgctg tgttcaggag gccacatata cagcccctcc   2820
cagccacacc tgcccctgct ctggggcctg ctgagccggc tgccctgggc acccggttcc   2880
aggcagcaca gacgtggggc atccccagaa agactccatc ccaggaccag gttcccctcc   2940
gtgctcttcg agagggtgtc agtgagcaga ctgcacccca agctcccgac tccaggtccc   3000
ctgatcttgg gcctgtttcc catgggattc aagagggaca gccccagctt tgtgtgtgtt   3060
```

-continued

```
taagcttagg aatgcccttt atggaaaggg ctatgtggga gagtcagcta tcttgtctgg   3120

ttttcttgag acctcagatg tgtgttcagc agggctgaaa gcttttattc tttaataatg   3180

agaaatgtat attttactaa taaattattg accgagttct gtagattctt gttaga       3236
```

<210> SEQ ID NO 60
<211> LENGTH: 60
<212> TYPE: DNA
<213> ORGANISM: Homo sapiens
<220> FEATURE:
<223> OTHER INFORMATION: NM_001109

<400> SEQUENCE: 60

```
ctttatggaa agggctatgt gggagagtca gctatcttgt ctggttttct tgagacctca     60
```

<210> SEQ ID NO 61
<211> LENGTH: 1449
<212> TYPE: DNA
<213> ORGANISM: Homo sapiens
<220> FEATURE:
<223> OTHER INFORMATION: NM_001124

<400> SEQUENCE: 61

```
ctggatagaa cagctcaagc cttgccactt cgggcttctc actgcagctg ggcttggact     60

tcggagtttt gccattgcca gtgggacgtc tgagactttc tccttcaagt acttggcaga    120

tcactctctt agcagggtct gcgcttcgca gccgggatga agctggtttc cgtcgccctg    180

atgtacctgg gttcgctcgc cttcctaggc gctgacaccg ctcggttgga tgtcgcgtcg    240

gagtttcgaa agaagtggaa taagtgggct ctgagtcgtg ggaagaggga actgcggatg    300

tccagcagct accccaccgg gctcgctgac gtgaaggccg ggcctgccca gacccttatt    360

cggccccagg acatgaaggg tgcctctcga agccccgaag acagcagtcc ggatgccgcc    420

cgcatccgag tcaagcgcta ccgccagagc atgaacaact tccagggcct ccggagcttt    480

ggctgccgct tcgggacgtg cacggtgcag aagctggcac accagatcta ccagttcaca    540

gataaggaca aggacaacgt cgcccccagg agcaagatca gcccccaggg ctacggccgc    600

cggcgccggc gctccctgcc cgaggccggc ccgggtcgga ctctggtgtc ttctaagcca    660

caagcacacg gggctccagc ccccccgagt ggaagtgctc cccactttct ttaggattta    720

ggcgcccatg gtacaaggaa tagtcgcgca agcatcccgc tggtgcctcc cgggacgaag    780

gacttcccga gcggtgtggg gaccgggctc tgacagccct gcggagaccc tgagtccggg    840

aggcaccgtc cggcggcgag ctctggcttt gcaagggccc ctccttctgg gggcttcgct    900

tccttagcct tgctcaggtg caagtgcccc agggggcggg gtgcagaaga atccgagtgt    960

ttgccaggct taaggagagg agaaactgag aaatgaatgc tgagaccccc ggagcagggg   1020

tctgagccac agccgtgctc gcccacaaac tgatttctca cggcgtgtca ccccaccagg   1080

gcgcaagcct cactattact tgaactttcc aaaacctaaa gaggaaaagt gcaatgcgtg   1140

ttgtacatac agaggtaact atcaatattt aagtttgttg ctgtcaagat tttttttgta   1200

acttcaaata tagagatatt tttgtacgtt atatattgta ttaagggcat tttaaaagca   1260

attatattgt cctcccctat tttaagacgt gaatgtctca gcgaggtgta aagttgttcg   1320

ccgcgtggaa tgtgagtgtg tttgtgtgca tgaaagagaa agactgatta cctcctgtgt   1380

ggaagaagga aacaccgagt ctctgtataa tctatttaca taaaatgggt gatatgcgaa   1440

cagcaaacc                                                           1449
```

<210> SEQ ID NO 62
<211> LENGTH: 60
<212> TYPE: DNA
<213> ORGANISM: Homo sapiens
<220> FEATURE:
<223> OTHER INFORMATION: NM_001124

<400> SEQUENCE: 62
gaaggaaaca ccgagtctct gtataatcta tttacataaa atgggtgata tgcgaacagc 60

<210> SEQ ID NO 63
<211> LENGTH: 1619
<212> TYPE: DNA
<213> ORGANISM: Homo sapiens
<220> FEATURE:
<223> OTHER INFORMATION: NM_001168

<400> SEQUENCE: 63
ccgccagatt tgaatcgcgg gacccgttgg cagaggtggc ggcggcggca tgggtgcccc 60
gacgttgccc cctgcctggc agccctttct caaggaccac cgcatctcta cattcaagaa 120
ctggcccttc ttggagggct gcgcctgcac cccggagcgg atggccgagg ctggcttcat 180
ccactgcccc actgagaacg agccagactt ggcccagtgt ttcttctgct tcaaggagct 240
ggaaggctgg gagccagatg acgaccccat agaggaacat aaaaagcatt cgtccggttg 300
cgctttcctt tctgtcaaga agcagtttga agaattaacc cttggtgaat tttgaaact 360 ggacagagaa agagccaaga acaaaattgc aaaggaaacc aacaataaga agaaagaatt 420
tgaggaaact gcgaagaaag tgcgccgtgc catcgagcag ctggctgcca tggattgagg 480
cctctggccg gagctgcctg gtcccagagt ggctgcacca cttccagggt ttattccctg 540
gtgccaccag ccttcctgtg ggccccttag caatgtctta ggaaaggaga tcaacatttt 600
caaattagat gtttcaactg tgctcctgtt ttgtcttgaa agtggcacca gaggtgcttc 660
tgcctgtgca gcgggtgctg ctggtaacag tggctgcttc tctctctctc tctcttttt 720 gggggctcat ttttgctgtt ttgattcccg ggcttaccag gtgagaagtg agggaggaag 780
aaggcagtgt cccttttgct agagctgaca gctttgttcg cgtgggcaga gccttccaca 840
gtgaatgtgt ctggacctca tgttgttgag gctgtcacag tcctgagtgt ggacttggca 900
ggtgcctgtt gaatctgagc tgcaggttcc ttatctgtca cacctgtgcc tcctcagagg 960
acagtttttt tgttgttgtg tttttttgtt ttttttttt ggtagatgca tgacttgtgt 1020
gtgatgagag aatggagaca gagtccctgg ctcctctact gtttaacaac atggctttct 1080
tattttgttt gaattgttaa ttcacagaat agcacaaact acaattaaaa ctaagcacaa 1140
agccattcta agtcattggg gaaacggggt gaacttcagg tggatgagga gacagaatag 1200
agtgatagga agcgtctggc agatactcct tttgccactg ctgtgtgatt agacaggccc 1260
agtgagccgc ggggcacatg ctggccgctc ctccctcaga aaaaggcagt ggcctaaatc 1320
ctttttaaat gacttggctc gatgctgtgg gggactggct gggctgctgc aggccgtgtg 1380
tctgtcagcc caaccttcac atctgtcacg ttctccacac gggggagaga cgcagtccgc 1440
ccaggtcccc gctttctttg gaggcagcag ctcccgcagg gctgaagtct ggcgtaagat 1500
gatggatttg attcgccctc ctccctgtca tagagctgca gggtggattg ttacagcttc 1560
gctggaaacc tctggaggtc atctcggctg ttcctgagaa ataaaaagcc tgtcatttc 1619

<210> SEQ ID NO 64
<211> LENGTH: 60
<212> TYPE: DNA
<213> ORGANISM: Homo sapiens

<220> FEATURE:
<223> OTHER INFORMATION: NM_001168

<400> SEQUENCE: 64

```
ttcacagaat agcacaaact acaattaaaa ctaagcacaa agccattcta agtcattggg     60
```

<210> SEQ ID NO 65
<211> LENGTH: 1552
<212> TYPE: DNA
<213> ORGANISM: Homo sapiens
<220> FEATURE:
<223> OTHER INFORMATION: NM_001216

<400> SEQUENCE: 65

```
gcccgtacac accgtgtgct gggacacccc acagtcagcc gcatggctcc cctgtgcccc     60
agcccctggc tccctctgtt gatcccggcc cctgctccag gcctcactgt gcaactgctg    120
ctgtcactgc tgcttctgat gcctgtccat ccccagaggt tgccccggat gcaggaggat    180
tccccccttgg gaggaggctc ttctggggaa gatgacccac tgggcgagga ggatctgccc    240
agtgaagagg attcacccag agaggaggat ccacccggag aggaggatct acctggagag    300
gaggatctac ctggagagga ggatctacct gaagttaagc ctaaatcaga agaagagggc    360
tccctgaagt tagaggatct acctactgtt gaggctcctg gagatcctca agaaccccag    420
aataatgccc acagggacaa agaaggggat gaccagagtc attggcgcta tggaggcgac    480
ccgccctggc cccgggtgtc cccagcctgc gcgggccgct tccagtcccc ggtggatatc    540
cgcccccagc tcgccgcctt ctgcccggcc ctgcgccccc tggaactcct gggcttccag    600
ctcccgccgc tcccagaact gcgcctgcgc aacaatggcc acagtgtgca actgaccctg    660
cctcctgggc tagagatggc tctgggtccc gggcgggagt accgggctct gcagctgcat    720
ctgcactggg gggctgcagg tcgtccgggc tcggagcaca ctgtggaagg ccaccgtttc    780
cctgccgaga tccacgtggt tcacctcagc accgcctttg ccagagttga cgaggccttg    840
gggcgcccgg gaggcctggc cgtgttggcc gcctttctgg aggagggccc ggaagaaaac    900
agtgcctatg agcagttgct gtctcgcttg gaagaaatcg ctgaggaagg ctcagagact    960
caggtcccag gactggacat atctgcactc ctgccctctg acttcagccg ctacttccaa   1020
tatgaggggt ctctgactac accgccctgt gcccagggtg tcatctggac tgtgtttaac   1080
cagacagtga tgctgagtgc taagcagctc cacaccctct ctgacaccct gtggggacct   1140
ggtgactctc ggctacagct gaacttccga gcgacgcagc ctttgaatgg gcgagtgatt   1200
gaggcctcct tccctgctgg agtggacagc agtcctcggg ctgctgagcc agtccagctg   1260
aattcctgcc tggctgctgg tgacatccta gccctggttt ttggcctcct ttttgctgtc   1320
accagcgtcg cgttccttgt gcagatgaga aggcagcaca gaaggggaac caaagggggt   1380
gtgagctacc gcccagcaga ggtagccgag actggagcct agaggctgga tcttggagaa   1440
tgtgagaagc cagccagagg catctgaggg ggagccggta actgtcctgt cctgctcatt   1500
atgccacttc cttttaactg ccaagaaatt ttttaaaata aatatttata at           1552
```

<210> SEQ ID NO 66
<211> LENGTH: 60
<212> TYPE: DNA
<213> ORGANISM: Homo sapiens
<220> FEATURE:
<223> OTHER INFORMATION: NM_001216

<400> SEQUENCE: 66

```
tcctgtcctg ctcattatgc cacttccttt taactgccaa gaaatttttt aaaataaata     60
```

<210> SEQ ID NO 67
<211> LENGTH: 2653
<212> TYPE: DNA
<213> ORGANISM: Homo sapiens
<220> FEATURE:
<223> OTHER INFORMATION: NM_001254

<400> SEQUENCE: 67

```
gagcgcggct ggagtttgct gctgccgctg tgcagtttgt tcaggggctt gtggtggtga     60
gtccgagagg ctgcgtgtga gagacgtgag aaggatcctg cactgaggag gtggaaagaa    120
gaggattgct cgaggaggcc tggggtctgt gaggcagcgg agctgggtga aggctgcggg    180
ttccggcgag gcctgagctg tgctgtcgtc atgcctcaaa cccgatccca ggcacaggct    240
acaatcagtt ttccaaaaag gaagctgtct cgggcattga acaaagctaa aaactccagt    300
gatgccaaac tagaaccaac aaatgtccaa accgtaacct gttctcctcg tgtaaaagcc    360
ctgcctctca gccccaggaa acgtctgggc gatgacaacc tatgcaacac tccccattta    420
cctccttgtt ctccaccaaa gcaaggcaag aaagagaatg gtccccctca ctcacataca    480
cttaagggac gaagattggt atttgacaat cagctgacaa ttaagtctcc tagcaaaaga    540
gaactagcca aagttcacca aaacaaaata ctttcttcag ttagaaaaag tcaagagatc    600
acaacaaatt ctgagcagag atgtccactg aagaaagaat ctgcatgtgt gagactattc    660
aagcaagaag gcacttgcta ccagcaagca aagctggtcc tgaacacagc tgtcccagat    720
cggctgcctg ccagggaaag ggagatggat gtcatcagga atttcttgag ggaacacatc    780
tgtgggaaaa aagctggaag cctttacctt tctggtgctc ctggaactgg aaaaactgcc    840
tgcttaagcc ggattctgca agacctcaag aaggaactga aaggctttaa aactatcatg    900
ctgaattgca tgtccttgag gactgcccag gctgtattcc cagctattgc tcaggagatt    960
tgtcaggaag aggtatccag gccagctggg aaggacatga tgaggaaatt ggaaaaacat   1020
atgactgcag agaagggccc catgattgtg ttggtattgg acgagatgga tcaactggac   1080
agcaaaggcc aggatgtatt gtacacgcta tttgaatggc catggctaag caattctcac   1140
ttggtgctga ttggtattgc taataccctg gatctcacag atagaattct acctaggctt   1200
caagctagag aaaaatgtaa gccacagctg ttgaacttcc caccttatac cagaaatcag   1260
atagtcacta ttttgcaaga tcgacttaat caggtatcta gagatcaggt tctggacaat   1320
gctgcagttc aattctgtgc ccgcaaagtc tctgctgttt caggagatgt tcgcaaagca   1380
ctggatgttt gcaggagagc tattgaaatt gtagagtcag atgtcaaaag ccagactatt   1440
ctcaaaccac tgtctgaatg taaatcacct tctgagcctc tgattcccaa gagggttggt   1500
cttattcaca tatcccaagt catctcagaa gttgatggta acaggatgac cttgagccaa   1560
gaaggagcac aagattcctt ccctcttcag cagaagatct tggtttgctc tttgatgctc   1620
ttgatcaggc agttgaaaat caaagaggtc actctgggga agttatatga agcctacagt   1680
aaagtctgtc gcaaacagca ggtggcggct gtggaccagt cagagtgttt gtcactttca   1740
gggctcttgg aagccagggg cattttagga ttaaagagaa acaaggaaac ccgtttgaca   1800
aaggtgtttt tcaagattga agagaaagaa atagaacatg ctctgaaaga taaagcttta   1860
attggaaata tcttagctac tggattgcct taaattcttc tcttacaccc cacccgaaag   1920
tattcagctg gcatttagag agctacagtc ttcattttag tgctttacac attcgggcct   1980
gaaaacaaat atgacctttt ttacttgaag ccaatgaatt ttaatctata gattctttaa   2040
tattagcaca gaataatatc tttgggtctt actattttta cccataaaag tgaccaggta   2100
```

gacccttttt aattacattc actacttcta ccacttgtgt atctctagcc aatgtgcttg 2160
caagtgtaca gatctgtgta gaggaatgtg tgtatattta cctcttcgtt tgctcaaaca 2220
tgagtgggta tttttttgtt tgtttttttt gttgttgttg tttttgaggc gcgtctcacc 2280
ctgttgccca ggctggagtg caatggcgcg ttctctgctc actacagcac ccgcttccca 2340
ggttgaagtg attctcttgc ctcagcctcc cgagtagctg ggattacagg tgcccaccac 2400
cgcgcccagc taattttttta atttttagta gagacagggt tttaccatgt tggccaggct 2460
ggtcttgaac tcctgaccct caagtgatct gcccaccttg gcctccctaa gtgctgggat 2520
tataggcgtg agccaccatg ctcagccatt aaggtatttt gttaagaact ttaagtttag 2580
ggtaagaaga atgaaaatga tccagaaaaa tgcaagcaag tccacatgga gatttggagg 2640
acactggtta aag 2653

<210> SEQ ID NO 68
<211> LENGTH: 60
<212> TYPE: DNA
<213> ORGANISM: Homo sapiens
<220> FEATURE:
<223> OTHER INFORMATION: NM_001254

<400> SEQUENCE: 68
caaggaaacc cgtttgacaa aggtgttttt caagattgaa gagaaagaaa tagaacatgc 60

<210> SEQ ID NO 69
<211> LENGTH: 627
<212> TYPE: DNA
<213> ORGANISM: Homo sapiens
<220> FEATURE:
<223> OTHER INFORMATION: NM_001323

<400> SEQUENCE: 69
gcggccgcaa gctcggcact cacggctctg agggctccga cggcactgac ggccatggcg 60
cgttcgaacc tcccgctggc gctgggcctg gccctggtcg cattctgcct cctggcgctg 120
ccacgcgacg cccgggcccg gccgcaggag cgcatggtcg gagaactccg ggacctgtcg 180
cccgacgacc cgcaggtgca gaaggcggcg caggcggccg tggccagcta caacatgggc 240
agcaacagca tctactactt ccgagacacg cacatcatca aggcgcagag ccagctggtg 300
gccggcatca agtacttcct gacgatggag atggggagca cagactgccg caagaccagg 360
gtcactggag accacgtcga cctcaccact tgcccccctgg cagcaggggc gcagcaggag 420
aagctgcgct gtgactttga ggtccttgtg gttccctggc agaactcctc tcagctccta 480
aagcacaact gtgtgcagat gtgataagtc cccgagggcg aaggccattg ggtttggggc 540
catggtggag ggcacttcag gtccgtgggc cgtatctgtc acaataaatg gccagtgctg 600
cttcttgcaa aaaaaaaaaa aaaaaaa 627

<210> SEQ ID NO 70
<211> LENGTH: 60
<212> TYPE: DNA
<213> ORGANISM: Homo sapiens
<220> FEATURE:
<223> OTHER INFORMATION: NM_001323

<400> SEQUENCE: 70
atcaagtact tcctgacgat ggagatgggg agcacagact gccgcaagac cagggtcact 60

<210> SEQ ID NO 71
<211> LENGTH: 1812

<212> TYPE: DNA
<213> ORGANISM: Homo sapiens
<220> FEATURE:
<223> OTHER INFORMATION: NM_001428

<400> SEQUENCE: 71

```
tagctaggca ggaagtcggc gcgggcggcg cggacagtat ctgtgggtac ccggagcacg     60
gagatctcgc cggctttacg ttcacctcgg tgtctgcagc accctccgct tcctctccta    120
ggcgacgaga cccagtggct agaagttcac catgtctatt ctcaagatcc atgccaggga    180
gatctttgac tctcgcggga atcccactgt tgaggttgat ctcttcacct caaaaggtct    240
cttcagagct gctgtgccca gtggtgcttc aactggtatc tatgaggccc tagagctccg    300
ggacaatgat aagactcgct atatggggaa gggtgtctca aaggctgttg agcacatcaa    360
taaaactatt gcgcctgccc tggttagcaa gaaactgaac gtcacagaac aagagaagat    420
tgacaaactg atgatcgaga tggatggaac agaaaataaa tctaagtttg gtgcgaacgc    480
cattctgggg gtgtcccttg ccgtctgcaa agctggtgcc gttgagaagg gggtccccct    540
gtaccgccac atcgctgact tggctggcaa ctctgaagtc atcctgccag tcccggcgtt    600
caatgtcatc aatggcggtt ctcatgctgg caacaagctg gccatgcagg agttcatgat    660
cctcccagtc ggtgcagcaa acttcaggga agccatgcgc attggagcag aggtttacca    720
caacctgaag aatgtcatca aggagaaata tgggaaagat gccaccaatg tgggggatga    780
aggcgggttt gctcccaaca tcctggagaa taaagaaggc ctggagctgc tgaagactgc    840
tattgggaaa gctggctaca ctgataaggt ggtcatcggc atggacgtag cggcctccga    900
gttcttcagg tctgggaagt atgacctgga cttcaagtct cccgatgacc ccagcaggta    960
catctcgcct gaccagctgg ctgacctgta caagtccttc atcaaggact acccagtggt   1020
gtctatcgaa gatccctttg accaggatga ctggggagct tggcagaagt tcacagccag   1080
tgcaggaatc caggtagtgg gggatgatct cacagtgacc aacccaaaga ggatcgccaa   1140
ggccgtgaac gagaagtcct gcaactgcct cctgctcaaa gtcaaccaga ttggctccgt   1200
gaccgagtct cttcaggcgt gcaagctggc ccaggccaat ggttggggcg tcatggtgtc   1260
tcatcgttcg ggggagactg aagatacctt catcgctgac ctggttgtgg ggctgtgcac   1320
tgggcagatc aagactggtg ccccttgccg atctgagcgc ttggccaagt acaaccagct   1380
cctcagaatt gaagaggagc tgggcagcaa ggctaagttt gccggcagga acttcagaaa   1440
ccccttggcc aagtaagctg tgggcaggca agcccttcgg tcacctgttg gctacacaga   1500
cccctcccct cgtgtcagct caggcagctc gaggcccccg accaacactt gcaggggtcc   1560
ctgctagtta gcgccccacc gccgtggagt tcgtaccgct tccttagaac ttctacagaa   1620
gccaagctcc ctggagccct gttggcagct ctagctttgc agtcgtgtaa ttggcccaag   1680
tcattgtttt tctcgcctca ctttccacca agtgtctaga gtcatgtgag cctcgtgtca   1740
tctccggggt ggccacaggc tagatccccg gtggttttgt gctcaaaata aaaagcctca   1800
gtgacccatg ag                                                        1812
```

<210> SEQ ID NO 72
<211> LENGTH: 60
<212> TYPE: DNA
<213> ORGANISM: Homo sapiens
<220> FEATURE:
<223> OTHER INFORMATION: NM_001428

<400> SEQUENCE: 72

```
agctctagct tttgcagtcg tgtaatgggc ccaagtcatt gtttttctcg cctcactttc     60
```

<210> SEQ ID NO 73
<211> LENGTH: 8368
<212> TYPE: DNA
<213> ORGANISM: Homo sapiens
<220> FEATURE:
<223> OTHER INFORMATION: NM_001456

<400> SEQUENCE: 73
gcgatccggg cgccaccccg cggtcatcgg tcaccggtcg ctctcaggaa cagcagcgca 60
acctctgctc cctgcctcgc ctcccgcgcg cctaggtgcc tgcgacttta attaaagggc 120
cgtcccctcg ccgaggctgc agcaccgccc ccccggcttc tcgcgcctca aaatgagtag 180
ctcccactct cgggcgggcc agagcgcagc aggcgcggct ccgggcggcg gcgtcgacac 240
gcgggacgcc gagatgccgg ccaccgagaa ggacctggcg gaggacgcgc cgtggaagaa 300
gatccagcag aacactttca cgcgctggtg caacgagcac ctgaagtgcg tgagcaagcg 360
catcgccaac ctgcagacgg acctgagcga cgggctgcgg cttatcgcgc tgttggaggt 420
gctcagccag aagaagatgc accgcaagca caaccagcgg cccactttcc gccaaatgca 480
gcttgagaac gtgtcggtgg cgctcgagtt cctggaccgc gagagcatca aactggtgtc 540
catcgacagc aaggccatcg tggacgggaa cctgaagctg atcctgggcc tcatctggac 600
cctgatcctg cactactcca tctccatgcc catgtgggac gaggaggagg atgaggaggc 660
caagaagcag acccccaagc agaggctcct gggctggatc cagaacaagc tgccgcagct 720
gcccatcacc aacttcagcc gggactggca gagcggccgg gccctgggcg ccctggtgga 780
cagctgtgcc ccgggcctgt gtcctgactg ggactcttgg gacgccagca agcccgttac 840
caatgcgcga gaggccatgc agcaggcgga tgactggctg ggcatccccc aggtgatcac 900
ccccgaggag attgtggacc ccaacgtgga cgagcactct gtcatgacct acctgtccca 960
gttccccaag gccaagctga agccaggggc tcccttgcgc cccaaactga acccgaagaa 1020
agcccgtgcc tacgggccag gcatcgagcc cacaggcaac atggtgaaga agcgggcaga 1080
gttcactgtg gagaccagaa gtgctggcca gggagaggtg ctggtgtacg tggaggaccc 1140
ggccggacac caggaggagg caaaagtgac cgccaataac gacaagaacc gcaccttctc 1200
cgtctggtac gtccccgagg tgacggggac tcataaggtt actgtgctct ttgctggcca 1260
gcacatcgcc aagagcccct tcgaggtgta cgtggataag tcacagggtg acgccagcaa 1320
agtgacagcc caaggtcccg gcctggagcc cagtggcaac atcgccaaca agaccaccta 1380
ctttgagatc tttacggcag gagctggcac gggcgaggtc gaggttgtga tccaggaccc 1440
catgggacag aagggcacgg tagagcctca gctggaggcc cggggcgaca gcacataccg 1500
ctgcagctac cagcccacca tggagggcgt ccacaccgtg cacgtcacgt ttgccggcgt 1560
gcccatccct cgcagcccct acactgtcac tgttggccaa gcctgtaacc cgagtgcctg 1620
ccgggcggtt ggccggggcc tccagcccaa gggtgtgcgg gtgaaggaga cagctgactt 1680
caaggtgtac acaaagggcg ctggcagtgg ggagctgaag gtcaccgtga agggccccaa 1740
gggagaggag cgcgtgaagc agaaggacct gggggatggc gtgtatggct tcgagtatta 1800
ccccatggtc cctggaacct atatcgtcac catcacgtgg ggtggtcaga acatcgggcg 1860
cagtcccttc gaagtgaagg tgggcaccga gtgtggcaat cagaaggtac gggcctgggg 1920
ccctgggctg gagggcggcg tcgttggcaa gtcagcagac tttgtggtgg aggctatcgg 1980
ggacgacgtg ggcacgctgg gcttctcggt ggaagggcca tcgcaggcta agatcgaatg 2040
tgacgacaag ggcgacggct cctgtgatgt gcgctactgg ccgcaggagg ctggcgagta 2100

-continued

```
tgccgttcac gtgctgtgca acagcgaaga catccgcctc agccccttca tggctgacat   2160
ccgtgacgcg ccccaggact tccacccaga cagggtgaag gcacgtgggc ctggattgga   2220
gaagacaggt gtggccgtca acaagccagc agagttcaca gtggatgcca agcacggtgg   2280
caaggcccca cttcgggtcc aagtccagga caatgaaggc tgccctgtgg aggcgttggt   2340
caaggacaac ggcaatggca cttacagctg ctcctacgtg cccaggaagc cggtgaagca   2400
cacagccatg gtgtcctggg gaggcgtcag catccccaac agccccttca gggtgaatgt   2460
gggagctggc agccacccca acaaggtcaa agtatacggc cccggagtag ccaagacagg   2520
gctcaaggcc cacgagccca cctacttcac tgtggactgc gccgaggctg gccaggggga   2580
cgtcagcatc ggcatcaagt gtgcccctgg agtggtaggc cccgccgaag ctgacatcga   2640
cttcgacatc atccgcaatg acaatgacac cttcacggtc aagtacacgc cccggggggc   2700
tggcagctac accattatgg tcctctttgc tgaccaggcc acgcccacca gccccatccg   2760
agtcaaggtg gagccctctc atgacgccag taaggtgaag gccgagggcc ctggcctcag   2820
tcgcactggt gtcgagcttg gcaagcccac ccacttcaca gtaaatgcca aagctgctgg   2880
caaaggcaag ctggacgtcc agttctcagg actcaccaag ggggatgcag tgcgagatgt   2940
ggacatcatc gaccaccatg acaacaccta cacagtcaag tacacgcctg tccagcaggg   3000
tccagtaggc gtcaatgtca cttatggagg ggatcccatc cctaagagcc ctttctcagt   3060
ggcagtatct ccaagcctgg acctcagcaa gatcaaggtg tctggcctgg gagagaaggt   3120
ggacgttggc aaagaccagg agttcacagt caaatcaaag ggtgctggtg gtcaaggcaa   3180
agtggcatcc aagattgtgg gcccctcggg tgcagcggtg ccctgcaagg tggagccagg   3240
cctgggggct gacaacagtg tggtgcgctt cctgccccgt gaggaagggc cctatgaggt   3300
ggaggtgacc tatgacggcg tgcccgtgcc tggcagcccc tttcctctgg aagctgtggc   3360
cccaccaaag cctagcaagg tgaaggcgtt tgggccgggg ctgcagggag gcagtgcggg   3420
ctcccccgcc cgcttcacca tcgacaccaa gggcgccggc acaggtggcc tgggcctgac   3480
ggtggagggc ccctgtgagg cgcagctcga gtgcttggac aatggggatg gcacatgttc   3540
cgtgtcctac gtgcccaccg agcccgggga ctacaacatc aacatcctct tcgctgacac   3600
ccacatccct ggctccccat tcaaggccca cgtggttccc tgctttgacg catccaaagt   3660
caagtgctca ggccccgggc tggagcgggc caccgctggg gaggtgggcc aattccaagt   3720
ggactgctcg agcgcgggca gcgcggagct gaccattgag atctgctcgg aggcggggct   3780
tccggccgag gtgtacatcc aggaccacgg tgatggcacg cacaccatta cctacattcc   3840
cctctgcccc ggggcctaca ccgtcaccat caagtacggc ggccagcccg tgcccaactt   3900
ccccagcaag ctgcaggtgg aacctgcggt ggacacttcc ggtgtccagt gctatgggcc   3960
tggtattgag ggccagggtg tcttccgtga ggccaccact gagttcagtg tggacgcccg   4020
ggctctgaca cagaccggag ggccgcacgt caaggcccgt gtggccaacc cctcaggcaa   4080
cctgacggag acctacgttc aggaccgtgg cgatggcatg tacaaagtgg agtacacgcc   4140
ttacgaggag ggactgcact ccgtggacgt gacctatgac ggcagtcccg tgcccagcag   4200
ccccttccag gtgcccgtga ccgagggctg cgacccctcc cgggtgcgtg tccacgggcc   4260
aggcatccaa agtggcacca ccaacaagcc caacaagttc actgtggaga ccaggggagc   4320
tggcacgggc ggcctgggcc tggctgtaga gggcccctcc gaggccaaga tgtcctgcat   4380
ggataacaag gacggcagct gctcggtcga gtacatccct tatgaggctg gcacctacag   4440
cctcaacgtc acctatggtg gccatcaagt gccaggcagt cctttcaagg tccctgtgca   4500
```

```
tgatgtgaca gatgcgtcca aggtcaagtg ctctgggccc ggcctgagcc caggcatggt   4560
tcgtgccaac ctccctcagt ccttccaggt ggacacaagc aaggctggtg tggccccatt   4620
gcaggtcaaa gtgcaagggc ccaaaggcct ggtggagcca gtggacgtgg tagacaacgc   4680
tgatggcacc cagaccgtca attatgtgcc cagccgagaa gggccctaca gcatctcagt   4740
actgtatgga gatgaagagg taccccggag ccccttcaag gtcaaggtgc tgcctactca   4800
tgatgccagc aaggtgaagg ccagtggccc cgggctcaac accactggcg tgcctgccag   4860
cctgccccgtg gagttcacca tcgatgcaaa ggacgccggg gagggcctgc tggctgtcca   4920
gatcacggat cccgaaggca agccgaagaa gacacacatc caagacaacc atgacggcac   4980
gtatacagtg gcctacgtgc cagacgtgac aggtcgctac accatcctca tcaagtacgg   5040
tggtgacgag atccccttct ccccgtaccg cgtgcgtgcc gtgcccaccg gggacgccag   5100
caagtgcact gtcacagtgt caatcggagg tcacgggcta ggtgctggca tcggccccac   5160
cattcagatt ggggaggaga cggtgatcac tgtggacact aaggcggcag gcaaaggcaa   5220
agtgacgtgc accgtgtgca cgcctgatgg ctcagaggtg gatgtggacg tggtggagaa   5280
tgaggacggc actttcgaca tcttctacac ggccccccag ccgggcaaat acgtcatctg   5340
tgtgcgcttt ggtggcgagc acgtgcccaa cagccccttc caagtgacgg ctctggctgg   5400
ggaccagccc tcggtgcagc cccctctacg gtctcagcag ctggccccac agtacaccta   5460
cgcccagggc ggccagcaga cttgggcccc ggagaggccc ctggtgggtg tcaatgggct   5520
ggatgtgacc agcctgaggc cctttgacct tgtcatcccc ttcaccatca agaagggcga   5580
gatcacaggg gaggttcgga tgccctcagg caaggtggcg cagcccacca tcactgacaa   5640
caaagacggc accgtgaccg tgcggtatgc acccagcgag gctggcctgc acgagatgga   5700
catccgctat gacaacatgc acatcccagg aagccccttg cagttctatg tggattacgt   5760
caactgtggc catgtcactg cctatgggcc tggcctcacc catggagtag tgaacaagcc   5820
tgccaccttc accgtcaaca ccaaggatgc aggagagggg ggcctgtctc tggccattga   5880
gggcccgtcc aaagcagaaa tcagctgcac tgacaaccag gatgggacat gcagcgtgtc   5940
ctacctgcct gtgctgccgg gggactacag cattctagtc aagtacaatg aacagcacgt   6000
cccaggcagc cccttcactg ctcgggtcac aggtgacgac tccatgcgta tgtcccacct   6060
aaaggtcggc tctgctgccg acatccccat caacatctca gagacggatc tcagcctgct   6120
gacggccact gtggtcccgc cctcgggccg ggaggagccc tgtttgctga agcggctgcg   6180
taatggccac gtggggattt cattcgtgcc caaggagacg gggagcacc tggtgcatgt   6240
gaagaaaaat ggccagcacg tggccagcag ccccatcccg gtggtgatca gccagtcgga   6300
aattggggat gccagtcgtg ttcgggtctc tggtcagggc cttcacgaag gccacacctt   6360
tgagcctgca gagtttatca ttgatacccg cgatgcaggc tatggtgggc tcagcctgtc   6420
cattgagggc cccagcaagg tggacatcaa cacagaggac ctggaggacg ggacgtgcag   6480
ggtcacctac tgccccacag agccaggcaa ctacatcatc aacatcaagt ttgccgacca   6540
gcacgtgcct ggcagcccct tctctgtgaa ggtgacaggc gagggccggg tgaaagagag   6600
catcacccgc aggcgtcggg ctccttcagt ggccaacgtt ggtagtcatt gtgacctcag   6660
cctgaaaatc cctgaaatta gcatccagga tatgacagcc caggtgacca gcccatcggg   6720
caagacccat gaggccgaga tcgtggaagg ggagaaccac acctactgca tccgctttgt   6780
tcccgctgag atgggcacac acacagtcag cgtcaagtac aagggccagc acgtgcctgg   6840
gagccccttc cagttcaccg tggggcccct aggggaaggg ggagcccaca aggtccgagc   6900
```

```
tgggggccct ggcctggaga gagctgaagc tggagtgcca gccgaattca gtatctggac   6960
ccgggaagct ggtgctggag gcctggccat tgctgtcgag ggccccagca aggctgagat   7020
ctcttttgag gaccgcaagg acggctcctg tggtgtggct tatgtggtcc aggagccagg   7080
tgactacgaa gtctcagtca agttcaacga ggaacacatt cccgacagcc ccttcgtggt   7140
gcctgtggct tctccgtctg gcgacgcccg ccgcctcact gtttctagcc ttcaggagtc   7200
agggctaaag gtcaaccagc cagcctcttt tgcagtcagc ctgaacgggg ccaagggggc   7260
gatcgatgcc aaggtgcaca gcccctcagg agccctggag gagtgctatg tcacagaaat   7320
tgaccaagat aagtatgctg tgcgcttcat ccctcgggag aatggcgttt acctgattga   7380
cgtcaagttc aacggtaccc acatccctgg aagccccttc aagatccgag ttggggagcc   7440
tgggcatgga ggggacccag gcttggtgtc tgcttacgga gcaggtctgg aaggcggtgt   7500
cacagggaac ccagctgagt tcgtcgtgaa cacgagcaat gcgggagctg gtgccctgtc   7560
ggtgaccatt gacggcccct ccaaggtgaa gatggattgc caggagtgcc ctgagggcta   7620
ccgcgtcacc tataccccca tggcacctgg cagctacctc atctccatca agtacggcgg   7680
cccctaccac attgggggca gccccttcaa ggccaaagtc acaggccccc gtctcgtcag   7740
caaccacagc ctccacgaga catcatcagt gtttgtagac tctctgacca aggccacctg   7800
tgccccccag catggggccc cgggtcctgg gcctgctgac gccagcaagg tggtggccaa   7860
gggcctgggg ctgagcaagg cctacgtagg ccagaagagc agcttcacag tagactgcag   7920
caaagcaggc aacaacatgc tgctggtggg ggttcatggc ccaaggaccc cctgcgagga   7980
gatcctggtg aagcacgtgg gcagccggct ctacagcgtg tcctacctgc tcaaggacaa   8040
gggggagtac acactggtgg tcaaatgggg gcacgagcac atcccaggca gcccctaccg   8100
cgttgtggtg ccctgagtct ggggcccgtg ccagccggca gcccccaagc ctgccccgct   8160
acccaagcag ccccgccctc ttcccctcaa ccccggccca ggccgccctg gccgcccgcc   8220
tgtcactgca gctgcccctg ccctgtgccg tgctgcgctc acctgcctcc ccagccagcc   8280
gctgacctct cggctttcac ttgggcagag ggagccattt ggtggcgctg cttgtcttct   8340
ttggttctgg gaggggtgag ggatgggg                                       8368
```

```
<210> SEQ ID NO 74
<211> LENGTH: 60
<212> TYPE: DNA
<213> ORGANISM: Homo sapiens
<220> FEATURE:
<223> OTHER INFORMATION: NM_001456

<400> SEQUENCE: 74

tgacctctcg gctttcactt gggcagaggg agccatttgg tggcgctgct tgtcttcttt     60
```

```
<210> SEQ ID NO 75
<211> LENGTH: 1642
<212> TYPE: DNA
<213> ORGANISM: Homo sapiens
<220> FEATURE:
<223> OTHER INFORMATION: NM_001548

<400> SEQUENCE: 75

ccagatctca gaggagcctg gctaagcaaa accctgcaga acggctgcct aatttacagc     60
aaccatgagt acaaatggtg atgatcatca ggtcaaggat agtctggagc aattgagatg    120
tcactttaca tgggagttat ccattgatga cgatgaaatg cctgatttag aaaacagagt    180
cttggatcag attgaattcc tagacaccaa atacagtgtg ggaatacaca acctactagc    240
```

ctatgtgaaa cacctgaaag gccagaatga ggaagccctg aagagcttaa aagaagctga 300
aaacttaatg caggaagaac atgacaacca agcaaatgtg aggagtctgg tgacctgggg 360
caactttgcc tggatgtatt accacatggg cagactggca gaagcccaga cttacctgga 420
caaggtggag aacatttgca agaagctttc aaatcccttc cgctatagaa tggagtgtcc 480
agaaatagac tgtgaggaag gatgggcctt gctgaagtgt ggaggaaaga attatgaacg 540
ggccaaggcc tgctttgaaa aggtgcttga agtggaccct gaaaaccctg aatccagcgc 600
tgggtatgcg atctctgcct atcgcctgga tggctttaaa ttagccacaa aaaatcacaa 660
gccatttctt ttgcttcccc taaggcaggc tgtccgctta aatccagaca atggatatat 720
taaggttctc cttgccctga agcttcagga tgaaggacag gaagctgaag gagaaaagta 780
cattgaagaa gctctagcca acatgtcctc acagacctat gtctttcgat atgcagccaa 840
gttttaccga agaaaaggct ctgtggataa agctcttgag ttattaaaaa aggccttgca 900
ggaaacaccc acttctgtct tactgcatca ccagataggg ctttgctaca aggcacaaat 960
gatccaaatc aaggaggcta caaaagggca gcctagaggg cagaacagag aaaagctaga 1020
caaaatgata agatcagcca tatttcattt tgaatctgca gtggaaaaaa agcccacatt 1080
tgaggtggct catctagacc tggcaagaat gtatatagaa gcaggcaatc acagaaaagc 1140
tgaagagaat tttcaaaaat tgttatgcat gaaaccagtg gtagaagaaa caatgcaaga 1200
catacatttc tactatggtc ggtttcagga atttcaaaag aaatctgacg tcaatgcaat 1260
tatccattat ttaaaagcta taaaaataga acaggcatca ttaacaaggg ataaaagtat 1320
caattctttg aagaaattgg ttttaaggaa acttcggaga aaggcattag atctggaaag 1380
cttgagcctc cttgggttcg tctataaatt ggaaggaaat atgaatgaag ccctggagta 1440
ctatgagcgg gccctgagac tggctgctga ctttgagaac tctgtgagac aaggtcctta 1500
ggcacccaga tatcagccac tttcacattt catttcattt tatgctaaca tttactaatc 1560
atcttttctg cttactgttt tcagaaacat tataattcac tgtaatgatg taattcttga 1620
ataataaatc tgacaaaata tt 1642

<210> SEQ ID NO 76
<211> LENGTH: 60
<212> TYPE: DNA
<213> ORGANISM: Homo sapiens
<220> FEATURE:
<223> OTHER INFORMATION: NM_001548

<400> SEQUENCE: 76
gtatcaattc tttgaagaaa ttggttttaa ggaaacttcg gagaaaggca ttagatctgg 60

<210> SEQ ID NO 77
<211> LENGTH: 3344
<212> TYPE: DNA
<213> ORGANISM: Homo sapiens
<220> FEATURE:
<223> OTHER INFORMATION: NM_001605

<400> SEQUENCE: 77
ggtacagctg cgcgtctgcg ggaataggtg cagcgggccc ttggcggggg actctgaggg 60
aggagctggg gacggcgacc ctaggagagt tctttggggt gactttcaag atggactcta 120
ctctaacagc aagtgaaatc cggcagcgat ttatagattt cttcaagagg aacgagcata 180
cgtatgttca ctcgtctgcc accatcccat tggatgaccc cactttgctc tttgccaatg 240
caggcatgaa ccagtttaaa cccattttcc tgaacacaat tgacccatct caccccatgg 300

-continued

```
caaagctgag cagagctgcc aatacccaga agtgcatccg ggctgggggc aaacaaaatg    360
acctggacga tgtgggcaag gatgtctatc atcacacctt cttcgagatg ctgggctctt    420
ggtcttttgg agattacttt aaggaattgg catgtaagat ggctctggaa ctcctcaccc    480
aagagtttgg cattcccatt gaaagacttt atgttactta ctttggcggg gatgaagcag    540
ctggcttaga agcagatctg gaatgcaaac agatctggca aaatttgggg ctggatgaca    600
ccaaaatcct cccaggcaac atgaaggata acttctggga gatgggtgac acgggcccct    660
gtggtccttg cagtgagatc cactacgacc ggattggtgg tcgggacgcc gcacatcttg    720
tcaaccagga cgaccctaat gtgctggaga tctggaacct tgtgttcatc cagtataaca    780
gggaagctga tggcattctg aaacctcttc ccaagaaaag cattgacaca gggatgggcc    840
tggaacgact ggtatctgtg ctgcagaata agatgtccaa ctatgacact gaccttttttg    900
tcccttactt tgaagccatt cagaagggca caggtgcccg accatacact gggaaagttg    960
gtgctgagga tgccgatggg attgacatgg cctaccgggt gctggctgac catgctcgga   1020
ccatcactgt ggcactggct gatggtggcc ggcctgacaa cacagggcgt ggatatgtgt   1080
tgagacggat tctccgccga gctgtccgat acgcccatga aaagctcaat gccagcaggg   1140
gcttctttgc tacgttagtg gatgttgtcg tccagtccct gggagatgca tttcctgagc   1200
tgaagaagga cccagacatg gtgaaggaca tcattaatga agaagaggtg cagtttctca   1260
agactctcag cagagggcgt cgcatcctgg acaggaaaat tcagagcctg ggagacagca   1320
agaccattcc cggagacact gcttggctcc tctatgacac ctatgggttt ccagtggatc   1380
tgactggact gattgctgaa gagaagggcc tggtggtaga catggatggc tttgaagagg   1440
agaggaaact ggcccagctg aaatcacagg gcaagggagc tggtggggaa gacctcatta   1500
tgctggacat ttacgctatc gaagagctcc gggcacgggg tctggaggtc acagatgatt   1560
ccccaaagta caattaccat ttggactcca gtggtagcta tgtatttgag aacacagtgg   1620
ctacggtgat ggctctgcgc agggagaaga tgttcgtgga agaggtgtcc acaggccagg   1680
agtgtggagt ggtgctggac aagacctgtt tctatgctga gcaaggaggc cagatctatg   1740
acgaaggcta cctggtgaag gtggatgaca gcagtgaaga taaaacagag tttacagtga   1800
agaatgctca ggtccgagga gggtatgtgc tacacattgg aaccatctac ggtgacctga   1860
aagtggggga tcaggtctgg ctgtttattg atgagccccg acgaagaccc atcatgagca   1920
accacacagc tacgcacatt ctgaacttcg ccctgcgctc agtgcttggg gaagctgacc   1980
agaaaggctc attggttgct cctgaccgcc tcagatttga ctttactgcc aagggagcca   2040
tgtccaccca acagatcaag aaggctgaag agattgctaa tgagatgatt gaggcagcca   2100
aggccgtcta tacccaggat tgccccctgg cagcagcgaa agccatccag ggcctacggg   2160
ctgtgtttga tgagacctat cctgaccctg tgcgagtcgt ctccattggg gtcccggtgt   2220
ccgagttgct ggatgacccc tctgggcctg ctggctccct gacttctgtt gagttctgtg   2280
ggggaacgca cctgcggaac tcgagtcatg caggagcttt tgtgatcgtg acggaagaag   2340
ccattgccaa gggtatccgg aggattgtgg ctgtcacagg tgccgaggcc cagaaggccc   2400
tcaggaaagc agagagcttg aagaaatgtc tctctgtcat ggaagccaaa gtgaaggctc   2460
agactgctcc aaacaaggat gtgcagaggg agatcgctga ccttggagag gccctggcca   2520
ctgcagtcat cccccagtgg cagaaggatg aattgcggga gactctcaaa tccctaaaga   2580
aggtcatgga tgacttggac cgagccagca aagccgatgt ccagaaacga gtgttagaga   2640
agacgaagca gttcatcgac agcaacccca accagcctct tgtcatcctg gagatggaga   2700
```

gcggcgcctc agccaaggcc ctgaatgaag ccttgaagct cttcaagatg cactcccctc 2760
agacttctgc catgctcttc acggtggaca atgaggctgg caagatcacg tgcctgtgtc 2820
aagtccccca gaatgcagcc aatcggggct taaaagccag cgagtgggtg cagcaggtgt 2880
caggcttgat ggacggtaaa ggtggtggca aggatgtgtc tgcacaggcc acaggcaaga 2940
acgttggctg cctgcaggag gcgctgcagc tggccacttc cttcgcccag ctgcgcctcg 3000
gggatgtaaa gaactgagtg gggaaggagg aggctcccac tggatccatc cgtccagcca 3060
agagctcttc atctgctaca agaacatttg aatcttggga cctttaaaga gcccctccta 3120
acccagcagt aactggaaca cacttgggag cagtcctatg tctcagtgcc ccttaaattt 3180
ctgccctgag ccctccacgt cagtgccatc ggtctagaac cactaacccc gcattgctgt 3240
tgatcgtcac gctcgcatct atagataacg gctctccaga cctgagcttt ccgcgtcagc 3300
aagtaggaat cgtttttgct gcagagaata aaaggaccac gtgc 3344

<210> SEQ ID NO 78
<211> LENGTH: 60
<212> TYPE: DNA
<213> ORGANISM: Homo sapiens
<220> FEATURE:
<223> OTHER INFORMATION: NM_001605

<400> SEQUENCE: 78
gccaagagct cttcatctgc tacaagaaca tttgaatctt gggaccttta aagagcccct 60

<210> SEQ ID NO 79
<211> LENGTH: 417
<212> TYPE: DNA
<213> ORGANISM: Homo sapiens
<220> FEATURE:
<223> OTHER INFORMATION: NM_001645

<400> SEQUENCE: 79
acctcccaac caagccctcc agcaaggatt caggagtgcc cctcgggcct cgccatgagg 60
ctcttcctgt cgctcccggt cctggtggtg gttctgtcga tcgtcttgga aggcccagcc 120
ccagcccagg ggaccccaga cgtctccagt gccttggata agctgaagga gtttggaaac 180
acactggagg acaaggctcg ggaactcatc agccgcatca aacagagtga actttctgcc 240
aagatgcggg agtggttttc agagacattt cagaaagtga aggagaaact caagattgac 300
tcatgaggac ctgaagggtg acatccagga ggggcctctg aaatttccca caccccagcg 360
cctgtgctga ggactcccgc catgtggccc caggtgccac caataaaaat cctaccg 417

<210> SEQ ID NO 80
<211> LENGTH: 60
<212> TYPE: DNA
<213> ORGANISM: Homo sapiens
<220> FEATURE:
<223> OTHER INFORMATION: NM_001645

<400> SEQUENCE: 80
aaacagagtg aactttctgc caagatgcgg gagtggtttt cagagacatt tcagaaagtg 60

<210> SEQ ID NO 81
<211> LENGTH: 1389
<212> TYPE: DNA
<213> ORGANISM: Homo sapiens
<220> FEATURE:
<223> OTHER INFORMATION: NM_001809

<400> SEQUENCE: 81

```
cgcggacttc tgccaagcac cggctcatgt gaggctcgcg gcacagcgtt ctctgggctc     60
cccagaagcc agcctttcgc tcccggaccc ggcagcccga gcaggagccg tgggaccggg    120
cgccagcacc ctctgcggcg tgtcatgggc ccgcgccgcc ggagccgaaa gcccgaggcc    180
ccgaggaggc gcagcccgag cccgaccccg acccccggcc cctcccggcg gggcccctcc    240
ttaggcgctt cctcccatca acacagtcgg cggagacaag gttggctaaa ggagatccga    300
aagcttcaga agagcacaca cctcttgata aggaagctgc ccttcagccg cctggcaaga    360
gaaatatgtg ttaaattcac tcgtggtgtg gacttcaatt ggcaagccca ggccctattg    420
gccctacaag aggcagcaga agcatttcta gttcatctct ttgaggacgc ctatctcctc    480
accttacatg caggccgagt tactctcttc ccaaaggatg tgcaactggc ccggaggatc    540
cggggccttg aggagggact cggctgagct cctgcaccca gtgtttctgt cagtctttcc    600
tgctcagcca ggggggatga taccggggac tctccagagc catgactaga tccaatggat    660
tctgcgatgc tgtctggact ttgctgtctc tgaacagtat gtgtgtgttg ctttaaatat    720
ttttcttttt tttgagaagg agaagactgc atgactttcc tctgtaacag aggtaatata    780
tgagacaatc aacaccgttc caaaggcctg aaaataattt tcagataaag agactccaag    840
gttgacttta gtttgtgagt tactcatgtg actatttgag gattttgaaa acatcagatt    900
tgctgtggta tgggagaaaa ggttatgtac ttattatttt agctctttct gtaatattta    960
catttttac catatgtaca tttgtacttt tattttacac ataagggaaa aaataagacc    1020
actttgagca gttgcctgga aggctgggca tttccatcat atagacctct gcccttcaga   1080
gtagcctcac cattagtggc agcatcatgt aactgagtgg actgtgcttg tcaacggatg   1140
tgtagctttt cagaaactta attggggatg aatagaaaac ctgtaagctt tgatgttctg   1200
gttacttcta gtaaattcct gtcaaaatca attcagaaat tctaacttgg agaatttaac   1260
attttactct tgtaaatcat agaagatgta tcataacagt tcagaatttt aaagtacatt   1320
ttcgatgctt ttatgggtat ttttgtagtt tctttgtaga gagataataa aaatcaaaat   1380
atttaatga                                                           1389
```

<210> SEQ ID NO 82
<211> LENGTH: 60
<212> TYPE: DNA
<213> ORGANISM: Homo sapiens
<220> FEATURE:
<223> OTHER INFORMATION: NM_001809

<400> SEQUENCE: 82

```
ggggatgaat agaaaacctg taagctttga tgttctggtt acttctagta aattcctgtc     60
```

<210> SEQ ID NO 83
<211> LENGTH: 2205
<212> TYPE: DNA
<213> ORGANISM: Homo sapiens
<220> FEATURE:
<223> OTHER INFORMATION: NM_001909

<400> SEQUENCE: 83

```
gcgcacgccg gccgcgccca cgtgaccggt ccgggtgcaa acacgcgggt cagctgatcc     60
ggcccaactg cggcgtcatc ccggctataa gcgcacggcc tcggcgaccc tctccgaccc    120
ggccgccgcc gccatgcagc cctccagcct tctgccgctc gccctctgcc tgctggctgc    180
acccgcctcc gcgctcgtca ggatcccgct gcacaagttc acgtccatcc gccggaccat    240
gtcggaggtt gggggctctg tggaggacct gattgccaaa ggccccgtct caaagtactc    300
```

```
ccaggcggtg ccagccgtga ccgaggggcc cattcccgag gtgctcaaga actacatgga    360
cgcccagtac tacggggaga ttggcatcgg gacgcccccc cagtgcttca cagtcgtctt    420
cgacacgggc tcctccaacc tgtgggtccc ctccatccac tgcaaactgc tggacatcgc    480
ttgctggatc caccacaagt acaacagcga caagtccagc acctacgtga agaatggtac    540
ctcgtttgac atccactatg gctcgggcag cctctccggg tacctgagcc aggacactgt    600
gtcggtgccc tgccagtcag cgtcgtcagc ctctgccctg ggcggtgtca aagtggagag    660
gcaggtcttt ggggaggcca ccaagcagcc aggcatcacc ttcatcgcag ccaagttcga    720
tggcatcctg ggcatggcct acccccgcat ctccgtcaac aacgtgctgc ccgtcttcga    780
caacctgatg cagcagaagc tggtggacca gaacatcttc tccttctacc tgagcaggga    840
cccagatgcg cagcctgggg gtgagctgat gctgggtggc acagactcca agtattacaa    900
gggttctctg tcctacctga atgtcacccg caaggcctac tggcaggtcc acctggacca    960
ggtggaggtg gccagcgggc tgaccctgtg caaggagggc tgtgaggcca ttgtggacac   1020
aggcacttcc ctcatggtgg gcccggtgga tgaggtgcgc gagctgcaga aggccatcgg   1080
ggccgtgccg ctgattcagg gcgagtacat gatcccctgt gagaaggtgt ccaccctgcc   1140
cgcgatcaca ctgaagctgg gaggcaaagg ctacaagctg tccccagagg actacacgct   1200
caaggtgtcg caggccggga agaccctctg cctgagcggc ttcatgggca tggacatccc   1260
gccacccagc gggccactct ggatcctggg cgacgtcttc atcggccgct actacactgt   1320
gtttgaccgt gacaacaaca gggtgggctt cgccgaggct gcccgcctct agttcccaag   1380
gcgtccgcgc gccagcacag aaacagagga gagtcccaga gcaggaggcc cctggcccag   1440
cggcccctcc cacacacacc cacacactcg cccgcccact gtcctgggcg ccctggaagc   1500
cggcggccca agcccgactt gctgttttgt tctgtggttt tcccctccct gggttcagaa   1560
atgctgcctg cctgtctgtc tctccatctg tttggtgggg gtagagctga tccagagcac   1620
agatctgttt cgtgcattgg aagaccccac ccaagcttgg cagccgagct cgtgtatcct   1680
ggggctccct tcatctccag ggagtcccct ccccggccct accagcgccc gctgggctga   1740
gcccctaccc cacaccaggc cgtcctcccg ggccctccct tggaaacctg ccctgcctga   1800
gggcccctct gcccagcttg ggcccagctg ggctctgcca ccctacctgt tcagtgtccc   1860
gggcccgttg aggatgaggc cgctagaggc ctgaggatga gctggaagga gtgagagggg   1920
acaaaaccca ccttgttgga gcctgcaggg tggtgctggg actgagccag tcccaggggc   1980
atgtattggc ctggaggtgg ggttgggatt gggggctggt gccagccttc ctctgcagct   2040
gacctctgtt gtcctcccct tgggcggctg agagccccag ctgacatgga aatacagttg   2100
ttggcctccg gcctcccctc aaaaaaaaaa aaaaaaaaaa aaaaaaaaaa aaaaaaaaaa   2160
aaaaaaaaaa aaaaaaaaaa aaaaaaaaaa aaaaaaaaaa aaaaa                   2205
```

<210> SEQ ID NO 84
<211> LENGTH: 60
<212> TYPE: DNA
<213> ORGANISM: Homo sapiens
<220> FEATURE:
<223> OTHER INFORMATION: NM_001909

<400> SEQUENCE: 84

```
tctgtttggt gggggtagag ctgatccaga gcacagatct gtttcgtgca ttggaagacc     60
```

<210> SEQ ID NO 85
<211> LENGTH: 817

<212> TYPE: DNA
<213> ORGANISM: Homo sapiens
<220> FEATURE:
<223> OTHER INFORMATION: NM_002038

<400> SEQUENCE: 85
gaaccgttta ctcgctgctg tgcccatcta tcagcaggct ccgggctgaa gattgcttct 60
cttctctcct ccaaggtcta gtgacggagc ccgcgcgcgg cgccaccatg cggcagaagg 120
cggtatcgct tttcttgtgc tacctgctgc tcttcacttg cagtggggtg gaggcaggta 180
agaaaaagtg ctcggagagc tcggacagcg gctccgggtt ctggaaggcc ctgaccttca 240
tggccgtcgg aggaggactc gcagtcgccg ggctgcccgc gctgggcttc accggcgccg 300
gcatcgcggc caactcggtg gctgcctcgc tgatgagctg gtctgcgatc ctgaatgggg 360
gcggcgtgcc cgccgggggg ctagtggcca cgctgcagag cctcggggct ggtggcagca 420
gcgtcgtcat aggtaatatt ggtgccctga tgggctacgc cacccacaag tatctcgata 480
gtgaggagga tgaggagtag ccagcagctc ccagaacctc ttcttccttc ttggcctaac 540
tcttccagtt aggatctaga actttgcctt tttttttttt tttttttttt tttgagatgg 600
gttctcacta tattgtccag gctagagtgc agtggctatt cacagatgcg aacatagtac 660
actgcagcct ccaactccta gcctcaagtg atcctcctgt ctcaacctcc caagtaggat 720
tacaagcatg cgccgacgat gcccagaatc cagaactttg tctatcactc tccccaacaa 780
cctagatgtg aaaacagaat aaacttcacc cagaaaa 817

<210> SEQ ID NO 86
<211> LENGTH: 60
<212> TYPE: DNA
<213> ORGANISM: Homo sapiens
<220> FEATURE:
<223> OTHER INFORMATION: NM_002038

<400> SEQUENCE: 86
agctcccaga acctcttctt ccttcttggc ctaactcttc cagttaggat ctagaacttt 60

<210> SEQ ID NO 87
<211> LENGTH: 1283
<212> TYPE: DNA
<213> ORGANISM: Homo sapiens
<220> FEATURE:
<223> OTHER INFORMATION: NM_002046

<400> SEQUENCE: 87
ctctctgctc ctcctgttcg acagtcagcc gcatcttctt ttgcgtcgcc agccgagcca 60
catcgctcag acaccatggg gaaggtgaag gtcggagtca acggatttgg tcgtattggg 120
cgcctggtca ccagggctgc ttttaactct ggtaaagtgg atattgttgc catcaatgac 180
cccttcattg acctcaacta catggtttac atgttccaat atgattccac ccatggcaaa 240
ttccatggca ccgtcaaggc tgagaacggg aagcttgtca tcaatggaaa tcccatcacc 300
atcttccagg agcgagatcc ctccaaaatc aagtggggcg atgctggcgc tgagtacgtc 360
gtggagtcca ctggcgtctt caccaccatg gagaaggctg gggctcattt gcaggggggga 420 gccaaaaggg tcatcatctc tgccccctct gctgatgccc ccatgttcgt catgggtgtg 480
aaccatgaga agtatgacaa cagcctcaag atcatcagca atgcctcctg caccaccaac 540
tgcttagcac ccctggccaa ggtcatccat gacaactttg gtatcgtgga aggactcatg 600
accacagtcc atgccatcac tgccacccag aagactgtgg atggcccctc cgggaaactg 660
tggcgtgatg gccgcggggc tctccagaac atcatccctg cctctactgg cgctgccaag 720
gctgtgggca aggtcatccc tgagctgaac gggaagctca ctggcatggc cttccgtgtc 780
cccactgcca acgtgtcagt ggtggacctg acctgccgtc tagaaaaacc tgccaaatat 840
gatgacatca agaaggtggt gaagcaggcg tcggagggcc ccctcaaggg catcctgggc 900
tacactgagc accaggtggt ctcctctgac ttcaacagcg acacccactc ctccaccttt 960
gacgctgggg ctggcattgc cctcaacgac cactttgtca agctcatttc ctggtatgac 1020
aacgaatttg gctacagcaa cagggtggtg gacctcatgg cccacatggc ctccaaggag 1080
taagacccct ggaccaccag ccccagcaag agcacaagag gaagagagag accctcactg 1140
ctggggagtc cctgccacac tcagtccccc accacactga atctcccctc ctcacagttg 1200
ccatgtagac cccttgaaga ggggaggggc ctagggagcc gcaccttgtc atgtaccatc 1260
aataaagtac cctgtgctca acc 1283

<210> SEQ ID NO 88
<211> LENGTH: 60
<212> TYPE: DNA
<213> ORGANISM: Homo sapiens
<220> FEATURE:
<223> OTHER INFORMATION: NM_002046

<400> SEQUENCE: 88
ctcaacgacc actttgtcaa gctcatttcc tggtatgaca acgaatttgg ctacagcaac 60

<210> SEQ ID NO 89
<211> LENGTH: 1610
<212> TYPE: DNA
<213> ORGANISM: Homo sapiens
<220> FEATURE:
<223> OTHER INFORMATION: NM_002061

<400> SEQUENCE: 89
ggcacgaggc tgcggccgca gtagccggag ccggagccgc agccaccggt gccttccttt 60
cccgccgccg cccagccgcc gtccggcctc cctcgggccc gagcgcagac caggctccag 120
ccgcgcggcg ccggcagcct cgcgctccct ctcgggtctc tctcgggcct cgggcaccgc 180
gtcctgtggg cggccgcctg cctgcccgcc cgcccgcagc cccttgcctg ccggcccctg 240
ggcggcccgt gccatgggca ccgacagccg cgcggccaag gcgctcctgg cgcgggcccg 300
caccctgcac ctgcagacgg ggaacctgct gaactggggc cgcctgcgga agaagtgccc 360
gtccacgcac agcgaggagc ttcatgattg tatccaaaaa accttgaatg aatggagttc 420
ccaaatcaac ccagatttgg tcagggagtt tccagatgtc ttggaatgca ctgtatctca 480
tgcagtagaa aagataaatc ctgatgaaag agaagaaatg aaagtttctg caaaactgtt 540
cattgtagaa tcaaactctt catcatcaac tagaagtgca gttgacatgg cctgttcagt 600
ccttggagtt gcacagctgg attctgtgat cattgcttca cctcctattg aagatggagt 660
taatctttcc ttggagcatt tacagcctta ctgggaggaa ttagaaaact tagttcagag 720
caaaaagatt gttgccatag gtacctctga tctagacaaa acacagttgg aacagctgta 780
tcagtgggca caggtaaaac caaatagtaa ccaagttaat cttgcctcct gctgtgtgat 840
gccaccagat ttgactgcat ttgctaaaca atttgacata cagctgttga ctcacaatga 900
tccaaaagaa ctgctttctg aagcaagttt ccaagaagct cttcaggaaa gcattcctga 960
cattcaagcg cacgagtggg tgccgctgtg gctactgcgg tattcggtca ttgtgaaaag 1020
tagaggaatt atcaaatcaa aaggctacat tttacaagct aaaagaaggg gttcttaact 1080
gacttaggag cataacttac ctgtaatttc cttcaatatg agagaaaatt gagatgtgta 1140
aaatctagtt actgcctgta aatggtgtca ttgaggcaga tattctttcg tcatatttga 1200
cagtatgttg tctgtcaagt tttaaatact tatcttgcct ccatatcaat ccattctcat 1260
gaacctctgt attgctttcc ttaaactatt gttttctaat tgaaattgtc tataaagaaa 1320
atacttgcaa tatatttttc ctttattttt atgactaata taaatcaaga aaatttgttg 1380
ttagatatat tttggcctag gtatcagggt aatgtatata catatttttt atttccaaaa 1440
aaaattcatt aattgcttct taactcttat tataaccaag caatttaatt acaattgtta 1500
aaactgaaat actggaagaa gatatttttc ctgtcattga tgagatatat cagagtaact 1560
ggagtagctg ggatttacta gtagtgtaaa taaaattcac tcttcaatac 1610

<210> SEQ ID NO 90
<211> LENGTH: 60
<212> TYPE: DNA
<213> ORGANISM: Homo sapiens
<220> FEATURE:
<223> OTHER INFORMATION: NM_002061

<400> SEQUENCE: 90
ctgacttagg agcataactt acctgtaatt tccttcaata tgagagaaaa ttgagatgtg 60

<210> SEQ ID NO 91
<211> LENGTH: 873
<212> TYPE: DNA
<213> ORGANISM: Homo sapiens
<220> FEATURE:
<223> OTHER INFORMATION: NM_002106

<400> SEQUENCE: 91
cgcagtttga atcgcggtgc gacgaaggag taggtggtgg gatctcaccg tgggtccgat 60
tagccttttc tctgccttgc ttgcttgagc ttcagcggaa ttcgaaatgg ctggcggtaa 120
ggctggaaag gactccggaa aggccaagac aaaggcggtt tcccgctcgc agagagccgg 180
cttgcagttc ccagtgggcc gtattcatcg acacctaaaa tctaggacga ccagtcatgg 240
acgtgtgggc gcgactgccg ctgtgtacag cgcagccatc ctggagtacc tcaccgcaga 300
ggtacttgaa ctggcaggaa atgcatcaaa agacttaaag gtaaagcgta ttacccctcg 360
tcacttgcaa cttgctattc gtggagatga agaattggat tctctcatca aggctacaat 420
tgctggtggt ggtgtcattc cacacatcca caaatctctg attgggaaga aaggacaaca 480
gaagactgtc taaaggatgc ctggattcct tgttatctca ggactctaaa tactctaaca 540
gctgtccagt gttggtgatt ccagtggact gtatctctgt gaaaaacaca attttgcctt 600
tttgtaattc tatttgagca agttggaagt ttaattagct ttccaaccaa ccaaatttct 660
gcattcgagt cttaaccata tttaagtgtt actgtggctt caaagaagct attgattctg 720
aagtagtggg ttttgattga gttgactgtt tttaaaaaac tgtttggatt ttaattgtga 780
tgcagaagtt atagtaacaa acatttggtt ttgtacagac attatttcca ctctggtgga 840
taagttcaat aaaggtcata tcccaaacta aaa 873

<210> SEQ ID NO 92
<211> LENGTH: 60
<212> TYPE: DNA
<213> ORGANISM: Homo sapiens
<220> FEATURE:
<223> OTHER INFORMATION: NM_002106

<400> SEQUENCE: 92
cgagtcttaa ccatatttaa gtgttactgt ggcttcaaag aagctattga ttctgaagta 60

<210> SEQ ID NO 93
<211> LENGTH: 4204
<212> TYPE: DNA
<213> ORGANISM: Homo sapiens
<220> FEATURE:
<223> OTHER INFORMATION: NM_002205

<400> SEQUENCE: 93
caggacaggg aagagcgggc gctatgggga gccggacgcc agagtcccct ctccacgccg 60
tgcagctgcg ctggggcccc cggcgccgac ccccgctcgt gccgctgctg ttgctgctcg 120
tgccgccgcc acccagggtc gggggcttca acttagacgc ggaggcccca gcagtactct 180
cggggccccc gggctccttc ttcggattct cagtggagtt ttaccggccg ggaacagacg 240
gggtcagtgt gctggtggga gcacccaagg ctaataccag ccagccagga gtgctgcagg 300
gtggtgctgt ctacctctgt ccttggggtg ccagccccac acagtgcacc cccattgaat 360
ttgacagcaa aggctctcgg ctcctggagt cctcactgtc cagctcagag ggagaggagc 420
ctgtggagta caagtccttg cagtggttcg gggcaacagt tcgagcccat ggctcctcca 480
tcttggcatg cgctccactg tacagctggc gcacagagaa ggagccactg agcgaccccg 540
tgggcacctg ctacctctcc acagataact tcacccgaat tctggagtat gcaccctgcc 600
gctcagattt cagctgggca gcaggacagg gttactgcca aggaggcttc agtgccgagt 660
tcaccaagac tggccgtgtg gttttaggtg gaccaggaag ctatttctgg caaggccaga 720
tcctgtctgc cactcaggag cagattgcag aatcttatta ccccgagtac ctgatcaacc 780
tggttcaggg gcagctgcag actcgccagg ccagttccat ctatgatgac agctacctag 840
gatactctgt ggctgttggt gaattcagtg gtgatgacac agaagacttt gttgctggtg 900
tgcccaaagg gaacctcact tacggctatg tcaccatcct taatggctca gacattcgat 960
ccctctacaa cttctcaggg gaacagatgg cctcctactt tggctatgca gtggccgcca 1020
cagacgtcaa tggggacggg ctggatgact tgctggtggg ggcacccctg ctcatggatc 1080
ggacccctga cgggcggcct caggaggtgg gcagggtcta cgtctacctg cagcacccag 1140
ccggcataga gcccacgccc acccttaccc tcactggcca tgatgagttt ggccgatttg 1200
gcagctcctt gacccccctg gggacctgg accaggatgg ctacaatgat gtggccatcg 1260
gggctccctt tggtggggag acccagcagg gagtagtgtt tgtatttcct gggggcccag 1320
gagggctggg ctctaagcct tcccaggttc tgcagcccct gtgggcagcc agccacaccc 1380
cagacttctt tggctctgcc cttcgaggag gccgagacct ggatggcaat ggatatcctg 1440
atctgattgt ggggtccttt ggtgtggaca aggctgtggt atacaggggc cgccccatcg 1500
tgtccgctag tgcctccctc accatcttcc ccgccatgtt caacccagag gagcggagct 1560
gcagcttaga ggggaaccct gtggcctgca tcaaccttag cttctgcctc aatgcttctg 1620
gaaaacacgt tgctgactcc attggtttca cagtggaact tcagctggac tggcagaagc 1680
agaagggagg ggtacggcgg gcactgttcc tggcctccag gcaggcaacc ctgacccaga 1740
ccctgctcat ccagaatggg gctcgagagg attgcagaga gatgaagatc tacctcagga 1800
acgagtcaga atttcgagac aaactctcgc cgattcacat cgctctcaac ttctccttgg 1860
acccccaagc cccagtggac agccacggcc tcaggccagc cctacattat cagagcaaga 1920
gccggataga ggacaaggct cagatcttgc tggactgtgg agaagacaac atctgtgtgc 1980
ctgacctgca gctggaagtg tttggggagc agaaccatgt gtacctgggt gacaagaatg 2040
ccctgaacct cactttccat gcccagaatg tgggtgaggg tggcgcctat gaggctgagc 2100

```
ttcgggtcac cgcccctcca gaggctgagt actcaggact cgtcagacac ccagggaact   2160
tctccagcct gagctgtgac tactttgccg tgaaccagag ccgcctgctg gtgtgtgacc   2220
tgggcaaccc catgaaggca ggagccagtc tgtggggtgg ccttcggttt acagtccctc   2280
atctccggga cactaagaaa accatccagt ttgacttcca gatcctcagc aagaatctca   2340
acaactcgca aagcgacgtg gtttcctttc ggctctccgt ggaggctcag gcccaggtca   2400
ccctgaacgg tgtctccaag cctgaggcag tgctattccc agtaagcgac tggcatcccc   2460
gagaccagcc tcagaaggag gaggacctgg gacctgctgt ccaccatgtc tatgagctca   2520
tcaaccaagg ccccagctcc attagccagg gtgtgctgga actcagctgt ccccaggctc   2580
tggaaggtca gcagctccta tatgtgacca gagttacggg actcaactgc accaccaatc   2640
accccattaa cccaaagggc ctggagttgg atcccgaggg ttccctgcac caccagcaaa   2700
aacgggaagc tccaagccgc agctctgctt cctcgggacc tcagatcctg aaatgcccgg   2760
aggctgagtg tttcaggctg cgctgtgagc tcgggcccct gcaccaacaa gagagccaaa   2820
gtctgcagtt gcatttccga gtctgggcca agactttctt gcagcgggag caccagccat   2880
ttagcctgca gtgtgaggct gtgtacaaag ccctgaagat gccctaccga atcctgcctc   2940
ggcagctgcc ccaaaaagag cgtcaggtgg ccacagctgt gcaatggacc aaggcagaag   3000
gcagctatgg cgtcccactg tggatcatca tcctagccat cctgtttggc ctcctgctcc   3060
taggtctact catctacatc ctctacaagc ttggattctt caaacgctcc ctcccatatg   3120
gcaccgccat ggaaaaagct cagctcaagc ctccagccac ctctgatgcc tgagtcctcc   3180
caatttcaga ctcccattcc tgaagaacca gtcccccacc cctcattcta ctgaaaagga   3240
ggggtctggg tacttcttga aggtgctgac ggccagggag aagctcctct ccccagccca   3300
gagacatact tgaagggcca gagccagggg ggtgaggagc tggggatccc tccccccccat   3360
gcactgtgaa ggacccttgt ttacacatac cctcttcatg gatgggggaa ctcagatcca   3420
gggacagagg cccagcctcc ctgaagcctt tgcattttgg agagtttcct gaaacaactg   3480
gaaagataac taggaaatcc attcacagtt ctttgggcca gacatgccac aaggacttcc   3540
tgtccagctc caacctgcaa agatctgtcc tcagccttgc cagagatcca aaagaagccc   3600
ccagtaagaa cctggaactt ggggagttaa gacctggcag ctctggacag ccccaccctg   3660
gtgggccaac aaagaacact aactatgcat ggtgccccag gaccagctca ggacagatgc   3720
cacaaggata gatgctggcc cagggccaga gcccagctcc aaggggaatc agaactcaaa   3780
tggggccaga tccagcctgg ggtctggagt tgatctggaa cccagactca gacattggca   3840
ccaatccagg cagatccagg actatatttg ggcctgctcc agacctgatc ctggaggccc   3900
agttcaccct gatttaggag aagccaggaa tttcccagga cctgaagggg ccatgatggc   3960
aacagatctg gaacctcagc ctggccagac acaggccctc cctgttcccc agagaaaggg   4020
gagcccactg tcctgggcct gcagaatttg ggttctgcct gccagctgca ctgatgctgc   4080
ccctcatctc tctgcccaac ccttccctca ccttggcacc agacacccag gacttattta   4140
aactctgttg caagtgcaat aaatctgacc cagtgccccc actgaccaga actagaaaaa   4200
aaaa                                                                4204
```

<210> SEQ ID NO 94
<211> LENGTH: 60
<212> TYPE: DNA
<213> ORGANISM: Homo sapiens
<220> FEATURE:
<223> OTHER INFORMATION: NM_002205

<400> SEQUENCE: 94
ttggcaccag acacccagga cttatttaaa ctctgttgca agtgcaataa atctgaccca 60

<210> SEQ ID NO 95
<211> LENGTH: 1976
<212> TYPE: DNA
<213> ORGANISM: Homo sapiens
<220> FEATURE:
<223> OTHER INFORMATION: NM_002266

<400> SEQUENCE: 95
gccacacggt ctttgagctg agtcgaggtg gaccctttga acgcagtcgc cctacagccg 60
ctgattcccc ccgcatcgcc tcccgtggaa gcccaggccc gcttcgcagc tttctccctt 120
tgtctcataa ccatgtccac caacgagaat gctaatacac cagctgcccg tcttcacaga 180
ttcaagaaca agggaaaaga cagtacagaa atgaggcgtc gcagaataga ggtcaatgtg 240
gagctgagga aagctaagaa ggatgaccag atgctgaaga ggagaaatgt aagctcattt 300
cctgatgatg ctacttctcc gctgcaggaa aaccgcaaca accagggcac tgtaaattgg 360
tctgttgatg acattgtcaa aggcataaat agcagcaatg tggaaaatca gctccaagct 420
actcaagctg ccaggaaact actttccaga gaaaaacagc cccccataga caacataatc 480
cgggctggtt tgattccgaa atttgtgtcc ttcttgggca gaactgattg tagtcccatt 540
cagtttgaat ctgcttgggc actcactaac attgcttctg ggacatcaga acaaaccaag 600
gctgtggtag atggaggtgc catcccagca ttcatttctc tgttggcatc tccccatgct 660
cacatcagtg aacaagctgt ctgggctcta ggaaacattg caggtgatgg ctcagtgttc 720
cgagacttgg ttattaagta cggtgcagtt gacccactgt tggctctcct tgcagttcct 780
gatatgtcat ctttagcatg tggctactta cgtaatctta cctggacact ttctaatctt 840
tgccgcaaca agaatcctgc acccccgata gatgctgttg agcagattct tcctacctta 900
gttcggctcc tgcatcatga tgatccagaa gtgttagcag atacctgctg ggctatttcc 960
taccttactg atggtccaaa tgaacgaatt ggcatggtgg tgaaaacagg agttgtgccc 1020
caacttgtga agcttctagg agcttctgaa ttgccaattg tgactcctgc cctaagagcc 1080
atagggaata ttgtcactgg tacagatgaa cagactcagg ttgtgattga tgcaggagca 1140
ctcgccgtct ttcccagcct gctcaccaac cccaaaacta acattcagaa ggaagctacg 1200
tggacaatgt caaacatcac agccggccgc caggaccaga tacagcaagt tgtgaatcat 1260
ggattagtcc cattccttgt cagtgttctc tctaaggcag attttaagac acaaaaggaa 1320
gctgtgtggg ccgtgaccaa ctataccagt ggtggaacag ttgaacagat tgtgtacctt 1380
gttcactgtg gcataataga accgttgatg aacctcttaa ctgcaaaaga taccaagatt 1440
attctggtta tcctggatgc catttcaaat atctttcagg ctgctgagaa actaggtgaa 1500
actgagaaac ttagtataat gattgaagaa tgtggaggct tagacaaaat tgaagctcta 1560
caaaaccatg aaaatgagtc tgtgtataag gcttcgttaa gcttaattga gaagtatttc 1620
tctgtagagg aagaggaaga tcaaaacgtt gtaccagaaa ctacctctga aggctacact 1680
ttccaagttc aggatggggc tcctgggacc tttaactttt agatcatgta gctgagacat 1740
aaatttgttg tgtactacgt ttggtatttt gtcttattgt ttctctacta agaactcttt 1800
cttaaatgtg gtttgttact gtagcacttt ttacactgaa actatacttg aacagttcca 1860
actgtacata catactgtat gaagcttgtc ctctgactag gtttctaatt tctatgtgga 1920
atttcctatc ttgcagcatc ctgtaaataa acattcaagt ccacccttaa aaaaaa 1976

<210> SEQ ID NO 96
<211> LENGTH: 60
<212> TYPE: DNA
<213> ORGANISM: Homo sapiens
<220> FEATURE:
<223> OTHER INFORMATION: NM_002266

<400> SEQUENCE: 96
tgagtctgtg tataaggctt cgttaagctt aattgagaag tatttctctg tagaggaaga 60

<210> SEQ ID NO 97
<211> LENGTH: 1145
<212> TYPE: DNA
<213> ORGANISM: Homo sapiens
<220> FEATURE:
<223> OTHER INFORMATION: NM_002346

<400> SEQUENCE: 97
gctccggcca gccgcggtcc agagcgcgcg aggttcgggg agctccgcca ggctgctggt 60
acctgcgtcc gcccggcgag caggacaggc tgctttggtt tgtgacctcc aggcaggacg 120
gccatcctct ccagaatgaa gatcttcttg ccagtgctgc tggctgccct tctgggtgtg 180
gagcgagcca gctcgctgat gtgcttctcc tgcttgaacc agaagagcaa tctgtactgc 240
ctgaagccga ccatctgctc cgaccaggac aactactgcg tgactgtgtc tgctagtgcc 300
ggcattggga atctcgtgac atttggccac agcctgagca agacctgttc cccggcctgc 360
cccatcccag aaggcgtcaa tgttggtgtg gcttccatgg gcatcagctg ctgccagagc 420
tttctgtgca atttcagtgc ggccgatggc gggctgcggg caagcgtcac cctgctgggt 480
gccgggctgc tgctgagcct gctgccggcc ctgctgcggt ttggcccctg accgcccaga 540
ccctgtcccc cgatccccca gctcaggaag gaaagcccag ccctttctgg atcccacagt 600
gtatgggagc ccctgactcc tcacgtgcct gatctgtgcc cttggtccca ggtcaggccc 660
accccctgca cctccacctg ccccagcccc tgcctctgcc caagtgggcc agctgccctc 720
acttctgggg tggatgatgt gaccttcctt gggggactgc ggaagggacg agggttccct 780
ggagtcttac ggtccaacat cagaccaagt cccatggaca tgctgacagg gtccccaggg 840
agaccgtgtc agtagggatg tgtgcctggc tgtgtacgtg ggtgtgcagt gcacgtgaga 900
gcacgtggcg gcttctgggg gccatgtttg gggagggagg tgtgccagca gcctggagag 960
cctcagtccc tgtagccccc tgccctggca cagctgcatg cacttcaagg gcagcctttg 1020
ggggttgggg tttctgccac ttccgggtct aggccctgcc caaatccagc cagtcctgcc 1080
ccagcccacc cccacattgg agccctcctg ctgctttggt gcctcaaata aatacagatg 1140
tcccc 1145

<210> SEQ ID NO 98
<211> LENGTH: 60
<212> TYPE: DNA
<213> ORGANISM: Homo sapiens
<220> FEATURE:
<223> OTHER INFORMATION: NM_002346

<400> SEQUENCE: 98
ggttccctgg agtcttacgg tccaacatca gaccaagtcc catggacatg ctgacagggt 60

<210> SEQ ID NO 99
<211> LENGTH: 1390
<212> TYPE: DNA
<213> ORGANISM: Homo sapiens

<220> FEATURE:
<223> OTHER INFORMATION: NM_002358

<400> SEQUENCE: 99
gggaagtgct gttggagccg ctgtggttgc tgtccgcgga gtggaagcgc gtgcttttgt 60
ttgtgtccct ggccatggcg ctgcagctct cccgggagca gggaatcacc ctgcgcggga 120
gcgccgaaat cgtggccgag ttcttctcat tcggcatcaa cagcatttta tatcagcgtg 180
gcatatatcc atctgaaacc tttactcgag tgcagaaata cggactcacc ttgcttgtaa 240
ctactgatct tgagctcata aaatacctaa ataatgtggt ggaacaactg aaagattggt 300
tatacaagtg ttcagttcag aaactggttg tagttatctc aaatattgaa agtggtgagg 360
tcctggaaag atggcagttt gatattgagt gtgacaagac tgcaaaagat gacagtgcac 420
ccagagaaaa gtctcagaaa gctatccagg atgaaatccg ttcagtgatc agacagatca 480
cagctacggt gacatttctg ccactgttgg aagtttcttg ttcatttgat ctgctgattt 540
atacagacaa agatttggtt gtacctgaaa aatgggaaga gtcgggacca cagtttatta 600
ccaattctga ggaagtccgc cttcgttcat ttactactac aatccacaaa gtaaatagca 660
tggtggccta caaaattcct gtcaatgact gaggatgaca tgaggaaaat aatgtaattg 720
taattttgaa atgtggtttt cctgaaatca ggtcatctat agttgatatg ttttatttca 780
ttggttaatt tttacatgga gaaaaccaaa atgatactta ctgaactgtg tgtaattgtt 840
cctttatttt tttggtacct atttgactta ccatggagtt aacatcatga atttattgca 900
cattgttcaa aaggaaccag gaggtttttt tgtcaacatt gtgatgtata ttcctttgaa 960
gatagtaact gtagatggaa aaacttgtgc tataaagcta gatgctttcc taaatcagat 1020
gttttggtca agtagtttga ctcagtatag gtagggagat atttaagtat aaaatacaac 1080
aaaggaagtc taaatattca gaatctttgt taaggtcctg aaagtaactc ataatctata 1140
aacaatgaaa tattgctgta tagctccttt tgaccttcat ttcatgtata gttttcccta 1200
ttgaatcagt ttccaattat ttgactttaa tttatgtaac ttgaacctat gaagcaatgg 1260
atatttgtac tgtttaatgt tctgtgatac agaactctta aaaatgtttt ttcatgtgtt 1320
ttataaaatc aagttttaag tgaaagtgag gaaataaagt taagtttgtt ttaaaaaaaa 1380
aaaaaaaaaa 1390

<210> SEQ ID NO 100
<211> LENGTH: 60
<212> TYPE: DNA
<213> ORGANISM: Homo sapiens
<220> FEATURE:
<223> OTHER INFORMATION: NM_002358

<400> SEQUENCE: 100
atgctttcct aaatcagatg ttttggtcaa gtagtttgac tcagtatagg tagggagata 60

<210> SEQ ID NO 101
<211> LENGTH: 1821
<212> TYPE: DNA
<213> ORGANISM: Homo sapiens
<220> FEATURE:
<223> OTHER INFORMATION: NM_002422

<400> SEQUENCE: 101
acaaggaggc aggcaagaca gcaaggcata gagacaacat agagctaagt aaagccagtg 60
gaaatgaaga gtcttccaat cctactgttg ctgtgcgtgg cagtttgctc agcctatcca 120
ttggatggag ctgcaagggg tgaggacacc agcatgaacc ttgttcagaa atatctagaa 180
aactactacg acctcaaaaa agatgtgaaa cagtttgtta ggagaaagga cagtggtcct 240
gttgttaaaa aaatccgaga aatgcagaag ttccttggat tggaggtgac ggggaagctg 300
gactccgaca ctctggaggt gatgcgcaag cccaggtgtg gagttcctga tgttggtcac 360
ttcagaacct ttcctggcat cccgaagtgg aggaaaaccc accttacata caggattgtg 420
aattatacac cagatttgcc aaaagatgct gttgattctg ctgttgagaa agctctgaaa 480
gtctgggaag aggtgactcc actcacattc tccaggctgt atgaaggaga ggctgatata 540
atgatctctt ttgcagttag agaacatgga gacttttacc cttttgatgg acctggaaat 600
gttttggccc atgcctatgc ccctgggcca gggattaatg gagatgccca ctttgatgat 660
gatgaacaat ggacaaagga tacaacaggg accaatttat ttctcgttgc tgctcatgaa 720
attggccact ccctgggtct ctttcactca gccaacactg aagctttgat gtacccactc 780
tatcactcac tcacagacct gactcggttc cgcctgtctc aagatgatat aaatggcatt 840
cagtccctct atggacctcc ccctgactcc cctgagaccc ccctggtacc cacggaacct 900
gtccctccag aacctgggac gccagccaac tgtgatcctg ctttgtcctt tgatgctgtc 960
agcactctga ggggagaaat cctgatcttt aaagacaggc acttttggcg caaatccctc 1020
aggaagcttg aacctgaatt gcatttgatc tcttcatttt ggccatctct tccttcaggc 1080
gtggatgccg catatgaagt tactagcaag gacctcgttt tcatttttaa aggaaatcaa 1140
ttctgggcca tcagaggaaa tgaggtacga gctggatacc caagaggcat ccacacccta 1200
ggtttccctc caaccgtgag gaaaatcgat gcagccattt ctgataagga aaagaacaaa 1260
acatatttct ttgtagagga caaatactgg agatttgatg agaagagaaa ttccatggag 1320
ccaggctttc ccaagcaaat agctgaagac tttccaggga ttgactcaaa gattgatgct 1380
gtttttgaag aatttgggtt cttttatttc tttactggat cttcacagtt ggagtttgac 1440
ccaaatgcaa agaaagtgac acacactttg aagagtaaca gctggcttaa ttgttgaaag 1500
agatatgtag aaggcacaat atgggcactt taaatgaagc taataattct tcacctaagt 1560
ctctgtgaat tgaaatgttc gttttctcct gcctgtgctg tgactcgagt cacactcaag 1620
ggaacttgag cgtgaatctg tatcttgccg gtcattttta tgttattaca gggcattcaa 1680
atgggctgct gcttagcttg caccttgtca catagagtga tctttcccaa gagaagggga 1740
agcactcgtg tgcaacagac aagtgactgt atctgtgtag actatttgct tatttaataa 1800
agacgatttg tcagttgttt t 1821

<210> SEQ ID NO 102
<211> LENGTH: 60
<212> TYPE: DNA
<213> ORGANISM: Homo sapiens
<220> FEATURE:
<223> OTHER INFORMATION: NM_002422

<400> SEQUENCE: 102
tgtagaaggc acaatatggg cactttaaat gaagctaata attcttcacc taagtctctg 60

<210> SEQ ID NO 103
<211> LENGTH: 2787
<212> TYPE: DNA
<213> ORGANISM: Homo sapiens
<220> FEATURE:
<223> OTHER INFORMATION: NM_002462

<400> SEQUENCE: 103
agagcggagg ccgcactcca gcactgcgca gggaccgcct tggaccgcag ttgccggcca 60

```
ggaatcccag tgtcacggtg gacacgcctc cctcgcgccc ttgccgccca cctgctcacc    120
cagctcaggg gctttggaat tctgtggcca cactgcgagg agatcggttc tgggtcggag    180
gctacaggaa gactcccact ccctgaaatc tggagtgaag aacgccgcca tccagccacc    240
attccaagga ggtgcaggag aacagctctg tgataccatt taacttgttg acattacttt    300
tatttgaagg aacgtatatt agagcttact ttgcaaagaa ggaagatggt tgtttccgaa    360
gtggacatcg caaaagctga tccagctgct gcatccccacc ctctattact gaatggagat    420
gctactgtgg cccagaaaaa tccaggctcg gtggctgaga acaacctgtg cagccagtat    480
gaggagaagg tgcgcccctg catcgacctc attgactccc tgcgggctct aggtgtggag    540
caggacctgg ccctgccagc catcgccgtc atcggggacc agagctcggg caagagctcc    600
gtgttggagg cactgtcagg agttgccctt cccagaggca gcgggatcgt gaccagatgc    660
ccgctggtgc tgaaactgaa gaaacttgtg aacgaagata agtggagagg caaggtcagt    720
taccaggact acgagattga gatttcggat gcttcagagg tagaaaagga aattaataaa    780
gcccagaatg ccatcgccgg ggaaggaatg ggaatcagtc atgagctaat caccctggag    840
atcagctccc gagatgtccc ggatctgact ctaatagacc ttcctggcat aaccagagtg    900
gctgtgggca atcagcctgc tgacattggg tataagatca agacactcat caagaagtac    960
atccagaggc aggagacaat cagcctggtg gtggtcccca gtaatgtgga catcgccacc   1020
acagaggctc tcagcatggc ccaggaggtg gacccccgagg gagacaggac catcggaatc   1080
ttgacgaagc ctgatctggt ggacaaagga actgaagaca aggttgtgga cgtggtgcgg   1140
aacctcgtgt tccacctgaa gaagggttac atgattgtca agtgccgggg ccagcaggag   1200
atccaggacc agctgagcct gtccgaagcc ctgcagagag agaagatctt ctttgagaac   1260
cacccatatt tcagggatct gctggaggaa ggaaaggcca cggttccctg cctggcagaa   1320
aaacttacca gcgagctcat cacacatatc tgtaaatctc tgccccctgtt agaaaatcaa   1380
atcaaggaga ctcaccagag aataacagag gagctacaaa agtatggtgt cgacataccg   1440
gaagacgaaa atgaaaaaat gttcttcctg atagataaaa ttaatgcctt taatcaggac   1500
atcactgctc tcatgcaagg agaggaaact gtaggggagg aagacattcg gctgtttacc   1560
agactccgac acgagttcca caaatggagt acaataattg aaaacaattt tcaagaaggc   1620
cataaaattt tgagtagaaa aatccagaaa tttgaaaatc agtatcgtgg tagagagctg   1680
ccaggctttg tgaattacag gacatttgag acaatcgtga aacagcaaat caaggcactg   1740
gaagagccgg ctgtggatat gctacacacc gtgacggata tggtccggct tgctttcaca   1800
gatgtttcga taaaaaattt tgaagagttt tttaacctcc acagaaccgc caagtccaaa   1860
attgaagaca ttagagcaga acaagagaga gaaggtgaga agctgatccg cctccacttc   1920
cagatggaac agattgtcta ctgccaggac caggtataca ggggtgcatt gcagaaggtc   1980
agagagaagg agctggaaga agaaaagaag aagaaatcct gggattttgg ggctttccag   2040
tccagctcgg caacagactc ttccatggag gagatctttc agcacctgat ggcctatcac   2100
caggaggcca gcaagcgcat ctccagccac atccctttga tcatccagtt cttcatgctc   2160
cagacgtacg gccagcagct tcagaaggcc atgctgcagc tcctgcagga caaggacacc   2220
tacagctggc tcctgaagga gcggagcgac accagcgaca agcggaagtt cctgaaggag   2280
cggcttgcac ggctgacgca ggctcggcgc cggcttgccc agttccccgg ttaaccacac   2340
tctgtccagc cccgtagacg tgcacgcaca ctgtctgccc ccgttcccgg gtagccactg   2400
gactgacgac ttgagtgctc agtagtcaga ctggatagtc cgtctctgct tatccgttag   2460
```

```
ccgtggtgat ttagcaggaa gctgtgagag cagtttggtt tctagcatga agacagagcc   2520

ccaccctcag atgcacatga gctggcggga ttgaaggatg ctgtcttcgt actgggaaag   2580

ggattttcag ccctcagaat cgctccacct tgcagctctc cccttctctg tattcctaga   2640

aactgacaca tgctgaacat cacagcttat ttcctcattt ttataatgtc ccttcacaaa   2700

cccagtgttt taggagcatg agtgccgtgt gtgtgcgtcc tgtcggagcc ctgtctcctc   2760

tctctgtaat aaactcattt ctagcag                                       2787
```

<210> SEQ ID NO 104
<211> LENGTH: 60
<212> TYPE: DNA
<213> ORGANISM: Homo sapiens
<220> FEATURE:
<223> OTHER INFORMATION: NM_002462

<400> SEQUENCE: 104

```
actgacacat gctgaacatc acagcttatt tcctcatttt tataatgtcc cttcacaaac     60
```

<210> SEQ ID NO 105
<211> LENGTH: 2808
<212> TYPE: DNA
<213> ORGANISM: Homo sapiens
<220> FEATURE:
<223> OTHER INFORMATION: NM_002759

<400> SEQUENCE: 105

```
gcggcggcgg cggcgcagtt tgctcatact ttgtgacttg cggtcacagt ggcattcagc     60

tccacacttg gtagaaccac aggcacgaca agcatagaaa catcctaaac aatcttcatc    120

gaggcatcga ggtccatccc aataaaaatc aggagaccct ggctatcata gaccttagtc    180

ttcgctggta tactcgctgt ctgtcaacca gcggttgact ttttttaagc cttctttttt    240

ctcttttacc agtttctgga gcaaattcag tttgccttcc tggatttgta aattgtaatg    300

acctcaaaac tttagcagtt cttccatctg actcaggttt gcttctctgg cggtcttcag    360

aatcaacatc cacacttccg tgattatctg cgtgcatttt ggacaaagct tccaaccagg    420

atacgggaag aagaaatggc tggtgatctt tcagcaggtt tcttcatgga ggaacttaat    480

acataccgtc agaagcaggg agtagtactt aaatatcaag aactgcctaa ttcaggacct    540

ccacatgata ggaggtttac atttcaagtt ataatagatg gaagagaatt tccagaaggt    600

gaaggtagat caaagaagga agcaaaaaat gccgcagcca aattagctgt tgagatactt    660

aataaggaaa agaaggcagt tagtccttta ttattgacaa caacgaattc ttcagaagga    720

ttatccatgg ggaattacat aggccttatc aatagaattg cccagaagaa aagactaact    780

gtaaattatg aacagtgtgc atcggggggtg catgggccag aaggatttca ttataaatgc    840

aaaatgggac agaaagaata tagtattggt acaggttcta ctaaacagga agcaaaacaa    900

ttggccgcta aacttgcata tcttcagata ttatcagaag aaacctcagt gaaatctgac    960

tacctgtcct ctggttcttt tgctactacg tgtgagtccc aaagcaactc tttagtgacc   1020

agcacactcg cttctgaatc atcatctgaa ggtgacttct cagcagatac atcagagata   1080

aattctaaca gtgacagttt aaacagttct tcgttgctta tgaatggtct cagaaataat   1140

caaaggaagg caaaaagatc tttggcaccc agatttgacc ttcctgacat gaaagaaaca   1200

aagtatactg tggacaagag gtttggcatg gattttaaag aaatagaatt aattggctca   1260

ggtggatttg gccaagtttt caaagcaaaa cacagaattg acggaaagac ttacgttatt   1320

aaacgtgtta aatataataa cgagaaggcg gagcgtgaag taaaagcatt ggcaaaactt   1380
```

gatcatgtaa atattgttca ctacaatggc tgttgggatg gatttgatta tgatcctgag 1440
accagtgatg attctcttga gagcagtgat tatgatcctg agaacagcaa aaatagttca 1500
aggtcaaaga ctaagtgcct tttcatccaa atggaattct gtgataaagg gaccttggaa 1560
caatggattg aaaaaagaag aggcgagaaa ctagacaaag ttttggcttt ggaactcttt 1620
gaacaaataa caaaaggggt ggattatata cattcaaaaa aattaattca tagagatctt 1680
aagccaagta atatattctt agtagataca aaacaagtaa agattggaga ctttggactt 1740
gtaacatctc tgaaaaatga tggaaagcga acaaggagta agggaacttt gcgatacatg 1800
agcccagaac agatttcttc gcaagactat ggaaaggaag tggacctcta cgctttgggg 1860
ctaattcttg ctgaacttct tcatgtatgt gacactgctt ttgaaacatc aaagtttttc 1920
acagacctac gggatggcat catctcagat atatttgata aaaaagaaaa aactcttcta 1980
cagaaattac tctcaaagaa acctgaggat cgacctaaca catctgaaat actaaggacc 2040
ttgactgtgt ggaagaaaag cccagagaaa aatgaacgac acacatgtta gagcccttct 2100
gaaaaagtat cctgcttctg atatgcagtt ttccttaaat tatctaaaat ctgctaggga 2160
atatcaatag atatttacct tttattttaa tgtttccttt aattttttac tatttttact 2220
aatctttctg cagaaacaga aaggttttct tctttttgct tcaaaaacat tcttacattt 2280
tactttttcc tggctcatct ctttattctt tttttttttt ttaaagacag agtctcgctc 2340
tgttgcccag gctggagtgc aatgacacag tcttggctca ctgcaacttc tgcctcttgg 2400
gttcaagtga ttctcctgcc tcagcctcct gagtagctgg attacaggca tgtgccaccc 2460
acccaactaa tttttgtgtt tttaataaag acagggtttc accatgttgg ccaggctggt 2520
ctcaaactcc tgacctcaag taatccacct gcctcggcct cccaaagtgc tgggattaca 2580
gggatgagcc accgcgccca gcctcatctc tttgttctaa agatggaaaa accaccccca 2640
aattttcttt ttatactatt aatgaatcaa tcaattcata tctatttatt aaatttctac 2700
cgcttttagg ccaaaaaaat gtaagatcgt tctctgcctc acatagctta caagccagct 2760
ggagaaatat ggtactcatt aaaaaaaaaa aaaaagtgat gtacaacc 2808

<210> SEQ ID NO 106
<211> LENGTH: 60
<212> TYPE: DNA
<213> ORGANISM: Homo sapiens
<220> FEATURE:
<223> OTHER INFORMATION: NM_002759

<400> SEQUENCE: 106
tcgttctctg cctcacatag cttacaagcc agctggagaa atatggtact cattaaaaaa 60

<210> SEQ ID NO 107
<211> LENGTH: 1678
<212> TYPE: DNA
<213> ORGANISM: Homo sapiens
<220> FEATURE:
<223> OTHER INFORMATION: NM_002811

<400> SEQUENCE: 107
aagaaggagg ccgcgcgagg gctgacgaac cggaagaaga ggaactgggc ctgaaagggt 60
accggtgacc gctactgctg ccggtgtttg cgtgtggcag ggagccaggc ctggcgagcg 120
gggtgtgtcg cgatgccgga gctggcagtg cagaaggtgg tggtccaccc cctggtgctg 180
ctcagtgtgg tggatcattt caaccgaatc ggcaaggttg gaaaccagaa gcgtgttgtt 240
ggtgtgcttt tggggtcatg gcaaaagaaa gtacttgatg tatcgaacag ttttgcagtt 300 cctttttgatg aagatgacaa agacgattct gtatggtttt tagaccatga ttatttggaa 360
aacatgtatg gaatgtttaa gaaagtcaat gccagggaaa gaatagttgg ctggtaccac 420
acaggcccta aactacacaa gaatgacatt gccatcaacg aactcatgaa aagatactgt 480
cctaattccg tattggtcat cattgatgtg aagccgaagg acctagggct gcctacagaa 540
gcgtacattt cagtggaaga agtccatgat gatggaactc caacctcgaa aacatttgaa 600
cacgtgacca gtgaaattgg agcagaggaa gctgaggaag ttggagttga acacttgtta 660
cgagatatca aagacacgac ggtgggcact ctgtcccagc ggatcacaaa ccaggtccat 720
ggtttgaagg gactgaactc caagcttctg gatatcagga gctacctgga aaaagtcgcc 780
acaggcaagc tgcccatcaa ccaccagatc atctaccagc tgcaggacgt cttcaacctg 840
ctgccagatg tcagcctgca ggagttcgtc aaggcctttt acctgaagac caatgaccag 900
atggtggtag tgtacttggc ctcgctgatc cgttccgtgg tcgccctgca caacctcatc 960
aacaacaaga ttgccaaccg ggatgcagag aagaaagaag ggcaggagaa agaagagagc 1020
aaaaaggata ggaaagagga caaggagaaa gataaagata aggaaaagag tgatgtaaag 1080
aaagaggaga aaaaggagaa aaagtaaaac atgtattaaa tagctttttt aatttgtaaa 1140
ttaaaatctt acaaactaaa tcagtgtgct gctagagggt tctttttcac ttgacatgct 1200
tattagaaag ctgacccaac aagagctctc tgcctccggt cactcttgct gtggtgctac 1260
gtggaagtga atggagactg atctcaaatc tgaactgcag ctttcgctgc tgtgagttgg 1320
ggatatgata gtcagctcag gcttcagatt gtatgagaaa aatgaagaga agtcaacaaa 1380
tattttggta ctcttcattc atttatctct aaaaccagga gttgaatttt cctcatcttg 1440
aaagactctt ggggtctgtt tctggtattt tacaaaattg ctaagtggaa tgcatgaatt 1500
gcattatgtt ctctggtaac acgtagagtt cagacccttc tgaactctgt tgataatacc 1560
acaccatgtt ctggacccat agctctggca tcctcagggg ttgtgatcca gctccatata 1620
ttgtttacct tcaaagatac aattaaatgg cttgattttt aaaaaaaaaa aaaaaaaa 1678

<210> SEQ ID NO 108
<211> LENGTH: 60
<212> TYPE: DNA
<213> ORGANISM: Homo sapiens
<220> FEATURE:
<223> OTHER INFORMATION: NM_002811

<400> SEQUENCE: 108
aaattgctaa gtggaatgca tgaattgcat tatgttctct ggtaacacgt agagttcaga 60

<210> SEQ ID NO 109
<211> LENGTH: 846
<212> TYPE: DNA
<213> ORGANISM: Homo sapiens
<220> FEATURE:
<223> OTHER INFORMATION: NM_002888

<400> SEQUENCE: 109
ccacgtccgg ggtgccgagc caactttcct gcgtccatgc agccccgccg gcaacggctg 60
cccgctccct ggtccgggcc caggggcccg cgccccaccg ccccgctgct cgcgctgctg 120
ctgttgctcg ccccggtggc ggcgcccgcg gggtccgggg gccccgacga ccctgggcag 180
cctcaggatg ctggggtccc gcgcaggctc ctgcagcaga aggcgcgcgc ggcgcttcac 240
ttcttcaact tccggtccgg ctcgcccagc gcgctgcgag tgctggccga ggtgcaggag 300
ggccgcgcgt ggattaatcc aaaagaggga tgtaaagttc acgtggtctt cagcacagag 360
cgctacaacc cagagtcttt acttcaggaa ggtgagggac gtttggggaa atgttctgct 420
cgagtgtttt tcaagaatca gaaacccaga ccaaccatca atgtaacttg tacacggctc 480
atcgagaaaa agaaaagaca acaagaggat tacctgcttt acaagcaaat gaagcaactg 540
aaaaacccct tggaaatagt cagcatacct gataatcatg gacatattga tccctctctg 600
agactcatct gggatttggc tttccttgga agctcttacg tgatgtggga aatgacaaca 660
caggtgtcac actactactt ggcacagctc actagtgtga ggcagtgggt aagaaaaacc 720
tgaaaattaa cttgtgccac aagagttaca atcaaagtgg tctccttaga ctgaattcat 780
gtgaacttct aatttcatat caagagttgt aatcacattt atttcaataa atatgtgagt 840
tcctgc 846

<210> SEQ ID NO 110
<211> LENGTH: 60
<212> TYPE: DNA
<213> ORGANISM: Homo sapiens
<220> FEATURE:
<223> OTHER INFORMATION: NM_002888

<400> SEQUENCE: 110
aaagaaaaga caacaagagg attacctgct ttacaagcaa atgaagcaac tgaaaaaccc 60

<210> SEQ ID NO 111
<211> LENGTH: 1054
<212> TYPE: DNA
<213> ORGANISM: Homo sapiens
<220> FEATURE:
<223> OTHER INFORMATION: NM_003090

<400> SEQUENCE: 111
gaattccgcg ggaggccacg ggctttccac agcgcggggg aacgggaggc tgcaggatgg 60
tcaagctgac ggcggagctg atcgagcagg cggcgcagta caccaacgcg gtgcgcgacc 120
gggagctgga cctccggggg tataaaattc ccgtcattga aaatctaggt gctacgttag 180
accagtttga tgctattgat ttttctgaca atgagatcag gaaactggat ggttttcctt 240
tgttgagaag actgaaaaca ttgttagtga acaacaacag aatatgccgt ataggtgagg 300
gacttgatca ggctctgccc tgtctgacag aactcattct caccaataat agtctcgtgg 360
aactgggtga tctggaccct ctggcatctc tcaaatcgct gacttaccta agtatcctaa 420
gaaatccggt aaccaataag aagcattaca gattgtatgt gatttataaa gttccgcaag 480
tcagagtact ggatttccag aaagtgaaac taaaagagcg tcaggaagca gagaaaatgt 540
tcaagggcaa acggggtgca cagcttgcaa aggatattgc caggagaagc aaaactttta 600
atccaggtgc tggtttgcca actgacaaaa agagaggtgg gccatctcca ggggatgtag 660
aagcaatcaa gaatgccata gcaaatgctt caactctggc tgaagtggag aggctgaagg 720
ggttgctgca gtctggtcag atccctggca gagaacgcag atcagggccc actgatgatg 780
gtgaagaaga gatggaagaa gacacagtca caaacgggtc ctgagcagtg aggcagatgt 840
ataataatag gccctcttgg aacaagtctt gcttttcgaa catggtataa tagccttgtt 900
tgtgttagca aagtggaatc tatcagcatt gttgaaatgc ttaagactgc tgctgataat 960
tttgtaatat aagttttgaa atctaaatgt caattttcta caaattataa aaataaactc 1020
cactctctat gctaaaaaaa aaaaaaagga attc 1054

<210> SEQ ID NO 112
<211> LENGTH: 60

<212> TYPE: DNA
<213> ORGANISM: Homo sapiens
<220> FEATURE:
<223> OTHER INFORMATION: NM_003090

<400> SEQUENCE: 112
taatagcctt gtttgtgtta gcaaagtgga atctatcagc attgttgaaa tgcttaagac 60

<210> SEQ ID NO 113
<211> LENGTH: 2033
<212> TYPE: DNA
<213> ORGANISM: Homo sapiens
<220> FEATURE:
<223> OTHER INFORMATION: NM_003158

<400> SEQUENCE: 113
gaattccggg actgagctct tgaagacttg ggtccttggt cgcaggtgga gcgacgggtc 60
tcactccatt gcccaggcca gagtgcggga tatttgataa gaaacttcag tgaaggccgg 120
gcgcggtgct catgcccgta atcccagcat tttcggaggc cgaggcatca tggaccgatc 180
taaagaaaac tgcatttcag gacctgttaa ggctacagct ccagttggag gtccaaaacg 240
tgttctcgtg actcagcaat ttccttgtca gaatccatta cctgtaaata gtggccaggc 300
tcagcgggtc ttgtgtcctt caaattcttc ccagcgcgtt cctttgcaag cacaaaagct 360
tgtctccagt cacaagccgg ttcagaatca gaagcagaag caattgcagg caaccagtgt 420
acctcatcct gtctccaggc cactgaataa cacccaaaag agcaagcagc ccctgccatc 480
gcacctgaaa ataatcctga ggaggaactg gcatcaaaac agaaaaatga agaatcaaaa 540
agaggcagtg gctttggaag actttgaaat tggtcgccct ctgggtaaag gaaagtttgg 600
taatgtttat ttggcaagag aaaagcaaag caagtttatt ctggctctta aagtgttatt 660
taaagctcag ctggagaaag ccggagtgga gcatcagctc agaagagaag tagaaataca 720
gtcccacctt cggcatccta atattcttag actgtatggt tatttccatg atgctaccag 780
agtctaccta attctggaat atgcaccact tggaacagtt tatagagaac ttcagaaact 840
ttcaaagttt gatgagcaga gaactgctaa cttatataac agaattgcaa atgccctgtc 900
ttactgtcat tcgaagagag ttattcatag agacattaag ccagagaact tacttcttgg 960
atcagctgga gagcttaaaa ttgcagattt tgggtggtca gtacatgctc catcttccag 1020
gaggaccact ctctgtggca ccctggacta cctgcccccct gaaatgattg aaggtcggat 1080
gcatgatgag aaggtggatc tctggagcct tggagttctt tgctatgaat ttttagttgg 1140
gaagcctcct tttgaggcaa acacatacca agagacctac aaaagaatat cacgggttga 1200
attcacattc cctgactttg taacagaggg agccagggac ctcatttcaa gactgttgaa 1260
gcataatccc agccagaggc caatgctcag agaagtactt gaacacccct ggatcacagc 1320
aaattcatca aaaccatcaa attgccaaaa caaagaatca gctagcaaac agtcttagga 1380
atcgtgcagg gggagaaatc cttgagccag ggctgccata taacctgaca ggaacatgct 1440
actgaagttt attttaccat tgactgctgc cctcaatcta gaacgctaca caagaaatat 1500
tttgttttta ctcagcaggt gtgccttaac ctccctattc agaaagctcc acatcaataa 1560
acatgacact ctgaagtgaa agtagccacg agaattgtgc tacttatact ggaacataat 1620
ctggaggcaa ggttcgactg cagtcgaacc ttgcctccag attatgaacc agtataagta 1680
gcacaattct cgtggctact ttcacttcag agtgtcatgt ttattgatgt ggagctttct 1740
gaatagggag gttaaggcac acctgctgag taaaacaaat atttcttgtg tagcgttctt 1800
aggaatctgg tgtctgtccg gccccggtag gcctgttggg tttctagtcc tccttaccat 1860
catctccata tgagagtgtg aaaataggaa cacgtgctct acctccattt agggatttgc 1920
ttgggataca gaagaggcca tgtgtctcag agctgttaag ggcttatttt tttaaaacat 1980
tggagtcata gcatgtgtgt aaactttaaa tatgcaggcc ttcgtggctc gag 2033

<210> SEQ ID NO 114
<211> LENGTH: 60
<212> TYPE: DNA
<213> ORGANISM: Homo sapiens
<220> FEATURE:
<223> OTHER INFORMATION: NM_003158

<400> SEQUENCE: 114
ttgggtttct agtcctcctt accatcatct ccatatgaga gtgtgaaaat aggaacacgt 60

<210> SEQ ID NO 115
<211> LENGTH: 1421
<212> TYPE: DNA
<213> ORGANISM: Homo sapiens
<220> FEATURE:
<223> OTHER INFORMATION: NM_003258

<400> SEQUENCE: 115
acttactgcg ggacggcctt ggagagtact cgggttcgtg aacttcccgg aggcgcaatg 60
agctgcatta acctgcccac tgtgctgccc ggctccccca gcaagacccg ggggcagatc 120
caggtgattc tcgggccgat gttctcagga aaaagcacag agttgatgag acgcgtccgt 180
cgcttccaga ttgctcagta caagtgcctg gtgatcaagt atgccaaaga cactcgctac 240
agcagcagct tctgcacaca tgaccggaac accatggagg cgctgcccgc ctgcctgctc 300
cgagacgtgg cccaggaggc cctgggcgtg gctgtcatag gcatcgacga ggggcagttt 360
ttccctgaca tcatggagtt ctgcgaggcc atggccaacg ccgggaagac cgtaattgtg 420
gctgcactgg atgggacctt ccagaggaag ccatttgggg ccatcctgaa cctggtgccg 480
ctggccgaga gcgtggtgaa gctgacggcg gtgtgcatgg agtgcttccg ggaagccgcc 540
tataccaaga ggctcggcac agagaaggag gtcgaggtga ttgggggagc agacaagtac 600
cactccgtgt gtcggctctg ctacttcaag aaggcctcag gccagcctgc cgggccggac 660
aacaaagaga actgcccagt gccaggaaag ccaggggaag ccgtggctgc caggaagctc 720
tttgccccac agcagattct gcaatgcagc cctgccaact gagggacctg caagggccgc 780
ccgctccctt cctgccactg ccgcctactg gacgctgccc tgcatgctgc ccagccactc 840
caggaggaag tcgggaggcg tggagggtga ccacaccttg gccttctggg aactctcctt 900
tgtgtggctg ccccacctgc cgcatgctcc ctcctctcct acccactggt ctgcttaaag 960
cttccctctc agctgctggg acgatcgccc aggctggagc tggccccgct tggtggcctg 1020
ggatctggca cactccctct ccttggggtg agggacagag ccccacgctg ttgacatcag 1080
cctgcttctt cccctctgcg gctttcactg ctgagtttct gttctccctg ggaagcctgt 1140
gccagcacct ttgagccttg gcccacactg aggcttaggc ctctctgcct gggatgggct 1200
cccaccctcc cctgaggatg gcctggattc acgccctctt gtttcctttt gggctcaaag 1260
cccttcctac ctctggtgat ggtttccaca ggaacaacag catctttcac caagatgggt 1320
ggcaccaacc ttgctgggac ttggatccca ggggcttatc tcttcaagtg tggagagggc 1380
agggtccacg cctctgctgt agcttatgaa attaactaat t 1421

<210> SEQ ID NO 116
<211> LENGTH: 60

<212> TYPE: DNA
<213> ORGANISM: Homo sapiens
<220> FEATURE:
<223> OTHER INFORMATION: NM_003258

<400> SEQUENCE: 116
cttcctacct ctggtgatgg tttccacagg aacaacagca tctttcacca agatgggtgg 60

<210> SEQ ID NO 117
<211> LENGTH: 913
<212> TYPE: DNA
<213> ORGANISM: Homo sapiens
<220> FEATURE:
<223> OTHER INFORMATION: NM_003311

<400> SEQUENCE: 117
agagccggcg ccgtcaccgc ccgcattgcc gctcccagtc ccgcgctcgg cacgacatga 60
aatcccccga cgaggtgcta cgcgagggcg agttggagaa gcgcagcgac agcctcttcc 120
agctatggaa gaagaagcgc ggggtgctca cctccgaccg cctgagcctg ttccccgcca 180
gcccccgcgc gcgccccaag gagctgcgct tccactccat cctcaaggtg gactgcgtgg 240
agcgcacggg caagtacgtg tacttcacca tcgtcaccac cgaccacaag gagatcgact 300
tccgctgcgc gggcgagagc tgctggaacg cggccatcgc gctggcgctc atcgatttcc 360
agaaccgccg cgccctgcag gactttcgca gccgccagga acgcaccgca cccgccgcac 420
ccgccgagga cgccgtggct gccgcggccg ccgcaccctc cgagccctcg gagccctcca 480
ggccatcccc gcagcccaaa ccccgcacgc catgagcccg ccgcgggcca tacgctggac 540
gagtcggacc gaggctagga cgtggccggc gctctccagc cctgcagcag aagaacttcc 600
cgtgcgcgcg gatcctcgct ccgttgcacg ggcgccttaa gttattggac tatctaatat 660
ctatgtattt atttcgctgg ttctttgtag tcacatattt tatagtctta atatcttgtt 720
tttgcatcac tgtgcccatt gcaaataaat cacttggcca gtttgctttt ctaccatccg 780
gctgtggctc agtgagactc ctgctgggag ggtggaggcc caggaatggg cgggcaggac 840
accctcatcc agtcctgcgg ggctggtgtg aaaggcgctg ggaaccggct ttgaatgaat 900
aaatgaatcg tgt 913

<210> SEQ ID NO 118
<211> LENGTH: 60
<212> TYPE: DNA
<213> ORGANISM: Homo sapiens
<220> FEATURE:
<223> OTHER INFORMATION: NM_003311

<400> SEQUENCE: 118
atttcgctgg ttctttgtag tcacatattt tatagtctta atatcttgtt tttgcatcac 60

<210> SEQ ID NO 119
<211> LENGTH: 1723
<212> TYPE: DNA
<213> ORGANISM: Homo sapiens
<220> FEATURE:
<223> OTHER INFORMATION: NM_003376

<400> SEQUENCE: 119
tcgcggaggc ttggggcagc cgggtagctc ggaggtcgtg gcgctggggg ctagcaccag 60
cgctctgtcg ggaggcgcag cggttaggtg gaccggtcag cggactcacc ggccagggcg 120
ctcggtgctg gaatttgata ttcattgatc cgggttttat ccctcttctt ttttcttaaa 180 cattttttttt taaaactgta ttgtttctcg ttttaattta tttttgcttg ccattcccca 240

```
cttgaatcgg gccgacggct tggggagatt gctctacttc cccaaatcac tgtggatttt    300

ggaaaccagc agaaagagga aagaggtagc aagagctcca gagagaagtc gaggaagaga    360

gagacggggt cagagagagc gcgcgggcgt gcgagcagcg aaagcgacag gggcaaagtg    420

agtgacctgc ttttgggggt gaccgccgga gcgcggcgtg agccctcccc cttgggatcc    480

cgcagctgac cagtcgcgct gacggacaga cagacagaca ccgcccccag ccccagctac    540

cacctcctcc ccggccggcg gcggacagtg gacgcggcgg cgagccgcgg gcaggggccg    600

gagcccgcgc ccggaggcgg ggtggagggg gtcggggctc gcggcgtcgc actgaaactt    660

ttcgtccaac ttctgggctg ttctcgcttc ggaggagccg tggtccgcgc gggggaagcc    720

gagccgagcg gagccgcgag aagtgctagc tcgggccggg aggagccgca gccggaggag    780

ggggaggagg aagaagagaa ggaagaggag agggggccgc agtggcgact cggcgctcgg    840

aagccgggct catggacggg tgaggcggcg gtgtgcgcag acagtgctcc agccgcgcgc    900

gctccccagg ccctggcccg ggcctcgggc cggggaggaa gagtagctcg ccgaggcgcc    960

gaggagagcg ggccgcccca cagcccgagc cggagaggga gcgcgagccg cgccggcccc   1020

ggtcgggcct ccgaaaccat gaactttctg ctgtcttggg tgcattggag ccttgccttg   1080

ctgctctacc tccaccatgc caagtggtcc caggctgcac ccatggcaga aggaggaggg   1140

cagaatcatc acgaagtggt gaagttcatg gatgtctatc agcgcagcta ctgccatcca   1200

atcgagaccc tggtggacat cttccaggag taccctgatg agatcgagta catcttcaag   1260

ccatcctgtg tgcccctgat gcgatgcggg ggctgctgca atgacgaggg cctggagtgt   1320

gtgcccactg aggagtccaa catcaccatg cagattatgc ggatcaaacc tcaccaaggc   1380

cagcacatag gagagatgag cttcctacag cacaacaaat gtgaatgcag accaaagaaa   1440

gatagagcaa gacaagaaaa aaaatcagtt cgaggaaagg gaaaggggca aaaacgaaag   1500

cgcaagaaat cccggtataa gtcctggagc gttccctgtg ggccttgctc agagcggaga   1560

aagcatttgt ttgtacaaga tccgcagacg tgtaaatgtt cctgcaaaaa cacagactcg   1620

cgttgcaagg cgaggcagct tgagttaaac gaacgtactt gcagatgtga caagccgagg   1680

cggtgagccg ggcaggagga aggagcctcc ctcagggttt cgg                     1723
```

<210> SEQ ID NO 120
<211> LENGTH: 60
<212> TYPE: DNA
<213> ORGANISM: Homo sapiens
<220> FEATURE:
<223> OTHER INFORMATION: NM_003376

<400> SEQUENCE: 120

```
ccagcacata ggagagatga gcttcctaca gcacaacaaa tgtgaatgca gaccaaagaa     60
```

<210> SEQ ID NO 121
<211> LENGTH: 2834
<212> TYPE: DNA
<213> ORGANISM: Homo sapiens
<220> FEATURE:
<223> OTHER INFORMATION: NM_003406

<400> SEQUENCE: 121

```
gcccactccc accgccagct ggaaccctgg ggactacgac gtccctcaaa ccttgcttct     60

aggagataaa aagaacatcc agtcatggat aaaaatgagc tggttcagaa ggccaaactg    120

gccgagcagg ctgagcgata tgatgacatg gcagcctgca tgaagtctgt aactgagcaa    180

ggagctgaat tatccaatga ggagaggaat cttctctcag ttgcttataa aaatgttgta    240
```

```
ggagcccgta ggtcatcttg gagggtcgtc tcaagtattg aacaaaagac ggaaggtgct    300
gagaaaaaac agcagatggc tcgagaatac agagagaaaa ttgagacgga gctaagagat    360
atctgcaatg atgtactgtc tcttttggaa aagttcttga tccccaatgc ttcacaagca    420
gagagcaaag tcttctattt gaaaatgaaa ggagattact accgttactt ggctgaggtt    480
gccgctggtg atgacaagaa agggattgtc gatcagtcac aacaagcata ccaagaagct    540
tttgaaatca gcaaaaagga aatgcaacca acacatccta tcagactggg tctggccctt    600
aacttctctg tgttctatta tgagattctg aactccccag agaaagcctg ctctcttgca    660
aagacagctt ttgatgaagc cattgctgaa cttgatacat taagtgaaga gtcatacaaa    720
gacagcacgc taataatgca attactgaga gacaacttga cattgtggac atcggatacc    780
caaggagacg aagctgaagc aggagaagga ggggaaaatt aaccggcctt ccaacttttg    840
tctgcctcat tctaaaattt acacagtaga ccatttgtca tccatgctgt cccacaaata    900
gtttttttgtt tacgatttat gacaggttta tgttacttct atttgaattt ctatatttcc    960
catgtggttt ttatgtttaa tattagggga gtagagccag ttaacattta gggagttatc   1020
tgttttcatc ttgaggtggc caatatgggg atgtggaatt tttatacaag ttataagtgt   1080
ttggcatagt acttttggta cattgtggct tcaaaagggc cagtgtaaaa ctgcttccat   1140
gtctaagcaa agaaaactgc ctacatactg gtttgtcctg gcggggaata aaagggatca   1200
ttggttccag tcacaggtgt agtaattgtg ggtactttaa ggtttggagc acttacaagg   1260
ctgtggtaga atcatacccc atggatacca catattaaac catgtatatc tgtggaatac   1320
tcaatgtgta cacctttgac tacagctgca gaagtgttcc tttagacaaa gttgtgaccc   1380
attttactct ggataagggc agaaacggtt cacattccat tatttgtaaa gttacctgct   1440
gttagctttc attattttg ctacactcat tttatttgta tttaaatgtt ttaggcaacc   1500
taagaacaaa tgtaaaagta aagatgcagg aaaaatgaat tgcttggtat tcattacttc   1560
atgtatatca agcacagcag taaaacaaaa acccatgtat ttaacttttt tttaggattt   1620
ttgcttttgt gatttttttt ttttttttt gatacttgcc taacatgcat gtgctgtaaa   1680
aatagttaac agggaaataa cttgagatga tggctagctt tgtttaatgt cttatgaaat   1740
tttcatgaac aatccaagca taattgttaa gaacacgtgt attaaattca tgtaagtgga   1800
ataaaagttt tatgaatgga cttttcaact actttctcta cagcttttca tgtaaattag   1860
tcttggttct gaaacttctc taaaggaaat tgtacatttt ttgaaattta ttccttattc   1920
cctcttggca gctaatgggc tcttaccaag tttaaacaca aaatttatca taacaaaaat   1980
actactaata taactactgt ttccatgtcc catgatcccc tctcttcctc cccaccctga   2040
aaaaaatgag ttcctatttt ttctgggaga ggggggggatt gattagaaaa aaatgtagtg   2100
tgttccattt aaaattttgg catatggcat tttctaactt aggaagccac aatgttcttg   2160
gcccatcatg acattgggta gcattaactg taagttttgt gcttccaaat cactttttgg   2220
tttttaagaa tttcttgata ctcttatagc ctgccttcaa ttttgatcct ttattctttc   2280
tatttgtcag gtgcacaaga ttaccttcct gttttagcct tctgtcttgt caccaaccat   2340
tcttacttgg tggccatgta cttggaaaaa ggccgcatga tctttctggc tccactcagt   2400
gtctaaggca ccctgcttcc tttgcttgca tcccacagac tatttccctc atcctattta   2460
ctgcagcaaa tctctcctta gttgatgaga ctgtgtttat ctccctttaa aaccctacct   2520
atcctgaatg gtctgtcatt gtctgccttt aaaatccttc ctctttcttc ctcctctatt   2580
ctctaaataa tgatggggct aagttatacc caaagctcac tttacaaaat atttcctcag   2640
```

tactttgcag aaaacaccaa acaaaaatgc cattttaaaa aaggtgtatt ttttctttta 2700
gaatgtaagc tcctcaagag cagggacaat gttttctgta tgttctattg tgcctagtac 2760
actgtaaatg ctcaataaat attgatgatg ggaggcagtg agtcttgatg ataagggtga 2820
gaaactgaaa tccc 2834

<210> SEQ ID NO 122
<211> LENGTH: 60
<212> TYPE: DNA
<213> ORGANISM: Homo sapiens
<220> FEATURE:
<223> OTHER INFORMATION: NM_003406

<400> SEQUENCE: 122
tttagccttc tgtcttgtca ccaaccattc ttacttggtg gccatgtact tggaaaaagg 60

<210> SEQ ID NO 123
<211> LENGTH: 1938
<212> TYPE: DNA
<213> ORGANISM: Homo sapiens
<220> FEATURE:
<223> OTHER INFORMATION: NM_003504

<400> SEQUENCE: 123
gatttggcgg gagtcttgac cgccgccggg ctcttggtac ctcagcgcga gcgccaggcg 60
tccggccgcc gtggctatgt tcgtgtccga tttccgcaaa gagttctacg aggtggtcca 120
gagccagagg gtccttctct tcgtggcctc ggacgtggat gctctgtgtg cgtgcaagat 180
ccttcaggcc ttgttccagt gtgaccacgt gcaatatacg ctggttccag tttctgggtg 240
gcaagaactt gaaactgcat ttcttgagca taaagaacag tttcattatt ttattctcat 300
aaactgtgga gctaatgtag acctattgga tattcttcaa cctgatgaag acactatatt 360
ctttgtgtgt gacacccata ggccagtcaa tgtcgtcaat gtatacaacg atacccagat 420
caaattactc attaaacaag atgatgacct tgaagttccc gcctatgaag acatcttcag 480
ggatgaagag gaggatgaag agcattcagg aaatgacagt gatgggtcag agccttctga 540
gaagcgcaca cggttagaag aggagatagt ggagcaaacc atgcggagga ggcagcggcg 600
agagtgggag gcccggagaa gagacatcct ctttgactac gagcagtatg aatatcatgg 660
gacatcgtca gccatggtga tgtttgagct ggcttggatg ctgtccaagg acctgaatga 720
catgctgtgg tgggccatcg ttggactaac agaccagtgg gtgcaagaca agatcactca 780
aatgaaatac gtgactgatg ttggtgtcct gcagcgccac gtttcccgcc acaaccaccg 840
gaacgaggat gaggagaaca cactctccgt ggactgcaca cggatctcct ttgagtatga 900
cctccgcctg gtgctctacc agcactggtc cctccatgac agcctgtgca acaccagcta 960
taccgcagcc aggttcaagc tgtggtctgt gcatggacag aagcggctcc aggagttcct 1020
tgcagacatg ggtcttcccc tgaagcaggt gaagcagaag ttccaggcca tggacatctc 1080
cttgaaggag aatttgcggg aaatgattga agagtctgca aataaatttg ggatgaagga 1140
catgcgcgtg cagactttca gcattcattt tgggttcaag cacaagtttc tggccagcga 1200
cgtggtcttt gccaccatgt ctttgatgga gagccccgag aaggatggct cagggacaga 1260
tcacttcatc caggctctgg acagcctctc caggagtaac ctggacaagc tgtaccatgg 1320
cctggaactc gccaagaagc agctgcgagc cacccagcag accattgcca gctgcctttg 1380
caccaacctc gtcatctccc aggggccttt cctgtactgc tctctcatgg agggcactcc 1440
agatgtcatg ctgttctcta ggccggcatc cctaagcctg ctcagcaaac acctgctcaa 1500
gtcctttgtg tgttcgacaa agaaccggcg ctgcaaactg ctgcccctgg tgatggctgc 1560
ccccctgagc atggagcatg gcacagtgac cgtggtgggc atccccccag agaccgacag 1620
ctcggacagg aagaactttt ttgggagggc gtttgagaag gcagcggaaa gcaccagctc 1680
ccggatgctg cacaaccatt ttgacctctc agtaattgag ctgaaagctg aggatcggag 1740
caagtttctg gacgcactta tttccctcct gtcctaggaa tttgattctt ccagaatgac 1800
cttcttattt atgtaactgg ctttcattta gattgtaagt tatggacatg atttgagatg 1860
tagaagccat tttttattaa ataaaatgct tattttaggc tccgtcccca aaaaaaaaaa 1920
aaaaaaaaaa aaaaaaa 1938

<210> SEQ ID NO 124
<211> LENGTH: 60
<212> TYPE: DNA
<213> ORGANISM: Homo sapiens
<220> FEATURE:
<223> OTHER INFORMATION: NM_003504

<400> SEQUENCE: 124
caagtttctg gacgcactta tttccctcct gtcctaggaa tttgattctt ccagaatgac 60

<210> SEQ ID NO 125
<211> LENGTH: 2346
<212> TYPE: DNA
<213> ORGANISM: Homo sapiens
<220> FEATURE:
<223> OTHER INFORMATION: NM_003600

<400> SEQUENCE: 125
acaaggcagc ctcgctcgag cgcaggccaa tcggctttct agctagaggg tttaactcct 60
atttaaaaag aagaaccttt gaattctaac ggctgagctc ttggaagact tgggtccttg 120
ggtcgcaggt gggagccgac gggtgggtag accgtggggg atatctcagt ggcggacgag 180
gacggcgggg acaaggggcg gctggtcgga gtggcggagc gtcaagtccc ctgtcggttc 240
ctccgtccct gagtgtcctt ggcgctgcct tgtgcccgcc cagcgccttt gcatccgctc 300
ctgggcaccg aggcgccctg taggatactg cttgttactt attacagcta gaggcatcat 360
ggaccgatct aaagaaaact gcatttcagg acctgttaag gctacagctc cagttggagg 420
tccaaaacgt gttctcgtga ctcagcaatt tccttgtcag aatccattac ctgtaaatag 480
tggccaggct cagcgggtct tgtgtccttc aaattcttcc cagcgcattc ctttgcaagc 540
acaaaagctt gtctccagtc acaagccggt tcagaatcag aagcagaagc aattgcaggc 600
aaccagtgta cctcatcctg tctccaggcc actgaataac acccaaaaga gcaagcagcc 660
cctgccatcg gcacctgaaa ataatcctga ggaggaactg gcatcaaaac agaaaaatga 720
agaatcaaaa aagaggcagt gggctttgga agactttgaa attggtcgcc ctctgggtaa 780
aggaaagttt ggtaatgttt atttggcaag agaaaagcaa agcaagttta ttctggctct 840
taaagtgtta tttaaagctc agctggagaa agccggagtg gagcatcagc tcagaagaga 900
agtagaaata cagtcccacc ttcggcatcc taatattctt agactgtatg gttatttcca 960
tgatgctacc agagtctacc taattctgga atatgcacca cttggaacag tttatagaga 1020
acttcagaaa ctttcaaagt ttgatgagca gagaactgct acttatataa cagaattggc 1080
aaatgccctg tcttactgtc attcgaagag agttattcat agagacatta agccagagaa 1140
cttacttctt ggatcagctg gagagcttaa aattgcagat tttgggtggt cagtacatgc 1200
tccatcttcc aggaggacca ctctctgtgg caccctggac tacctgcccc ctgaaatgat 1260
tgaaggtcgg atgcatgatg agaaggtgga tctctggagc cttggagttc tttgctatga 1320
atttttagtt gggaagcctc cttttgaggc aaacacatac caagagacct acaaaagaat 1380
atcacgggtt gaattcacat tccctgactt tgtaacagag ggagccaggg acctcatttc 1440
aagactgttg aagcataatc ccagccagag gccaatgctc agagaagtac ttgaacaccc 1500
ctggatcaca gcaaattcat caaaaccatc aaattgccaa aacaaagaat cagctagcaa 1560
acagtcttag gaatcgtgca gggggagaaa tccttgagcc agggctgcca tataacctga 1620
caggaacatg ctactgaagt ttattttacc attgactgct gccctcaatc tagaacgcta 1680
cacaagaaat atttgtttta ctcagcaggt gtgccttaac ctccctattc agaaagctcc 1740
acatcaataa acatgacact ctgaagtgaa agtagccacg agaattgtgc tacttatact 1800
ggttcataat ctggaggcaa ggttcgactg cagccgcccc gtcagcctgt gctaggcatg 1860
gtgtcttcac aggaggcaaa tccagagcct ggctgtgggg aaagtgacca ctctgccctg 1920
accccgatca gttaaggagc tgtgcaataa ccttcctagt acctgagtga gtgtgtaact 1980
tattgggttg gcgaagcctg gtaaagctgt tggaatgagt atgtgattct ttttaagtat 2040
gaaaataaag atatatgtac agacttgtat tttttctctg gtggcattcc tttaggaatg 2100
ctgtgtgtct gtccggcacc ccggtaggcc tgattgggtt tctagtcctc cttaaccact 2160
tatctcccat atgagagtgt gaaaaatagg aacacgtgct ctacctccat ttagggattt 2220
gcttgggata cagaagaggc catgtgtctc agagctgtta agggcttatt tttttaaaac 2280
attggagtca tagcatgtgt gtaaacttta aatatgcaaa taaataagta tctatgtcta 2340
aaaaaa 2346

<210> SEQ ID NO 126
<211> LENGTH: 60
<212> TYPE: DNA
<213> ORGANISM: Homo sapiens
<220> FEATURE:
<223> OTHER INFORMATION: NM_003600

<400> SEQUENCE: 126
agagtgtgaa aaataggaac acgtgctcta cctccattta gggatttgct tgggatacag 60

<210> SEQ ID NO 127
<211> LENGTH: 853
<212> TYPE: DNA
<213> ORGANISM: Homo sapiens
<220> FEATURE:
<223> OTHER INFORMATION: NM_003641

<400> SEQUENCE: 127
ctagtcctga cttcacttct gatgaggaag cctctctcct tagccttcag cctttcctcc 60
caccctgcca taagtaattt gatcctcaag aagttaaacc acacctcatt ggtccctggc 120
taattcacca atttacaaac agcaggaaat agaaacttaa gagaaataca cacttctgag 180
aaactgaaac gacaggggaa aggaggtctc actgagcacc gtcccagcat ccggacacca 240
cagcggccct tcgctccacg cagaaaacca cacttctcaa accttcactc aacacttcct 300
tccccaaagc cagaagatgc acaaggagga acatgaggtg gctgtgctgg gggcaccccc 360
cagcaccatc cttccaaggt ccaccgtgat caacatccac agcgagacct ccgtgcccga 420
ccatgtcgtc tggtccctgt tcaacaccct cttcttgaac tggtgctgtc tgggcttcat 480
agcattcgcc tactccgtga agtctaggga caggaagatg gttggcgacg tgaccggggc 540
ccaggcctat gcctccaccg ccaagtgcct gaacatctgg gccctgattc tgggcatcct 600

-continued catgaccatt ggattcatcc tgtcactggt attcggctct gtgacagtct accatattat 660
gttacagata atacaggaaa aacggggtta ctagtagccg cccatagcct gcaacctttg 720
cactccactg tgcaatgctg gccctgcacg ctggggctgt tgcccctgcc cccttggtcc 780
tgcccctaga tacagcagtt tatacccaca cacctgtcta cagtgtcatt caataaagtg 840
cacgtgcttg tga 853

<210> SEQ ID NO 128
<211> LENGTH: 60
<212> TYPE: DNA
<213> ORGANISM: Homo sapiens
<220> FEATURE:
<223> OTHER INFORMATION: NM_003641

<400> SEQUENCE: 128
attatgttac agataataca ggaaaaacgg ggttactagt agccgcccat agcctgcaac 60

<210> SEQ ID NO 129
<211> LENGTH: 1280
<212> TYPE: DNA
<213> ORGANISM: Homo sapiens
<220> FEATURE:
<223> OTHER INFORMATION: NM_003756

<400> SEQUENCE: 129
gaaagatggc gtcccgcaag gaaggtaccg gctctactgc cacctcttcc agctccaccg 60
ccggcgcagc agggaaaggc aaaggcaaag gcggctcggg agattcagcc gtgaagcaag 120
tgcagataga tggccttgtg gtattaaaga taatcaaaca ttatcaagaa gaaggacaag 180
gaactgaagt tgttcaagga gtgcttttgg gtctggttgt agaagatcgg cttgaaatta 240
ccaactgctt tcctttccct cagcacacag aggatgatgc tgactttgat gaagtccaat 300
atcagatgga aatgatgcgg agccttcgcc atgtaaacat tgatcatctt cacgtgggct 360
ggtatcagtc cacatactat ggctcattcg ttacccgggc actcctggac tctcagttta 420
gttaccagca tgccattgaa gaatctgtcg ttctcattta tgatcccata aaaactgccc 480
aaggatctct ctcactaaag gcatacagac tgactcctaa actgatggaa gtttgtaaag 540
aaaaggattt ttcccctgaa gcattgaaaa aagcaaatat cacctttgag tacatgtttg 600
aagaagtgcc gattgtaatt aaaaattcac atctgatcaa tgtcctaatg tgggaacttg 660
aaaagaagtc agctgttgca gataaacatg aattgctcag ccttgccagc agcaatcatt 720
tggggaagaa tctacagttg ctgatggaca gagtggatga aatgagccaa gatatagtta 780
aatacaacac atacatgagg aatactagta aacaacagca gcagaaacat cagtatcagc 840
agcgtcgcca gcaggagaat atgcagcgcc agagccgagg agaacccccg ctccctgagg 900
aggacctgtc caaactcttc aaaccaccac agccgcctgc caggatggac tcgctgctca 960
ttgcaggcca gataaacact tactgccaga acatcaagga gttcactgcc caaaacttag 1020
gcaagctctt catggcccag gctcttcaag aatacaacaa ctaagaaaag gaagtttcca 1080
gaaaagaagt taacatgaac tcttgaagtc acaccaggc aactcttgga agaaatatat 1140
ttgcatattg aaaagcacag aggatttctt tagtgtcatt gccgattttg gctataacag 1200
tgtctttcta gccataataa aataaaaaaa aaaaaaaaaa aaaaaaaaaa aaaaaaaaaa 1260
aaaaaaaaaa aaaaaaaaaa 1280

<210> SEQ ID NO 130
<211> LENGTH: 60

<212> TYPE: DNA
<213> ORGANISM: Homo sapiens
<220> FEATURE:
<223> OTHER INFORMATION: NM_003756

<400> SEQUENCE: 130
tgagccaaga tatagttaaa tacaacacat acatgaggaa tactagtaaa caacagcagc 60

<210> SEQ ID NO 131
<211> LENGTH: 839
<212> TYPE: DNA
<213> ORGANISM: Homo sapiens
<220> FEATURE:
<223> OTHER INFORMATION: NM_003832

<400> SEQUENCE: 131
aagccacagg ctccctggct ggcgtcagct aaagtggctg ttgggtgtcc gcaggcttct 60
gcctggccgc cgccgcctat aagctaccag gaggagcttt acgacttccc gtcctgcggg 120
aagtggcggg cacgatcgca aggtagcgca gaagcttctc aatggccagc gccagctgca 180
gccccggcgg cgcactcgcc tcacctgagc ctgggaggaa aattcttcca aggatgatct 240
cccactcaga gctgaggaag cttttctact cagcagatgc tgtgtgtttt gatgttgaca 300
gcacggtcat cagtgaagaa ggaatcggat gctttcattg gatttggagg aaatgtgatc 360
aggcaacaag tcaaggataa cgccaaatgg tatatcactg attttgtaga gctgctggga 420
gaaccggaag aataacatcc attgtcatac agctccaaac aacttcagat gaatttttac 480
aagttacaca gattgatact gtttgcttac aattgcctat tacaacttgc tataaaaagt 540
tggtacagat gatctgcact gtcaagtaaa ctacagttag gaatcctcaa agattggttt 600
gtttgttttt aactgtagtt ccagtattat atgatcacta tcgatttcct ggagagtttt 660
gtaatctgaa ttctttatgt atattcctag ctatatttca tacaaagtgt tttaagagtg 720
gagagtcaat taaacacctt tactcttagg aatatagatt cggcagcctt cagtgaatat 780
tggttttttt ccctttggta tgtcaataaa agtttatcca tgtgtcagaa aaaaaaaaa 839

<210> SEQ ID NO 132
<211> LENGTH: 60
<212> TYPE: DNA
<213> ORGANISM: Homo sapiens
<220> FEATURE:
<223> OTHER INFORMATION: NM_003832

<400> SEQUENCE: 132
gaagaaggaa tcggatgctt tcattggatt tggaggaaat gtgatcaggc aacaagtcaa 60

<210> SEQ ID NO 133
<211> LENGTH: 3128
<212> TYPE: DNA
<213> ORGANISM: Homo sapiens
<220> FEATURE:
<223> OTHER INFORMATION: NM_003981

<400> SEQUENCE: 133
gcttcgcccc gtggcgcggt ttgaaatttt gcggggctca acggctcgcg gagcggctac 60
gcggagtgac atcgccggtg tttgcgggtg gttgttgctc tcggggccgt gtggagtagg 120
tctggacctg gactcacggc tgcttggagc gtccgccatg aggagaagtg aggtgctggc 180
ggaggagtcc atagtatgtc tgcagaaagc cctaaatcac cttcgggaaa tatgggagct 240
aattgggatt ccagaggacc agcggttaca aagaactgag gtggtaaaga agcatatcaa 300
ggaactcctg gatatgatga ttgctgaaga ggaaagcctg aaggaaagac tcatcaaaag 360

```
catatccgtc tgtcagaaag agctgaacac tctgtgcagc gagttacatg ttgagccatt    420
tcaggaagaa ggagagacga ccatcttgca actagaaaaa gatttgcgca cccaagtgga    480
attgatgcga aaacagaaaa aggagagaaa acaggaactg aagctacttc aagagcaaga    540
tcaagaactg tgcgaaattc tttgtatgcc ccactatgat attgacagtg cctcagtgcc    600
cagcttagaa gagctgaacc agttcaggca acatgtgaca actttgaggg aaacaaaggc    660
ttctaggcgt gaggagtttg tcagtataaa gagacagatc atactgtgta tggaagaatt    720
agaccacacc ccagacacaa gctttgaaag agatgtggtg tgtgaagacg aagatgcctt    780
ttgtttgtct ttggagaata ttgcaacact acaaaagttg ctacggcagc tggaaatgca    840
gaaatcacaa aatgaagcag tgtgtgaggg gctgcgtact caaatccgag agctctggga    900
caggttgcaa atacctgaag aagaaagaga agctgtggcc accattatgt ctgggtcaaa    960
ggccaaggtc cggaaagcgc tgcaattaga agtggatcgg ttggaagaac tgaaaatgca   1020
aaacatgaag aaagtgattg aggcaattcg agtggagctg gttcagtact gggaccagtg   1080
cttttatagc caggagcaga gacaagcttt tgccccttc tgtgctgagg actacacaga   1140
aagtctgctc cagctccacg atgctgagat tgtgcggtta aaaaactact atgaagttca   1200
caaggaactc tttgaaggtg tccagaagtg ggaagaaacc tggaggcttt tcttagagtt   1260
tgagagaaaa gcttcagatc caaatcgatt tacaaaccga ggaggaaatc ttctaaaaga   1320
agaaaaacaa cgagccaagc tccagaaaat gctgcccaag ctggaagaag agttgaaggc   1380
acgaattgaa ttgtgggaac aggaacattc aaaggcattt atggtgaatg ggcagaaatt   1440
catggagtat gtggcagaac aatgggagat gcatcgattg gagaaagaga gagccaagca   1500
ggaaagacaa ctgaagaaca aaaaacagac agagacagag atgctgtatg gcagcgctcc   1560
tcgaacacct agcaagcggc gaggactggc tcccaataca ccgggcaaag cacgtaagct   1620
gaacactacc accatgtcca atgctacggc caatagtagc attcggccta tctttggagg   1680
gacagtctac cactcccccg tgtctcgact tcctccttct ggcagcaagc cagtcgctgc   1740
ttccacctgt tcagggaaga aaacaccccg tactggcagg catggagcca acaaggagaa   1800
cctggagctc aacggcagca tcctgagtgg tgggtaccct ggctcggccc ccctccagcg   1860
caacttcagc attaattctg ttgccagcac ctattctgag tttgcgaagg atccgtccct   1920
ctctgacagt tccactgttg ggcttcagcg agaactttca aaggcttcca aatctgatgc   1980
tacttctgga atcctcaatt caaccaacat ccagtcctga gaagccctga tcagtcaacc   2040
agctgtggct tcctgtgcct agactggacc taattatatg ggggtgactt tagtttttct   2100
tcagcttagg cgtgcttgaa accttggcca ggttccatga ccatgggcct aacttaaaga   2160
tgtgaatgag tgttacagtt gaaagcccat cataggttta gtggtcctag gagacttggt   2220
tttgacttat atacatgaaa agtttatggc aagaagtgca aattttagca tatggggcct   2280
gacttctcta ccacataatt ctacttgctg aagcatgatc aaagcttgtt ttatttcacc   2340
actgtaggaa aatgattgac tatgcccatc cctgggggta attttggcat gtatacctgt   2400
aactagtaat taacatcttt tttgtttagg catgttcaat taatgctgta gctatcatag   2460
ctttgctctt acctgaagcc ttgtccccac cacacaggac agccttcctc ctgaagagaa   2520
tgtctttgtg tgtccgaagt tgagatggcc tgccctactg ccaaagaggt gacaggaagg   2580
ctgggagcag ctttgttaaa ttgtgttcag ttctgttaca cagtgcattg ccctttgttg   2640
gggtatgca tgtatgaaca cacatgcttg tcggaacgct ttctcggcgt ttgtcccttg   2700
gctctcatct cccccattcc tgtgcctact ttgcctgagt tcttctaccc ccgcagttgc   2760
```

cagccacatt gggagtctgt ttgttccaat gggttgagct gtctttgtcg tggagatctg 2820
gaactttgca catgtcacta ctggggaggt gttcctgctc tagcttccac gatgaggcgc 2880
cctctttacc tatcctctca atcactactc ttcttgaagc actattattt attcttccgc 2940
tgtctgcctg cagcagtact actgtcaaca tagtgtaaat ggttctcaaa agcttaccag 3000
tgtggacttg gtgttagcca cgctgtttac tcatacagta cgtgtcctgt ttttaaaata 3060
tacaattatt cttaaaaata aattaaaatc tgtatactta catttcaaaa agaaaaaaaa 3120
aaaaaaaa 3128

<210> SEQ ID NO 134
<211> LENGTH: 60
<212> TYPE: DNA
<213> ORGANISM: Homo sapiens
<220> FEATURE:
<223> OTHER INFORMATION: NM_003981

<400> SEQUENCE: 134
tgcagcagta ctactgtcaa catagtgtaa atggttctca aaagcttacc agtgtggact 60

<210> SEQ ID NO 135
<211> LENGTH: 1816
<212> TYPE: DNA
<213> ORGANISM: Homo sapiens
<220> FEATURE:
<223> OTHER INFORMATION: NM_004029

<400> SEQUENCE: 135
ggcacccagg gtccggcctg cgccttcccg ccaggcctgg acactggttc aacacctgtg 60
acttcatgtg tgcgcgccgg ccacacctgc agtcacacct gtagcccccct ctgccaagag 120 atccataccg aggcagcgtc ggtggctaca agccctcagt ccacacctgt ggacacctgt 180
gacacctggc cacacgacct gtggccgcgg cctggcgtct gctgcgacag gagcccttac 240
ctcccctgtt ataacacctg accgccacct aactgcccct gcagaaggag caatggcctt 300
ggctcctgag agggcagccc cacgcgtgct gttcggagag tggctccttg gagagatcag 360
cagcggctgc tatgaggggc tgcagtggct ggacgaggcc cgcacctgtt tccgcgtgcc 420
ctggaagcac ttcgcgcgca aggacctgag cgaggccgac gcgcgcatct tcaaggcctg 480
ggctgtggcc cgcggcaggt ggccgcctag cagcagggga ggtggcccgc cccccgaggc 540
tgagactgcg gagcgcgccg gctggaaaac caacttccgc tgcgcactgc gcagcacgcg 600
tcgcttcgtg atgctgcggg ataactcggg ggacccggcc gacccgcaca aggtgtacgc 660
gctcagccgg gagctgtgct ggcgagaagg cccaggcacg gaccagactg aggcagaggc 720
ccccgcagct gtcccaccac cacagggtgg gcccccaggg ccattcttgg cacacacaca 780
tgctggactc caagccccag gccccctccc tgccccagct ggtgacaagg gggacctcct 840
gctccaggca gtgcaacaga gctgcctggc agaccatctg ctgacagcgt catgggggc 900 agatccagtc ccaaccaagg ctcctggaga gggacaagaa gggcttcccc tgactggggc 960
ctgtgctgga ggcgaggccg cggccccaga gtccccgcac caggcagagc cgtacctgtc 1020
accctcccca agcgcctgca ccgcggtgca agagcccagc ccaggggcgc tggacgtgac 1080
catcatgtac aagggccgca cggtgctgca gaaggtggtg ggacacccga gctgcacgtt 1140
cctatacggc cccccagacc cagctgtccg ggccacagac ccccagcagg tagcattccc 1200
cagccctgcc gagctcccgg accagaagca gctgcgctac acggaggaac tgctgcggca 1260
cgtggcccct gggttgcacc tggagcttcg gggccacag ctgtgggccc ggcgcatggg 1320
caagtgcaag gtgtactggg aggtgggcgg acccccaggc tccgccagcc cctccacccc 1380
agcctgcctg ctgcctcgga actgtgacac ccccatcttc gacttcagag tcttcttcca 1440
agagctggtg gaattccggg cacggcagcg ccgtggctcc ccacgctata ccatctacct 1500
gggcttcggg caggacctgt cagctgggag gcccaaggag aagagcctgg tcctggtgaa 1560
gctggaaccc tggctgtgcc gagtgcacct agagggcacg cagcgtgagg gtgtgtcttc 1620
cctggatagc agcagcctca gcctctgcct gtccagcgcc aacagcctct atgacgacat 1680
cgagtgcttc cttatggagc tggagcagcc cgcctagaac ccagtctaat gagaactcca 1740
gaaagctgga gcagcccacc tagagctggc cgcggccgcc cagtctaata aaaagaactc 1800
cagaacaaaa aaaaaa 1816

<210> SEQ ID NO 136
<211> LENGTH: 60
<212> TYPE: DNA
<213> ORGANISM: Homo sapiens
<220> FEATURE:
<223> OTHER INFORMATION: NM_004029

<400> SEQUENCE: 136
agcagcccac ctagagctgg ccgcggccgc ccagtctaat aaaaagaact ccagaacaaa 60

<210> SEQ ID NO 137
<211> LENGTH: 2121
<212> TYPE: DNA
<213> ORGANISM: Homo sapiens
<220> FEATURE:
<223> OTHER INFORMATION: NM_004203

<400> SEQUENCE: 137
tggaattttt ggcgcgagca gctccgcgcg cgttcacggg ccgttccccc tcacgggagt 60
cctccgcccg ggcgtccgga acagtcgacg gcagactccg gcccgctgag ccacccgagg 120
ggtcccgtgg cctccgcgga cccggaatct gggccctcgc ggacccgcgc cccgcccagt 180
cgccccaggg cttccccaca cccacggagt gaagtcagcc gcggccctgc ctgggaggaa 240
cttaccgtct accgggaaag gtggccagca gatgtgtcgg gcctggtgag agggtgaggc 300
gagacggccc gatcgcccag ggccccggaa gctgcggagg tcacccccgc ctggccttag 360
ctcagggaca ccctggattc acgtgggagc ccctgctcct gcctcccccg tcccaccact 420
gaggctgttg ggccaggcca gtcatgctag aacggcctcc tgcactggcc atgcccatgc 480
ccacggaggg caccccgcca cctctgagtg gcacccccat cccagtccca gcctacttcc 540
gccacgcaga acctggattc tccctcaaga ggcccagggg gctcagccgg agcctcccac 600
ctccgccccc tgccaagggc agcattccca tcagccgcct cttccctcct cggaccccag 660
gctggcacca gctgcagccc cggcgggtgt cattccgggg cgaggcctca gagactctgc 720
agagccctgg gtatgaccca agccggccag agtccttctt ccagcagagc ttccagaggc 780
tcagccgcct gggccatggc tcctacggag aggtcttcaa ggtgcgctcc aaggaggacg 840
gccggctcta tgcggtaaag cgttccatgt caccattccg gggccccaag gaccgggccc 900
gcaagttggc cgaggtgggc agccacgaga aggtggggca gcacccatgc tgcgtgcggc 960
tggagcaggc ctgggaggag ggcggcatcc tgtacctgca gacggagctg tgcgggccca 1020
gcctgcagca acactgtgag gcctggggtg ccagcctgcc tgaggcccag gtctggggct 1080
acctgcggga cacgctgctt gccctggccc atctgcacag ccagggcctg gtgcaccttg 1140
atgtcaagcc tgccaacatc ttcctggggc cccggggccg ctgcaagctg ggtgacttcg 1200
gactgctggt ggagctgggt acagcaggag ctggtgaggt ccaggaggga gaccccccgct 1260 acatggcccc cgagctgctg cagggctcct atgggacagc agcggatgtg ttcagtctgg 1320
gcctcaccat cctggaagtg gcatgcaaca tggagctgcc ccacggtggg gagggctggc 1380
agcagctgcg ccagggctac ctgccccctg agttcactgc cggtctgtct tccgagctgc 1440
gttctgtcct tgtcatgatg ctggagccag accccaagct gcgggccacg gccgaggccc 1500
tgctggcact gcctgtgttg aggcagccgc gggcctgggg tgtgctgtgg tgcatggcag 1560
cggaggccct gagccgaggg tgggccctgt ggcaggccct gcttgccctg ctctgctggc 1620
tctggcatgg gctggctcac cctgccagct ggctacagcc cctgggcccg ccagccaccc 1680
cgcctggctc accaccctgc agtttgctcc tggacagcag cctctccagc aactgggatg 1740
acgacagcct agggccttca ctctcccctg aggctgtcct ggcccggact gtggggagca 1800
cctccacccc ccggagcagg tgcacaccca gggatgccct ggacctaagt gacatcaact 1860
cagagcctcc tcggggctcc ttcccctcct ttgagcctcg gaacctcctc agcctgtttg 1920
aggacaccct agacccaacc tgagccccag actctgcctc tgcactttta accttttatc 1980
ctgtgtctct cccgtcgccc ttgaaagctg gggcccctcg ggaactccca tggtcttctc 2040
tgcctggccg tgtctaataa aaagtatttg aaccttggga gcacccaagc ttgctcatgt 2100
ggcaaaaaaa aaaaaaaaaa a 2121

<210> SEQ ID NO 138
<211> LENGTH: 60
<212> TYPE: DNA
<213> ORGANISM: Homo sapiens
<220> FEATURE:
<223> OTHER INFORMATION: NM_004203

<400> SEQUENCE: 138
ctggccgtgt ctaataaaaa gtatttgaac cttgggagca cccaagcttg ctcatgtggc 60

<210> SEQ ID NO 139
<211> LENGTH: 1982
<212> TYPE: DNA
<213> ORGANISM: Homo sapiens
<220> FEATURE:
<223> OTHER INFORMATION: NM_004207

<400> SEQUENCE: 139
ggcgagaggc gggctgaggc ggcccagcgg cggcaggtga ggcggaacca accctcctgg 60
ccatgggagg ggccgtggtg gacgagggcc ccacaggcgt caaggcccct gacggcggct 120
ggggctgggc cgtgctcttc ggctgtttcg tcatcactgg cttctcctac gccttcccca 180
aggccgtcag tgtcttcttc aaggagctca tacaggagtt tgggatcggc tacagcgaca 240
cagcctggat ctcctccatc ctgctggcca tgctctacgg gacaggtccg ctctgcagtg 300
tgtgcgtgaa ccgctttggc tgccggcccg tcatgcttgt ggggggtctc tttgcgtcgc 360
tgggcatggt ggctgcgtcc ttttgccgga gcatcatcca ggtctacctc accactgggg 420
tcatcacggg gttgggtttg gcactcaact tccagccctc gctcatcatg ctgaaccgct 480
acttcagcaa gcggcgcccc atggccaacg ggctggcggc agcaggtagc cctgtcttcc 540
tgtgtgccct gagcccgctg gggcagctgc tgcaggaccg ctacggctgg cggggcggct 600
tcctcatcct gggcggcctg ctgctcaact gctgcgtgtg tgccgcactc atgaggcccc 660
tggtggtcac ggcccagccg ggctcggggc cgccgcgacc ctcccggcgc ctgctagacc 720
tgagcgtctt ccgggaccgc ggctttgtgc tttacgccgt ggccgcctcg gtcatggtgc 780
tggggctctt cgtcccgccc gtgttcgtgg tgagctacgc caaggacctg ggcgtgcccg 840
acaccaaggc cgccttcctg ctcaccatcc tgggcttcat tgacatcttc gcgcggccgg 900
ccgcgggctt cgtggcgggg cttgggaagg tgcggcccta ctccgtctac ctcttcagct 960
tctccatgtt cttcaacggc ctcgcggacc tggcgggctc tacggcgggc gactacggcg 1020
gcctcgtggt cttctgcatc ttctttggca tctcctacgg catggtgggg gccctgcagt 1080
tcgaggtgct catggccatc gtgggcaccc acaagttctc cagtgccatt ggcctggtgc 1140
tgctgatgga ggcggtggcc gtgctcgtcg ggcccccttc gggaggcaaa ctcctggatg 1200
cgacccacgt ctacatgtac gtgttcatcc tggcgggggc cgaggtgctc acctcctccc 1260
tgattttgct gctgggcaac ttcttctgca ttaggaagaa gcccaaagag ccacagcctg 1320
aggtggcggc cgcggaggag gagaagctcc acaagcctcc tgcagactcg ggggtggact 1380
tgcgggaggt ggagcatttc ctgaaggctg agcctgagaa aaacggggag gtggttcaca 1440
ccccggaaac aagtgtctga gtggctgggc ggggccggca ggcacaggga ggaggtacag 1500
aagccggcaa cgcttgctat ttattttaca aactggactg gctcaggcag ggccacggct 1560
gggctccagc tgccggccca gcggatcgtc gcccgatcag tgttttgagg gggaaggtgg 1620
cggggtggga accgtgtcat tccagagtgg atctgcggtg aagccaagcc gcaaggttac 1680
aaggcatcct caccaggggc cccgcctgct gctcccaggt ggcctgcggc cactgctatg 1740
ctcaaggacc tggaaaccca tgcttcgaga caacgtgact ttaatgggag ggtgggtggg 1800
ccgcagacag gctggcaggg caggtgctgc gtggggccct ctccagcccg tcctaccctg 1860
ggctcacatg gggcctgtgc ccacccctct tgagtgtctt ggggacagct ctttccaccc 1920
ctggaagatg gaaataaacc tgcgtgtggg tggagtgttc tcgtgccgaa ttcaaaaagc 1980
tt 1982

<210> SEQ ID NO 140
<211> LENGTH: 60
<212> TYPE: DNA
<213> ORGANISM: Homo sapiens
<220> FEATURE:
<223> OTHER INFORMATION: NM_004207

<400> SEQUENCE: 140
cctcttgagt gtcttgggga cagctctttc cacccctgga agatggaaat aaacctgcgt 60

<210> SEQ ID NO 141
<211> LENGTH: 2054
<212> TYPE: DNA
<213> ORGANISM: Homo sapiens
<220> FEATURE:
<223> OTHER INFORMATION: NM_004209

<400> SEQUENCE: 141
cgggaggcgg cagcggctgc agcgttggta gcatcagcat cagcatcagc ggcagcggca 60
gcggcctcgg gcggggccgg ccggacggac aggcggacag aaggcgccag gggcgcgcgt 120
cccgcccggg ccggccatgg agggcgcctc cttcggcgcg ggccgcgcag gggccgccct 180
ggaccccgtg agctttgcgc ggcggcccca gaccctgctc cgggtcgcgt cctgggtgtt 240
ctccatcgcc gtcttcgggc ccatcgtcaa cgagggctac gtgaacaccg acagcggccc 300
cgagctgcgc tgcgtgttca acgggaacgc gggcgcctgc cgcttcggcg tcgcgctggg 360
cctcggagcc ttcctcgcct gcgccgcctt cctgctgctc gatgtgcgct tccagcaaat 420
cagcagcgtc cgcgaccgcc ggcgcgcggt gttgctggac ctgggcttct caggactctg 480

-continued gtccttcctg tggttcgtgg gcttctgctt cctcaccaat cagtggcagc gcacggcgcc 540
agggccggcc acgacgcagg cgggggacgc ggcgcgggcc gccatcgcct tcagcttctt 600
ctccatcctc agctgggtgg cgctcaccgt gaaggccctg cagcggttcc gcctgggcac 660
cgacatgtca ctcttcgcca ccgaacagct gagcaccggg gcgagccagg cctaccccgg 720
ctatccggtg ggcagcggcg tggagggcac cgagacctac cagagcccgc ccttcaccga 780
gaccctggac accagcccca aagggtacca ggtgcccgcc tactagcggc tggcaggcac 840
agaccagggc tccaaggcca ccccaccaac gcaggcccca gggtctccgg gacctccctt 900
gggtccttcc agctcagtgc cgcggacaga gtaggtggcc gctttgcgcc atccggggcc 960
aagagggggt ggacccgcgt gtctgggctg cccctgccaa gttcccccag tccctcagca 1020
cctggcccca ggactgaggt cctgagaagg ggatagcact gcccaggacg tgtgtcccta 1080
gcctggaatg gactggcctg gggaaggctt tcccctcttg ggccacacct gctcactctg 1140
gggttggggg tccagctgcc ctctacgatc aggtgcaggg gctgcccagg acaaagcggg 1200
ggcaggggaa agacaccacc ctcgccccaa gactggggat cctggccact gttcccatcc 1260
catgtccctg tgggtagtga ctgtctcgtt tctgtcatgg tggtgcgtcc cgtccggagc 1320
cactctccac tttctctcac aggctgctag aacagcccag ccctgtcagt gttgtgatca 1380
tggtccagtc ttcgggtttc acctcctagt actccacaag ctgctcctct ctctgtggcc 1440
ccggcccctg cccaggtgtg ggtggttctg gccaggaagg cacaaggtag ctgtgggcca 1500
agacaccagc cctgtcctag cccttcagta agaccttgcc aggagaggag aaggatgcct 1560
gggtgccagg caagacaagc ccctcagcag gagagaggcc cagaggctcc agctggccac 1620
cgtgccccac aagatggccc ctgtgtggtt ccctttacct tggcttcctg gcccagtccc 1680
tgcctctcca cctgcaccct gcttcctggc ccagtcccag gttggagtcc ctctgcatag 1740
ctgactactc atgcattgct caaagctggc ttttcacatt aagtcaacac caaacgtggt 1800
tgccacattt catcagacag acacctccct ctggagatgc agttgagtga caaccttgtt 1860
acattgtagc ctagaccaat tctgtgtgga tatttaagtg aacatgttta caatttttgt 1920
atatatcact ctctccctct cctgaaagac cagagattgt gtattttcag tgtcccatgt 1980
tccgactgca ccttctttac aataaagact gtaactgagc tgactgtgaa aaaaaaaaaa 2040
aaaaaaaaaa aaaa 2054

<210> SEQ ID NO 142
<211> LENGTH: 60
<212> TYPE: DNA
<213> ORGANISM: Homo sapiens
<220> FEATURE:
<223> OTHER INFORMATION: NM_004209

<400> SEQUENCE: 142
gatgcagttg agtgacaacc ttgttacatt gtagcctaga ccaattctgt gtggatattt 60

<210> SEQ ID NO 143
<211> LENGTH: 1224
<212> TYPE: DNA
<213> ORGANISM: Homo sapiens
<220> FEATURE:
<223> OTHER INFORMATION: NM_004217

<400> SEQUENCE: 143
ggccgggaga gtagcagtgc cttggacccc agctctcctc cccctttctc tctaaggatg 60
gcccagaagg agaactccta cccctggccc tacggccgac agacggctcc atctggcctg 120
agcaccctgc cccagcgagt cctccggaaa gagcctgtca ccccatctgc acttgtcctc 180
atgagccgct ccaatgtcca gcccacagct gcccctggcc agaaggtgat ggagaatagc 240
agtgggacac ccgacatctt aacgcggcac ttcacaattg atgactttga gattgggcgt 300
cctctgggca aaggcaagtt tggaaacgtg tacttggctc gggagaagaa aagccatttc 360
atcgtggcgc tcaaggtcct cttcaagtcc cagatagaga aggagggcgt ggagcatcag 420
ctgcgcagag agatcgaaat ccaggcccac ctgcaccatc ccaacatcct gcgtctctac 480
aactattttt atgaccggag gaggatctac ttgattctag agtatgcccc ccgcggggag 540
ctctacaagg agctgcagaa gagctgcaca tttgacgagc agcgaacagc cacgatcatg 600
gaggagttgg cagatgctct aatgtactgc catgggaaga aggtgattca cagagacata 660
aagccagaaa atctgctctt agggctcaag ggagagctga agattgctga cttcggctgg 720
tctgtgcatg cgccctccct gaggaggaag acaatgtgtg gcaccctgga ctacctgccc 780
ccagagatga ttgaggggcg catgcacaat gagaaggtgg atctgtggtg cattggagtg 840
ctttgctatg agctgctggt ggggaaccca ccctttgaga gtgcatcaca caacgagacc 900
tatcgccgca tcgtcaaggt ggacctaaag ttccccgctt ctgtgcccac gggagcccag 960
gacctcatct ccaaactgct caggcataac ccctcggaac ggctgcccct ggcccaggtc 1020
tcagcccacc cttgggtccg ggccaactct cggagggtgc tgcctccctc tgcccttcaa 1080
tctgtcgcct gatggtccct gtcattcact cgggtgcgtg tgtttgtatg tctgtgtatg 1140
tataggggaa agaagggatc cctaactgtt cccttatctg ttttctacct cctcctttgt 1200
ttaataaagg ctgaagcttt ttgt 1224

<210> SEQ ID NO 144
<211> LENGTH: 60
<212> TYPE: DNA
<213> ORGANISM: Homo sapiens
<220> FEATURE:
<223> OTHER INFORMATION: NM_004217

<400> SEQUENCE: 144
gtctgtgtat gtatagggga aagaagggat ccctaactgt tcccttatct gttttctacc 60

<210> SEQ ID NO 145
<211> LENGTH: 983
<212> TYPE: DNA
<213> ORGANISM: Homo sapiens
<220> FEATURE:
<223> OTHER INFORMATION: NM_004335

<400> SEQUENCE: 145
gtggaattca tggcatctac ttcgtatgac tattgcagag tgcccatgga agacggggat 60
aagcgctgta agcttctgct ggggatagga attctggtgc tcctgatcat cgtgattctg 120
ggggtgccct tgattatctt caccatcaag gccaacagcg aggcctgccg ggacggcctt 180
cgggcagtga tggagtgtcg caatgtcacc catctcctgc aacaagagct gaccgaggcc 240
cagaagggct ttcaggatgt ggaggcccag gccgccacct gcaaccacac tgtgatggcc 300
ctaatggctt ccctggatgc agagaaggcc caaggacaaa agaaagtgga ggagcttgag 360
ggagagatca ctacattaaa ccataagctt caggacgcgt ctgcagaggt ggagcgactg 420
agaagagaaa accaggtctt aagcgtgaga atcgcggaca agaagtacta ccccagctcc 480
caggactcca gctccgctgc ggcgccccag ctgctgattg tgctgctggg cctcagcgct 540
ctgctgcagt gagatcccag gaagctggca catcttggaa ggtccgtcct gctcggcttt 600
tcgcttgaac attcccttga tctcatcagt tctgagcggg tcatggggca acacggttag 660
cggggagagc acggggtagc cggagaaggg cctctggagc aggtctggag gggccatggg 720
gcagtcctgg gtgtggggac acagtcgggt tgacccaggg ctgtctccct ccagagcctc 780
cctccggaca atgagtcccc cctcttgtct cccaccctga gattgggcat ggggtgcggt 840
gtggggggca tgtgctgcct gttgttatgg gttttttttg cggggggggt tgcttttttc 900
tggggtcttt gagctccaaa aaataaacac ttcctttgag ggagagcaaa aaaaaaaaaa 960
aaaaaaaaaa aaaaaaaaaa aaa 983

<210> SEQ ID NO 146
<211> LENGTH: 60
<212> TYPE: DNA
<213> ORGANISM: Homo sapiens
<220> FEATURE:
<223> OTHER INFORMATION: NM_004335

<400> SEQUENCE: 146
ggttgctttt ttctggggtc tttgagctcc aaaaaataaa cacttccttt gagggagagc 60

<210> SEQ ID NO 147
<211> LENGTH: 3446
<212> TYPE: DNA
<213> ORGANISM: Homo sapiens
<220> FEATURE:
<223> OTHER INFORMATION: NM_004336

<400> SEQUENCE: 147
ttctagtttg cggttcaggt ttgccgctgc cggccagcgt cctctggcca tggacacccc 60
ggaaaatgtc cttcagatgc ttgaagccca catgcagagc tacaagggca atgaccctct 120
tggtgaatgg gaaagataca tacagtgggt agaagagaat tttcctgaga ataaagaata 180
cttgataact ttactagaac atttaatgaa ggaattttta gataagaaga aataccacaa 240
tgacccaaga ttcatcagtt attgtttaaa atttgctgag tacaacagtg acctccatca 300
attttttgag tttctgtaca accatgggat tggaaccctg tcatcccctc tgtacattgc 360
ctgggcgggg catctggaag cccaaggaga gctgcagcat gccagtgctg tccttcagag 420
aggaattcaa aaccaggctg aacccagaga gttcctgcaa caacaataca ggttatttca 480
gacacgcctc actgaaaccc atttgccagc tcaagctaga acctcagaac ctctgcataa 540
tgttcaggtt ttaaatcaaa tgataacatc aaaatcaaat ccaggaaata acatggcctg 600
catttctaag aatcagggtt cagagctttc tggagtgata tcttcagctt gtgataaaga 660
gtcaaatatg gaacgaagag tgatcacgat ttctaaatca gaatattctg tgcactcatc 720
tttggcatcc aaagttgatg ttgagcaggt tgttatgtat tgcaaggaga agcttattcg 780
tggggaatca gaattttcct ttgaagaatt gagagcccag aaatacaatc aacggagaaa 840
gcatgagcaa tgggtaaatg aagacagaca ttatatgaaa aggaaagaag caaatgcttt 900
tgaagaacag ctattaaaac agaaaatgga tgaacttcat aagaagttgc atcaggtggt 960
ggagacatcc catgaggatc tgcccgcttc ccaggaaagg tccgaggtta atccagcacg 1020
tatggggcca agtgtaggct cccagcagga actgagagcg ccatgtcttc cagtaaccta 1080
tcagcagaca ccagtgaaca tggaaaagaa cccaagagag gcacctcctg ttgttcctcc 1140
tttggcaaat gctatttctg cagctttggt gtccccagcc accagccaga gcattgctcc 1200
tcctgttcct ttgaaagccc agacagtaac agactccatg tttgcagtgg ccagcaaaga 1260
tgctggatgt gtgaataaga gtactcatga attcaagcca cagagtggag cagagatcaa 1320
agaagggtgt gaaacacata aggttgccaa cacaagttct tttcacacaa ctccaaacac 1380
atcactggga atggttcagg caacgccatc caaagtgcag ccatcaccca ccgtgcacac 1440
aaaagaagca ttaggtttca tcatgaatat gtttcaggct cctacacttc ctgatatttc 1500
tgatgacaaa gatgaatggc aatctctaga tcaaaatgaa gatgcatttg aagcccagtt 1560
tcaaaaaaat gtaaggtcat ctggggcttg gggagtcaat aagatcatct cttctttgtc 1620
atctgctttt catgtgtttg aagatggaaa caaagaaaat tatggattac cacagcctaa 1680
aaataaaccc acaggagcca ggacctttgg agaacgctct gtcagcagac ttccttcaaa 1740
accaaaggag gaagtgcctc atgctgaaga gtttttggat gactcaactg tatggggtat 1800
tcgctgcaac aaaaccctgg cacccagtcc taagagccca ggagacttca catctgctgc 1860
acaacttgcg tctacaccat tccacaagct tccagtggag tcagtgcaca ttttagaaga 1920
taaagaaaat gtggtagcaa aacagtgtac ccaggcgact ttggattctt gtgaggaaaa 1980
catggtggtg ccttcaaggg atggaaaatt cagtccaatt caagagaaaa gcccaaaaca 2040
ggccttgtcg tctcacatgt attcagcatc cttacttcgt ctgagccagc ctgctgcagg 2100
tggggtactt acctgtgagg cagagttggg cgttgaggct tgcagactca cagacactga 2160
cgctgccatt gcagaagatc caccagatgc tattgctggg ctccaagcag aatggatgca 2220
gatgagttca cttgggactg ttgatgctcc aaacttcatt gttgggaacc catgggatga 2280
taagctgatt ttcaaacttt tatctgggct ttctaaacca gtgagttcct atccaaatac 2340
ttttgaatgg caatgtaaac ttccagccat caagcccaag actgaatttc aattgggttc 2400
taagctggtc tatgtccatc accttcttgg agaaggagcc tttgcccagg tgtacgaagc 2460
tacccaggga gatctgaatg atgctaaaaa taaacagaaa tttgttttaa aggtccaaaa 2520
gcctgccaac ccctgggaat tctacattgg gacccagttg atggaaagac taaagccatc 2580
tatgcagcac atgtttatga agttctattc tgcccactta ttccagaatg gcagtgtatt 2640
agtaggagag ctctacagct atggaacatt attaaatgcc attaacctct ataaaaatac 2700
ccctgaaaaa gtgatgcctc aaggtcttgt catctctttt gctatgagaa tgctttacat 2760
gattgagcaa gtgcatgact gtgaaatcat tcatggagac attaaaccag acaatttcat 2820
acttggaaac ggatttttgg aacaggatga tgaagatgat ttatctgctg gcttggcact 2880
gattgacctg ggtcagagta tagatatgaa actttttcca aaaggaacta tattcacagc 2940
aaagtgtgaa acatctggtt ttcagtgtgt tgagatgctc agcaacaaac catggaacta 3000
ccagatcgat tactttgggg ttgctgcaac agtatattgc atgctctttg gcacttacat 3060
gaaagtgaaa aatgaaggag gagagtgtaa gcctgaaggt ctttttagaa ggcttcctca 3120
tttggatatg tggaatgaat tttttcatgt tatgttgaat attccagatt gtcatcatct 3180
tccatctttg gatttgttaa ggcaaaagct gaagaaagta tttcaacaac actatactaa 3240
caagattagg gccctacgta ataggctaat tgtactgctc ttagaatgta agcgttcacg 3300
aaaataaaat ttggatatag acagtcctta aaaatcacac tgtaaatatg aatctgctca 3360
ctttaaacct gttttttttt catttattgt ttatgtaaat gtttgttaaa aataaatccc 3420
atggaatatt tccatgtaaa aaaaaa 3446

<210> SEQ ID NO 148
<211> LENGTH: 60
<212> TYPE: DNA
<213> ORGANISM: Homo sapiens
<220> FEATURE:
<223> OTHER INFORMATION: NM_004336

<400> SEQUENCE: 148
ttagggccct acgtaatagg ctaattgtac tgctcttaga atgtaagcgt tcacgaaaat 60

<210> SEQ ID NO 149
<211> LENGTH: 739
<212> TYPE: DNA
<213> ORGANISM: Homo sapiens
<220> FEATURE:
<223> OTHER INFORMATION: NM_004345

<400> SEQUENCE: 149
taaagcaaac cccagcccac accctggcag gcagccaggg atgggtggat caggaaggct 60
cctggttggg cttttgcatc aggctcaggc tgggcataaa ggaggctcct gtgggctaga 120
gggaggcaga catggggacc atgaagaccc aaagggatgg ccactccctg gggcggtggt 180
cactggtgct cctgctgctg ggcctggtga tgcctctggc catcattgcc caggtcctca 240
gctacaagga agctgtgctt cgtgctatag atggcatcaa ccagcggtcc tcggatgcta 300
acctctaccg cctcctggac ctggacccca ggcccacgat ggatggggac ccagacacgc 360
caaagcctgt gagcttcaca gtgaaggaga cagtgtgccc caggacgaca cagcagtcac 420
cagaggattg tgacttcaag aaggacgggc tggtgaagcg gtgtatgggg acagtgaccc 480
tcaaccaggc caggggctcc tttgacatca gttgtgataa ggataacaag agatttgccc 540
tgctgggtga tttcttccgg aaatctaaag agaagattgg caaagagttt aaaagaattg 600
tccagagaat caaggatttt ttgcggaatc ttgtacccag gacagagtcc tagtgtgtgc 660
cctaccctgg ctcaggcttc tggctctga gaaataaact atgagagcaa tttcaaaaaa 720
aaaaaaaaaa aaaaaaaaa 739

<210> SEQ ID NO 150
<211> LENGTH: 60
<212> TYPE: DNA
<213> ORGANISM: Homo sapiens
<220> FEATURE:
<223> OTHER INFORMATION: NM_004345

<400> SEQUENCE: 150
gcaaagagtt taaaagaatt gtccagagaa tcaaggattt tttgcggaat cttgtaccca 60

<210> SEQ ID NO 151
<211> LENGTH: 1432
<212> TYPE: DNA
<213> ORGANISM: Homo sapiens
<220> FEATURE:
<223> OTHER INFORMATION: NM_004577

<400> SEQUENCE: 151
gaggaaaatt cttccagcga tggtctccca ctcagagctg aggaagcttt tctactcagc 60
agatgctgtg tgttttgatg ttgacagcac ggtcatcaga gaagaaggaa tcgatgagct 120
agccaaaatc tgtggcgttg aggacgcggt gtcagaaatg acacggcgag ccatgggcgg 180
ggcagtgcct ttcaaagctg ctctcacaga gcgcttagcc ctcatccagc cctccaggga 240
gcaggtgcag agactcatag cagagcaacc cccacacctg acccccggca taagggagct 300
ggtaagtcgc ctacaggagc gaaatgttca ggttttccta atatctggtg gctttaggag 360
tattgtagag catgttgctt caaagctcaa tatcccagca accaatgtat ttgccaatag 420
gctgaaattc tactttaacg gtgaatatgc aggttttgat gagacgcagc caacagctga 480
atctggtgga aaaggaaaag tgattaaact tttaaaggaa aaatttcatt ttaagaaaat 540
aatcatgatt ggagatggtg ccacagatat ggaagcctgt cctcctgctg atgctttcat 600
tggatttgga ggaaatgtga tcaggcaaca agtcaaggat aacgccaaat ggtatatcac 660
tgattttgta gagctgctgg gagaactgga agaataacat ccattgtcgt acagctccaa 720
acaacttcag atgaattttt acaagttata cagattgata ctgtttgctt acagttgcct 780
attacaactt gctatagaaa gttggtacaa atgatctgta ctttaaacta cagttaggaa 840
tcctagaaga ttgctttttt ttttttttta actgtagttc cagtattata tgatgactat 900
tgatttcctg gagaggtttt tttttttttt gagacagaat cttgctctgt tgcccaggct 960
ggagtgcagt ggcgcggtct cggctcactg caagctctgc ctcccaggtt cacgccattc 1020
tcctgcctca gcctcccgag tagctgggac tacaggcacc cgccaccaca tccggctaat 1080
tttttgtatt tttagtagag acggggtttg accgtgttag ccaggatggt cttgatctcc 1140
tgaccttgtg atccgcctgc ctcagcctcc caaagtgctg ggattacagg cttgggccac 1200
cgcgcccagc caatgtccta gagagttttg tgatctgaat tctttatgta tatttgtagc 1260
tatatttcat acaaagtgct ttaagtgtgg agagtcaatt aaacaccttt actcttagaa 1320
atacggattc ggcagccttc agtgaatatt ggtttctctt tggtatgtca ataaaagttt 1380
atccgtatgt cagaacggat ttgtggaaaa aaaaaaaaaa aaaaaaaaaa aa 1432

<210> SEQ ID NO 152
<211> LENGTH: 60
<212> TYPE: DNA
<213> ORGANISM: Homo sapiens
<220> FEATURE:
<223> OTHER INFORMATION: NM_004577

<400> SEQUENCE: 152
tagaaatacg gattcggcag ccttcagtga atattggttt ctctttggta tgtcaataaa 60

<210> SEQ ID NO 153
<211> LENGTH: 1530
<212> TYPE: DNA
<213> ORGANISM: Homo sapiens
<220> FEATURE:
<223> OTHER INFORMATION: NM_004701

<400> SEQUENCE: 153
aatcctggaa caaggctaca gcgtcgaaga tccccagcgc tgcgggctcg gagagcagtc 60
ctaacggcgc ctcgtacgct agtgtcctcc cttttcagtc cgcgtccctc cctgggccgg 120
gctggcactc ttgccttccc cgtccctcat ggcgctgctc cgacgcccga cggtgtccag 180
tgatttggag aatattgaca caggagttaa ttctaaagtt aagagtcatg tgactattag 240
gcgaactgtt ttagaagaaa ttggaaatag agttacaacc agagcagcac aagtagctaa 300
gaaagctcag aacaccaaag ttccagttca acccaccaaa acaacaaatg tcaacaaaca 360
actgaaacct actgcttctg tcaaaccagt acagatggaa aagttggctc caaagggtcc 420
ttctcccaca cctgaggatg tctccatgaa ggaagagaat ctctgccaag ctttttctga 480
tgccttgctc tgcaaaatcg aggacattga taacgaagat tgggagaacc ctcagctctg 540
cagtgactac gttaaggata tctatcagta tctcaggcag ctggaggttt tgcagtccat 600
aaacccacat ttcttagatg gaagagatat aaatggacgc atgcgtgcca tcctagtgga 660
ttggctggta caagtccact ccaagtttag gcttctgcag gagactctgt acatgtgcgt 720
tggcattatg gatcgatttt tacaggttca gccagtttcc cggaagaagc ttcaattagt 780
tgggattact gctctgctct tggcttccaa gtatgaggag atgttttctc caaatattga 840
agactttgtt tacatcacag acaatgctta taccagttcc caaatccgag aaatggaaac 900
tctaattttg aaagaattga aatttgagtt gggtcgaccc ttgccactac acttcttaag 960
gcgagcatca aaagccgggg aggttgatgt tgaacagcac actttagcca agtatttgat 1020
ggagctgact ctcatcgact atgatatggt gcattatcat ccttctaagg tagcagcagc 1080
tgcttcctgc ttgtctcaga aggttctagg acaaggaaaa tggaacttaa agcagcagta 1140
ttacacagga tacacagaga atgaagtatt ggaagtcatg cagcacatgg ccaagaatgt 1200
ggtgaaagta aatgaaaact taactaaatt catcgccatc aagaataagt atgcaagcag 1260
caaactcctg aagatcagca tgatccctca gctgaactca aaagccgtca aagaccttgc 1320
ctccccactg ataggaaggt cctaggctgc cgtgggccct ggggatgtgt gcttcattgt 1380 gcccttttc ttattggttt agaactcttg attttgtaca tagtcctctg gtctatctca 1440
tgaaacctct tctcagacca gttttctaaa catatattga ggaaaaataa agcgattggt 1500
ttttcttaag gtaaaaaaaa aaaaaaaaaa 1530

<210> SEQ ID NO 154
<211> LENGTH: 60
<212> TYPE: DNA
<213> ORGANISM: Homo sapiens
<220> FEATURE:
<223> OTHER INFORMATION: NM_004701

<400> SEQUENCE: 154
agaactcttg attttgtaca tagtcctctg gtctatctca tgaaacctct tctcagacca 60

<210> SEQ ID NO 155
<211> LENGTH: 2536
<212> TYPE: DNA
<213> ORGANISM: Homo sapiens
<220> FEATURE:
<223> OTHER INFORMATION: NM_004702

<400> SEQUENCE: 155
agcgggtgcg gggcgggacc ggcccggcct atatattggg ttggcgccgg cgccagctga 60
gccgagcggt agctggtctg gcgaggtttt atacacctga aagaagagaa tgtcaagacg 120
aagtagccgt ttacaagcta agcagcagcc ccagcccagc cagacggaat ccccccaaga 180
agcccagata atccaggcca agaagaggaa aactacccag gatgtcaaaa gaagtctggc 240
taaacatgtt aaaaaaggag agcagatatg ttcatgacaa acattttgaa gttctgcatt 300
ctgacttgga accacagatg aggtccatac ttctagactg gcttttagag gtatgtgaag 360
tatacacact tcatagggaa acattttatc ttgcacaaga ctttttttgat agatttatgt 420 tgacacaaaa ggatataaat aaaaatatgc ttcaactcat tggaattacc tcattattca 480
ttgcttccaa acttgaggaa atctatgctc ctaaactcca agagtttgct tacgtcactg 540
atggtgcttg cagtgaagag gatatcttaa ggatggaact cattatatta aaggctttaa 600
aatgggaact ttgtcctgta acaatcatct cctggctaaa tctctttctc caagttgatg 660
ctcttaaaga tgctcctaaa gttcttctac ctcagtattc tcaggaaaca ttcattcaaa 720
tagctcagct ttagatctg tgtattctag ccattgattc attagagttc cagtacagaa 780
tactgactgc tgctgccttg tgccatttta cctccattga agtggttaag aaagcctcag 840
gtttggagtg ggacagtatt tcagaatgtg tagattggat ggtacctttt gtcaatgtag 900
taaaaagtac tagtccagtg aagctgaaga cttttaagaa gattcctatg gaagacagac 960
ataatatcca gacacataca aactatttgg ctatgctgga ggaagtaaat tacataaaca 1020
ccttcagaaa agggggacag ttgtcaccag tgtgcaatgg aggcattatg acaccaccga 1080
agagcactga aaaaccacca ggaaaacact aaagaagata actaagcaaa caagttggaa 1140
ttcaccaaga ttgggtagaa ctggtatcac tgaactacta aagttttaca gaaagtagtg 1200
ctgtgattga ttgccctagc caattcacaa gttacactgc cattctgatt ttaaaactta 1260
caattggcac taaagaatac atttaattat ttcctatgtt agctgttaaa gaaacagcag 1320
gacttgttta caaagatgtc ttcattccca aggttactgg atagaagcca accacagtct 1380
ataccatagc aatgtttttc ctttaatcca gtgttactgt gtttatcttg ataaactagg 1440
aattttgtca ctggagtttt ggactggata agtgctacct taaagggtat actaagtgat 1500
acagtacttt gaatctagtt gttagattct caaaattcct acactcttga ctagtgcaat 1560
ttggttcttg aaaattaaat ttaaacttgt ttacaaaggt ttagttttgt aataaggtga 1620
ctaatttatc tatagctgct atagcaagct attataaaac ttgaatttct acaaatggtg 1680
aaatttaatg ttttttaaac tagtttattt gccttgccat aacacatttt ttaactaata 1740
aggcttagat gaacatggtg ttcaacctgt gctctaaaca gtgggagtac caaagaaatt 1800
ataaacaaga taaatgctgt ggctccttcc taactggggc tttcttgaca tgtaggttgc 1860
ttggtaataa ccttttttgta tatcacaatt tgggtgaaaa acttaagtac cctttcaaac 1920
tatttatatg aggaagtcac tttactactc taagatatcc ctaaggaatt ttttttttta 1980
atttagtgtg actaaggctt tatttatgtt tgtgaaactg ttaaggtcct ttctaaattc 2040
ctccattgtg agataaggac agtgtcaaag tgataaagct taacacttga cctaaacttc 2100
tattttctta aggaagaaga gtattaaata tatactgact cctagaaatc tatttattaa 2160
aaaaagacat gaaaacttgc tgtacatagg ctagctattt ctaaatattt taaattagct 2220
tttctaaaaa aaaaatccag cctcataaag tagattagaa aactagattg ctagtttatt 2280
ttgttatcag atatgtgaat ctcttctccc tttgaagaaa ctatacattt attgttacgg 2340
tatgaagtct tctgtatagt ttgtttttaa actaatattt gtttcagtat tttgtctgaa 2400
aagaaaacac cactaattgt gtacatatgt attatataaa cttaaccttt taatactgtt 2460
tatttttagc ccattgttta aaaaataaaa gttaaaaaaa tttaactgct taaaagtaaa 2520
aaaaaaaaaa aaaaaa 2536

<210> SEQ ID NO 156
<211> LENGTH: 60
<212> TYPE: DNA
<213> ORGANISM: Homo sapiens
<220> FEATURE:
<223> OTHER INFORMATION: NM_004702

<400> SEQUENCE: 156
gtttgtgaaa ctgttaaggt cctttctaaa ttcctccatt gtgagataag gacagtgtca 60

<210> SEQ ID NO 157
<211> LENGTH: 1491
<212> TYPE: DNA
<213> ORGANISM: Homo sapiens
<220> FEATURE:
<223> OTHER INFORMATION: NM_004710

<400> SEQUENCE: 157
gcggcggcgg cagcggcggc gacggcgaca tggagagcgg ggcctacggc gcggccaagg 60
cgggcggctc cttcgacctg cggcgcttcc tgacgcagcc gcaggtggtg gcgcgcgccg 120
tgtgcttggt cttcgccttg atcgtgttct cctgcatcta tggtgagggc tacagcaatg 180

```
cccacgagtc taagcagatg tactgcgtgt tcaaccgcaa cgaggatgcc tgccgctatg    240
gcagtgccat cggggtgctg gccttcctgg cctcggcctt cttcttggtg gtcgacgcgt    300
atttcccccca gatcagcaac gccactgacc gcaagtacct ggtcattggt gacctgctct    360
tctcagctct ctggaccttc ctgtggtttg ttggtttctg cttcctcacc aaccagtggg    420
cagtcaccaa cccgaaggac gtgctggtgg gggccgactc tgtgagggca gccatcacct    480
tcagcttctt ttccatcttc tcctggggtg tgctggcctc cctggcctac cagcgctaca    540
aggctggcgt ggacgacttc atccagaatt acgttgaccc cactccggac cccaacactg    600
cctacgcctc ctacccaggt gcatctgtgg acaactacca acagccaccc ttcacccaga    660
acgcggagac caccgagggc taccagccgc cccctgtgta ctgagcggcg gttagcgtgg    720
gaagggggac agagagggcc ctcccctctg ccctggactt tcccatgagc ctcctggaac    780
tgccagcccc tctctttcac ctgttccatc ctgtgcagct gacacacagc taaggagcct    840
catagcctgg cgggggctgg cagagccaca ccccaagtgc ctgtgcccag agggcttcag    900
tcagccgctc actcctccag ggcatttttta ggaaagggtt ttcagctagt gtttttcctc    960
gcttttaatg acctcagccc cgcctgcagt ggctagaagc cagcaggtgc ccatgtgcta   1020
ctgacaagtg cctcagcttc cccccggccc gggtcaggcc gtgggagccg ctattatctg   1080
cgttctctgc caaagactcg tgggggccat cacacctgcc ctgtgcagcg gagccggacc   1140
aggctcttgt gtcctcactc aggtttgctt cccctgtgcc cactgctgta tgatctgggg   1200
gccaccaccc tgtgccggtg gcctctgggc tgcctcccgt ggtgtgaggg cggggctggt   1260
gctcatggca cttcctcctt gctcccaccc ctggcagcag ggaagggctt tgcctgacaa   1320
cacccagctt tatgtaaata ttctgcagtt gttacttagg aagcctgggg agggcagggg   1380
tgccccatgg ctcccagact ctgtctgtgc cgagtgtatt ataaaatcgt gggggagatg   1440
cccggcctgg gatgctgttt ggagacggaa taaatgtttt ctcattcagt a            1491
```

<210> SEQ ID NO 158
<211> LENGTH: 60
<212> TYPE: DNA
<213> ORGANISM: Homo sapiens
<220> FEATURE:
<223> OTHER INFORMATION: NM_004710

<400> SEQUENCE: 158

```
ttgcctgaca acacccagct ttatgtaaat attctgcagt tgttacttag gaagcctggg     60
```

<210> SEQ ID NO 159
<211> LENGTH: 3324
<212> TYPE: DNA
<213> ORGANISM: Homo sapiens
<220> FEATURE:
<223> OTHER INFORMATION: NM_004856

<400> SEQUENCE: 159

```
gcagagcacc gcgccttagc cgcgaagttc tagttcttgc tgccggtcct aacgtcccgc     60
agtcttcgcc agccagccgt cccgcatgcg cgtttgggcg gcgtggagcc tgctgccatg    120
aagtcagcga gagctaagac accccggaaa cctaccgtga aaaaagggtc ccaaacgaac    180
cttaaagacc cagttggggt atactgtagg gtgcgcccac tgggctttcc tgatcaagag    240
tgttgcatag aagtgatcaa taatacaact gttcagcttc atactcctga gggctacaga    300
ctcaaccgaa atggagacta taaggagact cagtattcat ttaaacaagt atttggcact    360
cacaccaccc agaaggaact ctttgatgtt gtggctaatc ccttggtcaa tgacctcatt    420
```

-continued

```
catggcaaaa atggtcttct ttttacatat ggtgtgacgg gaagtggaaa aactcacaca    480
atgactggtt ctccagggga aggagggctg cttcctcgtt gtttggacat gatctttaac    540
agtatagggt catttcaagc taaacgatat gttttcaaat ctaatgatag gaatagtatg    600
gatatacagt gtgaggttga tgccttatta gaacgtcaga aaagagaagc tatgcccaat    660
ccaaagactt cttctagcaa acgacaagta gatccagagt ttgcagatat gataactgta    720
caagaattct gcaaagcaga agaggttgat gaagatagtg tctatggtgt atttgtctct    780
tatattgaaa tatataataa ttacatatat gatctattgg aagaggtgcc gtttgatccc    840
ataaaaccca aacctccaca atctaaattg cttcgtgaag ataagaacca taacatgtat    900
gttgcaggat gtacagaagt tgaagtgaaa tctactgagg aggcttttga agttttctgg    960
agaggccaga aaaagagacg tattgctaat acccatttga atcgtgagtc cagccgttcc   1020
catagcgtgt tcaacattaa attagttcag gctcccttgg atgcagatgg agacaatgtc   1080
ttacaggaaa aagaacaaat cactataagt cagttgtcct tggtagatct tgctggaagt   1140
gaaagaacta accggaccag agcagaaggg aacagattac gtgaagctgg taatattaat   1200
cagtcactaa tgacgctaag aacatgtatg gatgtcctaa gagagaacca aatgtatgga   1260
actaacaaga tggttccata tcgagattca aagttaaccc atctgttcaa gaactacttt   1320
gatggggaag gaaaagtgcg gatgatcgtg tgtgtgaacc ccaaggctga agattatgaa   1380
gaaaacttgc aagtcatgag atttgcggaa gtgactcaag aagttgaagt agcaagacct   1440
gtagacaagg caatatgtgg tttaacgcct gggaggagat acagaaacca gcctcgaggt   1500
ccagttggaa atgaaccatt ggttactgac gtggttttgc agagttttcc acctttgccg   1560
tcatgcgaaa ttttggatat caacgatgag cagacacttc caaggctgat tgaagcctta   1620
gagaaacgac ataacttacg acaaatgatg attgatgagt ttaacaaaca atctaatgct   1680
tttaaagctt tgttacaaga atttgacaat gctgttttaa gtaaagaaaa ccacatgcaa   1740
gggaaactaa atgaaaagga gaagatgatc tcaggacaga aattggaaat agaacgactg   1800
gaaaagaaaa acaaaacttt agaatataag attgagattt tagagaaaac aactactatc   1860
tatgaggaag ataaacgcaa tttgcaacag gaacttgaaa ctcagaacca gaaacttcag   1920
cgacagtttt ctgacaaacg cagattagaa gccaggttgc aaggcatggt gacagaaacg   1980
acaatgaagt gggagaaaga atgtgagcgt agagtggcag ccaaacagct ggagatgcag   2040
aataaactct gggttaaaga tgaaaagctg aaacaactga aggctattgt tactgaacct   2100
aaaactgaga agccagagag accctctcgg gagcgagatc gagaaaaagt tactcaaaga   2160
tctgtttctc catcacctgt gcctttactc tttcaacctg atcagaacgc accaccaatt   2220
cgtctccgac acagacgatc acgctctgca ggagacagat gggtagatca taagcccgcc   2280
tctaacatgc aaactgaaac agtcatgcag ccacatgtcc ctcatgccat cacagtatct   2340
gttgcaaatg aaaaggcact agctaagtgt gagaagtaca tgctgaccca ccaggaacta   2400
gcctccgatg gggagattga aactaaacta attaagggtg atatttataa aacaaggggt   2460
ggtggacaat ctgttcagtt tactgatatt gagactttaa agcaagaatc accaaatggt   2520
agtcgaaaac gaagatcttc cacagtagca cctgcccaac cagatggtgc agagtctgaa   2580
tggaccgatg tagaaacaag gtgttctgtg gctgtggaga tgagagcagg atcccagctg   2640
ggacctggat atcagcatca cgcacaaccc aagcgcaaaa agccatgaac tgacagtccc   2700
agtactgaaa gaacattttc atttgtgtgg atgatttctc gaaagccatg ccagaagcag   2760
tcttccaggt catcttgtag aactccagct ttgttgaaaa tcacggacct cagctacatc   2820
```

atacactgac ccagagcaaa gctttcccta tggttccaaa gacaactagt attcaacaaa 2880
ccttgtatag tatatgtttt gccatattta atattaatag cagaggaaga ctcctttttt 2940
catcactgta tgaatttttt ataatgtttt tttaaaatat atttcatgta tacttataaa 3000
ctaattcaca caagtgtttg tcttagatga ttaaggaaga ctatatctag atcatgtctg 3060
atttttattt gtgacttctc cagccctggt ctgaatttct taaggtttta taaacaaatg 3120
ctgctattta ttagctgcaa gaatgcactt tagaactatt tgacaattca gactttcaaa 3180
ataaagatgt aaatgactgg ccaataataa ccattttagg aaggtgtttt gaattctgta 3240
tgtatatatt cactttctga catttagata tgccaaaaga attaaaatca aaagcactaa 3300
gaaataaaaa aaaaaaaaaa aaaa 3324

<210> SEQ ID NO 160
<211> LENGTH: 60
<212> TYPE: DNA
<213> ORGANISM: Homo sapiens
<220> FEATURE:
<223> OTHER INFORMATION: NM_004856

<400> SEQUENCE: 160
caaagctttc cctatggttc aaagacaact agtattcaac aaaccttgta tagtgtatgt 60

<210> SEQ ID NO 161
<211> LENGTH: 1536
<212> TYPE: DNA
<213> ORGANISM: Homo sapiens
<220> FEATURE:
<223> OTHER INFORMATION: NM_004900

<400> SEQUENCE: 161
acagagcttc aaaaaaagag cgggacaggg acaagcgtat ctaagaggct gaacatgaat 60
ccacagatca gaaatccgat ggagcggatg tatcgagaca cattctacga caactttgaa 120
aacgaaccca tcctctatgg tcggagctac acttggctgt gctatgaagt gaaaataaag 180
aggggccgct caaatctcct ttgggacaca ggggtctttc gaggccaggt gtatttcaag 240
cctcagtacc acgcagaaat gtgcttcctc tcttggttct gtggcaacca gctgcctgct 300
tacaagtgtt tccagatcac ctggtttgta tcctggaccc cctgcccgga ctgtgtggcg 360
aagctggccg aattcctgtc tgagcacccc aatgtcaccc tgaccatctc tgccgcccgc 420
ctctactact actgggaaag agattaccga agggcgctct gcaggctgag tcaggcagga 480
gcccgcgtga cgatcatgga ctatgaagaa tttgcatact gctgggaaaa ctttgtgtac 540
aatgaaggtc agcaattcat gccttggtac aaattcgatg aaaattatgc attcctgcac 600
cgcacgctaa aggagattct cagatacctg atggatccag acacattcac tttcaacttt 660
aataatgacc ctttggtcct tcgacggcgc cagacctact tgtgctatga ggtggagcgc 720
ctggacaatg gcacctgggt cctgatggac cagcacatgg gctttctatg caacgaggct 780
aagaatcttc tctgtggctt ttacggccgc catgcggagc tgcgcttctt ggacctggtt 840
ccttctttgc agttggaccc ggcccagatc tacagggtca cttggttcat ctcctggagc 900
ccctgcttct cctggggctg tgccggggaa gtgcgtgcgt tccttcagga gaacacacac 960
gtgagactgc gcatcttcgc tgcccgcatc tatgattacg acccccctata taaggaggcg 1020 ctgcaaatgc tgcgggatgc tggggcccaa gtctccatca tgacctacga tgagtttgag 1080
tactgctggg acacctttgt gtaccgccag ggatgtccct tccagccctg ggatggacta 1140
gaggagcaca gccaagccct gagtgggagg ctgcgggcca ttctccagaa tcagggaaac 1200
tgaaggatgg gcctcagtct ctaaggaagg cagagacctg ggttgagcag cagaataaaa 1260
gatcttcttc caagaaatgc aaacagaccg ttcaccacca tctccagctg ctcacagaca 1320
ccagcaaagc aatgtgctcc tgatcaagta gattttttaa aaatcagagt caattaattt 1380
taattgaaaa tttctcttat gttccaagtg tacaagagta agattatgct caatattccc 1440
agaatagttt tcaatgtatt aatgaagtga ttaattggct ccatatttag actaataaaa 1500
cattaagaat cttccataat tgtttccaca aacact 1536

<210> SEQ ID NO 162
<211> LENGTH: 60
<212> TYPE: DNA
<213> ORGANISM: Homo sapiens
<220> FEATURE:
<223> OTHER INFORMATION: NM_004900

<400> SEQUENCE: 162
tgctcacaga caccagcaaa gcaatgtgct cctgatcaag tagatttttt aaaaatcaga 60

<210> SEQ ID NO 163
<211> LENGTH: 1722
<212> TYPE: DNA
<213> ORGANISM: Homo sapiens
<220> FEATURE:
<223> OTHER INFORMATION: NM_004988

<400> SEQUENCE: 163
cgtagagttc ggccgaagga acctgaccca ggctctgtga ggaggcaagg ttttcagggg 60
acaggccaac ccagaggaca ggattccctg gaggccacag aggagcacca aggagaagat 120
ctgcctgtgg gtcttcattg cccagctcct gcccacactc ctgcctgctg ccctgacgag 180
agtcatcatg tctcttgagc agaggagtct gcactgcaag cctgaggaag cccttgaggc 240
ccaacaagag gccctgggcc tggtgtgtgt gcaggctgcc gcctcctcct cctctcctct 300
ggtcctgggc accctggagg aggtgcccac tgctgggtca acagatcctc cccagagtcc 360
tcagggagcc tccgcctttc ccactaccat caacttcact cgacagaggc aacccagtga 420
gggttccagc agccgtgaag aggaggggcc aagcacctct tgtatcctgg agtccttgtt 480
ccgagcagta atcactaaga aggtggctga tttggttggt tttctgctcc tcaaatatcg 540
agccagggag ccagtcacaa aggcagaaat gctggagagt gtcatcaaaa attacaagca 600
ctgttttcct gagatcttcg gcaaagcctc tgagtccttg cagctggtct ttggcattga 660
cgtgaaggaa gcagacccca ccggccactc ctatgtcctt gtcacctgcc taggtctctc 720
ctatgatggc ctgctgggtg ataatcagat catgcccaag acaggcttcc tgataattgt 780
cctggtcatg attgcaatgg agggcggcca tgctcctgag gaggaaatct gggaggagct 840
gagtgtgatg gaggtgtatg atgggaggga gcacagtgcc tatggggagc ccaggaagct 900
gctcacccaa gatttggtgc aggaaaagta cctggagtac cggcaggtgc cggacagtga 960
tcccgcacgc tatgagttcc tgtggggtcc aagggccctt gctgaaacca gctatgtgaa 1020
agtccttgag tatgtgatca aggtcagtgc aagagttcgc tttttcttcc catccctgcg 1080
tgaagcagct ttgagagagg aggaagaggg agtctgagca tgagttgcag ccagggccag 1140
tgggaggggg actgggccag tgcaccttcc agggccgcgt ccagcagctt cccctgcctc 1200
gtgtgacatg aggcccattc ttcactctga agagagcggt cagtgttctc agtagtaggt 1260
ttctgttcta ttgggtgact tggagattta tctttgttct cttttggaat tgttcaaatg 1320
ttttttttta agggatggtt gaatgaactt cagcatccaa gtttatgaat gacagcagtc 1380
acacagttct gtgtatatag tttaagggta agagtcttgt gttttattca gattgggaaa 1440
tccattctat tttgtgaatt gggataataa cagcagtgga ataagtactt agaaatgtga 1500
aaaatgagca gtaaaataga tgagataaag aactaaagaa attaagagat agtcaattct 1560
tgccttatac ctcagtctat tctgtaaaat ttttaaagat atatgcatac ctggatttcc 1620
ttggcttctt tgagaatgta agagaaatta aatctgaata aagaattctt cctgttaaaa 1680
aaaaaaaaaa aaaaaaaaaa aaaaaaaaaa aaaaaaaaaa aa 1722

<210> SEQ ID NO 164
<211> LENGTH: 60
<212> TYPE: DNA
<213> ORGANISM: Homo sapiens
<220> FEATURE:
<223> OTHER INFORMATION: NM_004988

<400> SEQUENCE: 164
cagattggga aatccattct attttgtgaa ttgggataat aacagcagtg gaataagtac 60

<210> SEQ ID NO 165
<211> LENGTH: 2334
<212> TYPE: DNA
<213> ORGANISM: Homo sapiens
<220> FEATURE:
<223> OTHER INFORMATION: NM_004994

<400> SEQUENCE: 165
agacacctct gccctcacca tgagcctctg gcagcccctg gtcctggtgc tcctggtgct 60
gggctgctgc tttgctgccc ccagacagcg ccagtccacc cttgtgctct tccctggaga 120
cctgagaacc aatctcaccg acaggcagct ggcagaggaa tacctgtacc gctatggtta 180
cactcgggtg gcagagatgc gtggagagtc gaaatctctg gggcctgcgc tgctgcttct 240
ccagaagcaa ctgtccctgc ccgagaccgg tgagctggat agcgccacgc tgaaggccat 300
gcgaacccca cggtgcgggg tcccagacct gggcagattc caaacctttg agggcgacct 360
caagtggcac caccacaaca tcacctattg gatccaaaac tactcggaag acttgccgcg 420
ggcggtgatt gacgacgcct ttgcccgcgc cttcgcactg tggagcgcgg tgacgccgct 480
caccttcact cgcgtgtaca gccgggacgc agacatcgtc atccagtttg gtgtcgcgga 540
gcacggagac gggtatccct tcgacgggaa ggacgggctc ctggcacacg cctttcctcc 600
tggccccggc attcagggag acgcccattt cgacgatgac gagttgtggt ccctgggcaa 660
gggcgtcgtg gttccaactc ggtttggaaa cgcagatggc gcggcctgcc acttcccctt 720
catcttcgag ggccgctcct actctgcctg caccaccgac ggtcgctccg acggcttgcc 780
ctggtgcagt accacggcca actacgacac cgacgaccgg tttggcttct gccccagcga 840
gagactctac acccgggacg gcaatgctga tgggaaaccc tgccagtttc cattcatctt 900
ccaaggccaa tcctactccg cctgcaccac ggacggtcgc tccgacggct accgctggtg 960
cgccaccacc gccaactacg accgggacaa gctcttcggc ttctgcccga cccgagctga 1020
ctcgacggtg atggggggca actcggcggg ggagctgtgc gtcttcccct tcactttcct 1080
gggtaaggag tactcgacct gtaccagcga gggccgcgga gatgggcgcc tctggtgcgc 1140
taccacctcg aactttgaca gcgacaagaa gtggggcttc tgcccggacc aaggatacag 1200
tttgttcctc gtggcggcgc atgagttcgg ccacgcgctg ggcttagatc attcctcagt 1260
gccggaggcg ctcatgtacc ctatgtaccg cttcactgag gggcccccct tgcataagga 1320
cgacgtgaat ggcatccggc acctctatgg tcctcgccct gaacctgagc cacggcctcc 1380

```
aaccaccacc acaccgcagc ccacggctcc cccgacggtc tgccccaccg gacccccccac   1440
tgtccacccc tcagagcgcc ccacagctgg ccccacaggt ccccccctcag ctggccccac   1500
aggtcccccc actgctggcc cttctacggc cactactgtg cctttgagtc cggtggacga   1560
tgcctgcaac gtgaacatct tcgacgccat cgcggagatt gggaaccagc tgtatttgtt   1620
caaggatggg aagtactggc gattctctga gggcaggggg agccggccgc agggcccctt   1680
ccttatcgcc gacaagtggc ccgcgctgcc ccgcaagctg gactcggtct ttgaggagcc   1740
gctctccaag aagcttttct tcttctctgg gcgccaggtg tgggtgtaca caggcgcgtc   1800
ggtgctgggc ccgaggcgtc tggacaagct gggcctggga gccgacgtgg cccaggtgac   1860
cggggccctc cggagtggca gggggaagat gctgctgttc agcgggcggc gcctctggag   1920
gttcgacgtg aaggcgcaga tggtggatcc ccggagcgcc agcgaggtgg accggatgtt   1980
ccccggggtg cctttggaca cgcacgacgt cttccagtac cgagagaaag cctatttctg   2040
ccaggaccgc ttctactggc gcgtgagttc ccggagtgag ttgaaccagg tggaccaagt   2100
gggctacgtg acctatgaca tcctgcagtg ccctgaggac tagggctccc gtcctgcttt   2160
gcagtgccat gtaaatcccc actgggacca accctgggga aggagccagt ttgccggata   2220
caaactggta ttctgttctg gaggaaaggg aggagtggag gtgggctggg ccctctcttc   2280
tcacctttgt tttttgttgg agtgtttcta ataaacttgg attctctaac cttt         2334
```

<210> SEQ ID NO 166
<211> LENGTH: 60
<212> TYPE: DNA
<213> ORGANISM: Homo sapiens
<220> FEATURE:
<223> OTHER INFORMATION: NM_004994

<400> SEQUENCE: 166

```
ggccctctct tctcaccttt gtttttttgtt ggagtgtttc taataaactt ggattctcta     60
```

<210> SEQ ID NO 167
<211> LENGTH: 5329
<212> TYPE: DNA
<213> ORGANISM: Homo sapiens
<220> FEATURE:
<221> NAME/KEY: Modified_base
<222> LOCATION: 1 ... 5329
<223> OTHER INFORMATION: n = a,c,g, or t
<220> FEATURE:
<223> OTHER INFORMATION: NM_005063

<400> SEQUENCE: 167

```
gtggtgtcgg tgtcggcagc atccccggcg ccctgctgcg gtcgccggag ccctcggcct     60
ctgttctcct ccccctcccg cccttacctc cacgcgggac cgcccgcgcc agtcaactcc    120
tcgcactttg cccctgcttg gcagcggata aaagggggct gaggaaatac cggacacgtc    180
cacccgttgc cagctctagc ctttaaattc ccggctcggg acctccacgc accgggctag    240
cgccgacaac cagctagcgt gcaaggcgcc gcggctcagc gcgtaccggc gggcttcgaa    300
accgcagtcc tccggcgacc ccgaactccg ctccggagcc tcagcccccct ggaaagtgat    360
cccggcatcg gagagccaag atgccggccc acttgctgca ggacgatatc tctagctcct    420
ataccaccac caccaccatt acagcgcctc cctccagggt cctgcagaat ggaggagata    480
agttggagac gatgcccctc tacttggaag acgacattcg ccctgatata aaagatgata    540
tatatgaccc cacctacaag gataaggaag gcccaagccc caaggttgaa tatgtctgga    600
gaaacatcat ccttatgtct ctgctacact tgggagccct gtatgggatc actttgattc    660
```

ctacctgcaa gttctacacc tggctttggg gggtattcta ctattttgtc agtgccctgg 720
gcataacagc aggagctcat cgtctgtgga gccaccgctc ttacaaagct cggctgcccc 780
tacggctctt tctgatcatt gccaacacaa tggcattcca gaatgatgtc tatgaatggg 840
ctcgtgacca ccgtgcccac cacaagtttt cagaaacaca tgctgatcct cataattccc 900
gacgtggctt tttcttctct cacgtgggtt ggctgcttgt gcgcaaacac ccagctgtca 960
aagagaaggg gagtacgcta gacttgtctg acctagaagc tgagaaactg gtgatgttcc 1020
agaggaggta ctacaaacct ggcttgctgc tgatgtgctt catcctgccc acgcttgtgc 1080
cctggtattt ctggggtgaa acttttcaaa acagtgtgtt cgttgccact ttcttgcgat 1140
atgctgtggt gcttaatgcc acctggctgg tgaacagtgc tgcccacctc ttcggatatc 1200
gtccttatga caagaacatt agcccccggg agaatatcct ggtttcactt ggagctgtgg 1260
gtgagggctt ccacaactac caccactcct ttccctatga ctactctgcc agtgagtacc 1320
gctggcacat caacttcacc acattcttca ttgattgcat ggccgccctc ggtctggcct 1380
atgaccggaa gaaagtctcc aaggccgcca tcttggccag gattaaaaga accggagatg 1440
gaaactacaa gagtggctga gtttggggtc cctcaggttc ctttttcaaa aaccagccag 1500
gcagaggttt taatgtctgt ttattaacta ctgaataatg ctaccaggat gctaaagatg 1560
atgatgttaa cccattccag tacagtattc ttttaaaatt caaaagtatt gaaagccaac 1620
aactctgcct ttatgatgct aagctgatat tatttcttct cttatcctct ctctcttcta 1680
ggcccattgt cctccttttc actttaatcg ccctcctttc ccttattgcc tcccaggcaa 1740
gcagctggtc agtctttgct cagtgtccag cttccaaagc ctagacaacc tttctgtagc 1800
ctaaaacgaa tggtctttgc tccagataac tctctttcct tgagctgttg tgagctttga 1860
agtaggtggc ttgagctaga gataaaacag aatcttctgg gtagtcccct gttgattatc 1920
ttcagcccag gcttttgcta gatggaatgg aaaagcaact tcatttgaca caaagcttct 1980
aaagcnaggt aaattgtcgg gggagagagt tagcatgtat gaatgtaagg atgagggaag 2040
cgaaggaacc tctcgccatg atcagacata cagctgccta cctaatgagg acttcaagcc 2100
ccaccacata gcatgcttcc tttctctcct ggctcggggt aaaaagtggc tgcggtgttt 2160
ggcaatgcta attcaatgcc gcaacatata gttgaggccg aggataaaga aaagacattt 2220
taagtttgta gtaaaagtgg tctctgctgg ggaagggttt tcttttcttt ttttctttaa 2280
taacaaggag atttcttagt tcatatatca agaagtcttg aagttgggtg tttccagaat 2340
tggtaaaaac agcagctcat agaattttga gtattccatg agctgctcat tacagttctt 2400
tcctctttct gctctgccat cttcaggata ttggttcttc ccctcatagt aataagatgg 2460
ctgtggcatt tccaaacatc caaaaaaagg gaaggattta aggaggtgaa gtcgggtcaa 2520
aaataaaata tatatacata tatacattgc ttagaacgtt aaactattag agtatttccc 2580
ttccaaagag ggatgtttgg aaaaaactct gaaggagagg aggaattagt tgggatgcca 2640
atttcctctc cactgctgga catgagatgg agaggctgag ggacaggatc tataggcagc 2700
ttctaagagc gaacttcaca taggaaggga tctgagaaca cgttcagggg ttgagaaggt 2760
tactgagtga gttattggga gtcttaataa actagatatt aggtccattc attaattagt 2820
tccagtttct ccttgaaatg agtaaaaact agaaggcttc tctccacagt gttgtgcccc 2880
ttcactcatt tttttttgag gagaaggggg tctctgttaa catctagcct aaagtataca 2940
aactgcctgg ggggcagggt taggaatctc ttcactaccc tgattcttga ttcctggctc 3000
taccctgtct gtcccttttc tttgaccaga tctttctctt ccctgaacgt tttcttcttt 3060
ccctggacag gcagcctcct ttgtgtgtat tcagaggcag tgatgacttg ctgtccaggc 3120
agctccctcc tgcacacaga atgctcaggg tcactgaacc actgcttctc ttttgaaagt 3180
agagctagct gccactttca cgtggcctcc gcagtgtctc cacctacacc cctgtgctcc 3240
cctgccacac tgatggctca agacaaggct ggcaaaccct cccagaaaca tctctggccc 3300
agaaagcctc tctctccctc cctctctcat gagaagccaa gcgctcatgt tgagccagtg 3360
ggccagccac agagcaaaag agggtttatt ttcagtcccc tctctctggg tcagaaccag 3420
agggcatgct gaatgccccc tgcttacttg gtgagggtgc cccgcctgag tcagtgctct 3480
cagctggcag tgcaatgctt gtagaagtag gaggaaacag ttctcactgg gaagaagcaa 3540
gggcaagaac ccaagtgcct cacctcgaaa ggaggccctg ttccctggag tcagggtgaa 3600
ctgcaaagct ttggctgaga cctgggattt gagataccac aaaccctgct gaacacagtg 3660
tctgttcagc aaactaacca gcattcccta cagcctaggg cagacaatag tatagaagtc 3720
tggaaaaaaa caaaaacaga atttgagaac cttggaccac tcctgtccct gtagctcagt 3780
catcaaagca gaagtctggc tttgctctat taagattgga aatgtacact accaaacact 3840
cagtccactg ttgagcccca gtgctggaag ggaggaaggc ctttcttctg tgttaattgc 3900
gtagaggcta caggggttag cctggactaa aggcatcctt gtctttgagc tattcacctc 3960
agtagaaaag gatctaaggg aagatcactg tagtttagtt ctgttgacct gtgcacctac 4020
cccttggaaa tgtctgctgg tatttctaat tccacaggtc atcagatgcc tgcttgataa 4080
tatataaaca ataaaaacaa ctttcacttc ttcctattgt aatcgtgtgc catggatctg 4140
atctgtacca tgaccctaca taaggctgga tggcacctca ggctgagggc cccaatgtat 4200
gtgtggctgt gggtgtgggt gggagtgtgt ctgctgagta aggaacacga ttttcaagat 4260
tctaaagctc aattcaagtg acacattaat gataaactca gatctgatca agagtccgga 4320
tttctaacag tccttgcttt ggggggtgtg ctggcaactt agctcaggtg ccttacatct 4380
tttctaatca cagtgttgca tatgagcctg ccctcactcc ctctgcagaa tccctttgca 4440
cctgagaccc tactgaagtg gctggtagaa aaaggggcct gagtggagga ttatcagtat 4500
cacgatttgc aggattccct tctgggcttc attctggaaa cttttgttag ggctgctttt 4560
cttaagtgcc cacatttgat ggagggtgga aataatttga atgtatttga tttataagtt 4620
tttttttttt tttgggttaa aagatggttg tagcatttaa aatggaaaat tttctccttg 4680
gtttgctagt atcttgggtg tattctctgt aagtgtagct caaataggtc atcatgaaag 4740
gttaaaaaag cgaggtggcc atgttatgct ggtggttgcc agggcctcca accactgtgc 4800
cactgacttg ctgtgtgacc ctgggcaagt cacttaacta taaggtgcct cagttttcct 4860
tctgttaaaa tggggataat aatactgacc tacctcaaag ggcagttttg aggcatgact 4920
aatgcttttt agaaagcatt ttgggatcct tcagcacagg aattctcaag acctgagtat 4980
tttttataat aggaatgtcc accatgaact tgatacgtcc gtgtgtccca gatgctgtca 5040
ttagtctata tggttctcca agaaactgaa tgaatccatt ggagaagcgg tggataacta 5100
gccagacaaa atttgagaat acataaacaa cgcattgcca cggaaacata cagaggatgc 5160
cttttctgtg attgggtggg attttttccc tttttatgtg ggatatagta gttacttgtg 5220
acaagaataa ttttggaata atttctatta atatcaactc tgaagctaat tgtactaatc 5280
tgagattgtg tttgttcata ataaaagtga agtgaatctg attgcactg 5329

<210> SEQ ID NO 168
<211> LENGTH: 60

<212> TYPE: DNA
<213> ORGANISM: Homo sapiens
<220> FEATURE:
<223> OTHER INFORMATION: NM_005063

<400> SEQUENCE: 168
aataatgcta ccaggatgct aaagatgatg atgttaaccc attccagtac agtattcttt 60

<210> SEQ ID NO 169
<211> LENGTH: 634
<212> TYPE: DNA
<213> ORGANISM: Homo sapiens
<220> FEATURE:
<223> OTHER INFORMATION: NM_005101

<400> SEQUENCE: 169
cggctgagag gcagcgaact catctttgcc agtacaggag cttgtgccgt ggcccacagc 60
ccacagccca cagccatggg ctgggacctg acggtgaaga tgctggcggg caacgaattc 120
caggtgtccc tgagcagctc catgtcggtg tcagagctga aggcgcagat cacccagaag 180
attggcgtgc acgccttcca gcagcgtctg gctgtccacc cgagcggtgt ggcgctgcag 240
gacagggtcc cccttgccag ccagggcctg ggccctggca gcacggtcct gctggtggtg 300
gacaaatgcg acgaacctct gagcatcctg gtgaggaata acaagggccg cagcagcacc 360
tacgaggtcc ggctgacgca gaccgtggcc cacctgaagc agcaagtgag cgggctggag 420
ggtgtgcagg acgacctgtt ctggctgacc ttcgagggga agcccctgga ggaccagctc 480
ccgctggggg agtacggcct caagcccctg agcaccgtgt tcatgaatct gcgcctgcgg 540
ggaggcggca cagagcctgg cgggcggagc taagggcctc caccagcatc cgagcaggat 600
caagggccgg aaataaaggc tgttgtaaga gaat 634

<210> SEQ ID NO 170
<211> LENGTH: 60
<212> TYPE: DNA
<213> ORGANISM: Homo sapiens
<220> FEATURE:
<223> OTHER INFORMATION: NM_005101

<400> SEQUENCE: 170
tggtggtgga caaatgcgac gaacctctga gcatcctggt gaggaataac aagggccgca 60

<210> SEQ ID NO 171
<211> LENGTH: 1339
<212> TYPE: DNA
<213> ORGANISM: Homo sapiens
<220> FEATURE:
<223> OTHER INFORMATION: NM_005139

<400> SEQUENCE: 171
gaattccgat tagtgtgatc tcagctcaag gcaaaggtgg gatatcatgg catctatctg 60
ggttggacac cgaggaacag taagagatta tccagacttt agcccatcag tggatgctga 120
agctattcag aaagcaatca gaggaattgg aactgatgag aaaatgctca tcagcattct 180
gactgagagg tcaaatgcac agcggcagct gattgttaag gaatatcaag cagcatatgg 240
aaaggagctg aaagatgact tgaagggtga tctctctggc cactttgagc atctcatggt 300
ggccctagtg actccaccag cagtctttga tgcaaagcag ctaaagaaat ccatgaaggg 360
cgcgggaaca aacgaagatg ccttgattga aatcttaact accaggacaa gcaggcaaat 420
gaaggatatc tctcaagcct attatacagt atacaagaag agtcttggag atgacattag 480
ttccgaaaca tctggtgact tccggaaagc tctgttgact ttggcagatg gcagaagaga 540
tgaaagtctg aaagtggatg agcatctggc caaacaagat gcccagattc tctataaagc 600
tggtgagaac agatggggca cggatgaaga caaattcact gagatcctgt gtttaaggag 660
ctttcctcaa ttaaaactaa catttgatga atacagaaat atcagccaaa aggacattgt 720
ggacagcata aaaggagaat tatctgggca ttttgaagac ttactgttgg ccatagttaa 780
ttgtgtgagg aacacgccgg cctttttagc cgaaagactg catcgagcct tgaagggtat 840
tggaactgat gagtttactc tgaaccgaat aatggtgtcc agatcagaaa ttgacctttt 900
ggacattcga acagagttca agaagcatta tggctattcc ctatattcag caattaaatc 960
ggatacttct ggagactatg aaatcacact cttaaaaatc tgtggtggag atgactgaac 1020
caagaagata atctccaaag gtccacgatg ggctttccca acagctccac cttacttctt 1080
ctcatactat ttaagagaac aagcaaatat aaacagcaac ttgtgttcct aacaggaatt 1140
ttcattgttc tataacaaca acaacaaaag cgattattat tttagagcat ctcatttata 1200
atgtagcagc tcataaatga aattgaaaat ggtattaaag atctgcaact actatccaac 1260
ttatatttct gctttcaaag ttaagaatct ttatagttct actccattaa atataaagca 1320
agataataaa acggaattc 1339

<210> SEQ ID NO 172
<211> LENGTH: 60
<212> TYPE: DNA
<213> ORGANISM: Homo sapiens
<220> FEATURE:
<223> OTHER INFORMATION: NM_005139

<400> SEQUENCE: 172
ttcagcaatt aaatcggata cttctggaga ctatgaaatc acactcttaa aaatctgtgg 60

<210> SEQ ID NO 173
<211> LENGTH: 1582
<212> TYPE: DNA
<213> ORGANISM: Homo sapiens
<220> FEATURE:
<223> OTHER INFORMATION: NM_005165

<400> SEQUENCE: 173
ccgagctgtg cttgtggctg cggctgctaa ctggctgcgc acagggagct gtcaccatgc 60
ctcactcgta cccagccctt tctgctgagc agaagaagga gttgtctgac attgccctgc 120
ggattgtagc cccgggcaaa ggcattctgg ctgcggatga gtctgtaggc agcatggcca 180
agcggctgag ccaaattggg gtggaaaaca cagaggagaa ccgccggctg taccgccagg 240
tcctgttcag tgctgatgac cgtgtgaaaa agtgcattgg aggcgtcatt ttcttccatg 300
agaccctcta ccagaaagat gataatggtg ttcccttcgt ccgaaccatc caggataagg 360
gcatcgtcgt gggcatcaag gttgacaagg gtgtggtgcc tctagctggg actgatggag 420
aaaccaccac tcaagggctg gatgggctct cagaacgctg tgcccaatac aagaaggatg 480
gtgctgactt tgccaagtgg cgctgtgtgc tgaaaatcag tgagcgtaca ccctctgcac 540
ttgccattct ggagaacgcc aacgtgctgg cccgttatgc cagtatctgc cagcagaatg 600
gcattgtgcc tattgtggaa cctgaaatat tgcctgatgg agaccacgac ctcaaacgtt 660
gtcagtatgt tacagagaag gtcttggctg ctgtgtacaa ggccctgagt gaccatcatg 720
tatacctgga ggggaccctg ctcaagccca acatggtgac cccgggccat gcctgtccca 780
tcaagtatac cccagaggag attgccatgg caactgtcac tgccctgcgt cgcactgtgc 840
ccccagctgt cccaggagtg accttcctgt ctggggggtca gagcgaagaa gaggcatcat 900
tcaacctcaa tgccatcaac cgctgccccc ttccccgacc ctgggcgctt accttctcct 960
atgggcgtgc cctgcaagcc tctgcactca atgcctggcg agggcaacgg gacaatgctg 1020
gggctgccac tgaggagttc atcaagcggg ctgaggtgaa tgggcttgca gcccagggca 1080
agtatgaagg cagtggagaa gatggtggag cagcagcaca gtcactctac attgccaacc 1140
atgcctactg agtatccact ccataccaca gcccttggcc cagccatctg cacccacttt 1200
tgcttgtagt catggccagg gccaaatagc tatgcagagc agagatgcct tcacctggca 1260
ccaacttgtc ttcctttctc tcttcccttc ccctctctca ttgctgcacc tgggaccata 1320
ggatgggagg atagggagcc cctcatgact gagggcagaa gaaattgcta gaagtcagaa 1380
caggatggct gggtctcccc ctacctcttc cagctcccac aatttcccca tgatgaggta 1440
gcttctccct gggctctcct tcttgcctgc cctgtctcct gggatcagag ggtagtacag 1500
aagccctgac tcatgccttg agtacatacc atacagcaaa taaatggtag caaaacaaaa 1560
aaaaaaaaaa aaaaaaaaaa aa 1582

<210> SEQ ID NO 174
<211> LENGTH: 60
<212> TYPE: DNA
<213> ORGANISM: Homo sapiens
<220> FEATURE:
<223> OTHER INFORMATION: NM_005165

<400> SEQUENCE: 174
gagggtagta cagaagccct gactcatgcc ttgagtacat accatacagc aaataaatgg 60

<210> SEQ ID NO 175
<211> LENGTH: 451
<212> TYPE: DNA
<213> ORGANISM: Homo sapiens
<220> FEATURE:
<223> OTHER INFORMATION: NM_005213

<400> SEQUENCE: 175
acttccctgt tcactttggt tccagcatcc tgtccagcaa agaagcaatc agccaaaatg 60
atacctggag gcttatctga ggccaaaccc gccactccag aaatccagga gattgttgat 120
aaggttaaac cacagcttga agaaaaaaca aatgagactt atggaaaatt ggaagctgtg 180
cagtataaaa ctcaagttgt tgctggaaca aattactaca ttaaggtacg agcaggtgat 240
aataaatata tgcacttgaa agtattcaaa agtcttcccg gacaaaatga ggacttggta 300
cttactggat accaggttga caaaaacaag gatgacgagc tgacgggctt ttagcagcat 360
gtacccaaag tgttctgatt ccttcaactg gctactgagt catgatcctt gctgataaat 420
ataaccatca ataaagaagc attcttttcc a 451

<210> SEQ ID NO 176
<211> LENGTH: 60
<212> TYPE: DNA
<213> ORGANISM: Homo sapiens
<220> FEATURE:
<223> OTHER INFORMATION: NM_005213

<400> SEQUENCE: 176
aactggctac tgagtcatga tccttgctga taaatataac catcaataaa gaagcattct 60

<210> SEQ ID NO 177
<211> LENGTH: 366
<212> TYPE: DNA
<213> ORGANISM: Homo sapiens

<220> FEATURE:
<223> OTHER INFORMATION: NM_005218

<400> SEQUENCE: 177
gtcagctcag cctccaaagg agccagcctc tccccagttc ctgaaatcct gagtgttgcc 60
tgccagtcgc catgagaact tcctaccttc tgctgtttac tctctgctta cttttgtctg 120
agatggcctc aggtggtaac tttctcacag gccttggcca cagatctgat cattacaatt 180
gcgtcagcag tggagggcaa tgtctctatt ctgcctgccc gatctttacc aaaattcaag 240
gcacctgtta cagagggaag gccaagtgct gcaagtgagc tgggagtgac cagaagaaat 300
gacgcagaag tgaaatgaac tttttataag cattctttta ataaaggaaa attgcttttg 360
aagtat 366

<210> SEQ ID NO 178
<211> LENGTH: 60
<212> TYPE: DNA
<213> ORGANISM: Homo sapiens
<220> FEATURE:
<223> OTHER INFORMATION: NM_005218

<400> SEQUENCE: 178
gggagtgacc agaagaaatg acgcagaagt gaaatgaact tttataagc attcttttaa 60

<210> SEQ ID NO 179
<211> LENGTH: 1519
<212> TYPE: DNA
<213> ORGANISM: Homo sapiens
<220> FEATURE:
<223> OTHER INFORMATION: NM_005326

<400> SEQUENCE: 179
ctgcctcgga acgctgtccc ccgcagcgac ggcccgttcc acctcgcgat ctgccgggta 60
cccgggcggc gtggcgctcg gcctccaggg atccactgtg cggtgccaaa aaagaggcgg 120
aggctcgcgg cacagctctc ccggcgcagc tctcgggccg ccgccgccgc tcccaggccc 180
gtctcccggc ccgtggcagt cggggctcgc ggacaaaaca agttgagcgc gagcgcgttg 240
attggttggc ggacggtgcg aggtggacgc tgattggctg agggcagcgc gaggcgggcg 300
ctgattggct gcgacgcgcc gacgccggtg ttttgcagtc ctgggcagct cggcagtcca 360
gcccggcccg ggtcatggtg gtgggccgag ggctgctcgg ccgccgcagc ctcgccgcgc 420
tgggagccgc ctgcgcccgc cgaggcctcg gtccagccct gctgggagtt ttctgccaca 480
cagatttgcg gaagaacctg accgtggacg agggcaccat gaaggtagag gtgctgcctg 540
ccctgaccga caactacatg tacctggtca ttgatgatga gaccaaggag gctgccattg 600
tggatccggt gcagccccag aaggtcgtgg acgcggcgag aaagcacggg gtgaaactga 660
ccacagtgct caccacccac caccactggg accatgctgg cgggaatgag aaactggtca 720
agctggagtc gggactgaag gtgtacgggg gtgacgaccg tatcggggcc ctgactcaca 780
agatcactca cctgtccaca ctgcaggtgg ggtctctgaa cgtcaagtgc ctggcgaccc 840
cgtgccacac ttcaggacac atttgttact tcgtgagcaa gcccggaggc tcggagcccc 900
ctgccgtgtt cacaggtgac accttgtttg tggctggctg cgggaagttc tatgaaggga 960
ctgcggatga gatgtgtaaa gctctgctgg aggtcttggg ccggctcccc ccggacacaa 1020
gagtctactg tggccacgag tacaccatca acaacctcaa gtttgcacgc cacgtggagc 1080
ccggcaatgc cgccatccgg gagaagctgg cctgggccaa ggagaagtac agcatcgggg 1140
agcccacagt gccatccacc ctggcagagg agtttaccta caacccccttc atgagagtga 1200 gggagaagac ggtgcagcag cacgcaggtg agacggaccc ggtgaccacc atgcgggccg 1260
tgcgcaggga gaaggaccag ttcaagatgc cccgggactg aggccgccct gcaccttcag 1320
cggatttggg gattaggctc ttttaggtaa ctggctttcc tgctggtccg tgcgggaaat 1380
tcagtcttga tttaacctta attttacagc ccttggcttg tgttatcgga cattctaatg 1440
catatttata agagaagttt aacaagtatt tattcccata aaaaaaaaaa aaaaaaaaaa 1500
aaaaaaaaaa aaaaaaaaa 1519

<210> SEQ ID NO 180
<211> LENGTH: 60
<212> TYPE: DNA
<213> ORGANISM: Homo sapiens
<220> FEATURE:
<223> OTHER INFORMATION: NM_005326

<400> SEQUENCE: 180
cttgtgttat cggacattct aatgcatatt tataagagaa gtttaacaag tatttattcc 60

<210> SEQ ID NO 181
<211> LENGTH: 3378
<212> TYPE: DNA
<213> ORGANISM: Homo sapiens
<220> FEATURE:
<223> OTHER INFORMATION: NM_005461

<400> SEQUENCE: 181
acagctgcac cgccgagctg cgagcggctg cgagcgagag agcgtaagag caagagagct 60
agagagcgag caacgggcac tcgccccacg cctcccctca gccccaccgc gcgctccgct 120
tgcctctcca ccccgcccga ctctacccgg cccggtccct gcgcgggcac agcccagagc 180
tctggggcgg tgcaggcagc ctcgggactc tccggcgcgc cgccgcgtcc ccagacaaag 240
gcttggccgg cggccccggc ccgctgcgcc ctcgctcccc gcctccccag ctcttctccg 300
ctcttccccc ccgcgcttgg ctcggcgcgc tccggccggc cgcaaagttt cccgggcggc 360
agcggcggct gcgcctcgct tcagcgatgg ccgcggagct gagcatgggg ccagagctgc 420
ccaccagccc gctggccatg gagtatgtca acgacttcga cctgctcaag ttcgacgtga 480
agaaggagcc actggggcgc gcggagcgtc cgggcaggcc ctgcacacgc ctgcagccag 540
ccggctcggt gtcctccaca ccgctcagca ctccgtgtag ctccgtgccc tcgtcgccca 600
gcttcagccc gaccgaacag aagacacacc tcgaggatct gtactggatg gcgagcaact 660
accagcagat gaaccccgag gcgctcaacc tgacgcccga ggacgcggtg gaagcgctca 720
tcggctcgca cccagtgcca cagccgctgc aaagcttcga cagctttcgc ggcgctcacc 780
accaccacca tcaccaccac cctcacccgc accacgcgta cccgggcgcc ggcgtggccc 840
acgacgagct gggcccgcac gctcacccgc accatcacca tcatcaccaa gcgtcgccgc 900
cgccgtccag cgccgctagc ccggcgcaac agctgcccac tagccacccc gggcccgggc 960
cgcacgcgac ggcctcggcg acggcggcgg gcggcaacgg cagcgtggag gaccgcttct 1020
ccgacgacca gctcgtgtcc atgtccgtgc gcgagctgaa ccgccacctg cggggcttca 1080
ccaaggacga ggtgatccgc ctgaagcaga agcggcggac cctgaagaac cggggctacg 1140
cccagtcttg caggtataaa cgcgtccagc agaagcacca cctggagaat gagaagacgc 1200
agctcattca gcaggtggag cagcttaagc aggaggtgtc ccggctggcc cgcgagagag 1260
acgcctacaa ggtcaagtgc gagaaactcg ccaactccgg cttcagggag gcgggctcca 1320
ccagcgacag cccctcctct cccgagttct ttctgtgagt cgtggccggt cctggccccc 1380
gcccttgccc cggcccggac tccctgtccc acgtccctag tcccagacta ccccggaccc 1440
tgtccctgcc gcggccccag ccttgacctg tttgacttga gcgagaggga ggaagggcgc 1500
gcgggccgcg ggcgacgggc gggtgcgcgg gcgggcaggg gaccttggct aaggcgagag 1560
tagcgcacgc cagcgccgcc tcctagactc gagcagagcc ggagagagag acgagagggt 1620
gggaggtccc ggagtaactt ctctccaggc tgaagggcgg cgaggcatag tcccgagaag 1680
tcaccaaggc catctggaga ctcctggctt tctgaacttt gcgcgttaag ccgggacagc 1740
tgctttgctg cccggagagt agtccgcgcc aggaagagag caacgaggaa aggagaggga 1800
ctctggcgtc ccggcaggcg agaggcgagg ctgagcgaaa gaaggaagga cagacggacc 1860
tgtctgtcag agttcggaga acactggctc tcagccctga gacacaggcc tcagttagga 1920
cgctcggcgc ccaaatctca tcagttttat tgcctgctcg attatataga aaaatacaaa 1980
aaatctgcat taaaaatatt aatcctgcat gctggacatg tatggtaata atttctattt 2040
tgtaccattt tcttgtttaa ctttagcatg ttgttgatca tggatcatac tccccttgtt 2100
tctttgggtg agaagggatc gcagtttgga aactccggcg gctgcgtgcg gggtttcagt 2160
cccagctgta ggcttgtaaa tacccgcccc gccaaaccgc atagagaacg tggcagcaag 2220
ctgagggtct ttgtttgggt ttattattac ggtatttttg tttgtaagtt aaaaagaaaa 2280
aaaaaaagaa aaagttccgg gcattttgca tcagaaaaca actttgtctt ggggcacact 2340
tggaagttgc atgttttctt tccttccctt atccccattc ggtcctcttt ttcctctctc 2400
gctttagttt tcaaccttgt tggtgctgag agagagaacc gagaggtccc agtacaaggg 2460
cagggcaggg cagggaagct gccaagctcc gcaccccaga ggagtgttct ggactacagc 2520
cttgtcttat ggtcaaattg atacccttaa taagaaagga aaggaaagga aaacagatcc 2580
tcccctctgc tttttattgt aaccagaatc accctgaggt cccttctgaa ccctctgggc 2640
ctgcgctaat tgtaggagcc acagcgctcc tagggtgaga ggcttagcca tccctgaccc 2700
tggcagtgca ctggtaagca gacactgcac tgaaccaact gctatgctca gaatgtacca 2760
gaaacccaaa cattggcaag taattttgca actttcaagt gcgttcttta gaccaatgca 2820
ttgcgtttct ttccctgctt ttgagatagt aggaagagtt cttggtggtg tcccccccct 2880
tcaattcttc agttgtatag tagttatagg gaagatatgg gtgtttttct ttattattac 2940
tttttttttt ctgcaggtca gtaaaaggat ttaagttgca ctgacaaaaa taccaaaata 3000
aaagtgtatt tttaagttcc catttgaaat tgctggcgct gctggccgga tgcatttttg 3060
agtttgtatt agttgataaa ttaacagtaa taacaagatt gtatgaaccg catggtgctt 3120
gcagttttaa atattgtgga tatttgtcct gcatcagaaa cgagctttgg tttttacaga 3180
ttcaactgtg ttgaaatcaa acctgccgca acagaaattg tttttatttc atgtaaaata 3240
agggatcaat ttcaaaccct gcttatgata tgaaaatatt aaaacctagt ctattgtagt 3300
tttattcaga ctggtttctg ttttttggtt attaaaatgg tttcctattt tgcttattaa 3360
aaaaaaaaaa aaaaaaaa 3378

<210> SEQ ID NO 182
<211> LENGTH: 60
<212> TYPE: DNA
<213> ORGANISM: Homo sapiens
<220> FEATURE:
<223> OTHER INFORMATION: NM_005461

<400> SEQUENCE: 182
atttgtcctg catcagaaac gagctttggt ttttacagat tcaactgtgt tgaaatcaaa 60

<210> SEQ ID NO 183
<211> LENGTH: 597
<212> TYPE: DNA
<213> ORGANISM: Homo sapiens
<220> FEATURE:
<223> OTHER INFORMATION: NM_005532

<400> SEQUENCE: 183
agctgaagtt gaggatctct tactctctaa gccacggaat taacccgagc aggcatggag 60
gcctctgctc tcacctcatc agcagtgacc agtgtggcca aagtggtcag ggtggcctct 120
ggctctgccg tagttttgcc cctggccagg attgctacag ttgtgattgg aggagttgtg 180
gccatggcgg ctgtgcccat ggtgctcagt gccatgggct tcactgcggc gggaatcgcc 240
tcgtcctcca tagcagccaa gatgatgtcc gcggcggcca ttgccaatgg gggtggagtt 300
gcctcgggca gccttgtggg tactctgcag tcactgggag caactggact ctccggattg 360
accaagttca tcctgggctc cattgggtct gccattgcgg ctgtcattgc gaggttctac 420
tagctccctg cccctcgccc tgcagagaag agaaccatgc caggggagaa ggcacccagc 480
catcctgacc cagcgaggag ccaactatcc caaatatacc tgggtgaaat ataccaaatt 540
ctgcatctcc agaggaaaat aagaaataaa gatgaattgt tgcaactctt aaaaaaa 597

<210> SEQ ID NO 184
<211> LENGTH: 60
<212> TYPE: DNA
<213> ORGANISM: Homo sapiens
<220> FEATURE:
<223> OTHER INFORMATION: NM_005532

<400> SEQUENCE: 184
agccaactat cccaaatata cctgggtgaa atataccaaa ttctgcatct ccagaggaaa 60

<210> SEQ ID NO 185
<211> LENGTH: 1661
<212> TYPE: DNA
<213> ORGANISM: Homo sapiens
<220> FEATURE:
<223> OTHER INFORMATION: NM_005566

<400> SEQUENCE: 185
tgctgcagcc gctgccgccg attccggatc tcattgccac gcgcccccga cgaccgcccg 60
acgtgcattc ccgattcctt ttggttccaa gtccaatatg gcaactctaa aggatcagct 120
gatttataat cttctaaagg aagaacagac cccccagaat aagattacag ttgttggggt 180
tggtgctgtt ggcatggcct gtgccatcag tatcttaatg aaggacttgg cagatgaact 240
tgctcttgtt gatgtcatcg aagacaaatt gaagggagag atgatggatc tccaacatgg 300
cagccttttc cttagaacac caaagattgt ctctggcaaa gactataatg taactgcaaa 360
ctccaagctg gtcattatca cggctggggc acgtcagcaa gagggagaaa gccgtcttaa 420
tttggtccag cgtaacgtga acatatttaa attcatcatt cctaatgttg taaaatacag 480
cccgaactgc aagttgctta ttgtttcaaa tccagtggat atcttgacct acgtggcttg 540
gaagataagt ggttttccca aaaaccgtgt tattggaagt ggttgcaatc tggattcagc 600
ccgattccgt tacctgatgg gggaaaggct gggagttcac ccattaagct gtcatgggtg 660
ggtccttggg gaacatggag attccagtgt gcctgtatgg agtggaatga atgttgctgg 720
tgtctctctg aagactctgc acccagattt agggactgat aaagataagg aacagtggaa 780
agaggttcac aagcaggtgg ttgagagtgc ttatgaggtg atcaaactca aaggctacac 840
atcctgggct attggactct ctgtagcaga tttggcagag agtataatga agaatcttag 900
gcgggtgcac ccagtttcca ccatgattaa gggtctttac ggaataaagg atgatgtctt 960
ccttagtgtt ccttgcattt tgggacagaa tggaatctca gaccttgtga aggtgactct 1020
gacttctgag gaagaggccc gtttgaagaa gagtgcagat acactttggg ggatccaaaa 1080
ggagctgcaa ttttaaagtc ttctgatgtc atatcatttc actgtctagg ctacaacagg 1140
attctaggtg gaggttgtgc atgttgtcct ttttatctga tctgtgatta aagcagtaat 1200
attttaagat ggactgggaa aaacatcaac tcctgaagtt agaaataaga atggtttgta 1260
aaatccacag ctatatcctg atgctggatg gtattaatct tgtgtagtct tcaactggtt 1320
agtgtgaaat agttctgcca cctctgacgc accactgcca atgctgtacg tactgcattt 1380
gccccttgag ccaggtggat gtttaccgtg tgttatataa cttcctggct ccttcactga 1440
acatgcctag tccaacattt tttcccagtg agtcacatcc tgggatccag tgtataaatc 1500
caatatcatg tcttgtgcat aattcttcca aaggatctta ttttgtgaac tatatcagta 1560
gtgtacatta ccatataatg taaaaagatc tacatacaaa caatgcaacc aactatccaa 1620
gtgttatacc aactaaaacc cccaataaac cttgaacagt g 1661

<210> SEQ ID NO 186
<211> LENGTH: 60
<212> TYPE: DNA
<213> ORGANISM: Homo sapiens
<220> FEATURE:
<223> OTHER INFORMATION: NM_005566

<400> SEQUENCE: 186
catcaactcc tgaagttaga aataagaatg gtttgtaaaa tccacagcta tatcctgatg 60

<210> SEQ ID NO 187
<211> LENGTH: 2993
<212> TYPE: DNA
<213> ORGANISM: Homo sapiens
<220> FEATURE:
<223> OTHER INFORMATION: NM_005689

<400> SEQUENCE: 187
gggcctgcag ttggcagaag ggtcccgggc ccagagccag cggggccgtg ctgagacggc 60
gtacgtgccc tgcgtgagtg cgtggcggcg gcgcgtgcgc taggggagtg ggcggtgagg 120
cctggtccac gtgcgtccct tcccgggacc cccgcagctt ggcgcccagc ggctacgtga 180
gccaaggcac ccggatgtcc gcgcccctct ccgagtgaca agtcccggcc tccggtcccg 240
cagtgcccgc agcctcggcc ggcgtccacg cattgccatg gtgactgtgg gcaactactg 300
cgaggccgaa gggcccgtgg gtccggcctg gatgcaggat ggcctgagtc cctgcttctt 360
cttcacgctc gtgccctcga cgcggatggc tctagggact ctggccttgg tgctggctct 420
tccctgcaga cgccgggagc ggcccgctgg tgctgattcg ctgtcttggg gggccggccc 480
tcgcatctct ccctacgtgc tgcagctgct tctggccaca cttcaggcgg cgctgcccct 540
ggccggcctg gctggccggg tgggcactgc ccggggggcc ccactgccaa gctatctact 600
tctggcctcc gtgctggaga gtctggccgg cgcctgtggc ctgtggctgc ttgtcgtgga 660
gcggagccag gcacggcagc gtctggcaat gggcatctgg atcaagttca ggcacagccc 720
tggtctcctg ctcctctgga ctgtggcgtt tgcagctgag aacttggccc tggtgtcttg 780
gaacagccca cagtggtggt gggcaagggc agacttgggc caacaggttc agtttagcct 840
gtgggtgctg cggtatgtgg tctctggagg gctgtttgtc ctgggtctct gggcccctgg 900

```
acttcgtccc cagtcctata cattgcaggt tcatgaagag gaccaagatg tggaaaggag    960
ccaggttcgg tcagcagccc aacagtctac ctggcgagat tttggcagga agctccgcct   1020
cctgagtggc tacctgtggc ctcgagggag tccagctctg cagctggtgg tgctcatctg   1080
cctggggctc atgggtttgg aacgggcact caatgtgttg gtgcctatat tctataggaa   1140
cattgtgaac ttgctgactg agaaggcacc ttggaactct ctggcctgga ctgttaccag   1200
ttacgtcttc ctcaagttcc tccagggggg tggcactggc agtacaggct tcgtgagcaa   1260
cctgcgcacc ttcctgtgga tccgggtgca gcagttcacg tctcggcggg tggagctgct   1320
catcttctcc cacctgcacg agctctcact gcgctggcac ctggggcgcc gcacagggga   1380
ggtgctgcgg atcgcggatc ggggcacatc cagtgtcaca gggctgctca gctacctggt   1440
gttcaatgtc atccccacgc tggccgacat catcattggc atcatctact tcagcatgtt   1500
cttcaacgcc tggtttggcc tcattgtgtt cctgtgcatg agtctttacc tcaccctgac   1560
cattgtggtc actgagtgga gaaccaagtt tcgtcgtgct atgaacacac aggagaacgc   1620
tacccgggca cgagcagtgg actctctgct aaacttcgag acggtgaagt attacaacgc   1680
cgagagttac gaagtggaac gctatcgaga ggccatcatc aaatatcagg gtttggagtg   1740
gaagtcgagc gcttcactgg ttttactaaa tcagacccag aacctggtga ttgggctcgg   1800
gctcctcgcc ggctccctgc tttgcgcata ctttgtcact gagcagaagc tacaggttgg   1860
ggactatgtg ctctttggca cctacattat ccagctgtac atgcccctca attggtttgg   1920
cacctactac aggatgatcc agaccaactt cattgacatg gagaacatgt ttgacttgct   1980
gaaagaggag acagaagtga aggaccttcc tggagcaggg ccccttcgct ttcagaaggg   2040
ccgtattgag tttgagaacg tgcacttcag ctatgccgat gggcgggaga ctctgcagga   2100
cgtgtctttc actgtgatgc ctggacagac acttgccctg gtgggcccat ctggggcagg   2160
gaagagcaca attttgcgcc tgctgtttcg cttctacgac atcagctctg gctgcatccg   2220
aatagatggg caggacattt cacaggtgac ccaggcctct ctccggtctc acattggagt   2280
tgtgccccaa gacactgtcc tctttaatga caccatcgcc gacaatatcc gttacggccg   2340
tgtcacagct gggaatgatg aggtggaggc tgctgctcag gctgcaggca tccatgatgc   2400
cattatggct ttccctgaag ggtacaggac acaggtgggc gagcggggac tgaagctgag   2460
cggcggggag aagcagcgcg tcgccattgc ccgcaccatc ctcaaggctc cgggcatcat   2520
tctgctggat gaggcaacgt cagcgctgga tacatctaat gagagggcca tccaggcttc   2580
tctggccaaa gtctgtgcca accgcaccac catcgtagtg gcacacaggc tctcaactgt   2640
ggtcaatgct gaccagatcc tcgtcatcaa ggatggctgc atcgtggaga ggggacgaca   2700
cgaggctctg ttgtcccgag gtggggtgta tgctgacatg tggcagctgc agcagggaca   2760
ggaagaaacc tctgaagaca ctaagcctca gaccatggaa cggtgacaaa agtttggcca   2820
cttccctctc aaagactaac ccagaaggga ataagatgtg tctcctttcc ctggcttatt   2880
tcatcctggt cttggggtat ggtgctagct atggtaaggg aaagggacct ttccgaaaaa   2940
catcttttgg ggaaataaaa atgtggactg tgaaaaaaaa aaaaaaaaaa aaa          2993
```

<210> SEQ ID NO 188
<211> LENGTH: 60
<212> TYPE: DNA
<213> ORGANISM: Homo sapiens
<220> FEATURE:
<223> OTHER INFORMATION: NM_005689

<400> SEQUENCE: 188
ggaaagggac ctttccgaaa aacatctttt ggggaaataa aaatgtggac tgtgaaaaaa 60

<210> SEQ ID NO 189
<211> LENGTH: 1830
<212> TYPE: DNA
<213> ORGANISM: Homo sapiens
<220> FEATURE:
<223> OTHER INFORMATION: NM_005749

<400> SEQUENCE: 189
ggggagttga aacctaattt tgtggcgtag cagctatgca gcttgaaatc caagtagcac 60
taaattttat tatttcgtat ttgtacaata agcttcccag gagacgtgtc aacatttttg 120
gtgaagaact tgaaagactt cttaagaaga aatatgaagg gcactggtat cctgaaaagc 180
catacaaagg atcggggttt agatgtatac acatagggga gaaagtggac ccagtgattg 240
aacaagcatc caaagagagt ggtttggaca ttgatgatgt tcgtggcaat ctgccacagg 300
atcttagtgt ttggatcgac ccatttgagg tttcttacca aattggtgaa aagggaccag 360
tgaaggtgct ttacgtggat gataataatg aaaatggatg tgagttggat aaggagatca 420
aaaacagctt taacccagag gcccaggttt ttatgcccat aagtgaccca gcctcatcag 480
tgtccagctc tccatcgcct ccttttggtc actctgctgc tgtaagccct accttcatgc 540
cccggtccac tcagccttta acctttacca ctgccacttt tgctgccacc aagttcggct 600
ctaccaaaat gaagaatagt ggccgtagca acaaggttgc acgtacttct cccatcaacc 660
tcggcttgaa tgtgaatgac ctcttgaagc agaaagccat ctcttcctca atgcactctc 720
tgtatgggct tggcttgggt agccagcagc agccacagca acagcagcag ccagcccagc 780
cgccaccgcc accaccacca ccacagcagc aacaacagca gaaaacctct gctctttctc 840
ctaatgccaa ggaatttatt tttcctaata tgcagggtca aggtagtagt accaatggaa 900
tgttcccagg tgacagcccc cttaacctca gtcctctcca gtacagtaat gcctttgatg 960
tgtttgcagc ctatggaggc ctcaatgaga agtcttttgt agatggcttg aattttagct 1020
taaataacat gcagtattct aaccagcaat tccagcctgt tatggctaac taaaaaaaag 1080
aaaatgtatc gtacaagtta aaatgcacgg gcccaagggg gatttttttt ttcacctcct 1140
tgagaatttt tttttttaag cttatagtaa ggatacattc aagcttggtt aaaaaaaataa 1200 taataaaaca tgcatcattt ttcatttgcc aaccaagcac aaagttattt tatactgact 1260
gtatatttta aagtatactc tcagatatgg cctcttacag tatttaagat atagcaagga 1320
catggctgat tttttttttat aaaaattggc actaataagt gggtttattg gtcttttcta 1380
attgtataat ttaatttagt acaaagtttg taaaatatca gaggatatat atatattgtt 1440
tctacgacat ggtattgcat ttatatcttt ttactacagt gatctgtgac agcagcagct 1500
tcatgttgta tttttttttac tgaaattgta aaatatccat cttaaagaca tcaactattc 1560
taaaaattgt gtacaggata ttcctttagt ggtggaatta aaatgtacga atacttgctt 1620
tttcaaaaaa atgtattttc tgttaaaagt ttaaagattt ttgctatata ttatggaaga 1680
aaaatgtaat cgtaaatatt aattttgtac ctatattgtg caatacttga aaaaaacggt 1740
ataaaagtat tttgagtcag tgtcttacat gttaagaggg actgaaatag tttatattaa 1800
gtttgtatta aaattcttta aaattaaaaa 1830

<210> SEQ ID NO 190
<211> LENGTH: 60
<212> TYPE: DNA
<213> ORGANISM: Homo sapiens

<220> FEATURE:
<223> OTHER INFORMATION: NM_005749

<400> SEQUENCE: 190
aaacctctgc tctttctcct aatgccaagg aatttatttt tcctaatatg cagggtcaag 60

<210> SEQ ID NO 191
<211> LENGTH: 1534
<212> TYPE: DNA
<213> ORGANISM: Homo sapiens
<220> FEATURE:
<223> OTHER INFORMATION: NM_005804

<400> SEQUENCE: 191
ggaagcgcag caactcgtgt ctgagcgccc ggcggaaaac cgaagttgga agtgtctctt 60
agcagcgcgc ggagaagaac ggggagccag catcatggca gaacaggatg tggaaaacga 120
tcttttggat tacgatgaag aggaagagcc ccaggctcct caagagagca caccagctcc 180
ccctaagaaa gacatcaagg gatcctacgt ttccatccac agctctggct tccgggactt 240
tctgctgaag ccggagctcc tgcgggccat cgtggactgt ggctttgagc atccttctga 300
ggtccagcat gagtgcattc cccaggccat cctgggcatg gacgtcctgt gccaggccaa 360
gtccgggatg ggcaagacag cggtcttcgt gctggccacc ctacagcaga ttgagcctgt 420
caacggacag gtgacggtcc tggtcatgtg ccacacgagg gagctggcct tccagatcag 480
caaggaatat gagcgctttt ccaagtacat gcccagcgtc aaggtgtctg tgttcttcgg 540
tggtctctcc atcaagaagg atgaagaagt gttgaagaag aactgtcccc atgtcgtggt 600
ggggaccccg ggccgcatcc tggcgctcgt gcggaatagg agcttcagcc taaagaatgt 660
gaagcacttt gtgctggacg agtgtgacaa gatgctggag cagctggaca tgcggcggga 720
tgtgcaggag atcttccgcc tgacaccaca cgagaagcag tgcatgatgt tcagcgccac 780
cctgagcaag gacatccggc ctgtgtgcag gaagttcatg caggatccca tggaggtgtt 840
tgtggacgac gagaccaagc tcacgctgca cggcctgcag cagtactacg tcaaactcaa 900
agacagtgag aagaaccgca agctctttga tctcttggat gtgctggagt ttaaccaggt 960
gataatcttc gtcaagtcag tgcagcgctg catggccctg gcccagctcc tcgtggagca 1020
gaacttcccg gccatcgcca tccaccgggg catggcccag gaggagcgcc tgtcacgcta 1080
tcagcagttc aaggatttcc agcggcggat cctggtggcc accaatctgt ttggccgggg 1140
gatggacatc gagcgagtca acatcgtctt taactacgac atgcctgagg actcggacac 1200
ctacctgcac cgggtggccc gggcgggtcg ctttggcacc aaaggcctag ccatcacttt 1260
tgtgtctgac gagaatgatg ccaaaatcct caatgacgtc caggaccggt ttgaagttaa 1320
tgtggcagaa cttccagagg aaatcgacat ctccacatac atcgagcaga gccggtaacc 1380
accacgtgcc agagccgccc acccggagcc gcccgcatgc agcttcacct cccctttcca 1440
ggcgccactg ttgagaagct agagattgta tgagaataaa cttgttatta tggaaaaaaa 1500
aaaaaaaaaa aaaaaaaaaa aaaaaaaaaa aaaa 1534

<210> SEQ ID NO 192
<211> LENGTH: 60
<212> TYPE: DNA
<213> ORGANISM: Homo sapiens
<220> FEATURE:
<223> OTHER INFORMATION: NM_005804

<400> SEQUENCE: 192
gttgagaagc tagagattgt atgagaataa agtgttatta tgaaatgaag aagcctcacc 60

<210> SEQ ID NO 193
<211> LENGTH: 1416
<212> TYPE: DNA
<213> ORGANISM: Homo sapiens
<220> FEATURE:
<221> NAME/KEY: Modified_base
<222> LOCATION: 1 ... 1416
<223> OTHER INFORMATION: n = a,c,g, or t
<220> FEATURE:
<223> OTHER INFORMATION: NM_005945

<400> SEQUENCE: 193

```
aggaattccg gaattccgga attccgatgg atggaacaga aaataaatct aagtttggtg     60
cgaacgccat tctgggggtg tcccttgccg tctgcaaagc tggtgccgtt gagaaggggg    120
tcccctgtac cgccacatcg cgtacttggc tggcaacttc gaagtcatcc tgccagtccc    180
ggcgttcaag tgtcatcatc aatggcggtt ctcatgctgg caacaagctg gccatgcaga    240
gtctgtcctc ccagtcggtg cagcaaactc agggaagcca tgccgcattg gagcagaggt    300
ttaccacaac ctgaagaatg tcatcaagga gaaatatggg aaagatgcca ccaatgtggg    360
gatttgcgcg ggtttgctcc caacatcctg gagaataaag aaggcctgga gctgctgaag    420
actgctattg gaaagcctgg cctacactgt aaaggtggtc atggcatgga cgtagcggcc    480
tccgagttct tcaggtcagg gaactatgac ctggacttca agtctcccga tgaccccagc    540
aggtacatct cgcctgacca gctggctgac ctgtacaagt ccttcatcaa ggactaccca    600
gtggtgtcta tcgaagatcc ctttgaccag gatgactggg gagcttcaga agttcacagc    660
cagtgcagga atccaggtag tggggggatg actcacagtg accaacccaa agaggatcgc    720
caaggcgtga acgagaagtc ctgcaactgc ctcctgctca aagtcaacca gattggctcc    780
gtgaccgagt ctcttcaggc gtgcaagctg gcccaggcca atggttgggg cgtcatggtg    840
tctcatcgtt cgggggagac tgaagatacc ttcatcgctg acctggttgt ggggctgtgc    900
actggggcag atcaagactg gtgccccttg ccgatcacgc gcttggccaa gtacaaccag    960
ctcctcagaa ttgaagagga gctgggcagc aaggctaagt ttgccggcag gaacttcaga   1020
aacccettgg ccaagtaagc tgtgggcagg caagccttcg gtcacctgtt ggctacagac   1080
ccctcccctg gtgtcagctc aggcagctcg aggcccccga ccaacacttg caggggtccc   1140
tgctagttag cgcccaccgc cgtggagttc gtaccgcttc cttagaactc tacagaagcc   1200
aagctccctg gaagccctgt tggcagctct agctttgcag ttgtgtaatt ggcccaagtc   1260
attgtttttc tcgccttact ttccaccaag tgtctagagt catgtgagcc tngtgtcatc   1320
tccggggtgg ccacaggcta gatccccggt ggttttgtgc tcaaaataaa aagcctcagt   1380
gacccatgaa aaaaaaaaag gaattccgga attccg                              1416
```

<210> SEQ ID NO 194
<211> LENGTH: 60
<212> TYPE: DNA
<213> ORGANISM: Homo sapiens
<220> FEATURE:
<223> OTHER INFORMATION: NM_005945

<400> SEQUENCE: 194

```
ttgtgtaatt ggcccaagtc attgtttttc tcgccttact ttccaccaag tgtctagagt     60
```

<210> SEQ ID NO 195
<211> LENGTH: 961
<212> TYPE: DNA
<213> ORGANISM: Homo sapiens

<220> FEATURE:
<223> OTHER INFORMATION: NM_006014

<400> SEQUENCE: 195
ggcgaccacg gtgtcttcaa aagccccgtc agggttggct tcctggggcc ggaccgactg 60
tgggtcagtt tgcaccagcg ctctggaatc gagttacgcg cgaaagggca gagtttctgg 120
aggaaaccgc agcctctcaa ccgctgaccg ggtctcagaa ggcccccggc agggccgctt 180
ggcgggaact gaccacgcgc cagtcaggct ctccagggac ctgcgcaggc gcgtgtgggc 240
ggagtcgtgc gcagggggcg gggcttcggg aaggagccac agagagggcg gggcgtagga 300
cctgcgcttc gggggtggag tcggagcggc gcggcggcgg tcatgcggga cgcggatgca 360
gacgcaggcg gaggcgctga cggcggggat ggccggggtg gccacagctg ccgcgggggc 420
gtggacacag ccgcagctcc ggccggtgga gctcccccag cgcacgcgcc aggtccgggc 480
agagacgccg cgtctgcggc caggggggtca cgaatgcggc cgcacatatt caccctcagc 540
gtgcctttcc cgaccccctt ggaggcggaa atcgcccatg ggtccctggc accagatgcc 600
gagccccacc aaagggtggt tgggaaggat ctcacagtga gtggcaggat cctggtcgtc 660
cgctggaaag ctgaagactg tcgcctgctc cgaatttccg tcatcaactt tcttgaccag 720
ctttccctgg tggtgcggac catgcagcgc tttgggcccc ccgtttcccg ctaagcctgg 780
cctgggcaaa tggagcgagg tcccactttg cgtctccttg taggcagtgc gtccatcctt 840
ccctagggca ggaattccca cagttgctac tttcctggga gggcctcatg ttttatctgg 900
ttcttaaatg tttgttacta cagaaaataa aactgcgcta ctaaaaaaaa aaaaaaaaaa 960
a 961

<210> SEQ ID NO 196
<211> LENGTH: 60
<212> TYPE: DNA
<213> ORGANISM: Homo sapiens
<220> FEATURE:
<223> OTHER INFORMATION: NM_006014

<400> SEQUENCE: 196
ggcctcatgt tttatctggt tcttaaatgt ttgttactac agaaaataaa actgaggtat 60

<210> SEQ ID NO 197
<211> LENGTH: 1648
<212> TYPE: DNA
<213> ORGANISM: Homo sapiens
<220> FEATURE:
<223> OTHER INFORMATION: NM_006086

<400> SEQUENCE: 197
atgcgggaga tcgtgcacat ccaggccggc cagtgcggca accagatcgg ggccaagttc 60
tgggaagtca tcagtgatga gcatggcatc gaccccagcg gcaactacgt gggcgactcg 120
gacttgcagc tggagcggat cagcgtctac tacaacgagg cctcttctca caagtacgtg 180
cctcgagcca ttctggtgga cctggaaccc ggaaccatgg acagtgtccg ctcaggggcc 240
tttggacatc tcttcaggcc tgacaatttc atctttggtc agagtggggc cggcaacaac 300
tgggccaagg gtcactacac ggagggggcg gagctggtgg attcggtcct ggatgtggtg 360
cggaaggagt gtgaaaactg cgactgcctg cagggcttcc agctgaccca ctcgctgggg 420
ggggggacgg gctccggcat gggcacgttg ctcatcagca aggtgcgtga ggagtatccc 480
gaccgcatca tgaacacctt cagcgtcgtg ccctcaccca aggtgtcaga cacggtggtg 540
gaaccctaca acgccacgct gtccatccac cagctggtgg aaaacacgga tgaaacctac 600
tgcatcgaca acgaggcgct ctacgacatc tgcttccgca ccctcaagct ggccacgccc 660
acctacgggg acctcaacca cctggtatcg gccaccatga gcggagtcac cacctccttg 720
cgcttcccgg gccagctcaa cgctgacctg cgcaagctgg ccgtcaacat ggtgcccttc 780
ccgcgcctgc acttcttcat gcccggcttc gcccccctca ccaggcgggg cagccagcag 840
taccgggccc tgaccgtgcc cgagctcacc cagcagatgt tcgatgccaa gaacatgatg 900
gccgcctgcg acccgcgcca cggccgctac ctgacggtgg ccaccgtgtt ccggggccgc 960
atgtccatga aggaggtgga cgagcagatg ctggccatcc agagcaagaa cagcagctac 1020
ttcgtggagt ggatccccaa caacgtgaag gtggccgtgt gtgacatccc gccccgcggc 1080
ctcaagatgt cctccacctt catcgggaac agcacggcca tccaggagct gttcaagcgc 1140
atctccgagc agttcacggc catgttccgg cgcaaggcct tcctgcactg gtacacgggc 1200
gagggcatgg acgagatgga gttcaccgag gccgagagca acatgaacga cctggtgtcc 1260
gagtaccagc agtaccagga cgccacggcc gaggaagagg gcgagatgta cgaagacgac 1320
gaggaggagt cggaggccca gggccccaag tgaaactgct cgcagctgga gtgagaggca 1380
ggtggcggcc ggggccgaag ccagcagtgt ctaaaccccc ggagccatct tgctgccgac 1440
accctgcttt ccccatcgcc ctagggctcc cttgccgccc tcctgcagta tttatggcct 1500
cgtcctcccc cacctaggcc acgtgtgagc tgctcctgtc tctgtcttat tgcagctcca 1560
ggcctgacgt tttacggttt tgttttttac tggtttgtgt ttatattttc ggggatactt 1620
aataaatcta ttgctgtcag ataccctt 1648

<210> SEQ ID NO 198
<211> LENGTH: 60
<212> TYPE: DNA
<213> ORGANISM: Homo sapiens
<220> FEATURE:
<223> OTHER INFORMATION: NM_006086

<400> SEQUENCE: 198
tttttactgg tttgtgttta tattttcggg gatacttaat aaatctattg ctgtcagata 60

<210> SEQ ID NO 199
<211> LENGTH: 3074
<212> TYPE: DNA
<213> ORGANISM: Homo sapiens
<220> FEATURE:
<223> OTHER INFORMATION: NM_006096

<400> SEQUENCE: 199
aacaaacctc gcctggctcc cagctggtgc tgaagctcgt cagttcacca tccgccctcg 60
gcttccgcgg ggcgctgggc cgccagcctc ggcaccgtcc tttcctttct ccctcgcgtt 120
aggcaggtga cagcagggac atgtctcggg agatgcagga tgtagacctc gctgaggtga 180
agcctttggt ggagaaaggg gagaccatca ccggcctcct gcaagagttt gatgtccagg 240
agcaggacat cgagacttta catggctctg ttcacgtcac gctgtgtggg actcccaagg 300
gaaaccggcc tgtcatcctc acctaccatg acatcggcat gaaccacaaa acctgctaca 360
accccctctt caactacgag gacatgcagg agatcaccca gcactttgcc gtctgccacg 420
tggacgcccc tggccagcag gacggcgcag cctccttccc cgcagggtac atgtacccct 480
ccatggatca gctggctgaa atgcttcctg gagtccttca acagtttggg ctgaaaagca 540
ttattggcat gggaacagga gcaggcgcct acatcctaac tcgatttgct ctaaacaacc 600
ctgagatggt ggagggcctt gtccttatca acgtgaaccc ttgtgcggaa ggctggatgg 660

-continued

```
actgggccgc ctccaagatc tcaggatgga cccaagctct gccggacatg gtggtgtccc    720
accttttggg gaaggaagaa atgcagagta acgtggaagt ggtccacacc taccgccagc    780
acattgtgaa tgacatgaac ccgggcaacc tgcacctgtt catcaatgcc tacaacagcc    840
ggcgcgacct ggagattgag cgaccaatgc cgggaaccca cacagtcacc ctgcagtgcc    900
ctgctctgtt ggtggttggg gacagctcgc ctgcagtgga tgccgtggtg gagtgcaact    960
caaaattgga cccaacaaag accactctcc tcaagatggc ggactgtggc ggcctcccgc   1020
agatctccca gccggccaag ctcgctgagg ccttcaagta cttcgtgcag ggcatgggat   1080
acatgccctc ggctagcatg acccgcctga tgcggtcccg cacagcctct ggttccagcg   1140
tcacttctct ggatggcacc cgcagccgct cccacaccag cgagggcacc cgaagccgct   1200
cccacaccag cgagggcacc cgcagccgct cgcacaccag cgagggggcc cacctggaca   1260
tcacccccaa ctcgggtgct gctgggaaca gcgccgggcc caagtccatg gaggtctcct   1320
gctaggcggc ctgcccagct gccgccccg gactctgatc tctgtagtgg cccccctcctc  1380
cccggcccct tttcgccccc tgcctgccat actgcgccta actcggtatt aatccaaagc   1440
ttattttgta agagtgagct ctggtggaga caaatgaggt ctattacgtg ggtgccctct   1500
ccaaaggcgg ggtggcggtg gaccaaagga aggaagcaag catctccgca tcgcatcctc   1560
ttccattaac cagtggccgg ttgccactct cctcccctcc ctcagagaca ccaaactgcc   1620
aaaaacaaga cgcgtagcag cacacacttc acaaagccaa gcctaggccg ccctgagcat   1680
cctggttcaa acgggtgcct ggtcagaagg ccagccgccc acttcccgtt tcctctttaa   1740
ctgaggagaa gctgatccag tttccggaaa caaaatcctt ttctcatttg gggagggggg   1800
taatagtgac atgcaggcac ctcttttaaa caggcaaaac aggaaggggg aaaaggtggg   1860
attcatgtcg aggctagagg catttggaac aacaaatcta cgtagttaac ttgaagaaac   1920
cgatttttaa agttggtgca tctagaaagc tttgaatgca gaagcaaaca agcttgattt   1980
ttctagcatc ctcttaatgt gcagcaaaag caggcgacaa aatctcctgg ctttacagac   2040
aaaaatattt cagcaaacgt tggcatcat ggtttttgaa ggctttagtt ctgctttctg    2100
cctctcctcc acagccccaa cctcccaccc ctgatacatg agccagtgat tattcttgtt   2160
cagggagaag atcatttaga tttgttttgc attccttaga atggagggca acattccaca   2220
gctgccctgg ctgtgatgag tgtccttgca ggggccggag taggagcact ggggtggggg   2280
tggaattggg gttactcgat gtaagggatt ccttgttgtt gtgttgagat ccagtgcagt   2340
tgtgatttct gtggatccca gcttggttcc aggaattttg tgtgattggc ttaaatccag   2400
ttttcaatct tcgacagctg ggctggaacg tgaactcagt agctgaacct gtctgacccg   2460
gtcacgttct tggatcctca gaactctttg ctcttgtcgg ggtgggggtg ggaactcacg   2520
tggggagcgg tggctgagaa aatgtaagga ttctggaata catattccat gggactttcc   2580
ttccctctcc tgcttcctct tttcctgctc cctaaccttt cgccgaatgg ggcagcacca   2640
ctgacgtttc tgggcggcca gtgcggctgc caggttcctg tactactgcc ttgtactttt   2700
cattttggct caccgtggat ttttctcatag gaagtttggt cagagtgaat tgaatattgt  2760
aagtcagcca ctgggacccg aggatttctg ggaccccgca gttgggagga ggaagtagtc   2820
cagccttcca ggtggcgtga gaggcaatga ctcgttacct gccgcccatc accttggagg   2880
ccttccctgg ccttgagtag aaaagtcggg gatcggggca agagaggctg agtacggatg   2940
ggaaactatt gtgcacaagt ctttccagag gagtttctta atgagatatt tgtatttatt   2980
tccagaccaa taaatttgta actttgcagc ggaaaaaaaa aaaaaaaaaa aaaaaaaaaa   3060
```

aaaaaaaaaa aaaa 3074

<210> SEQ ID NO 200
<211> LENGTH: 60
<212> TYPE: DNA
<213> ORGANISM: Homo sapiens
<220> FEATURE:
<223> OTHER INFORMATION: NM_006096

<400> SEQUENCE: 200
gagtacggat gggaaactat tgtgcacaag tctttccaga ggagtttctt aatgagatat 60

<210> SEQ ID NO 201
<211> LENGTH: 2148
<212> TYPE: DNA
<213> ORGANISM: Homo sapiens
<220> FEATURE:
<223> OTHER INFORMATION: NM_006115

<400> SEQUENCE: 201
gcttcagggt acagctcccc cgcagccaga agccgggcct gcagcgcctc agcaccgctc 60
cgggacaccc cacccgcttc ccaggcgtga cctgtcaaca gcaacttcgc ggtgtggtga 120
actctctgag gaaaaaccat tttgattatt actctcagac gtgcgtggca acaagtgact 180
gagacctaga aatccaagcg ttggaggtcc tgaggccagc ctaagtcgct tcaaaatgga 240
acgaaggcgt ttgtggggtt ccattcagag ccgatacatc agcatgagtg tgtggacaag 300
cccacggaga cttgtggagc tggcagggca gagcctgctg aaggatgagg ccctggccat 360
tgccgccctg gagttgctgc ccagggagct cttcccgcca ctcttcatgg cagcctttga 420
cgggagacac agccagaccc tgaaggcaat ggtgcaggcc tggcccttca cctgcctccc 480
tctgggagtg ctgatgaagg gacaacatct tcacctggag accttcaaag ctgtgcttga 540
tggacttgat gtgctccttg cccaggaggt tcgccccagg aggtggaaac ttcaagtgct 600
ggatttacgg aagaactctc atcaggactt ctggactgta tggtctggaa acagggccag 660
tctgtactca tttccagagc cagaagcagc tcagcccatg acaaagaagc gaaaagtaga 720
tggtttgagc acagaggcag agcagccctt cattccagta gaggtgctcg tagacctgtt 780
cctcaaggaa ggtgcctgtg atgaattgtt ctcctacctc attgagaaag tgaagcgaaa 840
gaaaaatgta ctacgcctgt gctgtaagaa gctgaagatt tttgcaatgc ccatgcagga 900
tatcaagatg atcctgaaaa tggtgcagct ggactctatt gaagatttgg aagtgacttg 960
tacctggaag ctacccacct tggcgaaatt ttctccttac ctgggccaga tgattaatct 1020
gcgtagactc ctcctctccc acatccatgc atcttcctac atttccccgg agaaggaaga 1080
gcagtatatc gcccagttca cctctcagtt cctcagtctg cagtgcctgc aggctctcta 1140
tgtggactct ttatttttcc ttagaggccg cctggatcag ttgctcaggc acgtgatgaa 1200
ccccttggaa accctctcaa taactaactg ccggctttcg gaaggggatg tgatgcatct 1260
gtcccagagt cccagcgtca gtcagctaag tgtcctgagt ctaagtgggg tcatgctgac 1320
cgatgtaagt cccgagcccc tccaagctct gctggagaga gcctctgcca ccctccagga 1380
cctggtcttt gatgagtgtg ggatcacgga tgatcagctc cttgccctcc tgccttccct 1440
gagccactgc tcccagctta caaccttaag cttctacggg aattccatct ccatatctgc 1500
cttgcagagt ctcctgcagc acctcatcgg gctgagcaat ctgacccacg tgctgtatcc 1560
tgtccccctg gagagttatg aggacatcca tggtaccctc cacctggaga ggcttgccta 1620
tctgcatgcc aggctcaggg agttgctgtg tgagttgggg cggcccagca tggtctggct 1680
tagtgccaac ccctgtcctc actgtgggga cagaaccttc tatgacccgg agcccatcct 1740
gtgcccctgt ttcatgccta actagctggg tgcacatatc aaatgcttca ttctgcatac 1800
ttggacacta aagccaggat gtgcatgcat cttgaagcaa caaagcagcc acagtttcag 1860
acaaatgttc agtgtgagtg aggaaaacat gttcagtgag gaaaaaacat tcagacaaat 1920
gttcagtgag gaaaaaaagg ggaagttggg gataggcaga tgttgacttg aggagttaat 1980
gtgatctttg gggagataca tcttatagag ttagaaatag aatctgaatt tctaaaggga 2040
gattctggct tgggaagtac atgtaggagt taatccctgt gtagactgtt gtaaagaaac 2100
tgttgaaaat aaagagaagc aatgtgaagc aaaaaaaaaa aaaaaaaa 2148

<210> SEQ ID NO 202
<211> LENGTH: 60
<212> TYPE: DNA
<213> ORGANISM: Homo sapiens
<220> FEATURE:
<223> OTHER INFORMATION: NM_006115

<400> SEQUENCE: 202
tggggagata catcttatag agttagaaat agaatctgaa tttctaaagg gagattctgg 60

<210> SEQ ID NO 203
<211> LENGTH: 1051
<212> TYPE: DNA
<213> ORGANISM: Homo sapiens
<220> FEATURE:
<223> OTHER INFORMATION: NM_006332

<400> SEQUENCE: 203
ggaccgccgc ctggttaaag gcgcttattt cccaggcagc cgctgcagtc gccacacctt 60
tgcccctgct gcgatgaccc tgtcgccact tctgctgttc ctgccaccgc tgctgctgct 120
gctggacgtc cccacggcgg cggtgcaggc gtcccctctg caagcgttag acttctttgg 180
gaatgggcca ccagttaact acaagacagg caatctatac ctgcgggggc ccctgaagaa 240
gtccaatgca ccgcttgtca atgtgaccct ctactatgaa gcactgtgcg gtggctgccg 300
agccttcctg atccgggagc tcttcccaac atggctgttg gtcatggaga tcctcaatgt 360
cacgctggtg ccctacggaa acgcacagga acaaaatgtc agtggcaggt gggagttcaa 420
gtgccagcat ggagaagagg agtgcaaatt caacaaggtg gaggcctgcg tgttggatga 480
acttgacatg gagctagcct tcctgaccat tgtctgcatg gaagagtttg aggacatgga 540
gagaagtctg ccactatgcc tgcagctcta cgccccaggg ctgtcgccag acactatcat 600
ggagtgtgca atgggggacc gcggcatgca gctcatgcac gccaacgccc agcggacaga 660
tgctctccag ccaccacacg agtatgtgcc ctgggtcacc gtcaatggga aacccttgga 720
agatcagacc cagctcctta cccttgtctg ccagttgtac cagggcaaga agccggatgt 780
ctgcccttcc tcaaccagct ccctcaggag tgtttgcttc aagtgatggc cggtgagctg 840
cggagagctc atggaaggcg agtgggaacc cggctgcctg cctttttttc tgatccagac 900
cctcggcacc tgctacttac caactggaaa attttatgca tcccatgaag cccagataca 960
caaaattcca ccccatgatc aagaatcctg ctccactaag aatggtgcta aagtaaaact 1020
agtttaataa gcaaaaaaaa aaaaaaaaaa a 1051

<210> SEQ ID NO 204
<211> LENGTH: 60
<212> TYPE: DNA
<213> ORGANISM: Homo sapiens

<220> FEATURE:
<223> OTHER INFORMATION: NM_006332

<400> SEQUENCE: 204
aaattccacc cctagatcaa gaatcctgct ccactaagaa tggtgctaaa gtaaaactag 60

<210> SEQ ID NO 205
<211> LENGTH: 1714
<212> TYPE: DNA
<213> ORGANISM: Homo sapiens
<220> FEATURE:
<223> OTHER INFORMATION: NM_006417

<400> SEQUENCE: 205
ggggcatttt gtgcctgcct agctatccag acagagcagc taccctcagc tctagctgat 60
actacagaca gtacaacaga tcaagaagta tggcagtgac aactcgtttg acacggttgc 120
acgaaaagat cctgcaaaat cattttggag ggaagcggct tagccttctc tataagggta 180
gtgtccatgg attccgtaat ggagttttgc ttgacagatg ttgtaatcaa gggcctactc 240
taacagtgat ttatagtgaa gatcatatta ttggagcata tgcggaagag agttaccagg 300
aaggaaagta tgcttccatc atcctttttg cacttcaaga tactaaaatt tcagaatgga 360
aactaggact atgtacacca gaaacactgt tttgttgtga tgttacaaaa tataactccc 420
caactaattt ccagatagat ggaagaaata gaaaagtgat tatggactta aagacaatgg 480
aaaatcttgg acttgctcaa aattgtacta tctctattca ggattatgaa gtttttcgat 540
gcgaagattc actggatgaa agaaagataa aaggggtcat tgagctcagg aagagcttac 600
tgtctgcctt gagaacttat gaaccatatg gatccctggt tcaacaaata cgaattctgc 660
tgctgggtcc aattggagct gggaagtcca gctttttcaa ctcagtgagg tctgttttcc 720
aagggcatgt aacgcatcag gctttggtgg gcactaatac aactgggata tctgagaagt 780
ataggacata ctctattaga gacgggaaag atggcaaata cctgccgttt attctgtgtg 840
actcactggg gctgagtgag aaagaaggcg gcctgtgcag ggatgacata ttctatatct 900
tgaacggtaa cattcgtgat agataccagt ttaatcccat ggaatcaatc aaattaaatc 960
atcatgacta cattgattcc ccatcgctga aggacagaat tcattgtgtg gcatttgtat 1020
ttgatgccag ctctattcaa tacttctcct ctcagatgat agtaaagatc aaaagaattc 1080
gaagggagtt ggtaaacgct ggtgtggtac atgtggcttt gctcactcat gtggatagca 1140
tggatttgat tacaaaaggt gaccttatag aaatagagag atgtgagcct gtgaggtcca 1200
agctagagga agtccaaaga aaacttggat ttgctctttc tgacatctcg gtggttagca 1260
attattcctc tgagtgggag ctggaccctg taaaggatgt tctaattctt tctgctctga 1320
gacgaatgct atgggctgca gatgacttct tagaggattt gccttttgag caaataggga 1380
atctaaggga ggaaattatc aactgtgcac aaggaaaaaa atagatatgt gaaaggttca 1440
cgtaaatttc ctcacatcac agaagattaa aattcagaaa ggagaaaaca cagaccaaag 1500
agaagtatct aagaccaaag ggatgtgttt tattaatgtc taggatgaag aaatgcatag 1560
aacattgtag tacttgtaaa taactagaaa taacatgatt tagtcataat tgtgaaaaat 1620
agtaataatt tttcttggat ttatgttctg tatctgtgaa aaaataaatt tcttataaaa 1680
ctcggaaaaa aaaaaaaaaa aaaaaaaaaa aaaa 1714

<210> SEQ ID NO 206
<211> LENGTH: 60
<212> TYPE: DNA
<213> ORGANISM: Homo sapiens

<220> FEATURE:
<223> OTHER INFORMATION: NM_006417

<400> SEQUENCE: 206
atgacatatt ctatatcttg aacggtaaca ttcgtgatag ataccagttt aatcccatgg 60

<210> SEQ ID NO 207
<211> LENGTH: 3791
<212> TYPE: DNA
<213> ORGANISM: Homo sapiens
<220> FEATURE:
<223> OTHER INFORMATION: NM_006461

<400> SEQUENCE: 207
acagacggcg ggtgaacatg gcgtcctcga cttggtctga gacgtgatag gcctgccttc 60
tggttgaaga tgtggcgagt gaaaaaactg agcctcagcc tgtcgccttc gccccagacg 120
ggaaaaccat ctatgagaac tcctctccgt gaacttaccc tgcagcccgg tgccctcacc 180
acctctggaa aaagatcccc cgcttgctcc tcgctgaccc catcactgtg caagctgggg 240
ctgcaggaag gcagcaacaa ctcgtctcca gtggattttg taaataacaa gaggacagac 300
ttatcttcag aacatttcag tcattcctca aagtggctag aaacttgtca gcatgaatca 360
gatgagcagc ctctagatcc aattccccaa attagctcta ctcctaaaac gtctgaggaa 420
gcagtagacc cactgggcaa ttatatggtt aaaaccatcg tccttgtacc atctccactg 480
gggcagcaac aagacatgat atttgaggcc cgtttagata ccatggcaga gacaaacagc 540
atatctttaa atggaccttt gagaacagac gatctggtga gagaggaggt ggcaccctgc 600
atgggagaca ggttttcaga agttgctgct gtatctgaga aacctatctt tcaggaatct 660
ccgtcccatc tcttagagga gtctccacca aatccctgtt ctgaacaact acattgctcc 720
aaggaaagcc tgagcagtag aactgaggct gtgcgtgagg acttagtacc ttctgaaagt 780
aacgccttct tgccttcctc tgttctctgg ctttcccctt caactgcctt ggcagcagat 840
ttccgtgtca atcatgtgga cccagaggag gaaattgtag agcatggagc tatggaggaa 900
agagaaatga ggtttcccac acatcctaag gagtctgaaa cagaagatca agcacttgtc 960
tcaagtgtgg aagatattct gtccacatgc ctgacaccaa atctagtaga aatggaatcc 1020
caagaagctc caggcccagc agtagaagat gttggtagga ttcttggctc tgatacagag 1080
tcttggatgt ccccactggc ctggctggaa aaaggtgtaa atacctccgt catgctggaa 1140
aatctccgcc aaagcttatc ccttccctcg atgcttcggg atgctgcaat tggcactacc 1200
cctttctcta cttgctcggt ggggacttgg tttactcctt cagcaccaca ggaaaagagt 1260
acaaacacat cccagacagg cctggttggc accaagcaca gtacttctga gacagagcag 1320
ctcctgtgtg gccggcctcc agatctgact gccttgtctc gacatgactt ggaagataac 1380
ctgctgagct ctcttgtcat tgtggagttt ctctcccgcc agcttcggga ctggaagagc 1440
cagctggctg tccctcaccc agaaacccag gacagtagca cacagactga cacatctcac 1500
agtgggataa ctaataaact tcagcatctt aaggagagcc atgagatggg acaggcccta 1560
cagcaggcca gaaatgtcat gcaatcatgg gtgcttatct ctaaagagct gatatccttg 1620
cttcacctat ccctgttgca tttagaagaa gataagacta ctgtgaatca ggagtctcgg 1680
cgtgcagaaa cattggtctg ttgctgtttt gatttgctga agaaattgag ggcaaagctc 1740
cagagcctca aagcagaaag ggaggaggca aggcacagag aggaaatggc tctcagaggc 1800
aaggatgcgg cagagatagt gttggaggct ttctgtgcac acgccagcca gcgcatcagc 1860
cagctggaac aggacctagc atccatgcgg gaattcagag gccttctgaa ggatgcccag 1920
acccaactgg tagggcttca tgccaagcaa gaagagctgg ttcagcagac agtgagtctt 1980
acttctacct tgcaacaaga ctggaggtcc atgcaactgg attatacaac atggacagct 2040
ttgctgagtc ggtcccgaca actcacagag aaactcacag tcaagagcca gcaagccctg 2100
caggaacgtg atgtggcaat tgaggaaaag caggaggttt ctagggtgct ggaacaagtc 2160
tctgcccagt tagaggagtg caaaggccaa acagaacaac tggagttgga aaacattcgt 2220
ctagcaacag atctccgggc tcagttgcag attctggcca acatggacag ccagctaaaa 2280
gagctacaga gtcagcatac ccattgtgcc caggacctgg ctatgaagga tgagttactc 2340
tgccagctta cccagagcaa tgaggagcag gctgctcaat gcgtaaagga agagatggca 2400
ctaaaacaca tgcaggcaga actgcagcag caacaagctg tcctggccaa agaggtgcgg 2460
gacctgaaag agaccttgga gtttgcagac caggagaatc aggttgctca cctggagctg 2520
ggtcaggttg agtgtcaatt gaaaaccaca ctggaagtgc tccgggagcg cagcttgcag 2580
tgtgagaacc tcaaggacac tgtagagaac ctaacggcta aactggccag caccatagca 2640
gataaccagg agcaagatct ggagaaaaca cggcagtact ctcaaaagct agggctgctg 2700
actgagcaac tacagagcct gactctcttt ctacagacaa aactaaagga gaagactgaa 2760
caagagaccc ttctgctgag tacagcctgt cctcccaccc aggaacaccc tctgcctaat 2820
gacaggacct tcctgggaag catcttgaca gcagtggcag atgaagagcc agaatcaact 2880
cctgtgccct tgcttggaag tgacaagagt gctttcaccc gagtagcatc aatggtttcc 2940
cttcagcccg cagagacccc aggcatggag gagagcctgg cagaaatgag tattatgact 3000
actgagcttc agagtctttg ttccctgcta caagagtcta aagaagaagc catcaggact 3060
ctgcagcgaa aaatttgtga gctgcaagct aggctgcagg cccaggaaga acagcatcag 3120
gaagtccaga aggcaaaaga agcagacata gagaagctga accaggcctt gtgcttgcgc 3180
tacaagaatg aaaaggagct ccaggaagtg atacagcaga atgagaagat cctagaacag 3240
atagacaaga gtggcgagct cataagcctt agagaggagg tgacccacct tacccgctca 3300
cttcggcgtg cggagacaga gaccaaagtg ctccaggagg cctggcaggc cagctggact 3360
ccaactgcca gcctatggcc accaattgga tccaggagaa agtgtggctc tctcaggagg 3420
tggacaaact gagagtgatg ttcctggaga tgaaaaatga gaaggaaaac tcctgatcaa 3480
gttccagagc ccatagaaat atcctagagg agaaccttcg gcgctctgac aaggagttag 3540
aaaaactaga tgacattgtt cagcatattt ataagaccct gctctctatt ccagaggtgg 3600
tgaggggatg caaagaacta cagggattgc tggaatttct gagctaagaa actgaaagcc 3660
agaatttgtt tcacctcttt ttacctgcaa tacccctta ccccaatacc aagaccaact 3720
ggcatagagc caactgagat aaatgctatt taaataaagt gtatttaatg aaaaaaaaaa 3780
aaaaaaaaaa a 3791

<210> SEQ ID NO 208
<211> LENGTH: 60
<212> TYPE: DNA
<213> ORGANISM: Homo sapiens
<220> FEATURE:
<223> OTHER INFORMATION: NM_006461

<400> SEQUENCE: 208
ctgacaagga gttagaaaaa ctagatgaca ttgttcagca tatttataag accctgctct 60

<210> SEQ ID NO 209
<211> LENGTH: 2856

<212> TYPE: DNA
<213> ORGANISM: Homo sapiens
<220> FEATURE:
<223> OTHER INFORMATION: NM_006516

<400> SEQUENCE: 209

```
tagtcgcggg tccccgagtg agcacgccag ggagcaggag accaaacgac gggggtcgga     60
gtcagagtcg cagtgggagt ccccggaccg gagcacgagc ctgagcggga gagcgccgct    120
cgcacgcccg tcgccacccg cgtacccggc gcagccagag ccaccagcgc agcgctgcca    180
tggagcccag cagcaagaag ctgacgggtc gcctcatgct ggctgtggga ggagcagtgc    240
ttggctccct gcagtttggc tacaacactg gagtcatcaa tgccccccag aaggtgatcg    300
aggagttcta caaccagaca tgggtccacc gctatgggga gagcatcctg cccaccacgc    360
tcaccacgct ctggtccctc tcagtggcca tcttttctgt tgggggcatg attggctcct    420
tctctgtggg ccttttcgtt aaccgctttg gccggcggaa ttcaatgctg atgatgaacc    480
tgctggcctt cgtgtccgcc gtgctcatgg gcttctcgaa actgggcaag tcctttgaga    540
tgctgatcct gggccgcttc atcatcggtg tgtactgcgg cctgaccaca ggcttcgtgc    600
ccatgtatgt gggtgaagtg tcacccacag cctttcgtgg ggccctgggc accctgcacc    660
agctgggcat cgtcgtcggc atcctcatcg cccaggtgtt cggcctggac tccatcatgg    720
gcaacaagga cctgtggccc ctgctgctga gcatcatctt catcccggcc ctgctgcagt    780
gcatcgtgct gcccttctgc cccgagagtc cccgcttcct gctcatcaac cgcaacgagg    840
agaaccgggc caagagtgtg ctaaagaagc tgcgcgggac agctgacgtg acccatgacc    900
tgcaggagat gaaggaagag agtcggcaga tgatgcggga gaagaaggtc accatcctgg    960
agctgttccg ctcccccgcc taccgccagc ccatcctcat cgctgtggtg ctgcagctgt   1020
cccagcagct gtctggcatc aacgctgtct tctattactc cacgagcatc ttcgagaagg   1080
cgggggtgca gcagcctgtg tatgccacca ttggctccgg tatcgtcaac acggccttca   1140
ctgtcgtgtc gctgtttgtg gtggagcgag caggccggcg gaccctgcac ctcataggcc   1200
tcgctggcat ggcgggttgt gccatactca tgaccatcgc gctagcactg ctggagcagc   1260
taccctggat gtcctatctg agcatcgtgg ccatctttgg ctttgtggcc ttctttgaag   1320
tgggtcctgg ccccatccca tggttcatcg tggctgaact cttcagccag ggtccacgtc   1380
cagctgccat tgccgttgca ggcttctcca actggacctc aaatttcatt gtgggcatgt   1440
gcttccagta tgtggagcaa ctgtgtggtc cctacgtctt catcatcttc actgtgctcc   1500
tggttctgtt cttcatcttc acctacttca aagttcctga gactaaaggc cggaccttcg   1560
atgagatcgc ttccggcttc cggcaggggg gagccagcca aagtgataag acacccgagg   1620
agctgttcca tcccctgggg gctgattccc aagtgtgagt cgccccagat caccagcccg   1680
gcctgctccc agcagcccta aggatctctc aggagcacag gcagctggat gagacttcca   1740
aacctgacag atgtcagccg agccgggcct ggggctcctt tctccagcca gcaatgatgt   1800
ccagaagaat attcaggact taacggctcc aggattttaa caaaagcaag actgttgctc   1860
aaatctattc agacaagcaa caggttttat aatttttttta ttactgattt tgttattttt   1920
atatcagcct gagtctcctg tgcccacatc ccaggcttca ccctgaatgg ttccatgcct   1980
gagggtggag actaagccct gtcgagacac ttgccttctt cacccagcta atctgtaggg   2040
ctggacctat gtcctaagga cacactaatc gaactatgaa ctacaaagct tctatcccag   2100
gaggtggcta tggccacccg ttctgctggc ctggatctcc ccactctagg ggtcaggctc   2160
cattaggatt tgccccttcc catctcttcc tacccaacca ctcaaattaa tctttcttta   2220
```

cctgagacca gttgggagca ctggagtgca gggaggagag gggaagggcc agtctgggct 2280
gccgggttct agtctccttt gcactgaggg ccacactatt accatgagaa gagggcctgt 2340
gggagcctgc aaactcactg ctcaagaaga catggagact cctgccctgt tgtgtataga 2400
tgcaagatat ttatatatat ttttggttgt caatattaaa tacagacact aagttatagt 2460
atatctggac aagccaactt gtaaatacac cacctcactc ctgttactta cctaaacaga 2520
tataaatggc tggtttttag aaacatggtt ttgaaatgct tgtggattga gggtaggagg 2580
tttggatggg agtgagacag aagtaagtgg ggttgcaacc actgcaacgg cttagacttc 2640
gactcaggat ccagtccctt acacgtacct ctcatcagtg tcctcttgct caaaaatctg 2700
tttgatccct gttacccaga gaatatatac attctttatc ttgacattca aggcatttct 2760
atcacatatt tgatagttgg tgttcaaaaa aacactagtt ttgtgccagc cgtgatgctc 2820
aggcttgaaa tcgcattatt ttgaatgtga agggaa 2856

<210> SEQ ID NO 210
<211> LENGTH: 60
<212> TYPE: DNA
<213> ORGANISM: Homo sapiens
<220> FEATURE:
<223> OTHER INFORMATION: NM_006516

<400> SEQUENCE: 210
aaacagatat aaatggctgg tttttagaaa catggttttg aaatgcttgt ggattgaggg 60

<210> SEQ ID NO 211
<211> LENGTH: 576
<212> TYPE: DNA
<213> ORGANISM: Homo sapiens
<220> FEATURE:
<223> OTHER INFORMATION: NM_006607

<400> SEQUENCE: 211
atggctactc tgatctacgt tgataaggaa attggagaac caggcacccg tgtggctgcc 60
aaggatgtgc tgaagctgga gtctagacct tcaatcaaag cattagatgg gatatctcaa 120
gttttaacac cacgttttgg caaaacatac gatgctccat cagccttacc taaagctacc 180
agaaaggctt tgggcactgt caacagagct acagaaaagt cagtaaagac caatggaccc 240
agaaaacaaa aacagccaag cttttctgcc aaaaagatga ccgagaagac tgttaaaaca 300
aaaagttctg ttcctgcctc agatgacgcc tatccagaaa tagaaaaatt ctttcccttc 360
aatcttctag actttgagag ttttgacctg cctgaagagc gccagattgc acacctcccc 420
ttgagtggag tgcctctcat gatccttgat gaggagggag agcttgaaaa gctgtttcag 480
ctgggccccc cttcacctgt gaaaatgccc tctccaccat gggaatgcaa tctgtttgca 540
gtctccttca agcattctgt cgaccctgga tgttga 576

<210> SEQ ID NO 212
<211> LENGTH: 60
<212> TYPE: DNA
<213> ORGANISM: Homo sapiens
<220> FEATURE:
<223> OTHER INFORMATION: NM_006607

<400> SEQUENCE: 212
cgcctatcca gaaatagaaa aattctttcc cttcaatctt ctagactttg agagttttga 60

<210> SEQ ID NO 213
<211> LENGTH: 2058

<212> TYPE: DNA
<213> ORGANISM: Homo sapiens
<220> FEATURE:
<223> OTHER INFORMATION: NM_006820

<400> SEQUENCE: 213
gcacgaggaa gccacagatc tcttaagaac tttctgtctc caaaccgtgg ctgctcgata 60
aatcagacag aacagttaat cctcaattta agcctgatct aacccctaga aacagatata 120
gaacaatgga agtgacaaca agattgacat ggaatgatga aaatcatctg cgcaactgct 180
tggaaatgtt tctttgagtc ttctctataa gtctagtgtt catggaggta gcattgaaga 240
tatggttgaa agatgcagcc gtcagggatg tactataaca atggcttaca ttgattacaa 300
tatgattgta gcctttatgc ttggaaatta tattaattta cgtgaaagtt ctacagagcc 360
aaatgattcc ctatggtttt cacttcaaaa gaaaaatgac accactgaaa tagaaacttt 420
actcttaaat acagcaccaa aaattattga tgagcaactg gtgtgtcgtt tatcgaaaac 480
ggatattttc attatatgtc gagataataa aatttatcta gataaaatga taacaagaaa 540
cttgaaacta aggttttatg gccaccgtca gtatttggaa tgtgaagttt ttcgagttga 600
aggaattaag gataacctag acgacataaa gaggataatt aaagccagag agcacagaaa 660
taggcttcta gcagacatca gagactatag gccctatgca gacttggttt cagaaattcg 720
tattcttttg gtgggtccag ttgggtctgg aaagtccagt tttttcaatt cagtcaagtc 780
tatttttcat ggccatgtga ctggccaagc cgtagtgggg tctgatacca ccagcataac 840
cgagcggtat aggatatatt ctgttaaaga tggaaaaaat ggaaaatctc tgccatttat 900
gttgtgtgac actatggggc tagatggggc agaaggagca ggactgtgca tggatgacat 960
tccccacatc ttaaaaggtt gtatgccaga cagatatcag tttaattccc gtaaaccaat 1020
tacacctgag cattctactt ttatcacctc tccatctctg aaggacagga ttcactgtgt 1080
ggcttatgtc ttagacatca actctattga caatctctac tctaaaatgt tggcaaaagt 1140
gaagcaagtt cacaaagaag tattaaactg tggtatagca tatgtggcct tgcttactaa 1200
agtggatgat tgcagtgagg ttcttcaaga caacttttta aacatgagta gatctatgac 1260
ttctcaaagc cgggtcatga atgtccataa aatgctaggc attcctattt ccaatatttt 1320
gatggttgga aattatgctt cagatttgga actggacccc atgaaggata ttctcatcct 1380
ctctgcactg aggcagatgc tgcgggctgc agatgatttt ttagaagatt tgcctcttga 1440
ggaaactggt gcaattgaga gagcgttaca gccctgcatt tgagataagt tgccttgatt 1500
ctgacatttg gcccagcctg tactggtgtg ccgcaatgag agtcaatctc tattgacagc 1560
ctgcttcaga ttttgctttt gttcgttttg ccttctgtcc ttggaacagt catatctcaa 1620
gttcaaaggc caaaacctga gaagcggtgg gctaagatag gtcctactgc aaaccacccc 1680
tccatatttc cgtaccattt acaattcagt ttctgtgaca tctttttaaa ccactggagg 1740
aaaaatgaga tattctctaa tttattcttc tataacactc tatatagagc tatgtgagta 1800
ctaatcacat tgaataatag ttataaaatt attgtataga catctgcttc ttaaacagat 1860
tgtgagttct ttgagaaaca gcgtggattt tacttatctg tgtattcaca gagcttagca 1920
cagtgcctgg taatgagcaa gcatacttgc cattactttt ccttcccact ctctccaaca 1980
tcacattcac tttaaatttt tctgtatata gaaaggaaaa ctagcctggg caacatgatg 2040
aaaccccatc tccactgc 2058

<210> SEQ ID NO 214
<211> LENGTH: 60

<212> TYPE: DNA
<213> ORGANISM: Homo sapiens
<220> FEATURE:
<223> OTHER INFORMATION: NM_006820

<400> SEQUENCE: 214
tgagttcttt gagaaacagc gtggatttta cttatctgtg tattcacaga gcttagcaca 60

<210> SEQ ID NO 215
<211> LENGTH: 2825
<212> TYPE: DNA
<213> ORGANISM: Homo sapiens
<220> FEATURE:
<223> OTHER INFORMATION: NM_006845

<400> SEQUENCE: 215
gcgaaattga ggtttcttgg tattgcgcgt ttctcttcct tgctgactct ccgaatggcc 60
atggactcgt cgcttcaggc ccgcctgttt cccggtctcg ctatcaagat ccaacgcagt 120
aatggtttaa ttcacagtgc caatgtaagg actgtgaact tggagaaatc ctgtgtttca 180
gtggaatggg cagaaggagg tgccacaaag ggcaaagaga ttgattttga tgatgtggct 240
gcaataaacc cagaactctt acagcttctt cccttacatc cgaaggacaa tctgcccttg 300
caggaaaatg taacaatcca gaaacaaaaa cggagatccg tcaactccaa aattcctgct 360
ccaaaagaaa gtcttcgaag ccgctccact cgcatgtcca ctgtctcaga gcttcgcatc 420
acggctcagg agaatgacat ggaggtggag ctgcctgcag ctgcaaactc ccgcaagcag 480
ttttcagttc ctcctgcccc cactaggcct tcctgccctg cagtggctga aataccattg 540
aggatggtca gcgaggagat ggaagagcaa gtccattcca tccgtggcag ctcttctgca 600
aaccctgtga actcagttcg gaggaaatca tgtcttgtga aggaagtgga aaaaatgaag 660
aacaagcgag aagagaagaa ggcccagaac tctgaaatga gaatgaagag agctcaggag 720
tatgacagta gttttccaaa ctgggaattt gcccgaatga ttaaagaatt tcgggctact 780
ttggaatgtc atccacttac tatgactgat cctatcgaag agcacagaat atgtgtctgt 840
gttaggaaac gcccactgaa taagcaagaa ttggccaaga aagaaattga tgtgatttcc 900
attcctagca agtgtctcct cttggtacat gaacccaagt tgaaagtgga cttaacaaag 960
tatctggaga accaagcatt ctgctttgac tttgcatttg atgaaacagc ttcgaatgaa 1020
gttgtctaca ggttcacagc aaggccactg gtacagacaa tctttgaagg tggaaaagca 1080
acttgttttg catatggcca gacaggaagt ggcaagacac atactatggg cggagacctc 1140
tctgggaaag cccagaatgc atccaaaggg atctatgcca tggcctcccg ggacgtcttc 1200
ctcctgaaga atcaaccctg ctaccggaag ttgggcctgg aagtctatgt gacattcttc 1260
gagatctaca atgggaagct gtttgacctg ctcaacaaga aggccaagct gcgcgtgctg 1320
gaggacggca agcaacaggt gcaagtggtg gggctgcagg agcatctggt taactctgct 1380
gatgatgtca tcaagatgct cgacatgggc agcgcctgca gaacctctgg gcagacattt 1440
gccaactcca attcctcccg ctcccacgcg tgcttccaaa ttattcttcg agctaaaggg 1500
agaatgcatg gcaagttctc tttggtagat ctggcaggga atgagcgagg cgcagacact 1560
tccagtgctg accggcagac ccgcatggag ggcgcagaaa tcaacaagag tctcttagcc 1620
ctgaaggagt gcatcagggc cctgggacag aacaaggctc acaccccgtt ccgtgagagc 1680
aagctgacac aggtgctgag ggactccttc attggggaga actctaggac ttgcatgatt 1740
gccacgatct caccaggcat aagctcctgt gaatatactt taaacaccct gagatatgca 1800
gacagggtca aggagctgag cccccacagt gggcccagtg gagagcagtt gattcaaatg 1860
gaaacagaag agatggaagc ctgctctaac ggggcgctga ttccaggcaa tttatccaag 1920
gaagaggagg aactgtcttc ccagatgtcc agctttaacg aagccatgac tcagatcagg 1980
gagctggagg agaaggctat ggaagagctc aaggagatca tacagcaagg accagactgg 2040
cttgagctct ctgagatgac cgagcagcca gactatgacc tggagacctt tgtgaacaaa 2100
gcggaatctg ctctggccca gcaagccaag catttctcag ccctgcgaga tgtcatcaag 2160
gccttacgcc tggccatgca gctggaagag caggctagca gacaaataag cagcaagaaa 2220
cggccccagt gacgactgca aataaaaatc tgtttggttt gacacccagc ctcttccctg 2280
gccctcccca gagaactttg ggtacctggt gggtctaggc agggtctgag ctgggacagg 2340
ttctggtaaa tgccaagtat gggggcatct gggcccaggg cagctgggga gggggtcaga 2400
gtgacatggg acactccttt tctgttcctc agttgtcgcc ctcacgagag gaaggagctc 2460
ttagttaccc ttttgtgttg cccttctttc catcaagggg aatgttctca gcatagagct 2520
ttctccgcag catcctgcct gcgtggactg gctgctaatg gagagctccc tggggttgtc 2580
ctggctctgg ggagagagac ggagccttta gtacagctat ctgctggctc taaaccttct 2640
acgcctttgg gccgagcact gaatgtcttg tactttaaaa aaatgtttct gagacctctt 2700
tctactttac tgtctcccta gagtcctaga ggatccctac tgttttctgt tttatgtgtt 2760
tatacattgt atgtaacaat aaagagaaaa aataaaaaaa aaaaaaaaaa aaaaaaaaaa 2820
aaaaa 2825

<210> SEQ ID NO 216
<211> LENGTH: 60
<212> TYPE: DNA
<213> ORGANISM: Homo sapiens
<220> FEATURE:
<223> OTHER INFORMATION: NM_006845

<400> SEQUENCE: 216
aaatgtttct gagacctctt tctactttac tgtctcccta gagtcctaga ggatccctac 60

<210> SEQ ID NO 217
<211> LENGTH: 823
<212> TYPE: DNA
<213> ORGANISM: Homo sapiens
<220> FEATURE:
<223> OTHER INFORMATION: NM_007019

<400> SEQUENCE: 217
aaacgcgggc gggcgggccc gcagtcctgc agttgcagtc gtgttctccg agttcctgtc 60
tctctgccaa cgccgcccgg atggcttccc aaaaccgcga cccagccgcc actagcgtcg 120
ccgccgcccg taaaggagct gagccgagcg gggcgccgc ccggggtccg gtgggcaaaa 180
ggctacagca ggagctgatg accctcatga tgtctggcga taaagggatt tctgccttcc 240
ctgaatcaga caacctttc aaatgggtag ggaccatcca tggagcagct ggaacagtat 300
atgaagacct gaggtataag ctctcgctag agttccccag tggctaccct tacaatgcgc 360
ccacagtgaa gttcctcacg ccctgctatc accccaacgt ggacacccag ggtaacatat 420
gcctggacat cctgaaggaa aagtggtctg ccctgtatga tgtcaggacc attctgctct 480
ccatccagag ccttctagga gaacccaaca ttgatagtcc cttgaacaca catgctgccg 540
agctctggaa aaaccccaca gcttttaaga agtacctgca agaaacctac tcaaagcagg 600
tcaccagcca ggagccctga cccaggctgc ccagcctgtc cttgtgtcgt ctttttaatt 660
tttccttaga tggtctgtcc tttttgtgat ttctgtatag gactctttat cttgagctgt 720
ggtatttttg ttttgttttt gtcttttaaa ttaagcctcg gttgagccct tgtatattaa 780
ataaatgcat ttttgtcctt ttttagacaa aaaaaaaaaa aaa 823

<210> SEQ ID NO 218
<211> LENGTH: 60
<212> TYPE: DNA
<213> ORGANISM: Homo sapiens
<220> FEATURE:
<223> OTHER INFORMATION: NM_007019

<400> SEQUENCE: 218
tggaaaaacc ccacagcttt taagaagtac ctgcaagaaa cctactcaaa gcaggtcacc 60

<210> SEQ ID NO 219
<211> LENGTH: 2831
<212> TYPE: DNA
<213> ORGANISM: Homo sapiens
<220> FEATURE:
<223> OTHER INFORMATION: NM_007183

<400> SEQUENCE: 219
gaattccgga caggacgtga agatagttgg gtttggaggc ggccgccagg cccaggcccg 60
gtggacctgc cgccatgcag gacggtaact tcctgctgtc ggccctgcag cctgaggccg 120
gcgtgtgctc cctggcgctg ccctctgacc tgcagctgga ccgccggggc gccgaggggc 180
cggaggccga gcggctgcgg gcagcccgcg tccaggagca ggtccgcgcc cgcctcttgc 240
agctgggaca gcagccgcgg cacaacgggg ccgctgagcc cgagcctgag gccgagactg 300
ccagaggcac atccaggggg cagtaccaca ccctgcaggc tggcttcagc tctcgctctc 360
agggcctgag tggggacaag acctcgggct tccggcccat cgccaagccg gcctacagcc 420
cagcctcctg gtcctcccgc tccgccgtgg atctgagctg cagtcggagg ctgagttcag 480
cccacaatgg gggcagcgcc tttggggccg ctgggtacgg gggtgcccag cccacccctc 540
ccatgcccac caggcccgtg tccttccatg agcgcggtgg ggttgggagc cgggccgact 600
atgacacact ctccctgcgc tcgctgcggc tggggcccgg gggcctggac gaccgctaca 660
gcctggtgtc tgagcagctg gagcccgcgg ccacctccac ctacagggcc tttgcgtacg 720
agcgccaggc cagctccagc tccagccggg caggggggct ggactggccc gaggccactg 780
aggtttcccc gagccggacc atccgtgccc ctgccgtgcg gaccctgcag cgattccaga 840
gcagccaccg gagccgcggg gtaggcgggg cagtgccggg ggccgtcctg gagccagtgg 900
ctcgagcgcc atctgtgcgc agcctcagcc tcagcctggc tgactcgggc cacctgccgg 960
acgtgcatgg gttcaacagc tacggtagcc accgaaccct gcagagactc agcagcggtt 1020
ttgatgacat tgacctgccc tcagcagtca agtacctcat ggcttcagac cccaacctgc 1080
aggtgctggg agcggcctac atccagcaca agtgctacag cgatgcagcc gccaagaagc 1140
aggcccgcag ccttcaggcc gtgcctaggc tggtgaagct cttcaaccac gccaaccagg 1200
aagtgcagcg ccatgccaca ggtgccatgc gcaacctcat ctacgacaac gctgacaaca 1260
agctggccct ggtggaggag aacgggatct tcgagctgct gcggacactg cgggagcagg 1320
atgatgagct tcgcaaaaat gtcacaggga tcctgtggaa cctttcatcc agcgaccacc 1380
tgaaggaccg cctggccaga gacacgctgg agcagctcac ggacctggtg ttgagccccc 1440
tgtcgggggc tgggggtccc cccctcatcc agcagaacgc ctcggaggcg gagatcttct 1500
acaacgccac cggcttcctc aggaacctca gctcagcctc tcaggccact cgccagaaga 1560
tgcgggagtg ccacgggctg gtggacgccc tggtcacctc tatcaaccac gccctggacg 1620
cgggcaaatg cgaggacaag agcgtggaga acgcggtgtg cgtcctgcgg aacctgtcct 1680
accgcctcta cgacgagatg ccgccgtccg cgctgcagcg gctggagggt cgcggccgca 1740
gggacctggc gggggcgccg ccgggagagg tcgtgggctg cttcacgccg cagagccggc 1800
ggctgcgcga gctgcccctc gccgccgatg cgctcacctt cgcggaggtg tccaaggacc 1860
ccaagggcct cgagtggctg tggagccccc agatcgtggg gctgtacaac cggctgctgc 1920
agcgctgcga gctcaaccgg cacacgacgg aggcggccgc cggggcgctg cagaacatca 1980
cggcaggcga ccgcaggtgg gcgggggtgc tgagccgcct ggccctggag caggagcgta 2040
ttctgaaccc cctgctagac cgtgtcagga ccgccgacca ccaccagctg cgctcactga 2100
ctggcctcat ccgaaacctg tctcggaacg ctaggaacaa ggacgagatg tccacgaagg 2160
tggtgagcca cctgatcgag aagctgccag gcagcgtggg tgagaagtcg cccccagccg 2220
aggtgctggt caacatcata gctgtgctca acaacctggt ggtggccagc cccatcgctg 2280
cccgagacct gctgtatttt gacggactcc gaaagctcat cttcatcaag aagaagcggg 2340
acagccccga cagtgagaag tcctcccggg cagcatccag cctcctggcc aacctgtggc 2400
agtacaacaa gctccaccgt gactttcggg cgaagggcta tcggaaggag gacttcctgg 2460
gcccataggt gaagccttct ggaggagaag gtgacgtggc ccagcgtcca agggacagac 2520
tcagctccag gctgcttggc agcccagcct ggaggagaag gctaatgacg gaggggcccc 2580
tcgctggggc ccctgtgtgc atctttgagg gtcctgggcc accaggaggg gcagggtctt 2640
atagctgggg acttggcttc cgcagggcag ggggtggggc agggctcaag gctgctctgg 2700
tgtatggggt ggtgacccag tcacattggc agaggtgggg gttggctgtg gcctggcagt 2760
atcttgggat agccagcact gggaataaag atggccatga acagtcacaa aaaaaaaaaa 2820
aaaaggaatt c 2831

<210> SEQ ID NO 220
<211> LENGTH: 60
<212> TYPE: DNA
<213> ORGANISM: Homo sapiens
<220> FEATURE:
<223> OTHER INFORMATION: NM_007183

<400> SEQUENCE: 220
ctggcagtat cttgggatag ccagcactgg gaataaagat ggccatgaac agtcacaaaa 60

<210> SEQ ID NO 221
<211> LENGTH: 2815
<212> TYPE: DNA
<213> ORGANISM: Homo sapiens
<220> FEATURE:
<223> OTHER INFORMATION: NM_007267

<400> SEQUENCE: 221
aggaagcgga ggaaggtgaa gtaggaccga attcctgtgc cgaagaggcc tgcagtggga 60
gagcaggatg gggctccgg aggtggcgcc caggctctga gctaccctag gtctgcagac 120
tagcgggcat tggccagaga catggcccag ccactggcct tcatcctcga tgtccctgag 180
accccagggg accagggcca gggccccagc ccctatgatg aaagcgaagt gcacgactcc 240
ttccagcagc tcatccagga gcagagccag tgcacggccc aggaggggct ggagctgcag 300
cagagagagc gggaggtgac aggaagtagc cagcagacac tctggcggcc cgagggcacc 360
cagagcacgg ccacactccg catcctggcc agcatgccca gccgcaccat tggccgcagc 420
cgaggtgcca tcatctccca gtactacaac cgcacggtgc agcttcggtg caggagcagc 480

-continued

```
cggcccctgc tcgggaactt tgtccgctcc gcctggccca gcctccgcct gtacgacctg    540
gagctggacc ccacggccct ggaggaggag gagaagcaga gcctcctggt gaaggagttc    600
cagagcctgg cagtggcaca gcgggaccac atgcttcgcg ggatgccctt aagcctggct    660
gagaaacgca gcctgcgaga gaagagcagg accccgaggg ggaagtggag gggccagccg    720
ggcagcggcg gggtctgctc ctgctgtggc cggctcagat atgcctgcgt gctggccttg    780
cacagcctgg gcctggcgct gctctccgcc ctgcaggccc tgatgccgtg gcgctacgcc    840
ctgaagcgca tcgggggcca gttcggctcc agcgtgctct cctacttcct ctttctcaag    900
accctgctgg ctttcaatgc cctcctgctg ctgctgctgg tggccttcat catgggccct    960
caggtcgcct tcccacccgc cctgccgggc cctgccccg tctgcacagg cctggagctc   1020
ctcacaggcg cgggttgctt cacccacacc gtcatgtact acggccacta cagtaacgcc   1080
acgctgaacc agccgtgtgg cagcccctg gatggcagcc agtgcacacc cagggtgggt   1140
ggcctgccct acaacatgcc cctggcctac ctctccactg tgggcgtgag cttctttatc   1200
acctgcatca ccctggtgta cagcatggct cactctttcg gggagagcta ccgggtgggc   1260
agcacctctg gcatccacgc catcaccgtc ttctgctcct gggactacaa ggtgacgcag   1320
aagcgggcct cccgcctcca gcaggacaat attcgcaccc ggctgaagga gctgctggcc   1380
gagtggcagc tgcggcacag ccccaggagc gtgtgcggga ggctgcggca ggcggctgtg   1440
ctggggcttg tgtggctgct gtgtctgggg accgcgctgg gctgcgccgt ggccgtccac   1500
gtcttctcgg agttcatgat ccagagtcca gaggctgctg gccaggaggc tgtgctgctg   1560
gtcctgcccc tggtggttgg cctcctcaac ctgggggccc cctacctgtg ccgtgtcctg   1620
gccgccctgg agccgcatga ctccccggta ctggaggtgt acgtggccat ctgcaggaac   1680
ctcatcctca agctggccat cctggggaca ctgtgctacc actggctggg ccgcagggtg   1740
ggcgtcctgc agggccagtg ctgggaggat tttgtgggcc aggagctgta ccggttcctg   1800
gtgatggact tcgtcctcat gttgctggac acgctttttg ggaactggt gtggaggatt   1860
atctccgaga agaagctgaa gaggaggcgg aagccggagt ttgacattgc ccggaatgtc   1920
ctggagctga tttatgggca gactctgacc tggctggggg tgctcttctc gcccctcctc   1980
cccgccgtgc agatcatcaa gctgctgctc gtcttctatg tcaagaagac cagccttctg   2040
gccaactgcc aggcgccgcg ccggccctgg ctggcctcac acatgagcac cgtcttcctc   2100
acgctgctct gcttccccgc cttcctgggc gccgctgtct tcctctgcta cgccgtctgg   2160
caggtgaagc cctcgagcac ctgcggcccc ttccggaccc tggacaccat gtacgaggcc   2220
ggcagggtgt gggtgcgcca cctggaggcg gcaggcccca gggtctcctg gctgccctgg   2280
gtgcaccggt acctgatgga aaacaccttc tttgtcttcc tggtgtcagc cctgctgctg   2340
gccgtgatct acctcaacat ccaggtggtg cggggccagc gcaaggtcat ctgcctgctc   2400
aaggagcaga tcagcaatga gggtgaggac aaaatcttct taatcaacaa gcttcactcc   2460
atctacgaga ggaaggagag ggaggagagg agcagggttg ggacaaccga ggaggctgcg   2520
gcacccctg ccctgctcac agatgaacag gatgcctagg gggacggcga tgggcctcac   2580
gggcccgccc agcaccctga gaccacactg ttgcctccca gtgaccctgc tgggacacca   2640
ggacaaggaa gacagtttcg cctctcgaaa gccgcagctg cgcctaggct ggagctggaa   2700
gggtgggtga atccggcttg ggcatcccca atgaactctg ccctgcctgg gactctattt   2760
attctgatta aaggggtttt gcaaatggga aaaaaaaaaa aaaaaaaaaa aaaaa        2815
```

<210> SEQ ID NO 222
<211> LENGTH: 60
<212> TYPE: DNA
<213> ORGANISM: Homo sapiens
<220> FEATURE:
<223> OTHER INFORMATION: NM_007267

<400> SEQUENCE: 222
ggtgaggaca aaatcttctt aatcaacaag cttcactcca tctacgagag gaaggagagg 60

<210> SEQ ID NO 223
<211> LENGTH: 1893
<212> TYPE: DNA
<213> ORGANISM: Homo sapiens
<220> FEATURE:
<223> OTHER INFORMATION: NM_007274

<400> SEQUENCE: 223
atttaccgcc gcgcggagag tgagggccca agtccgccct gctccgccac ttaggccgcc 60
ccagacgctt ccctcggggc tgccaccggg tcgggcgcgg ctgccgcggc tagcgggcct 120
tccccgcacc ggcgcggccc aaccgccacc gaaccttctg gaagcggcgg ctgcctgggc 180
ccccacgccg ccagaatcgt acgcccgcgc gagctctctg cagccttggc ggcctgggag 240
gcggggctcg gggtggggcc ggcgcggggg cggggtcggc gcggggaggc cgcgttcgat 300
tcgcccccgg cgcgcaggcc ccgcctcacc agccccatcg ctccacctct gccctccccc 360
tttatggcgc ggcccgggct cattcattcc gcgccgggcc tgccagacac ctgcgccctt 420
ctgcagccgc ccgccgcatc cgccgccgca gcccccagca tgtcgggccc agacgtcgag 480
acgccgtccg ccatccagat ctgccggatc atgcggccag atgatgccaa cgtggccggc 540
aatgtccacg gggggaccat cctgaagatg atcgaggagg caggcgccat catcagcacc 600
cggcattgca acagccagaa cggggagcgc tgtgtggccg ccctggctcg tgtcgagcgc 660
accgacttcc tgtctcccat gtgcatcggt gaggtggcgc atgtcagcgc ggagatcacc 720
tacacctcca agcactctgt ggaggtgcag gtcaacgtga tgtccgaaaa catcctcaca 780
ggtgccaaaa agctgaccaa taaggccacc ctgtggtatg tgcccctgtc gctgaagaat 840
gtggacaagg tcctcgaggt gcctcctgtt gtgtattccc ggcaggagca ggaggaggag 900
ggccggaagc ggtatgaagc ccagaagctg gagcgcatgg agaccaagtg gaggaacggg 960
gacatcgtcc agccagtcct caacccagag ccgaacactg tcagctacag ccagtccagc 1020
ttgatccacc tggtggggcc ttcagactgc accctgcacg gctttgtgca cggaggtgtg 1080
accatgaagc tcatggatga ggtcgccggg atcgtggctg cacgccactg caagaccaac 1140
atcgtcacag cttccgtgga cgccattaat tttcatgaca agatcagaaa aggctgcgtc 1200
atcaccatct cgggacgcat gaccttcacg agcaataagt ccatggagat cgaggtgttg 1260
gtggacgccg accctgttgt ggacagctct cagaagcgct accgggccgc cagtgccttc 1320
ttcacctacg tgtcgctgag ccaggaaggc aggtcgctgc ctgtgcccca gctggtgccc 1380
gagaccgagg acgagaagaa gcgctttgag gaaggcaaag ggcggtacct gcagatgaag 1440
gcgaagcgac agggccacgc ggagcctcag ccctagactc cctcctcctg ccactggtgc 1500
ctcgagtagc catggcaacg ggcccagtgt ccagtcactt agaagttccc cccttggcca 1560
aaaacccaat tcacattgag agctggtgtt gtctgaagtt ttcgtatcac agtgttaacc 1620
tgtactctct cctgcaaacc tacacaccaa agctttattt atatcattcc agtatcaatg 1680
ctacacagtg ttgtcccgag cgccgggagg cgttgggcag aaaccctcgg gaatgcttcc 1740
gagcacgctg tagggtatgg gaagaaccca gcaccactaa taaagctgct gcttggctgg 1800
aaaaaaaaaa aaaaaaaaaa aaaaaaaaaa aaaaaaaaaa aaaaaaaaaa aaaaaaaaaa 1860
aaaaaaaaaa aaaaaaaaaa aaaaaaaaaa aaa 1893

<210> SEQ ID NO 224
<211> LENGTH: 60
<212> TYPE: DNA
<213> ORGANISM: Homo sapiens
<220> FEATURE:
<223> OTHER INFORMATION: NM_007274

<400> SEQUENCE: 224
acctacacac caaagcttta tttatatcat tccagtatca atgctacaca gtgttgtccc 60

<210> SEQ ID NO 225
<211> LENGTH: 4157
<212> TYPE: DNA
<213> ORGANISM: Homo sapiens
<220> FEATURE:
<223> OTHER INFORMATION: NM_007315

<400> SEQUENCE: 225
agcggggcgg ggcgccagcg ctgccttttc tcctgccggg tagtttcgct ttcctgcgca 60
gagtctgcgg aggggctcgg ctgcaccggg gggatcgcgc ctggcagacc ccagaccgag 120
cagaggcgac ccagcgcgct cgggagaggc tgcaccgccg cgcccccgcc tagcccttcc 180
ggatcctgcg cgcagaaaag tttcatttgc tgtatgccat cctcgagagc tgtctaggtt 240
aacgttcgca ctctgtgtat ataacctcga cagtcttggc acctaacgtg ctgtgcgtag 300
ctgctccttt ggttgaatcc ccaggccctt gttggggcac aaggtggcag gatgtctcag 360
tggtacgaac ttcagcagct tgactcaaaa ttcctggagc aggttcacca gctttatgat 420
gacagttttc ccatggaaat cagacagtac ctggcacagt ggttagaaaa gcaagactgg 480
gagcacgctg ccaatgatgt ttcatttgcc accatccgtt ttcatgacct cctgtcacag 540
ctggatgatc aatatagtcg cttttctttg gagaataact tcttgctaca gcataacata 600
aggaaaagca agcgtaatct tcaggataat tttcaggaag acccaatcca gatgtctatg 660
atcatttaca gctgtctgaa ggaagaaagg aaaattctgg aaaacgccca gagatttaat 720
caggctcagt cggggaatat tcagagcaca gtgatgttag acaaacagaa agagcttgac 780
agtaaagtca gaaatgtgaa ggacaaggtt atgtgtatag agcatgaaat caagagcctg 840
gaagatttac aagatgaata tgacttcaaa tgcaaaacct tgcagaacag agaacacgag 900
accaatggtg tggcaaagag tgatcagaaa caagaacagc tgttactcaa gaagatgtat 960
ttaatgcttg acaataagag aaaggaagta gttcacaaaa taatagagtt gctgaatgtc 1020
actgaactta cccagaatgc cctgattaat gatgaactag tggagtggaa gcggagacag 1080
cagagcgcct gtattggggg gccgcccaat gcttgcttgg atcagctgca gaactggttc 1140
actatagttg cggagagtct gcagcaagtt cggcagcagc ttaaaaagtt ggaggaattg 1200
gaacagaaat acacctacga acatgaccct atcacaaaaa acaaacaagt gttatgggac 1260
cgcaccttca gtcttttcca gcagctcatt cagagctcgt ttgtggtgga aagacagccc 1320
tgcatgccaa cgcaccctca gaggccgctg gtcttgaaga caggggtcca gttcactgtg 1380
aagttgagac tgttggtgaa attgcaagag ctgaattata atttgaaagt caaagtctta 1440
tttgataaag atgtgaatga gagaaataca gtaaaaggat ttaggaagtt caacattttg 1500
ggcacgcaca caaaagtgat gaacatggag gagtccacca atggcagtct ggcggctgaa 1560
tttcggcacc tgcaattgaa agaacagaaa aatgctggca ccagaacgaa tgagggtcct 1620
ctcatcgtta ctgaagagct tcactccctt agttttgaaa cccaattgtg ccagcctggt 1680
ttggtaattg acctcgagac gacctctctg cccgttgtgg tgatctccaa cgtcagccag 1740
ctcccgagcg gttgggcctc catcctttgg tacaacatgc tggtggcgga acccaggaat 1800
ctgtccttct tcctgactcc accatgtgca cgatgggctc agctttcaga agtgctgagt 1860
tggcagtttt cttctgtcac caaaagaggt ctcaatgtgg accagctgaa catgttggga 1920
gagaagcttc ttggtcctaa cgccagcccc gatggtctca ttccgtggac gaggttttgt 1980
aaggaaaata taaatgataa aaattttccc ttctggcttt ggattgaaag catcctagaa 2040
ctcattaaaa aacacctgct ccctctctgg aatgatgggt gcatcatggg cttcatcagc 2100
aaggagcgag agcgtgccct gttgaaggac cagcagccgg ggaccttcct gctgcggttc 2160
agtgagagct cccgggaagg ggccatcaca ttcacatggg tggagcggtc ccagaacgga 2220
ggcgaacctg acttccatgc ggttgaaccc tacacgaaga aagaactttc tgctgttact 2280
ttccctgaca tcattcgcaa ttacaaagtc atggctgctg agaatattcc tgagaatccc 2340
ctgaagtatc tgtatccaaa tattgacaaa gaccatgcct ttggaaagta ttactccagg 2400
ccaaaggaag caccagagcc aatggaactt gatggcccta aaggaactgg atatatcaag 2460
actgagttga tttctgtgtc tgaagttcac ccttctagac ttcagaccac agacaacctg 2520
ctccccatgt ctcctgagga gtttgacgag gtgtctcgga tagtgggctc tgtagaattc 2580
gacagtatga tgaacacagt atagagcatg aatttttttc atcttctctg gcgacagttt 2640
tccttctcat ctgtgattcc ctcctgctac tctgttcctt cacatcctgt gtttctaggg 2700
aaatgaaaga aaggccagca aattcgctgc aacctgttga tagcaagtga atttttctct 2760
aactcagaaa catcagttac tctgaagggc atcatgcatc ttactgaagg taaaattgaa 2820
aggcattctc tgaagagtgg gtttcacaag tgaaaaacat ccagatacac ccaaagtatc 2880
aggacgagaa tgagggtcct ttgggaaagg agaagttaag caacatctag caaatgttat 2940
gcataaagtc agtgcccaac tgttataggt tgttggataa atcagtggtt atttagggaa 3000
ctgcttgacg taggaacggt aaatttctgt gggagaattc ttacatgttt tctttgcttt 3060
aagtgtaact ggcagttttc cattggttta cctgtgaaat agttcaaagc caagtttata 3120
tacaattata tcagtcctct ttcaaaggta gccatcatgg atctggtagg gggaaaatgt 3180
gtattttatt acatctttca cattggctat ttaaagacaa agacaaattc tgtttcttga 3240
gaagagaata ttagctttac tgtttgttat ggcttaatga cactagctaa tatcaataga 3300
aggatgtaca tttccaaatt cacaagttgt gtttgatatc caaagctgaa tacattctgc 3360
tttcatcttg gtcacataca attattttta cagttctccc aagggagtta ggctattcac 3420
aaccactcat tcaaaagttg aaattaacca tagatgtaga taaactcaga aatttaattc 3480
atgtttctta aatgggctac tttgtccttt ttgttattag ggtggtattt agtctattag 3540
ccacaaaatt gggaaaggag tagaaaaagc agtaactgac aacttgaata atacaccaga 3600
gataatatga gaatcagatc atttcaaaac tcatttccta tgtaactgca ttgagaactg 3660
catatgtttc gctgatatat gtgtttttca catttgcgaa tggttccatt ctctctcctg 3720
tactttttcc agacactttt ttgagtggat gatgtttcgt gaagtatact gtatttttac 3780
ctttttcctt ccttatcact gacacaaaaa gtagattaag agatgggttt gacaaggttc 3840
ttccctttta catactgctg tctatgtggc tgtatcttgt ttttccacta ctgctaccac 3900
aactatatta tcatgcaaat gctgtattct tctttggtgg agataaagat ttcttgagtt 3960
ttgttttaaa attaaagcta aagtatctgt attgcattaa atataatatg cacacagtgc 4020
tttccgtggc actgcataca atctgaggcc tcctctctca gtttttatat agatggcgag 4080
aacctaagtt tcagttgatt ttacaattga aatgactaaa aaacaaagaa gacaacatta 4140
aaacaatatt gtttcta 4157

<210> SEQ ID NO 226
<211> LENGTH: 60
<212> TYPE: DNA
<213> ORGANISM: Homo sapiens
<220> FEATURE:
<223> OTHER INFORMATION: NM_007315

<400> SEQUENCE: 226
atcagatcat ttcaaaactc atttcctatg taactgcatt gagaactgca tatgtttcgc 60

<210> SEQ ID NO 227
<211> LENGTH: 1696
<212> TYPE: DNA
<213> ORGANISM: Homo sapiens
<220> FEATURE:
<223> OTHER INFORMATION: NM_009587

<400> SEQUENCE: 227
caaaggactt cctagtgggt gtgaaaggca gcggtggcca cagaggcggc ggagagatgg 60
ccttcagcgg ttcccaggct ccctacctga gtccagctgt ccccttttct gggactattc 120
aaggaggtct ccaggacgga cttcagatca ctgtcaatgg gaccgttctc agctccagtg 180
gaaccaggtt tgctgtgaac tttcagactg gcttcagtgg aaatgacatt gccttccact 240
tcaaccctcg gtttgaagat ggagggtacg tggtgtgcaa cacgaggcag aacggaagct 300
gggggcccga ggagaggaag acacacatgc ctttccagaa ggggatgccc tttgacctct 360
gcttcctggt gcagagctca gatttcaagg tgatggtgaa cgggatcctc ttcgtgcagt 420
acttccaccg cgtgcccttc caccgtgtgg acaccatctc cgtcaatggc tctgtgcagc 480
tgtcctacat cagcttccag aaccccccgca cagtccctgt tcagcctgcc ttctccacgg 540
tgccgttctc ccagcctgtc tgtttcccac ccaggcccag gggcgcaga caaaaacctc 600 ccggcgtgtg gcctgccaac ccggctccca ttacccagac agtcatccac acagtgcaga 660
gcgcccctgg acagatgttc tctactcccg ccatcccacc tatgatgtac ccccaccccg 720
cctatccgat gcctttcatc accaccattc tgggagggct gtacccatcc aagtccatcc 780
tcctgtcagg cactgtcctg cccagtgctc agaggttcca catcaacctg tgctctggga 840
accacatcgc cttccacctg aacccccgtt ttgatgagaa tgctgtggtc cgcaacaccc 900
agatcgacaa ctcctggggg tctgaggagc gaagtctgcc ccgaaaaatg cccttcgtcc 960
gtggccagag cttctcagtg tggatcttgt gtgaagctca ctgcctcaag gtggccgtgg 1020
atggtcagca cctgtttgaa tactaccatc gcctgaggaa cctgcccacc atcaacagac 1080
tggaagtggg gggcgacatc cagctgaccc atgtgcagac ataggcggct tcctggccct 1140
ggggccgggg gctggggtgt ggggcagtct gggtcctctc atcatcccca cttcccaggc 1200
ccagcctttc caaccctgcc tgggatctgg gctttaatgc agaggccatg tccttgtctg 1260
gtcctgcttc tggctacagc caccctggaa cggagaaggc agctgacggg gattgccttc 1320
ctcagccgca gcagcacctg gggctccagc tgctggaatc ctaccatccc aggaggcagg 1380
cacagccagg gagaggggag gagtgggcag tgaagatgaa gccccatgct cagtcccctc 1440
ccatccccca cgcagctcca ccccagtccc aagccaccag ctgtctgctc ctggtgggag 1500
gtggcctcct cagcccctcc tctctgacct ttaacctcac tctcaccttg caccgtgcac 1560
caacccttca cccctcctgg aaagcaggcc tgatggcttc ccactggcct ccaccacctg 1620
accagagtgt tctcttcaga ggactggctc ctttcccagt gtccttaaaa taaagaaatg 1680
aaaatgcttg ttggca 1696

<210> SEQ ID NO 228
<211> LENGTH: 60
<212> TYPE: DNA
<213> ORGANISM: Homo sapiens
<220> FEATURE:
<223> OTHER INFORMATION: NM_009587

<400> SEQUENCE: 228
cagaggactg gctcctttcc cagtgtcctt aaaataaaga aatgaaaatg cttgttggca 60

<210> SEQ ID NO 229
<211> LENGTH: 6552
<212> TYPE: DNA
<213> ORGANISM: Homo sapiens
<220> FEATURE:
<223> OTHER INFORMATION: NM_012291

<400> SEQUENCE: 229
atgaggagct tcaaaagagt caactttggg actctgctaa gcagccagaa ggaggctgaa 60
gagttgctgc ccgacttgaa ggagttcctg tccaaccctc cagctggttt tcccagcagc 120
cgatctgatg ctgagaggag acaagcttgt gatgccatcc tgagggcttg caaccagcag 180
ctgactgcta agctagcttg ccctaggcat ctggggagcc tgctggagct ggcagagctg 240
gcctgtgatg gctacttagt gtctacccca cagcgtcctc ccctctacct ggaacgaatt 300
ctctttgtct tactgcggaa tgctgctgca caaggaagcc cagaggccac actccgcctt 360
gctcagcccc tccatgcctg cttggtgcag tgctctcgcg aggctgctcc ccaggactat 420
gaggccgtgg ctcggggcag cttttctctg ctttggaagg gggcagaagc cctgttggaa 480
cggcgagctg catttgcagc tcggctgaag gccttgagct tcctagtact cttggaggat 540
gaaagtaccc cttgtgaggt tcctcacttt gcttctccaa cagcctgtcg agcggtagct 600
gcccatcagc tatttgatgc cagtggccat ggtctaaatg aagcagatgc tgatttccta 660
gatgacctgc tctccaggca cgtgatcaga gccttggtgg gtgagagagg gagctcttct 720
gggcttcttt ctccccagag ggccctctgc ctcttggagc tcaccttgga acactgccgt 780
cgcttttgct ggagccgcca ccatgacaaa gccatcagcg cagtggagaa ggctcacagt 840
tacctaagga acaccaatct agcccctagc cttcagctat gtcagctggg ggttaagctg 900
ctgcaggttg gggaggaagg acctcaggca gtggccaagc ttctgatcaa ggcatcagct 960
gtcctgagca agagtatgga ggcaccatca cccccacttc gggcattgta tgagagctgc 1020
cagttcttcc tttcaggcct ggaacgaggc accaagaggc gctatagact tgatgccatt 1080
ctgagcctct ttgcttttct tggagggtac tgctctcttc tgcagcagct gcgggatgat 1140
ggtgtgtatg gggctcctc caagcaacag cagtcttttc ttcagatgta ctttcaggga 1200
cttcacctct acactgtggt ggtttatgac tttgcccaag gctgtcagat agttgatttg 1260
gctgacctga cccaactagt ggacagttgt aaatctaccg ttgtctggat gctggaggcc 1320
ttagagggcc tgtcgggcca agagctgacg gaccacatgg ggatgaccgc ttcttacacc 1380
agtaatttgg cctacagctt ctatagtcac aagctctatg ccgaggcctg tgccatctct 1440
gagccgctct gtcagcacct gggtttggtg aagccaggca cttatcccga ggtgcctcct 1500
gagaagttgc acaggtgctt ccggctacaa gtagagagtt tgaagaaact gggtaaacag 1560

-continued

```
gcccagggct gcaagatggt gattttgtgg ctggcagccc tgcaaccctg tagccctgaa   1620
cacatggctg agccagtcac tttctgggtt cgggtcaaga tggatgcggc cagggctgga   1680
gacaaggagc tacagctaaa gactctgcga gacagcctca gtggctggga cccggagacc   1740
ctggccctcc tgctgaggga ggagctgcag gcctacaagg cggtgcgggc cgacactgga   1800
caggaacgct tcaacatcat ctgtgacctc ctggagctga gccccgagga gacaccagcc   1860
ggggcctggg cacgagccac ccacctggta gaactggctc aggtgctctg ctaccacgac   1920
tttacgcagc agaccaactg ctctgctctg gatgctatcc gggaagccct gcagcttctg   1980
gactctgtga ggcctgaggc ccaggccaga gatcagcttc tggacgataa agcacaggcc   2040
ttgctgtggc tttacatctg tactctggaa gccaaaatac aggaaggtat cgagcgggat   2100
cggagagccc aggcccctgg taacttggag gaatttgaag tcaatgacct gaactatgaa   2160
gataaactcc aggaagatcg tttcctatac agtaacattg ccttcaacct ggctgcagat   2220
gctgctcagt ccaaatgcct ggaccaagcc ctggccctgt ggaaggagct gcttacaaag   2280
gggcaggccc cagctgtacg gtgtctccag cagacagcag cctcactgca gatcctagca   2340
gccctctacc agctggtggc aaagcccatg caggctctgg aggtcctcct gctgctacgg   2400
attgtctctg agagactgaa ggaccactcg aaggcagctg gctcctcctg ccacatcacc   2460
cagctcctcc tgaccctcgg ctgtcccagc tatgcccagt tacacctgga agaggcagca   2520
tcgagcctga agcatctcga tcagactact gacacatacc tgctcctttc cctgacctgt   2580
gatctgcttc gaagtcaact ctactggact caccagaagg tgaccaaggg tgtctctctg   2640
ctgctgtctg tgcttcggga tcctgccctc cagaagtcct ccaaggcttg gtacttgctg   2700
cgtgtccagg tcctgcagct ggtggcagct taccttagcc tcccgtcaaa caacctctca   2760
cactccctgt gggagcagct ctgtgcccaa ggctggcaga cacctgagat agctctcata   2820
gactcccata agctcctccg aagcatcatc ctcctgctga tgggcagtga cattctctca   2880
actcagaaag cagctgtgga gacatcgttt ttggactatg gtgaaaatct ggtacaaaaa   2940
tggcaggttc tttcagaggt gctgagctgc tcagagaagc tggtctgcca cctgggccgc   3000
ctgggtagtg tgagtgaagc caaggccttt tgcttggagg ccctaaaact tacaacaaag   3060
ctgcagatac cacgccagtg tgccctgttc ctggtgctga agggcgagct ggagctggcc   3120
cgcaatgaca ttgatctctg tcagtcggac ctgcagcagg ttctgttctt gcttgagtct   3180
tgcacagagt ttggtggggt gactcagcac ctggactctg tgaagaaggt ccacctgcag   3240
aaggggaagc agcaggccca ggtcccctgt cctccacagc tcccagagga ggagctcttc   3300
ctaagaggcc ctgctctaga gctggtggcc actgtggcca aggagcctgg ccccatagca   3360
ccttctacaa actcctcccc agtcttgaaa accaagcccc agcccatacc caacttcctg   3420
tcccattcac ccacctgtga ctgctcgctc tgcgccagcc ctgtcctcac agcagtctgt   3480
ctgcgctggg tattggtcac ggcaggggtg aggctggcca tgggccacca agcccagggt   3540
ctggatctgc tgcaggtcgt gctgaagggc tgtcctgaag ccgctgagcg cctcacccaa   3600
gctctccaag cttccctgaa tcataaaaca ccccccctcct tggttccaag cctcttggat   3660
gagatcttgg ctcaagcata cacactgttg gcactggagg gcctgaacca gccatcaaac   3720
gagagcctgc agaaggttct acagtcaggg ctgaagtttg tagcagcacg gataccccac   3780
ctagagccct ggcgagccag cctgctcttg atttgggccc tcacaaaact aggtggcctc   3840
agctgctgta ctacccaact tttgcaagc tcctggggct ggcagccacc attaataaaa   3900
agtgtccctg gctcagagcc ctctaagact cagggccaaa aacgttctgg acgagggcgc   3960
```

```
caaaagttag cctctgctcc cctgcgcctc aataatacct ctcagaaagg tctggaaggt   4020
agaggactgc cctgcacacc taaacccccca gaccggatca ggcaagctgg ccctcatgtc  4080
cccttcacgg tgtttgagga agtctgccct acagagagca agcctgaagt accccaggcc   4140
cccagggtac aacagagagt ccagacgcgc ctcaaggtga acttcagtga tgacagtgac   4200
ttggaagacc ctgtctcagc tgaggcctgg ctggcagagg agcctaagag acggggcact   4260
gcttcccggg gccgggggcg agcaaggaag ggcctgagcc taaagacgga tgccgtggtt   4320
gccccaggta gtgcccctgg gaaccctggc ctgaatggca ggagccggag ggccaagaag   4380
gtggcatcaa gacattgtga ggagcggcgt ccccagaggg ccagtgacca ggccaggcct   4440
ggccctgaga tcatgaggac catccctgag gaagaactga ctgacaactg gagaaaaatg   4500
agctttgaga tcctcagggg ctctgacggg gaagactcag cctcaggtgg gaagactcca   4560
gctccgggcc ctgaggcagc ttctggagaa tgggagctgc tgaggctgga ttccagcaag   4620
aagaagctgc ccagcccatg cccagacaag gagagtgaca aggaccttgg tcctcggctc   4680
cagctcccct cagcccccgt agccactggt ctttctaccc tggactccat ctgtgactcc   4740
ctgagtgttg ctttccgggg cattagtcac tgtcctccta gtgggctcta tgcccacctc   4800
tgccgcttcc tggccttgtg cctgggccac cgggatcctt atgccactgc tttccttgtc   4860
accgagtctg tctccatcac ctgtcgccac cagctgctca cccacctcca cagacagctc   4920
agcaaggccc agaagcaccg aggatcactt gaaatagcag accagctgca ggggctgagc   4980
cttcaggaga tgcctggaga tgtccccctg gcccgcatcc agcgcctctt ttccttcagg   5040
gctttggaat ctggccactt cccccagcct gaaaaggaga gtttccagga gcgcctggct   5100
ctgatcccca gtggggtgac tgtgtgtgtg ttggccctgg ccaccctcca gcccggaacc   5160
gtgggcaaca ccctcctgct gacccggctg gaaaaggaca gtcccccagt cagtgtgcag   5220
attcccactg gccagaacaa gcttcatctg cgttcagtcc tgaatgagtt tgatgccatc   5280
cagaaggcac agaaagagaa cagcagctgt actgacaagc gagaatggtg gacagggcgg   5340
ctggcactgg accacaggat ggaggttctc atcgcttccc tagagaagtc tgtgctgggc   5400
tgctggaagg ggctgctgct gccgtccagt gaggagcccg gccctgccca ggaggcctcc   5460
cgcctacagg agctgctaca ggactgtggc tggaaatatc ctgaccgcac tctgctgaaa   5520
atcatgctca gtggtgccgg tgccctcacc cctcaggaca ttcaggccct ggcctacggg   5580
ctgtgcccaa cccagccaga gcgagcccag gagctcctga atgaggcagt aggacgtcta   5640
cagggcctga cagtaccaag caatagccac cttgtcttgg tcctagacaa ggacttgcag   5700
aagctgccgt gggaaagcat gcccagcctc caagcactgc ctgtcacccg gctgccctcc   5760
ttccgcttcc tactcagcta ctccatcatc aaagagtatg gggcctcgcc agtgctgagt   5820
caaggggtgg atccacgaag taccttctat gtcctgaacc ctcacaataa cctgtcaagc   5880
acagaggagc aatttcgagc caatttcagc agtgaagctg gctggagagg agtggttggg   5940
gaggtgccaa gacctgaaca ggtgcaggaa gccctgacaa agcatgattt gtatatctat   6000
gcagggcatg gggctggtgc ccgcttcctt gatgggcagg ctgtcctgcg gctgagctgt   6060
cgggcagtgg ccctgctgtt tggctgtagc agtgcggccc tggctgtgca tggaaacctg   6120
gagggggctg gcatcgtgct caagtacatc atggctggtt gccccttgtt tctgggtaat   6180
ctctgggatg tgactgaccg cgacattgac cgctacacgg aagctctgct gcaaggctgg   6240
cttggagcag gcccaggggc ccccccttctc tactatgtaa accaggcccg ccaagctccc   6300
cgactcaagt atcttattgg ggctgcacct atagcctatg gcttgcctgt ctctctgcgg   6360
```

taaccccatg gagctgtctt attgatgcta gaagcctcat aactgttcta cctccaaggt 6420
tagatttaat ccttaggata actcttttaa agtgattttc cccagtgttt tatatgaaac 6480
atttcctttt gatttaacct cagtataata aagatacatc atttaaaccc tgaaaaaaaa 6540
aaaaaaaaaa aa 6552

<210> SEQ ID NO 230
<211> LENGTH: 60
<212> TYPE: DNA
<213> ORGANISM: Homo sapiens
<220> FEATURE:
<223> OTHER INFORMATION: NM_012291

<400> SEQUENCE: 230
agcctcataa ctgttctacc tccaaggtta gatttaatcc ttaggataac tcttttaaag 60

<210> SEQ ID NO 231
<211> LENGTH: 6317
<212> TYPE: DNA
<213> ORGANISM: Homo sapiens
<220> FEATURE:
<223> OTHER INFORMATION: NM_013261

<400> SEQUENCE: 231
tagtaagaca ggtgccttca gttcactctc agtaaggggc tggttgcctg catgagtgtg 60
tgctctgtgt cactgtggat tggagttgaa aaagcttgac tggcgtcatt caggagctgg 120
atggcgtggg acatgtgcaa ccaggactct gagtctgtat ggagtgacat cgagtgtgct 180
gctctggttg gtgaagacca gcctctttgc ccagatcttc ctgaacttga tctttctgaa 240
ctagatgtga acgacttgga tacagacagc tttctgggtg gactcaagtg gtgcagtgac 300
caatcagaaa taatatccaa tcagtacaac aatgagcctt caaacatatt tgagaagata 360
gatgaagaga atgaggcaaa cttgctagca gtcctcacag agacactaga cagtctccct 420
gtggatgaag acggattgcc ctcatttgat gcgctgacag atggagacgt gaccactgac 480
aatgaggcta gtccttcctc catgcctgac ggcacccctc caccccagga ggcagaagag 540
ccgtctctac ttaagaagct cttactggca ccagccaaca ctcagctaag ttataatgaa 600
tgcagtggtc tcagtaccca gaaccatgca aatcacaatc acaggatcag aacaaaccct 660
gcaattgtta agactgagaa ttcatggagc aataaagcga agagtatttg tcaacagcaa 720
aagccacaaa gacgtccctg ctcggagctt ctcaaatatc tgaccacaaa cgatgaccct 780
cctcacacca aacccacaga gaacagaaac agcagcagag acaaatgcac ctccaaaaag 840
aagtcccaca cacagtcgca gtcacaacac ttacaagcca aaccaacaac tttatctctt 900
cctctgaccc cagagtcacc aaatgacccc aagggttccc catttgagaa caagactatt 960
gaacgcacct taagtgtgga actctctgga actgcaggcc taactccacc caccactcct 1020
cctcataaag ccaaccaaga taaccctttt agggcttctc caaagctgaa gtcctcttgc 1080
aagactgtgg tgccaccacc atcaaagaag cccaggtaca gtgagtcttc tggtacacaa 1140
ggcaataact ccaccaagaa agggccggag caatccgagt tgtatgcaca actcagcaag 1200
tcctcagtcc tcactggtgg acacgaggaa aggaagacca agcggcccag tctgcggctg 1260
tttggtgacc atgactattg ccagtcaatt aattccaaaa cagaaatact cattaatata 1320
tcacaggagc tccaagactc tagacaacta gaaaataaag atgtctcctc tgattggcag 1380
gggcagattt gttcttccac agattcagac cagtgctacc tgagagagac tttggaggca 1440
agcaagcagg tctctccttg cagcacaaga aaacagctcc aagaccagga aatccgagcc 1500

```
gagctgaaca agcacttcgg tcatcccagt caagctgttt ttgacgacga agcagacaag   1560

accggtgaac tgagggacag tgatttcagt aatgaacaat tctccaaact acctatgttt   1620

ataaattcag gactagccat ggatggcctg tttgatgaca gcgaagatga aagtgataaa   1680

ctgagctacc cttgggatgg cacgcaatcc tattcattgt tcaatgtgtc tccttcttgt   1740

tcttctttta actctccatg tagagattct gtgtcaccac ccaaatcctt attttctcaa   1800

agaccccaaa ggatgcgctc tcgttcaagg tccttttctc gacacaggtc gtgttcccga   1860

tcaccatatt ccaggtcaag atcaaggtct ccaggcagta gatcctcttc aagatcctgc   1920

tattactatg agtcaagcca ctacagacac cgcacgcacc gaaattctcc cttgtatgtg   1980

agatcacgtt caagatcgcc ctacagccgt cggcccaggt atgacagcta cgaggaatat   2040

cagcacgaga ggctgaagag ggaagaatat cgcagagagt atgagaagcg agagtctgag   2100

agggccaagc aaagggagag gcagaggcag aaggcaattg aagagcgccg tgtgatttat   2160

gtcggtaaaa tcagacctga cacaacacgg acagaactga gggaccgttt tgaagttttt   2220

ggtgaaattg aggagtgcac agtaaatctg cgggatgatg gagacagcta tggtttcatt   2280

acctaccgtt atacctgtga tgcttttgct gctcttgaaa atggatacac tttgcgcagg   2340

tcaaacgaaa ctgactttga gctgtacttt tgtggacgca agcaattttt caagtctaac   2400

tatgcagacc tagattcaaa ctcagatgac tttgaccctg cttccaccaa gagcaagtat   2460

gactctctgg attttgatag tttactgaaa gaagctcaga gaagcttgcg caggtaacat   2520

gttccctagc tgaggatgac agagggatgg cgaatacctc atgggacagc gcgtccttcc   2580

ctaaagacta ttgcaagtca tacttaggaa tttctcctac tttacactct ctgtacaaaa   2640

acaaaacaaa acaacaacaa tacaacaaga acaacaacaa caataacaac aatggtttac   2700

atgaacacag ctgctgaaga ggcaagagac agaatgatat ccagtaagca catgtttatt   2760

catgggtgtc agctttgctt ttcctggagt ctcttggtga tggagtgtgc gtgtgtgcat   2820

gtatgtgtgt gtgtatgtat gtgtgtggtg tgtgtgcttg gtttagggga agtatgtgtg   2880

ggtacatgtg aggactgggg gcacctgacc agaatgcgca agggcaaacc atttcaaatg   2940

gcagcagttc catgaagaca cgcttaaaac ctagaacttc aaaatgttcg tattctattc   3000

aaaaggaaat atatatatat atatatatat atatatatat atatataaat taaaaaggaa   3060

agaaaactaa caaccaacca accaaccaac caaccacaaa ccaccctaaa atgacagccg   3120

ctgatgtctg ggcatcagcc tttgtactct gttttttaa gaaagtgcag aatcaacttg   3180

aagcaagctt tctctcataa cgtaatgatt atatgacaat cctgaagaaa ccacaggttc   3240

catagaacta atatcctgtc tctctctctc tctctctctc tctcttttt ttttcttttt   3300

ccttttgcca tggaatctgg gtgggagagg atactgcggg caccagaatg ctaaagtttc   3360

ctaacatttt gaagtttctg tagttcatcc ttaatcctga cacccatgta aatgtccaaa   3420

atgttgatct tccactgcaa atttcaaaag ccttgtcaat ggtcaagcgt gcagcttgtt   3480

cagcggttct ttctgaggag cggacaccgg gttacattac taatgagagt tgggtagaac   3540

tctctgagat gtgttcagat agtgtaattg ctacattctc tgatgtagtt aagtatttac   3600

agatgttaaa tggagtattt ttattttatg tatatactat acaacaatgt tcttttttgt   3660

tacagctatg cactgtaaat gcagccttct tttcaaaact gctaaatttt tcttaatcaa   3720

gaatattcaa atgtaattat gaggtgaaac aattattgta cactaacata tttagaagct   3780

gaacttactg cttatatata tttgattgta aaaacaaaaa gacagtgtgt gtgtctgttg   3840

agtgcaacaa gagcaaaatg atgctttccg cacatccatc ccttaggtga gcttcaatct   3900
```

aagcatcttg tcaagaaata tcctagtccc ctaaaggtat taaccacttc tgcgatattt 3960
ttccacattt tcttgtcgct tgtttttctt tgaagtttta tacactggat ttgttagggg 4020
aatgaaattt tctcatctaa aatttttcta gaagatatca tgattttatg taaagtctct 4080
caatgggtaa ccattaagaa atgtttttat tttctctatc aacagtagtt ttgaaactag 4140
aagtcaaaaa tctttttaaa atgctgtttt gttttaattt ttgtgatttt aatttgatac 4200
aaaatgctga ggtaataatt atagtatgat ttttacaata attaatgtgt gtctgaagac 4260
tatctttgaa gccagtattt ctttcccttg gcagagtatg acgatggtat ttatctgtat 4320
tttttacagt tatgcatcct gtataaatac tgatatttca ttcctttgtt tactaaagag 4380
acatatttat cagttgcaga tagcctattt attataaatt atgagatgat gaaaataata 4440
aagccagtgg aaattttcta cctaggatgc atgacaattg tcaggttgga gtgtaagtgc 4500
ttcatttggg aaattcagct tttgcagaag cagtgtttct acttgcacta gcatggcctc 4560
tgacgtgacc atggtgttgt tcttgatgac attgcttctg ctaaatttaa taaaaacttc 4620
agaaaaacct ccattttgat catcaggatt tcatctgagt gtggagtccc tggaatggaa 4680
ttcagtaaca tttggagtgt gtattcaagt ttctaaattg agattcgatt actgtttggc 4740
tgacatgact tttctggaag acatgataca cctactactc aattgttctt ttcctttctc 4800
tcgcccaaca cgatcttgta agatggattt cacccccagg ccaatgcagc taattttgat 4860
agctgcattc atttatcacc agcatattgt gttctgagtg aatccactgt ttgtcctgtc 4920
ggatgcttgc ttgatttttt ggcttcttat ttctaagtag atagaaagca ataaaaatac 4980
tatgaaatga aagaacttgt tcacaggttc tgcgttacaa cagtaacaca tctttaatcc 5040
gcctaattct tgttgttctg taggttaaat gcaggtattt taactgtgtg aacgccaaac 5100
taaagtttac agtctttctt tctgaatttt gagtatcttc tgttgtagaa taataataaa 5160
aagactatta agagcaataa attattttta agaaatcgag atttagtaaa tcctattatg 5220
tgttcaagga ccacatgtgt tctctatttt gcctttaaat ttttgtgaac caattttaaa 5280
tacattctcc tttttgccct ggattgttga catgagtgga atacttggtt tcttttctta 5340
cttatcaaaa gacagcacta cagatatcat attgaggatt aatttatccc ccctaccccc 5400
agcctgacaa atattgttac catgaagata gttttcctca atggacttca aattgcatct 5460
agaattagtg gagcttttgt atcttctgca gacactgtgg gtagcccatc aaaatgtaag 5520
ctgtgctcct ctcattttta tttttatttt tttgggagag aatatttcaa atgaacacgt 5580
gcaccccatc atcactggag gcaaatttca gcatagatct gtaggatttt tagaagaccg 5640
tgggccattg ccttcatgcc gtggtaagta ccacatctac aattttggta accgaactgg 5700
tgctttagta atgtggattt ttttcttttt taaaagagat gtagcagaat aattcttcca 5760
gtgcaacaaa atcaattttt tgctaaacga ctccgagaac aacagttggg ctgtcaacat 5820
tcaaagcagc agagagggaa ctttgcacta ttggggtatg atgtttgggt cagttgataa 5880
aaggaaacct tttcatgcct ttagatgtga gcttccagta ggtaatgatt atgtgtcctt 5940
tcttgatggc tgtaatgaga acttcaatca ctgtagtcta agacctgatc tatagatgac 6000
ctagaatagc catgtactat aatgtgatga ttctaaattt gtacctatgt gacagacatt 6060
ttcaataatg tgaactgctg atttgatgga gctactttaa gatttgtagg tgaaagtgta 6120
atactgttgg ttgaactatg ctgaagaggg aaagtgagcg attagttgag cccttgccgg 6180
gcctttttc cacctgccaa ttctacatgt attgttgtgg ttttattcat tgtatgaaaa 6240
ttcctgtgat ttttttaaa tgtgcagtac acatcagcct cactgagcta ataaagggaa 6300
acgaatgttt caaatct 6317

<210> SEQ ID NO 232
<211> LENGTH: 60
<212> TYPE: DNA
<213> ORGANISM: Homo sapiens
<220> FEATURE:
<223> OTHER INFORMATION: NM_013261

<400> SEQUENCE: 232
ctgtagtcta agacctgatc tatagatacc tagaatagcc atgtactata atgtgatgat 60

<210> SEQ ID NO 233
<211> LENGTH: 3237
<212> TYPE: DNA
<213> ORGANISM: Homo sapiens
<220> FEATURE:
<223> OTHER INFORMATION: NM_013277

<400> SEQUENCE: 233
gcgaagtgaa gggtggccca ggtggggcca ggctgactga atgtatctcc tagctatgga 60
ctaaataata catgggggga aataaacaag tattcatgag ggtgaaaatg tgacccagca 120
ggaaaattac aactattttc aattgacgtt gaataggatg agtcatggaa tttaagtgat 180
ttactgaaga ttatactact ggtagataga agagctaaag aaagatggat actatgatgc 240
tgaatgtgcg gaatctgttt gagcagcttg tgcgccgggt ggagattctc agtgaaggaa 300
atgaagtcca atttatccag ttggcgaagg actttgagga tttccgtaaa aagtggcaga 360
ggactgacca tgagctgggg aaatacaagg atcttttgat gaaagcagag actgagcgaa 420
gtgctctgga tgttaagctg aagcatgcac gtaatcaggt ggatgtagag atcaaacgga 480
gacagagagc tgaggctgac tgcgaaaagc tggaacgaca gattcagctg attcgagaga 540
tgctcatgtg tgacacatct ggcagcattc aactaagcga ggagcaaaaa tcagctctgg 600
cttttctcaa cagaggccaa ccatccagca gcaatgctgg gaacaaaaga ctatcaacca 660
ttgatgaatc tggttccatt ttatcagata tcagctttga caagactgat gaatcactgg 720
attgggactc ttctttggtg aagactttca aactgaagaa gagagaaaag aggcgctcta 780
ctagccgaca gtttgttgat ggtccccctg gacctgtaaa gaaaactcgt tccattggct 840
ctgcagtaga ccaggggaat gaatccatag ttgcaaaaac tacagtgact gttcccaatg 900
atggcgggcc catcgaagct gtgtccacta ttgagactgt gccatattgg accaggagcc 960
gaaggaaaac aggtacttta caaccttgga acagtgactc caccctgaac agcaggcagc 1020
tggagccaag aactgagaca gacagtgtgg gcacgccaca gagtaatgga gggatgcgcc 1080
tgcatgactt tgtttctaag acggttatta aacctgaatc ctgtgttcca tgtggaaagc 1140
ggataaaatt tggcaaatta tctctgaagt gtcgagactg tcgtgtggtc tctcatccag 1200
aatgtcggga ccgctgtccc cttccctgca ttcctaccct gataggaaca cctgtcaaga 1260
ttggagaggg aatgctggca gactttgtgt cccagacttc tccaatgatc ccctccattg 1320
ttgtgcattg tgtaaatgag attgagcaaa gaggtctgac tgagacaggc ctgtatagga 1380
tctctggctg tgaccgcaca gtaaaagagc tgaaagagaa attcctcaga gtgaaaactg 1440 taccccctcct cagcaaagtg gatgatatcc atgctatctg tagccttcta aaagactttc 1500
ttcgaaacct caaagaacct cttctgacct ttcgccttaa cagagccttt atggaagcag 1560
cagaaatcac agatgaagac aacagcatag ctgccatgta ccaagctgtt ggtgaactgc 1620
cccaggccaa cagggacaca ttagctttcc tcatgattca cttgcagaga gtggctcaga 1680
gtccacatac taaaatggat gttgccaatc tggctaaagt ctttggccct acaatagtgg 1740
cccatgctgt gcccaatcca gacccagtga caatgttaca ggacatcaag cgtcaaccca 1800
aggtggttga gcgcctgctt tccttgcctc tggagtattg gagtcagttc atgatggtgg 1860
agcaagagaa cattgacccc ctacatgtca ttgaaaactc aaatgccttt tcaacaccac 1920
agacaccaga tattaaagtg agtttactgg gacctgtgac cactcctgaa catcagcttc 1980
tcaagactcc ttcatctagt tccctgtcac agagagtccg ttccaccctc accaagaaca 2040
ctcctagatt tgggagcaaa agcaagtctg ccactaacct aggacgacaa ggcaactttt 2100
ttgcttctcc aatgctcaag tgaagtcaca tctgcctgtt acttcccagc attgactgac 2160
tataagaaag gacacatctg tactctgctc tgcagcctcc tgtactcatt actactttta 2220
gcattctcca ggcttttact caagtttaat tgtgcatgag ggttttatta aaactatata 2280
tatctcccct tccttctcct caagtcacat aatatcagca ctttgtgctg gtcattgttg 2340
ggagctttta gatgagacat ctttccaggg gtagaagggt tagtatggaa ttggttgtga 2400
ttctttttgg ggaagggggt tattgttcct ttggcttaaa gccaaatgct gctcatagaa 2460
tgatctttct ctagtttcat ttagaactga tttccgtgag acaatgacag aaaccctacc 2520
tatctgataa gattagcttg tctcagggtg ggaagtggga gggcagggca aagaaaggat 2580
tagaccagag gatttaggat gcctccttct aagaaccaga agttctcatt ccccattatg 2640
aactgagcta taatatggag ctttcataaa aatgggatgc attgaggaca gaactagtga 2700
tgggagtatg cgtagctttg atttggatga ttaggtcttt aatagtgttg agtggcacaa 2760
ccttgtaaat gtgaaagtac aactcgtatt tatctctgat gtgccgctgg ctgaactttg 2820
ggttcatttg gggtcaaagc cagtttttct tttaaaattg aattcattct gatgcttggc 2880
ccccataccc ccaaccttgt ccagtggagc ccaacttcta aaggtcaata tatcatcctt 2940
tggcatccca actaacaata aagagtaggc tataagggaa gattgtcaat attttgtggt 3000
aagaaaagct acagtcattt tttctttgca ctttggatgc tgaaattttt cccatggaac 3060
atagccacat ctagatagat gtgagctttt tcttctgtta aaattattct taatgtctgt 3120
aaaaacgatt ttcttctgta gaatgtttga cttcgtattg acccttatct gtaaaacacc 3180
tatttgggat aatatttgga aaaaaagtaa atagcttttt caaaatgaaa aaaaaaa 3237

<210> SEQ ID NO 234
<211> LENGTH: 60
<212> TYPE: DNA
<213> ORGANISM: Homo sapiens
<220> FEATURE:
<223> OTHER INFORMATION: NM_013277

<400> SEQUENCE: 234
ctcattcccc attatgaact gagctataat atggagcttt cataaaaatg ggatgcattg 60

<210> SEQ ID NO 235
<211> LENGTH: 1122
<212> TYPE: DNA
<213> ORGANISM: Homo sapiens
<220> FEATURE:
<223> OTHER INFORMATION: NM_013409

<400> SEQUENCE: 235
gctcctcgcc ccgcgcctgc ccccaggatg gtccgcgcga ggcaccagcc gggtgggctt 60
tgcctcctgc tgctgctgct ctgccagttc atggaggacc gcagtgccca ggctgggaac 120
tgctggctcc gtcaagcgaa gaacggccgc tgccaggtcc tgtacaagac cgaactgagc 180
aaggaggagt gctgcagcac cggccggctg agcacctcgt ggaccgagga ggacgtgaat 240
gacaacacac tcttcaagtg gatgattttc aacgggggcg cccccaactg catcccctgt 300
aaagaaacgt gtgagaacgt ggactgtgga cctgggaaaa aatgccgaat gaacaagaag 360
aacaaacccc gctgcgtctg cgccccggat tgttccaaca tcacctggaa gggtccagtc 420
tgcgggctgg atgggaaaac ctaccgcaat gaatgtgcac tcctaaaggc aagatgtaaa 480
gagcagccag aactggaagt ccagtaccaa ggcagatgta aaaagacttg tcgggatgtt 540
ttctgtccag gcagctccac atgtgtggtg gaccagacca ataatgccta ctgtgtgacc 600
tgtaatcgga tttgcccaga gcctgcttcc tctgagcaat atctctgtgg gaatgatgga 660
gtcacctact ccagtgcctg ccacctgaga aaggctacct gcctgctggg cagatctatt 720
ggattagcct atgagggaaa gtgtatcaaa gcaaagtcct gtgaagatat ccagtgcact 780
ggtgggaaaa aatgtttatg ggatttcaag gttgggagag gccggtgttc cctctgtgat 840
gagctgtgcc ctgacagtaa gtcggatgag cctgtctgtg ccagtgacaa tgccacttat 900
gccagcgagt gtgccatgaa ggaagctgcc tgctcctcag gtgtgctact ggaagtaaag 960
cactccggat cttgcaactc catttcggaa gacaccgagg aagaggagga agatgaagac 1020
caggactaca gctttcctat atcttctatt ctagagtggt aaactctcta taagtgttca 1080
gtgttcacat agcctttgtg caaaaaaaaa aaaaaaaaaa aa 1122

<210> SEQ ID NO 236
<211> LENGTH: 60
<212> TYPE: DNA
<213> ORGANISM: Homo sapiens
<220> FEATURE:
<223> OTHER INFORMATION: NM_013409

<400> SEQUENCE: 236
gaagatgaag accaggacta cagctttcct atatcttcta ttctagagtg gtaaactctc 60

<210> SEQ ID NO 237
<211> LENGTH: 11389
<212> TYPE: DNA
<213> ORGANISM: Homo sapiens
<220> FEATURE:
<223> OTHER INFORMATION: NM_014246

<400> SEQUENCE: 237
atggcgccgc cgccgccgcc cgtgctgccc gtgctgctgc tcctggccgc cgccgccgcc 60
ctgccggcga tggggctgcg agcggccgcc tgggagccgc gcgtacccgg cgggacccgc 120
gccttcgccc tccggcccgg ctgtacctac gcggtgggcg ccgcttgcac gccccgggcg 180
ccgcgggagc tgctggacgt gggccgcgat gggcggctgg caggacgtcg gcgcgtctcg 240
ggcgcggggc gcccgctgcc gctgcaagtc cgcttggtgg cccgcagtgc cccgacggcg 300
ctgagccgcc gcctgcgggc gcgcacgcac cttcccggct gcggagcccg tgcccggctc 360
tgcggaaccg gtgcccggct ctgcggggcg ctctgcttcc ccgtccccgg cggctgcgcg 420
gccgcgcagc attcggcgct cgcagctccg accaccttac ccgcctgccg ctgcccgccg 480
cgccccaggc cccgctgtcc cggccgtccc atctgcctgc cgccgggcgg ctcggtccgc 540
ctgcgtctgc tgtgcgccct gcggcgcgcg gctggcgccg tccgggtggg actggcgctg 600
gaggccgcca ccgcggggac gccctccgcg tcgccatccc catcgccgcc cctgccgccg 660
aacttgcccg aagcccgggc ggggccggcg cgacgggccc ggcggggcac gagcggcaga 720
gggagcctga agtttccgat gcccaactac caggtggcgt tgtttgagaa cgaaccggcg 780

```
ggcaccctca tcctccagct gcacgcgcac tacaccatcg agggcgagga ggagcgcgtg    840
agctattaca tggaggggct gttcgacgag cgctcccggg gctacttccg aatcgactct    900
gccacgggcg ccgtgagcac ggacagcgta ctggaccgcg agaccaagga gacgcacgtc    960
ctcagggtga aagccgtgga ctacagtacg ccgccgcgct cggccaccac ctacatcact   1020
gtcttggtca aagacaccaa cgaccacagc ccggtcttcg agcagtcgga gtaccgcgag   1080
cgcgtgcggg agaacctgga ggtgggctac gaggtgctga ccatccgcgc cagcgaccgc   1140
gactcgccca tcaacgccaa cttgcgttac cgcgtgttgg ggggcgcgtg ggacgtcttc   1200
cagctcaacg agagctctgg cgtggtgagc acacgggcgg tgctggaccg ggaggaggcg   1260
gccgagtacc agctcctggt ggaggccaac gaccaggggc gcaatccggg cccgctcagt   1320
gccacggcca ccgtgtacat cgaggtggag gacgagaacg acaactaccc ccagttcagc   1380
gagcagaact acgtggtcca ggtgcccgag gacgtggggc tcaacacggc tgtgctgcga   1440
gtgcaggcca cggaccggga ccagggccag aacgcggcca ttcactacag catcctcagc   1500
gggaacgtgg ccggccagtt ctacctgcac tcgctgagcg ggatcctgga tgtgatcaac   1560
cccttggatt tcgaggatgt ccagaaatac tcgctgagca ttaaggccca ggatgggggc   1620
cggcccccgc tcatcaattc ttcaggggtg gtgtctgtgc aggtgctgga tgtcaacgac   1680
aacgagccta tctttgtgag cagccccttc caggccacgg tgctggagaa tgtgcccctg   1740
ggctaccccg tggtgcacat tcaggcggtg gacgcggact ctggagagaa cgcccggctg   1800
cactatcgcc tggtggacac ggcctccacc tttctggggg gcggcagcgc tgggcctaag   1860
aatcctgccc ccacccctga cttccccttc cagatccaca acagctccgg ttggatcaca   1920
gtgtgtgccg agctggaccg cgaggaggtg gagcactaca gcttcggggt ggaggcggtg   1980
gaccacggct cgccccccat gagctcctcc accagcgtgt ccatcacggt gctggacgtg   2040
aatgacaacg acccggtgtt cacgcagccc acctacgagc ttcgtctgaa tgaggatgcg   2100
gccgtgggga gcagcgtgct gaccctgcag gcccgcgacc gtgacgccaa cagtgtgatt   2160
acctaccagc tcacaggcgg caacacccgg aaccgctttg cactcagcag ccagagaggg   2220
ggcggcctca tcaccctggc gctacctctg gactacaagc aggagcagca gtacgtgctg   2280
gcggtgacag catccgacgg cacacggtcg cacactgcgc atgtcctaat caacgtcact   2340
gatgccaaca cccacaggcc tgtctttcag agctcccatt acacagtgag tgtcagtgag   2400
gacaggcctg tgggcacctc cattgctacc ctcagtgcca acgatgagga cacaggagag   2460
aatgcccgca tcacctacgt gattcaggac cccgtgccgc agttccgcat tgaccccgac   2520
agtggcacca tgtacaccat gatggagctg gactatgaga accaggtcgc ctacacgctg   2580
accatcatgg cccaggacaa cggcatcccg cagaaatcag acaccaccac cctagagatc   2640
ctcatcctcg atgccaatga caatgcaccc cagttcctgt gggatttcta ccagggttcc   2700
atctttgagg atgctccacc ctcgaccagc atcctccagg tctctgccac ggaccgggac   2760
tcaggtccca atgggcgtct gctgtacacc ttccagggtg gggacgacgg cgatggggac   2820
ttctacatcg agcccacgtc cggtgtgatt cgcacccagc gccggctgga ccgggagaat   2880
gtggccgtgt acaacctttg ggctctggct gtggatcggg gcagtcccac tccccttagc   2940
gcctcggtag aaatccaggt gaccatcttg gacattaatg acaatgcccc catgtttgag   3000
aaggacgaac tggagctgtt tgttgaggag aacaacccag tggggtcggt ggtggcaaag   3060
attcgtgcta acgaccctga tgaaggccct aatgcccaga tcatgtatca gattgtggaa   3120
ggggacatgc ggcatttctt ccagctggac ctgctcaacg ggggacctgcg tgccatggtg   3180
```

-continued

```
gagctggact ttgaggtccg gcgggagtat gtgctggtgg tgcaggccac gtcggctccg   3240
ctggtgagcc gagccacggt gcacatcctt ctcgtggacc agaatgacaa cccgcctgtg   3300
ctgcccgact tccagatcct cttcaacaac tatgtcacca acaagtccaa cagtttcccc   3360
accggcgtga tcggctgcat cccggcccat gaccccgacg tgtcagacag cctcaactac   3420
accttcgtgc agggcaacga gctgcgcctg ttgctgctgg accccgccac gggcgaactg   3480
cagctcagcc gcgacctgga caacaaccgg ccgctggagg cgctcatgga ggtgtctgtg   3540
tctgatggca tccacagcgt cacggccttc tgcaccctgc gtgtcaccat catcacggac   3600
gacatgctga ccaacagcat cactgtccgc ctggagaaca tgtcccagga gaagttcctg   3660
tccccgctgc tggccctctt cgtggagggg gtggccgccg tgctgtccac caccaaggac   3720
gacgtcttcg tcttcaacgt ccagaacgac accgacgtca gctccaacat cctgaacgtg   3780
accttctcgg cgctgctgcc tggcggcgtc cgcggccagt tcttcccgtc ggaggacctg   3840
caggagcaga tctacctgaa tcggacgctg ctgaccacca tctccacgca gcgcgtgctg   3900
cccttcgacg acaacatctg cctgcgcgag ccctgcgaga actacatgaa gtgcgtgtcc   3960
gttctgcgat tcgacagctc cgcgcccttc ctcagctcca ccaccgtgct cttccggccc   4020
atccacccca tcaacggcct gcgctgccgc tgcccgcccg gcttcaccgg cgactactgc   4080
gagacggaga tcgacctctg ctactccgac ccgtgcggcg ccaacggccg ctgccgcagc   4140
cgcgagggcg gctacacctg cgagtgcttc gaggacttca ctggagagca ctgtgaggtg   4200
gatgcccgct caggccgctg tgccaacggg gtgtgcaaga acgggggcac ctgcgtgaac   4260
ctgctcatcg gcggcttcca ctgcgtgtgt cctcctggcg agtatgagag gccctactgt   4320
gaggtgacca ccaggagctt cccgccccag tccttcgtca ccttccgggg cctgagacag   4380
cgcttccact tcaccatctc cctcacgttt gccactcagg aaaggaacgg cttgcttctc   4440
tacaacggcc gcttcaatga gaagcacgac ttcatcgccc tggagatcgt ggacgagcag   4500
gtgcagctca ccttctctgc aggcgagaca acaacgaccg tggcaccgaa ggttcccagt   4560
ggtgtgagtg acgggcggtg gcactctgtg caggtgcagt actacaacaa gcccaatatt   4620
ggccacctgg gcctgcccca tgggccgtcc ggggaaaaga tggccgtggt gacagtggat   4680
gattgtgaca caaccatggc tgtgcgcttt ggaaaggaca tcgggaacta cagctgcgct   4740
gcccagggca ctcagaccgg ctccaagaag tccctggatc tgaccggccc tctactcctg   4800
gggggtgtcc ccaacctgcc agaagacttc ccagtgcaca accggcagtt cgtgggctgc   4860
atgcggaacc tgtcagtcga cggcaaaaat gtggacatgg ccggattcat cgccaacaat   4920
ggcacccggg aaggctgcgc tgctcggagg aacttctgcg atgggaggcg gtgtcagaat   4980
ggaggcacct gtgtcaacag gtggaatatg tatctgtgtg agtgtccact ccgattcggc   5040
gggaagaact gtgagcaagc catgcctcac ccccagctct tcagcggtga gagcgtcgtg   5100
tcctggagtg acctgaacat catcatctct gtgccctggt acctggggct catgttccgg   5160
acccggaagg aggacagcgt tctgatggag gccaccagtg gtgggcccac cagctttcgc   5220
ctccagatcc tgaacaacta cctccagttt gaggtgtccc acggcccctc cgatgtggag   5280
tccgtgatgc tgtccgggtt gcgggtgacc gacggggagt ggcaccacct gctgatcgag   5340
ctgaagaatg ttaaggagga cagtgagatg aagcacctgg tcaccatgac cttggactat   5400
gggatggacc agaacaaggc agatatcggg ggcatgcttc ccgggctgac ggtaaggagc   5460
gtggtggtcg gaggcgcctc tgaagacaag gtctccgtgc gccgtggatt ccgaggctgc   5520
atgcagggag tgaggatggg ggggacgccc accaacgtcg ccaccctgaa catgaacaac   5580
```

```
gcactcaagg tcagggtgaa ggacggctgt gatgtggacg acccctgtac ctcgagcccc   5640
tgtcccccca atagccgctg ccacgacgcc tgggaggact acagctgcgt ctgtgacaaa   5700
gggtaccttg gaataaactg tgtggatgcc tgtcacctga acccctgcga gaacatgggg   5760
gcctgcgtgc gctcccccgg ctccccgcag ggctacgtgt gcgagtgtgg gcccagtcac   5820
tacgggccgt actgtgagaa caaactcgac cttccgtgcc ccagaggctg gtgggggaac   5880
cccgtctgtg gaccctgcca ctgtgccgtc agcaaaggct ttgatcccga ctgtaataag   5940
accaacggcc agtgccaatg caaggagaat tactacaagc tcctagccca ggacacctgt   6000
ctgccctgcg actgcttccc ccatggctcc cacagccgca cttgcgacat ggccaccggg   6060
cagtgtgcct gcaagcccgg cgtcatcggc cgccagtgca accgctgcga caacccgttt   6120
gccgaggtca ccacgctcgg ctgtgaagtg atctacaatg gctgtcccaa agcatttgag   6180
gccggcatct ggtggccaca gaccaagttc gggcagccgg ctgcggtgcc atgccctaag   6240
ggatccgttg gaaatgcggt ccgacactgc agcggggaga agggctggct gcccccagag   6300
ctctttaact gtaccaccat ctccttcgtg gacctcaggg ccatgaatga gaagctgagc   6360
cgcaatgaga cgcaggtgga cggcgccagg gccctgcagc tggtgagggc gctgcgcagt   6420
gctacacagc acacgggcac gctctttggc aatgacgtgc gcacggccta ccagctgctg   6480
ggccacgtcc ttcagcacga gagctggcag cagggcttcg acctggcagc cacgcaggac   6540
gccgactttc acgaggacgt catccactcg ggcagcgccc tcctggcccc agccaccagg   6600
gcggcgtggg agcagatcca gcggagcgag ggcggcacgg cacagctgct ccggcgcctc   6660
gagggctact tcagcaacgt ggcacgcaac gtgcggcgga cgtacctgcg gcccttcgtc   6720
atcgtcaccg ccaacatgat tcttgctgtc gacatctttg acaagttcaa ctttacggga   6780
gccagggtcc cgcgattcga caccatccat gaagagttcc ccagggagct ggagtcctcc   6840
gtctccttcc cagccgactt cttcagacca cctgaagaaa aagaaggccc cctgctgagg   6900
ccggctggcc ggaggaccac cccgcagacc acgcgcccgg ggcctggcac cgagagggag   6960
gccccgatca gcaggcggag gcgacaccct gatgacgctg gccagttcgc cgtcgctctg   7020
gtcatcattt accgcaccct ggggcagctc ctgcccgagc gctacgaccc cgaccgtcgc   7080
agcctccggt tgcctcaccg gcccatcatt aataccccga tggtgagcac gctggtgtac   7140
agcgaggggg ctccgctccc gagacccctg gagaggcccg tcctggtgga gttcgccctg   7200
ctggaggtgg aggagcgaac caagcctgtc tgcgtgttct ggaaccactc cctggccgtt   7260
ggtgggacgg gagggtggtc tgcccggggc tgcgagctcc tgtccaggaa ccggacacat   7320
gtcgcctgcc agtgcagcca cacagccagc tttgcggtgc tcatggatat ctccaggcgt   7380
gagaacgggg aggtcctgcc tctgaagatt gtcacctatg ccgctgtgtc cttgtcactg   7440
gcagccctgc tggtggcctt cgtcctcctg agcctggtcc gcatgctgcg ctccaacctg   7500
cacagcattc acaagcacct cgccgtggcg ctcttcctct ctcagctggt gttcgtgatt   7560
gggatcaacc agacggaaaa cccgtttctg tgcacagtgg ttgccatcct cctccactac   7620
atctacatga gcacctttgc ctggaccctc gtggagagcc tgcatgtcta ccgcatgctg   7680
accgaggtgc gcaacatcga cacggggccc atgcggttct actacgtcgt gggctggggc   7740
atcccggcca ttgtcacagg actggcggtc ggcctggacc cccagggcta cgggaacccc   7800
gacttctgct ggctgtcgct tcaagacacc ctgatttgga gctttgcggg gcccatcgga   7860
gctgttataa tcatcaacac agtcacttct gtcctatctg caaaggtttc ctgccaaaga   7920
aagcaccatt attatgggaa aaaagggatc gtctccctgc tgaggaccgc attcctcctg   7980
```

ctgctgctca tcagcgccac ctggctgctg gggctgctgg ctgtgaaccg cgatgcactg 8040
agctttcact acctcttcgc catcttcagc ggcttacagg gccccttcgt cctccttttc 8100
cactgcgtgc tcaaccagga ggtccggaag cacctgaagg gcgtgctcgg cgggaggaag 8160
ctgcacctgg aggactccgc caccaccagg gccaccctgc tgacgcgctc cctcaactgc 8220
aacaccacct tcggtgacgg gcctgacatg ctgcgcacag acttgggcga gtccaccgcc 8280
tcgctggaca gcatcgtcag ggatgaaggg atccagaagc tcggcgtgtc ctctgggctg 8340
gtgaggggca gccacggaga gccagacgcg tccctcatgc ccaggagctg caaggatccc 8400
cctggccacg attccgactc agatagcgag ctgtccctgg atgagcagag cagctcttac 8460
gcctcctcac actcgtcaga cagcgaggac gatggggtgg gagctgagga aaaatgggac 8520
ccggccaggg gcgccgtcca cagcaccccc aaaggggacg ctgtggccaa ccacgttccg 8580
gccggctggc ccgaccagag cctggctgag agtgacagtg aggaccccag cggcaagccc 8640
cgcctgaagg tggagaccaa ggtcagcgtg gagctgcacc gcgaggagca gggcagtcac 8700
cgtggagagt accccccgga ccaggagagc gggggcgcag ccaggcttgc tagcagccag 8760
cccccagagc agaggaaagg catcttgaaa aataaagtca cctacccgcc gccgctgacg 8820
ctgacggagc agacgctgaa gggccggctc cgggagaagc tggccgactg tgagcagagc 8880
cccacatcct cgcgcacgtc ttccctgggc tctggcggcc ccgactgcgc catcacagtc 8940
aagagccctg ggagggagcc ggggcgtgac cacctcaacg gggtggccat gaatgtgcgc 9000
actgggagcg cccaggccga tggctccgac tctgagaaac cgtgaggcaa gcccgtcacc 9060
ccacacaggc tgcggcatca ccctcagacc ttggagccca aggggccact gcccttgaag 9120
tggagtgggc ccagagtgtg gcggtcccca tggtggcagc cccccgactg atcatccaga 9180
cacaaaggtc ttggttctcc caggagctca gggcctgtca gacctggtga caagtgccaa 9240
aggccacagg catgagggag gcgtggacca ctgggccagc accgctgagt cctaagactg 9300
cagtcaaagc cagaactgag aggggacccc agactgggcc cagaggctgg ccagagttca 9360
ggaacgccgg gcacagacca aagaccgcgg tccagccccg cccaggcggg catctcatgg 9420
cagtgcggac ccgtggctgg cagcccgggc agtcctttgc aaaggcaccc cttgtcttaa 9480
aatcacttcg ctatgtggga aaggtggaga tacttttata tatttgtatg ggactctgag 9540
gaggtgcaac ctgtatatat attgcattcg tgctgacttt gttatcccga gagatccatg 9600
caatgatctc ttgctgtctt ctctgtcaag attgcacagt tgtacttgaa tctggcatgt 9660
gttgacgaaa ctggtgcccc agcagatcaa aggtgggaaa tacgtcagca gtggggctaa 9720
aaccaagcgg ctagaagccc tacagctgcc ttcggccagg aagtgaggat ggtgtgggcc 9780
ctccccgccg gccccctggg tccccagtgt tcgctgtgtg tgcgtttgtc ctctgctgcc 9840
atctgccccg gctgtgtgaa ttcaagacag ggcagtgcag cactaggcag gtgtgaggag 9900
ccctgctgag gtcactgtgg ggcacggttg ccacacggct gtcatttttc acctggtcat 9960
tctgtgacca ccaccccctc ccctcaccgc ctcccaggtg gcccgggagc tgcaggtggg 10020
gatggctttg tcctttgctc ctgctccccg tgggacctgg gaccttaaag cgttgcaggt 10080
tcctgatttg gacagaggtg tggggccttc caggccgtta catacctcct gccaattctc 10140
taactctctg agactgcgag gatctccagg cagggttctc ccctctggag tctgaccaat 10200
tacttcattt tgcttcaaat ggccaattgt gcagagggac aaagccacag ccacactctt 10260
caacggttac caaactgttt ttggaaattc acaccaaggt cgggcccact gcaggcagct 10320
ggcacagcgt ggcccgaggg gctgtggaac gggtcccgga actgtcagac atgtttgatt 10380
ttagcgtttc ctttgttctt caaatcaggt gcccaaataa gtgatcagca cagctgcttc 10440
caaataggag aaaccataaa ataggatgaa aatcaagtaa aatgcaaaga tgtccacact 10500
gttttaaact tgaccctgat gaaaatgtga gcactgttag cagatgccta tgggagagga 10560
aaagcgtatc tgaaaatggt ccaggacagg aggatgaaat gagatcccag agtcctcaca 10620
cctgaatgaa ttatacatgt gccttaccag gtgagtggtc tttcgaagat aaaaaactct 10680
agtcccttta aacgtttgcc cctggcgttt cctaagtacg aaaaggtttt taagtcttcg 10740
aacagtctcc tttcatgact ttaacaggat tctgcccct gaggtgtaat ttttttgttc 10800 tattttttc cacgtactcc acagccaaca tcacgaggtg taatttttaa tttgatcaga 10860
actgttacca aaaaacaact gtcagtttta ttgagatggg aaaaatgtaa acctattttt 10920
attacttaag actttatggg agagattaga cactggaggt ttttaacaga acgtgtattt 10980
attaatgttc aaaacactgg aattacaaat gagaagagtc tacaataaat taagattttt 11040
gaatttgtac ttctgcggtg ctggtttttc tccacaaaca cccccgcccc tccccatgcc 11100
cagggtggcc gtggaaggga cggtttacgg acgtgcagct gagctgtccg tgtcccatgc 11160
tccctcagcc agtggaacgt gccggaactt tttgtccatt ccctagtagg cctgccacag 11220
cctagatggg cagtttttgt ctttcaccaa atttgaggac ttttttttt tgccattatt 11280 tcttcagttt tcttttcttg cactgatctt tctcctctcc ttctgtgact ccagtgactc 11340
agacgttaga cctcttgatg ttttcccact ggtccctgag gctctgttc 11389

<210> SEQ ID NO 238
<211> LENGTH: 60
<212> TYPE: DNA
<213> ORGANISM: Homo sapiens
<220> FEATURE:
<223> OTHER INFORMATION: NM_014246

<400> SEQUENCE: 238
gggagagatt agacactgga ggtttttaac agaacgtgta tttattaatg ttcaaaacac 60

<210> SEQ ID NO 239
<211> LENGTH: 4372
<212> TYPE: DNA
<213> ORGANISM: Homo sapiens
<220> FEATURE:
<223> OTHER INFORMATION: NM_014314

<400> SEQUENCE: 239
tagttattaa agttcctatg cagctccgcc tcgcgtccgg cctcatttcc tcggaaaatc 60
cctgctttcc ccgctcgcca cgccctcctc ctacccggct ttaaagctag tgaggcacag 120
cctgcgggga acgtagctag ctgcaagcag aggccggcat gaccaccgag cagcgacgca 180
gcctgcaagc cttccaggat tatatccgga agaccctgga ccctacctac atcctgagct 240
acatggcccc ctggtttagg gaggaagagg tgcagtatat tcaggctgag aaaaacaaca 300
agggcccaat ggaggctgcc acactttttc tcaagttcct gttggagctc caggaggaag 360
gctggttccg tggctttttg gatgccctag accatgcagg ttattctgga ctttatgaag 420
ccattgaaag ttgggatttc aaaaaaattg aaaagttgga ggagtataga ttacttttaa 480
aacgtttaca accagaattt aaaaccagaa ttatcccaac cgatatcatt tctgatctgt 540
ctgaatgttt aattaatcag gaatgtgaag aaattctaca gatttgctct actaagggga 600
tgatggcagg tgcagagaaa ttggtggaat gccttctcag atcagacaag gaaaactggc 660
ccaaaacttt gaaacttgct ttggagaaag aaaggaacaa gttcagtgaa ctgtggattg 720

-continued

```
tagagaaagg tataaaagat gttgaaacag aagatcttga ggataagatg gaaacttctg    780
acatacagat tttctaccaa gaagatccag aatgccagaa tcttagtgag aattcatgtc    840
caccttcaga agtgtctgat acaaacttgt acagcccatt taaaccaaga aattaccaat    900
tagagcttgc tttgcctgct atgaaaggaa aaaacacaat aatatgtgct cctacaggtt    960
gtggaaaaac ctttgtttca ctgcttatat gtgaacatca tcttaaaaaa ttcccacaag   1020
gacaaaaggg gaaagttgtc tttttgcga atcagatccc agtgtatgaa cagcagaaat   1080
ctgtattctc aaaatacttt gaaagacatg ggtatagagt tacaggcatt tctggagcaa   1140
cagctgagaa tgtcccagtg gaacagattg ttgagaacaa tgacatcatc attttaactc   1200
cacagattct tgtgaacaac cttaaaaagg gaacgattcc atcactatcc atctttactt   1260
tgatgatatt tgatgaatgc cacaacacta gtaaacaaca cccgtacaat atgatcatgt   1320
ttaattatct agatcagaaa cttggaggat cttcaggccc actgccccag gtcattgggc   1380
tgactgcctc ggttggtgtt ggggatgcca aaaacacaga tgaagccttg gattatatct   1440
gcaagctgtg tgcttctctt gatgcgtcag tgatagcaac agtcaaacac aatctggagg   1500
aactggagca agttgtttat aagccccaga agtttttcag gaaagtggaa tcacggatta   1560
gcgacaaatt taaatacatc atagctcagc tgatgaggga cacagagagt ctggcaaaga   1620
gaatctgcaa agacctcgaa aacttatctc aaattcaaaa tagggaattt ggaacacaga   1680
aatatgaaca atggattgtt acagttcaga aagcatgcat ggtgttccag atgccagaca   1740
aagatgaaga gagcaggatt tgtaaagccc tgtttttata cacttcacat ttgcggaaat   1800
ataatgatgc cctcattatc agtgagcatg cacgaatgaa agatgctctg gattacttga   1860
aagacttctt cagcaatgtc cgagcagcag gattcgatga gattgagcaa gatcttactc   1920
agagatttga agaaaagctg caggaactag aaagtgtttc cagggatccc agcaatgaga   1980
atcctaaact tgaagacctc tgcttcatct tacaagaaga gtaccactta aacccagaga   2040
caataacaat tctctttgtg aaaaccagag cacttgtgga cgctttaaaa aattggattg   2100
aaggaaatcc taaactcagt tttctaaaac ctggcatatt gactggacgt ggcaaaacaa   2160
atcagaacac aggaatgacc ctcccggcac agaagtgtat attggatgca ttcaaagcca   2220
gtggagatca caatattctg attgccacct cagttgctga tgaaggcatt gacattgcac   2280
agtgcaatct tgtcatcctt tatgagtatg tgggcaatgt catcaaaatg atccaaacca   2340
gaggcagagg aagagcaaga ggtagcaagt gcttccttct gactagtaat gctggtgtaa   2400
ttgaaaaaga acaaataaac atgtacaaag aaaaaatgat gaatgactct attttacgcc   2460
ttcagacatg ggacgaagca gtatttaggg aaaagattct gcatatacag actcatgaaa   2520
aattcatcag agatagtcaa gaaaaaccaa aacctgtacc tgataaggaa aataaaaaac   2580
tgctctgcag aaagtgcaaa gccttggcat gttacacagc tgacgtaaga gtgatagagg   2640
aatgccatta cactgtgctt ggagatgctt ttaaggaatg ctttgtgagt agaccacatc   2700
ccaagccaaa gcagttttca agttttgaaa aaagagcaaa gatattctgt gcccgacaga   2760
actgcagcca tgactgggga atccatgtga agtacaagac atttgagatt ccagttataa   2820
aaattgaaag ttttgtggtg gaggatattg caactggagt tcagacactg tactcgaagt   2880
ggaaggactt tcattttgag aagataccat ttgatccagc agaaatgtcc aaatgatatc   2940
aggtcctcaa tcttcagcta cagggaatga gtaactttga gtggagaaga aacaaacata   3000
gtgggtataa tcatggatcg cttgtacccc tgtgaaaata tatttttttaa aaatatcttt   3060
agcagtttgt actatattat atatgcaaag cacaaatgag tgaatcacag cactgagtat   3120
```

tttgtaggcc aacagagctc atagtacttg ggaaaaatta aaaagcctca tttctagcct 3180
tctttttaga gtcaactgcc aacaaacaca cagtaatcac tctgtacaca ctgggataga 3240
tgaatgaatg gaatgttggg aatttttatc tccctttgtc tccttaacct actgtaaact 3300
ggcttttgcc cttaacaatc tactgaaatt gttcttttga aggttaccag tgactctggt 3360
tgccaaatcc actgggcact tcttaacctt ctatttgacc tctgcgcatt tggccctgtt 3420
gagcactctt cttgaagctc tccctgggct tctctctctt ctagttctat tctagtcttt 3480
ttttattgag tcctcctctt tgctgatccc ttccaagggt tcaatatata tacatgtata 3540
tactgtacat atgtatatgt aactaatata catacataca ggtatgtata tgtaatggtt 3600
atatgtactc atgttcctgg tgtagcaacg tgtggtatgg ctacacagag aacatgagaa 3660
cataaagcca tttttatgct tactactaaa agctgtccac tgtagagttg ctgtatgtag 3720
caatgtgtat ccactctaca gtggtcagct tttagtagag agcataaaaa tgataaaata 3780
cttcttgaaa acttagttta ctatacatct tgccctatta atatgttctc ttaacgtgtg 3840
ccattgttct ctttgaccat tttcctataa tgatgttgat gttcaacacc tggactgaat 3900
gtctgttctc agatcccttg gatgttacag atgaggcagt ctgactgtcc tttctacttg 3960
aaagattaga atatgtatcc aaatggcatt cacgtgtcac ttagcaaggt ttgctgatgc 4020
ttcaaagagc ttagtttgcg gtttcctgga cgtggaaaca agtatctgag ttccctggag 4080
atcaacggga tgaggtgtta cagctgcctc cctcttcatg caatctggtg agcagtggtg 4140
caggcgggga gccagagaaa cttgccagtt atataacttc tctttggctt ttcttcatct 4200
gtaaaacaag gataatactg aactgtaagg gttagtggag agtttttaat taaaagaatg 4260
tgtgaaaagt acatgacaca gtagttgctt gataatagtt actagtagta gtattcttac 4320
taagacccaa tacaaatgga ttatttaaac caaaaaaaaa aaaaaaaaaa aa 4372

<210> SEQ ID NO 240
<211> LENGTH: 60
<212> TYPE: DNA
<213> ORGANISM: Homo sapiens
<220> FEATURE:
<223> OTHER INFORMATION: NM_014314

<400> SEQUENCE: 240
agttcagaca ctgtactcga agtggaagga ctttcatttt gagaagatac catttgatcc 60

<210> SEQ ID NO 241
<211> LENGTH: 1647
<212> TYPE: DNA
<213> ORGANISM: Homo sapiens
<220> FEATURE:
<223> OTHER INFORMATION: NM_014321

<400> SEQUENCE: 241
gcgcgcgggt ttcgttgacc cgcggcgttc acgggaattg ttcgctttag tgccggcgcc 60
atggggtcgg agctgatcgg gcgcctagcc ccgcgcctgg gcctcgccga gcccgacatg 120
ctgaggaaag cagaggagta cttgcgcctg tcccgggtga agtgtgtcgg cctctccgca 180
cgcaccacgg agaccagcag tgcagtcatg tgcctggacc ttgcagcttc ctggatgaag 240
tgccccttgg acagggctta tttaattaaa ctttctggtt tgaacaagga gacatatcag 300
agctgtctta aatcttttga gtgtttactg ggcctgaatt caaatattgg aataagagac 360
ctagctgtac agtttagctg tatagaagca gtgaacatgg cttcaaagat actaaaaagc 420
tatgagtcca gtcttcccca gacacagcaa gtggatcttg acttatccag gccacttttc 480

```
acttctgctg cactgctttc agcatgcaag attctaaagc tgaaagtgga taaaaacaaa    540

atggtagcca catccggtgt aaaaaaagct atatttgatc gactgtgtaa acaactagag    600

aagattggac agcaggtcga cagagaacct ggagatgtag ctactccacc acggaagaga    660

aagaagatag tggttgaagc cccagcaaag gaaatggaga aggtagagga gatgccacat    720

aaaccacaga aagatgaaga tctgacacag gattatgaag aatggaaaag aaaaattttg    780

gaaaatgctg ccagtgctca aaaggctaca gcagagtgat ttcagcttcc aaactggtat    840

acattccaaa ctgatagtac attgccatct ccaggaagac ttgacggctt tgggattttg    900

tttaaacttt tataataagg atcctaagac tgttgccttt aaatagcaaa gcagcctacc    960

tggaggctaa gtctgggcag tgggctggcc cctggtgtga gcattagacc agccacagtg   1020

cctgattggt atagccttat gtgctttcct acaaaatgga attggaggcc gggcgcagtg   1080

gctcacgcct gtaatcccag cactttggga ggccaaggtg ggtggatcac ctgaggtcag   1140

gagctcgaga ccagcctggc caacatggtg aaaccccatc tctactaaaa atacaaaaat   1200

tagccaggtg tgatggtgca tgcctgtaat cccagctcct cagtaggctg agacaggagc   1260

atcacttgaa cgtgggaggc agaggttgca gtgagccgag attgcaccac cgcactccag   1320

cctgggtgac agagcgagac ttatctcata aataaataga tagatactcc agcctgggtg   1380

acagagcgag acttatagat agatagatag atagatggat agatagatag atagatagat   1440

agatagataa acggaattgg agccattttg ctttaagtga atggcagtcc cttgtcttat   1500

tcagaatata aaattcagtc tgaatggcat cttacagatt ttacttcaat ttttgtgtac   1560

ggtatttttt atttgactaa atcaatatat tgtacagcct aagttaataa atgttattta   1620

tatatgcaaa aaaaaaaaaa aaaaaaa                                       1647
```

<210> SEQ ID NO 242
<211> LENGTH: 60
<212> TYPE: DNA
<213> ORGANISM: Homo sapiens
<220> FEATURE:
<223> OTHER INFORMATION: NM_014321

<400> SEQUENCE: 242

```
tgctttaagt gaatggcagt cccttgtctt attcagaata taaaattcag tctgaatggc     60
```

<210> SEQ ID NO 243
<211> LENGTH: 1455
<212> TYPE: DNA
<213> ORGANISM: Homo sapiens
<220> FEATURE:
<223> OTHER INFORMATION: NM_014364

<400> SEQUENCE: 243

```
ggcggtccgc acgcacctcg gtaacatcac agcaggtcca ggccaatgat aaccttataa     60

gaggccatgt cgaagcgcga catcgtcctc accaatgtca ccgttgtcca gttgctgcga    120

cagccgtgcc cggtgaccag agcaccgccc ccacctgagc ctaaggctga agtagagccc    180

cagccacaac cagagcccac accagtcagg gaggaaataa agccaccacc gccaccactg    240

cctcctcacc ccgctactcc tcctcctaag atggtgtctg tggcccggga gctgactgtg    300

ggcatcaatg gatttggacg catcggtcgc ctggtcctgc gcgcctgcat ggagaagggt    360

gttaaggtgg tggctgtgaa tgatccattc attgacccgg aatacatggt gtacatgttt    420

aagtatgact ccacccacgg ccgatacaag ggaagtgtgg aattcaggaa tggacaactg    480

gtcgtggaca accatgagat ctctgtctac cagtgcaaag agcccaaaca gatcccctgg    540
```

agggctgtcg ggagccccta cgtggtggag tccacaggcg tgtacctctc catacaggca 600
gcttcggacc acatctctgc aggtgctcaa cgtgtggtca tctccgcgcc ctcaccggat 660
gcaccaatgt tcgtcatggg tgtcaatgaa aatgactata accctggctc catgaacatt 720
gtgagcaacg cgtcctgcac caccaactgt ttggctcccc tcgccaaagt catccacgag 780
cgatttggga tcgtggaagg gttgatgacc acagtccatt cctacacggc cacccagaag 840
acagtggacg ggccatcaag gaaggcctgg cgagatgggc ggggtgccca ccagaacatc 900
atcccagcct ccactggggc tgcgaaagct gtgaccaaag tcatcccaga gctcaaaggg 960
aagctgacag ggatggcgtt ccgggtacca accccggatg tgtctgtcgt ggacctgacc 1020
tgccgcctcg cccagcctgc cccctactca gccatcaagg aggctgtaaa agcagcagcc 1080
aaggggccca tggctggcat ccttgcctac accgaggatg aggtcgtctc tacggacttc 1140
ctcggtgata cccactcgtc catcttcgat gctaaggccg gcattgcgct caatgacaat 1200
ttcgtgaagc tcatttcatg gtacgacaac gaatatggct acagtcaccg ggtggtcgac 1260
ctcctccgct acatgttcag ccgagacaag tgaaacggga aggtcctttc tttccttccc 1320
aggggccggg gccggaacat gtgcctcccg ttccagcatc tggctgcccg ggggaggaag 1380
gacacccggg gcgggcgccc cacgccgatg ggtccatggt gaaataaaaa acagtgctcg 1440
aaaaaaaaaa aaaaa 1455

<210> SEQ ID NO 244
<211> LENGTH: 60
<212> TYPE: DNA
<213> ORGANISM: Homo sapiens
<220> FEATURE:
<223> OTHER INFORMATION: NM_014364

<400> SEQUENCE: 244
cgctcaatga caatttcgtg aagctcattt catggtacga caacgaatat ggctacagtc 60

<210> SEQ ID NO 245
<211> LENGTH: 935
<212> TYPE: DNA
<213> ORGANISM: Homo sapiens
<220> FEATURE:
<223> OTHER INFORMATION: NM_014462

<400> SEQUENCE: 245
gaagtgggta agggtaatat ggaggagctt ccggcaggcc ccggcggctg aaagccgggg 60
cagaagtgct ggtctcggtc gggattccgg gcttggtccc accgaggcgg cgactgcggt 120
aggagggaag aggttttgga cgcgctggcc tcccgccgct gtgcattgca gcattatttc 180
agttcaaaat gaactatatg cctggcaccg ccagcctcat cgaggacatt gacaaaaagc 240
acttggttct gcttcgagat ggaaggacac ttataggctt tttaagaagc attgatcaat 300
ttgcaaactt agtgctacat cagactgtgg agcgtattca tgtgggcaaa aaatacggtg 360
atattcctcg agggattttt gtggtcagag gagaaaatgt ggtcctacta ggagaaatag 420
acttggaaaa ggagagtgac acacccctcc agcaagtatc cattgaagaa attctagaag 480
aacaaagggt ggaacagcag accaagctgg aagcagagaa gttgaaagtg caggccctga 540
aggaccgagg tctttccatt cctcgagcag atactcttga tgagtactaa tcttttgccc 600
agaggctgtt ggctcttgaa gagtaggggc tgtcactgag tgaaagtgac atcctggcca 660
cctcacgcat ttgatcacag actgtagagt tttgaaaagt cacttttatt tttaattatt 720
ttacatatgc aacatgaaga aatcgtgtag gtgggttttt tttttaataa caaaatcact 780
gtttaaagaa acagtggcat agactccttc acacatcact gtggcaccag caactacttc 840
tttatattgt tcttcatatc ccaaattaga gtttacaggg acagtcttca tttacttgta 900
aataaaatat gaatctcaaa aaaaaaaaaa aaaaa 935

<210> SEQ ID NO 246
<211> LENGTH: 60
<212> TYPE: DNA
<213> ORGANISM: Homo sapiens
<220> FEATURE:
<223> OTHER INFORMATION: NM_014462

<400> SEQUENCE: 246
ttaataacaa aatcactgtt taaagaaaca gtggcataga ctccttcaca catcactgtg 60

<210> SEQ ID NO 247
<211> LENGTH: 890
<212> TYPE: DNA
<213> ORGANISM: Homo sapiens
<220> FEATURE:
<223> OTHER INFORMATION: NM_014501

<400> SEQUENCE: 247
ggcggaccga agaacgcagg aagggggccg gggggacccg cccccggccg gccgcagcca 60
tgaactccaa cgtggagaac ctacccccgc acatcatccg cctggtgtac aaggaggtga 120
cgacactgac cgcagaccca cccgatggca tcaaggtctt tcccaacgag gaggacctca 180
ccgacctcca ggtcaccatc gagggccctg aggggacccc atatgctgga ggtctgttcc 240
gcatgaaact cctgctgggg aaggacttcc ctgcctcccc acccaagggc tacttcctga 300
ccaagatctt ccacccgaac gtgggcgcca atggcgagat ctgcgtcaac gtgctcaaga 360
gggactggac ggctgagctg ggcatccgac acgtactgct gaccatcaag tgcctgctga 420
tccaccctaa ccccgagtct gcactcaacg aggaggcggg ccgcctgctc ttggagaact 480
acgaggagta tgcggctcgg gcccgtctgc tcacagagat ccacgggggc gccggcgggc 540
ccagcggcag ggccgaagcc ggtcgggccc tggccagtgg cactgaagct tcctccaccg 600
accctggggc cccagggggc ccgggagggg ctgagggtcc catggccaag aagcatgctg 660
gcgagcgcga taagaagctg gcggccaaga aaaagacgga caagaagcgg gcgctgcggg 720
cgctgcggcg gctgtagtgg gctctcttcc tccttccacc gtgaccccaa cctctcctgt 780
cccctccctc caactctgtc tctaagttat ttaaattatg gctggggtcg ggagggtac 840 agggggcact gggacctgga tttgtttttc taaataaagt tggaaaagca 890

<210> SEQ ID NO 248
<211> LENGTH: 60
<212> TYPE: DNA
<213> ORGANISM: Homo sapiens
<220> FEATURE:
<223> OTHER INFORMATION: NM_014501

<400> SEQUENCE: 248
acacgtactg ctgaccatca agtgcctgct gatccaccct aaccccgagt ctgcactcaa 60

<210> SEQ ID NO 249
<211> LENGTH: 1182
<212> TYPE: DNA
<213> ORGANISM: Homo sapiens
<220> FEATURE:
<223> OTHER INFORMATION: NM_016095

<400> SEQUENCE: 249

-continued

```
gcggccggcg gcgtctcctc ccgggacgct gaggggcccg aggagaccgt gaggctctgg      60

cctgcagctc gcgccgccat ggacgctgcc gaggtcgaat tcctcgccga gaaggagctg     120

gttaccatta tccccaactt cagtctggac aagatctacc tcatcggggg ggacctgggg     180

ccttttaacc ctggtttacc cgtggaagtg cccctgtggc tggcgattaa cctgaaacaa     240

agacagaaat gtcgcctgct ccctccagag tggatggatg tagaaaagtt ggagaagatg     300

agggatcatg aacgaaagga agaaactttt accccaatgc ccagccctta ctacatggaa     360

cttacgaagc tcctgttaaa tcatgcttca gacaacatcc cgaaggcaga cgaaatccgg     420

accctggtca aggatatgtg ggacactcgt atagccaaac tccgagtgtc tgctgacagc     480

tttgtgagac agcaggaggc acatgccaag ctggataact tgaccttgat ggagatcaac     540

accagcggga ctttcctcac acaagcgctc aaccacatgt acaaactccg cacgaacctc     600

cagcctctgg agagtactca gtctcaggac ttctagagaa aggcctggtg caggcggctt     660

gctgggggat gtgagcgctc aggatgtgat gaggtactcg tggttctgga gctctagaaa     720

cacttctgat gcatgaaaaa tgtgtgatgg tgcaaggaat ggattcagga tgttgttgga     780

gaaacaagtt tgtgattagt ccttaaaact tagctccctg ggacattctt caattccaca     840

tctgtttcta gaaaccagcc ctttttcccc ccacttttga gaaataaaaa agccttaggt     900

aaataagtca ttctccctag cagagccact tgggtctcct gcatggaagc cgtcacactt     960

gggcaggtgt tcagtgactg gtaggtgtag atacagcagg agtggccatg tggtccacgg    1020

ctttttaccc cttcttgatc ctgatttctt gggctgaatt tagactctct cacagaggtg    1080

gctcacagag aaggatggca gatggtgcag ccaacaatgc tgaccggtgc ttatcctcta    1140

agccctgatc cacaataaaa atggacccaa ctcaaaaaaa aa                       1182
```

<210> SEQ ID NO 250
<211> LENGTH: 60
<212> TYPE: DNA
<213> ORGANISM: Homo sapiens
<220> FEATURE:
<223> OTHER INFORMATION: NM_016095

<400> SEQUENCE: 250

```
atggattcag gatgttgttg gagaaacaag tttgtgatta gtccttaaaa cttagctccc      60
```

<210> SEQ ID NO 251
<211> LENGTH: 704
<212> TYPE: DNA
<213> ORGANISM: Homo sapiens
<220> FEATURE:
<223> OTHER INFORMATION: NM_016185

<400> SEQUENCE: 251

```
tgcagcggtg gtcggctgtt gggtgtggag tttcccagcg cccctcgggt ccgacccttt      60

gagcgttctg ctccggcgcc agcctacctc gctcctcggc gccatgacca caaccaccac     120

cttcaaggga gtcgacccca acagcaggaa tagctcccga gttttgcggc ctccaggtgg     180

tggatccaat ttttcattag gttttgatga accaacagaa caacctgtga ggaagaacaa     240

aatggcctct aatatctttg ggacacctga agaaaatcaa gcttcttggg ccaagtcagc     300

aggtgccaag tctagtggtg gcagggaaga cttggagtca tctggactgc agagaaggaa     360

ctcctctgaa gcaagctccg gagacttctt agatctgaag ggagaaggtg atattcatga     420

aaatgtggac acagacttgc caggcagcct ggggcagagt gaagagaagc ccgtgcctgc     480

tgcgcctgtg cccagcccgg tggccccggc cccagtgcca tccagaagaa atccccctgg     540
```

cggcaagtcc agcctcgtct tgggttagct ctgactgtcc tgaacgctgt cgttctgtct 600
gtttcctcca tgcttgagaa ctgcacaact tgagcctgac tgtacatctt cttggatttg 660
tttcattaaa aagaagcact ttatgtaaaa aaaaaaaaaa aaaa 704

<210> SEQ ID NO 252
<211> LENGTH: 60
<212> TYPE: DNA
<213> ORGANISM: Homo sapiens
<220> FEATURE:
<223> OTHER INFORMATION: NM_016185

<400> SEQUENCE: 252
tgaaccaaca gaacaacctg tgaggaagaa caaaatggcc tctaatatct ttgggacacc 60

<210> SEQ ID NO 253
<211> LENGTH: 2268
<212> TYPE: DNA
<213> ORGANISM: Homo sapiens
<220> FEATURE:
<221> NAME/KEY: Modified_base
<222> LOCATION: 1 ... 2268
<223> OTHER INFORMATION: n = a,c,g, or t
<220> FEATURE:
<223> OTHER INFORMATION: NM_016359

<400> SEQUENCE: 253
gggatttgaa ccncgctgac gaagtttggt gatccatctt ccgagtatcg ccgggatttc 60
gaatcgcgat gatcatcccc tctctagagg agctggactc cctcaagtac agtgacctgc 120
agaacttagc caagagtctg ggtctccggg ccaacctgag ggcaaccaag ttgttaaaag 180
ccttgaaagg ctacattaaa catgaggcaa gaaaaggaaa tgagaatcag gatgaaagtc 240
aaacttctgc atcctcttgt gatgagactg agatacagat cagcaaccag gaagaagctg 300
agagacagcc acttggccat gtcaccaaaa caaggagaag gtgcaagact gtccgtgtgg 360
accctgactc acagcagaat cattcagaga taaaaataag taatcccact gaattccaga 420
atcatgaaaa gcaggaaagc caggatctca gagctactgc aaaagttcct tctccaccag 480
acgagcacca agaagctgag aatgctgttt cctcaggtaa cagagattca aaggtacctt 540
cagaaggaaa gaaatctctc tacacagatg agtcatccaa acctggaaaa aataaaagaa 600
ctgcaatcac tactccaaac tttaagaagc ttcatgaagc tcattttaag gaaatggagt 660
ccattgatca atatattgag agaaaaagaa acattttgaa gaacacaatt ccatgaatga 720
actgaagcag cagcccatca ataagggagg ggtcaggact ccagtacctc caagaggaag 780
actctctgtg gcttctactc ccatcagcca acgacgctcg caaggccggt cttgtggccc 840
tgcaagtcag agtaccttgg gtctgaaggg gtcactcaag cgctctgcta tctctgcagc 900
taaaacgggt gtcaggtttt cagctgctac taaagataat gagcataagc gttcactgac 960
caagactcca gccagaaagt ctgcacatgt gaccgtgtct gggggcaccc caaaaggcga 1020
ggctgtgctt gggacacaca aattaaagac catcacgggg aattctgctg ctgttattac 1080
cccattcaag ttgacaactg aggcaacgca gactccagtc tccaataaga aaccagtgtt 1140
tgatcttaaa gcaagtttgt ctcgtcccct caactatgaa ccacacaaag gaaagctaaa 1200
accatggggg caatctaaag aaaataatta tctaaatcaa catgtcaaca gaattaactt 1260
ctacaagaaa acttacaaac aaccccatct ccagacaaag gaagagcaac ggaagaaacg 1320
cgagcaagaa cgaaaggaga agaaagcaaa ggttttggga atgcgaaggg gcctcatttt 1380
ggctgaagat taataatttt ttaatatctt gtaaatattc ctgtattctc aactttttc 1440 cttttgtaaa tttttttttt tttgctgtca tccccacttt agtcacgaga tctttttctg 1500
ctaactgttc atagtctgtg tagtgtccat gggttcttca tgtgctatga tctctgaaaa 1560
gacgttatca ccttaaagct caaattcttt gggatggttt ttacttaagt ccattaacaa 1620
ttcaggtttc taacgagacc catcctaaaa ttctgtttct agatttttaa tgtcaagttc 1680
ccaagttccc cctgctggtt ctaatattaa cagaactgca gtcttctgct agccaatagc 1740
atttacctga tggcagctag ttatgcaagc ttcaggagaa tttgaacaat aacaagaata 1800
gggtaagctg ggatagaaag gccacctctt cactctctat agaatatagt aacctttatg 1860
aaacggggcc atatagtttg gttatgacat caatatttta cctaggtgaa attgtttagg 1920
cttatgtacc ttcgttcaaa tatcctcatg taattgccat ctgtcactca ctatattcac 1980
aaaaataaaa ctctacaact cattctaaca ttgcttactt aaaagctaca tagccctatc 2040
gaaatgcgag gattaatgct ttaatgcttt tagagacagg gtctcactgt gttgcccagg 2100
ctggtctcaa actccaccaa atgtacttct tattcatttt atggaaaaga ctaggctttg 2160
cttagtatca tgtccatgtt tccttcacct cagtggagct tctgagtttt atactgctca 2220
agatcgtcat aaataaaatt ttttctcatt gtcaaaaaaa aaaaaaaa 2268

<210> SEQ ID NO 254
<211> LENGTH: 60
<212> TYPE: DNA
<213> ORGANISM: Homo sapiens
<220> FEATURE:
<223> OTHER INFORMATION: NM_016359

<400> SEQUENCE: 254
acattgctta cttaaaagct acatagccct atcgaaatgc gaggattaat gctttaatgc 60

<210> SEQ ID NO 255
<211> LENGTH: 1590
<212> TYPE: DNA
<213> ORGANISM: Homo sapiens
<220> FEATURE:
<223> OTHER INFORMATION: NM_016816

<400> SEQUENCE: 255
gaggcagttc tgttgccact ctctctcctg tcaatgatgg atctcagaaa taccccagcc 60
aaatctctgg acaagttcat tgaagactat ctcttgccag acacgtgttt ccgcatgcaa 120
atcgaccatg ccattgacat catctgtggg ttcctgaagg aaaggtgctt ccgaggtagc 180
tcctaccctg tgtgtgtgtc caaggtggta aagggtggct cctcaggcaa gggcaccacc 240
ctcagaggcc gatctgacgc tgacctggtt gtcttcctca gtcctctcac cacttttcag 300
gatcagttaa atcgccgggg agagttcatc caggaaatta ggagacagct ggaagcctgt 360
caaagagaga gagcactttc cgtgaagttt gaggtccagg ctccacgctg gggcaacccc 420
cgtgcgctca gcttcgtact gagttcgctc cagctcgggg agggggtgga gttcgatgtg 480
ctgcctgcct ttgatgccct gggtcagttg actggcagct ataaacctaa cccccaaatc 540
tatgtcaagc tcatcgagga gtgcaccgac ctgcagaaag agggcgagtt ctccacctgc 600
ttcacagaac tacagagaga cttcctgaag cagcgcccca ccaagctcaa gagcctcatc 660
cgcctagtca agcactggta ccaaaattgt aagaagaagc ttgggaagct gccacctcag 720
tatgccctgg agctcctgac ggtctatgct tgggagcgag ggagcatgaa aacacatttc 780
aacacagccc aaggatttcg gacggtcttg gaattagtca taaactacca gcaactctgc 840
atctactgga caaagtatta tgactttaaa aaccccatta ttgaaaagta cctgagaagg 900
cagctcacga aacccaggcc tgtgatcctg gacccggcgg accctacagg aaacttgggt 960
ggtggagacc caaagggttg gaggcagctg gcacaagagg ctgaggcctg gctgaattac 1020
ccatgcttta agaattggga tgggtcccca gtgagctcct ggattctgct ggctgaaagc 1080
aacagtacag acgatgagac cgacgatccc aggacgtatc agaaatatgg ttacattgga 1140
acacatgagt accctcattt ctctcataga cccagcacgc tccaggcagc atccacccca 1200
caggcagaag aggactggac ctgcaccatc ctctgaatgc cagtgcatct tgggggaaag 1260
ggctccagtg ttatctggac cagttccttc attttcaggt gggactcttg atccagagaa 1320
gacaaagctc ctcagtgagc tggtgtataa tccaagacag aacccaagtc tcctgactcc 1380
tggccttcta tgccctctat cctatcatag ataacattct ccacagcctc acttcattcc 1440
acctattctc tgaaaatatt ccctgagaga gaacagagag atttagataa gagaatgaaa 1500
ttccagcctt gactttcttc tgtgcacctg atgggagggt aatgtctaat gtattatcaa 1560
taacaataaa aataaagcaa ataccaaaaa 1590

<210> SEQ ID NO 256
<211> LENGTH: 60
<212> TYPE: DNA
<213> ORGANISM: Homo sapiens
<220> FEATURE:
<223> OTHER INFORMATION: NM_016816

<400> SEQUENCE: 256
cgatcccagg acgtatcaga aatatggtta cattggaaca catgagtacc ctcatttctc 60

<210> SEQ ID NO 257
<211> LENGTH: 2905
<212> TYPE: DNA
<213> ORGANISM: Homo sapiens
<220> FEATURE:
<223> OTHER INFORMATION: NM_016817

<400> SEQUENCE: 257
cggcagccag ctgagagcaa tgggaaatgg ggagtcccag ctgtcctcgg tgcctgctca 60
gaagctgggt tggtttatcc aggaatacct gaagccctac gaagaatgtc agacactgat 120
cgacgagatg gtgaacacca tctgtgacgt ctgcaggaac cccgaacagt tccccctggt 180
gcagggagtg gccataggtg gctcctatgg acggaaaaca gtcttaagag gcaactccga 240
tggtaccctt gtccttttct tcagtgactt aaaacaattc caggatcaga agagaagcca 300
acgtgacatc ctcgataaaa ctggggataa gctgaagttc tgtctgttca cgaagtggtt 360
gaaaaacaat ttcgagatcc agaagtccct tgatgggtcc accatccagg tgttcacaaa 420
aaatcagaga atctctttcg aggtgctggc cgccttcaac gctctgagct taaatgataa 480
tcccagcccc tggatctatc gagagctcaa aagatccttg gataagacaa atgccagtcc 540
tggtgagttt gcagtctgct tcactgaact ccagcagaag tttttgaca accgtcctgg 600 aaaactaaag gatttgatcc tcttgataaa gcactggcat caacagtgcc agaaaaaaat 660
caaggattta ccctcgctgt ctccgtatgc cctggagctg cttacggtgt atgcctggga 720
acaggggtgc agaaaagaca actttgacat tgctgaaggc gtcagaacgg ttctggagct 780
gatcaaatgc caggagaagc tgtgtatcta ttggatggtc aactacaact ttgaagatga 840
gaccatcagg aacatcctgc tgcaccagct ccaatcagcg aggccagtaa tcttggatcc 900
agttgaccca accaataatg tgagtggaga taaaatatgc tggcaatggc tgaaaaaaga 960
agctcaaacc tggttgactt ctcccaacct ggataatgag ttacctgcac catcttggaa 1020
tgtcctgcct gcaccactct tcacgacccc aggccacctt ctggataagt tcatcaagga 1080
gtttctccag cccaacaaat gcttcctaga gcagattgac agtgctgtta acatcatccg 1140
tacattcctt aaagaaaact gcttccgaca atcaacagcc aagatccaga ttgtccgggg 1200
aggatcaacc gccaaaggca cagctctgaa gactggctct gatgccgatc tcgtcgtgtt 1260
ccataactca cttaaaagct acacctccca aaaaaacgag cggcacaaaa tcgtcaagga 1320
aatccatgaa cagctgaaag ccttttggag ggagaaggag gaggagcttg aagtcagctt 1380
tgagcctccc aagtggaagg ctcccagggt gctgagcttc tctctgaaat ccaaagtcct 1440
caacgaaagt gtcagctttg atgtgcttcc tgcctttaat gcactgggtc agctgagttc 1500
tggctccaca cccagccccg aggtttatgc agggctcatt gatctgtata aatcctcgga 1560
cctcccggga ggagagtttt ctacctgttt cacagtcctg cagcgaaact tcattcgctc 1620
ccggcccacc aaactaaagg atttaattcg cctggtgaag cactggtaca aagagtgtga 1680
aaggaaactg aagccaaagg ggtctttgcc cccaaagtat gccttggagc tgctcaccat 1740
ctatgcctgg gagcagggga gtggagtgcc ggattttgac actgcagaag gtttccggac 1800
agtcctggag ctggtcacac aatatcagca gctcggcatc ttctggaagg tcaattacaa 1860
ctttgaagat gagaccgtga ggaagtttct actgagccag ttgcagaaaa ccaggcctgt 1920
gatcttggac ccaggcgaac ccacaggtga cgtgggtgga ggggaccgtt ggtgttggca 1980
tcttctggac aaagaagcaa aggttaggtt atcctctccc tgcttcaagg atgggactgg 2040
aaacccaata ccaccttgga aagtgccgac aatgcagaca ccaggaagtt gtggagctag 2100
gatccatcct attgtcaatg agatgttctc atccagaagc catagaatcc tgaataataa 2160
ttctaaaaga aacttctgga gatcatctgg caatcgcttt taaagactcg gctcaccgtg 2220
agaaagagtc actcacatcc attcttccct tgatggtccc tattcctcct tcccttgcct 2280
tcttggactt cttgaaatca atcaagactg caaacccttt cataaagctg ccttgctgaa 2340
ctcctctctg caggagccct gcttaaaata gttgatgtca tcactttatg tgcatcttat 2400
ttctgtcaac ttgtattttt ttttcttgta tttttccaat tagctcctcc tttttccttc 2460
cagtctaaaa aaggaatcct ctgtgtcttc aaagcaaagc tctttacttt ccccttggtt 2520
ctcataactc tgtgatcttg ctctcggtgc ttccaactca tccacgtcct gtctgtttcc 2580
tctgtataca aaaccctttc tgcccctgct gacacagaca tcctctatgc cagcagccag 2640
gccaaccctt tcattagaac ttcaagctct ccaaaggctc agattataac tgttgtcata 2700
tttatatgag gctgttgtct tttccttctg agcctgcctt tatcccccca cccaggagta 2760
tcctcttgcc aaagcaaaag actttttcct tggctttagc cttaaagata cttgaaggtc 2820
taggtgcttt aacctcacat accctcactt aaacttttat cactgttgca tataccagtt 2880
gtgatacaat aaagaatgta tctgg 2905

<210> SEQ ID NO 258
<211> LENGTH: 60
<212> TYPE: DNA
<213> ORGANISM: Homo sapiens
<220> FEATURE:
<223> OTHER INFORMATION: NM_016817

<400> SEQUENCE: 258
aaggtctagg tgctttaacc tcacataccc tcacttaaac ttttatcact gttgcatata 60

<210> SEQ ID NO 259
<211> LENGTH: 2054

<212> TYPE: DNA
<213> ORGANISM: Homo sapiens
<220> FEATURE:
<223> OTHER INFORMATION: NM_017414

<400> SEQUENCE: 259
gggaagctcg ggccggcagg gtttccccgc acgctggcgc ccagctcccg gcgcggaggc 60
cgctgtaagt ttcgctttcc attcagtgga aaacgaaagc tgggcggggt gccacgagcg 120
cggggccaga ccaaggcggg cccggagcgg aacttcggtc ccagctcggt ccccggctca 180
gtcccgacgt ggaactcagc agcggaggct ggacgcttgc atggcgcttg agagattcca 240
tcgtgcctgg ctcacataag cgcttcctgg aagtgaagtc gtgctgtcct gaacgcgggc 300
caggcagctg cggcctgggg gttttggagt gatcacgaat gagcaaggcg tttgggctcc 360
tgaggcaaat ctgtcagtcc atcctggctg agtcctcgca gtccccggca gatcttgaag 420
aaaagaagga agaagacagc aacatgaaga gagagcagcc cagagagcgt cccagggcct 480
gggactaccc tcatggcctg gttggtttac acaacattgg acagacctgc tgccttaact 540
ccttgattca ggtgttcgta atgaatgtgg acttcaccag gatattgaag aggatcacgg 600
tgcccagggg agctgacgag cagaggagaa gcgtcccttt ccagatgctt ctgctgctgg 660
agaagatgca ggacagccgg cagaaagcag tgcggcccct ggagctggcc tactgcctgc 720
agaagtgcaa cgtgcccttg tttgtccaac atgatgctgc ccaactgtac ctcaaactct 780
ggaacctgat taaggaccag atcactgatg tgcacttggt ggagagactg caggccctgt 840
atacgatccg ggtgaaggac tccttgattt gcgttgactg tgccatggag agtagcagaa 900
acagcagcat gctcaccctc ccactttctc tttttgatgt ggactcaaag cccctgaaga 960
cactggagga cgccctgcac tgcttcttcc agcccaggga gttatcaagc aaaagcaagt 1020
gcttctgtga gaactgtggg aagaagaccc gtgggaaaca ggtcttgaag ctgacccatt 1080
tgccccagac cctgacaatc cacctcatgc gattctccat caggaattca cagacgagaa 1140
agatctgcca ctccctgtac ttcccccaga gcttggattt cagccagatc cttccaatga 1200
agcgagagtc ttgtgatgct gaggagcagt ctggagggca gtatgagctt tttgctgtga 1260
ttgcgcacgt gggaatggca gactccggtc attactgtgt ctacatccgg aatgctgtgg 1320
atggaaaatg gttctgcttc aatgactcca atatttgctt ggtgtcctgg gaagacatcc 1380
agtgtaccta cggaaatcct aactaccact ggcaggaaac tgcatatctt ctggtttaca 1440
tgaagatgga gtgctaatgg aaatgcccaa aaccttcaga gattgacacg ctgtcatttt 1500
ccatttccgt tcctggatct acggagtctt ctaagagatt ttgcaatgag gagaagcatt 1560
gttttcaaac tatataactg agccttattt ataattaggg atattatcaa aatatgtaac 1620
catgaggccc ctcaggtcct gatcagtcag aatggatgct ttcaccagca gacccggcca 1680
tgtggctgct cggtcctggg tgctcgctgc tgtgcaagac attagccctt tagttatgag 1740
cctgtgggaa cttcaggggt tcccagtggg gagagcagtg gcagtgggag gcatctgggg 1800
gccaaaggtc agtggcaggg ggtatttcag tattatacaa ctgctgtgac cagacttgta 1860
tactggctga atatcagtgc tgtttgtaat ttttcacttt gagaaccaac attaattcca 1920
tatgaatcaa gtgttttgta actgctattc atttattcag caaatattta ttgatcatct 1980
cttctccata agatagtgtg ataaacacag tcatgaataa agttattttc cacaaaaaaa 2040
aaaaaaaaaa aaaa 2054

<210> SEQ ID NO 260
<211> LENGTH: 60

<212> TYPE: DNA
<213> ORGANISM: Homo sapiens
<220> FEATURE:
<223> OTHER INFORMATION: NM_017414

<400> SEQUENCE: 260
tgagcatctc ttctccataa gatagtgtga taaacacggt catgaataaa gttattttcc 60

<210> SEQ ID NO 261
<211> LENGTH: 3638
<212> TYPE: DNA
<213> ORGANISM: Homo sapiens
<220> FEATURE:
<223> OTHER INFORMATION: NM_017523

<400> SEQUENCE: 261
ggtagatgcg gctgtgacag cagcaaagaa tgacggccaa gggcgacagc aggggctggc 60
catgctgtaa aggggcttct tgggagggtc cagcctcagg aatcaagggg aactcctgag 120
ccgagaattc tgaagatctc ctccctccct gaagctgtgg gctgggccat cggaaaactt 180
tcagttttgt ttccttgcct gcaagaaacg aaactcaacc gaaagcctgc agagagcaga 240
acatggaagg agacttctcg gtgtgcagga actgtaaaag acatgtagtc tctgccaact 300
tcaccctcca tgaggcttac tgcctgcggt tcctggtcct gtgtccggag tgtgaggagc 360
ctgtccccaa ggaaaccatg gaggagcact gcaagcttga gcaccagcag gttgggtgta 420
cgatgtgtca gcagagcatg cagaagtcct cgctggagtt tcataaggcc aatgagtgcc 480
aggagcgccc tgttgagtgt aagttctgca aactggacat gcagctcagc aagctggagc 540
tccacgagtc ctactgtggc agccggacag agctctgcca aggctgtggc cagttcatca 600
tgcaccgcat gctcgcccag cacagagatg tctgtcgcag tgaacaggcc cagctcggga 660
aaggggaaag aatttcagct cctgaaaggg aaatctactg tcattattgc aaccaaatga 720
ttccagaaaa taagtatttc caccatatgg gtaaatgttg tccagactca gagtttaaga 780
aacactttcc tgttggaaat ccagaaattc ttccttcatc tcttccaagt caagctgctg 840
aaaatcaaac ttccacgatg gagaaagatg ttcgtccaaa gacaagaagt ataaacagat 900
ttcctcttca ttctgaaagt tcatcaaaga aagcaccaag aagcaaaaac aaaaccttgg 960
atccactttt gatgtcagag cccaagccca ggaccagctc ccctagagga gataaagcag 1020
cctatgacat tctgaggaga tgttctcagt gtggcatcct gcttcccctg ccgatcctaa 1080
atcaacatca ggagaaatgc cggtggttag cttcatcaaa aggaaaacaa gtgagaaatt 1140
tcagctagat ttggaaaagg aaaggtacta caaattcaaa agatttcact tttaacactg 1200
gcattcctgc ctacttgctg tggtggtctt gtgaaaggtg atgggtttta ttcgttgggc 1260
tttaaaagaa aaggtttggc agaactaaaa acaaaactca cgtatcatct caatagatac 1320
agaaaaggct tttgataaaa ttcaacttga cttcatgtta aaaaccctca acaaaccagg 1380
cgtcgaagga acatacctca aaataataag agccatctat gacaaaacca cagccaacat 1440
catactgaat gagcaaaagc tggagcatta ctcttgagaa gtagaacaag gcacttcagt 1500
cctattcaac atagtactgg aagtcctcgc cacagcaatc aggcaagaga aagaaataaa 1560
aggcaaccaa aaagaaagga agtcgaagta tctctgtttg cagacgatat gattctatat 1620
ctagaaaacc ccatgatctt ggcccaaaag ctcctagatc tgataaacaa cttcagctaa 1680
ctttcaggag acaaaatcaa tatacaaaat atggtagcat ttttatacac caacgacatc 1740
caagctgaga gccaaatcaa gaatgcaatc ctattcacaa ttgccacaaa aagaataaaa 1800
tacctaggaa tacagctaac cagggagatg aaagatctct acaacaaaaa ttacaaaaca 1860
ctgctgaaag aaatcagaga tgacacaaat ggaaaaacat tccatactta tggataggaa 1920
gaatcaatat tgttaaaatg gccatactac ccaaagcaat ttatagattc aatgctattc 1980
ctatcaaact accaataaca ttcttcacag aatcagaaaa aaaaagcatt aaaatttatt 2040
tgaaaccaaa aaagagccca aaaagccaaa gcaatcctaa gcaaaaagaa caaagctgga 2100
ggcatcgcat tacccaactt caaactatac tacagggcta cagtaaccaa aactgcatga 2160
tactggtaca aaagcatggt gctggtacaa aagcagacac atagatcaat ggaacagaat 2220
agagggccca gaaataaagc tacacaccta caaccatcta atctttgaca aagttgacaa 2280
aaatacgcaa tggggaaaga attccccatt cagtaagtgg tactgggata actagctagc 2340
catatgcaga ggattgaaac tgaaccactt ccttacacca tatgcaaaaa tcaactcaag 2400
atggattaaa gacttaaatg taaaacccca aactataaaa actctggaag ataacctagg 2460
caataccatt ctggacatag gaacggaaaa agatttcatg acaaagatcc caaaaataat 2520
tgtaacgaaa gcaaaaattg acaaatggga catgattaaa cagaattacc atttgactca 2580
gcaatcccat tattggttat atacccaaag gaatctaaat cattctgtca taaagacata 2640
tatacacaaa tgttcacggc agcactatac acaatcgcaa agtcagggaa tcaaactaaa 2700
tgtccatcag tggtagaaag gataaagaaa atgtggtggc agggagtggt ggctcatgtc 2760
tgtaatccca gcactttggg aggctgaggc gggtggttca cctgaggtca ggagtttgag 2820
accagcctgg ccaacatggc gaaactccgt ctccgctaaa aatacgaaaa ttagccaggc 2880
gtggtggcga gcacctgtca tcccagctac ttgggaggcc taggcgtgag aatcgcttga 2940
acctggaagg tggtggttgc agtgagccga gatcctgcca ctgcactcca gcctgggcaa 3000
ccaagcgaga ctctgcctta aaaaaaaaaa aaagaaaatg tggcacatat acaccatgga 3060
atactatgca gccataaaaa agaatgggat catgtcctgt gcagcaacgt ggatggagct 3120
ggaagccatt atcctaaatg aactcactca gaaacagaaa accaaatacc acatgttctc 3180
acttataagt agaagctaaa cattgagtac acatggatac aaagaaggga accgcagaca 3240
ctggggccta cctgaggtcg gagcatggaa ggagggtgag gatcaaaaaa ctacctatct 3300
ggtactatgc tttttatctg gatgatgaaa taatctgtac aacaaaccct ggtgacatgc 3360
aatttaccta tatagcaagc ctacacatgt gcccctgaac ctaaaaaaaa agttaaaaga 3420
aaaacgtttg gattattttc cctctttcga acaaagacat tggtttgccc aaggactaca 3480
aataaaccaa cgggaaaaaa gaaaggttcc agttttgtct gaaaattctg attaagcctc 3540
tgggccctac agcctggaga acctggagaa tcctacaccc acagaacccg gctttgtccc 3600
caaagaataa aaacacctct ctaaaaaaaa aaaaaaaa 3638

<210> SEQ ID NO 262
<211> LENGTH: 60
<212> TYPE: DNA
<213> ORGANISM: Homo sapiens
<220> FEATURE:
<223> OTHER INFORMATION: NM_017523

<400> SEQUENCE: 262
ttggaaaagg aaaggtacta caaattcaaa agatttcact tttaacactg gcattcctgc 60

<210> SEQ ID NO 263
<211> LENGTH: 2461
<212> TYPE: DNA
<213> ORGANISM: Homo sapiens
<220> FEATURE:
<223> OTHER INFORMATION: NM_018410

<400> SEQUENCE: 263
atgctgggta cgctgcgcgc catggagggc gaggacgtgg aagacgacca gctgctgcag 60
aagctcaggg ccagtcgccg ccgcttccag aggcgcatgc agcggctgat agagaagtac 120
aaccagccct tcgaggacac cccggtggtg caaatggcca cgctgaccta cgagacgcca 180
cagggattga gaatttgggg tggaagacta ataaaggaaa gaaacaaagg agagatccag 240
gactcctcca tgaagcccgc ggacaggaca gatggctccg tgcaagctgc agcctggggt 300
cctgagcttc cctcgcaccg cacagtcctg ggagccgatt caaaaagcgg tgaggtcgat 360
gccacgtcag accaggaaga gtcagttgct tgggccttag cacctgcagt gcctcaaagc 420
cctttgaaaa atgaattaag aaggaaatac ttgacccaag tggatatact gctacaaggt 480
gcagagtatt ttgagtgtgc aggtaacaga gctggaaggg atgtacgtgt gactccgctg 540
ccttcactgg cctcacctgc cgtgcctgcc cccggatact gcagtcgtat ctccggaaag 600
agtcctggtg acccagcgaa accagcttca tctcccagag aatgggatcc tttgcatcct 660
tcctccacag acatggcctt agtacctaga aatgacagcc tctccctaca agagaccagt 720
agcagcagct tcttaagcag ccagcccttt gaagatgatg acatttgcaa tgtgaccatc 780
agtgacctgt acgcagggat gctgcactcc atgagccggc tgttgagcac aaagccatca 840
agcatcatct ccaccaaaac gttcatcatg caaaactgga actgcaggag gaggcacaga 900
tataagagca ggatgaacaa aacatattgc aaaggagcca gacgttctca gaggagctcc 960
aaggagaact tcataccctg ctctgagcct gtgaaaggga caggggcatt aagagattgc 1020
aagaacgtat tagatgtttc ttgccgtaag acaggtttaa aattggaaaa agcttttctt 1080
gaagtcaaca gaccccaaat ccataagtta gatccaagtt ggaaggagcg caaagtgaca 1140
ccctcgaagt attcttcctt gatttacttc gactccagtg caacatataa tcttgatgag 1200
gaaaatagat ttaggacatt aaaatggtta atttctcctg taaaaatagt ttccagacca 1260
acaatacgac agggccatgg agagaaccgt cagagggaga ttgaaatccg atttgatcag 1320
cttcatcggg aatattgcct gagtcccagg aaccagcctc gccggatgtg cctcccggac 1380
tcctgggcca tgaacatgta cagagggggt cctgcgagtc ctggtggcct tcagggctta 1440
gaaacccgca ggctgagttt accttccagc aaagcaaaag caaaaagttt aagtgaggct 1500
tttgaaaacc taggcaaaag atctctggaa gcaggtaggt gcctgcccaa gagcgattca 1560
tcttcatcac ttccaaagac caaccccaca cacagcgcaa ctcgcccgca gcagacatct 1620
gaccttcacg ttcagggaaa tagttctgga atatttagaa agtcagtgtc acccagcaaa 1680
actctttcag tcccagataa agaagtgcca ggccacggaa ggaatcgtta cgatgaaatt 1740
aaagaagaat ttgacaagct tcatcaaaag tattgcctca aatctcctgg gcagatgaca 1800
gtgcctttat gtattggagt gtctacagat aaagcaagta tggaagttcg atatcaaaca 1860
gaaggcttct taggaaaatt aaatccagac cctcacttcc agggtttcca gaagttgcca 1920
tcatcacccc tggggtgcag aaaaagtcta ctgggctcaa ctgcaattga ggctccttca 1980
tctacatgtg ttgctcgtgc catcacgagg gatggcacga gggaccatca gttccctgca 2040
aaaagaccca ggctatcaga accccagggc tccggacgcc agggcaattc cctgggtgcc 2100
tcagatgggg tggacaacac cgtcagaccg ggagaccagg gcagctcttc acagcccaac 2160
tcagaagaga gaggagagaa cacgtcttac aggatggaag agaaaagtga tttcatgcta 2220
gaaaaattgg aaactaaaag tgtgtagcta ggttatttcg gagtgttatt tatcttccca 2280
cttgctctct gtttgtattt ttgttttgtt tttgattctt gagactgtga ggacttggtt 2340
gacttctctg cccttaaagt aaatattagt gaaattggtt ccatcagaga taacctcgag 2400
ttcttggtgt agaaattatg tgaataaagt tgctcaatta gaaaaaaaaa aaaaaaaaaa 2460
a 2461

<210> SEQ ID NO 264
<211> LENGTH: 60
<212> TYPE: DNA
<213> ORGANISM: Homo sapiens
<220> FEATURE:
<223> OTHER INFORMATION: NM_018410

<400> SEQUENCE: 264
agtgatttca tgctagaaaa attggaaact aaaagtgtgt agctaggtta tttcggagtg 60

<210> SEQ ID NO 265
<211> LENGTH: 1405
<212> TYPE: DNA
<213> ORGANISM: Homo sapiens
<220> FEATURE:
<223> OTHER INFORMATION: NM_018455

<400> SEQUENCE: 265
cacctcgctc gcagcctccc cagcgcagca gcccggctgt gggcctgcgg cagccgggtc 60
ttcctggtcc ccacctcctg gggccgacgg gcggcaggaa ggggctcggc gggacgcgcc 120
gtcagggacc tgaggaggaa caacggaacg cgttcggaac ggcctggact cccgagactc 180
acccgactcg tggccacacc gggagaactg aagcggcagt agccggcgga gacgcccgac 240
ccgaaggccg gctgctaggg agcagacagc tgaaccgctt gccagacgcc gaaacccagt 300
gacgccctcc accgctccac cgtgctcccg gctccccgcc cccgccgccc gcgggcccca 360
aggcgcatgc gccgcctgtc ctggaggggc ccatttccgt ccgtcgtggg gggaggcaca 420
gtgagtccac tggggcacgg cagcgtctaa gccacaagcc gagcacataa gccaggtcct 480
aacggagcct atgtgtaagt ccactactgg tgcaaggttg cacacttcta agaagagcgg 540
cgtggggggc tcggcgacct tcgcttcagt cgctccccccg tgcagtcccc tgtgcccaag 600
acacagcctg atgcttgtgc tccggtgggc ggagcttgga ggcggcggga actgcaattg 660
gtggctttga aggcgcggcg agcgggaaca gctcttgagg agtgagactg caggagatgt 720
gggccgtgcc aaagagatgg atgagactgt tgctgagttc atcaagagga ccatcttgaa 780
aatccccatg aatgaactga caacaatcct gaaggcctgg gattttttgt ctgaaaatca 840
actgcagact gtaaatttcc gacagagaaa ggaatctgta gttcagcact tgatccatct 900
gtgtgaggaa aagcgtgcaa gtatcagtga tgctgccctg ttagacatca tttatatgca 960
atttcatcag caccagaaag tttgggatgt ttttcagatg agtaaaggac caggtgaaga 1020
tgttgacctt tttgatatga aacaatttaa aaattcgttc aagaaaattc ttcagagagc 1080
attaaaaaat gtgacagtca gcttcagaga aactgaggag aatgcagtct ggattcgaat 1140
tgcctgggga acacagtaca caaagccaaa ccagtacaaa cctacctacg tggtgtacta 1200
ctcccagact ccgtacgcct tcacgtcctc ctccatgctg aggcgcaata caccgcttct 1260
gggtcaggag ttagaagcta ctgggaaaat ctacctccga caagaggaga tcattttaga 1320
tattaccgaa atgaagaaag cttgcaatta gtgaacatga aaggaaaata aaaattcctc 1380
acagtcaaaa aaaaaaaaaa aaaaa 1405

<210> SEQ ID NO 266
<211> LENGTH: 60

<212> TYPE: DNA
<213> ORGANISM: Homo sapiens
<220> FEATURE:
<223> OTHER INFORMATION: NM_018455

<400> SEQUENCE: 266
ccgacaagag gagatcattt tagatattac cgaaatgaag aaagcttgca attagtgaac 60

<210> SEQ ID NO 267
<211> LENGTH: 927
<212> TYPE: DNA
<213> ORGANISM: Homo sapiens
<220> FEATURE:
<223> OTHER INFORMATION: NM_018465

<400> SEQUENCE: 267
ggcagcgggc gaaaggagcc ggggcctgga ggtttgcgta ccggtcgcct ggtcccggca 60
ccagcgccgc ccagtgtggt ttcccataag gaagctcttc ttcctgcttg gcttccacct 120
ttaacccttc cacctgggag cgtcctctaa cacattcaga ctacaagtcc agacccagga 180
gagcaaggcc cagaaagagg tcaaaatggg gtttatattt tcaaaatcta tgaatgaaag 240
catgaaaaat caaaaggagt tcatgcttat gaatgctcga cttcagctgg aaaggcagct 300
catcatgcag agtgaaatga gggaaagaca aatggccatg cggattgcgt ggtctcggga 360
attcctcaaa tattttggaa ctttttttgg ccttgcagcc atctctttaa cagctggagc 420
gattaaaaaa aagaagccag ccttcctggt cccgattgtt ccattaagct ttatcctcac 480
ctaccagtat gacttgggct atggaaccct tttagaaaga atgaaaggtg aagctgagga 540
catactggaa acagaaaaga gtaaattgca gctgccaaga ggaatgatca cttttgaaag 600
cattgaaaaa gccagaaagg aacagagtag attcttcata gacaaatgaa atcatgctta 660
ccaatcaaat ctcaaagcac agaattattg acttgaatca tggtttttac agttttttaa 720
atgctcaaga ttttgatatt atagatttta ttttaaaata ttaaaatgca agatagtttt 780
gagctatttt aaaataaaat ttataacatt caacacaaaa tcatggaggt gctctaaata 840
acttttagat ttcctctctc tgtgtgcatt accaatatct aagtgtaaaa ttaataaatt 900
gttttgaatt cctggaaaaa aaaaaaa 927

<210> SEQ ID NO 268
<211> LENGTH: 60
<212> TYPE: DNA
<213> ORGANISM: Homo sapiens
<220> FEATURE:
<223> OTHER INFORMATION: NM_018465

<400> SEQUENCE: 268
ggaacagagt agattcttca tagacaaatg aaatcatgct taccaatcaa atctcaaagc 60

<210> SEQ ID NO 269
<211> LENGTH: 1047
<212> TYPE: DNA
<213> ORGANISM: Homo sapiens
<220> FEATURE:
<223> OTHER INFORMATION: NM_018487

<400> SEQUENCE: 269
cccacttctc cagccagcgc cccagccctc ccgccgcccg ctcgcaggtc ccgaggagcg 60
cagactgtgt ccctgacaat gggaacagcc gacagtgatg agatggcccc ggaggcccca 120
cagcacaccc acatcgatgt gcacatccac caggagtctg ccctggccaa gctcctgctc 180
acctgctgct ctgcgctgcg gccccgggcc acccaggcca ggggcagcag ccggctgctg 240
gtggcctcgt gggtgatgca gatcgtgctg ggggatcttga gtgcagtcct aggaggattt 300
ttctacatcc gcgactacac cctcctcgtc acctcgggag ctgccatctg gacaggggct 360
gtggctgtgc tggctggagc tgctgccttc atttacgaga aacggggtgg tacatactgg 420
gccctgctga ggactctgct aacgctggca gctttctcca cagccatcgc tgccctcaaa 480
ctttggaatg aagatttccg atatggctac tcttattaca acagtgcctg ccgcatctcc 540
agctcgagtg actggaacac tccagccccc actcagagtc cagaagaagt cagaaggcta 600
cacctatgta cctccttcat ggacatgctg aaggccttgt tcagaaccct tcaggccatg 660
ctcttgggtg tctggattct gctgcttctg gcatctctga cccctctgtg gctgtactgc 720
tggagaatgt tcccaaccaa agggaaaaga gaccagaagg aaatgttgga agtgagtgga 780
atctagccat gcctctcctg attattagtg cctggtgctt ctgcaccggg cgtccctgca 840
tctgactgct ggaagaagaa ccagactgag gaaaagaggc tcttcaacag ccccagttat 900
cctggcccca tgaccgtggc cacagccctg ctccagcagc acttgcccat tccttacacc 960
ccttccccat cctgctccgc ttcatgtccc ctcctgagta gtcatgtgat aataaactct 1020
catgttattg ttcccaggaa aaaaaaa 1047

<210> SEQ ID NO 270
<211> LENGTH: 60
<212> TYPE: DNA
<213> ORGANISM: Homo sapiens
<220> FEATURE:
<223> OTHER INFORMATION: NM_018487

<400> SEQUENCE: 270
aaccaaaggg aaaagagacc agaaggaaat gttggaagtg agtggaatct agccatgcct 60

<210> SEQ ID NO 271
<211> LENGTH: 2280
<212> TYPE: DNA
<213> ORGANISM: Homo sapiens
<220> FEATURE:
<223> OTHER INFORMATION: U17077

<400> SEQUENCE: 271
ccgcccgcca ccagctacgc cccgtccgac gtgccctcgg gggtcgcgct gttcctcacc 60
atccctttcg ccttcttcct gcccgagctg atatttgggt tcttggtctg gaccatggta 120
gccgccaccc acatagtata ccccttgctg caaggatggg tgatgtatgt ctcgctcacc 180
tcgtttctca tctccttgat gttcctgttg tcttacttgt ttggatttta caaaagattt 240
gaatcctgga gagttctgga cagcctgtac cacgggacca ctggcatcct gtacatgagc 300
gctgccgtcc tacaagtaca tgccacgatt gtttctgaga aactgctgga cccaagaatt 360
tactacatta attcggcagc ctcgttcttc gccttcatcg ccacgctgct ctacattctc 420
catgccttca gcatctatta ccactgatgc acaggcgcca ggccaagggg gaaatgctct 480
ttgaaagctc caattattgg tccccaaaag cagcttccaa cgtttgccat ctggatgaca 540
aacggaagat ccactaaaac gtccacggga ttaacagaac gtccttgcag actgagcgat 600
gacaccacac tttgtttgga catttaaatt cactctgctg aataggagga agcttttctt 660
tttcctggga aaacaactgt ctcttggaat tatctgacca tgaacttgct cttctagaca 720
actcacatca aagccctcac tccactaatg gagaatccta gccccactaa tgccaagtct 780
gtttggggat tttgcctcag ctatgggctt ccctagagta ggtctagggg aatactcagt 840
ctgatctttt ttttgtttgt tttattttgt tttttttgag acggagtctc gctcttcctc 900
caaggctgga gtgcagtgac gcgatctcca ctcactgcag gctccgcctc ccgggttccc 960
gccattctcc tgcctcagcc tcccgagtag ccgggactac aggcgcccac caccatgccc 1020
ggctaattta gttgtatttt tagtagagat ggggtttcac cgtattagcc aggatggtct 1080
cgatctcctg acctcgtgat ccgcccgcct cggcctccca aagtgctggg attacaggcg 1140
tgagccaccg tgcccggcct gattctctta aaattgaaga ggtgctgcca aggccttcag 1200
atctaacgca gatgcataga ccttgttcct ggtacttgtt cagcctgtgc tggggagccg 1260
tggtcccgag ttccctggga ggctgacagg gtcaagccac cctgcccacc accctcccac 1320
ttcccctccc ctttcctctc cagcattagg attcaaggga aatctgcatg aagccaattt 1380
tgagggtaga cgtgtgggga aaataaatca ttatacagta agacctgggg cttgaggggt 1440
ggggaatggg gagggaaggg catagcctgc tcctccatga gtctgacatc tcggaaactg 1500
agcagctgcc ggacgcctgg gtcaggaatc caagacccca cctcttaagg actggttcct 1560
cagaaagcac cctcagggaa aaaggtgaaa acattacatc cgtggattct cctgccacaa 1620
ccgcattgga agaaaaggct gccgcaacat ctcagcgagg agtgaaggac ccatgtccca 1680
ggaaccgcgc tgcgccacct gcactcaccc ccctcacatt ctcttaagca cccggtggcc 1740
ctccgaggct ggcggaatgg tggtgcccac ggggttgggc aagggctcac caggacctca 1800
acgggcaaag ttgtgcacac taaaatatca aatcaaggtg cttggtttta aagtaaatgt 1860
ttttctaaag aaagctgtgt tcttctgttg acccagacga atagggcaca gccctgtaac 1920
tgcacgtgcc ttctgtcatt gggaatgaaa taaattatta cgagaaaggg acttgtccta 1980
actggtttga ggccttacag ttttgtatct acatttttcc cctcctgggg tttgcgggga 2040
cagggacaga actacaggag tcatgggaaa gaaaattctg gcttcactac tgctcactgc 2100
tcactttctg atcactctga tacttttttt tttttttttt ttttgcaacc tgataccttg 2160
aaaagcttct atgtgtctct ccttttgttg cctggcagct gtctaggatg atcactgatt 2220
actatttact aagtagccac atgcaaataa aagttgtttg gtaaaatgga aaaaaaaaaa 2280

<210> SEQ ID NO 272
<211> LENGTH: 60
<212> TYPE: DNA
<213> ORGANISM: Homo sapiens
<220> FEATURE:
<223> OTHER INFORMATION: U17077

<400> SEQUENCE: 272
tcaccaggac ctcaacgggc aaagttgtgc acactaaaat atcaaatcaa ggtgcttggt 60

<210> SEQ ID NO 273
<211> LENGTH: 2554
<212> TYPE: DNA
<213> ORGANISM: Homo sapiens
<220> FEATURE:
<223> OTHER INFORMATION: X87949

<400> SEQUENCE: 273
aggtcgacgc cggccaagac agcacagaca gattgaccta ttggggtgtt tcgcgagtgt 60
gagagggaag cgccgcggcc tgtatttcta gacctgccct tcgcctggtt cgtggcgcct 120
tgtgaccccg ggcccctgcc gcctgcaagt cggaaattgc gctgtgctcc tgtgctacgg 180
cctgtggctg gactgcctgc tgctgcccaa ctggctggca agatgaagct ctccctggtg 240
gccgcgatgc tgctgctgct cagcgcggcg cgggccgagg aggaggacaa gaaggaggac 300
gtgggcacgg tggtcggcat cgacttgggg accacctact cctgcgtcgg cgtgttcaag 360

```
aacggccgcg tggagatcat cgccaacgat cagggcaacc gcatcacgcc gtcctatgtc    420
gccttcactc ctgaaggggga acgtctgatt ggcgatgccg ccaagaacca gctcacctcc    480
aaccccgaga acacggtctt tgacgccaag cggctcatcg gccgcacgtg gaatgacccg    540
tctgtgcagc aggacatcaa gttcttgccg ttcaaggtgg ttgaaaagaa aactaaacca    600
tacattcaag ttgatattgg aggtgggcaa acaaagacat ttgctcctga agaaatttct    660
gccatggttc tcactaaaat gaaagaaacc gctgaggctt atttgggaaa gaaggttacc    720
catgcagttg ttactgtacc agcctatttt aatgatgccc aacgccaagc aaccaaagac    780
gctggaacta ttgctggcct aaatgttatg aggatcatca acgagcctac ggcagctgct    840
attgcttatg gcctggataa gagggagggg gagaagaaca tcctggtgtt tgacctgggt    900
ggcggaacct tcgatgtgtc tcttctcacc attgacaatg gtgtcttcga agttgtggcc    960
actaatggag atactcatct gggtggagaa gactttgacc agcgtgtcat ggaacacttc   1020
atcaaactgt acaaaaagaa gacgggcaaa gatgtcagga aggacaatag agctgtgcag   1080
aaactccggc gcgaggtaga aaaggccaag gccctgtctt ctcagcatca agcaagaatt   1140
gaaattgagt ccttctatga aggagaagac ttttctgaga ccctgactcg ggccaaattt   1200
gaagagctca acatggatct gttccggtct actatgaagc ccgtccagaa agtgttggaa   1260
gattctgatt tgaagaagtc tgatattgat gaaattgttc ttgttggtgg ctcgactcga   1320
attccaaaga ttcagcaact ggttaaagag ttcttcaatg gcaaggaacc atcccgtggc   1380
ataaacccag atgaagctgt agcgtatggt gctgctgtcc aggctggtgt gctctctggt   1440
gatcaagata caggtgacct ggtactgctt catgtatgtc cccttacact tggtattgaa   1500
actgtaggag gtgtcatgac caaactgatt ccaagtaata cagtggtgcc taccaagaac   1560
tctcagatct tttctacagc ttctgataat caaccaactg ttacaatcaa ggtctatgaa   1620
ggtgaaagac ccctgacaaa agacaatcat cttctgggta catttgatct gactggaatt   1680
cctcctgctc ctcgtggggt cccacagatt gaagtcacct ttgagataga tgtgaatggt   1740
attcttcgag tgacagctga agacaagggt acagggaaca aaaataagat cacaatcacc   1800
aatgaccaga atcgcctgac acctgaagaa atcgaaagga tggttaatga tgctgagaag   1860
tttgctgagg aagacaaaaa gctcaaggag cgcattgata ctagaaatga gttggaaagc   1920
tatgcctatt ctctaaagaa tcagattgga gataaagaaa agctgggagg taaactttcc   1980
tctgaagata aggagaccat ggaaaaagct gtagaagaaa agattgaatg gctggaaagc   2040
caccaagatg ctgacattga agacttcaaa gctaagaaga aggaactgga agaaattgtt   2100
caaccaatta tcagcaaact ctatggaagt gcaggccctc ccccaactgg tgaagaggat   2160
acagcagaaa aagatgagtt gtagacactg atctgctagt gctgtaatat tgtaaatact   2220
ggactcagga acttttgtta ggaaaaaatt gaaagaactt aagtctcgaa tgtaattgga   2280
atcttcacct cagagtggag ttgaactgct atagcctaag cggctgttta ctgcttttca   2340
ttagcagttg ctcacatgtc tttgggtggg gggggagaag aagaattggc catcttaaaa   2400
agcgggtaaa aaacctgggt tagggtgtgt gttcaccttc aaaatgttct atttaacaac   2460
tgggtcatgt gcatctggtg taggaagttt tttctaccat aagtgacacc aataaatgtt   2520
tgttatttac actggtcaaa aaaaaaaaaa aaaa                                2554
```

<210> SEQ ID NO 274
<211> LENGTH: 60
<212> TYPE: DNA
<213> ORGANISM: Homo sapiens

<220> FEATURE:
<223> OTHER INFORMATION: X87949

<400> SEQUENCE: 274
aactttcctc tgaagataag gagaccatgg aaaaagctgt agaagaaaag attgaatggc 60

<210> SEQ ID NO 275
<211> LENGTH: 1359
<212> TYPE: DNA
<213> ORGANISM: Homo sapiens
<220> FEATURE:
<223> OTHER INFORMATION: Contig1632

<400> SEQUENCE: 275
ttttaagaca gttacctgtt gtgctgctgt tacaatatat aatgaaacca agtcagggga 60
gtgaatttat caatcttttg atgtaaagta aaaacgtagt tcacacttca ggagagaact 120
tcatagcaca atgtctttct ataagatatt tttaatgatt tagtatttta caacatttgt 180
ttaccatatt ttgatatacc atttttttct atctgcccag ttttattaaa aaaactatat 240
attattttct aaagaaacaa tcatattttt atacaaaatt atgttttcag gtaacgaaat 300
agatgtaggg tacagtggaa cataagcagt gttacccctg gctgggagtc agtattatac 360
aacaaatggt gagctggaac atgccctgtc tgtgctgtcc ctcctgtgct gggtcgcgga 420
tgtgtaggca acattgcctt atcacgctag gttcacctga cactttaaaa ggaaaaaaag 480
ttccatagag ttctgtggtc acaaaattgt tttgctttta tcaaatactt taatagaacc 540
aaagttgcag atattggaat gtatggaagt atctcagtct ctgcataaga ggattaaagt 600
atgaaaggat catttaatga ctgttttact tataagtcat taagtaatcc accatttctt 660
atggatgatg cttaagcctg gtgaggtttg tactctaagg agcccagatc ataatgcagt 720
gcatttcctt agcccttaga gtttcttgca aacatttaaa aaaagacata tttaagaaag 780
aaagataaag aaaaaacata tttaattact gtaaacaggt actgctttat gtttattttc 840
tctctacttc aaccaaaatc agatctttga ggttttgctg acattgttgg tggttttgca 900
catgttcttt ctaattggat ttatgaatag ttctatgggt tttcaaagat gaatcatgct 960
aagaacactt ctgctttttg atccactgtt tgcagcagaa ttatatatat gtataggaaa 1020
aatccacttt gaataatcca tgttttgtat ttggaaattg tttttaaaaa taaaaaggaa 1080
aggaaatata taaagctgtt atttattctg catttcttac atatctatcg cttgtcagta 1140
tacccgtttt ggtatatatt gcctctgcac atctacattt gtatatgcaa cagtgagctt 1200
tatatctaca taaactgtaa ataatccttt ctgtgaaagg atcatcatat caagatgata 1260
ccaaaagtat gtaaaaagaa acctgcatta ttttgtaatt atttcttata gatatttcat 1320
ggtaagatta gcagtcaata aagttacttt tttgcctttt 1359

<210> SEQ ID NO 276
<211> LENGTH: 60
<212> TYPE: DNA
<213> ORGANISM: Homo sapiens
<220> FEATURE:
<223> OTHER INFORMATION: Contig1632

<400> SEQUENCE: 276
gggttttcaa agatgaatca tgctaagaac acttctgctt tttgatccac tgtttgcagc 60

<210> SEQ ID NO 277
<211> LENGTH: 994
<212> TYPE: DNA
<213> ORGANISM: Homo sapiens
<220> FEATURE:
<223> OTHER INFORMATION: Contig3464

<400> SEQUENCE: 277
tgaatgtata tattaagact gtagctgaat tgcacatgaa atcagattgc caacttcttg 60
actttcaatg ttagacattt atccttaagt tgtgagcgat atatgtagca tgctgtgaaa 120
tgtctgttat agctctttaa ttcatcagta ttaatacaga attatcattt gcgtttcttg 180
gtacttttta ttcaatgtaa tcagaagctg tgatgttttg cctttgtagt cctgtgcttt 240
gttactgtaa tttttttttt tttttttacg aagcacgtga ctggactaat gtaaggcaga 300
tgacgtgatc tttaagactg ctatatatat cagtctctta ctctataagg ttttaaatta 360
gaataagctt ttatcaaata gataattgat gcaatttagg attcacgcaa gtttcagtgt 420
caaatggcgg tcttatagtt tcaattctga aaatagcaaa cttaataaac agccacttta 480
aacttgttct ggcaaaccag accctgctgt agatatagtc taaggtagtt aaccatataa 540
gccttttcaa ctcttaatgc cctccacatg aatcagcagt taagaaggtt ctagaaccca 600
tgaaagcttt tgtatgtatt actaggtttt gtttttctta tgtttgctga ttttacagtt 660
ctgactaaag ctgacctaaa tggatcagtt tatgtgtaat attctagtgc tttaatgact 720 cttttttttct ttggagggag ggtaacatta tttggacaga tgcagaagga actgttagtg 780
agtcaagaca aacacatctg aaataaagga actgtgtatt aacatgttaa caattcataa 840
ctgcactttt tatgacattt tgaaaatcta tttataggta cagaacaatg ggttttgtta 900
aactgtatca catttatact tgcagaaatt tatttcattg ttattagtag gaattttatt 960
ggttcaataa aattggcaaa actgaacacc aaaa 994

<210> SEQ ID NO 278
<211> LENGTH: 60
<212> TYPE: DNA
<213> ORGANISM: Homo sapiens
<220> FEATURE:
<223> OTHER INFORMATION: Contig3464

<400> SEQUENCE: 278
ctgctgtaga tatagtctaa ggtagttaac catataagcc ttttcaactc ttaatgccct 60

<210> SEQ ID NO 279
<211> LENGTH: 423
<212> TYPE: DNA
<213> ORGANISM: Homo sapiens
<220> FEATURE:
<223> OTHER INFORMATION: Contig14683

<400> SEQUENCE: 279
tatgttatgg atatcttatt ttagagtaag aatataaggc atagccatat ttatgaaggt 60
agtaatactc tactaatcaa tacttagaag tttttgttat gactaatctg aatgcttttt 120
agtttttcct taatctagtt atgttggtaa tttataagtc agttttcaga ttaggaaaga 180
aggtatttga gggtgttcca tttccactga atagtaagat gatgcttact tagatttcca 240
cagctgtttg aaagctctgt atttggctat aacggaaaac tttgttaggg atgcttgatg 300
ttttgtgttt tgtttctaaa ggaagacagt gttttgttcc ttctttagaa aacttgaaga 360
atagaataat gagtccagga ttaatttggg ataaagtctt ttacttcata aattctgatt 420
ctg 423

<210> SEQ ID NO 280
<211> LENGTH: 60

<212> TYPE: DNA
<213> ORGANISM: Homo sapiens
<220> FEATURE:
<223> OTHER INFORMATION: Contig14683

<400> SEQUENCE: 280
aggaagacag tgttttgttc cttctttaga aaacttgaag aatagaataa tgagtccagg 60

<210> SEQ ID NO 281
<211> LENGTH: 391
<212> TYPE: DNA
<213> ORGANISM: Homo sapiens
<220> FEATURE:
<223> OTHER INFORMATION: Contig28552

<400> SEQUENCE: 281
atgccattga tgtgaagaag gtgtctgtgg aagactttct tactgacctg aataacttca 60
gaaccacatt catgcaagca ataaaggaga atatcaaaaa aagagaagca gaggaaaaag 120
aaaaacgtgt cagaatagct aaagaattag cagagcgaga aagactcgaa cgccaacaaa 180
agaaaaagcg tttattagaa atgaagactg agggtgatga gacaggagtg atggataatc 240
tgctggaggc cttgcagtcc ggggctgcct tccgcgacag aagaaaaagg acaccgatgc 300
caaaagatgt tcggcagagt ctcagtccaa tgtctcagag gcctgttctg aaagtttgta 360
accatggtaa taaaccgtat ttataaattg c 391

<210> SEQ ID NO 282
<211> LENGTH: 60
<212> TYPE: DNA
<213> ORGANISM: Homo sapiens
<220> FEATURE:
<223> OTHER INFORMATION: Contig28552

<400> SEQUENCE: 282
aagactttct tactgacctg aataacttca gaaccacatt catgcaagca ataaaggaga 60

<210> SEQ ID NO 283
<211> LENGTH: 450
<212> TYPE: DNA
<213> ORGANISM: Homo sapiens
<220> FEATURE:
<223> OTHER INFORMATION: Contig28947

<400> SEQUENCE: 283
ctcatccaag gagctggggc agacttcatt gattctagag agacctgttt cagtgcctac 60
tcatccctgc cctctggtgc cagcctcctt accatcacgg cttcactgag gtgtaggtgg 120
gtttttctta aacaggagac agtctctccc ctcttacctc aacttcttgg ggtgggaatc 180
agtgatactg gagatggcta gttgctgtgt tacgggtttg agttacattt ggctataaaa 240
caatcttgtt gggaaaaatg tgggggagag gacttcttcc tacacgcgca ttgagacaga 300
ttccaactgg ttaatgatat tgtttgtaag aaagagattc tgttggttga ctgcctaaag 360
agaaaggtgg gatggccttc agattatacc agcttagcta gcattactaa ccaactgatg 420
gaagctctga aaataaaaga tcttgaaccc 450

<210> SEQ ID NO 284
<211> LENGTH: 60
<212> TYPE: DNA
<213> ORGANISM: Homo sapiens
<220> FEATURE:
<223> OTHER INFORMATION: Contig28947

<400> SEQUENCE: 284
agacagattc caactggtta atgatattgt ttgtaagaaa gagattctgt tggttgactg 60

<210> SEQ ID NO 285
<211> LENGTH: 439
<212> TYPE: DNA
<213> ORGANISM: Homo sapiens
<220> FEATURE:
<223> OTHER INFORMATION: Contig30875

<400> SEQUENCE: 285
agaaatcaat gacagttgac aggaagagag gacgcataca acaggcaaaa gaggaatgcc 60
cagcagtctt ggtccttgcg gtgcaatact ggccttgagg ccaagtcagc aggggattcg 120
tagtcactaa cttctaactg aggcagggaa gtaccatgtt ctggaaaagg tccaaagaaa 180
caggaataga ggcagtgtag caagaggcag atttttggtg ccaaatagat ttgaatcctg 240
gttctgcttc ttcctttgta gagtatgata ttggttcttt cctcccaaag ctattataaa 300
gactaaatat gtacacaaat ctttgggatg tctgacatat aaatgcttaa caataggtat 360
ttgctggtat tattacaaat gaatttgctt atttttgagc cacttctatg tctgtccatt 420
aaaccaaaat gtgttctgc 439

<210> SEQ ID NO 286
<211> LENGTH: 60
<212> TYPE: DNA
<213> ORGANISM: Homo sapiens
<220> FEATURE:
<223> OTHER INFORMATION: Contig30875

<400> SEQUENCE: 286
ggttctttcc tcccaaagct attataaaga ctaaatatgt acacaaatct ttgggatgtc 60

<210> SEQ ID NO 287
<211> LENGTH: 338
<212> TYPE: DNA
<213> ORGANISM: Homo sapiens
<220> FEATURE:
<223> OTHER INFORMATION: Contig31221

<400> SEQUENCE: 287
gggaagttac actgcttcac accacaaggc cgtgggaaat cttggaggtt ctgtgccttt 60
ctgtcacctc tactttttgc agctgtgatt gcactgtccc gcacatgtga ctacaagcat 120
cactggcaag gaccctttaa atggtgaaaa tgggcagatg aatagcaata agtggacctt 180
tgttactctt ctgagttaga aaaattctaa tttagtacac tctgaacaaa gcttattata 240
cttacttaag atgtgttttg atttggtgtt cagaaagcaa cctgacaatg ataatactgt 300
aactatgata aaattgagaa taaaaagatt ttatttag 338

<210> SEQ ID NO 288
<211> LENGTH: 60
<212> TYPE: DNA
<213> ORGANISM: Homo sapiens
<220> FEATURE:
<223> OTHER INFORMATION: Contig31221

<400> SEQUENCE: 288
aaatgggcag atgaatagca ataagtggac ctttgttact cttctgagtt agaaaaattc 60

<210> SEQ ID NO 289
<211> LENGTH: 417
<212> TYPE: DNA
<213> ORGANISM: Homo sapiens
<220> FEATURE:
<223> OTHER INFORMATION: Contig31288

<400> SEQUENCE: 289
gaatcacttg agcccgggag gttgaggctg cagtgagctg tgtttatacc actgcactcc 60
agcctgctgg gtaacagagc aagactccat ctcaaaaaga aaagaaaaaa tgctttgcta 120
cataatgagg ccaggcaaaa aaaaaaaaag tcctgtggaa atcatataga caaacatttg 180
caaagctgct actgccattg taccagtgtt aaaatgtgtt ctaccttgca tcttttactg 240
atttttatga cagattttat attgtaacca tttgagaact ctgtaagtgc tatggcttcc 300
ttaaactacg atttatcata tgctcccagt gtttactttg agactgaatg gcaaccagag 360
aatgtaaaca accaaggtgc atctggttat gttttaaaat aaagattaat aaaagtt 417

<210> SEQ ID NO 290
<211> LENGTH: 60
<212> TYPE: DNA
<213> ORGANISM: Homo sapiens
<220> FEATURE:
<223> OTHER INFORMATION: Contig31288

<400> SEQUENCE: 290
ggcttcctta aactacgatt tatcatatgc tcccagtgtt tactttgaga ctgaatggca 60

<210> SEQ ID NO 291
<211> LENGTH: 394
<212> TYPE: DNA
<213> ORGANISM: Homo sapiens
<220> FEATURE:
<223> OTHER INFORMATION: Contig31646

<400> SEQUENCE: 291
gctgctacac cccatgtaaa aagcggaaaa taaaatgaag attttccagc gcaagatgcg 60
gtactggttg cttccacctt ttttggcaat tgtttatttc tgcaccattg tccaaggtca 120
agtggctcca cccacaaggt taagatataa tgtaatatct catgacagta tacagatttc 180
atggaaggct ccaagaggga aatttggtgg ttacaaactt cttgtgactc caacttcagg 240
tggaaaaact aaccagctga atctgcagaa cactgcaact aaagcaatta ttcaaggcct 300
tatgccagac cagaattaca cagttcaaat tattgcatac aataaagata aagaaagcaa 360
gccagctcaa ggccaattca gaattaaaga ttta 394

<210> SEQ ID NO 292
<211> LENGTH: 60
<212> TYPE: DNA
<213> ORGANISM: Homo sapiens
<220> FEATURE:
<223> OTHER INFORMATION: Contig31646

<400> SEQUENCE: 292
gccagaccag aattacacag ttcaaattat tgcatacaat aaagataaag aaagcaagcc 60

<210> SEQ ID NO 293
<211> LENGTH: 357
<212> TYPE: DNA
<213> ORGANISM: Homo sapiens
<220> FEATURE:
<223> OTHER INFORMATION: Contig37562

<400> SEQUENCE: 293
caattatttc aagtgcacct tattaacaaa agtatcagtg gatccaacat aaaattttat 60
agtactaaat gtcaagccta actgtgaatt ttgttctgta tcttaagtaa atttatgata 120
atgttctcga gctatcaaca aaatatatgt acttttgtga gctatgaatt ttctaattaa 180
attttacatg ctataacatg atttttacat gaatgatact ttgtttataa ctatcaaatg 240
tcagtatttt actacaattt tattataaag tgtacattat cactaaatga acttcgattt 300
taaaaatcaa attagcttta gttgtatatt attttttaca aataaagata gacttgt 357

<210> SEQ ID NO 294
<211> LENGTH: 60
<212> TYPE: DNA
<213> ORGANISM: Homo sapiens
<220> FEATURE:
<223> OTHER INFORMATION: Contig37562

<400> SEQUENCE: 294
atcaaatgtc agtattttac tacaatttta ttataaagtg tacattatca ctaaatgaac 60

<210> SEQ ID NO 295
<211> LENGTH: 351
<212> TYPE: DNA
<213> ORGANISM: Homo sapiens
<220> FEATURE:
<223> OTHER INFORMATION: Contig37895

<400> SEQUENCE: 295
aatagagaca cctctaatta attaaagcgg atgccctccc cactcctccc aggatttgac 60
tcggagcaca aactcttcac aaaccaaaat gtcaggacac catcgccagt gtccactggc 120
cactgctgtt ggtgtgaggc agccaggagc ccctcagaac tagtaagtct gagaagaggc 180
tgcacggggc ctaggagagg gagaaatgag cccgtccaag gtgaattcct tgattctcca 240
ttgtgagtgc accaagaaca agcactccct ccgactgact ctcgcctacc aggatctgga 300
acaccttcca ttaatttatt cgttcattca ataaatattt attgactgac t 351

<210> SEQ ID NO 296
<211> LENGTH: 60
<212> TYPE: DNA
<213> ORGANISM: Homo sapiens
<220> FEATURE:
<223> OTHER INFORMATION: Contig37895

<400> SEQUENCE: 296
ctctcgccta ccaggatctg gaacaccttc cattaattta ttcgttcatt caataaatat 60

<210> SEQ ID NO 297
<211> LENGTH: 418
<212> TYPE: DNA
<213> ORGANISM: Homo sapiens
<220> FEATURE:
<223> OTHER INFORMATION: Contig38288

<400> SEQUENCE: 297
gacaagtaaa tgggggccgt tgggacggcg ggtgcctgga gggcagctct gggctcagcg 60
ggcagtgctt agagcacagg cccctctgtt gggggatggg gaggagagca gtctgccctt 120
gggagcgtag gccccaggga gacttctaaa gcccccccctg tcgtctgctc ttcacccagc 180
accacagagg cacctgctgc acacacaagc atctcactcg gcccacggag ggggccaggc 240
ttcctttgcc tgaagctgtt ttgggaaggg tctccacaca ggcactgatc tcccaagctt 300
tggtcatgat gtcttttacc atttgataat tttaaacatt gtttttaaac ccaaaacatt 360
tagtggtccg ttgcctctga agatgtaaac aaacaaatac actatttctg ggaacatt 418

<210> SEQ ID NO 298
<211> LENGTH: 60
<212> TYPE: DNA
<213> ORGANISM: Homo sapiens
<220> FEATURE:
<223> OTHER INFORMATION: Contig38288

<400> SEQUENCE: 298
tttagtggtc cgttgcctct gaagatgtaa acaaacaaat acactatttc tgggaacatt 60

<210> SEQ ID NO 299
<211> LENGTH: 413
<212> TYPE: DNA
<213> ORGANISM: Homo sapiens
<220> FEATURE:
<223> OTHER INFORMATION: Contig38901

<400> SEQUENCE: 299
tacatttttg tttaatgttg ggcctgaggt taactgtgac catggtccag cttgagtggc 60
ttctggagca gccacatttt caaggactgt ccaaaagcca gccagttcag ggctcaggcc 120
tcacccattg cccactcctg gggagaccat cacctggctc atcgtttcca ccaagagtgc 180
cccacaggag tgccccacag acccgctgga ccagcctgct gcgggtcctg gccaggggtc 240
tggctaacgg tgagggctga ctctgaactg tctctcagtc tccagaaagt gttcaagcct 300
gttgtgttcc caaatctgat tcctcctatt gtcttgtaaa tcaaactcta agtgaaaact 360
tcccatttgt cccttcaaag attttttttt attaaatggt tttttaagat cct 413

<210> SEQ ID NO 300
<211> LENGTH: 60
<212> TYPE: DNA
<213> ORGANISM: Homo sapiens
<220> FEATURE:
<223> OTHER INFORMATION: Contig38901

<400> SEQUENCE: 300
tgttcccaaa tctgattcct cctattgtct tgtaaatcaa actctaagtg aaaacttccc 60

<210> SEQ ID NO 301
<211> LENGTH: 434
<212> TYPE: DNA
<213> ORGANISM: Homo sapiens
<220> FEATURE:
<223> OTHER INFORMATION: Contig40434

<400> SEQUENCE: 301
gaatggtgaa agagagatgc cgtgttttga aagtaagatg atgaaatgaa tttttaattc 60
aagaaacatt cagaaacata ggaattaaaa cttagagaaa tgatctaatt tccctgttca 120
cacaaacttt acactttaat ctgatgattg gatattttat tttagtgaaa catcatcttg 180
ttagctaact ttaaaaaatg gatgtagaat gattaaaggt tggtatgatt tttttttaat 240
gtatcagttt gaacctagaa tattgaatta aaatgctgtc tcagtatttt aaaagcaaaa 300
aaggaatgga ggaaaattgc atcttagacc atttttatat gcagtgtaca atttgctggg 360
ctagaaatga gataaagatt atttattttt gttcatatct tgtacttttc tattaaaatc 420
attttatgaa atcc 434

<210> SEQ ID NO 302
<211> LENGTH: 60
<212> TYPE: DNA
<213> ORGANISM: Homo sapiens
<220> FEATURE:
<223> OTHER INFORMATION: Contig40434

<400> SEQUENCE: 302
aaggaatgga ggaaaattgc atcttagacc atttttatat gcagtgtaca atttgctggg 60

<210> SEQ ID NO 303
<211> LENGTH: 391
<212> TYPE: DNA
<213> ORGANISM: Homo sapiens
<220> FEATURE:
<223> OTHER INFORMATION: Contig40552

<400> SEQUENCE: 303
caccaagccc tgctccggca cctcgaatcc ctggcgacca tgagtcacca gctccaagcc 60
ttactgtgcc cccagaccaa gagctccatc ccccgccctc tgcagcgttt gtctagcgcc 120
cttgcagctc cagagccccc tggcccagcc cgtgactcct ctttggggcc tacagatgaa 180
gctggctctg agtgtccctt ccctagaaag gcctgaccct ccttacccac cagaacaggg 240
gttttgatgc cctcactagt gttgaagcct gttccagaga gaggtgggac tgcaaggaga 300
ggatggtcag ccctacccac ctgccctgtt tgagcttcct gtttgacaat gtttgctgtt 360 gatttttgt tcaataaaga atttggtaaa a 391

<210> SEQ ID NO 304
<211> LENGTH: 60
<212> TYPE: DNA
<213> ORGANISM: Homo sapiens
<220> FEATURE:
<223> OTHER INFORMATION: Contig40552

<400> SEQUENCE: 304
tttgagcttc ctgtttgaca atgtttgctg ttgatttttt gttcaataaa gaatttggta 60

<210> SEQ ID NO 305
<211> LENGTH: 495
<212> TYPE: DNA
<213> ORGANISM: Homo sapiens
<220> FEATURE:
<223> OTHER INFORMATION: Contig41413

<400> SEQUENCE: 305
aaatattctt aatagggcta ctttgaatta atctgccttt atgtttggga gaagaaagct 60
gagacattgc atgaaagatg atgagagata aatgttgatc ttttggcccc atttgttaat 120
tgtattcagt atttgaacgt cgtcctgttt gttgttagtt ttcttcatca tttattgtat 180
agacaatttt taaatctctg taatatgata cattttccta tcttttaagt tattgttacc 240
taaagttaat ccagattata tggtccttat atgtgtacaa cattaaaatg aaaggctttg 300
tcttgcattg tgaggtacag gcggaagttg gaatcaggtt ttaggattct gtctctcatt 360
agctgaataa tgtgaggatt aacttctgcc agctcagacc atttcctaat cagttgaaag 420
ggaaacaagt atttcagtct caaaattgaa taatgcacaa gtcttaagtg attaaaataa 480
aactgttctt atgtc 495

<210> SEQ ID NO 306
<211> LENGTH: 60
<212> TYPE: DNA
<213> ORGANISM: Homo sapiens
<220> FEATURE:
<223> OTHER INFORMATION: Contig41413

<400> SEQUENCE: 306
cagctcagac catttcctaa tcagttgaaa gggaaacaag tatttcagtc tcaaaattga 60

<210> SEQ ID NO 307
<211> LENGTH: 409
<212> TYPE: DNA
<213> ORGANISM: Homo sapiens
<220> FEATURE:
<223> OTHER INFORMATION: Contig41538

<400> SEQUENCE: 307
aaaaaaaaaa aaaaaaaaaa aaagagttgt tttctcatgt tcattatagt tcattacagt 60
tacatagtcc gaaggtctta caactaatca ctggtagcaa taaatgcttc aggcccacat 120
gatgctgatt agttctcagt tttcattcag ttcacaatat aaccaccatt cctgccctcc 180
ctgccaaggg tcataaatgg tgactgccta acaacaaaat ttgcagtctc atctcatttt 240
catccagact tctggaactc aaagattaac ttttgactaa ccctggaata tctcttatct 300
cacttatagc ttcaggcatg tatttatatg tattcttgat agcaatacca taatcaatgt 360
gtattcctga tagtaatgct acaataaatc caaacatttc aactctgtt 409

<210> SEQ ID NO 308
<211> LENGTH: 60
<212> TYPE: DNA
<213> ORGANISM: Homo sapiens
<220> FEATURE:
<223> OTHER INFORMATION: Contig41538

<400> SEQUENCE: 308
ctcatgttca ttatagttca ttacagttac atagtccgaa ggtcttacaa ctaatcactg 60

<210> SEQ ID NO 309
<211> LENGTH: 552
<212> TYPE: DNA
<213> ORGANISM: Homo sapiens
<220> FEATURE:
<223> OTHER INFORMATION: Contig41887

<400> SEQUENCE: 309
ctgaagacta cgaccatgaa atcacagggc tgcgggtgtc tgtaggtctt ctcctggtga 60
aaagtgtcca ggtgaaactt ggagactcct gggacgtgaa actgggagcc ttaggtggga 120
atacccagga agtcaccctg cagccaggcg aatacatcac aaaagtcttt gtcgccttcc 180
aagctttcct ccggggtatg gtcatgtaca ccagcaagga ccgctatttc tattttggga 240
agcttgatgg ccagatctcc tctgcctacc ccagccaaga ggggcaggtg ctggtgggca 300
tctatggcca gtatcaactc cttggcatca agagcattgg ctttgaatgg aattatccac 360
tagaggagcc gaccactgag ccaccagtta atctcacata ctcagcaaac tcacccgtgg 420
gtcgctaggg tggggtatgg ggccatccga gctgaggcca tctgtgtggt ggtggctgat 480
ggtactggag taactgagtc gggacgctga atctgaatcc accaataaat aaagcttctg 540
cagaatcagt gc 552

<210> SEQ ID NO 310
<211> LENGTH: 60
<212> TYPE: DNA
<213> ORGANISM: Homo sapiens
<220> FEATURE:
<223> OTHER INFORMATION: Contig41887

<400> SEQUENCE: 310
tactggagta actgagtcgg gacgctgaat ctgaatccac caataaataa agcttctgca 60

<210> SEQ ID NO 311
<211> LENGTH: 745
<212> TYPE: DNA
<213> ORGANISM: Homo sapiens
<220> FEATURE:
<223> OTHER INFORMATION: Contig42342

<400> SEQUENCE: 311
gcagtaaaga caggacgcac ccatgtcaca agaggagcac aggcaggggt gttggtgttg 60
gggcagccct cagggtctcc agacccagcc ccactcacac agcagcctag gaaggaaggg 120
cagagtccca ggtgtcagct ggtgggtctc ccaggagctg cccctccctg gaagtcacag 180
gacaggaatg acagatcagg gaactgcagg aagctgccac ctctggggtc agaatatgcc 240
cagcctgcgg gggctctcta tcggggtctt cgagagccag acagcctgcc ttgtgctgca 300
tacctggctt tgctctgtgc agaacccagc acacgtgatt ttgtgtgaca tgccagcagc 360
ctggctccca ggacaggagg cctgccctgg gggaggggct gcaggaggag ggggggcagg 420
cacccatgag tctgtccagc cttgtcacag atgcatcgcc caagctgcgg tcctgatttc 480
agctcacctc agagtaaatc agaataaact gcacccagac tttcacgaat gcatgttgac 540
gctttcagtt caccccttc tttgctaact ttcttcctat tttcttctaa tgcgagagct 600
tattaattcc atatttatca ttttgaataa cttttctcct ttttagtaac aaaatgtact 660
tcactcttag taaaatgtat ttactatttt agtaacaaaa atatacttgc ctaatcatgt 720
ttaaaatata gtgatgtgaa aaatt 745

<210> SEQ ID NO 312
<211> LENGTH: 60
<212> TYPE: DNA
<213> ORGANISM: Homo sapiens
<220> FEATURE:
<223> OTHER INFORMATION: Contig42342

<400> SEQUENCE: 312
cacccagact ttcacgaatg catgttgacg ctttcagttc accccttct ttgctaactt 60

<210> SEQ ID NO 313
<211> LENGTH: 398
<212> TYPE: DNA
<213> ORGANISM: Homo sapiens
<220> FEATURE:
<223> OTHER INFORMATION: Contig43645

<400> SEQUENCE: 313
agttcaaagg cagataaatc tgtaaattat tttatcctat ctaccatttc ttaagaagac 60
attactccaa aataattaaa tttaaggctt tatcaggtct gcatatagaa tcttaaattc 120
taataaagtt tcatgttaat gtcataggat ttttaaaaga gctataggta atttctgtat 180
aatatgtgta tattaaaatg taattgattt cagttgaaag tattttaaag ctgataaata 240
gcattagggt tctttgcaat gtggtatcta gctgtattat tggttttatt tactttaaac 300
attttgaaaa gcttatactg gcagcctaga aaaacaaaca attaatgtat ctttatgtcc 360
ctggcacatg aataaacttt gctgtggttt actaatct 398

<210> SEQ ID NO 314
<211> LENGTH: 60
<212> TYPE: DNA
<213> ORGANISM: Homo sapiens
<220> FEATURE:
<223> OTHER INFORMATION: Contig43645

<400> SEQUENCE: 314
gaaaagctta tactggcagc ctagaaaaac aaacaattaa tgtatcttta tgtccctggc 60

<210> SEQ ID NO 315
<211> LENGTH: 478
<212> TYPE: DNA
<213> ORGANISM: Homo sapiens
<220> FEATURE:
<223> OTHER INFORMATION: Contig44289

<400> SEQUENCE: 315
ctaaaaacaa cactcatcag tcttgggaaa tttgaacttt gatcaactta actaaagaag 60
gaagggtagt aagaattttt caaatacaaa tatttgccaa ttcacagatg ataacattta 120
aggccttcaa aagtaagggt ttttccttgt ttctccagtc agcttttgtc aactctaata 180
gttttttcat aaacattttt tatttgtata attgcaacag tttaagaaat tatcacaact 240
atttagaaac atttaaaatg ttctttttga tataagctat atacttggaa aaatacattg 300
gtatctaaaa tttgaggtgt gttaagactg ctttttgttt taaaaaatgg tttacattca 360
aatttttgaa gtgttttatg cttcatatgg ctaagttgta gtttggcaga gttaacagca 420
taagaataaa catgctgtaa ttttaaaaga tgctttgaat aaaaatttat tttaattt 478

<210> SEQ ID NO 316
<211> LENGTH: 60
<212> TYPE: DNA
<213> ORGANISM: Homo sapiens
<220> FEATURE:
<223> OTHER INFORMATION: Contig44289

<400> SEQUENCE: 316
catcagtctt gggaaatttg aactttgatc aacttaacta aagaaggaag ggtagtaaga 60

<210> SEQ ID NO 317
<211> LENGTH: 556
<212> TYPE: DNA
<213> ORGANISM: Homo sapiens
<220> FEATURE:
<223> OTHER INFORMATION: Contig44909

<400> SEQUENCE: 317
accatctggg atttctacag cctgggtacc catagccaca ccaaggcttc tgggagattc 60
tgcagggtca gctttccagg ctgttcccaa atagctccct gcctccccac tgcccctaaa 120
gccacagcag aagagccatt catctcataa acaaaaagga agaggaaaga atgaggaagg 180
accctgtgca aggttatttg caggcaggga tgggcttgta cctgacagca cccacccctg 240
tgtggccccc aggccctcat caccctcaga cccctcctaa gcagttccct cattgctctt 300
tggactaggc tgacagcagg aagagcaggg cccatgaccg ggtggaagtt cagttttggt 360
gtctgcttca agagggggtt ttacactctg attccaggac aagcactctg aggcgggtgg 420
gggagagaaa ccctggctct tcacccaggt ttcacacaca tgtaaatgaa acactatgtt 480
agtatctaac acactcctgg atacagaaca caagtcttgg cacatatgtg atggaaataa 540
agtgttttgc aatctt 556

<210> SEQ ID NO 318
<211> LENGTH: 60
<212> TYPE: DNA
<213> ORGANISM: Homo sapiens
<220> FEATURE:
<223> OTHER INFORMATION: Contig44909

<400> SEQUENCE: 318
tcacccaggt ttcacacaca tgtaaatgaa acactatgtt agtatctaac acactcctgg 60

<210> SEQ ID NO 319
<211> LENGTH: 710
<212> TYPE: DNA
<213> ORGANISM: Homo sapiens
<220> FEATURE:
<223> OTHER INFORMATION: Contig45032

<400> SEQUENCE: 319
aaagataggc ttctaagtta aggcaaatca ttcattctgt cattaaacaa atacaaacca 60
ggcacctgtc atatgccaag tgatattcaa aatggcccat gtagaccttt gtgaagtatg 120
tggcctaaca gacattaaac aaatgtctgt gaaactgaca taataaagta aggtaagtta 180
tatgtgagac attctctttt tataataatt cctgtaaagc agtacttact taggtaatga 240
tatcatactg ttttgtttta tatttttcct aagagctaaa acgtcatcct ctcttcagtg 300
atgtggactg ggaaaatctg cagcatcaga ctatgccttt catcccccag ccagatgatg 360
aaacagatac ctcctatttt gaagccagga atactgctca gcacctgacc gtatctggat 420
ttagtctgta gcacaaaaat tttcctttta gtctagcctc gtgttataga atgaacttgc 480
ataattatat actccttaat actagattga tctaaggggg aaagatcatt atttaaccta 540
gttcaatgtg cttttaatgt acgttacagc tttcacagag ttaaaaggct gaaaggaata 600
tagtcagtaa tttatcttaa cctcaaaact gtatataaat cttcaaagct tttttcatct 660
atttattttg tttattgcac tttatgaaaa ctgaagcatc aataaaatta 710

<210> SEQ ID NO 320
<211> LENGTH: 60
<212> TYPE: DNA
<213> ORGANISM: Homo sapiens
<220> FEATURE:
<223> OTHER INFORMATION: Contig45032

<400> SEQUENCE: 320
ttaacctagt tcaatgtgct tttaatgtac gttacagctt tcacagagtt aaaaggctga 60

<210> SEQ ID NO 321
<211> LENGTH: 726
<212> TYPE: DNA
<213> ORGANISM: Homo sapiens
<220> FEATURE:
<223> OTHER INFORMATION: Contig46218

<400> SEQUENCE: 321
atacatattg ctttagagag caggtaggtg gccatgtgtt cagcagtgtg tccttaagaa 60
aataccatct ttctaagcca ctggaatttt tactttacta tttttaacat taatggatgt 120
caggtcatca acctcaagtc tttacatatc catgtatatt ccatatatat tgtttatata 180
ggcccaagtt tctccttaat tgggatctat atactaccag cacaacatca aaaacatgta 240
attgaataca tcagagctat atatgtaagg aaatgactgg tgaccccatt atcatcattg 300
ttgaattcat gttaagtaga ccctctaggg gaccataagg caattgagca cataacgaaa 360
aatgatgcaa taagaatgta tgcactctct ttgccaaatg catgtgcttt tgtgtaacgt 420
ggatgtaaac agaattgcag tgctgccgaa attcttgatc ttggctaaga gagtattttt 480
ccccttgtaa ttatgactct gagataaaat tgccattttg aaatttccaa agtaacaact 540
ttttttattt tatgaataaa cttgggattg caatttctct gatctgacaa tcaataactt 600
taacaaagat ctaaataagt gtttcaagga aagttttcct aagcaaatgt aatattacct 660
catttgggca tcattactct gttaattcta tatcaaagga aataaacttg ctacttgcac 720
taaatg 726

<210> SEQ ID NO 322
<211> LENGTH: 60
<212> TYPE: DNA
<213> ORGANISM: Homo sapiens
<220> FEATURE:
<223> OTHER INFORMATION: Contig46218

<400> SEQUENCE: 322
accataaggc aattgagcac ataacgaaaa atgatgcaat aagaatgtat gcactctctt 60

<210> SEQ ID NO 323
<211> LENGTH: 580
<212> TYPE: DNA
<213> ORGANISM: Homo sapiens
<220> FEATURE:
<223> OTHER INFORMATION: Contig47096

<400> SEQUENCE: 323
ggtggtctct catccttgtg tgctgctctg ctaagagatg tccaaggcgg agccggggca 60
agatccttcc agactcatct gtcagagccc caagcccttt agacccagag cccaaggacc 120
atgcctttgg gacattagga ctgcagcctt tgcttctgtg tattttggag ttttggtgac 180
ttttgtcacc tggacacact catttgttag ccatagtggg ttcccttggt cagcaacagt 240
gcatgtacct ctggatgtca tctgaggtga gaccaccgag gccttttctc tctgtgtaca 300
gaggggagtt aggagttgct ggactggatg cattacgagg actggggaca gggtagaggg 360
acatccaggg atcagggcat gagtgggggc aaccccccgg cctctgccct ggcatggtct 420
ccgcatgggc tgaggtgtag ctgattggct gccacatttc ggccatgctg gctggcgtgc 480
ccatgttgca gatattttcc cgagttcccc agaatggatg gtattgaatc tcagccacat 540
gcaacactgt gtccagcatt ctttgcaata aatacttttt 580

<210> SEQ ID NO 324
<211> LENGTH: 60
<212> TYPE: DNA
<213> ORGANISM: Homo sapiens
<220> FEATURE:
<223> OTHER INFORMATION: Contig47096

<400> SEQUENCE: 324
atattttccc gagttcccca gaatggatgg tattgaatct cagccacatg caacactgtg 60

<210> SEQ ID NO 325
<211> LENGTH: 632
<212> TYPE: DNA
<213> ORGANISM: Homo sapiens
<220> FEATURE:
<223> OTHER INFORMATION: Contig47563

<400> SEQUENCE: 325
gccatctagt ctgtggtttt ctgttgaagc agtctgaatt gactaaaaca gtcacttgga 60
gtagttataa accactttcc tgttgaaagc agaacatgct gattcaactg ttttgttcaa 120
tagcaatgat agattttgtt taagtcccct acactttctt atttctaaat gatcaagagt 180
acacttcctg gcagtgatta aggagtgtgt atctaacaga aaaaatatat ataccctgtg 240
aacccgaata tggaattcag attgtttctg ccctcagtat catacttaaa aaacaagcat 300
acaaacaaac ataagggaac aaacagcaac cataacaaaa acaaaccttt aaaggtgggt 360
ttttgctgtg ataaatgaat acggtactct gaaggagaaa aaagtttctc aaatgagctt 420
aaactgcaag tgatttaaaa attagagaat ataattctta aagctattga aagtttcaac 480
cagaaaacct caagtgaatt ttgtatgtaa atgaaatctt gaatgtaagt tctgtgattc 540
tttaagcaaa caattagctg aaaacttggt attgttgtag tttatgtagt aagtgacttg 600
gcacccatca gaaaataaag ggcattaaat tg 632

<210> SEQ ID NO 326
<211> LENGTH: 60
<212> TYPE: DNA
<213> ORGANISM: Homo sapiens
<220> FEATURE:
<223> OTHER INFORMATION: Contig47563

<400> SEQUENCE: 326
agcaaacaat tagctgaaaa cttggtattg ttgtagttta tgtagtaagt gacttggcac 60

<210> SEQ ID NO 327
<211> LENGTH: 540
<212> TYPE: DNA
<213> ORGANISM: Homo sapiens
<220> FEATURE:
<223> OTHER INFORMATION: Contig48913

<400> SEQUENCE: 327
accagagggt gtcccttttc cacagtaatg ggatcggctg gtgtgccttc agggaggaag 60
agggaggtgg tcaagcttga aaaactggct ttaggatggt tctgactttg ttctccctcc 120
ccaagtgttc tcaacctcca ttctgcagtg ttcagagttt tagggaaagg gtttgggtgc 180
cccagcatcc aggtgttgtg tggcttagcg catgtgaagt gaaaaccttc tggggttgtt 240
tggaagcagc tttctggttc ttgtgattgt atcctgaggt cccagaaccc tattctccca 300
cgaggatcct cagtgaccat ggtggccaca cgcctggcca gcctgctggc tcctgggtga 360
gctgaagaac cttgcctgtg gcacttttcg agggtgagct ggaaccgaga gaacatggtc 420
cccgtgctgg gactcatgcg ggtcatttcc tgccggcctg gtttcgcctg gtcgtgtctt 480
tatgagcacc atgtaagcct ccttgtattg agataattgg gcattaaaca ttaaactgca 540

<210> SEQ ID NO 328
<211> LENGTH: 60
<212> TYPE: DNA
<213> ORGANISM: Homo sapiens
<220> FEATURE:
<223> OTHER INFORMATION: Contig48913

<400> SEQUENCE: 328
tatgagcacc atgtaagcct ccttgtattg agataattgg gcattaaaca ttaaactgca 60

<210> SEQ ID NO 329
<211> LENGTH: 534
<212> TYPE: DNA
<213> ORGANISM: Homo sapiens
<220> FEATURE:
<223> OTHER INFORMATION: Contig49169

<400> SEQUENCE: 329
cctaatgtta acatttttaa aaatacatat ttgggactct tattatcaag gttctaccta 60
tgttaattta caattcatgt ttcaagacat ttgccaaatg tattaccgat gcctctgaaa 120
agggggtcac tgggtctcat agactgatat gaagtcgaca tatttatagt gcttagagac 180
caaactaatg gaaggcagac tatttacagc ttagtatatg tgtacttaag tctatgtgaa 240
cagagaaatg cctcccgtag tgtttgaaag cgttaagctg ataatgtaat taacaactgc 300
tgagagatca aagattcaac ttgccataca cctcaaattc ggagaaacag ttaatttggg 360
caaatctaca gttctgtttt tgctactcta ttgtcattcc tgtttaatac tcactgtact 420
tgtatttgag acaaataggt gatactgaat tttatactgt tttctacttt tccattaaaa 480
cattggcacc tcaatgataa agaaatttaa ggtataaaat taaatgtaaa aatt 534

<210> SEQ ID NO 330
<211> LENGTH: 60
<212> TYPE: DNA
<213> ORGANISM: Homo sapiens
<220> FEATURE:
<223> OTHER INFORMATION: Contig49169

<400> SEQUENCE: 330
catacacctc aaattcggag aaacagttaa tttgggcaaa tctacagttc tgtttttgct 60

<210> SEQ ID NO 331
<211> LENGTH: 602
<212> TYPE: DNA
<213> ORGANISM: Homo sapiens
<220> FEATURE:
<223> OTHER INFORMATION: Contig49388

<400> SEQUENCE: 331
tgtcagtgga ggggtctctg cagccaactg agactatctt gctgtgccct gagccttcct 60
agggtttaga agaacagcat tcaaaattcc ccgtcctgtc agtgtttgcc ttcgcacctc 120
ctcccctaaa gcagcgcggg gggcaaataa gaccccaccc ctccctgcag cttcacaggg 180
acgcttcctt ccctccccgc aaccacccca ggctcccctg ggaggctgca gttgtggtac 240
acgtccccgg tgctgggttg gccgtgactc gggggcgggg cgatcgggtc tcagcccctg 300
ccttccccag tctctgggtc acccgaattt tcccacccct gcttctcccc gaggaggttg 360
agctcttgag caagttggga cttgggccgg ggcctggaag aatgattggc tgggaggccg 420
cgggagggag gccaggaggc ccggaccagt tgggaggagt gagcaggccc cgggggaggg 480
ggatgagcgc agtttgctcg ctttcctccc ctgccggccc cctccgcccc cacacacact 540
cgggacgtct tcattgaaga ttcacttaca aaggaatgtt tcactaaata aaagaaaacc 600
ag 602

<210> SEQ ID NO 332
<211> LENGTH: 60
<212> TYPE: DNA
<213> ORGANISM: Homo sapiens
<220> FEATURE:
<223> OTHER INFORMATION: Contig49388

<400> SEQUENCE: 332
cgggacgtct tcattgaaga ttcacttaca aaggaatgtt tcactaaata aaagaaaacc 60

<210> SEQ ID NO 333
<211> LENGTH: 562
<212> TYPE: DNA
<213> ORGANISM: Homo sapiens
<220> FEATURE:
<223> OTHER INFORMATION: Contig50728

<400> SEQUENCE: 333
gcgaatttgg gccccttgat cctctgatgg gagctgaaag gatgagaggt gggcatctag 60
atttagggag gctgttcagg ctttgcaggt cccttacctg aacacataga aaccctggag 120
ctgtgactgt gtccatgtgt gtgtgtttgt ctgtgtgtgt tgcgggggat gggcacctgc 180
atgaatgtgg tagagaaaat ggctctgctc agagggaaga tacgcatagc aaggcaggga 240
ccagaggaat cacaggcgcc tggagagcag ccgggcaccg cctccaggga cctgccggct 300
tccctcagtc ctccaggggc ccagcactct tcctttaggc cctgtgagcg tcccttgtca 360
ggatacattc tctcattttg ctgaagctga tttgattggg tgtctgtttc tcgcagccaa 420
aagagctctg aatgaggaaa gtgcttctgt gctaactccc cgcgtctcct gaatttcagt 480
cattcatgta cccgcctcga aatttttgca atatctgtgt accaactgtc catttactta 540
ataaagaagt tttctttaaa tt 562

<210> SEQ ID NO 334
<211> LENGTH: 60
<212> TYPE: DNA
<213> ORGANISM: Homo sapiens
<220> FEATURE:
<223> OTHER INFORMATION: Contig50728

<400> SEQUENCE: 334
tttgattggg tgtctgtttc tcgcagccaa aagagctctg aatgaggaaa gtgcttctgt 60

<210> SEQ ID NO 335
<211> LENGTH: 400
<212> TYPE: DNA
<213> ORGANISM: Homo sapiens
<220> FEATURE:
<223> OTHER INFORMATION: AI497657

<400> SEQUENCE: 335 ttttttttt tgcacttatg gtatttattg ttggaagatt gagtacctta atgcacacca 60
atgctcagat gacttggggg cacatagggg actgctgtca ccatgcctca ctcctgcagg 120
gaaggggctg ccctactaaa accccagcgg gcccagtgct gtgtccagaa caggtcctta 180
tattactgca gcccacaatg gaactactga gtaggagcca aaagaggagg gagcaggaag 240
aggtggcatt tggagagggg agaccgcacc cacaggtctg ccacagcgcg tcaacggtat 300
ggggtacttt tacagtcaag ttgacttcgg tgtccgccca ccatctacct ttgtaggacc 360
actgaaacaa gggacatcca ccacggccca cagccggggc 400

<210> SEQ ID NO 336
<211> LENGTH: 60
<212> TYPE: DNA
<213> ORGANISM: Homo sapiens
<220> FEATURE:
<223> OTHER INFORMATION: AI497657

<400> SEQUENCE: 336
gagcattggt gtgcattaag gtactcaatc ttccaacaat aaataccata agtgcaaaaa 60

<210> SEQ ID NO 337
<211> LENGTH: 475
<212> TYPE: DNA
<213> ORGANISM: Homo sapiens
<220> FEATURE:
<223> OTHER INFORMATION: Contig50950

<400> SEQUENCE: 337
ctggaagagg ctcccaaccc agagtgtccc tgtgggaggc aggcagaagg tgacaattga 60
cacgatttcc tgcacgcgtc ctcctctacc ttggaagcag ttagaatcta ccaggcacag 120
atgaggccgc ccttgcctga cggagcttga tgagcagccc ttggtctccg gttccaggac 180
tgagagccca gctgcctctg cccacccttc cccaggcctc tgccagcctc tggctgcacg 240
gtcaggccct gccccatggc aggcctgcca gagcttggct ggggacccct cccgcctctg 300
gctccctgat gggctggatg taacttgtgt cttctagccc cttaaggagc ccaggtgttt 360
taaggaatga attggtcact gcatcttgta tcgattatgg ttctgagaaa agcaaatatc 420
acttttggct gcattaaaag aagcatcata tataaaataa agaagatgaa ggtct 475

<210> SEQ ID NO 338
<211> LENGTH: 60
<212> TYPE: DNA
<213> ORGANISM: Homo sapiens
<220> FEATURE:
<223> OTHER INFORMATION: Contig50950

<400> SEQUENCE: 338
gtcactgcat cttgtatcga ttatggttct gagaaaagca aatatcactt ttggctgcat 60

<210> SEQ ID NO 339
<211> LENGTH: 860
<212> TYPE: DNA
<213> ORGANISM: Homo sapiens
<220> FEATURE:
<223> OTHER INFORMATION: Contig51660

<400> SEQUENCE: 339
ggatggcaac cttcagctag actgcctggc tcaagggtgg aagcaatacc aacagagagc 60
atttggctgg ttccggtgtt cctcctgcca gcgaagttgg gcttccgcca agtgcagatt 120
ctgtgccaca cgtactggga gcactggaca tcccagggtc aggtgcgtat gaggctcttt 180
ggccaaaggt gccagaagtg ctcctggtcc caatatgaga tgcctgagtt ctcctcggat 240
agcaccatga ggattctgag caacctggtg cagcatatac tgaagaaata ctatggaaat 300
ggcatgagga agtctccaga aatgccagta atcctggaag tgtccctgga aggatcccat 360
gacacagcca attgtgaggc atgcactttg ggcatatgtg gacagggctt aaaaagctac 420
atgacaaagc cgtccaaatc cctactcccc cacctaaaga ctgggaattc ctcacctgga 480
attggtgctg tgtacctcgc aaaccaagcc aagaaccagt cagatgaggc aaaagaggct 540
aaggggagtg ggtatgagaa attagggccc agtcgagacc cagatccact gaacatctgt 600
gtctttattt tgctgcttgt atttattgta gtcaaatgct ttacatcaga atgatgaaaa 660
taggcttgcc actttctctt attttaattc catggtagtc aatgaactgg ctgccacttt 720
aatataactg aaaattcatt ttgagaccaa gcaggatcaa gtttgtagaa taaacactgg 780
tttcctagcc atcctctgaa aacagtatga aacatgacca agtacataat ggatttagta 840
ataaatattg tcgaattgct 860

<210> SEQ ID NO 340
<211> LENGTH: 60
<212> TYPE: DNA
<213> ORGANISM: Homo sapiens
<220> FEATURE:
<223> OTHER INFORMATION: Contig51660

<400> SEQUENCE: 340
gctgcttgta tttattgtag tcaaatgctt tacatcagaa tgatgaaaat aggcttgcca 60

<210> SEQ ID NO 341
<211> LENGTH: 608
<212> TYPE: DNA
<213> ORGANISM: Homo sapiens
<220> FEATURE:
<223> OTHER INFORMATION: Contig52490

<400> SEQUENCE: 341
atcgtggcta gcggacagac acgagcctct tgggaatacc ttgtccatca cgtcatggcc 60
atgggtgcct tcttctccgg catcttttgg agcagctttg tcggtggggg tgtcttaaca 120
ctactggtgg aagtcagcaa catcttcctc accattcgca tgatgatgaa aatcagtaat 180
gcccaggatc atctcctcta ccgggttaac aagtatgtga acctggtcat gtactttctc 240
ttccgcctgg cccctcaggc ctacctcacc catttcttct tgcgttatgt gaaccagagg 300
accctgggca ccttcctgct gggtatcctg ctcatgctgg acgtgatgat cataatctac 360
ttttcccgcc tcctccgctc tgacttctgc cctgagcatg tccccaagaa gcaacacaaa 420
gacaagttct tgactgagaa ctgagtgagg ggcacagagc ctgggacaac aaaaacggac 480
aaggccagaa acagcttcat atggacactg ggacttagcc ccaagcctgg gtgtcctctg 540
aggccagcct ctccaccttc tgagcctgcg cccacactat tgaaaacact aatgaaagta 600
ctcctctg 608

<210> SEQ ID NO 342
<211> LENGTH: 60
<212> TYPE: DNA
<213> ORGANISM: Homo sapiens
<220> FEATURE:
<223> OTHER INFORMATION: Contig52490

<400> SEQUENCE: 342
ccaggatcat ctcctctacc gggttaacaa gtatgtgaac ctggtcatgt actttctctt 60

<210> SEQ ID NO 343
<211> LENGTH: 1282
<212> TYPE: DNA
<213> ORGANISM: Homo sapiens
<220> FEATURE:
<223> OTHER INFORMATION: Contig53598

<400> SEQUENCE: 343
catgccagca cctttgaacc ggtctcttag aagaagacac acatcctggg tgtacagtgg 60
tgaaatgggg agtgggtgcc cattctgaaa aacgaggcat tcctgctcat tccctctgct 120
tagctggtgg gcaggggaga gagggaaatg ccaaaaactt ggagtgaagg atgatgctat 180
tttttatttt taaatatatc ttcaggttat tttcttactg ttgcttcaga tctaatgtaa 240
aaggcagatg tcccctcctc tccacccccg acgctgaccc cggcctcagt cacggctctt 300
tgcatgatca cagttctgtg ttctggcctg tggcagggcc gggaagggcc gctggcttcc 360
gaacagacgt ggttgctctc cacgaggcgc atggggagcc cgcgggccct aagctttgtc 420
gcagatgtca tcattggcag aattacttgt cttgaaaaat aagtagcatt gctgaaacac 480
acaaccgaat tctctacgat ggccatttgc tcattgtctt tcctctgtgt gtagtgagtg 540
accctggcag tgtttgcctg ctcagagtgg cccctcagaa caacagggct ggccttggaa 600
aaaccccaaa acaggactgt ggtgacaact ctggtcaggt gtgatttgac atgagggccg 660
gaggcggttg ctgacggcag gactggagag gctgcgtgcc cggcactggc agcgaggctc 720
gtgtgtcccc caggcagatc tgggcacttt cccaacccag gtttatgcgt ctccagggaa 780
gcctcggtgc cagagtggtg ggcagatctg accatcccca cagaccagaa acaaggaatt 840
tctgggatta cccagtcccc cttcaaccca gttgatgtaa ccacctcatt ttttacaaat 900
acagaatcta ttctactcag gctatgggcc tcgtcctcac tcagttattg cgagtgttgc 960
tgtccgcatg ctccgggccc cacgtggctc ctgtgctcta gatcatggtg actcccccgc 1020
cctgtggttg gaatcgatgc cacggattgc aggccaaatt tcagatcgtg tttccaaaca 1080
cccttgctgt gccctttaat gggattgaaa gcacttttac cacatggaga aatatatttt 1140
taatttgtga tgcttttcta caaggtccac tatttctgag tttaatgtgt ttccaacact 1200
taaggagact ctaatgaaag ctgatgaatt ttcttttctg tccaaacaag taaaataaaa 1260
ataaaagtct atttagatgt tg 1282

<210> SEQ ID NO 344
<211> LENGTH: 60
<212> TYPE: DNA
<213> ORGANISM: Homo sapiens
<220> FEATURE:
<223> OTHER INFORMATION: Contig53598

<400> SEQUENCE: 344
ccactatttc tgagtttaat gtgtttccaa cacttaagga gactctaatg aaagctgatg 60

<210> SEQ ID NO 345
<211> LENGTH: 601
<212> TYPE: DNA
<213> ORGANISM: Homo sapiens
<220> FEATURE:
<223> OTHER INFORMATION: Contig53641

<400> SEQUENCE: 345
tggaggctgt ggatgatgct ttcaagacaa tggatgtgga tatggccgag gaacatgcca 60
gggcccagat gagggcccag atgaatatcg gggatgaagc gctgattgga cggtggagct 120
gggatgacat acaagtcgag ctcctgacct gggatgagga cggagatttt ggcgatgcct 180
gggccaggat ccccctttgct ttctgggcca gataccatca gtacattctg aatagcaacc 240
gtgccaacag gagggccacg tggagagctg gcgtcagcag tggcaccaat ggaggggcca 300
gcaccagcgt cctagatggc cccagcacca gctccaccat ccggaccaga aatgctgcca 360
gagctggcgc cagcttcttc tcctggatcc agcaccgttg acgaactgca gcgatcttac 420
tggccaagcc agagcgcctc ctctcagatt ccttctcgac acagcaccct aggcggcttc 480
ttcctgtcag tcggaggtgg catgcaagat gaagctctct ttgctcttcc tgctttcatt 540
ttgtgctttt ccttgtgttt tcatgttttg ggtatcagtg ttacattaaa gttgcaaaat 600
t 601

<210> SEQ ID NO 346
<211> LENGTH: 60
<212> TYPE: DNA
<213> ORGANISM: Homo sapiens
<220> FEATURE:
<223> OTHER INFORMATION: Contig53641

<400> SEQUENCE: 346
ctttcatttt gtgcttttcc ttgtgttttc atgttttggg tatcagtgtt acattaaagt 60

<210> SEQ ID NO 347
<211> LENGTH: 751
<212> TYPE: DNA
<213> ORGANISM: Homo sapiens
<220> FEATURE:
<223> OTHER INFORMATION: Contig54242

<400> SEQUENCE: 347
aattactcaa agaaggagcc atttcagtta actcaagtga atgaaagact tttggaatct 60
gcagtgggtc cttccctgtt gaccatttgg taacttgtaa tctgaccaaa aactcttgag 120
ctgcaacagg ccttgccaga gggctcagga tgggaaagga agaaggggat aggaaaagaa 180
gaggtaattt tacatttccc ctttaaagta aattttagcc aactcatcat tctgaaatgt 240
ccctataaag aatgagtcga actagaccag aagccagcct actccttctt acatagcttc 300
tccaacaggg gtagcaatga cctgtccact tcaaacacag ataaggcctg ccatcctcat 360
tggttaaagg cacacgtgag actttcagtg ggctctgctg agaaggaagg cagcccagga 420
gtcaggtatg caggcattgc attgtcagtg tctgctctca gagtttacac attcaattgc 480
ttccaagggt gaatctcctg ctctgtgaat gctatcagac cccaaaggcc aaccttgggc 540
tgggtctatg tacgttcttc cgaagcactg atgatcaaaa ttgaagacac attcagaggt 600
ttgattggtt gagattaact ggtgtggtgg ttggtgtatg tatgttttat ttttatgtct 660
ttgtatgtag ttctacataa tgcaaattgt gctttctgat ggacaagacc tcataactgt 720
gattaatatc aataaaaagg ggatgttgtg g 751

<210> SEQ ID NO 348
<211> LENGTH: 60
<212> TYPE: DNA
<213> ORGANISM: Homo sapiens
<220> FEATURE:
<223> OTHER INFORMATION: Contig54242

<400> SEQUENCE: 348
gtaaatttta gccaactcat cattctgaaa tgtccctata aagaatgagt cgaactagac 60

<210> SEQ ID NO 349
<211> LENGTH: 637
<212> TYPE: DNA
<213> ORGANISM: Homo sapiens
<220> FEATURE:
<223> OTHER INFORMATION: Contig54661

<400> SEQUENCE: 349
ggcagtgatg tctatgttga gattaactta tgtattgagg aaaatttgaa gtttattttt 60
tcgatgaata aggctgtcaa atgatttagt atagattaat gacatctttt ttagaaatat 120
taaagtgagt attcctcatt atgtcatcat ttctgataat tagagtgcta atttgaatgt 180
tagataatgt ttccacatct atacctattt ctttctaggg cacttctgac cctggggctt 240
ggggatggcc tttaggccac agtagtgtct gtgttaagtt cactaaatgt gtatttaatg 300
agaaacattc ctatgtaaaa atgtgtgtat gtgaacgtat gcatacattt ttattgtgca 360
cctgtacatt gtgaagaagt agtttggaaa tttgtaaagc acaaaccata aaagagtgtg 420
gagttattaa atgatgtagc acaaatgtaa tgtttagctt ataaaaggtc ctttctattt 480
tctatggcaa agactttgac acttgaaaaa taaaaccaat atttgattta tttttgtaag 540
tatttaggat attattttaa ataaatgatt gtccattatc aatataatag ttgtgaaatg 600
atttaagtaa ataaacttta tgcttctgtg tctgttg 637

<210> SEQ ID NO 350
<211> LENGTH: 60
<212> TYPE: DNA
<213> ORGANISM: Homo sapiens
<220> FEATURE:
<223> OTHER INFORMATION: Contig54661

<400> SEQUENCE: 350
ctgtacattg tgaagaagta gtttggaaat ttgtaaagca caaaccataa aagagtgtgg 60

<210> SEQ ID NO 351
<211> LENGTH: 924
<212> TYPE: DNA
<213> ORGANISM: Homo sapiens
<220> FEATURE:
<223> OTHER INFORMATION: Contig55188

<400> SEQUENCE: 351
gcgacaagta ccgcaagcgg gcactcatcc tggtgtcact gctggccttt gccggcctct 60
tcgccgccct cgtgctgtgg ctgtacatct accccattaa ctggccctgg atcgagcacc 120
tcacctgctt ccccttcacc agccgcttct gcgagaagta tgagctggac caggtgctgc 180
actgaccgct gggccacacg gctgcccctc agccctgctg gaacagggtc tgcctgcgag 240
ggctgccctc tgcagagcgc tctctgtgtg ccagagagcc agagacccaa gacagggccc 300
gggctctgga cctgggtgcc cccctgccag gcgaggctga ctccgcgtga gatggttggt 360
taaggcgggg tttttctggg gcgtgaggcc tgtgagatcc tgacccaagc tcaggcacac 420
ccaaggcacc tgcctctctg agtcttgggt ctcagttcct aatatcccgc tccttgctga 480
gaccatctcc tggggcaggg tccttttctt cccaggtcct cagcgctgcc tctgctggtg 540
ccttctcccc cactactact ggagcgtgcc cttgctgggg acgtggctgt gccctcagtt 600
gcccccaggg ctgggtgccc accatgcccc ttcctctttc tcctcctacc tctgccctgt 660
gagcccatcc ataaggctct cagatgggac attgtgggaa aggctttggc catggtctgg 720
gggcagagaa caagggggga gacacaagta gacctcaggt agaacgacac tgggcggagc 780
caccccaggg cctgctccca gggagtgctc gaggcgcatc aggcccgttt tttaccagtt 840
tatatcacgg tcttcatttt taaaagtaac gctaactttg tacggacgat gtctcatgga 900
ttaaataata ttctttatgg cagt 924

<210> SEQ ID NO 352
<211> LENGTH: 60
<212> TYPE: DNA
<213> ORGANISM: Homo sapiens
<220> FEATURE:
<223> OTHER INFORMATION: Contig55188

<400> SEQUENCE: 352
agtaacgcta actttgtacg gacgatgtct catggattaa ataatattct ttatggcagt 60

<210> SEQ ID NO 353
<211> LENGTH: 699
<212> TYPE: DNA
<213> ORGANISM: Homo sapiens
<220> FEATURE:
<223> OTHER INFORMATION: Contig55353

<400> SEQUENCE: 353
tgattatgcc aagagctcta aacagaagtt tgagaaggta aaaattaagt tgtagtatct 60
gagttgtttt tattttcttc ctttggtgtt tatgaaggta ttcataagaa ctttaatttc 120
aggggaaaaa atgcctgatt tgctattttt gacatttcct cgtctcttaa gaagtcagtt 180
aaatatgttt tcatagttta tattcctgtt tcatagatta ctgtgaaaca tgtatttaaa 240
cctatgaatt ataaaatagt atttagattc tagcgtgagt taaatagatt agtcatatat 300
cttttagatt tgtggatttg acatgtaaat tatgtgttgt gtataagtaa gttagttact 360
aaacatatgg catggttatt gataaacttg ttgctatttt tttccaaatg ctatcagtgt 420
ttgtggactt ttaaaaatta gtttgaattt tggaatgttc tgtgataaaa tataatttca 480
actattttgt acatttaaat atgccatgtt gtatatgtct gtatttaaaa atgttgtaaa 540
tatctgcatt ttaagaatta tgaaagattt tcctcaaaaa tgacagaact ctccatactt 600
aattgtgaca cattataaga tatctgattt taagcttttg gattttgttc taaaaattaa 660
gtttaaacat gctgaaaatt ccataaaaat aaaattttg 699

<210> SEQ ID NO 354
<211> LENGTH: 60
<212> TYPE: DNA
<213> ORGANISM: Homo sapiens
<220> FEATURE:
<223> OTHER INFORMATION: Contig55353

<400> SEQUENCE: 354
taaaatagta tttagattct agcgtgagtt aaatagatta gtcatatatc ttttagattt 60

<210> SEQ ID NO 355
<211> LENGTH: 809
<212> TYPE: DNA
<213> ORGANISM: Homo sapiens
<220> FEATURE:
<223> OTHER INFORMATION: Contig56503

<400> SEQUENCE: 355
gcatgtgaga tgagtgactg ccggtgaatg tgtccacagt tgagaggttg gagcaggatg 60
agggaatcct gtcaccatca ataatcactt gtggagcgcc actctgccca agacgccacc 120
tgggcggaca gcatggagct ctccatggcc aggctgcctg tgtgcatgtt ccctgtctgg 180
tgcccctttg cccgcctcct gcaaacctca cagggtcccc acacaacagt gccctccaga 240
agcagcccct cggaggcaga ggaaggaaaa tggggatggc tggggctctc tccatcctcc 300
ttttctcctt gccttcgcat ggctggcctt cccctccaaa acctccattc ccctgctgcc 360
agcccctttg ccatagcctg attttgggga ggaggaaggg gcgatttgag ggagaagggg 420
agaaagctta tggctgggtc tggtttcttc ccttcccaga gggtcttact gttccagggt 480
ggccccaggg caggcagggg ccacactatg cctgcgccct ggtaaaggtg acccctgcca 540
tttaccagca gccctggcat gttcctgccc cacaggaata gaatggaggg agctccagaa 600
actttccatc ccaaaggcag tctccgtggt tgaagcagac tggatttttg ctctgcccct 660 gacccettgt ccctctttga gggaggggag ctatgctagg actccaacct cagggactcg 720
ggtggcctgc gctagcttct tttgatactg aaaactttta aggtgggagg gtggcaaggg 780
atgtgcttaa taaatcaatt ccaagcctc 809

<210> SEQ ID NO 356
<211> LENGTH: 60
<212> TYPE: DNA
<213> ORGANISM: Homo sapiens
<220> FEATURE:
<223> OTHER INFORMATION: Contig56503

<400> SEQUENCE: 356
gaaaactttt aaggtgggag ggtggcaagg gatgtgctta ataaatcaat tccaagcctc 60

<210> SEQ ID NO 357
<211> LENGTH: 976
<212> TYPE: DNA
<213> ORGANISM: Homo sapiens
<220> FEATURE:
<223> OTHER INFORMATION: Contig56678

<400> SEQUENCE: 357
gaaggatata ctttgttata acttattatt ttgttctctg taaatacaag atgtttatag 60
gaaatatgta ttctgaactc tatctgcaga atgagtcact acaccaaaat agttctatta 120
tttagaatgt gttaatttta aagggacctg ataggtattt atttacatat gcgatccaca 180
tttgtgtgaa agcatgtgat catactaacc cagcctcctg gaatgtcgct gtacgatgat 240
tgatgtcttt ttctcagtcc atagttacaa ttgtttagta tgctaatcag tccagttccc 300
tgaggtttaa gatcaaatat aaattactct gcttttcgac tcattcaggt agcattgtac 360
ctgaacctga ttgctacttt ttcatcttaa atattatatt tcctcatcta atctgccttc 420
ccctcatcca cagacatttg gagaaggaaa tgggagggtg tctgttatcc ctttctcttt 480
gctttgtccc cgttgttaga ctggcagcgt cagttgctcg gtgggcttgg ttagagccgt 540
gggtgaggca ggtggctggc ggggacaggg agaggctgag agggaagtgg tggcatttac 600
tgctctgaca cttccactgt ccctgctggg gatgctgggg ccaaggcctg tggggcctgt 660
gaactgcaca gccaggagca aggaacccac taaatactcc gtcacctcca tgtcccctct 720
acagtgttaa attattacat aagcaggtga aaggtagaag gcgaattatg tgagtaaata 780
tggtctgttt tctcttcagc aaaaatgact atttttgtgt gtgactaatt tatttttatt 840
attgtaaaga tacaataaac cggttgaaat atctgctttg ttgacaagcg tgtgctttct 900
ctggccttat tcgcgttctg ttctcctgca aatagcgccc tctaaaaaga agagtcagac 960
aataaactgg ttgaaa 976

<210> SEQ ID NO 358
<211> LENGTH: 60
<212> TYPE: DNA
<213> ORGANISM: Homo sapiens
<220> FEATURE:
<223> OTHER INFORMATION: Contig56678

<400> SEQUENCE: 358
tattacataa gcaggtgaaa ggtagaaggc gaattatgtg agtaaatatg gtctgttttc 60

<210> SEQ ID NO 359
<211> LENGTH: 1118
<212> TYPE: DNA
<213> ORGANISM: Homo sapiens
<220> FEATURE:
<223> OTHER INFORMATION: Contig57584

<400> SEQUENCE: 359
agctgttgtg catccagagg tggaattggg gcccggcatt ccctcctcgt cccgggctgg 60
cccttgcccc caccctgcaa ctcctggttg agatgggctc agccaagagc gtcccagtca 120
caccagcgcg gcctccgccg acaacaagca tctggctcga gtggcggacc cccgttcacc 180
tagtgctggc atcctgcgca ctcccatcca ggtggagagc tctccacagc caggcctacc 240
agcaggggag caactggagg gtcttaaaca tgcccaggac tcagatcccc gctctcctac 300
tcttggtatt gcacggacac ctatgaagac cagcagtgga gaccccccaa gcccactggt 360
gaaacagctg agtgaagtat ttgaaactga agactctaaa tcaaatcttc ccccagagcc 420
tgttctgccc ccagaggcac ctttatcttc tgaattggac ttgcctctgg gtacccagtt 480
atctgttgag gaacagatgc caccttggaa ccagactgag ttcccctcca aacaggtgtt 540
ttccaaggag gaagcaagac agcccacaga aacccctgtg gccagccaga gctccgacaa 600
gccctcaagg gaccctgaga ctcccagatc ttcaggttct atgcgcaata gatggaaacc 660
aaacagcagc aaggtactag ggagatcccc cctcaccatc ctgcaggatg acaactcccc 720
tggcaccctg acactacgac agggtaagcg gccttcaccc ctaagtgaaa atgttagtga 780
actaaaggaa ggagccattc ttggaactgg acgacttctg aaaactggag gacgagcatg 840
ggagcaaggc caggaccatg acaaggaaaa tcagcacttt cccttggtgg agagctaggc 900
cctgcatggc cccagcaatg cagtcaccca gggcctggtg atatctgtgt cctctcaccc 960
cttctttccc agggatactg aggaatggct tgttttctta gactcctcct cagctaccaa 1020
actgggactc acagctttat tgggctttct ttgtgtcttg tgtgtttctt ttatattaaa 1080
ggaagtaatt ttaaatgtta ctttaaaaag gtatatgt 1118

<210> SEQ ID NO 360
<211> LENGTH: 60
<212> TYPE: DNA
<213> ORGANISM: Homo sapiens
<220> FEATURE:
<223> OTHER INFORMATION: Contig57584

<400> SEQUENCE: 360
aggaatggct tgttttctta gactcctcct cagctaccaa actgggactc acagctttat 60

<210> SEQ ID NO 361
<211> LENGTH: 859
<212> TYPE: DNA
<213> ORGANISM: Homo sapiens
<220> FEATURE:
<223> OTHER INFORMATION: Contig63649

<400> SEQUENCE: 361
gtcgcagggt accagtgtgc ggagttcctg ttgccaagct gaaggtggcc ctgggcaggc 60
acaggtgtgg tcatatcttc agccaacagg accatcctcc ggagggccac ctctggggac 120
ttcctacggg aagagagtga cagatttggt gcttctgtgt gtttctgccg cttcagtggg 180
gccgctgcgg gagacagcgg gtggatcctc cagcagcctg tctgctgagc ctgccttctc 240
aagtctactg ttaaaatcag gaccgggtcg tgtccgagcc tacaggccct gtctccgctc 300
cccaggcctg caggagttga gggctgcacc tgctcgctgg agagggagag gcagatttag 360
tggacgcctg gcatggactc ggactggcct ttggaagctc cctgccctga cgggttgcct 420
gtcaccactg cgaagtgagg cttggaggac ctgcacctga gaaaggctgt gtgtggtctt 480
gggtccacac ctgccagagc taacttactg ccagacggcg acttactgtg ggccaccctc 540
agtgaaccgg ggtgtcctca gctggcccta cagagcactt ctgtgctggg gatgagtagg 600
aactctgggc gaggagggtc ccagcgccgc ccctcgatac agccctgctc tgccctctgc 660
ccgtacttat accaggtggg atccctgccc tgcattgcct ggggattggc tgggcttggg 720
cacgccctgc tgtggaactg gatgttttca gggagcccag cctttcctca tgtcaacaca 780
gttcacaata tagttttcaa agtacagttt aaaactcaaa agtaaacttt tcagcaactc 840
aaaaaaaaaa aaaaaaaaa 859

<210> SEQ ID NO 362
<211> LENGTH: 60
<212> TYPE: DNA
<213> ORGANISM: Homo sapiens
<220> FEATURE:
<223> OTHER INFORMATION: Contig63649

<400> SEQUENCE: 362
cagcctttcc tcatgtcaac acagttcaca atatagtttt caaagtacag tttaaaactc 60

<210> SEQ ID NO 363
<211> LENGTH: 1170
<212> TYPE: DNA
<213> ORGANISM: Homo sapiens
<220> FEATURE:
<223> OTHER INFORMATION: Contig63525

<400> SEQUENCE: 363
gccatggctc cctgggcgga gcgagcactc gcggctgaac ccgctgcgcg cggtgtggct 60
cacgctgacc gccgccttcc tgctgaccct actgctgcag ctcctgccgc ccggcctgct 120
cccgggctgc gcgatcttcc aggacctgat ccgctatggg aaaaccaagt gtggggagcc 180
gtcgcgcccc gccgcctgcc gagcctttga tgtccccaag agatattttt cccactttta 240
tatcatctca gtgctgtgga atggcttcct gctttggtgc cttactcaat ctctgttcct 300
gggagcacct tttccaagct ggcttcatgg tttgctcaga attctcgggg cggcacagtt 360
ccagggaggg gagctggcac tgtctgcatt cttagtgcta gtatttctgt ggctgcacag 420
cttacgaaga ctcttcgagt gcctctacgt cagtgtcttc tccaatgtca tgattcacgt 480
cgtgcagtac tgttttggac ttgtctatta tgtccttgtt ggcctaactg tgctgagcca 540
agtgccaatg gatggcagga atgctacata acagggaaaa atctattgat gcaagcacgg 600
tggttccata ttcttgggat gatgatgttc atctggtcat ctgcccatca gtataagtgc 660
catgttattc tcggcaatct caggaaaaat aaagcaggag tggtcattca ctgtaaccac 720
aggatcccat ttggagactg gtttgaatat gtttcttccc ctaactactt agcagagctg 780
atgatctacg tttccatggc cgtcaccttt gggttccaca acttaacttg gtggctagtg 840
gtgacaaatg tcttctttaa tcaggccctg tctgcctttc tcagccacca attctacaaa 900
agcaaatttg tctcttaccc gaagcatagg aaagctttcc taccattttt gttttaagtt 960
aacctcagtc atgaagaatg caaaccaggt gatggtttca atgcctaagg acagtgaagt 1020
ctggagccca aagtacagtt tcagcaaagc tgtttgaaac tctccattcc atttctatac 1080
cccacaagtt ttcactgaat gagcatgcag tgccactcaa gaaaatgaat ctccaaagta 1140
tcttcaaaga attaattact aatggcagat 1170

<210> SEQ ID NO 364
<211> LENGTH: 60
<212> TYPE: DNA
<213> ORGANISM: Homo sapiens
<220> FEATURE:
<223> OTHER INFORMATION: Contig63525

<400> SEQUENCE: 364
ctcttacccg aagcatagga aagctttcct accatttttg ttttaagtta acctcagtca 60

<210> SEQ ID NO 365
<211> LENGTH: 632
<212> TYPE: DNA
<213> ORGANISM: Homo sapiens
<220> FEATURE:
<223> OTHER INFORMATION: Contig64688

<400> SEQUENCE: 365
aagaatgcta agatgatttc agatatcgaa aagaaaaggc agcgtatgat tgaagtccag 60
gatgaactgc ttcggttaga gccacagctg aaacaactac aaacaaaata tgatgaactt 120
aaagagagaa agtcttccct taggaatgca gcatatttct tatctaattt aaaacagctt 180
tatcaagatt attcagatgt tcaagctcaa gaaccaaacg taaaggaaac gtatgattca 240
tccagccttc cagctctgtt atttaaagca agaacacttc tgggagccga aagccatctg 300

-continued

```
cgaaatatca accatcagtt agagaagctc cttgaccagg gatgagaaga gcagtctact    360

aaaatgtgcc tataggaaga ctagtctcat gctgttacct tctgaaactg tacctttata    420

aatcaattgt tttgcaaaga agttatggcc tacttagaat ctaaaatttg ttattcaaat    480

taaatggctg tgaacaatgt taaatagcat cagtttgtcc aatagtttta aaggccataa    540

tcatcttttc tggttaatat cttgagtaat tttaaaatgt tgacacctta atcggtccca    600

ggtatgagcc ataataaact tgtaaaatta ag                                 632


<210> SEQ ID NO 366
<211> LENGTH: 60
<212> TYPE: DNA
<213> ORGANISM: Homo sapiens
<220> FEATURE:
<223> OTHER INFORMATION: Contig64688

<400> SEQUENCE: 366

ggctgtgaac aatgttaaat agcatcagtt tgtccaatag ttttaaaggc cataatcatc     60
```